United States Patent
Verweij et al.

(10) Patent No.: US 11,773,393 B2
(45) Date of Patent: *Oct. 3, 2023

(54) TREATMENT OF LIVER DISEASES WITH CELL DEATH INDUCING DFFA LIKE EFFECTOR B (CIDEB) INHIBITORS

(71) Applicant: Regeneron Pharmaceuticals, Inc., Tarrytown, NY (US)

(72) Inventors: Niek Verweij, Tarrytown, NY (US); Luca Andrea Lotta, Tarrytown, NY (US); Aris Baras, Tarrytown, NY (US); Mary Haas, Tarrytown, NY (US); Jonas Nielsen, Tarrytown, NY (US); Olukayode Sosina, Tarrytown, NY (US); Adam Locke, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/709,705

(22) Filed: Mar. 31, 2022

(65) Prior Publication Data

US 2022/0282253 A1 Sep. 8, 2022

Related U.S. Application Data

(63) Continuation of application No. 17/560,008, filed on Dec. 22, 2021.

(60) Provisional application No. 63/257,137, filed on Oct. 19, 2021, provisional application No. 63/246,101, filed on Sep. 20, 2021, provisional application No. 63/149,258, filed on Feb. 13, 2021, provisional application No. 63/129,725, filed on Dec. 23, 2020.

(51) Int. Cl.

| | |
|---|---|
| *C12N 15/113* | (2010.01) |
| *A61P 1/16* | (2006.01) |
| *A61K 31/7088* | (2006.01) |
| *A61K 38/46* | (2006.01) |
| *C12Q 1/6883* | (2018.01) |

(52) U.S. Cl.
CPC ........ *C12N 15/113* (2013.01); *A61K 31/7088* (2013.01); *A61K 38/465* (2013.01); *A61P 1/16* (2018.01); *C12N 15/1137* (2013.01); *C12Q 1/6883* (2013.01); *C12N 2310/122* (2013.01); *C12N 2310/14* (2013.01); *C12N 2310/531* (2013.01); *C12N 2320/31* (2013.01); *C12Q 2600/106* (2013.01); *C12Q 2600/158* (2013.01)

(58) Field of Classification Search
CPC ............. C12N 15/113; C12N 15/1137; C12N 2310/14; C12N 2320/31; C12N 2320/34; C12Q 2600/156; C12Q 2600/158

USPC ............... 435/6.1, 91.1, 91.31, 455, 458; 514/44 A, 44 R; 536/23.1, 24.5
See application file for complete search history.

(56) References Cited

U.S. PATENT DOCUMENTS

| | | |
|---|---|---|
| 7,341,749 B2 | 3/2008 | Hall et al. |
| 8,445,207 B2 | 5/2013 | Ryu et al. |
| 9,205,064 B2 | 12/2015 | Narain et al. |
| 9,896,731 B2 | 2/2018 | Narain et al. |
| 10,351,915 B2 | 7/2019 | Narain et al. |
| 10,519,504 B2 | 12/2019 | Narain et al. |
| 10,980,932 B2 | 4/2021 | Le et al. |
| 11,021,545 B2 | 6/2021 | Kwon et al. |
| 11,028,446 B2 | 6/2021 | Narain et al. |
| 11,078,247 B2 | 8/2021 | Fotin-Mleczek et al. |
| 2009/0215853 A1 | 8/2009 | Hall et al. |
| 2010/0173024 A1 | 7/2010 | McDaniel |
| 2010/0226980 A1 | 9/2010 | Moreau |
| 2011/0020312 A1 | 1/2011 | Narain et al. |
| 2011/0027247 A1 | 2/2011 | Narain et al. |
| 2011/0064739 A1 | 3/2011 | Borlak et al. |
| 2011/0123986 A1 | 5/2011 | Narain et al. |
| 2012/0015839 A1 | 1/2012 | Chinnaiyan |
| 2013/0203615 A1 | 8/2013 | Groskopf et al. |
| 2013/0252845 A1 | 9/2013 | Son et al. |
| 2014/0079836 A1 | 3/2014 | McDaniel |
| 2014/0342946 A1 | 11/2014 | Kuriakose et al. |
| 2015/0337390 A1 | 11/2015 | Groskopf et al. |
| 2016/0145693 A1 | 5/2016 | Narain et al. |
| 2017/0137879 A1 | 5/2017 | Narain et al. |
| 2018/0334721 A1 | 11/2018 | Narain et al. |
| 2019/0010554 A1 | 1/2019 | Narain et al. |
| 2019/0071795 A1 | 3/2019 | Nerenberg et al. |
| 2020/0010880 A1 | 1/2020 | Ku et al. |
| 2021/0002725 A1 | 1/2021 | Narain et al. |
| 2021/0047752 A1 | 2/2021 | Nerenberg et al. |
| 2021/0002296 A1 | 7/2021 | Mainolfi et al. |

FOREIGN PATENT DOCUMENTS

| | | | |
|---|---|---|---|
| WO | 2012149386 | 11/2012 | |
| WO | WO-2012149386 A1 * | 11/2012 | ............. C07H 21/04 |
| WO | 2013022872 | 2/2013 | |
| WO | 2014089121 | 6/2014 | |
| WO | 2016130806 | 8/2016 | |
| WO | WO-2016130806 A2 * | 8/2016 | ......... A61K 31/7125 |
| WO | 2017067477 | 4/2017 | |
| WO | 2019075181 | 4/2019 | |
| WO | WO-2019075181 A1 * | 4/2019 | ........... A61K 31/713 |

OTHER PUBLICATIONS

Abul-Husn et al (N. Engl. J. Med., vol. 378, No. 12, pp. 1096-1106 (2018)) (Year: 2018).*
U.S. Appl. No. 17/560,008.*
Li et al., "Cideb Regulates Diet-Induced Obesity, Liver Steatosis, and Insulin Sensitivity by Controlling Lipogenesis and Fatty Acid Oxidation", Diabetes, 2007, 56(10), pp. 2523-2532.
(Continued)

*Primary Examiner* — Jane J Zara
(74) *Attorney, Agent, or Firm* — Armstrong Teasdale LLP

(57) ABSTRACT

The present disclosure provides methods of treating subjects having a liver disease, and methods of identifying subjects having an increased risk of developing liver disease.

27 Claims, 19 Drawing Sheets
(18 of 19 Drawing Sheet(s) Filed in Color)
Specification includes a Sequence Listing.

(56) References Cited

OTHER PUBLICATIONS

Dong et al., "PNPLA3 Potential Therapeutic Target for Personalized Treatment of Chronic Liver Disease", Frontiers in Medicine, 2019, 6, pp. 1-11.
Linden et al., "Pnpla3 silencing with antisense oligonucleotides ameliorates nonalcoholic steatohepatitis and fibrosis in Pnpla3 I148M knock-in mice", Molecular Metabolism, 2019, 22, pp. 49-61.
International Search Report and Written Opinion dated Jun. 10, 2022 for International Patent Application No. PCT/US2021/064987.

* cited by examiner

US 11,773,393 B2

TREATMENT OF LIVER DISEASES WITH CELL DEATH INDUCING DFFA LIKE EFFECTOR B (CIDEB) INHIBITORS

REFERENCE TO A SEQUENCE LISTING

This application includes a Sequence Listing submitted electronically as a text file named 18923806201SEQ, created on Dec. 21, 2021, with a size of 2,576 kilobytes. The Sequence Listing is incorporated herein by reference.

FIELD

The present disclosure relates generally to the treatment of subjects having a liver disease with cell death inducing DFFA like effector B (CIDEB) inhibitors, patatin-like phospholipase domain containing 3 (PNPLA3) inhibitors, or hydroxysteroid 17-beta dehydrogenase 13 (HSD17B13) inhibitors, or any combination thereof, and methods of identifying subjects having an increased risk of developing a liver disease.

BACKGROUND

Chronic liver disease and liver cirrhosis are leading causes of morbidity and mortality in the United States, accounting for 38,170 deaths (1.5% of total deaths) in 2014 (Kochanek et al., Nat'l. Vital Stat. Rep., 2016, 65, 1-122). The most common etiologies of liver cirrhosis in the U.S. are alcoholic liver disease, chronic hepatitis C, and nonalcoholic fatty liver disease (NAFLD), together accounting for about 80% of patients awaiting liver transplant between 2004 and 2013 (Wong et al., Gastroenterology, 2015, 148, 547-555). The estimated prevalence of NAFLD in the U.S. is between 19 and 46 percent (Browning et al., Hepatology, 2004, 40, 1387-1395; Lazo et al., Am. J. Epidemiol., 2013, 178, 38-45; and Williams et al., Gastroenterology, 2011, 140, 124-131) and has been rising over time (Younossi et al., Clin. Gastroenterol. Hepatol., 2011, 9, 524-530), likely in conjunction with increased prevalence of obesity, which is one of its primary risk factors (Cohen et al., Science, 2011, 332, 1519-1523). While significant advances have been made in the treatment of hepatitis C, there are currently no evidence-based treatments for alcoholic or nonalcoholic liver disease or liver cirrhosis. Identifying naturally occurring genetic variants that protect from liver damage and liver disease outcomes can be a pathway to identify novel therapeutic targets for liver disease (Abul-Husn et al. N. Engl. J. Med., 2018, 378, 1096-106).

CIDEB is expressed in the liver and small intestine and has been shown to play roles in regulating various aspects of lipid metabolism. CIDEB may participate in lipid metabolism by regulating lipid droplet fusion and very low density lipoprotein (VLDL) lipidation by interacting with ApoB. CIDEB is also required for the biogenesis of VLDL transport vesicles and for chylomicron lipidation in the small intestine. In addition, CIDEB regulates hepatic SREBP activation (master regulators of lipid metabolism) by selectively promoting ER-to-Golgi delivery of the SREBP/SCAP complex. Sterol depletion induces SCAP to interact with CIDEB, which also binds Sec12, the GEF of Sar1, thereby enriching SCAP/SREBP at ER exit sites and increasing the packaging of SREBP/SCAP into COPII-coated vesicles.

SUMMARY

The present disclosure provides methods of treating a subject having a liver disease or at risk of developing a liver disease, the methods comprising administering a CIDEB inhibitor to the subject.

The present disclosure also provides methods of treating a subject with a CIDEB inhibitor, wherein the subject has a liver disease or is at risk of developing a liver disease, the methods comprising the steps of: determining whether the subject has a CIDEB variant nucleic acid molecule by: obtaining or having obtained a biological sample from the subject; and performing or having performed a sequence analysis on the biological sample to determine if the subject has a genotype comprising the CIDEB variant nucleic acid molecule; and administering or continuing to administer the CIDEB inhibitor in a standard dosage amount to a CIDEB reference subject; and administering or continuing to administer the CIDEB inhibitor in a dosage amount that is the same as or less than a standard dosage amount to a subject that is heterozygous or homozygous for the CIDEB variant nucleic acid molecule; wherein the presence of a genotype having the CIDEB variant nucleic acid molecule indicates the subject has a decreased risk of developing the liver disease or has a decreased risk of developing a more severe form of the liver disease.

The present disclosure also provides methods of identifying a subject having an increased risk of developing a liver disease, the methods comprising: determining or having determined the presence or absence of a CIDEB variant nucleic acid molecule in a biological sample obtained from the subject; wherein: when the subject is CIDEB reference, the subject has an increased risk of developing the liver disease; and when the subject is heterozygous or homozygous for the CIDEB variant nucleic acid molecule, the subject has a decreased risk of developing the liver disease or has a decreased risk of developing a more severe form of the liver disease.

The present disclosure also provides therapeutic compositions that treat or inhibit a liver disease for use in the treatment of a liver disease in a subject having a CIDEB variant nucleic acid molecule comprising: 14:24305635:A: AGTAG, 14:24305641:A:C, 14:24305650:G:A, 14:24305657:C:A, 14:24305662:G:T, 14:24305667:T:C, 14:24305671:C:A, 14:24305671:C:G, 14:24305701:A:T, 14:24305709:C:T, 14:24305718:A:G, 14:24305721:T:C, 14:24305728:G:GGCCTT, 14:24305743:T:C, 14:24305948: T:C, 14:24305966:C:T, 14:24305974:T:C, 14:24305980: TCA:T, 14:24305988:C:T, 14:24306014:C:T, 14:24306034: A:C, 14:24306041:C:G, 14:24306044:G:A, 14:24306047: G:A, 14:24306051:T:G, 14:24306064:T:C, 14:24306074:A: G, 14:24306077:G:C, 14:24306082:A:G, 14:24306083:T:A, 14:24306095:G:A, 14:24306122:A:G, 14:24306134:C:G, 14:24306373:C:G, 14:24306379:T:C, 14:24306382:G:A, 14:24306383:G:T, 14:24306426:T:G, 14:24306437:C:G, 14:24306439:G:C, 14:24306442:A:G, 14:24306444:A:G, 14:24306457:C:T, 14:24306463:C:T, 14:24306469:C:T, 14:24306480:A:G, 14:24306486:A:C, 14:24306504:A:G, 14:24306519:A:G, 14:24307382:G:C, 14:24307405:A:G, 14:24307417:A:T, 14:24307421:T:A, 14:24307441:C:A, 14:24307444:A:C, 14:24307444:A:G, 14:24307450:C: CGCTG, 14:24307461:TG:T, 14:24307469:AG:A, 14:24307474:C:T, 14:24307475:A:G, 14:24307833:G:C, 14:24307851:T:TAC, 14:24306426:T:C, 14:24307849:G:C, 14:24307448:G:T, 14:24305671:C:T, 14:24305663:C:T, 14:24305686:C:G, 14:24307829:A:C, 14:24307818:CT-GAG:C, 14:24307856:C:T, 14:24306423:T:C, 14:24306061:AC:A, 14:24307390:C:T, 14:24306382:G:T, 14:24306373:C:T, 14:24305733:T:C, 14:24307858:T:C, 14:24306387:C:T, 14:24305637:T:C, 14:24306062:C:T, 14:24307853:C:G, 14:24307450:C:G, 14:24306052:TG:T, 14:24305673:G:A, 14:24306043:C:T, 14:24307834:G:A, 14:24306417:C:T, 14:24307451:G:A, 14:24307436:A:C, 14:24305953:ACTTT:A, 14:24306489:G:T, 14:24307441:C:T, 14:24306375:C:T, 14:24305657:C:G, 14:24306427:C:T, 14:24306524:C:T, 14:24307516:C:A, 14:24307840:G:C, 14:24307501:A:G, 14:24305968:A:C, 14:24305986:C:T, 14:24307441:C:G, 14:24307459:G:T, 14:24306017:T:A, 14:24307424:G:A, 14:24306072:G:T, 14:24307423:C:T, 14:24307450:C:T, 14:24306420:G:A, 14:24307454:G:A, 14:24305653:C:T, 14:24307442:G:A, 14:24306002:C:T, 14:24306076:C:T, 14:24305664:C:T, 14:24305961:TG:T, 14:24305706:A:G, 14:24305946:C:T, 14:24306455:G:C, 14:24307468:G:A, 14:24307825:A:C, 14:24306110:G:A, 14:24305710:C:T, 14:24307483:C:T, 14:24306459:A:G, 14:24305754:C:T, 14:24305650:G:C, 14:24305691:C:T, 14:24306508:G:C, 14:24306039:G:T, 14:24306139:T:C, 14:24306391:T:C, 14:24306373:C:A, 14:24307498:C:T, 14:24307415:G:A, 14:24306138:CTG:C, 14:24307453:T:C, 14:24305692:G:A, 14:24305683:C:G, 14:24307484:G:A, 14:24307385:C:T, 14:24306519:A:T, 14:24307839:A:C, 14:24305965:C:T, 14:24305988:CAT:C, 14:24306087:C:G, 14:24307439:C:T, 14:24307477:A:C, 14:24306436:G:T, 14:24306507:A:G, 14:24307397:C:T, 14:24307495:G:A, 14:24306034:A:T, 14:24306013:G:A, 14:24307381:A:G, 14:24306383:G:C, 14:24305638:A:G, 14:24307420:G:A, 14:24306020:C:T, 14:24306470:A:C, 14:24307435:C:T, 14:24306469:C:G, 14:24306451:C:T, 14:24306403:G:A, 14:24307515:C:G, 14:24307489:A:G, 14:24307414:C:T, 14:24306483:A:G, 14:24305755:G:A, 14:24305766:C:T, 14:24306064:T:G, 14:24307516:C:G, 14:24305766:C:G, 14:24306489:G:A, 14:24306097:T:C, 14:24305763:T:G, 14:24307447:G:A, 14:24307402:G:A, 14:24305972:C:G, 14:24306423:T:G, 14:24305974:T:TG, 14:24307411:T:C, 14:24306121:T:C, 14:24307516:C:T, 14:24306424:C:T, 14:24306039:G:C, 14:24307853:C:A, 14:24306388:A:G, 14:24305990:T:C, 14:24307822:G:GT, 14:24305640:G:A, 14:24307418:T:C, 14:24305758:G:C, 14:24306131:C:T, 14:24305953:A:G, 14:24305730:C:A, 14:24306418:A:G, 14:24306059:AC:A, 14:24307842:G:A, 14:24307837:T:G, 14:24306095:G:T, 14:24306109:C:T, 14:24307822:G:A, 14:24306077:G:A, 14:24307824:A:T, 14:24306080:C:T, 14:24305649:C:T, 14:24306433:G:GA, 14:24306420:G:C, 14:24305658:T:G, 14:24306472:C:T, 14:24307412:TC:T, 14:24306062:C:A, 14:24306044:G:C, 14:24306047:G:T, 14:24306126:CAG:C, 14:24306449:C:G, 14:24307391:G:A, or 14:24307857:A:C, according to GRCh38/hg38 human genome assembly coordinates.

The present disclosure also provides compositions comprising a CIDEB inhibitor, a PNPLA3 inhibitor, or an HSD17B13 inhibitor, or any combination thereof, for use in the treatment of a liver disease in a subject having a CIDEB variant nucleic acid molecule comprising: 14:24305635:A:AGTAG, 14:24305641:A:C, 14:24305650:G:A, 14:24305657:C:A, 14:24305662:G:T, 14:24305667:T:C, 14:24305671:C:A, 14:24305671:C:G, 14:24305701:A:T, 14:24305709:C:T, 14:24305718:A:G, 14:24305721:T:C, 14:24305728:G:GGCCTT, 14:24305743:T:C, 14:24305948:T:C, 14:24305966:C:T, 14:24305974:T:C, 14:24305980:TCA:T, 14:24305988:C:T, 14:24306014:C:T, 14:24306034:A:C, 14:24306041:C:G, 14:24306044:G:A, 14:24306047:G:A, 14:24306051:T:G, 14:24306064:T:C, 14:24306074:A:G, 14:24306077:G:C, 14:24306082:A:G, 14:24306083:T:A, 14:24306095:G:A, 14:24306122:A:G, 14:24306134:C:G, 14:24306373:C:G, 14:24306379:T:C, 14:24306382:G:A, 14:24306383:G:T, 14:24306426:T:G, 14:24306437:C:G, 14:24306439:G:C, 14:24306442:A:G, 14:24306444:A:G, 14:24306457:G:A, 14:24306463:C:T, 14:24306469:C:T, 14:24306480:A:G, 14:24306486:A:C, 14:24306504:A:G, 14:24306519:A:G, 14:24307382:G:C, 14:24307405:A:G, 14:24307417:A:T, 14:24307421:T:A, 14:24307441:C:A, 14:24307444:A:C, 14:24307444:A:G, 14:24307450:C:CGCTG, 14:24307461:TG:T, 14:24307469:AG:A, 14:24307474:C:T, 14:24307475:A:G, 14:24307833:G:C, 14:24307851:T:TAC, 14:24306426:T:C, 14:24307849:G:C, 14:24307448:G:T, 14:24305671:C:T, 14:24305663:C:T, 14:24305686:C:G, 14:24307829:A:C, 14:24307818:CTGAG:C, 14:24307856:C:T, 14:24306423:T:C, 14:24306061:AC:A, 14:24307390:C:T, 14:24306382:G:T, 14:24306373:C:T, 14:24305733:T:C, 14:24307858:T:C, 14:24306387:C:T, 14:24305637:T:C, 14:24306062:C:T, 14:24307853:C:G, 14:24307450:C:G, 14:24306052:TG:T, 14:24305673:G:A, 14:24306043:C:T, 14:24307834:G:A, 14:24306417:C:T, 14:24307451:G:A, 14:24307436:A:C, 14:24305953:ACTTT:A, 14:24306489:G:T, 14:24307441:C:T, 14:24306375:C:T, 14:24305657:C:G, 14:24306427:C:T, 14:24306524:C:T, 14:24307516:C:A, 14:24307840:G:C, 14:24307501:A:G, 14:24305968:A:C, 14:24305986:C:T, 14:24307441:C:G, 14:24307459:G:T, 14:24306017:T:A, 14:24307424:G:A, 14:24306072:G:T, 14:24307423:C:T, 14:24307450:C:T, 14:24306420:G:A, 14:24307454:G:A, 14:24305653:C:T, 14:24307442:G:A, 14:24306002:C:T, 14:24306076:C:T, 14:24305664:C:T, 14:24305961:TG:T, 14:24305706:A:G, 14:24305946:C:T, 14:24306455:G:C, 14:24307468:G:A, 14:24307825:A:C, 14:24306110:G:A, 14:24305710:C:T, 14:24307483:C:T, 14:24306459:A:G, 14:24305754:C:T, 14:24305650:G:C, 14:24305691:C:T, 14:24306508:G:C, 14:24306039:G:T, 14:24306139:T:C, 14:24306391:T:C, 14:24306373:C:A, 14:24307498:C:T, 14:24307415:G:A, 14:24306138:CTG:C, 14:24307453:T:C, 14:24305692:G:A, 14:24305683:C:G, 14:24307484:G:A, 14:24307385:C:T, 14:24306519:A:T, 14:24307839:A:C, 14:24305965:C:T, 14:24305988:CAT:C, 14:24306087:C:G, 14:24307439:C:T, 14:24307477:A:C, 14:24306436:G:T, 14:24306507:A:G, 14:24307397:C:T, 14:24307495:G:A, 14:24306034:A:T, 14:24306013:G:A, 14:24307381:A:G, 14:24306383:G:C, 14:24305638:A:G, 14:24307420:G:A, 14:24306020:C:T, 14:24306470:A:C, 14:24307435:C:T, 14:24306469:C:G, 14:24306451:C:T, 14:24306403:G:A, 14:24307515:C:G, 14:24307489:A:G, 14:24307414:C:T, 14:24306483:A:G, 14:24305755:G:A, 14:24305766:C:T, 14:24306064:T:G, 14:24307516:C:G, 14:24305766:C:G, 14:24306489:G:A, 14:24306097:T:C, 14:24305763:T:G, 14:24307447:G:A, 14:24307402:G:A, 14:24305972:C:G, 14:24306423:T:G, 14:24305974:T:TG, 14:24307411:T:C, 14:24306121:T:C, 14:24307516:C:T, 14:24306424:C:T, 14:24306039:G:C, 14:24307853:C:A, 14:24306388:A:G, 14:24305990:T:C, 14:24307822:G:GT, 14:24305640:G:A, 14:24307418:T:C, 14:24305758:G:C, 14:24306131:C:T, 14:24305953:A:G, 14:24305730:C:A, 14:24306418:A:G, 14:24306059:AC:A, 14:24307842:G:A, 14:24307837:T:G, 14:24306095:G:T, 14:24306109:C:T, 14:24307822:G:A, 14:24306077:G:A, 14:24307824:A:T, 14:24306080:C:T, 14:24305649:C:T, 14:24306433:G:GA, 14:24306420:G:C, 14:24305658:T:G, 14:24306472:C:T, 14:24307412:TC:T, 14:24306062:C:A, 14:24306044:G:C, 14:24306047:G:T, 14:24306126:CAG:C, 14:24306449:C:G, 14:24307391:G:A, or 14:24307857:A:C, according to GRCh38/hg38 human genome assembly coordinates.

The present disclosure also provides methods of treating a subject having a liver disease or at risk of developing a liver disease, wherein the subject is heterozygous or homozygous for a PNPLA3 variant nucleic acid molecule encoding PNPLA3 Ile148Met or Ile144Met polypeptide, the methods comprising administering to the subject: i) a CIDEB inhibitor; ii) a combination of a CIDEB inhibitor and a PNPLA3 inhibitor; iii) a combination of a CIDEB inhibitor and an HSD17B13 inhibitor; or iv) a combination of a CIDEB inhibitor, a PNPLA3 inhibitor, and an HSD17B13 inhibitor.

The present disclosure also provides methods of treating a subject having a liver disease or at risk of developing a liver disease, wherein: when the subject is homozygous for a nucleic acid molecule encoding a reference HSD17B13 polypeptide or a functional HSD17B13 polypeptide, the subject is administered: i) a CIDEB inhibitor in an amount that is the same as or greater than a standard dosage amount; ii) a combination of a CIDEB inhibitor in an amount that is the same as or greater than a standard dosage amount and a PNPLA3 inhibitor; iii) a combination of a CIDEB inhibitor in an amount that is the same as or greater than a standard dosage amount and an HSD17B13 inhibitor; or iv) a combination of a CIDEB inhibitor in an amount that is the same as or greater than a standard dosage amount, aPNPLA3 inhibitor, and an HSD17B13 inhibitor; and when the subject is not homozygous for a nucleic acid molecule encoding a reference HSD17B13 polypeptide or a functional HSD17B13 polypeptide (i.e., is a carrier for a loss-of-function HSD17B13), the subject is administered: i) a CIDEB inhibitor in an amount that is less than a standard dosage amount; ii) a combination of a CIDEB inhibitor in an amount that is less than a standard dosage amount and a PNPLA3 inhibitor; iii) a combination of a CIDEB inhibitor in an amount that is less than a standard dosage amount and an HSD17B13 inhibitor; or iv) a combination of a CIDEB inhibitor in an amount that is less than a standard dosage amount, aPNPLA3 inhibitor, and an HSD17B13 inhibitor.

The present disclosure also provides methods of treating a subject with a CIDEB inhibitor, wherein the subject has a liver disease or is at risk of developing a liver disease, the methods comprising: determining whether the subject has a PNPLA3 variant nucleic acid molecule encoding a PNPLA3 Ile148Met or Ile144Met polypeptide by: obtaining or having obtained a biological sample from the subject; and performing or having performed a sequence analysis on the biological sample to determine if the subject has a genotype comprising the PNPLA3 variant nucleic acid molecule; and administering or continuing to administer the CIDEB inhibitor in an amount that is the same as or greater than a standard dosage amount, or in combination with an HSD17B13 inhibitor and/or a PNPLA3 inhibitor to a subject that is heterozygous or homozygous for the PNPLA3 variant nucleic acid molecule; wherein the presence of a genotype having the PNPLA3 variant nucleic acid molecule encoding a PNPLA3 Ile148Met or Ile144Met polypeptide indicates that the subject is a candidate for treatment with the CIDEB inhibitor.

The present disclosure also provides methods of treating a subject with a CIDEB inhibitor, wherein the subject has a liver disease or is at risk of developing a liver disease, the methods comprising: determining whether the subject has a nucleic acid molecule encoding a reference HSD17B13 polypeptide or a functional HSD17B13 polypeptide by: obtaining or having obtained a biological sample from the subject; and performing or having performed a sequence analysis on the biological sample to determine if the subject has a genotype comprising the nucleic acid molecule encoding the reference HSD17B13 polypeptide or a functional HSD17B13 polypeptide; and administering or continuing to administer the CIDEB inhibitor, or in combination with an HSD17B13 inhibitor and/or a PNPLA3 inhibitor, to a subject that is heterozygous or homozygous for the nucleic acid molecule encoding the reference HSD17B13 polypeptide or a functional HSD17B13 polypeptide; wherein the presence of a genotype having the nucleic acid molecule encoding the reference HSD17B13 polypeptide or a functional HSD17B13 polypeptide indicates the subject is a candidate for treatment with the CIDEB inhibitor.

The present disclosure also provides methods of treating a subject, wherein the subject is overweight, obese, has increased body mass index (BMI), has a high percentage of liver fat, or has high adiposity, the methods comprising administering to the subject a CIDEB inhibitor, or a CIDEB inhibitor in combination with a PNPLA3 inhibitor and/or an HSD17B13 inhibitor.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying figures, which are incorporated in and constitute a part of this specification, illustrate several aspects and together with the description serve to explain the principles of the present disclosure.

DESCRIPTION

Figure 1:
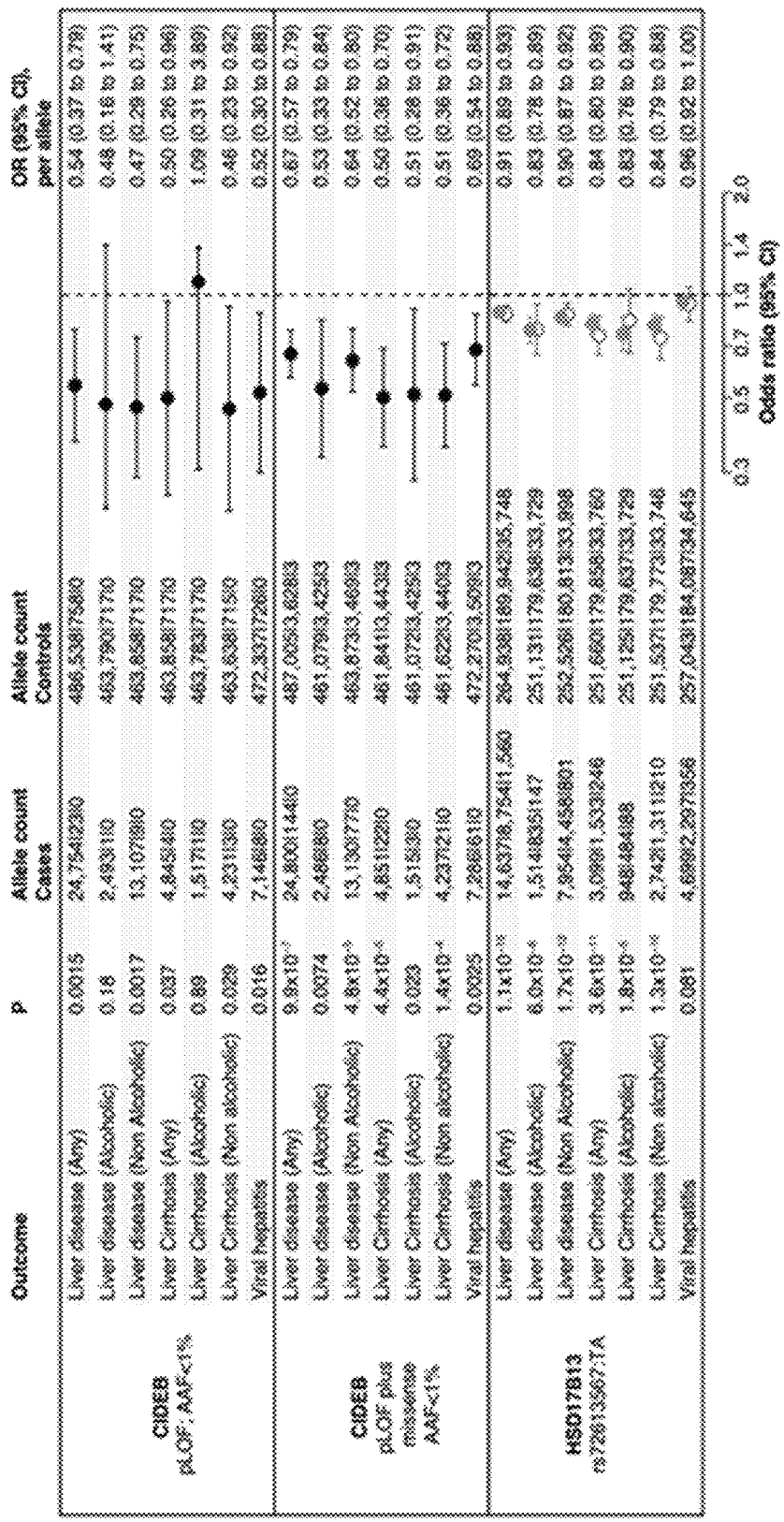
FIG. 1 shows an association of rare coding variants in CIDEB with liver disease risk. The Figure shows the association with liver disease across etiology and severity spectrum for rare pLOF variants in CIDEB (top), rare coding variants in CIDEB (middle) and the HSD17B13 splice variant (gray, heterozygous variant genotype compared with reference homozygous genotype; open circles, homozygous variant genotype compared with reference homozygous genotype). Abbreviations: OR; odds ratio, CI, confidence interval.

Various terms relating to aspects of the present disclosure are used throughout the specification and claims. Such terms are to be given their ordinary meaning in the art, unless otherwise indicated. Other specifically defined terms are to be construed in a manner consistent with the definitions provided herein.

Unless otherwise expressly stated, it is in no way intended that any method or aspect set forth herein be construed as requiring that its steps be performed in a specific order.

Accordingly, where a method claim does not specifically state in the claims or descriptions that the steps are to be limited to a specific order, it is in no way intended that an order be inferred, in any respect. This holds for any possible non-expressed basis for interpretation, including matters of logic with respect to arrangement of steps or operational flow, plain meaning derived from grammatical organization or punctuation, or the number or type of aspects described in the specification.

As used herein, the singular forms "a," "an" and "the" include plural referents unless the context clearly dictates otherwise.

As used herein, the term "about" means that the recited numerical value is approximate and small variations would not significantly affect the practice of the disclosed embodiments. Where a numerical value is used, unless indicated otherwise by the context, the term "about" means the numerical value can vary by ±10% and remain within the scope of the disclosed embodiments.

As used herein, the term "comprising" may be replaced with "consisting" or "consisting essentially of" in particular embodiments as desired.

As used herein, the terms "nucleic acid", "nucleic acid molecule", "nucleic acid sequence", "polynucleotide", or "oligonucleotide" can comprise a polymeric form of nucleotides of any length, can comprise DNA and/or RNA, and can be single-stranded, double-stranded, or multiple stranded. One strand of a nucleic acid also refers to its complement.

As used herein, the term "subject" includes any animal, including mammals. Mammals include, but are not limited to, farm animals (such as, for example, horse, cow, pig), companion animals (such as, for example, dog, cat), laboratory animals (such as, for example, mouse, rat, rabbits), and non-human primates (such as, for example, apes and monkeys). In some embodiments, the subject is a human. In some embodiments, the subject is a patient under the care of a physician.

It has been observed in accordance with the present disclosure that a gene burden of particular CIDEB variations (i.e., CIDEB variant nucleic acid molecules) associate with a decreased risk of developing a liver disease. It is believed that variants in CIDEB genes or proteins have not been significantly associated with liver disease or markers of liver damage in previous exome-sequencing association studies. Therefore, it is believed that humans having a liver disease or at risk of developing a liver disease may be treated with CIDEB inhibitors. Accordingly, the present disclosure provides methods for leveraging the identification of subjects who do not have such protective CIDEB variant nucleic acid molecules who, thus, are at risk of developing a liver disease, and to stratify the risk in such subjects of developing liver disease, such that subjects at risk or subjects with active disease may be treated with CIDEB inhibitors.

In any of the embodiments described herein, the CIDEB variant nucleic acid molecules can be any CIDEB nucleic acid molecule (such as, for example, genomic nucleic acid molecule, mRNA molecule, or cDNA molecule) encoding a CIDEB polypeptide having a partial loss-of-function, a complete loss-of-function, a predicted partial loss-of-function, or a predicted complete loss-of-function, or encoding a missense polypeptide, or resulting in the absence of an encoded polypeptide, or having an impact on the CIDEB mRNA sequence or expression. For example, the CIDEB variant nucleic acid molecules can be any of the CIDEB variant nucleic acid molecules described herein. A CIDEB variant nucleic acid molecule can be a variant that is predicted to result in the premature truncation of the CIDEB polypeptide (including, but not limited to, frameshift mutations, insertions or deletions, stop-gain, stop-lost, start-lost, splice site variants or large chromosomal or sub-chromosomal re-arrangements affecting the CIDEB gene). CIDEB variant nucleic acid molecules can include, but are not limited to, in-frame insertions or deletions in the CIDEB gene or variants in the untranslated regions of the CIDEB gene. A missense variant is a variant predicted to result in the change of an amino acid sequence of the CIDEB polypeptide.

For purposes of the present disclosure, any particular subject, such as a human, can be categorized as having one of three CIDEB genotypes: i) CIDEB reference; ii) heterozygous for a CIDEB variant nucleic acid molecule, and iii) homozygous for a CIDEB variant nucleic acid molecule. A subject is CIDEB reference when the subject does not have a copy of a CIDEB variant nucleic acid molecule. A subject is heterozygous for a CIDEB variant nucleic acid molecule when the subject has a single copy of a CIDEB variant nucleic acid molecule. A CIDEB variant nucleic acid molecule is any CIDEB nucleic acid molecule (such as, a genomic nucleic acid molecule, an mRNA molecule, or a cDNA molecule) encoding a CIDEB polypeptide having a partial loss-of-function, a complete loss-of-function, a predicted partial loss-of-function, or a predicted complete loss-of-function, or encoding a missense polypeptide, or having an impact on the CIDEB mRNA sequence. A subject who has a CIDEB polypeptide having a partial loss-of-function (or predicted partial loss-of-function, or a missense) is hypomorphic for CIDEB (lower abundance or function of the gene compared to the reference sequence version). The CIDEB variant nucleic acid molecule can be any variant nucleic acid molecule described herein. A subject is homozygous for a CIDEB variant nucleic acid molecule when the subject has two copies of any of the CIDEB variant nucleic acid molecules.

For subjects that are genotyped or determined to be heterozygous or homozygous for a CIDEB variant nucleic acid molecule, such subjects have a decreased risk of developing a liver disease compared to CIDEB reference subjects. For subjects that are genotyped or determined to be CIDEB reference, such subjects have an increased risk of developing a liver disease compared to carriers of the aforementioned CIDEB variants. For subjects that are genotyped or determined to be CIDEB reference or are heterozygous for a CIDEB variant nucleic acid molecule, such subjects can be treated with one or more CIDEB inhibitors. Such subjects can also be treated with therapeutic agents used to treat a liver disease. For subjects that are genotyped or determined to be CIDEB reference or are heterozygous for a CIDEB variant nucleic acid molecule, such subjects can also be treated with a combination of a CIDEB inhibitor and a PNPLA3 inhibitor and/or an HSD17B13 inhibitor.

For subjects that are genotyped or determined to be CIDEB reference and are carriers of a PNPLA3 variant nucleic acid molecule encoding PNPLA3 Ile148Met or Ile144Met, such subjects have an increased risk of developing a liver disease compared to subjects who are either CIDEB reference or carriers of the aforementioned CIDEB variant types, but do not carry a PNPLA3 variant nucleic acid molecule encoding PNPLA3 Ile148Met or Ile144Met (PNPLA3 reference). For subjects that are genotyped or determined to be CIDEB reference or are heterozygous for a CIDEB variant nucleic acid molecule and to be carriers of a PNPLA3 variant nucleic acid molecule encoding PNPLA3 Ile148Met or Ile144Met, such subjects can be treated with a combination of one or more CIDEB inhibitors and/or one or more PNPLA3 inhibitors. Such subjects can also be treated with therapeutic agents used to treat a liver disease. Such subjects can also be treated with an HSD17B13 inhibitor.

For subjects that are genotyped or determined to be CIDEB reference and are carriers of a nucleic acid molecule encoding a reference HSD17B13 polypeptide or a functional HSD17B13 polypeptide, such subjects have an increased risk of developing a liver disease compared to subjects who are either CIDEB reference or heterozygous carriers of the aforementioned CIDEB variants, but do not carry a nucleic acid molecule encoding a reference HSD17B13 polypeptide or a functional HSD17B13 polypeptide. For subjects that are genotyped or determined to be CIDEB reference or are heterozygous for a CIDEB variant nucleic acid molecule and to be carriers of a nucleic acid molecule encoding a reference HSD17B13 polypeptide or a functional HSD17B13 polypeptide, such subjects can be treated with a combination of one or more CIDEB inhibitors and/or one or more HSD17B13 inhibitors. Such subjects can also be treated with therapeutic agents used to treat a liver disease. Such subjects can also be treated with a PNPLA3 inhibitor.

In any of the embodiments described herein, the CIDEB variant nucleic acid molecule can be any nucleic acid molecule (such as, for example, genomic nucleic acid molecule, mRNA molecule, or cDNA molecule) encoding a CIDEB polypeptide having a partial loss-of-function, a complete loss-of-function, a predicted partial loss-of-function, or a predicted complete loss-of-function, or encoding a missense polypeptide, or having an impact on the CIDEB mRNA sequence. In some embodiments, the CIDEB variant nucleic acid molecule is a variant that causes or is predicted to cause a nonsynonymous amino acid substitution in CIDEB and whose allele frequency is less than 1/100 alleles in the population from which the subject is selected. In some embodiments, the CIDEB variant nucleic acid molecule is any rare missense variant (allele frequency <1%; or 1 in 100 alleles) or any missense variant predicted or demonstrated to result in a change in CIDEB polypeptide sequence, folding, structure, abundance or function regardless of frequency, or any splice-site, stop-gain, start-loss, stop-loss, frameshift, or in-frame indel, or other frameshift CIDEB variant or any other variant predicted or demonstrated to result in a change in the amino acid sequence of the CIDEB polypeptide. In some embodiments, the subject has one or more of the following CIDEB variant nucleic acid molecules: 14:24305635:A:AGTAG, 14:24305641:A:C, 14:24305650:G:A, 14:24305657:C:A, 14:24305662:G:T, 14:24305667:T:C, 14:24305671:C:A, 14:24305671:C:G, 14:24305701:A:T, 14:24305709:C:T, 14:24305718:A:G, 14:24305721:T:C, 14:24305728:G:GGCCTT, 14:24305743:T:C, 14:24305948:T:C, 14:24305966:C:T, 14:24305974:T:C, 14:24305980:TCA:T, 14:24305988:C:T, 14:24306014:C:T, 14:24306034:A:C, 14:24306041:C:G, 14:24306044:G:A, 14:24306047:G:A, 14:24306051:T:G, 14:24306064:T:C, 14:24306074:A:G, 14:24306077:G:C, 14:24306082:A:G, 14:24306083:T:A, 14:24306095:G:A, 14:24306122:A:G, 14:24306134:C:G, 14:24306373:C:G, 14:24306379:T:C, 14:24306382:G:A, 14:24306383:G:T, 14:24306426:T:G, 14:24306437:C:G, 14:24306439:G:C, 14:24306442:A:G, 14:24306444:A:G, 14:24306457:C:T, 14:24306463:C:T, 14:24306469:C:T, 14:24306480:A:G, 14:24306486:A:C, 14:24306504:A:G, 14:24306519:A:G, 14:24307382:G:C, 14:24307405:A:G, 14:24307417:A:T, 14:24307421:T:A, 14:24307441:C:A, 14:24307444:A:C, 14:24307444:A:G, 14:24307450:CGCTG, 14:24307461:TG:T, 14:24307469:AG:A, 14:24307474:C:T, 14:24307475:A:G, 14:24307833:G:C, 14:24307851:T:TAC, 14:24306426:T:C, 14:24307849:G:C, 14:24307448:G:T, 14:24305671:C:T, 14:24305663:C:T, 14:24305686:C:G, 14:24307829:A:C, 14:24307818:CTGAG:C, 14:24307856:C:T, 14:24306423:T:C, 14:24306061:AC:A, 14:24307390:C:T, 14:24306382:G:T, 14:24306373:C:T, 14:24305733:T:C, 14:24307858:T:C, 14:24306387:C:T, 14:24305637:T:C, 14:24306062:C:T, 14:24307853:C:G, 14:24307450:C:G, 14:24306052:TG:T, 14:24305673:G:A, 14:24306043:C:T, 14:24307834:G:A, 14:24306417:C:T, 14:24307451:G:A, 14:24307436:A:C, 14:24305953:ACTTT:A, 14:24306489:G:T, 14:24307441:C:T, 14:24306375:C:T, 14:24305657:C:G, 14:24306427:C:T, 14:24306524:C:T, 14:24307516:C:A, 14:24307840:G:C, 14:24307501:A:G, 14:24305968:A:C, 14:24305986:C:T, 14:24307441:C:G, 14:24307459:G:T, 14:24306017:T:A, 14:24307424:G:A, 14:24306072:G:T, 14:24307423:C:T, 14:24307450:C:T, 14:24306420:G:A, 14:24307454:G:A, 14:24305653:C:T, 14:24307442:G:A, 14:24306002:C:T, 14:24306076:C:T, 14:24305664:C:T, 14:24305961:TG:T, 14:24305706:A:G, 14:24305946:C:T, 14:24306455:G:C, 14:24307468:G:A, 14:24307825:A:C, 14:24306110:G:A, 14:24305710:C:T, 14:24307483:C:T, 14:24306459:A:G, 14:24305754:C:T, 14:24305650:G:C, 14:24305691:C:T, 14:24306508:G:C, 14:24306039:G:T, 14:24306139:T:C, 14:24306391:T:C, 14:24306373:C:A, 14:24307498:C:T, 14:24307415:G:A, 14:24306138:CTG:C, 14:24307453:T:C, 14:24305692:G:A, 14:24305683:C:G, 14:24307484:G:A, 14:24307385:C:T, 14:24306519:A:T, 14:24307839:A:C, 14:24305965:C:T, 14:24305988:CAT:C, 14:24306087:C:G, 14:24307439:C:T, 14:24307477:A:C, 14:24306436:G:T, 14:24306507:A:G, 14:24307397:C:T, 14:24307495:G:A, 14:24306034:A:T, 14:24306013:G:A, 14:24307381:A:G, 14:24306383:G:C, 14:24305638:A:G, 14:24307420:G:A, 14:24306020:C:T, 14:24306470:A:C, 14:24307435:C:T, 14:24306469:C:G, 14:24306451:C:T, 14:24306403:G:A, 14:24307515:C:G, 14:24307489:A:G, 14:24307414:C:T, 14:24306483:A:G, 14:24305755:G:A, 14:24305766:C:T, 14:24306064:T:G, 14:24307516:C:G, 14:24305766:C:G, 14:24306489:G:A, 14:24306097:T:C, 14:24305763:T:G, 14:24307447:G:A, 14:24307402:G:A, 14:24305972:C:G, 14:24306423:T:G, 14:24305974:T:TG, 14:24307411:T:C, 14:24306121:T:C, 14:24307516:C:T, 14:24306424:C:T, 14:24306039:G:C, 14:24307853:C:A, 14:24306388:A:G, 14:24305990:T:C, 14:24307822:G:GT, 14:24305640:G:A, 14:24307418:T:C, 14:24305758:G:C, 14:24306131:C:T, 14:24305953:A:G, 14:24305730:C:A, 14:24306418:A:G, 14:24306059:AC:A, 14:24307842:G:A, 14:24307837:T:G, 14:24306095:G:T, 14:24306109:C:T, 14:24307822:G:A, 14:24306077:G:A, 14:24307824:A:T, 14:24306080:C:T, 14:24305649:C:T, 14:24306433:G:GA, 14:24306420:G:C, 14:24305658:T:G, 14:24306472:C:T, 14:24307412:TC:T, 14:24306062:C:A, 14:24306044:G:C, 14:24306047:G:T, 14:24306126:CAG:C, 14:24306449:C:G, 14:24307391:G:A, or 14:24307857:A:C (according to GRCh38/hg38 human genome assembly coordinates).

In any of the embodiments described herein, the CIDEB variant nucleic acid molecules have one or more variations at the indicated positions of chromosome 14 using the nucleotide sequence of the CIDEB reference genomic nucleic acid molecule (SEQ ID NO:1; ENSG00000136305.11 in the GRCh38/hg38 human genome assembly, for which position 24,311,422 of chromosome 14 is the first nucleotide in SEQ ID NO:1).

In any of the embodiments described herein, the CIDEB variant nucleic acid molecules can be mRNA and cDNA molecules having the corresponding variant positions referring to the reference genomic sequence as a reference sequence.

The nucleotide sequences of CIDEB reference mRNA molecules produced through alternative splicing are set forth in SEQ ID NOs:2-12. The variant nucleotides at their respective variant positions for the variant genomic nucleic acid molecules described herein also have corresponding variant nucleotides at their respective variant positions for the variant mRNA molecules based upon the CIDEB reference mRNA sequences according to SEQ ID NOs:2-12. Any of these CIDEB variant mRNA molecules can be detected in any of the methods described herein.

The nucleotide sequences of CIDEB reference cDNA molecules produced through alternative splicing are set forth in SEQ ID NOs:13-23. The variant nucleotides at their respective variant positions for the variant genomic nucleic acid molecules described herein also have corresponding variant nucleotides at their respective variant positions for the variant cDNA molecules based upon the CIDEB reference cDNA sequences according to SEQ ID NOs:13-23. Any of these CIDEB variant cDNA molecules can be detected in any of the methods described herein.

The amino acid sequence of a CIDEB reference polypeptide is set forth in SEQ ID NO:24. Using the translated nucleotide sequence of either the CIDEB mRNA or cDNA molecules, the CIDEB variant polypeptides have corresponding translated variant amino acids at variant positions. Any of these CIDEB predicted loss-of-function polypeptides can be detected in any of the methods described herein.

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. The amino acid sequence follows the standard convention of beginning at the amino terminus of the sequence and proceeding forward (i.e., from left to right in each line) to the carboxy terminus.

As used herein, the phrase "corresponding to" or grammatical variations thereof when used in the context of the numbering of a particular nucleotide or nucleotide sequence or position refers to the numbering of a specified reference sequence when the particular nucleotide or nucleotide sequence is compared to a reference sequence. In other words, the residue (such as, for example, nucleotide or amino acid) number or residue (such as, for example, nucleotide or amino acid) position of a particular polymer is designated with respect to the reference sequence rather than by the actual numerical position of the residue within the particular nucleotide or nucleotide sequence. For example, a particular nucleotide sequence can be aligned to a reference sequence by introducing gaps to optimize residue matches between the two sequences. In these cases, although the gaps are present, the numbering of the residue in the particular nucleotide or nucleotide sequence is made with respect to the reference sequence to which it has been aligned. A variety of computational algorithms exist that can be used for performing a sequence alignment to identify a nucleotide or amino acid position in one polymeric molecule that corresponds to a nucleotide or amino acid position in another polymeric molecule. For example, by using the NCBI BLAST algorithm (Altschul et al., Nucleic Acids Res., 1997, 25, 3389-3402) or CLUSTALW software (Sievers and Higgins, Methods Mol. Biol., 2014, 1079, 105-116) sequence alignments may be performed. However, sequences can also be aligned manually.

Any one or more (i.e., any combination) of the variants recited herein can be used within any of the methods described herein to determine whether a subject has an increased or decreased risk of developing a liver disease. The combinations of particular variants can form a gene-burden or "mask" used for statistical analysis of the particular correlation of CIDEB and higher or lower risk of developing a liver disease or liver damage (e.g., as quantified by liver biomarkers or imaging related variables).

In any of the embodiments described herein, the CIDEB predicted loss-of-function polypeptide can be any CIDEB polypeptide having a partial loss-of-function, a complete loss-of-function, a predicted partial loss-of-function, or a predicted complete loss-of-function, or missense polypeptide.

In any of the embodiments described herein, the liver disease is a fatty liver disease (such as, for example, alcoholic fatty liver disease (AFLD), non-alcoholic fatty liver disease (NAFLD) or non-alcoholic steatohepatitis (NASH)), liver cirrhosis, liver fibrosis, an increased liver enzyme (such as, for example, alanine transaminase (ALT) or aspartate transaminase (AST)), simple steatosis, steatohepatitis, parenchymal liver disease, viral hepatitis, or hepatocellular carcinoma, or any of the complications of such conditions (including, but not limited to, heart or metabolic disease related to NASH or NAFLD, portal vein hypertension or thrombosis, esophageal or gastric varices or bleeding from those varices, and other liver-disease related co-morbidities). In some embodiments, the liver disease is a fatty liver disease. In some embodiments, the liver disease is AFLD. In some embodiments, the liver disease is NAFLD. In some embodiments, the liver disease is NASH. In some embodiments, the liver disease is liver cirrhosis. In some embodiments, the liver disease is liver fibrosis. In some embodiments, the liver disease is an increased liver enzyme. In some embodiments, the liver disease is increased ALT. In some embodiments, the liver disease is increased AST. In some embodiments, the liver disease is simple steatosis. In some embodiments, the liver disease is steatohepatitis. In some embodiments, the liver disease is parenchymal liver disease. In some embodiments, the liver disease is viral hepatitis. In some embodiments, the liver disease is hepatocellular carcinoma. In some embodiments, the liver disease is liver damage quantified by a liver biomarker (e.g., liver transaminase), a change in a liver biomarker, by liver imaging, or by liver histology.

Symptoms of liver disease include, but are not limited to, enlarged liver, fatigue, pain in the upper right abdomen, abdominal swelling (ascites), enlarged blood vessels just beneath the skin's surface, enlarged breasts in men, enlarged spleen, red palms, and yellowing of the skin and eyes (jaundice), pruritus, dark urine color, pale stool color nausea or vomiting, loss of appetite, and tendency to bruise easily. Testing for liver diseases can involve blood tests, imaging of the liver, and biopsy of the liver. An individual is at increased risk of a liver disease if the subject has at least one known risk-factor (e.g., genetic factor such as a disease-causing mutation) placing individuals with that risk factor at a statistically significant greater risk of developing the disease than individuals without the risk factor. Risk factors for liver diseases are also well known and can include, for example, excessive alcohol use, obesity, high cholesterol, high levels of triglycerides in the blood, polycystic ovary syndrome, sleep apnea, type 2 diabetes, underactive thyroid (hypothyroidism), underactive pituitary gland (hypopituitarism), and metabolic syndromes including raised blood lipids.

The present disclosure provides methods of treating a subject having a liver disease or at risk of developing a liver disease, the methods comprising administering a CIDEB inhibitor to the subject.

The present disclosure also provides methods of treating a subject having a liver disease or at risk of developing a liver disease, wherein the subject is heterozygous or homozygous for a nucleic acid molecule encoding PNPLA3 Ile148Met or Ile144Met, the methods comprising administering: i) a CIDEB inhibitor in an amount that is the same as or greater than a standard dosage amount; ii) a combination of a CIDEB inhibitor in an amount that is the same as or greater than a standard dosage amount and a PNPLA3 inhibitor; iii) a combination of a CIDEB inhibitor in an amount that is the same as or greater than a standard dosage amount and an HSD17B13 inhibitor; or iv) a combination of a CIDEB inhibitor in an amount that is the same as or greater than a standard dosage amount, aPNPLA3 inhibitor, and an HSD17B13 inhibitor.

The present disclosure also provides methods of treating a subject having a liver disease or at risk of developing a liver disease, wherein: when the subject is homozygous for a nucleic acid molecule encoding a reference HSD17B13 polypeptide or a functional HSD17B13 polypeptide, the subject is administered: i) a CIDEB inhibitor in an amount that is the same as or greater than a standard dosage amount; ii) a combination of a CIDEB inhibitor in an amount that is the same as or greater than a standard dosage amount and a PNPLA3 inhibitor; iii) a combination of a CIDEB inhibitor in an amount that is the same as or greater than a standard dosage amount and an HSD17B13 inhibitor; or iv) a combination of a CIDEB inhibitor in an amount that is the same as or greater than a standard dosage amount, aPNPLA3 inhibitor, and an HSD17B13 inhibitor; and when the subject is not homozygous for a nucleic acid molecule encoding a reference HSD17B13 polypeptide or a functional HSD17B13 polypeptide (i.e., is a carrier for a loss-of-function HSD17B13), the subject is administered: i) a CIDEB inhibitor in an amount that is less than a standard dosage amount; ii) a combination of a CIDEB inhibitor in an amount that is less than a standard dosage amount and a PNPLA3 inhibitor; iii) a combination of a CIDEB inhibitor in an amount that is less than a standard dosage amount and an HSD17B13 inhibitor; or iv) a combination of a CIDEB inhibitor in an amount that is less than a standard dosage amount, aPNPLA3 inhibitor, and an HSD17B13 inhibitor.

The present disclosure also provides methods of treating a subject having a liver disease or at risk of developing a liver disease, wherein the subject is heterozygous or homozygous for a nucleic acid molecule encoding a PNPLA3 Ile148Met or Ile144Met polypeptide and is heterozygous or homozygous for a nucleic acid molecule encoding a reference HSD17B13 polypeptide or a functional HSD17B13 polypeptide, the methods comprising administering a combination of a CIDEB inhibitor, a PNPLA3 inhibitor, and/or an HSD17B13 inhibitor to the subject.

In these methods, the subject can have any one or more of the liver diseases disclosed herein. In some embodiments, the liver disease is a fatty liver disease. In some embodiments, the liver disease is NAFLD or NASH. In some embodiments, the liver disease is NAFLD. In some embodiments, the liver disease is NASH. In some embodiments, the liver disease is liver cirrhosis. In some embodiments, the liver disease is fibrosis. In some embodiments, the liver disease is an increased liver enzyme. In some embodiments, the liver enzyme is ALT. In some embodiments, the liver enzyme is AST.

The present disclosure also provides methods of treating a subject having a liver disease or at risk of developing a liver disease, the methods comprising determining a nonalcoholic fatty liver disease (NAFLD) activity score (or NASH-CRN nonalcoholic fatty-liver disease activity score or NAS (NASH-CRN nonalcoholic fatty-liver disease activity score)), and when the NAFLD activity score is greater than a pre-determined score, administering to the subject a CIDEB inhibitor, a PNPLA3 inhibitor, or an HSD17B13 inhibitor, or any combination thereof, as described herein. The NAFLD activity score is defined by histological examinations from liver biopsies and scored based on the NASH Clinical Research Network system: steatosis Grade 0 (<5% parenchymal involvement), steatosis Grade 1 (5 to <34%), steatosis Grade 2 (34 to <67%), and steatosis Grade 3 (>67%); lobular inflammation Grade 0 (no foci), lobular inflammation Grade 1 (mild, <2 foci per 200× field), lobular inflammation Grade 2 (moderate, 2-4 foci per 200× field), lobular inflammation Grade 3 (severe, >4 foci per 200× field); ballooning Grade 0 (none), ballooning Grade 1 (few balloon cells), ballooning Grade 2 (many cells/prominent ballooning); fibrosis Stage 0 (none), fibrosis Stage 1 (perisinusoidal or periportal fibrosis), fibrosis Stage 2 (perisinusoidal and periportal fibrosis), fibrosis Stage 3 (bridging fibrosis), and fibrosis Stage 4 (cirrhosis). 5) Nonalcoholic fatty liver disease (NAFLD) activity score (NAS) defined as the unweighted sum of the scores for steatosis (0-3), lobular inflammation (0-3), and ballooning (0-2), thus ranging from 0-8. In some embodiments, the pre-determined NAFLD activity score is greater than 0. In some embodiments, the pre-determined NAFLD activity score is greater than 1. In some embodiments, the pre-determined NAFLD activity score is greater than 2. In some embodiments, the pre-determined NAFLD activity score is greater than 3. In some embodiments, the pre-determined NAFLD activity score is greater than 4. In some embodiments, the pre-determined NAFLD activity score is greater than 5.

In some embodiments, the CIDEB inhibitor comprises an inhibitory nucleic acid molecule. Examples of inhibitory nucleic acid molecules include, but are not limited to, antisense nucleic acid molecules, small interfering RNAs (siRNAs), and short hairpin RNAs (shRNAs). Such inhibitory nucleic acid molecules can be designed to target any region of a CIDEB mRNA. In some embodiments, the antisense RNA, siRNA, or shRNA hybridizes to a sequence within a CIDEB genomic nucleic acid molecule or mRNA molecule and decreases expression of the CIDEB polypeptide in a cell in the subject. In some embodiments, the CIDEB inhibitor comprises an antisense RNA that hybridizes to a CIDEB genomic nucleic acid molecule or mRNA molecule and decreases expression of the CIDEB polypeptide in a cell in the subject. In some embodiments, the CIDEB inhibitor comprises an siRNA that hybridizes to a CIDEB genomic nucleic acid molecule or mRNA molecule and decreases expression of the CIDEB polypeptide in a cell in the subject. In some embodiments, the CIDEB inhibitor comprises an shRNA that hybridizes to a CIDEB genomic nucleic acid molecule or mRNA molecule and decreases expression of the CIDEB polypeptide in a cell in the subject.

The inhibitory nucleic acid molecules described herein can be targeted to various CIDEB transcripts. For example, the inhibitory nucleic acid molecules described herein can be targeted to the CIDEB transcripts (derived from chromosome 14; Ensembl Gene ID=ENSG00000136305; hgnc symbol=CIDEB; from top to bottom=Transcript A, Transcript B, Transcript C, Transcript D, Transcript E, and Transcript F) in Table 1.

TABLE 1

| Ensembl Transcript id | Transcript Start | Transcript End | Name | Coordinates | Length |
|---|---|---|---|---|---|
| ENST00000258807 | 24305187 | 24311422 | CIDEB_258807 | chr14: 24311422-24305187 | 6235 |
| ENST00000336557 | 24305187 | 24311395 | CIDEB_336557 | chr14: 24311395-24305187 | 6208 |
| ENST00000554411 | 24305096 | 24308263 | CIDEB_554411 | chr14: 24308263-24305096 | 3167 |
| ENST00000555471 | 24310087 | 24310718 | CIDEB_555471 | chr14: 24310718-24310087 | 631 |
| ENST00000555817 | 24310799 | 24311430 | CIDEB_555817 | chr14: 24311430-24310799 | 631 |
| ENST00000556756 | 24305606 | 24306461 | CIDEB_556756 | chr14: 24306461-24305606 | 855 |

Additional CIDEB transcripts include, but are not limited to those of the following Ensembl Gene IDs=ENST00000555471, ENST00000555817, ENST00000556756, ENST00000258807, ENS100000336557, and ENST00000554411.

In some embodiments, the antisense nucleic acid molecules targeted to Transcript A comprise or consist of the nucleotide sequences shown in Table 2.

TABLE 2

| Sequence | SEQ ID NO: |
|---|---|
| ACCACGCAGUCAACCUUCUG | 115 |
| UACCACGCAGUCAACCUUCU | 116 |
| CUACCACGCAGUCAACCUUC | 117 |
| CCUACCACGCAGUCAACCUU | 118 |
| CCCUACCACGCAGUCAACCU | 119 |
| UUGCCUUCGGCUUGCUCUGG | 120 |
| CUUGCCUUCGGCUUGCUCUG | 121 |
| GCUUGCCUUCGGCUUGCUCU | 122 |
| UGCUUGCCUUCGGCUUGCUC | 123 |
| GUGCUUGCCUUCGGCUUGCU | 124 |
| UCGUGCUUGCCUUCGGCUUG | 125 |
| AUCGUGCUUGCCUUCGGCUU | 126 |
| CAUCGUGCUUGCCUUCGGCU | 127 |
| AGCGCCAUCGUGCUUGCCUU | 128 |
| UGGUGAGCGCCAUCGUGCUU | 129 |
| CUGAUGCUCGGCUGCUACAG | 130 |
| GCUGAUGCUCGGCUGCUACA | 131 |
| UUUCGGGCUGAUGCUCGGCU | 132 |
| UCCUUUCGGGCUGAUGCUCG | 133 |
| UUCCUUUCGGGCUGAUGCUC | 134 |
| CUUCCUUUCGGGCUGAUGCU | 135 |
| GCUUCCUUUCGGGCUGAUGC | 136 |
| UGCUUCCUUUCGGGCUGAUG | 137 |
| GUGCUUCCUUUCGGGCUGAU | 138 |
| CGUGCUUCCUUUCGGGCUGA | 139 |
| UCGUGCUUCCUUUCGGGCUG | 140 |
| UUCGUGCUUCCUUUCGGGCU | 141 |
| UUUCGUGCUUCCUUUCGGGC | 142 |
| CUUUCGUGCUUCCUUUCGGG | 143 |
| GCUUUCGUGCUUCCUUUCGG | 144 |
| AUGUACGCCAGCGUGCUGCU | 145 |
| UCAGCAUGUACGCCAGCGUG | 146 |
| AGGCGGUGUACUACGUGUGC | 147 |
| AAGGCGGUGUACUACGUGUG | 148 |
| CAAGGCGGUGUACUACGUGU | 149 |
| GCAAGGCGGUGUACUACGUG | 150 |
| UGCAAGGCGGUGUACUACGU | 151 |
| CUGCAAGGCGGUGUACUACG | 152 |
| GCUGCAAGGCGGUGUACUAC | 153 |
| GGCUGCAAGGCGGUGUACUA | 154 |
| GCUCUUUGUGGCCUUCCUGA | 155 |
| CGCUCUUUGUGGCCUUCCUG | 156 |
| CUUCGUGGUGUGGAGCUUGG | 157 |
| GGCUUCGUGGUGUGGAGCUU | 158 |
| CAACGGCUUCGUGGUGUGGA | 159 |
| UGGCAACGGCUUCGUGGUGU | 160 |
| UGAGCUGGAAGACUUCGCGG | 161 |
| CUGAGCUGGAAGACUUCGCG | 162 |
| GCUGAGCUGGAAGACUUCGC | 163 |
| ACACUGCUGAGCUGGAAGAC | 164 |

TABLE 2-continued

| Sequence | SEQ ID NO: |
|---|---|
| CGAGACACUGCUGAGCUGGA | 165 |
| ACGAGACACUGCUGAGCUGG | 166 |
| AACGAGACACUGCUGAGCUG | 167 |
| GAACGAGACACUGCUGAGCU | 168 |
| GGAACGAGACACUGCUGAGC | 169 |
| GGGAACGAGACACUGCUGAG | 170 |
| AGGGAACGAGACACUGCUGA | 171 |
| CAGGGAACGAGACACUGCUG | 172 |
| CCAGGGAACGAGACACUGCU | 173 |
| AAGGAUGUCGGUCUGCUACC | 174 |
| GAAGGAUGUCGGUCUGCUAC | 175 |
| AGAAGGAUGUCGGUCUGCUA | 176 |
| UAGGCCCAGAAGGAUGUCGG | 177 |
| GUAGGCCCAGAAGGAUGUCG | 178 |
| UGUAGGCCCAGAAGGAUGUC | 179 |
| CUGUAGGCCCAGAAGGAUGU | 180 |
| CCUGUAGGCCCAGAAGGAUG | 181 |
| ACCUGUAGGCCCAGAAGGAU | 182 |
| CUUCUCAUCGGGCAUCACAG | 183 |
| CCUUCUCAUCGGGCAUCACA | 184 |
| ACCUUCUCAUCGGGCAUCAC | 185 |
| CACCUUCUCAUCGGGCAUCA | 186 |
| GCACCUUCUCAUCGGGCAUC | 187 |
| GGCACCUUCUCAUCGGGCAU | 188 |
| UGGCACCUUCUCAUCGGGCA | 189 |
| AUGGCACCUUCUCAUCGGGC | 190 |
| CAUGGCACCUUCUCAUCGGG | 191 |
| GCAUGGCACCUUCUCAUCGG | 192 |
| GGCAUGGCACCUUCUCAUCG | 193 |
| GAGGCAUGGCACCUUCUCAU | 194 |
| GGAGGCAUGGCACCUUCUCA | 195 |
| GACUCCCAGGCAGAAAAGAG | 196 |
| GGACUCCCAGGCAGAAAAGA | 197 |
| AGGACUCCCAGGCAGAAAAG | 198 |
| UCAGGACUCCCAGGCAGAAA | 199 |
| GAAGUCAGGACUCCCAGGCA | 200 |
| GUGGAAGUCAGGACUCCCAG | 201 |
| UCGUGGAAGUCAGGACUCCC | 202 |
| CUCGUGGAAGUCAGGACUCC | 203 |
| CCUCGUGGAAGUCAGGACUC | 204 |
| UGGGUCCUCGUGGAAGUCAG | 205 |
| CUGGGUCCUCGUGGAAGUCA | 206 |
| UCUGGGUCCUCGUGGAAGUC | 207 |
| GUCUGGGUCCUCGUGGAAGU | 208 |
| AAGAAGGAGUUGUGUUUGAG | 209 |
| CCAAGAAGGAGUUGUGUUUG | 210 |
| GUUCCAAGAAGGAGUUGUGU | 211 |
| GGUUCCAAGAAGGAGUUGUG | 212 |
| CAGGUCAACUGACUGGGAGC | 213 |
| UGCCUGUUUACCACUGAGCU | 214 |
| AUGCCUGUUUACCACUGAGC | 215 |
| UAUGCCUGUUUACCACUGAG | 216 |
| UUAUGCCUGUUUACCACUGA | 217 |
| UUUAUGCCUGUUUACCACUG | 218 |
| CUUUAUGCCUGUUUACCACU | 219 |
| ACUUUAUGCCUGUUUACCAC | 220 |
| UAGAGAUAGUGACAGCCUGG | 221 |
| GUAGAGAUAGUGACAGCCUG | 222 |
| UGGUGGUAGAGAUAGUGACA | 223 |
| GUGGUGGUAGAGAUAGUGAC | 224 |
| UAGAGGAGUGGUGGUAGAGA | 225 |
| ACUAGAGGAGUGGUGGUAGA | 226 |
| AGACUAGAGGAGUGGUGGUA | 227 |
| CAGACUAGAGGAGUGGUGGU | 228 |
| CCAGACUAGAGGAGUGGUGG | 229 |
| GCCAGACUAGAGGAGUGGUG | 230 |
| GGCCAGACUAGAGGAGUGGU | 231 |
| GCCCAGAUGUGCUAGAAUGG | 232 |
| UGCCCAGAUGUGCUAGAAUG | 233 |
| UUGCCCAGAUGUGCUAGAAU | 234 |
| UUUGCCCAGAUGUGCUAGAA | 235 |
| UUUUGCCCAGAUGUGCUAGA | 236 |
| CCAGUUUUGCCCAGAUGUGC | 237 |
| AUCCAGUUUUGCCCAGAUGU | 238 |
| CCAUCCAGUUUUGCCCAGAU | 239 |
| CACCAUCCAGUUUUGCCCAG | 240 |

TABLE 2-continued

| Sequence | SEQ ID NO: |
|---|---|
| CCACCAUCCAGUUUUGCCCA | 241 |
| CCCACCAUCCAGUUUUGCCC | 242 |
| UUGCUCCCAGCUUGGUAAGU | 243 |
| GCUUGCUCCCAGCUUGGUAA | 244 |
| AUCCUGCUUGCUCCCAGCUU | 245 |
| AAUCCUGCUUGCUCCCAGCU | 246 |
| CAAUCCUGCUUGCUCCCAGC | 247 |
| CCAAUCCUGCUUGCUCCCAG | 248 |
| AACCUUUCAGCUUCUCCAGG | 249 |
| UAACCUUUCAGCUUCUCCAG | 250 |
| UUAACCUUUCAGCUUCUCCA | 251 |
| ACUGCUGCUUAACCUUUCAG | 252 |
| UACUGCUGCUUAACCUUUCA | 253 |
| CUACUGCUGCUUAACCUUUC | 254 |
| CCUACUGCUGCUUAACCUUU | 255 |
| GCCUACUGCUGCUUAACCUU | 256 |
| CAGGACAGGAGUAGGCACCU | 257 |
| ACAGGACAGGAGUAGGCACC | 258 |
| GCACAGGACAGGAGUAGGCA | 259 |
| AUAGGCACAGGACAGGAGUA | 260 |
| GAUAGGCACAGGACAGGAGU | 261 |
| UGAUAGGCACAGGACAGGAG | 262 |
| ACCCUCUGCAAAUGUGAUAG | 263 |
| CUUACCCUCUGCAAAUGUGA | 264 |
| GUCUUACCCUCUGCAAAUGU | 265 |
| UGUCUUACCCUCUGCAAAUG | 266 |
| UUGUCUUACCCUCUGCAAAU | 267 |
| CUUGUCUUACCCUCUGCAAA | 268 |
| UCUUGUCUUACCCUCUGCAA | 269 |
| CAUUCUUGUCUUACCCUCUG | 270 |
| CCCAUUCUUGUCUUACCCUC | 271 |
| GAGCCUCAUCUUGUCCCUCC | 272 |
| UGAGCCUCAUCUUGUCCCUC | 273 |
| UGCGUUGGUGAUGGGAAGGA | 274 |
| GUGCGUUGGUGAUGGGAAGG | 275 |
| GGUGCGUUGGUGAUGGGAAG | 276 |
| GGGUGCGUUGGUGAUGGGAA | 277 |
| UGGGUGCGUUGGUGAUGGGA | 278 |

| Sequence | SEQ ID NO: |
|---|---|
| UCUCACAUGCCUGGACGCCU | 279 |
| CAAGGCAGGCUCUCACAUGC | 280 |
| UGCUGUUUCCUGGCAAGGCA | 281 |
| UUGUGCUGUUUCCUGGCAAG | 282 |
| CUUGUGCUGUUUCCUGGCAA | 283 |
| ACCACCAGGGAAUCUUACUG | 284 |
| UCCACCACCAGGGAAUCUUA | 285 |
| AUUUCCUUCCACCACCAGGG | 286 |
| UAUUUCCUUCCACCACCAGG | 287 |
| CCUAUUUCCUUCCACCACCA | 288 |
| AGUCCUCCUAUUUCCUUCCA | 289 |
| AGAGUCCUCCUAUUUCCUUC | 290 |
| AGCAGAGUCCUCCUAUUUCC | 291 |
| CAGCAGAGUCCUCCUAUUUC | 292 |
| AUUCAGCAGAGUCCUCCUAU | 293 |
| ACCAGGAUUCAGCAGAGUCC | 294 |
| GACCAGGAUUCAGCAGAGUC | 295 |
| GGACCAGGAUUCAGCAGAGU | 296 |
| CAGGACCAGGAUUCAGCAGA | 297 |
| CAGAAGCAGGACCAGGAUUC | 298 |
| ACAGAAGCAGGACCAGGAUU | 299 |
| AACAGAAGCAGGACCAGGAU | 300 |
| AGAACAGAAGCAGGACCAGG | 301 |
| GGGAGGGAUGAGAACAGAAG | 302 |
| CAGGCAACAUACACACUGCA | 303 |
| CCAGGCAACAUACACACUGC | 304 |
| ACCAGGCAACAUACACACUG | 305 |
| AGACCAGGCAACAUACACAC | 306 |
| GAGAGACCAGGCAACAUACA | 307 |
| CCAGAGAGACCAGGCAACAU | 308 |
| UUGUUUGGGUCACCUCUGCA | 309 |
| GUUGUUUGGGUCACCUCUGC | 310 |
| AGUUGUUUGGGUCACCUCUG | 311 |
| UGAGUUGUUUGGGUCACCUC | 312 |
| CUGAGUUGUUUGGGUCACCU | 313 |
| GACUGAGUUGUUUGGGUCAC | 314 |
| AAACAGGCAAGGAUAAGGCA | 315 |
| ACAUGGAAAAGCUGUCAUUG | 316 |

TABLE 2-continued

| Sequence | SEQ ID NO: |
|---|---|
| CCUUACAUGGAAAAGCUGUC | 317 |
| GCCUUACAUGGAAAAGCUGU | 318 |
| CUCCUGGAACCUAGCACCAU | 319 |
| CCUCCUGGAACCUAGCACCA | 320 |
| UCCUCCUGGAACCUAGCACC | 321 |
| AACCAUUAUGCCUCCAUGCA | 322 |
| UAACCAUUAUGCCUCCAUGC | 323 |
| CUAACCAUUAUGCCUCCAUG | 324 |
| CCUAACCAUUAUGCCUCCAU | 325 |
| CCCUAACCAUUAUGCCUCCA | 326 |
| ACUCCCUAACCAUUAUGCCU | 327 |
| GACUCCCUAACCAUUAUGCC | 328 |
| UGACUCCCUAACCAUUAUGC | 329 |
| AUGACUCCCUAACCAUUAUG | 330 |
| CAUGACUCCCUAACCAUUAU | 331 |
| GGGCCUCUUCAUGGUUGUGU | 332 |
| UGGUGCAGCCUGGUAAUGGG | 333 |
| CUGGUGCAGCCUGGUAAUGG | 334 |
| CCUGGUGCAGCCUGGUAAUG | 335 |
| AUCCUGGUGCAGCCUGGUAA | 336 |
| UAUCCUGGUGCAGCCUGGUA | 337 |
| GUAUCCUGGUGCAGCCUGGU | 338 |
| UGUAUCCUGGUGCAGCCUGG | 339 |
| UCUUGUAUCCUGGUGCAGCC | 340 |
| GUCUUGUAUCCUGGUGCAGC | 341 |
| UGUCUUGUAUCCUGGUGCAG | 342 |
| UUGUCUUGUAUCCUGGUGCA | 343 |
| CUUGUCUUGUAUCCUGGUGC | 344 |
| UCUUGUCUUGUAUCCUGGUG | 345 |
| UUCUUGUCUUGUAUCCUGGU | 346 |
| UUUCUUGUCUUGUAUCCUGG | 347 |
| CCUUUCUUGUCUUGUAUCCU | 348 |
| ACUCAUCCUUUCCUUUCUUG | 349 |
| CCUACUCAUCCUUUCCUUUC | 350 |
| CCCUACUCAUCCUUUCCUUU | 351 |
| UCCCUACUCAUCCUUUCCUU | 352 |
| GCUUCUUAGUAUGUCCCUAC | 353 |
| GCUGCUUCUUAGUAUGUCCC | 354 |
| GGCUGCUUCUUAGUAUGUCC | 355 |
| GGGCUGCUUCUUAGUAUGUC | 356 |
| AGGGCUGCUUCUUAGUAUGU | 357 |
| GAGAGGGCUGCUUCUUAGUA | 358 |
| UCCAAGAGGAGAGGGCUGCU | 359 |
| UUGACUUUUCCAAGAGGAGA | 360 |
| AGCUCUAUCCAUCUGCCAGG | 361 |
| GCUGUUACUUGAGCAGAGGC | 362 |
| GGCUGUUACUUGAGCAGAGG | 363 |
| UGGCUGUUACUUGAGCAGAG | 364 |
| CUGGCUGUUACUUGAGCAGA | 365 |
| UCUGGCUGUUACUUGAGCAG | 366 |
| CCUCAAGUUCUGGCUGUUAC | 367 |
| ACCUCAAGUUCUGGCUGUUA | 368 |
| CAACCUCAAGUUCUGGCUGU | 369 |
| GCAACCUCAAGUUCUGGCUG | 370 |
| AGCAACCUCAAGUUCUGGCU | 371 |
| CAAGCAACCUCAAGUUCUGG | 372 |
| CCAAGCAACCUCAAGUUCUG | 373 |
| CCCAAGCAACCUCAAGUUCU | 374 |
| ACUAAGACAGUGCUCCUGGU | 375 |
| CAAACUAAGACAGUGCUCCU | 376 |
| AGCUCUGCUUUGGAAGAACC | 377 |
| CCCUUAGCUCAAGCUCUGCU | 378 |
| GCCCUUAGCUCAAGCUCUGC | 379 |
| AAGCCCUUAGCUCAAGCUCU | 380 |
| CAAGCCCUUAGCUCAAGCUC | 381 |
| CCAAGCCCUUAGCUCAAGCU | 382 |
| CCCAAGCCCUUAGCUCAAGC | 383 |
| GUACCCAAGCCCUUAGCUCA | 384 |
| UGUACCCAAGCCCUUAGCUC | 385 |
| CUGUACCCAAGCCCUUAGCU | 386 |
| CCUGUACCCAAGCCCUUAGC | 387 |
| ACCUGUACCCAAGCCCUUAG | 388 |
| UCACCUGUACCCAAGCCCUU | 389 |
| AUCACCUGUACCCAAGCCCU | 390 |
| GGAUCACCUGUACCCAAGCC | 391 |
| CUCAAGAAUACAGGAUCACC | 392 |

TABLE 2-continued

| Sequence | SEQ ID NO: |
|---|---|
| CUUAGCUCAAGAAUACAGGA | 393 |
| CCUUAGCUCAAGAAUACAGG | 394 |
| GCCCUUAGCUCAAGAAUACA | 395 |
| AGCCCUUAGCUCAAGAAUAC | 396 |
| AAGCCCUUAGCUCAAGAAUA | 397 |
| CAAGCCCUUAGCUCAAGAAU | 398 |
| CCAAGCCCUUAGCUCAAGAA | 399 |
| CCCAAGCCCUUAGCUCAAGA | 400 |
| GUACCCAAGCCCUUAGCUCA | 401 |
| UGUACCCAAGCCCUUAGCUC | 402 |
| CUGUACCCAAGCCCUUAGCU | 403 |
| CCUGUACCCAAGCCCUUAGC | 404 |
| ACCUGUACCCAAGCCCUUAG | 405 |
| UCACCUGUACCCAAGCCCUU | 406 |
| AUCACCUGUACCCAAGCCCU | 407 |
| GGAUCACCUGUACCCAAGCC | 408 |
| UAACCUCCCAAAUACAGGAU | 409 |
| UACCUUAUGCCCUCACUUCC | 410 |
| UUACCUUAUGCCCUCACUUC | 411 |
| UUUACCUUAUGCCCUCACUU | 412 |
| UUUUACCUUAUGCCCUCACU | 413 |
| UUGUUUUACCUUAUGCCCUC | 414 |
| CUUGUUUUACCUUAUGCCCU | 415 |
| UUAAUGGCUUUCCUCUCUCU | 416 |
| ACUCUUAAUGGCUUUCCUCU | 417 |
| UACUCUUAAUGGCUUUCCUC | 418 |
| CAUACUCUUAAUGGCUUUCC | 419 |
| GAAGGGACUUAACAUACUCU | 420 |
| UGAAGGGACUUAACAUACUC | 421 |
| ACUGAAGGGACUUAACAUAC | 422 |
| CUACUGAAGGGACUUAACAU | 423 |
| GCCUACUGAAGGGACUUAAC | 424 |
| GGCCUACUGAAGGGACUUAA | 425 |
| UUCUCAGAGGUUCCCAAGGC | 426 |
| UUUUCUCAGAGGUUCCCAAG | 427 |
| ACUUUUCUCAGAGGUUCCCA | 428 |
| UACUUUUCUCAGAGGUUCCC | 429 |
| GGGCAAUCUAUACUUUUCUC | 430 |

TABLE 2-continued

| Sequence | SEQ ID NO: |
|---|---|
| UGUCUUGGGCAAUCUAUACU | 431 |
| CCAGUCUUUUGUCUUGGGCA | 432 |
| GCCAGUCUUUUGUCUUGGGC | 433 |
| UGCCAGUCUUUUGUCUUGGG | 434 |
| CUGCCAGUCUUUUGUCUUGG | 435 |
| UCACCCUGCCAGUCUUUUGU | 436 |
| AUCACCCUGCCAGUCUUUUG | 437 |
| GCCCACUCAUUAAGUACAUU | 438 |
| CUGUAGCCCACUCAUUAAGU | 439 |
| CGCUGUAGCCCACUCAUUAA | 440 |
| ACGCUGUAGCCCACUCAUUA | 441 |
| UACGCUGUAGCCCACUCAUU | 442 |
| AUACGCUGUAGCCCACUCAU | 443 |
| GAUACGCUGUAGCCCACUCA | 444 |
| GGAUACGCUGUAGCCCACUC | 445 |
| AGGAUACGCUGUAGCCCACU | 446 |
| GAGGAUACGCUGUAGCCCAC | 447 |
| UGAGGAUACGCUGUAGCCCA | 448 |
| GUGAGGAUACGCUGUAGCCC | 449 |
| UGUGAGGAUACGCUGUAGCC | 450 |
| CUGUUGUGAGGAUACGCUGU | 451 |
| UCUGUUGUGAGGAUACGCUG | 452 |
| GUCUGUUGUGAGGAUACGCU | 453 |
| UGUCUGUUGUGAGGAUACGC | 454 |
| ACUGUCUGUUGUGAGGAUAC | 455 |
| CACUGUCUGUUGUGAGGAUA | 456 |
| CAACUCUCUCUCACUGUCUG | 457 |
| AACAACUCUCUCUCACUGUC | 458 |
| AGAACAACUCUCUCUCACUG | 459 |
| GUAGAACAACUCUCUCUCAC | 460 |
| GGUAGAACAACUCUCUCUCA | 461 |
| CAGGUAGAACAACUCUCUCU | 462 |
| CCAGGUAGAACAACUCUCUC | 463 |
| ACCCAGGUAGAACAACUCUC | 464 |
| UAUACCCAGGUAGAACAACU | 465 |
| AUAUACCCAGGUAGAACAAC | 466 |
| GGAUAUACCCAGGUAGAACA | 467 |
| GUUUUGGAUAUACCCAGGUA | 468 |

TABLE 2-continued

| Sequence | SEQ ID NO: |
|---|---|
| CCUUGUUUUGGAUAUACCCA | 469 |
| CCCUUGUUUUGGAUAUACCC | 470 |
| CCUCGUAAACUCCAUACCCU | 471 |
| CCCUCGUAAACUCCAUACCC | 472 |
| ACCCUCGUAAACUCCAUACC | 473 |
| AACCCUCGUAAACUCCAUAC | 474 |
| GAACCCUCGUAAACUCCAUA | 475 |
| UGAACCCUCGUAAACUCCAU | 476 |
| UUGAACCCUCGUAAACUCCA | 477 |
| CUUGAACCCUCGUAAACUCC | 478 |
| CCUUGAACCCUCGUAAACUC | 479 |
| ACCUUGAACCCUCGUAAACU | 480 |
| UACCUUGAACCCUCGUAAAC | 481 |
| AUACCUUGAACCCUCGUAAA | 482 |
| AAUACCUUGAACCCUCGUAA | 483 |
| AAAUACCUUGAACCCUCGUA | 484 |
| CAAAUACCUUGAACCCUCGU | 485 |
| CCAAAUACCUUGAACCCUCG | 486 |
| ACCAAAUACCUUGAACCCUC | 487 |
| AACCAAAUACCUUGAACCCU | 488 |
| GAACCAAAUACCUUGAACCC | 489 |
| UGAACCAAAUACCUUGAACC | 490 |
| CCCUGAACCAAAUACCUUGA | 491 |
| GGCCCUGAACCAAAUACCUU | 492 |
| UGGCCCUGAACCAAAUACCU | 493 |
| UAUUCAGGUUGUUGCCCAAA | 494 |
| GGUAUUCAGGUUGUUGCCCA | 495 |
| AGGUAUUCAGGUUGUUGCCC | 496 |
| AAGGUAUUCAGGUUGUUGCC | 497 |
| AAAGGUAUUCAGGUUGUUGC | 498 |
| UAACUUGAUUGCCCUGUGAC | 499 |
| GUAACUUGAUUGCCCUGUGA | 500 |
| AGUAACUUGAUUGCCCUGUG | 501 |
| CAGAGUAACUUGAUUGCCCU | 502 |
| ACAGAGUAACUUGAUUGCCC | 503 |
| CACAGAGUAACUUGAUUGCC | 504 |
| UGUCCUGACAAAGAAACACA | 505 |
| CAAUCCCUGCUUUCCUGCCA | 506 |
| ACAAUCCCUGCUUUCCUGCC | 507 |
| AACACAAUCCCUGCUUUCCU | 508 |
| GAACACAAUCCCUGCUUUCC | 509 |
| AAUGAACACAAUCCCUGCUU | 510 |
| AAAUGAACACAAUCCCUGCU | 511 |
| GUGAAACCCUCAAAUGAACA | 512 |
| AGUGAAACCCUCAAAUGAAC | 513 |
| CAGUGAAACCCUCAAAUGAA | 514 |
| ACAGUGAAACCCUCAAAUGA | 515 |
| GCAUGGAAGCUGAGACUCUC | 516 |
| UUGCAUGGAAGCUGAGACUC | 517 |
| CAGUUGCAUGGAAGCUGAGA | 518 |
| ACAGUUGCAUGGAAGCUGAG | 519 |
| GACAGUUGCAUGGAAGCUGA | 520 |
| AUGGACAGUUGCAUGGAAGC | 521 |
| GUGAUGGACAGUUGCAUGGA | 522 |
| CGUGAUGGACAGUUGCAUGG | 523 |
| CCGUGAUGGACAGUUGCAUG | 524 |
| GCCGUGAUGGACAGUUGCAU | 525 |
| AGCCGUGAUGGACAGUUGCA | 526 |
| CAGCCGUGAUGGACAGUUGC | 527 |
| GCAGCCGUGAUGGACAGUUG | 528 |
| UGCAGCCGUGAUGGACAGUU | 529 |
| UUGCAGCCGUGAUGGACAGU | 530 |
| GUUGCAGCCGUGAUGGACAG | 531 |
| CAGUUGCAGCCGUGAUGGAC | 532 |
| UCAGUUGCAGCCGUGAUGGA | 533 |
| UUCAGUUGCAGCCGUGAUGG | 534 |
| UUUCAGUUGCAGCCGUGAUG | 535 |
| AUUUCAGUUGCAGCCGUGAU | 536 |
| GAUUUCAGUUGCAGCCGUGA | 537 |
| UGAUUUCAGUUGCAGCCGUG | 538 |
| CUCUGAUUUCAGUUGCAGCC | 539 |
| UUAGCUUCUGGUGCGCUGUG | 540 |
| UUUAGCUUCUGGUGCGCUGU | 541 |
| CUUUAGCUUCUGGUGCGCUG | 542 |
| GACUUUAGCUUCUGGUGCGC | 543 |
| AGACUUUAGCUUCUGGUGCG | 544 |

TABLE 2-continued

| Sequence | SEQ ID NO: |
|---|---|
| AAGACUUUAGCUUCUGGUGC | 545 |
| UCAAGACUUUAGCUUCUGGU | 546 |
| AUCAAGACUUUAGCUUCUGG | 547 |
| GCAUCAAGACUUUAGCUUCU | 548 |
| AUGGCAUCAAGACUUUAGCU | 549 |
| GAUGGCAUCAAGACUUUAGC | 550 |
| AGGGAUGUCCUUUGAUGGCA | 551 |
| GCAGGGAUGUCCUUUGAUGG | 552 |
| GGCAGGGAUGUCCUUUGAUG | 553 |
| CGUGACAGAGAUGUGAAUGG | 554 |
| GGACGUGACAGAGAUGUGAA | 555 |
| UGGACGUGACAGAGAUGUGA | 556 |
| GUGGACGUGACAGAGAUGUG | 557 |
| AGUGGACGUGACAGAGAUGU | 558 |
| UAGUGGACGUGACAGAGAUG | 559 |
| UUAGUGGACGUGACAGAGAU | 560 |
| AUUAGUGGACGUGACAGAGA | 561 |
| GAUUAGUGGACGUGACAGAG | 562 |
| CGAUUAGUGGACGUGACAGA | 563 |
| CCGAUUAGUGGACGUGACAG | 564 |
| UGCCGAUUAGUGGACGUGAC | 565 |
| UUGCCGAUUAGUGGACGUGA | 566 |
| UUUGCCGAUUAGUGGACGUG | 567 |
| UUUUGCCGAUUAGUGGACGU | 568 |
| CUUUUGCCGAUUAGUGGACG | 569 |
| CCUUUUGCCGAUUAGUGGAC | 570 |
| UCCUUUUGCCGAUUAGUGGA | 571 |
| CUCCUUUUGCCGAUUAGUGG | 572 |
| UCUCCUUUUGCCGAUUAGUG | 573 |
| UUCUCCUUUUGCCGAUUAGU | 574 |
| UUUCUCCUUUUGCCGAUUAG | 575 |
| AGGUCAUCUUCUCUCACUUU | 576 |
| UUAGGUCAUCUUCUCUCACU | 577 |
| CUUAGGUCAUCUUCUCUCAC | 578 |
| ACACUUAGGUCAUCUUCUCU | 579 |
| CACACUUAGGUCAUCUUCUC | 580 |
| UCACACUUAGGUCAUCUUCU | 581 |
| GUCACACUUAGGUCAUCUUC | 582 |

TABLE 2-continued

| Sequence | SEQ ID NO: |
|---|---|
| AGUCACACUUAGGUCAUCUU | 583 |
| CAGUCACACUUAGGUCAUCU | 584 |
| GCAGUCACACUUAGGUCAUC | 585 |
| UGCAGUCACACUUAGGUCAU | 586 |
| AUUUUCCAGAGCUGCCUGCU | 587 |
| CUCACUGCUCUGGCUUCAUU | 588 |
| GCUCACUGCUCUGGCUUCAU | 589 |
| UUACCUGCUCUUUCCUUCCU | 590 |
| UGCUUACCUGCUCUUUCCUU | 591 |
| UUCCUGCUUACCUGCUCUUU | 592 |
| CUUCCUGCUUACCUGCUCUU | 593 |
| ACUGGCCUUCCUGCUUACCU | 594 |
| GACACUGGCCUUCCUGCUUA | 595 |
| CAUUAGGGUCCUGUCUGGGA | 596 |
| UCAUUAGGGUCCUGUCUGGG | 597 |
| AUCAUUAGGGUCCUGUCUGG | 598 |
| GAUCAUUAGGGUCCUGUCUG | 599 |
| GGAUCAUUAGGGUCCUGUCU | 600 |
| AUUCAGGAUCAUUAGGGUCC | 601 |
| GAUUCAGGAUCAUUAGGGUC | 602 |
| GGAUUCAGGAUCAUUAGGGU | 603 |
| AUGGAUUCAGGAUCAUUAGG | 604 |
| GAUACAUGGAUUCAGGAUCA | 605 |
| UGAUACAUGGAUUCAGGAUC | 606 |
| AUGGCAGGGCUUUGGAAAAU | 607 |
| CAUGGCAGGGCUUUGGAAAA | 608 |
| GCAUGGCAGGGCUUUGGAAA | 609 |
| CAGCAUGGCAGGGCUUUGGA | 610 |
| GAAGUGGGAUGGCAGCAUGG | 611 |
| GGAAGUGGGAUGGCAGCAUG | 612 |
| GGGAAGUGGGAUGGCAGCAU | 613 |
| UGGAGAAGCCAUAAGCUGCA | 614 |
| CUGGAGAAGCCAUAAGCUGC | 615 |
| ACUGGAGAAGCCAUAAGCUG | 616 |
| UACUGGAGAAGCCAUAAGCU | 617 |
| CUACUGGAGAAGCCAUAAGC | 618 |
| CCUACUGGAGAAGCCAUAAG | 619 |
| ACCUACUGGAGAAGCCAUAA | 620 |

TABLE 2-continued

| Sequence | SEQ ID NO: |
|---|---|
| CACCUACUGGAGAAGCCAUA | 621 |
| CCACCUACUGGAGAAGCCAU | 622 |
| GCCACCUACUGGAGAAGCCA | 623 |
| CUGCCACCUACUGGAGAAGC | 624 |
| GCUGCCACCUACUGGAGAAG | 625 |
| UGUGUGCUGCCACCUACU | 626 |
| CUGUGUGCUGCCACCUAC | 627 |
| UUAUGAGUGGCUCUGUGUGU | 628 |
| UUUAUGAGUGGCUCUGUGUG | 629 |
| AGUUUAUGAGUGGCUCUGUG | 630 |
| CAGUUUAUGAGUGGCUCUGU | 631 |
| GUUUCUGGCUCUCAGGCUCU | 632 |
| GGUUUCUGGCUCUCAGGCUC | 633 |
| CGGUUUCUGGCUCUCAGGCU | 634 |
| GGACGGUUUCUGGCUCUCAG | 635 |
| GGGACGGUUUCUGGCUCUCA | 636 |
| UGAAAUGUGACUUCUGGUGU | 637 |
| GGGAACCAUGUAAAAGGAUG | 638 |
| GUGAGGGUAGAUGGGAACCA | 639 |
| UUGUGAGGGUAGAUGGGAAC | 640 |
| GUUGUGAGGGUAGAUGGGAA | 641 |
| UGUUGUGAGGGUAGAUGGGA | 642 |
| AUGUGUGUCUUUGGUGAUGA | 643 |
| GGAGCUUGUAUGUGUGUCUU | 644 |
| UUGGAGCUUGUAUGUGUGUC | 645 |
| AUUGGAGCUUGUAUGUGUGU | 646 |
| CAUUGGAGCUUGUAUGUGUG | 647 |
| CCAUUGGAGCUUGUAUGUGU | 648 |
| GCCAUUGGAGCUUGUAUGUG | 649 |
| AGCCAUUGGAGCUUGUAUGU | 650 |
| CUGGAGGAAGAAUUGCCUGG | 651 |
| GUCCUGGAGGAAGAAUUGCC | 652 |
| GCCAGUAAGAAGGGCAAAGU | 653 |
| GGCCAGUAAGAAGGGCAAAG | 654 |
| GGAAUGAGUCAAGCCUGGAC | 655 |
| GGGAAUGAGUCAAGCCUGGA | 656 |
| GUGGGAAUGAGUCAAGCCUG | 657 |
| AAGGUGGGAAUGAGUCAAGC | 658 |

| Sequence | SEQ ID NO: |
|---|---|
| UCUCAGCCCAGGACAAGGUG | 659 |
| AUCUCAGCCCAGGACAAGGU | 660 |
| GCUGGGUGGUUCUCUCCUGU | 661 |
| UUCUGGGCUGGGUGGUUCUC | 662 |
| GAACUUCUGGGCUGGGUGGU | 663 |
| CGGAGAGUUCCUUCCCUGGA | 664 |
| ACCGGAGAGUUCCUUCCCUG | 665 |
| GACCGGAGAGUUCCUUCCCU | 666 |
| UGGACCGGAGAGUUCCUUCC | 667 |
| GUGGACCGGAGAGUUCCUUC | 668 |
| GGUGGACCGGAGAGUUCCUU | 669 |
| UGGUGGACCGGAGAGUUCCU | 670 |
| AUGGUGGACCGGAGAGUUCC | 671 |
| CAUGGUGGACCGGAGAGUUC | 672 |
| GAGCUGAGAGGUACUCCAUG | 673 |
| AGAGCUGAGAGGUACUCCAU | 674 |
| CAGAGCUGAGAGGUACUCCA | 675 |
| UUCAGAGCUGAGAGGUACUC | 676 |
| GGUUCAGAGCUGAGAGGUAC | 677 |
| GGGUUCAGAGCUGAGAGGUA | 678 |
| CACCUGAGUAAGUCACUGGG | 679 |
| UCACCUGAGUAAGUCACUGG | 680 |
| GUCACCUGAGUAAGUCACUG | 681 |
| AGUCACCUGAGUAAGUCACU | 682 |
| CAGUCACCUGAGUAAGUCAC | 683 |
| GCAGUCACCUGAGUAAGUCA | 684 |
| UUAGCAGUCACCUGAGUAAG | 685 |
| GUUAGCAGUCACCUGAGUAA | 686 |
| GGUUAGCAGUCACCUGAGUA | 687 |
| GGGUUAGCAGUCACCUGAGU | 688 |
| AGGGUUAGCAGUCACCUGAG | 689 |
| GAGGGUUAGCAGUCACCUGA | 690 |
| GGAGGGUUAGCAGUCACCUG | 691 |
| CGGAGGGUUAGCAGUCACCU | 692 |
| AGCGGAGGGUUAGCAGUCAC | 693 |
| GAGCGGAGGGUUAGCAGUCA | 694 |
| AGAGCGGAGGGUUAGCAGUC | 695 |
| UAGAGCGGAGGGUUAGCAGU | 696 |

TABLE 2-continued

| Sequence | SEQ ID NO: |
|---|---|
| GUAGAGCGGAGGGUUAGCAG | 697 |
| GGUAGAGCGGAGGGUUAGCA | 698 |
| AGGGUAGAGCGGAGGGUUAG | 699 |
| GAGGGUAGAGCGGAGGGUUA | 700 |
| AUUGUUGCCCUGCCUAUAUC | 701 |
| AGUAUUGUUGCCCUGCCUAU | 702 |
| GAGUAUUGUUGCCCUGCCUA | 703 |
| GGAGUAUUGUUGCCCUGCCU | 704 |
| UGGAGUAUUGUUGCCCUGCC | 705 |
| GUGGAGUAUUGUUGCCCUGC | 706 |
| AGUGGAGUAUUGUUGCCCUG | 707 |
| GAGUGGAGUAUUGUUGCCCU | 708 |
| UGAGUGGAGUAUUGUUGCCC | 709 |
| CUGAGUGGAGUAUUGUUGCC | 710 |
| GCUGAGUGGAGUAUUGUUGC | 711 |
| GGCUGAGUGGAGUAUUGUUG | 712 |
| GGGCUGAGUGGAGUAUUGUU | 713 |
| GGUACUGGUUAGUCUCCUAG | 714 |
| GGGUACUGGUUAGUCUCCUA | 715 |
| UUGACAAGCCCACUGUGGAG | 716 |
| UGGCUCAGGAGCUUGACAAG | 717 |
| GGUGGCUCAGGAGCUUGACA | 718 |
| UAGGGAUGAGGGAGAGACCA | 719 |
| UCGAUUAGGGAUGAGGGAGA | 720 |
| UAGAGGGCUAGGGAGGGAGA | 721 |
| GUAGAGUGGCUAGAGGGCUA | 722 |
| GGUAGAGUGGCUAGAGGGCU | 723 |
| UGAGGGUAGAGUGGCUAGAG | 724 |
| GAUGAGGGUAGAGUGGCUAG | 725 |
| CAUGAUGAGGGUAGAGUGGC | 726 |
| GCAUGAUGAGGGUAGAGUGG | 727 |
| GGGCAUGAUGAGGGUAGAGU | 728 |
| GGUAGUUGAAGAAAAGUC | 729 |
| CCAAACUCCGAGCUUAUAUU | 730 |
| UCCAAACUCCGAGCUUAUAU | 731 |
| GUCCAAACUCCGAGCUUAUA | 732 |
| CGUCCAAACUCCGAGCUUAU | 733 |
| CCGUCCAAACUCCGAGCUUA | 734 |

TABLE 2-continued

| Sequence | SEQ ID NO: |
|---|---|
| UCCGUCCAAACUCCGAGCUU | 735 |
| CUCCGUCCAAACUCCGAGCU | 736 |
| ACCCUCCGUCCAAACUCCGA | 737 |
| AGACCCUCCGUCCAAACUCC | 738 |
| CAGACCCUCCGUCCAAACUC | 739 |
| UCCAGACCCUCCGUCCAAAC | 740 |
| GUCCAGACCCUCCGUCCAAA | 741 |
| AGACACGGAAAGGUCGCUGG | 742 |
| CAGACACGGAAAGGUCGCUG | 743 |
| ACAGACACGGAAAGGUCGCU | 744 |
| CACAGACACGGAAAGGUCGC | 745 |
| UCACAGACACGGAAAGGUCG | 746 |
| AUCACAGACACGGAAAGGUC | 747 |
| GAUCACAGACACGGAAAGGU | 748 |
| UUGGCCUACUUACUUUGGCU | 749 |
| CUUGGCCUACUUACUUUGGC | 750 |
| ACUUGGCCUACUUACUUUGG | 751 |
| GAGGAACUUGGCCUACUUAC | 752 |
| CGAGGAACUUGGCCUACUUA | 753 |
| CCGAGGAACUUGGCCUACUU | 754 |
| ACCGAGGAACUUGGCCUACU | 755 |
| AACCGAGGAACUUGGCCUAC | 756 |
| GAACCGAGGAACUUGGCCUA | 757 |
| GGAACCGAGGAACUUGGCCU | 758 |
| AGGAACCGAGGAACUUGGCC | 759 |
| UAGGAACCGAGGAACUUGGC | 760 |
| AUAGGAACCGAGGAACUUGG | 761 |
| UAUAGGAACCGAGGAACUUG | 762 |
| AUCACAAGUUGCCACUGUUG | 763 |
| CAUCACAAGUUGCCACUGUU | 764 |
| AUCAUCACAAGUUGCCACUG | 765 |
| CAUCAUCACAAGUUGCCACU | 766 |
| CUGCUCCAUCAUCACAAGUU | 767 |
| UCUGCUCCAUCAUCACAAGU | 768 |
| CCCUCUGCUCCAUCAUCACA | 769 |
| UCAGCCCUCUGCUCCAUCAU | 770 |
| UGACUUCAGCCCUCUGCUCC | 771 |
| GUGACUUCAGCCCUCUGCUC | 772 |

TABLE 2-continued

| Sequence | SEQ ID NO: |
|---|---|
| UGUGACUUCAGCCCUCUGCU | 773 |
| GUGUGACUUCAGCCCUCUGC | 774 |
| UGUGUGACUUCAGCCCUCUG | 775 |
| GCCCACUCCGCUGCUUUUAG | 776 |
| GGCCCACUCCGCUGCUUUUA | 777 |
| AGGCCCACUCCGCUGCUUUU | 778 |
| UAGGCCCACUCCGCUGCUUU | 779 |
| UUAGGCCCACUCCGCUGCUU | 780 |
| AUUAGGCCCACUCCGCUGCU | 781 |
| UCAUUAGGCCCACUCCGCUG | 782 |
| CUCAUUAGGCCCACUCCGCU | 783 |
| AGCUCAUUAGGCCCACUCCG | 784 |
| CUCCCAUAGAAAAGCUCACU | 785 |
| GCUCCCAUAGAAAAGCUCAC | 786 |
| UGCUCCCAUAGAAAAGCUCA | 787 |
| CUGCUCCCAUAGAAAAGCUC | 788 |
| CCUGCUCCCAUAGAAAAGCU | 789 |
| UCCCUAUCUCCUGCUAACCC | 790 |
| CCUCGAACUCUCCCUAUCUC | 791 |
| CCCUCGAACUCUCCCUAUCU | 792 |
| UCCCUCGAACUCUCCCUAUC | 793 |
| GUCCCUCGAACUCUCCCUAU | 794 |
| CUUUCCAUACUAGCUUCUGA | 795 |
| CCUUUCCAUACUAGCUUCUG | 796 |
| ACCUUUCCAUACUAGCUUCU | 797 |
| CACACAAAUCACCUUUCCAU | 798 |
| GUCACACAAAUCACCUUUCC | 799 |
| UGUCACACAAAUCACCUUUC | 800 |
| UUUGACAGGCAGGAAGUGGC | 801 |
| GGUUUGACAGGCAGGAAGUG | 802 |
| AGGUUUGACAGGCAGGAAGU | 803 |
| AAGGUUUGACAGGCAGGAAG | 804 |
| AACUUCCCAAGGUUUGACAG | 805 |
| CAACUUCCCAAGGUUUGACA | 806 |
| GAACAACUUCCCAAGGUUUG | 807 |
| UGAACAACUUCCCAAGGUUU | 808 |
| GUAGGUUGAACAACUUCCCA | 809 |
| GGUAGGUUGAACAACUUCCC | 810 |
| UGGUAGGUUGAACAACUUCC | 811 |
| GGUUUUGGUAGGUUGAACAA | 812 |
| UGAGGUUUUGGUAGGUUGAA | 813 |
| CUGAGGUUUUGGUAGGUUGA | 814 |
| CCUACAUUAUCCUCUUACUC | 815 |
| GGACUUUACCUACAUUAUCC | 816 |
| GUAUGAGGACUUUACCUACA | 817 |
| GCCAGGUAUGAGGACUUUAC | 818 |
| UGCCAGGUAUGAGGACUUUA | 819 |
| GUGCCAGGUAUGAGGACUUU | 820 |
| CUGUGCCAGGUAUGAGGACU | 821 |
| UCUGUGCCAGGUAUGAGGAC | 822 |
| CCUCAAGAGUUCUCCAGAAG | 823 |
| CCCUCAAGAGUUCUCCAGAA | 824 |
| ACCCUCAAGAGUUCUCCAGA | 825 |
| ACACCCUCAAGAGUUCUCCA | 826 |
| CACACCCUCAAGAGUUCUCC | 827 |
| CCACACCCUCAAGAGUUCUC | 828 |
| CCCACACCCUCAAGAGUUCU | 829 |
| UUCCCACACCCUCAAGAGUU | 830 |
| CAAUGCUGCACCUCACUUCC | 831 |
| UACAAUGCUGCACCUCACUU | 832 |
| CUACAAUGCUGCACCUCACU | 833 |
| UCUACAAUGCUGCACCUCAC | 834 |
| AUCUACAAUGCUGCACCUCA | 835 |
| UAUCUACAAUGCUGCACCUC | 836 |
| CUUAUCUACAAUGCUGCACC | 837 |
| GUCUUAUCUACAAUGCUGCA | 838 |
| UGUCUUAUCUACAAUGCUGC | 839 |
| CUGUCUUAUCUACAAUGCUG | 840 |
| CACCCUUCUGUCUUAUCUAC | 841 |
| UCCACCCUUCUGUCUUAUCU | 842 |
| GUCCACCCUUCUGUCUUAUC | 843 |
| AGUCCACCCUUCUGUCUUAU | 844 |
| AAGUCCACCCUUCUGUCUUA | 845 |
| GAAAGCAAGCCAGGUUCUCA | 846 |
| GGAAAGCAAGCCAGGUUCUC | 847 |
| GGAAUUGGAAAGCAAGCCAG | 848 |

TABLE 2-continued

| Sequence | SEQ ID NO: |
|---|---|
| ACCAUGUCAUUGGCAUCUCC | 849 |
| UACCAUGUCAUUGGCAUCUC | 850 |
| CCUACCAUGUCAUUGGCAUC | 851 |
| UCCUACCAUGUCAUUGGCAU | 852 |
| CUCCUACCAUGUCAUUGGCA | 853 |
| GCUCCUACCAUGUCAUUGGC | 854 |
| UGCUCCUACCAUGUCAUUGG | 855 |
| UCUUUGCUCCUACCAUGUCA | 856 |
| CCUCUUUGCUCCUACCAUGU | 857 |
| UUCCUCUUUGCUCCUACCAU | 858 |
| UCUCCGUGUUCUUCAGUUUU | 859 |
| CUCUCCGUGUUCUUCAGUUU | 860 |
| AGCUCUCCGUGUUCUUCAGU | 861 |
| UGCAGCUCUCCGUGUUCUUC | 862 |
| GGUUGCAGCUCUCCGUGUUC | 863 |
| AGGUUGCAGCUCUCCGUGUU | 864 |
| AAAGGUUGCAGCUCUCCGUG | 865 |
| UAAAGGUUGCAGCUCUCCGU | 866 |
| CUAAAGGUUGCAGCUCUCCG | 867 |
| CCUAAAGGUUGCAGCUCUCC | 868 |
| UCCUAAAGGUUGCAGCUCUC | 869 |
| CUCCUAAAGGUUGCAGCUCU | 870 |
| CCUCCUAAAGGUUGCAGCUC | 871 |
| GCACUUUGAUACCUCCUAAA | 872 |
| GGCACUUUGAUACCUCCUAA | 873 |
| GAUGUCCCACUUUGACUUUC | 874 |
| UCGAUGUCCCACUUUGACUU | 875 |
| GUCGAUGUCCCACUUUGACU | 876 |
| GGUCGAUGUCCCACUUUGAC | 877 |
| UGGUCGAUGUCCCACUUUGA | 878 |
| UUGGUCGAUGUCCCACUUUG | 879 |
| AUUGGUCGAUGUCCCACUUU | 880 |
| CAUUGGUCGAUGUCCCACUU | 881 |
| AACAUCCAUCAGUUGGCUCU | 882 |
| CUGCCCAACAUCCAUCAGUU | 883 |
| AGCUGCCCAACAUCCAUCAG | 884 |
| UAGCUGCCCAACAUCCAUCA | 885 |
| UUAGCUGCCCAACAUCCAUC | 886 |
| UUUAGCUGCCCAACAUCCAU | 887 |
| CUUUAGCUGCCCAACAUCCA | 888 |
| CCUCUUUAGCUGCCCAACAU | 889 |
| CCCUCUUUAGCUGCCCAACA | 890 |
| UCCCUCUUUAGCUGCCCAAC | 891 |
| UUCCCUCUUUAGCUGCCCAA | 892 |
| CCUUCCCUCUUUAGCUGCCC | 893 |
| CCCUUCCCUCUUUAGCUGCC | 894 |
| GCAGGUCUUAUCCCAUGCCC | 895 |
| GGGCAGGUCUUAUCCCAUGC | 896 |
| AGGGCAGGUCUUAUCCCAUG | 897 |
| AAGGGCAGGUCUUAUCCCAU | 898 |
| GAAGGGCAGGUCUUAUCCCA | 899 |
| AGAAGGGCAGGUCUUAUCCC | 900 |
| CCAAUGGCAAGAAGCAAGAA | 901 |
| CCCAAUGGCAAGAAGCAAGA | 902 |
| GCCCAAUGGCAAGAAGCAAG | 903 |
| UCCAAUGCCUGCCCAAUGGC | 904 |
| CUCCAAUGCCUGCCCAAUGG | 905 |
| UCUCCAAUGCCUGCCCAAUG | 906 |
| GGUCUCCAAUGCCUGCCCAA | 907 |
| UAGGGUCUCCAAUGCCUGCC | 908 |
| GUAGGGUCUCCAAUGCCUGC | 909 |
| AGUAGGGUCUCCAAUGCCUG | 910 |
| CAGUAGGGUCUCCAAUGCCU | 911 |
| GCAGUAGGGUCUCCAAUGCC | 912 |
| AGCAGUAGGGUCUCCAAUGC | 913 |
| CAGCAGUAGGGUCUCCAAUG | 914 |
| UCAGCAGUAGGGUCUCCAAU | 915 |
| AUUCAGCAGUAGGGUCUCCA | 916 |
| CAUUCAGCAGUAGGGUCUCC | 917 |
| CCAUUCAGCAGUAGGGUCUC | 918 |
| UCCAUUCAGCAGUAGGGUCU | 919 |
| ACUCCAUUCAGCAGUAGGGU | 920 |
| CACUCCAUUCAGCAGUAGGG | 921 |
| GCACUCCAUUCAGCAGUAGG | 922 |
| AGCACUCCAUUCAGCAGUAG | 923 |
| UAGCACUCCAUUCAGCAGUA | 924 |

TABLE 2-continued

| Sequence | SEQ ID NO: |
|---|---|
| GUUAGCACUCCAUUCAGCAG | 925 |
| GGUUAGCACUCCAUUCAGCA | 926 |
| GGGUUAGCACUCCAUUCAGC | 927 |
| CAGGGUUAGCACUCCAUUCA | 928 |
| CCAGGGUUAGCACUCCAUUC | 929 |
| ACCAGGGUUAGCACUCCAUU | 930 |
| CACCAGGGUUAGCACUCCAU | 931 |
| GCACCAGGGUUAGCACUCCA | 932 |
| AGCACCAGGGUUAGCACUCC | 933 |
| UAGCACCAGGGUUAGCACUC | 934 |
| CUAGCACCAGGGUUAGCACU | 935 |
| UCUAGCACCAGGGUUAGCAC | 936 |
| CUCUAGCACCAGGGUUAGCA | 937 |
| CCUCUAGCACCAGGGUUAGC | 938 |
| UCCUCUAGCACCAGGGUUAG | 939 |
| CUCCUCUAGCACCAGGGUUA | 940 |
| CCUCCUCUAGCACCAGGGUU | 941 |
| UCCUCCUCUAGCACCAGGGU | 942 |
| GUUCCAUCCUCCUCUAGCAC | 943 |
| AAGUCCUCACUGUCCACUGC | 944 |
| GAAGUCCUCACUGUCCACUG | 945 |
| AGAAGUCCUCACUGUCCACU | 946 |
| AAGAAGUCCUCACUGUCCAC | 947 |
| GAAGAAGUCCUCACUGUCCA | 948 |
| GGAAGAAGUCCUCACUGUCC | 949 |
| UGGAAGAAGUCCUCACUGUC | 950 |
| CUGGAAGAAGUCCUCACUGU | 951 |
| AGCUGGAAGAAGUCCUCACU | 952 |
| ACUGCAACACCAUCAGGCAC | 953 |
| GACUGCAACACCAUCAGGCA | 954 |
| AGACUGCAACACCAUCAGGC | 955 |
| CAGACUGCAACACCAUCAGG | 956 |
| CCAGACUGCAACACCAUCAG | 957 |
| GACCAGACUGCAACACCAUC | 958 |
| CUCUGACCAGACUGCAACAC | 959 |
| AGCUCUGACCAGACUGCAAC | 960 |
| CCAGCUCUGACCAGACUGCA | 961 |
| UGUAGGGCUCCAGCUCUGAC | 962 |
| CUUGUAGGGCUCCAGCUCUG | 963 |
| CCUUGUAGGGCUCCAGCUCU | 964 |
| ACAGGCAUUGGAAGCAGCCC | 965 |
| GACAGGCAUUGGAAGCAGCC | 966 |
| AAGGACAGGCAUUGGAAGCA | 967 |
| AAAGGACAGGCAUUGGAAGC | 968 |
| UAAAGGACAGGCAUUGGAAG | 969 |
| CUAAAGGACAGGCAUUGGAA | 970 |
| GCUCUAAAGGACAGGCAUUG | 971 |
| AGCUCUAAAGGACAGGCAUU | 972 |
| AAGCUCUAAAGGACAGGCAU | 973 |
| AAAGCUCUAAAGGACAGGCA | 974 |
| GAAAGCUCUAAAGGACAGGC | 975 |
| CGGGAAAGCUCUAAAGGACA | 976 |
| CCGGGAAAGCUCUAAAGGAC | 977 |
| AGGGUUAAGCUAGAGAGGAA | 978 |
| UCAGGGUUAAGCUAGAGAGG | 979 |
| GAUCAGGGUUAAGCUAGAGA | 980 |
| GGAUCAGGGUUAAGCUAGAG | 981 |
| AGGAUCAGGGUUAAGCUAGA | 982 |
| CCCAGGAUCAGGGUUAAGCU | 983 |
| CAACUCCUCCUGCACCUGGU | 984 |
| ACAACUCCUCCUGCACCUGG | 985 |
| GACAAUUCCACAACUCCUCC | 986 |
| UGACAAUUCCACAACUCCUC | 987 |
| UUGACAAUUCCACAACUCCU | 988 |
| CUUGACAAUUCCACAACUCC | 989 |
| UCCUUGACAAUUCCACAACU | 990 |
| AUCCUUGACAAUUCCACAAC | 991 |
| CAUCCUUGACAAUUCCACAA | 992 |
| ACAUCCUUGACAAUUCCACA | 993 |
| GACAUCCUUGACAAUUCCAC | 994 |
| UGACAUCCUUGACAAUUCCA | 995 |
| UGUGUGACAUCCUUGACAAU | 996 |
| ACUGUGUGACAUCCUUGACA | 997 |
| ACUUUCUGUCCACUGUGUGA | 998 |
| CCUCGCUUGGACUUUCUGUC | 999 |
| CCCUCGCUUGGACUUUCUGU | 1000 |

TABLE 2-continued

| Sequence | SEQ ID NO: |
|---|---|
| UCCCUCGCUUGGACUUUCUG | 1001 |
| CUCCCUCGCUUGGACUUUCU | 1002 |
| CCUCCCUCGCUUGGACUUUC | 1003 |
| CCCUCCCUCGCUUGGACUUU | 1004 |
| UCCAUCAGCACUGGGUCAGA | 1005 |
| ACCACUAAUCUCCAUCAGCA | 1006 |
| CACCACUAAUCUCCAUCAGC | 1007 |
| CCACCACUAAUCUCCAUCAG | 1008 |
| CCCACCACUAAUCUCCAUCA | 1009 |
| ACCAGACACCCACCACUAAU | 1010 |
| UACCAGACACCCACCACUAA | 1011 |
| CUCAUACCAGACACCCACCA | 1012 |
| CCUCAUACCAGACACCCACC | 1013 |
| UCCUAUACCAGACACCCAC | 1014 |
| AUCCUCAUACCAGACACCCA | 1015 |
| GAUCCUCAUACCAGACACCC | 1016 |
| AGAUCCUCAUACCAGACACC | 1017 |
| UAGAUCCUCAUACCAGACAC | 1018 |
| GUAGAUCCUCAUACCAGACA | 1019 |
| AGUAGAUCCUCAUACCAGAC | 1020 |
| CAGUAGAUCCUCAUACCAGA | 1021 |
| UGCAGUAGAUCCUCAUACCA | 1022 |
| GUGCAGUAGAUCCUCAUACC | 1023 |
| AGUGCAGUAGAUCCUCAUAC | 1024 |
| ACUCUGUAGGACACCCUUGU | 1025 |
| CACUCUGUAGGACACCCUUG | 1026 |
| CCACUCUGUAGGACACCCUU | 1027 |
| UCCACUCUGUAGGACACCCU | 1028 |
| CUCCACUCUGUAGGACACCC | 1029 |
| ACUCCACUCUGUAGGACACC | 1030 |
| CACUCCACUCUGUAGGACAC | 1031 |
| AGCACUCCACUCUGUAGGAC | 1032 |
| UAUGACAGCACUCCACUCUG | 1033 |
| AUAUGACAGCACUCCACUCU | 1034 |
| UUGCUGUGCUUUGGGCCUCUC | 1035 |
| ACGUCAAAGGUGAAUCGGGC | 1036 |
| CACGUCAAAGGUGAAUCGGG | 1037 |
| ACACGUCAAAGGUGAAUCGG | 1038 |

TABLE 2-continued

| Sequence | SEQ ID NO: |
|---|---|
| UACACGUCAAAGGUGAAUCG | 1039 |
| GUACACGUCAAAGGUGAAUC | 1040 |
| GGCUGCCAAAGAGGUCUCGA | 1041 |
| UCAGGCUGCCAAAGAGGUCU | 1042 |
| CAUUCAGGCUGCCAAAGAGG | 1043 |
| GACAUUCAGGCUGCCAAAGA | 1044 |
| UGACAUUCAGGCUGCCAAAG | 1045 |
| CUUUGACAUUCAGGCUGCCA | 1046 |
| GCUUUGACAUUCAGGCUGCC | 1047 |
| CCGUAGAAUGUGGCUUUGAC | 1048 |
| GCCCGUAGAAUGUGGCUUUG | 1049 |
| UAGAGCCCGUAGAAUGUGGC | 1050 |
| GUAGAGCCCGUAGAAUGUGG | 1051 |
| AGUAGAGCCCGUAGAAUGUG | 1052 |
| AGAGUAGAGCCCGUAGAAUG | 1053 |
| UAGAGUAGAGCCCGUAGAAU | 1054 |
| AUAGAGUAGAGCCCGUAGAA | 1055 |
| CAUAGAGUAGAGCCCGUAGA | 1056 |
| UCAUAGAGUAGAGCCCGUAG | 1057 |
| CUCAUAGAGUAGAGCCCGUA | 1058 |
| GAAAGUCACAACUCAUAGAG | 1059 |
| CCUUGAAAGUCACAACUCAU | 1060 |
| AAGUCCUUGAAAGUCACAAC | 1061 |
| CCAAGUCCUUGAAAGUCACA | 1062 |
| UUCUUUGGGCCAAGUCCUUG | 1063 |
| UUUCUUUGGGCCAAGUCCUU | 1064 |
| UUGAUUUCUGACCUGAGUAC | 1065 |
| GUUGAUUUCUGACCUGAGUA | 1066 |
| GGGACUAUCCAACUGUAGGG | 1067 |
| GCAAGAGGACGAAUUAUGGG | 1068 |
| UGCAAGAGGACGAAUUAUGG | 1069 |
| GUGCAAGAGGACGAAUUAUG | 1070 |
| GGUGCAAGAGGACGAAUUAU | 1071 |
| GGGUGCAAGAGGACGAAUUA | 1072 |
| UGGGUGCAAGAGGACGAAUU | 1073 |
| GUGGGUGCAAGAGGACGAAU | 1074 |
| GGUGGGUGCAAGAGGACGAA | 1075 |
| UAGGUGGGUGCAAGAGGACG | 1076 |

TABLE 2-continued

| Sequence | SEQ ID NO: |
|---|---|
| GUAGGUGGGUGCAAGAGGAC | 1077 |
| GGUAGGUGGGUGCAAGAGGA | 1078 |
| CCACAAGCAAGAGCUAACUA | 1079 |
| ACUUUCCACAAGCAAGAGCU | 1080 |
| GACUUUCCACAAGCAAGAGC | 1081 |
| GGACUUUCCACAAGCAAGAG | 1082 |
| AGGACUUUCCACAAGCAAGA | 1083 |
| GAGGACUUUCCACAAGCAAG | 1084 |
| UGAGGACUUUCCACAAGCAA | 1085 |
| AUGAGGACUUUCCACAAGCA | 1086 |
| GAUGAGGACUUUCCACAAGC | 1087 |
| AGAUGAGGACUUUCCACAAG | 1088 |
| GAGAUGAGGACUUUCCACAA | 1089 |
| GGAGAUGAGGACUUUCCACA | 1090 |
| UGGGAGAUGAGGACUUUCCA | 1091 |
| GCUGGGAGAUGAGGACUUUC | 1092 |
| UCAAGCUGGGAGAUGAGGAC | 1093 |
| AAGCCAUCAAGCUGGGAGAU | 1094 |
| GAAGCCAUCAAGCUGGGAGA | 1095 |
| GGAGGAAGCCAUCAAGCUGG | 1096 |
| GGGAGGAAGCCAUCAAGCUG | 1097 |
| AACUUGGGAGGAAGCCAUCA | 1098 |
| AAACUUGGGAGGAAGCCAUC | 1099 |
| CAGCAGUGUGGAGGUCCAAC | 1100 |
| GCAGCAGUGUGGAGGUCCAA | 1101 |
| UGCAGCAGUGUGGAGGUCCA | 1102 |
| UUGCAGCAGUGUGGAGGUCC | 1103 |
| GGUGGAGGAAAUUCCCAGCA | 1104 |
| ACGAAGGGUGGAGGAAAUUC | 1105 |
| GACGAAGGGUGGAGGAAAUU | 1106 |
| AUGACGAAGGGUGGAGGAAA | 1107 |
| CAUGACGAAGGGUGGAGGAA | 1108 |
| GCAUGACGAAGGGUGGAGGA | 1109 |
| UGCAUGACGAAGGGUGGAGG | 1110 |
| CUGCAUGACGAAGGGUGGAG | 1111 |
| ACUGCAUGACGAAGGGUGGA | 1112 |
| CACUGCAUGACGAAGGGUGG | 1113 |
| CCACUGCAUGACGAAGGGUG | 1114 |

TABLE 2-continued

| Sequence | SEQ ID NO: |
|---|---|
| UCCACUGCAUGACGAAGGGU | 1115 |
| CUCCACUGCAUGACGAAGGG | 1116 |
| CCUCCACUGCAUGACGAAGG | 1117 |
| CCCUCCACUGCAUGACGAAG | 1118 |
| CUUAGUAGGAAUGGAGGCGG | 1119 |
| CCUUAGUAGGAAUGGAGGCG | 1120 |
| CCCUUAGUAGGAAUGGAGGC | 1121 |
| UCGGUUGGAAUGAUUCUGGG | 1122 |
| GUCGGUUGGAAUGAUUCUGG | 1123 |
| GGUCGGUUGGAAUGAUUCUG | 1124 |
| GGGUCGGUUGGAAUGAUUCU | 1125 |
| UGGGUCGGUUGGAAUGAUUC | 1126 |
| GUGGGUCGGUUGGAAUGAUU | 1127 |
| AGUGGGUCGGUUGGAAUGAU | 1128 |
| CAGUGGGUCGGUUGGAAUGA | 1129 |
| GCAGUGGGUCGGUUGGAAUG | 1130 |
| UGCAGUGGGUCGGUUGGAAU | 1131 |
| UUGCAGUGGGUCGGUUGGAA | 1132 |
| UUUGCAGUGGGUCGGUUGGA | 1133 |
| CUUUGCAGUGGGUCGGUUGG | 1134 |
| UCUUUGCAGUGGGUCGGUUG | 1135 |
| UAGUCUUUGCAGUGGGUCGG | 1136 |
| AUAGUCUUUGCAGUGGGUCG | 1137 |
| CUGUCAUAGUCUUUGCAGUG | 1138 |
| UGCUGUCAUAGUCUUUGCAG | 1139 |
| UCUAGCCUGUACUGUCUGCA | 1140 |
| AUCUAGCCUGUACUGUCUGC | 1141 |
| UAUCUAGCCUGUACUGUCUG | 1142 |
| UUAUCUAGCCUGUACUGUCU | 1143 |
| GUUAUCUAGCCUGUACUGUC | 1144 |
| GGUUAUCUAGCCUGUACUGU | 1145 |
| GGGUUAUCUAGCCUGUACUG | 1146 |
| UGGGUUAUCUAGCCUGUACU | 1147 |
| GUGGGUUAUCUAGCCUGUAC | 1148 |
| GGUGGGUUAUCUAGCCUGUA | 1149 |
| GGGUGGGUUAUCUAGCCUGU | 1150 |
| UGGGUGGGUUAUCUAGCCUG | 1151 |
| UUGGGUGGGUUAUCUAGCCU | 1152 |

TABLE 2-continued

| Sequence | SEQ ID NO: |
|---|---|
| AUUGGGUGGGUUAUCUAGCC | 1153 |
| AAUUGGGUGGGUUAUCUAGC | 1154 |
| AAAUUGGGUGGGUUAUCUAG | 1155 |
| GGAAAUUGGGUGGGUUAUCU | 1156 |
| GGGAAAUUGGGUGGGUUAUC | 1157 |
| GAAAGGUUCUGUCACGAGGG | 1158 |
| GCUGAAAGGUUCUGUCACGA | 1159 |
| UGCUGAAAGGUUCUGUCACG | 1160 |
| GGCGUUAUGCUGAAAGGUUC | 1161 |
| AGGCGUUAUGCUGAAAGGUU | 1162 |
| GAGGCGUUAUGCUGAAAGGU | 1163 |
| UGAGGCGUUAUGCUGAAAGG | 1164 |
| GUGAGGCGUUAUGCUGAAAG | 1165 |
| AUGUGAGGCGUUAUGCUGAA | 1166 |
| GAUGUGAGGCGUUAUGCUGA | 1167 |
| GGAUGUGAGGCGUUAUGCUG | 1168 |
| GGGAUGUGAGGCGUUAUGCU | 1169 |
| CUUGGGAUGUGAGGCGUUAU | 1170 |
| AGACUUGGGAUGUGAGGCGU | 1171 |
| UAGACUUGGGAUGUGAGGCG | 1172 |
| AUAGACUUGGGAUGUGAGGC | 1173 |
| UAUAGACUUGGGAUGUGAGG | 1174 |
| GGGUAUAGACUUGGGAUGUG | 1175 |
| AGGGUAUAGACUUGGGAUGU | 1176 |
| AAGGUGGCUAGGAAAGAACA | 1177 |
| AAAGGUGGCUAGGAAAGAAC | 1178 |
| GAAAGGUGGCUAGGAAAGAA | 1179 |
| ACAUCUUGAUCUUGGCCUUU | 1180 |
| GGCUGGGAUCAAGAUGCCUG | 1181 |
| GUCAGGCUGGGAUCAAGAUG | 1182 |
| AGUCAGGCUGGGAUCAAGAU | 1183 |
| CAGUCAGGCUGGGAUCAAGA | 1184 |
| AGCAGUCAGGCUGGGAUCAA | 1185 |
| GAUGUAGCAGCAGUCAGGCU | 1186 |
| GGAUUAGAUGUAGCAGCAGU | 1187 |
| GGGAUUAGAUGUAGCAGCAG | 1188 |
| GACAGGAGGCAUUGGUAGGG | 1189 |
| UUAGGGACAGGAGGCAUUGG | 1190 |
| UUUAGGGACAGGAGGCAUUG | 1191 |
| GAGUUUAGGGACAGGAGGCA | 1192 |
| GGAGUUUAGGGACAGGAGGC | 1193 |
| GCUGUCAUCAGUAUGCUGGG | 1194 |
| GGCUGUCAUCAGUAUGCUGG | 1195 |
| GGGCUGUCAUCAGUAUGCUG | 1196 |
| AGGGCUGUCAUCAGUAUGCU | 1197 |
| AGAGAGGGCUGUCAUCAGUA | 1198 |
| CAGAGAGGGCUGUCAUCAGU | 1199 |
| UCAGAGAGGGCUGUCAUCAG | 1200 |
| GUCAGAGAGGGCUGUCAUCA | 1201 |
| GGUAAAGUCAGAGAGGGCUG | 1202 |
| GGGAAGGGUAUGAAGACAGA | 1203 |

In some embodiments, the antisense nucleic acid molecules targeted to Transcript B comprise or consist of the nucleotide sequences shown in Table 3.

TABLE 3

| Sequence | SEQ ID NO: |
|---|---|
| UUGCCUUCGGCUUGCUCUGG | 1204 |
| CUUGCCUUCGGCUUGCUCUG | 1205 |
| GCUUGCCUUCGGCUUGCUCU | 1206 |
| UGCUUGCCUUCGGCUUGCUC | 1207 |
| GUGCUUGCCUUCGGCUUGCU | 1208 |
| UCGUGCUUGCCUUCGGCUUG | 1209 |
| AUCGUGCUUGCCUUCGGCUU | 1210 |
| CAUCGUGCUUGCCUUCGGCU | 1211 |
| AGCGCCAUCGUGCUUGCCUU | 1212 |
| UGGUGAGCGCCAUCGUGCUU | 1213 |
| CUGAUGCUCGGCUGCUACAG | 1214 |
| GCUGAUGCUCGGCUGCUACA | 1215 |
| UUUCGGGCUGAUGCUCGGCU | 1216 |
| UCCUUUCGGGCUGAUGCUCG | 1217 |
| UUCCUUUCGGGCUGAUGCUC | 1218 |
| CUUCCUUUCGGGCUGAUGCU | 1219 |
| GCUUCCUUUCGGGCUGAUGC | 1220 |
| UGCUUCCUUUCGGGCUGAUG | 1221 |
| GUGCUUCCUUUCGGGCUGAU | 1222 |

TABLE 3-continued

| Sequence | SEQ ID NO: |
|---|---|
| CGUGCUUCCUUUCGGGCUGA | 1223 |
| UCGUGCUUCCUUUCGGGCUG | 1224 |
| UUCGUGCUUCCUUUCGGGCU | 1225 |
| UUUCGUGCUUCCUUUCGGGC | 1226 |
| CUUUCGUGCUUCCUUUCGGG | 1227 |
| GCUUUCGUGCUUCCUUUCGG | 1228 |
| AUGUACGCCAGCGUGCUGCU | 1229 |
| UCAGCAUGUACGCCAGCGUG | 1230 |
| AGGCGGUGUACUACGUGUGC | 1231 |
| AAGGCGGUGUACUACGUGUG | 1232 |
| CAAGGCGGUGUACUACGUGU | 1233 |
| GCAAGGCGGUGUACUACGUG | 1234 |
| UGCAAGGCGGUGUACUACGU | 1235 |
| CUGCAAGGCGGUGUACUACG | 1236 |
| GCUGCAAGGCGGUGUACUAC | 1237 |
| GGCUGCAAGGCGGUGUACUA | 1238 |
| GCUCUUUGUGGCCUUCCUGA | 1239 |
| CGCUCUUUGUGGCCUUCCUG | 1240 |
| CUUCGUGGUGUGGAGCUUGG | 1241 |
| GGCUUCGUGGUGUGGAGCUU | 1242 |
| CAACGGCUUCGUGGUGUGGA | 1243 |
| UGGCAACGGCUUCGUGGUGU | 1244 |
| UGAGCUGGAAGACUUCGCGG | 1245 |
| CUGAGCUGGAAGACUUCGCG | 1246 |
| GCUGAGCUGGAAGACUUCGC | 1247 |
| ACACUGCUGAGCUGGAAGAC | 1248 |
| CGAGACACUGCUGAGCUGGA | 1249 |
| ACGAGACACUGCUGAGCUGG | 1250 |
| AACGAGACACUGCUGAGCUG | 1251 |
| GAACGAGACACUGCUGAGCU | 1252 |
| GGAACGAGACACUGCUGAGC | 1253 |
| GGGAACGAGACACUGCUGAG | 1254 |
| AGGGAACGAGACACUGCUGA | 1255 |
| CAGGGAACGAGACACUGCUG | 1256 |
| CCAGGGAACGAGACACUGCU | 1257 |
| AAGGAUGUCGGUCUGCUACC | 1258 |
| GAAGGAUGUCGGUCUGCUAC | 1259 |
| AGAAGGAUGUCGGUCUGCUA | 1260 |
| UAGGCCCAGAAGGAUGUCGG | 1261 |
| GUAGGCCCAGAAGGAUGUCG | 1262 |
| UGUAGGCCCAGAAGGAUGUC | 1263 |
| CUGUAGGCCCAGAAGGAUGU | 1264 |
| CCUGUAGGCCCAGAAGGAUG | 1265 |
| ACCUGUAGGCCCAGAAGGAU | 1266 |
| CUUCUCAUCGGGCAUCACAG | 1267 |
| CCUUCUCAUCGGGCAUCACA | 1268 |
| ACCUUCUCAUCGGGCAUCAC | 1269 |
| CACCUUCUCAUCGGGCAUCA | 1270 |
| GCACCUUCUCAUCGGGCAUC | 1271 |
| GGCACCUUCUCAUCGGGCAU | 1272 |
| UGGCACCUUCUCAUCGGGCA | 1273 |
| AUGGCACCUUCUCAUCGGGC | 1274 |
| CAUGGCACCUUCUCAUCGGG | 1275 |
| GCAUGGCACCUUCUCAUCGG | 1276 |
| GGCAUGGCACCUUCUCAUCG | 1277 |
| GAGGCAUGGCACCUUCUCAU | 1278 |
| GGAGGCAUGGCACCUUCUCA | 1279 |
| GACUCCCAGGCAGAAAAGAG | 1280 |
| GGACUCCCAGGCAGAAAAGA | 1281 |
| AGGACUCCCAGGCAGAAAAG | 1282 |
| UCAGGACUCCCAGGCAGAAA | 1283 |
| GAAGUCAGGACUCCCAGGCA | 1284 |
| GUGGAAGUCAGGACUCCCAG | 1285 |
| UCGUGGAAGUCAGGACUCCC | 1286 |
| CUCGUGGAAGUCAGGACUCC | 1287 |
| CCUCGUGGAAGUCAGGACUC | 1288 |
| UGGGUCCUCGUGGAAGUCAG | 1289 |
| CUGGGUCCUCGUGGAAGUCA | 1290 |
| UCUGGGUCCUCGUGGAAGUC | 1291 |
| GUCUGGGUCCUCGUGGAAGU | 1292 |
| AAGAAGGAGUUGUGUUUGAG | 1293 |
| CCAAGAAGGAGUUGUGUUUG | 1294 |
| GUUCCAAGAAGGAGUUGUGU | 1295 |
| GGUUCCAAGAAGGAGUUGUG | 1296 |
| CAGGUCAACUGACUGGGAGC | 1297 |
| UGCCUGUUUACCACUGAGCU | 1298 |

TABLE 3-continued

| Sequence | SEQ ID NO: |
|---|---|
| AUGCCUGUUUACCACUGAGC | 1299 |
| UAUGCCUGUUUACCACUGAG | 1300 |
| UUAUGCCUGUUUACCACUGA | 1301 |
| UUUAUGCCUGUUUACCACUG | 1302 |
| CUUUAUGCCUGUUUACCACU | 1303 |
| ACUUUAUGCCUGUUUACCAC | 1304 |
| UAGAGAUAGUGACAGCCUGG | 1305 |
| GUAGAGAUAGUGACAGCCUG | 1306 |
| UGGUGGUAGAGAUAGUGACA | 1307 |
| GUGGUGGUAGAGAUAGUGAC | 1308 |
| UAGAGGAGUGGUGGUAGAGA | 1309 |
| ACUAGAGGAGUGGUGGUAGA | 1310 |
| AGACUAGAGGAGUGGUGGUA | 1311 |
| CAGACUAGAGGAGUGGUGGU | 1312 |
| CCAGACUAGAGGAGUGGUGG | 1313 |
| GCCAGACUAGAGGAGUGGUG | 1314 |
| GGCCAGACUAGAGGAGUGGU | 1315 |
| GCCCAGAUGUGCUAGAAUGG | 1316 |
| UGCCCAGAUGUGCUAGAAUG | 1317 |
| UUGCCCAGAUGUGCUAGAAU | 1318 |
| UUUGCCCAGAUGUGCUAGAA | 1319 |
| UUUUGCCCAGAUGUGCUAGA | 1320 |
| CCAGUUUUGCCCAGAUGUGC | 1321 |
| AUCCAGUUUUGCCCAGAUGU | 1322 |
| CCAUCCAGUUUUGCCCAGAU | 1323 |
| CACCAUCCAGUUUUGCCCAG | 1324 |
| CCACCAUCCAGUUUUGCCCA | 1325 |
| CCCACCAUCCAGUUUUGCCC | 1326 |
| UUGCUCCCAGCUUGGUAAGU | 1327 |
| GCUUGCUCCCAGCUUGGUAA | 1328 |
| AUCCUGCUUGCUCCCAGCUU | 1329 |
| AAUCCUGCUUGCUCCCAGCU | 1330 |
| CAAUCCUGCUUGCUCCCAGC | 1331 |
| CCAAUCCUGCUUGCUCCCAG | 1332 |
| AACCUUUCAGCUUCUCCAGG | 1333 |
| UAACCUUUCAGCUUCUCCAG | 1334 |
| UUAACCUUUCAGCUUCUCCA | 1335 |
| ACUGCUGCUUAACCUUUCAG | 1336 |
| UACUGCUGCUUAACCUUUCA | 1337 |
| CUACUGCUGCUUAACCUUUC | 1338 |
| CCUACUGCUGCUUAACCUUU | 1339 |
| GCCUACUGCUGCUUAACCUU | 1340 |
| CAGGACAGGAGUAGGCACCU | 1341 |
| ACAGGACAGGAGUAGGCACC | 1342 |
| GCACAGGACAGGAGUAGGCA | 1343 |
| AUAGGCACAGGACAGGAGUA | 1344 |
| GAUAGGCACAGGACAGGAGU | 1345 |
| UGAUAGGCACAGGACAGGAG | 1346 |
| ACCCUCUGCAAAUGUGAUAG | 1347 |
| CUUACCCUCUGCAAAUGUGA | 1348 |
| GUCUUACCCUCUGCAAAUGU | 1349 |
| UGUCUUACCCUCUGCAAAUG | 1350 |
| UUGUCUUACCCUCUGCAAAU | 1351 |
| CUUGUCUUACCCUCUGCAAA | 1352 |
| UCUUGUCUUACCCUCUGCAA | 1353 |
| CAUUCUUGUCUUACCCUCUG | 1354 |
| CCCAUUCUUGUCUUACCCUC | 1355 |
| GAGCCUCAUCUUGUCCCUCC | 1356 |
| UGAGCCUCAUCUUGUCCCUC | 1357 |
| UGCGUUGGUGAUGGGAAGGA | 1358 |
| GUGCGUUGGUGAUGGGAAGG | 1359 |
| GGUGCGUUGGUGAUGGGAAG | 1360 |
| GGGUGCGUUGGUGAUGGGAA | 1361 |
| UGGGUGCGUUGGUGAUGGGA | 1362 |
| UCUCACAUGCCUGGACGCCU | 1363 |
| CAAGGCAGGCUCUCACAUGC | 1364 |
| UGCUGUUUCCUGGCAAGGCA | 1365 |
| UUGUGCUGUUUCCUGGCAAG | 1366 |
| CUUGUGCUGUUUCCUGGCAA | 1367 |
| ACCACCAGGGAAUCUUACUG | 1368 |
| UCCACCACCAGGGAAUCUUA | 1369 |
| AUUUCCUUCCACCACCAGGG | 1370 |
| UAUUUCCUUCCACCACCAGG | 1371 |
| CCUAUUUCCUUCCACCACCA | 1372 |
| AGUCCUCCUAUUUCCUUCCA | 1373 |
| AGAGUCCUCCUAUUUCCUUC | 1374 |

TABLE 3-continued

| Sequence | SEQ ID NO: |
|---|---|
| AGCAGAGUCCUCCUAUUUCC | 1375 |
| CAGCAGAGUCCUCCUAUUUC | 1376 |
| AUUCAGCAGAGUCCUCCUAU | 1377 |
| ACCAGGAUUCAGCAGAGUCC | 1378 |
| GACCAGGAUUCAGCAGAGUC | 1379 |
| GGACCAGGAUUCAGCAGAGU | 1380 |
| CAGGACCAGGAUUCAGCAGA | 1381 |
| CAGAAGCAGGACCAGGAUUC | 1382 |
| ACAGAAGCAGGACCAGGAUU | 1383 |
| AACAGAAGCAGGACCAGGAU | 1384 |
| AGAACAGAAGCAGGACCAGG | 1385 |
| GGGAGGGAUGAGAACAGAAG | 1386 |
| CAGGCAACAUACACACUGCA | 1387 |
| CCAGGCAACAUACACACUGC | 1388 |
| ACCAGGCAACAUACACACUG | 1389 |
| AGACCAGGCAACAUACACAC | 1390 |
| GAGAGACCAGGCAACAUACA | 1391 |
| CCAGAGAGACCAGGCAACAU | 1392 |
| UUGUUUGGGUCACCUCUGCA | 1393 |
| GUUGUUUGGGUCACCUCUGC | 1394 |
| AGUUGUUUGGGUCACCUCUG | 1395 |
| UGAGUUGUUUGGGUCACCUC | 1396 |
| CUGAGUUGUUUGGGUCACCU | 1397 |
| GACUGAGUUGUUUGGGUCAC | 1398 |
| AAACAGGCAAGGAUAAGGCA | 1399 |
| ACAUGGAAAAGCUGUCAUUG | 1400 |
| CCUUACAUGGAAAAGCUGUC | 1401 |
| GCCUUACAUGGAAAAGCUGU | 1402 |
| CUCCUGGAACCUAGCACCAU | 1403 |
| CCUCCUGGAACCUAGCACCA | 1404 |
| UCCUCCUGGAACCUAGCACC | 1405 |
| AACCAUUAUGCCUCCAUGCA | 1406 |
| UAACCAUUAUGCCUCCAUGC | 1407 |
| CUAACCAUUAUGCCUCCAUG | 1408 |
| CCUAACCAUUAUGCCUCCAU | 1409 |
| CCCUAACCAUUAUGCCUCCA | 1410 |
| ACUCCCUAACCAUUAUGCCU | 1411 |
| GACUCCCUAACCAUUAUGCC | 1412 |
| UGACUCCCUAACCAUUAUGC | 1413 |
| AUGACUCCCUAACCAUUAUG | 1414 |
| CAUGACUCCCUAACCAUUAU | 1415 |
| GGGCCUCUUCAUGGUUGUGU | 1416 |
| UGGUGCAGCCUGGUAAUGGG | 1417 |
| CUGGUGCAGCCUGGUAAUGG | 1418 |
| CCUGGUGCAGCCUGGUAAUG | 1419 |
| AUCCUGGUGCAGCCUGGUAA | 1420 |
| UAUCCUGGUGCAGCCUGGUA | 1421 |
| GUAUCCUGGUGCAGCCUGGU | 1422 |
| UGUAUCCUGGUGCAGCCUGG | 1423 |
| UCUUGUAUCCUGGUGCAGCC | 1424 |
| GUCUUGUAUCCUGGUGCAGC | 1425 |
| UGUCUUGUAUCCUGGUGCAG | 1426 |
| UUGUCUUGUAUCCUGGUGCA | 1427 |
| CUUGUCUUGUAUCCUGGUGC | 1428 |
| UCUUGUCUUGUAUCCUGGUG | 1429 |
| UUCUUGUCUUGUAUCCUGGU | 1430 |
| UUUCUUGUCUUGUAUCCUGG | 1431 |
| CCUUUCUUGUCUUGUAUCCU | 1432 |
| ACUCAUCCUUUCCUUUCUUG | 1433 |
| CCUACUCAUCCUUUCCUUUC | 1434 |
| CCCUACUCAUCCUUUCCUUU | 1435 |
| UCCCUACUCAUCCUUUCCUU | 1436 |
| GCUUCUAGUAUGUCCCUAC | 1437 |
| GCUGCUUCUUAGUAUGUCCC | 1438 |
| GGCUGCUUCUUAGUAUGUCC | 1439 |
| GGGCUGCUUCUUAGUAUGUC | 1440 |
| AGGGCUGCUUCUUAGUAUGU | 1441 |
| GAGAGGGCUGCUUCUUAGUA | 1442 |
| UCCAAGAGGAGAGGGCUGCU | 1443 |
| UUGACUUUCCAAGAGGAGA | 1444 |
| AGCUCUAUCCAUCUGCCAGG | 1445 |
| GCUGUUACUUGAGCAGAGGC | 1446 |
| GGCUGUUACUUGAGCAGAGG | 1447 |
| UGGCUGUUACUUGAGCAGAG | 1448 |
| CUGGCUGUUACUUGAGCAGA | 1449 |
| UCUGGCUGUUACUUGAGCAG | 1450 |

TABLE 3-continued

| Sequence | SEQ ID NO: |
|---|---|
| CCUCAAGUUCUGGCUGUUAC | 1451 |
| ACCUCAAGUUCUGGCUGUUA | 1452 |
| CAACCUCAAGUUCUGGCUGU | 1453 |
| GCAACCUCAAGUUCUGGCUG | 1454 |
| AGCAACCUCAAGUUCUGGCU | 1455 |
| CAAGCAACCUCAAGUUCUGG | 1456 |
| CCAAGCAACCUCAAGUUCUG | 1457 |
| CCCAAGCAACCUCAAGUUCU | 1458 |
| ACUAAGACAGUGCUCCUGGU | 1459 |
| CAAACUAAGACAGUGCUCCU | 1460 |
| AGCUCUGCUUUGGAAGAACC | 1461 |
| CCCUUAGCUCAAGCUCUGCU | 1462 |
| GCCCUUAGCUCAAGCUCUGC | 1463 |
| AAGCCCUUAGCUCAAGCUCU | 1464 |
| CAAGCCCUUAGCUCAAGCUC | 1465 |
| CCAAGCCCUUAGCUCAAGCU | 1466 |
| CCCAAGCCCUUAGCUCAAGC | 1467 |
| GUACCCAAGCCCUUAGCUCA | 1468 |
| UGUACCCAAGCCCUUAGCUC | 1469 |
| CUGUACCCAAGCCCUUAGCU | 1470 |
| CCUGUACCCAAGCCCUUAGC | 1471 |
| ACCUGUACCCAAGCCCUUAG | 1472 |
| UCACCUGUACCCAAGCCCUU | 1473 |
| AUCACCUGUACCCAAGCCCU | 1474 |
| GGAUCACCUGUACCCAAGCC | 1475 |
| CUCAAGAAUACAGGAUCACC | 1476 |
| CUUAGCUCAAGAAUACAGGA | 1477 |
| CCUUAGCUCAAGAAUACAGG | 1478 |
| GCCCUUAGCUCAAGAAUACA | 1479 |
| AGCCCUUAGCUCAAGAAUAC | 1480 |
| AAGCCCUUAGCUCAAGAAUA | 1481 |
| CAAGCCCUUAGCUCAAGAAU | 1482 |
| CCAAGCCCUUAGCUCAAGAA | 1483 |
| CCCAAGCCCUUAGCUCAAGA | 1484 |
| GUACCCAAGCCCUUAGCUCA | 1485 |
| UGUACCCAAGCCCUUAGCUC | 1486 |
| CUGUACCCAAGCCCUUAGCU | 1487 |
| CCUGUACCCAAGCCCUUAGC | 1488 |

TABLE 3-continued

| Sequence | SEQ ID NO: |
|---|---|
| ACCUGUACCCAAGCCCUUAG | 1489 |
| UCACCUGUACCCAAGCCCUU | 1490 |
| AUCACCUGUACCCAAGCCCU | 1491 |
| GGAUCACCUGUACCCAAGCC | 1492 |
| UAACCUCCCAAAUACAGGAU | 1493 |
| UACCUUAUGCCCUCACUUCC | 1494 |
| UUACCUUAUGCCCUCACUUC | 1495 |
| UUUACCUUAUGCCCUCACUU | 1496 |
| UUUUACCUUAUGCCCUCACU | 1497 |
| UUGUUUACCUUAUGCCCUC | 1498 |
| CUUGUUUACCUUAUGCCCU | 1499 |
| UUAAUGGCUUUCCUCUCUCU | 1500 |
| ACUCUUAAUGGCUUUCCUCU | 1501 |
| UACUCUUAAUGGCUUUCCUC | 1502 |
| CAUACUCUUAAUGGCUUUCC | 1503 |
| GAAGGGACUUAACAUACUCU | 1504 |
| UGAAGGGACUUAACAUACUC | 1505 |
| ACUGAAGGGACUUAACAUAC | 1506 |
| CUACUGAAGGGACUUAACAU | 1507 |
| GCCUACUGAAGGGACUUAAC | 1508 |
| GGCCUACUGAAGGGACUUAA | 1509 |
| UUCUCAGAGGUUCCCAAGGC | 1510 |
| UUUUCUCAGAGGUUCCCAAG | 1511 |
| ACUUUUCUCAGAGGUUCCCA | 1512 |
| UACUUUUCUCAGAGGUUCCC | 1513 |
| GGGCAAUCUAUACUUUUCUC | 1514 |
| UGUCUUGGGCAAUCUAUACU | 1515 |
| CCAGUCUUUUGUCUUGGGCA | 1516 |
| GCCAGUCUUUUGUCUUGGGC | 1517 |
| UGCCAGUCUUUUGUCUUGGG | 1518 |
| CUGCCAGUCUUUUGUCUUGG | 1519 |
| UCACCCUGCCAGUCUUUUGU | 1520 |
| AUCACCCUGCCAGUCUUUUG | 1521 |
| GCCCACUCAUUAAGUACAUU | 1522 |
| CUGUAGCCCACUCAUUAAGU | 1523 |
| CGCUGUAGCCCACUCAUUAA | 1524 |
| ACGCUGUAGCCCACUCAUUA | 1525 |
| UACGCUGUAGCCCACUCAUU | 1526 |

TABLE 3-continued

| Sequence | SEQ ID NO: |
|---|---|
| AUACGCUGUAGCCCACUCAU | 1527 |
| GAUACGCUGUAGCCCACUCA | 1528 |
| GGAUACGCUGUAGCCCACUC | 1529 |
| AGGAUACGCUGUAGCCCACU | 1530 |
| GAGGAUACGCUGUAGCCCAC | 1531 |
| UGAGGAUACGCUGUAGCCCA | 1532 |
| GUGAGGAUACGCUGUAGCCC | 1533 |
| UGUGAGGAUACGCUGUAGCC | 1534 |
| CUGUUGUGAGGAUACGCUGU | 1535 |
| UCUGUUGUGAGGAUACGCUG | 1536 |
| GUCUGUUGUGAGGAUACGCU | 1537 |
| UGUCUGUUGUGAGGAUACGC | 1538 |
| ACUGUCUGUUGUGAGGAUAC | 1539 |
| CACUGUCUGUUGUGAGGAUA | 1540 |
| CAACUCUCUCUCACUGUCUG | 1541 |
| AACAACUCUCUCUCACUGUC | 1542 |
| AGAACAACUCUCUCUCACUG | 1543 |
| GUAGAACAACUCUCUCUCAC | 1544 |
| GGUAGAACAACUCUCUCUCA | 1545 |
| CAGGUAGAACAACUCUCUCU | 1546 |
| CCAGGUAGAACAACUCUCUC | 1547 |
| ACCCAGGUAGAACAACUCUC | 1548 |
| UAUACCCAGGUAGAACAACU | 1549 |
| AUAUACCCAGGUAGAACAAC | 1550 |
| GGAUAUACCCAGGUAGAACA | 1551 |
| GUUUUGGAUAUACCCAGGUA | 1552 |
| CCUUGUUUUGGAUAUACCCA | 1553 |
| CCCUUGUUUUGGAUAUACCC | 1554 |
| CCUCGUAAACUCCAUACCCU | 1555 |
| CCCUCGUAAACUCCAUACCC | 1556 |
| ACCCUCGUAAACUCCAUACC | 1557 |
| AACCCUCGUAAACUCCAUAC | 1558 |
| GAACCCUCGUAAACUCCAUA | 1559 |
| UGAACCCUCGUAAACUCCAU | 1560 |
| UUGAACCCUCGUAAACUCCA | 1561 |
| CUUGAACCCUCGUAAACUCC | 1562 |
| CCUUGAACCCUCGUAAACUC | 1563 |
| ACCUUGAACCCUCGUAAACU | 1564 |
| UACCUUGAACCCUCGUAAAC | 1565 |
| AUACCUUGAACCCUCGUAAA | 1566 |
| AAUACCUUGAACCCUCGUAA | 1567 |
| AAAUACCUUGAACCCUCGUA | 1568 |
| CAAAUACCUUGAACCCUCGU | 1569 |
| CCAAAUACCUUGAACCCUCG | 1570 |
| ACCAAAUACCUUGAACCCUC | 1571 |
| AACCAAAUACCUUGAACCCU | 1572 |
| GAACCAAAUACCUUGAACCC | 1573 |
| UGAACCAAAUACCUUGAACC | 1574 |
| CCCUGAACCAAAUACCUUGA | 1575 |
| GGCCCUGAACCAAAUACCUU | 1576 |
| UGGCCCUGAACCAAAUACCU | 1577 |
| UAUUCAGGUUGUUGCCCAAA | 1578 |
| GGUAUUCAGGUUGUUGCCCA | 1579 |
| AGGUAUUCAGGUUGUUGCCC | 1580 |
| AAGGUAUUCAGGUUGUUGCC | 1581 |
| AAAGGUAUUCAGGUUGUUGC | 1582 |
| UAACUUGAUUGCCCUGUGAC | 1583 |
| GUAACUUGAUUGCCCUGUGA | 1584 |
| AGUAACUUGAUUGCCCUGUG | 1585 |
| CAGAGUAACUUGAUUGCCCU | 1586 |
| ACAGAGUAACUUGAUUGCCC | 1587 |
| CACAGAGUAACUUGAUUGCC | 1588 |
| UGUCCUGACAAAGAAACACA | 1589 |
| CAAUCCCUGCUUUCCUGCCA | 1590 |
| ACAAUCCCUGCUUUCCUGCC | 1591 |
| AACACAAUCCCUGCUUUCCU | 1592 |
| GAACACAAUCCCUGCUUUCC | 1593 |
| AAUGAACACAAUCCCUGCUU | 1594 |
| AAAUGAACACAAUCCCUGCU | 1595 |
| GUGAAACCCUCAAAUGAACA | 1596 |
| AGUGAAACCCUCAAAUGAAC | 1597 |
| CAGUGAAACCCUCAAAUGAA | 1598 |
| ACAGUGAAACCCUCAAAUGA | 1599 |
| GCAUGGAAGCUGAGACUCUC | 1600 |
| UUGCAUGGAAGCUGAGACUC | 1601 |
| CAGUUGCAUGGAAGCUGAGA | 1602 |

TABLE 3-continued

| Sequence | SEQ ID NO: |
|---|---|
| ACAGUUGCAUGGAAGCUGAG | 1603 |
| GACAGUUGCAUGGAAGCUGA | 1604 |
| AUGGACAGUUGCAUGGAAGC | 1605 |
| GUGAUGGACAGUUGCAUGGA | 1606 |
| CGUGAUGGACAGUUGCAUGG | 1607 |
| CCGUGAUGGACAGUUGCAUG | 1608 |
| GCCGUGAUGGACAGUUGCAU | 1609 |
| AGCCGUGAUGGACAGUUGCA | 1610 |
| CAGCCGUGAUGGACAGUUGC | 1611 |
| GCAGCCGUGAUGGACAGUUG | 1612 |
| UGCAGCCGUGAUGGACAGUU | 1613 |
| UUGCAGCCGUGAUGGACAGU | 1614 |
| GUUGCAGCCGUGAUGGACAG | 1615 |
| CAGUUGCAGCCGUGAUGGAC | 1616 |
| UCAGUUGCAGCCGUGAUGGA | 1617 |
| UUCAGUUGCAGCCGUGAUGG | 1618 |
| UUUCAGUUGCAGCCGUGAUG | 1619 |
| AUUUCAGUUGCAGCCGUGAU | 1620 |
| GAUUUCAGUUGCAGCCGUGA | 1621 |
| UGAUUUCAGUUGCAGCCGUG | 1622 |
| CUCUGAUUUCAGUUGCAGCC | 1623 |
| UUAGCUUCUGGUGCGCUGUG | 1624 |
| UUUAGCUUCUGGUGCGCUGU | 1625 |
| CUUUAGCUUCUGGUGCGCUG | 1626 |
| GACUUUAGCUUCUGGUGCGC | 1627 |
| AGACUUUAGCUUCUGGUGCG | 1628 |
| AAGACUUUAGCUUCUGGUGC | 1629 |
| UCAAGACUUUAGCUUCUGGU | 1630 |
| AUCAAGACUUUAGCUUCUGG | 1631 |
| GCAUCAAGACUUUAGCUUCU | 1632 |
| AUGGCAUCAAGACUUUAGCU | 1633 |
| GAUGGCAUCAAGACUUUAGC | 1634 |
| AGGGAUGUCCUUUGAUGGCA | 1635 |
| GCAGGGAUGUCCUUUGAUGG | 1636 |
| GGCAGGGAUGUCCUUUGAUG | 1637 |
| CGUGACAGAGAUGUGAAUGG | 1638 |
| GGACGUGACAGAGAUGUGAA | 1639 |
| UGGACGUGACAGAGAUGUGA | 1640 |
| GUGGACGUGACAGAGAUGUG | 1641 |
| AGUGGACGUGACAGAGAUGU | 1642 |
| UAGUGGACGUGACAGAGAUG | 1643 |
| UUAGUGGACGUGACAGAGAU | 1644 |
| AUUAGUGGACGUGACAGAGA | 1645 |
| GAUUAGUGGACGUGACAGAG | 1646 |
| CGAUUAGUGGACGUGACAGA | 1647 |
| CCGAUUAGUGGACGUGACAG | 1648 |
| UGCCGAUUAGUGGACGUGAC | 1649 |
| UUGCCGAUUAGUGGACGUGA | 1650 |
| UUUGCCGAUUAGUGGACGUG | 1651 |
| UUUUGCCGAUUAGUGGACGU | 1652 |
| CUUUUGCCGAUUAGUGGACG | 1653 |
| CCUUUUGCCGAUUAGUGGAC | 1654 |
| UCCUUUUGCCGAUUAGUGGA | 1655 |
| CUCCUUUUGCCGAUUAGUGG | 1656 |
| UCUCCUUUUGCCGAUUAGUG | 1657 |
| UUCUCCUUUUGCCGAUUAGU | 1658 |
| UUUCUCCUUUUGCCGAUUAG | 1659 |
| AGGUCAUCUUCUCUCACUUU | 1660 |
| UUAGGUCAUCUUCUCUCACU | 1661 |
| CUUAGGUCAUCUUCUCUCAC | 1662 |
| ACACUUAGGUCAUCUUCUCU | 1663 |
| CACACUUAGGUCAUCUUCUC | 1664 |
| UCACACUUAGGUCAUCUUCU | 1665 |
| GUCACACUUAGGUCAUCUUC | 1666 |
| AGUCACACUUAGGUCAUCUU | 1667 |
| CAGUCACACUUAGGUCAUCU | 1668 |
| GCAGUCACACUUAGGUCAUC | 1669 |
| UGCAGUCACACUUAGGUCAU | 1670 |
| AUUUUCCAGAGCUGCCUGCU | 1671 |
| CUCACUGCUCUGGCUUCAUU | 1672 |
| GCUCACUGCUCUGGCUUCAU | 1673 |
| UUACCUGCUCUUUCCUUCCU | 1674 |
| UGCUUACCUGCUCUUUCCUU | 1675 |
| UUCCUGCUUACCUGCUCUUU | 1676 |
| CUUCCUGCUUACCUGCUCUU | 1677 |
| ACUGGCCUUCCUGCUUACCU | 1678 |

TABLE 3-continued

| Sequence | SEQ ID NO: |
|---|---|
| GACACUGGCCUUCCUGCUUA | 1679 |
| CAUUAGGGUCCUGUCUGGGA | 1680 |
| UCAUUAGGGUCCUGUCUGGG | 1681 |
| AUCAUUAGGGUCCUGUCUGG | 1682 |
| GAUCAUUAGGGUCCUGUCUG | 1683 |
| GGAUCAUUAGGGUCCUGUCU | 1684 |
| AUUCAGGAUCAUUAGGGUCC | 1685 |
| GAUUCAGGAUCAUUAGGGUC | 1686 |
| GGAUUCAGGAUCAUUAGGGU | 1687 |
| AUGGAUUCAGGAUCAUUAGG | 1688 |
| GAUACAUGGAUUCAGGAUCA | 1689 |
| UGAUACAUGGAUUCAGGAUC | 1690 |
| AUGGCAGGGCUUUGGAAAAU | 1691 |
| CAUGGCAGGGCUUUGGAAAA | 1692 |
| GCAUGGCAGGGCUUUGGAAA | 1693 |
| CAGCAUGGCAGGGCUUUGGA | 1694 |
| GAAGUGGGAUGGCAGCAUGG | 1695 |
| GGAAGUGGGAUGGCAGCAUG | 1696 |
| GGGAAGUGGGAUGGCAGCAU | 1697 |
| UGGAGAAGCCAUAAGCUGCA | 1698 |
| CUGGAGAAGCCAUAAGCUGC | 1699 |
| ACUGGAGAAGCCAUAAGCUG | 1700 |
| UACUGGAGAAGCCAUAAGCU | 1701 |
| CUACUGGAGAAGCCAUAAGC | 1702 |
| CCUACUGGAGAAGCCAUAAG | 1703 |
| ACCUACUGGAGAAGCCAUAA | 1704 |
| CACCUACUGGAGAAGCCAUA | 1705 |
| CCACCUACUGGAGAAGCCAU | 1706 |
| GCCACCUACUGGAGAAGCCA | 1707 |
| CUGCCACCUACUGGAGAAGC | 1708 |
| GCUGCCACCUACUGGAGAAG | 1709 |
| UGUGUGUGCUGCCACCUACU | 1710 |
| CUGUGUGUGCUGCCACCUAC | 1711 |
| UUAUGAGUGGCUCUGUGUGU | 1712 |
| UUUAUGAGUGGCUCUGUGUG | 1713 |
| AGUUUAUGAGUGGCUCUGUG | 1714 |
| CAGUUUAUGAGUGGCUCUGU | 1715 |
| GUUUCUGGCUCUCAGGCUCU | 1716 |

TABLE 3-continued

| Sequence | SEQ ID NO: |
|---|---|
| GGUUUCUGGCUCUCAGGCUC | 1717 |
| CGGUUUCUGGCUCUCAGGCU | 1718 |
| GGACGGUUUCUGGCUCUCAG | 1719 |
| GGGACGGUUUCUGGCUCUCA | 1720 |
| UGAAAUGUGACUUCUGGUGU | 1721 |
| GGGAACCAUGUAAAAGGAUG | 1722 |
| GUGAGGGUAGAUGGGAACCA | 1723 |
| UUGUGAGGGUAGAUGGGAAC | 1724 |
| GUUGUGAGGGUAGAUGGGAA | 1725 |
| UGUUGUGAGGGUAGAUGGGA | 1726 |
| AUGUGUGUCUUUGGUGAUGA | 1727 |
| GGAGCUUGUAUGUGUGUCUU | 1728 |
| UUGGAGCUUGUAUGUGUGUC | 1729 |
| AUUGGAGCUUGUAUGUGUGU | 1730 |
| CAUUGGAGCUUGUAUGUGUG | 1731 |
| CCAUUGGAGCUUGUAUGUGU | 1732 |
| GCCAUUGGAGCUUGUAUGUG | 1733 |
| AGCCAUUGGAGCUUGUAUGU | 1734 |
| CUGGAGGAAGAAUUGCCUGG | 1735 |
| GUCCUGGAGGAAGAAUUGCC | 1736 |
| GCCAGUAAGAAGGGCAAAGU | 1737 |
| GGCCAGUAAGAAGGGCAAAG | 1738 |
| GGAAUGAGUCAAGCCUGGAC | 1739 |
| GGGAAUGAGUCAAGCCUGGA | 1740 |
| GUGGGAAUGAGUCAAGCCUG | 1741 |
| AAGGUGGGAAUGAGUCAAGC | 1742 |
| UCUCAGCCCAGGCAAGGUG | 1743 |
| AUCUCAGCCCAGGACAAGGU | 1744 |
| GCUGGGUGGUUCUCUCCUGU | 1745 |
| UUCUGGGCUGGGUGGUUCUC | 1746 |
| GAACUUCUGGGCUGGGUGGU | 1747 |
| CGGAGAGUUCCUUCCCUGGA | 1748 |
| ACCGGAGAGUUCCUUCCCUG | 1749 |
| GACCGGAGAGUUCCUUCCCU | 1750 |
| UGGACCGGAGAGUUCCUUCC | 1751 |
| GUGGACCGGAGAGUUCCUUC | 1752 |
| GGUGGACCGGAGAGUUCCUU | 1753 |
| UGGUGGACCGGAGAGUUCCU | 1754 |

TABLE 3-continued

| Sequence | SEQ ID NO: |
|---|---|
| AUGGUGGACCGGAGAGUUCC | 1755 |
| CAUGGUGGACCGGAGAGUUC | 1756 |
| GAGCUGAGAGGUACUCCAUG | 1757 |
| AGAGCUGAGAGGUACUCCAU | 1758 |
| CAGAGCUGAGAGGUACUCCA | 1759 |
| UUCAGAGCUGAGAGGUACUC | 1760 |
| GGUUCAGAGCUGAGAGGUAC | 1761 |
| GGGUUCAGAGCUGAGAGGUA | 1762 |
| CACCUGAGUAAGUCACUGGG | 1763 |
| UCACCUGAGUAAGUCACUGG | 1764 |
| GUCACCUGAGUAAGUCACUG | 1765 |
| AGUCACCUGAGUAAGUCACU | 1766 |
| CAGUCACCUGAGUAAGUCAC | 1767 |
| GCAGUCACCUGAGUAAGUCA | 1768 |
| UUAGCAGUCACCUGAGUAAG | 1769 |
| GUUAGCAGUCACCUGAGUAA | 1770 |
| GGUUAGCAGUCACCUGAGUA | 1771 |
| GGGUUAGCAGUCACCUGAGU | 1772 |
| AGGGUUAGCAGUCACCUGAG | 1773 |
| GAGGGUUAGCAGUCACCUGA | 1774 |
| GGAGGGUUAGCAGUCACCUG | 1775 |
| CGGAGGGUUAGCAGUCACCU | 1776 |
| AGCGGAGGGUUAGCAGUCAC | 1777 |
| GAGCGGAGGGUUAGCAGUCA | 1778 |
| AGAGCGGAGGGUUAGCAGUC | 1779 |
| UAGAGCGGAGGGUUAGCAGU | 1780 |
| GUAGAGCGGAGGGUUAGCAG | 1781 |
| GGUAGAGCGGAGGGUUAGCA | 1782 |
| AGGGUAGAGCGGAGGGUUAG | 1783 |
| GAGGGUAGAGCGGAGGGUUA | 1784 |
| AUUGUUGCCCUGCCUAUAUC | 1785 |
| AGUAUUGUUGCCCUGCCUAU | 1786 |
| GAGUAUUGUUGCCCUGCCUA | 1787 |
| GGAGUAUUGUUGCCCUGCCU | 1788 |
| UGGAGUAUUGUUGCCCUGCC | 1789 |
| GUGGAGUAUUGUUGCCCUGC | 1790 |
| AGUGGAGUAUUGUUGCCCUG | 1791 |
| GAGUGGAGUAUUGUUGCCCU | 1792 |

TABLE 3-continued

| Sequence | SEQ ID NO: |
|---|---|
| UGAGUGGAGUAUUGUUGCCC | 1793 |
| CUGAGUGGAGUAUUGUUGCC | 1794 |
| GCUGAGUGGAGUAUUGUUGC | 1795 |
| GGCUGAGUGGAGUAUUGUUG | 1796 |
| GGGCUGAGUGGAGUAUUGUU | 1797 |
| GGUACUGGUUAGUCUCCUAG | 1798 |
| GGGUACUGGUUAGUCUCCUA | 1799 |
| UUGACAAGCCCACUGUGGAG | 1800 |
| UGGCUCAGGAGCUUGACAAG | 1801 |
| GGUGGCUCAGGAGCUUGACA | 1802 |
| UAGGGAUGAGGGAGAGACCA | 1803 |
| UCGAUUAGGGAUGAGGGAGA | 1804 |
| UAGAGGGCUAGGGAGGGAGA | 1805 |
| GUAGAGUGGCUAGAGGGCUA | 1806 |
| GGUAGAGUGGCUAGAGGGCU | 1807 |
| UGAGGGUAGAGUGGCUAGAG | 1808 |
| GAUGAGGGUAGAGUGGCUAG | 1809 |
| CAUGAUGAGGGUAGAGUGGC | 1810 |
| GCAUGAUGAGGGUAGAGUGG | 1811 |
| GGGCAUGAUGAGGGUAGAGU | 1812 |
| GGUAGUUGAGAAGAAAAGUC | 1813 |
| CCAAACUCCGAGCUUAUAUU | 1814 |
| UCCAAACUCCGAGCUUAUAU | 1815 |
| GUCCAAACUCCGAGCUUAUA | 1816 |
| CGUCCAAACUCCGAGCUUAU | 1817 |
| CCGUCCAAACUCCGAGCUUA | 1818 |
| UCCGUCCAAACUCCGAGCUU | 1819 |
| CUCCGUCCAAACUCCGAGCU | 1820 |
| ACCCUCCGUCCAAACUCCGA | 1821 |
| AGACCCUCCGUCCAAACUCC | 1822 |
| CAGACCCUCCGUCCAAACUC | 1823 |
| UCCAGACCCUCCGUCCAAAC | 1824 |
| GUCCAGACCCUCCGUCCAAA | 1825 |
| AGACACGGAAAGGUCGCUGG | 1826 |
| CAGACACGGAAAGGUCGCUG | 1827 |
| ACAGACACGGAAAGGUCGCU | 1828 |
| CACAGACACGGAAAGGUCGC | 1829 |
| UCACAGACACGGAAAGGUCG | 1830 |

TABLE 3-continued

| Sequence | SEQ ID NO: |
|---|---|
| AUCACAGACACGGAAAGGUC | 1831 |
| GAUCACAGACACGGAAAGGU | 1832 |
| UUGGCCUACUUACUUUGGCU | 1833 |
| CUUGGCCUACUUACUUUGGC | 1834 |
| ACUUGGCCUACUUACUUUGG | 1835 |
| GAGGAACUUGGCCUACUUAC | 1836 |
| CGAGGAACUUGGCCUACUUA | 1837 |
| CCGAGGAACUUGGCCUACUU | 1838 |
| ACCGAGGAACUUGGCCUACU | 1839 |
| AACCGAGGAACUUGGCCUAC | 1840 |
| GAACCGAGGAACUUGGCCUA | 1841 |
| GGAACCGAGGAACUUGGCCU | 1842 |
| AGGAACCGAGGAACUUGGCC | 1843 |
| UAGGAACCGAGGAACUUGGC | 1844 |
| AUAGGAACCGAGGAACUUGG | 1845 |
| UAUAGGAACCGAGGAACUUG | 1846 |
| AUCACAAGUUGCCACUGUUG | 1847 |
| CAUCACAAGUUGCCACUGUU | 1848 |
| AUCAUCACAAGUUGCCACUG | 1849 |
| CAUCAUCACAAGUUGCCACU | 1850 |
| CUGCUCCAUCAUCACAAGUU | 1851 |
| UCUGCUCCAUCAUCACAAGU | 1852 |
| CCCUCUGCUCCAUCAUCACA | 1853 |
| UCAGCCCUCUGCUCCAUCAU | 1854 |
| UGACUUCAGCCCUCUGCUCC | 1855 |
| GUGACUUCAGCCCUCUGCUC | 1856 |
| UGUGACUUCAGCCCUCUGCU | 1857 |
| GUGUGACUUCAGCCCUCUGC | 1858 |
| UGUGUGACUUCAGCCCUCUG | 1859 |
| GCCCACUCCGCUGCUUUUAG | 1860 |
| GGCCCACUCCGCUGCUUUUA | 1861 |
| AGGCCCACUCCGCUGCUUUU | 1862 |
| UAGGCCCACUCCGCUGCUUU | 1863 |
| UUAGGCCCACUCCGCUGCUU | 1864 |
| AUUAGGCCCACUCCGCUGCU | 1865 |
| UCAUUAGGCCCACUCCGCUG | 1866 |
| CUCAUUAGGCCCACUCCGCU | 1867 |
| AGCUCAUUAGGCCCACUCCG | 1868 |

TABLE 3-continued

| Sequence | SEQ ID NO: |
|---|---|
| CUCCCAUAGAAAAGCUCACU | 1869 |
| GCUCCCAUAGAAAAGCUCAC | 1870 |
| UGCUCCCAUAGAAAAGCUCA | 1871 |
| CUGCUCCCAUAGAAAAGCUC | 1872 |
| CCUGCUCCCAUAGAAAAGCU | 1873 |
| UCCCUAUCUCCUGCUAACCC | 1874 |
| CCUCGAACUCUCCCUAUCUC | 1875 |
| CCCUCGAACUCUCCCUAUCU | 1876 |
| UCCCUCGAACUCUCCCUAUC | 1877 |
| GUCCCUCGAACUCUCCCUAU | 1878 |
| CUUUCCAUACUAGCUUCUGA | 1879 |
| CCUUUCCAUACUAGCUUCUG | 1880 |
| ACCUUUCCAUACUAGCUUCU | 1881 |
| CACACAAAUCACCUUUCCAU | 1882 |
| GUCACACAAAUCACCUUUCC | 1883 |
| UGUCACACAAAUCACCUUUC | 1884 |
| UUUGACAGGCAGGAAGUGGC | 1885 |
| GGUUUGACAGGCAGGAAGUG | 1886 |
| AGGUUUGACAGGCAGGAAGU | 1887 |
| AAGGUUUGACAGGCAGGAAG | 1888 |
| AACUUCCCAAGGUUUGACAG | 1889 |
| CAACUUCCCAAGGUUUGACA | 1890 |
| GAACAACUUCCCAAGGUUUG | 1891 |
| UGAACAACUUCCCAAGGUUU | 1892 |
| GUAGGUUGAACAACUUCCCA | 1893 |
| GGUAGGUUGAACAACUUCCC | 1894 |
| UGGUAGGUUGAACAACUUCC | 1895 |
| GGUUUUGGUAGGUUGAACAA | 1896 |
| UGAGGUUUUGGUAGGUUGAA | 1897 |
| CUGAGGUUUUGGUAGGUUGA | 1898 |
| CCUACAUUAUCCUCUUACUC | 1899 |
| GGACUUUACCUACAUUAUCC | 1900 |
| GUAUGAGGACUUUACCUACA | 1901 |
| GCCAGGUAUGAGGACUUUAC | 1902 |
| UGCCAGGUAUGAGGACUUUA | 1903 |
| GUGCCAGGUAUGAGGACUUU | 1904 |
| CUGUGCCAGGUAUGAGGACU | 1905 |
| UCUGUGCCAGGUAUGAGGAC | 1906 |

TABLE 3-continued

| Sequence | SEQ ID NO: |
|---|---|
| CCUCAAGAGUUCUCCAGAAG | 1907 |
| CCCUCAAGAGUUCUCCAGAA | 1908 |
| ACCCUCAAGAGUUCUCCAGA | 1909 |
| ACACCCUCAAGAGUUCUCCA | 1910 |
| CACACCCUCAAGAGUUCUCC | 1911 |
| CCACACCCUCAAGAGUUCUC | 1912 |
| CCCACACCCUCAAGAGUUCU | 1913 |
| UUCCCACACCCUCAAGAGUU | 1914 |
| CAAUGCUGCACCUCACUUCC | 1915 |
| UACAAUGCUGCACCUCACUU | 1916 |
| CUACAAUGCUGCACCUCACU | 1917 |
| UCUACAAUGCUGCACCUCAC | 1918 |
| AUCUACAAUGCUGCACCUCA | 1919 |
| UAUCUACAAUGCUGCACCUC | 1920 |
| CUUAUCUACAAUGCUGCACC | 1921 |
| GUCUUAUCUACAAUGCUGCA | 1922 |
| UGUCUUAUCUACAAUGCUGC | 1923 |
| CUGUCUUAUCUACAAUGCUG | 1924 |
| CACCCUUCUGUCUUAUCUAC | 1925 |
| UCCACCCUUCUGUCUUAUCU | 1926 |
| GUCCACCCUUCUGUCUUAUC | 1927 |
| AGUCCACCCUUCUGUCUUAU | 1928 |
| AAGUCCACCCUUCUGUCUUA | 1929 |
| GAAAGCAAGCCAGGUUCUCA | 1930 |
| GGAAAGCAAGCCAGGUUCUC | 1931 |
| GGAAUUGGAAAGCAAGCCAG | 1932 |
| ACCAUGUCAUUGGCAUCUCC | 1933 |
| UACCAUGUCAUUGGCAUCUC | 1934 |
| CCUACCAUGUCAUUGGCAUC | 1935 |
| UCCUACCAUGUCAUUGGCAU | 1936 |
| CUCCUACCAUGUCAUUGGCA | 1937 |
| GCUCCUACCAUGUCAUUGGC | 1938 |
| UGCUCCUACCAUGUCAUUGG | 1939 |
| UCUUUGCUCCUACCAUGUCA | 1940 |
| CCUCUUUGCUCCUACCAUGU | 1941 |
| UUCCUCUUUGCUCCUACCAU | 1942 |
| UCUCCGUGUUCUUCAGUUUU | 1943 |
| CUCUCCGUGUUCUUCAGUUU | 1944 |
| AGCUCUCCGUGUUCUUCAGU | 1945 |
| UGCAGCUCUCCGUGUUCUUC | 1946 |
| GGUUGCAGCUCUCCGUGUUC | 1947 |
| AGGUUGCAGCUCUCCGUGUU | 1948 |
| AAAGGUUGCAGCUCUCCGUG | 1949 |
| UAAAGGUUGCAGCUCUCCGU | 1950 |
| CUAAAGGUUGCAGCUCUCCG | 1951 |
| CCUAAAGGUUGCAGCUCUCC | 1952 |
| UCCUAAAGGUUGCAGCUCUC | 1953 |
| CUCCUAAAGGUUGCAGCUCU | 1954 |
| CCUCCUAAAGGUUGCAGCUC | 1955 |
| GCACUUUGAUACCUCCUAAA | 1956 |
| GGCACUUUGAUACCUCCUAA | 1957 |
| GAUGUCCCACUUUGACUUUC | 1958 |
| UCGAUGUCCCACUUUGACUU | 1959 |
| GUCGAUGUCCCACUUUGACU | 1960 |
| GGUCGAUGUCCCACUUUGAC | 1961 |
| UGGUCGAUGUCCCACUUUGA | 1962 |
| UUGGUCGAUGUCCCACUUUG | 1963 |
| AUUGGUCGAUGUCCCACUUU | 1964 |
| CAUUGGUCGAUGUCCCACUU | 1965 |
| AACAUCCAUCAGUUGGCUCU | 1966 |
| CUGCCCAACAUCCAUCAGUU | 1967 |
| AGCUGCCCAACAUCCAUCAG | 1968 |
| UAGCUGCCCAACAUCCAUCA | 1969 |
| UUAGCUGCCCAACAUCCAUC | 1970 |
| UUUAGCUGCCCAACAUCCAU | 1971 |
| CUUUAGCUGCCCAACAUCCA | 1972 |
| CCUCUUUAGCUGCCCAACAU | 1973 |
| CCCUCUUUAGCUGCCCAACA | 1974 |
| UCCCUCUUUAGCUGCCCAAC | 1975 |
| UUCCCUCUUUAGCUGCCCAA | 1976 |
| CCUUCCCUCUUUAGCUGCCC | 1977 |
| CCCUUCCCUCUUUAGCUGCC | 1978 |
| GCAGGUCUAUCCCAUGCCC | 1979 |
| GGGCAGGUCUUAUCCCAUGC | 1980 |
| AGGGCAGGUCUUAUCCCAUG | 1981 |
| AAGGGCAGGUCUUAUCCCAU | 1982 |

TABLE 3-continued

| Sequence | SEQ ID NO: |
|---|---|
| GAAGGGCAGGUCUUAUCCCA | 1983 |
| AGAAGGGCAGGUCUUAUCCC | 1984 |
| CCAAUGGCAAGAAGCAAGAA | 1985 |
| CCCAAUGGCAAGAAGCAAGA | 1986 |
| GCCCAAUGGCAAGAAGCAAG | 1987 |
| UCCAAUGCCUGCCCAAUGGC | 1988 |
| CUCCAAUGCCUGCCCAAUGG | 1989 |
| UCUCCAAUGCCUGCCCAAUG | 1990 |
| GGUCUCCAAUGCCUGCCCAA | 1991 |
| UAGGGUCUCCAAUGCCUGCC | 1992 |
| GUAGGGUCUCCAAUGCCUGC | 1993 |
| AGUAGGGUCUCCAAUGCCUG | 1994 |
| CAGUAGGGUCUCCAAUGCCU | 1995 |
| GCAGUAGGGUCUCCAAUGCC | 1996 |
| AGCAGUAGGGUCUCCAAUGC | 1997 |
| CAGCAGUAGGGUCUCCAAUG | 1998 |
| UCAGCAGUAGGGUCUCCAAU | 1999 |
| AUUCAGCAGUAGGGUCUCCA | 2000 |
| CAUUCAGCAGUAGGGUCUCC | 2001 |
| CCAUUCAGCAGUAGGGUCUC | 2002 |
| UCCAUUCAGCAGUAGGGUCU | 2003 |
| ACUCCAUUCAGCAGUAGGGU | 2004 |
| CACUCCAUUCAGCAGUAGGG | 2005 |
| GCACUCCAUUCAGCAGUAGG | 2006 |
| AGCACUCCAUUCAGCAGUAG | 2007 |
| UAGCACUCCAUUCAGCAGUA | 2008 |
| GUUAGCACUCCAUUCAGCAG | 2009 |
| GGUUAGCACUCCAUUCAGCA | 2010 |
| GGGUUAGCACUCCAUUCAGC | 2011 |
| CAGGGUUAGCACUCCAUUCA | 2012 |
| CCAGGGUUAGCACUCCAUUC | 2013 |
| ACCAGGGUUAGCACUCCAUU | 2014 |
| CACCAGGGUUAGCACUCCAU | 2015 |
| GCACCAGGGUUAGCACUCCA | 2016 |
| AGCACCAGGGUUAGCACUCC | 2017 |
| UAGCACCAGGGUUAGCACUC | 2018 |
| CUAGCACCAGGGUUAGCACU | 2019 |
| UCUAGCACCAGGGUUAGCAC | 2020 |
| CUCUAGCACCAGGGUUAGCA | 2021 |
| CCUCUAGCACCAGGGUUAGC | 2022 |
| UCCUCUAGCACCAGGGUUAG | 2023 |
| CUCCUCUAGCACCAGGGUUA | 2024 |
| CCUCCUCUAGCACCAGGGUU | 2025 |
| UCCUCCUCUAGCACCAGGGU | 2026 |
| GUUCCAUCCUCCUCUAGCAC | 2027 |
| AAGUCCUCACUGUCCACUGC | 2028 |
| GAAGUCCUCACUGUCCACUG | 2029 |
| AGAAGUCCUCACUGUCCACU | 2030 |
| AAGAAGUCCUCACUGUCCAC | 2031 |
| GAAGAAGUCCUCACUGUCCA | 2032 |
| GGAAGAAGUCCUCACUGUCC | 2033 |
| UGGAAGAAGUCCUCACUGUC | 2034 |
| CUGGAAGAAGUCCUCACUGU | 2035 |
| AGCUGGAAGAAGUCCUCACU | 2036 |
| ACUGCAACACCAUCAGGCAC | 2037 |
| GACUGCAACACCAUCAGGCA | 2038 |
| AGACUGCAACACCAUCAGGC | 2039 |
| CAGACUGCAACACCAUCAGG | 2040 |
| CCAGACUGCAACACCAUCAG | 2041 |
| GACCAGACUGCAACACCAUC | 2042 |
| CUCUGACCAGACUGCAACAC | 2043 |
| AGCUCUGACCAGACUGCAAC | 2044 |
| CCAGCUCUGACCAGACUGCA | 2045 |
| UGUAGGGCUCCAGCUCUGAC | 2046 |
| CUUGUAGGGCUCCAGCUCUG | 2047 |
| CCUUGUAGGGCUCCAGCUCU | 2048 |
| ACAGGCAUUGGAAGCAGCCC | 2049 |
| GACAGGCAUUGGAAGCAGCC | 2050 |
| AAGGACAGGCAUUGGAAGCA | 2051 |
| AAAGGACAGGCAUUGGAAGC | 2052 |
| UAAAGGACAGGCAUUGGAAG | 2053 |
| CUAAAGGACAGGCAUUGGAA | 2054 |
| GCUCUAAAGGACAGGCAUUG | 2055 |
| AGCUCUAAAGGACAGGCAUU | 2056 |
| AAGCUCUAAAGGACAGGCAU | 2057 |
| AAAGCUCUAAAGGACAGGCA | 2058 |

TABLE 3-continued

| Sequence | SEQ ID NO: |
|---|---|
| GAAAGCUCUAAAGGACAGGC | 2059 |
| CGGGAAAGCUCUAAAGGACA | 2060 |
| CCGGGAAAGCUCUAAAGGAC | 2061 |
| AGGGUUAAGCUAGAGAGGAA | 2062 |
| UCAGGGUUAAGCUAGAGAGG | 2063 |
| GAUCAGGGUUAAGCUAGAGA | 2064 |
| GGAUCAGGGUUAAGCUAGAG | 2065 |
| AGGAUCAGGGUUAAGCUAGA | 2066 |
| CCCAGGAUCAGGGUUAAGCU | 2067 |
| CAACUCCUCCUGCACCUGGU | 2068 |
| ACAACUCCUCCUGCACCUGG | 2069 |
| GACAAUUCCACAACUCCUCC | 2070 |
| UGACAAUUCCACAACUCCUC | 2071 |
| UUGACAAUUCCACAACUCCU | 2072 |
| CUUGACAAUUCCACAACUCC | 2073 |
| UCCUUGACAAUUCCACAACU | 2074 |
| AUCCUUGACAAUUCCACAAC | 2075 |
| CAUCCUUGACAAUUCCACAA | 2076 |
| ACAUCCUUGACAAUUCCACA | 2077 |
| GACAUCCUUGACAAUUCCAC | 2078 |
| UGACAUCCUUGACAAUUCCA | 2079 |
| UGUGUGACAUCCUUGACAAU | 2080 |
| ACUGUGUGACAUCCUUGACA | 2081 |
| ACUUUCUGUCCACUGUGUGA | 2082 |
| CCUCGCUUGGACUUUCUGUC | 2083 |
| CCCUCGCUUGGACUUUCUGU | 2084 |
| UCCCUCGCUUGGACUUUCUG | 2085 |
| CUCCCUCGCUUGGACUUUCU | 2086 |
| CCUCCCUCGCUUGGACUUUC | 2087 |
| CCCUCCCUCGCUUGGACUUU | 2088 |
| UCCAUCAGCACUGGGUCAGA | 2089 |
| ACCACUAAUCUCCAUCAGCA | 2090 |
| CACCACUAAUCUCCAUCAGC | 2091 |
| CCACCACUAAUCUCCAUCAG | 2092 |
| CCCACCACUAAUCUCCAUCA | 2093 |
| ACCAGACACCCACCACUAAU | 2094 |
| UACCAGACACCCACCACUAA | 2095 |
| CUCAUACCAGACACCCACCA | 2096 |
| CCUCAUACCAGACACCCACC | 2097 |
| UCCUCAUACCAGACACCCAC | 2098 |
| AUCCUCAUACCAGACACCCA | 2099 |
| GAUCCUCAUACCAGACACCC | 2100 |
| AGAUCCUCAUACCAGACACC | 2101 |
| UAGAUCCUCAUACCAGACAC | 2102 |
| GUAGAUCCUCAUACCAGACA | 2103 |
| AGUAGAUCCUCAUACCAGAC | 2104 |
| CAGUAGAUCCUCAUACCAGA | 2105 |
| UGCAGUAGAUCCUCAUACCA | 2106 |
| GUGCAGUAGAUCCUCAUACC | 2107 |
| AGUGCAGUAGAUCCUCAUAC | 2108 |
| ACUCUGUAGGACACCCUUGU | 2109 |
| CACUCUGUAGGACACCCUUG | 2110 |
| CCACUCUGUAGGACACCCUU | 2111 |
| UCCACUCUGUAGGACACCCU | 2112 |
| CUCCACUCUGUAGGACACCC | 2113 |
| ACUCCACUCUGUAGGACACC | 2114 |
| CACUCCACUCUGUAGGACAC | 2115 |
| AGCACUCCACUCUGUAGGAC | 2116 |
| UAUGACAGCACUCCACUCUG | 2117 |
| AUAUGACAGCACUCCACUCU | 2118 |
| UUGCUGUGCUUGGGCCUCUC | 2119 |
| ACGUCAAAGGUGAAUCGGGC | 2120 |
| CACGUCAAAGGUGAAUCGGG | 2121 |
| ACACGUCAAAGGUGAAUCGG | 2122 |
| UACACGUCAAAGGUGAAUCG | 2123 |
| GUACACGUCAAAGGUGAAUC | 2124 |
| GGCUGCCAAAGAGGUCUCGA | 2125 |
| UCAGGCUGCCAAAGAGGUCU | 2126 |
| CAUUCAGGCUGCCAAAGAGG | 2127 |
| GACAUUCAGGCUGCCAAAGA | 2128 |
| UGACAUUCAGGCUGCCAAAG | 2129 |
| CUUUGACAUUCAGGCUGCCA | 2130 |
| GCUUUGACAUUCAGGCUGCC | 2131 |
| CCGUAGAAUGUGGCUUUGAC | 2132 |
| GCCCGUAGAAUGUGGCUUUG | 2133 |
| UAGAGCCCGUAGAAUGUGGC | 2134 |

TABLE 3-continued

| Sequence | SEQ ID NO: |
|---|---|
| GUAGAGCCCGUAGAAUGUGG | 2135 |
| AGUAGAGCCCGUAGAAUGUG | 2136 |
| AGAGUAGAGCCCGUAGAAUG | 2137 |
| UAGAGUAGAGCCCGUAGAAU | 2138 |
| AUAGAGUAGAGCCCGUAGAA | 2139 |
| CAUAGAGUAGAGCCCGUAGA | 2140 |
| UCAUAGAGUAGAGCCCGUAG | 2141 |
| CUCAUAGAGUAGAGCCCGUA | 2142 |
| GAAAGUCACAACUCAUAGAG | 2143 |
| CCUUGAAAGUCACAACUCAU | 2144 |
| AAGUCCUUGAAAGUCACAAC | 2145 |
| CCAAGUCCUUGAAAGUCACA | 2146 |
| UUCUUUGGGCCAAGUCCUUG | 2147 |
| UUUCUUUGGGCCAAGUCCUU | 2148 |
| UUGAUUUCUGACCUGAGUAC | 2149 |
| GUUGAUUUCUGACCUGAGUA | 2150 |
| GGGACUAUCCAACUGUAGGG | 2151 |
| GCAAGAGGACGAAUUAUGGG | 2152 |
| UGCAAGAGGACGAAUUAUGG | 2153 |
| GUGCAAGAGGACGAAUUAUG | 2154 |
| GGUGCAAGAGGACGAAUUAU | 2155 |
| GGGUGCAAGAGGACGAAUUA | 2156 |
| UGGGUGCAAGAGGACGAAUU | 2157 |
| GUGGGUGCAAGAGGACGAAU | 2158 |
| GGUGGGUGCAAGAGGACGAA | 2159 |
| UAGGUGGGUGCAAGAGGACG | 2160 |
| GUAGGUGGGUGCAAGAGGAC | 2161 |
| GGUAGGUGGGUGCAAGAGGA | 2162 |
| CCACAAGCAAGAGCUAACUA | 2163 |
| ACUUCCACAAGCAAGAGCU | 2164 |
| GACUUCCACAAGCAAGAGC | 2165 |
| GGACUUUCCACAAGCAAGAG | 2166 |
| AGGACUUUCCACAAGCAAGA | 2167 |
| GAGGACUUUCCACAAGCAAG | 2168 |
| UGAGGACUUUCCACAAGCAA | 2169 |
| AUGAGGACUUUCCACAAGCA | 2170 |
| GAUGAGGACUUUCCACAAGC | 2171 |
| AGAUGAGGACUUUCCACAAG | 2172 |
| GAGAUGAGGACUUUCCACAA | 2173 |
| GGAGAUGAGGACUUUCCACA | 2174 |
| UGGGAGAUGAGGACUUUCCA | 2175 |
| GCUGGGAGAUGAGGACUUUC | 2176 |
| UCAAGCUGGGAGAUGAGGAC | 2177 |
| AAGCCAUCAAGCUGGGAGAU | 2178 |
| GAAGCCAUCAAGCUGGGAGA | 2179 |
| GGAGGAAGCCAUCAAGCUGG | 2180 |
| GGGAGGAAGCCAUCAAGCUG | 2181 |
| AACUUGGGAGGAAGCCAUCA | 2182 |
| AAACUUGGGAGGAAGCCAUC | 2183 |
| CAGCAGUGUGGAGGUCCAAC | 2184 |
| GCAGCAGUGUGGAGGUCCAA | 2185 |
| UGCAGCAGUGUGGAGGUCCA | 2186 |
| UUGCAGCAGUGUGGAGGUCC | 2187 |
| GGUGGAGGAAAUUCCCAGCA | 2188 |
| ACGAAGGGUGGAGGAAAUUC | 2189 |
| GACGAAGGGUGGAGGAAAUU | 2190 |
| AUGACGAAGGGUGGAGGAAA | 2191 |
| CAUGACGAAGGGUGGAGGAA | 2192 |
| GCAUGACGAAGGGUGGAGGA | 2193 |
| UGCAUGACGAAGGGUGGAGG | 2194 |
| CUGCAUGACGAAGGGUGGAG | 2195 |
| ACUGCAUGACGAAGGGUGGA | 2196 |
| CACUGCAUGACGAAGGGUGG | 2197 |
| CCACUGCAUGACGAAGGGUG | 2198 |
| UCCACUGCAUGACGAAGGGU | 2199 |
| CUCCACUGCAUGACGAAGGG | 2200 |
| CCUCCACUGCAUGACGAAGG | 2201 |
| CCCUCCACUGCAUGACGAAG | 2202 |
| CUUAGUAGGAAUGGAGGCGG | 2203 |
| CCUUAGUAGGAAUGGAGGCG | 2204 |
| CCCUUAGUAGGAAUGGAGGC | 2205 |
| UCGGUUGGAAUGAUUCUGGG | 2206 |
| GUCGGUUGGAAUGAUUCUGG | 2207 |
| GGUCGGUUGGAAUGAUUCUG | 2208 |
| GGGUCGGUUGGAAUGAUUCU | 2209 |
| UGGGUCGGUUGGAAUGAUUC | 2210 |

TABLE 3-continued

| Sequence | SEQ ID NO: |
|---|---|
| GUGGGUCGGUUGGAAUGAUU | 2211 |
| AGUGGGUCGGUUGGAAUGAU | 2212 |
| CAGUGGGUCGGUUGGAAUGA | 2213 |
| GCAGUGGGUCGGUUGGAAUG | 2214 |
| UGCAGUGGGUCGGUUGGAAU | 2215 |
| UUGCAGUGGGUCGGUUGGAA | 2216 |
| UUUGCAGUGGGUCGGUUGGA | 2217 |
| CUUUGCAGUGGGUCGGUUGG | 2218 |
| UCUUUGCAGUGGGUCGGUUG | 2219 |
| UAGUCUUUGCAGUGGGUCGG | 2220 |
| AUAGUCUUUGCAGUGGGUCG | 2221 |
| CUGUCAUAGUCUUUGCAGUG | 2222 |
| UGCUGUCAUAGUCUUUGCAG | 2223 |
| UCUAGCCUGUACUGUCUGCA | 2224 |
| AUCUAGCCUGUACUGUCUGC | 2225 |
| UAUCUAGCCUGUACUGUCUG | 2226 |
| UUAUCUAGCCUGUACUGUCU | 2227 |
| GUUAUCUAGCCUGUACUGUC | 2228 |
| GGUUAUCUAGCCUGUACUGU | 2229 |
| GGGUUAUCUAGCCUGUACUG | 2230 |
| UGGGUUAUCUAGCCUGUACU | 2231 |
| GUGGGUUAUCUAGCCUGUAC | 2232 |
| GGUGGGUUAUCUAGCCUGUA | 2233 |
| GGGUGGGUUAUCUAGCCUGU | 2234 |
| UGGGUGGGUUAUCUAGCCUG | 2235 |
| UUGGGUGGGUUAUCUAGCCU | 2236 |
| AUUGGGUGGGUUAUCUAGCC | 2237 |
| AAUUGGGUGGGUUAUCUAGC | 2238 |
| AAAUUGGGUGGGUUAUCUAG | 2239 |
| GGAAAUUGGGUGGGUUAUCU | 2240 |
| GGGAAAUUGGGUGGGUUAUC | 2241 |
| GAAAGGUUCUGUCACGAGGG | 2242 |
| GCUGAAAGGUUCUGUCACGA | 2243 |
| UGCUGAAAGGUUCUGUCACG | 2244 |
| GGCGUUAUGCUGAAAGGUUC | 2245 |
| AGGCGUUAUGCUGAAAGGUU | 2246 |
| GAGGCGUUAUGCUGAAAGGU | 2247 |
| UGAGGCGUUAUGCUGAAAGG | 2248 |

TABLE 3-continued

| Sequence | SEQ ID NO: |
|---|---|
| GUGAGGCGUUAUGCUGAAAG | 2249 |
| AUGUGAGGCGUUAUGCUGAA | 2250 |
| GAUGUGAGGCGUUAUGCUGA | 2251 |
| GGAUGUGAGGCGUUAUGCUG | 2252 |
| GGGAUGUGAGGCGUUAUGCU | 2253 |
| CUUGGGAUGUGAGGCGUUAU | 2254 |
| AGACUUGGGAUGUGAGGCGU | 2255 |
| UAGACUUGGGAUGUGAGGCG | 2256 |
| AUAGACUUGGGAUGUGAGGC | 2257 |
| UAUAGACUUGGGAUGUGAGG | 2258 |
| GGGUAUAGACUUGGGAUGUG | 2259 |
| AGGGUAUAGACUUGGGAUGU | 2260 |
| AAGGUGGCUAGGAAAGAACA | 2261 |
| AAAGGUGGCUAGGAAAGAAC | 2262 |
| GAAAGGUGGCUAGGAAAGAA | 2263 |
| ACAUCUUGAUCUUGGCCUUU | 2264 |
| GGCUGGGAUCAAGAUGCCUG | 2265 |
| GUCAGGCUGGGAUCAAGAUG | 2266 |
| AGUCAGGCUGGGAUCAAGAU | 2267 |
| CAGUCAGGCUGGGAUCAAGA | 2268 |
| AGCAGUCAGGCUGGGAUCAA | 2269 |
| GAUGUAGCAGCAGUCAGGCU | 2270 |
| GGAUUAGAUGUAGCAGCAGU | 2271 |
| GGGAUUAGAUGUAGCAGCAG | 2272 |
| GACAGGAGGCAUUGGUAGGG | 2273 |
| UUAGGGACAGGAGGCAUUGG | 2274 |
| UUUAGGGACAGGAGGCAUUG | 2275 |
| GAGUUUAGGGACAGGAGGCA | 2276 |
| GGAGUUUAGGGACAGGAGGC | 2277 |
| GCUGUCAUCAGUAUGCUGGG | 2278 |
| GGCUGUCAUCAGUAUGCUGG | 2279 |
| GGGCUGUCAUCAGUAUGCUG | 2280 |
| AGGGCUGUCAUCAGUAUGCU | 2281 |
| AGAGAGGGCUGUCAUCAGUA | 2282 |
| CAGAGAGGGCUGUCAUCAGU | 2283 |
| UCAGAGAGGGCUGUCAUCAG | 2284 |
| GUCAGAGAGGGCUGUCAUCA | 2285 |

TABLE 3-continued

| Sequence | SEQ ID NO: |
|---|---|
| GGUAAAGUCAGAGAGGGCUG | 2286 |
| GGGAAGGGUAUGAAGACAGA | 2287 |

In some embodiments, the antisense nucleic acid molecules targeted to Transcript C comprise or consist of the nucleotide sequences shown in Table 4.

TABLE 4

| Sequence | SEQ ID NO: |
|---|---|
| GUUUCUGGCUCUCAGGCUCU | 2288 |
| GGUUUCUGGCUCUCAGGCUC | 2289 |
| CGGUUUCUGGCUCUCAGGCU | 2290 |
| GGACGGUUUCUGGCUCUCAG | 2291 |
| GGGACGGUUUCUGGCUCUCA | 2292 |
| UGAAAUGUGACUUCUGGUGU | 2293 |
| GGGAACCAUGUAAAAGGAUG | 2294 |
| GUGAGGGUAGAUGGGAACCA | 2295 |
| UUGUGAGGGUAGAUGGGAAC | 2296 |
| GUUGUGAGGGUAGAUGGGAA | 2297 |
| UGUUGUGAGGGUAGAUGGGA | 2298 |
| AUGUGUGUCUUUGGUGAUGA | 2299 |
| GGAGCUUGUAUGUGUGUCUU | 2300 |
| UUGGAGCUUGUAUGUGUGUC | 2301 |
| AUUGGAGCUUGUAUGUGUGU | 2302 |
| CAUUGGAGCUUGUAUGUGUG | 2303 |
| CCAUUGGAGCUUGUAUGUGU | 2304 |
| GCCAUUGGAGCUUGUAUGUG | 2305 |
| AGCCAUUGGAGCUUGUAUGU | 2306 |
| CUGGAGGAAGAAUUGCCUGG | 2307 |
| GUCCUGGAGGAAGAAUUGCC | 2308 |
| GCCAGUAAGAAGGGCAAAGU | 2309 |
| GGCCAGUAAGAAGGGCAAAG | 2310 |
| GGAAUGAGUCAAGCCUGGAC | 2311 |
| GGGAAUGAGUCAAGCCUGGA | 2312 |
| GUGGGAAUGAGUCAAGCCUG | 2313 |
| AAGGUGGGAAUGAGUCAAGC | 2314 |
| UCUCAGCCCAGGACAAGGUG | 2315 |
| AUCUCAGCCCAGGACAAGGU | 2316 |
| GCUGGGUGGUUCUCUCCUGU | 2317 |

TABLE 4-continued

| Sequence | SEQ ID NO: |
|---|---|
| UUCUGGGCUGGGUGGUUCUC | 2318 |
| GAACUUCUGGGCUGGGUGGU | 2319 |
| CGGAGAGUUCCUUCCCUGGA | 2320 |
| ACCGGAGAGUUCCUUCCCUG | 2321 |
| GACCGGAGAGUUCCUUCCCU | 2322 |
| UGGACCGGAGAGUUCCUUCC | 2323 |
| GUGGACCGGAGAGUUCCUUC | 2324 |
| GGUGGACCGGAGAGUUCCUU | 2325 |
| UGGUGGACCGGAGAGUUCCU | 2326 |
| AUGGUGGACCGGAGAGUUCC | 2327 |
| CAUGGUGGACCGGAGAGUUC | 2328 |
| GAGCUGAGAGGUACUCCAUG | 2329 |
| AGAGCUGAGAGGUACUCCAU | 2330 |
| CAGAGCUGAGAGGUACUCCA | 2331 |
| UUCAGAGCUGAGAGGUACUC | 2332 |
| GGUUCAGAGCUGAGAGGUAC | 2333 |
| GGGUUCAGAGCUGAGAGGUA | 2334 |
| CACCUGAGUAAGUCACUGGG | 2335 |
| UCACCUGAGUAAGUCACUGG | 2336 |
| GUCACCUGAGUAAGUCACUG | 2337 |
| AGUCACCUGAGUAAGUCACU | 2338 |
| CAGUCACCUGAGUAAGUCAC | 2339 |
| GCAGUCACCUGAGUAAGUCA | 2340 |
| UUAGCAGUCACCUGAGUAAG | 2341 |
| GUUAGCAGUCACCUGAGUAA | 2342 |
| GGUUAGCAGUCACCUGAGUA | 2343 |
| GGGUUAGCAGUCACCUGAGU | 2344 |
| AGGGUUAGCAGUCACCUGAG | 2345 |
| GAGGGUUAGCAGUCACCUGA | 2346 |
| GGAGGGUUAGCAGUCACCUG | 2347 |
| CGGAGGGUUAGCAGUCACCU | 2348 |
| AGCGGAGGGUUAGCAGUCAC | 2349 |
| GAGCGGAGGGUUAGCAGUCA | 2350 |
| AGAGCGGAGGGUUAGCAGUC | 2351 |
| UAGAGCGGAGGGUUAGCAGU | 2352 |
| GUAGAGCGGAGGGUUAGCAG | 2353 |
| GGUAGAGCGGAGGGUUAGCA | 2354 |
| AGGGUAGAGCGGAGGGUUAG | 2355 |

TABLE 4-continued

| Sequence | SEQ ID NO: |
|---|---|
| GAGGGUAGAGCGGAGGGUUA | 2356 |
| AUUGUUGCCCUGCCUAUAUC | 2357 |
| AGUAUUGUUGCCCUGCCUAU | 2358 |
| GAGUAUUGUUGCCCUGCCUA | 2359 |
| GGAGUAUUGUUGCCCUGCCU | 2360 |
| UGGAGUAUUGUUGCCCUGCC | 2361 |
| GUGGAGUAUUGUUGCCCUGC | 2362 |
| AGUGGAGUAUUGUUGCCCUG | 2363 |
| GAGUGGAGUAUUGUUGCCCU | 2364 |
| UGAGUGGAGUAUUGUUGCCC | 2365 |
| CUGAGUGGAGUAUUGUUGCC | 2366 |
| GCUGAGUGGAGUAUUGUUGC | 2367 |
| GGCUGAGUGGAGUAUUGUUG | 2368 |
| GGGCUGAGUGGAGUAUUGUU | 2369 |
| GGUACUGGUUAGUCUCCUAG | 2370 |
| GGGUACUGGUUAGUCUCCUA | 2371 |
| UUGACAAGCCCACUGUGGAG | 2372 |
| UGGCUCAGGAGCUUGACAAG | 2373 |
| GGUGGCUCAGGAGCUUGACA | 2374 |
| UAGGGAUGAGGGAGAGACCA | 2375 |
| UCGAUUAGGGAUGAGGGAGA | 2376 |
| UAGAGGGCUAGGGAGGGAGA | 2377 |
| GUAGAGUGGCUAGAGGGCUA | 2378 |
| GGUAGAGUGGCUAGAGGGCU | 2379 |
| UGAGGGUAGAGUGGCUAGAG | 2380 |
| GAUGAGGGUAGAGUGGCUAG | 2381 |
| CAUGAUGAGGGUAGAGUGGC | 2382 |
| GCAUGAUGAGGGUAGAGUGG | 2383 |
| GGGCAUGAUGAGGGUAGAGU | 2384 |
| GGUAGUUGAGAAGAAAAGUC | 2385 |
| CCAAACUCCGAGCUUAUAUU | 2386 |
| UCCAAACUCCGAGCUUAUAU | 2387 |
| GUCCAAACUCCGAGCUUAUA | 2388 |
| CGUCCAAACUCCGAGCUUAU | 2389 |
| CCGUCCAAACUCCGAGCUUA | 2390 |
| UCCGUCCAAACUCCGAGCUU | 2391 |
| CUCCGUCCAAACUCCGAGCU | 2392 |
| ACCCUCCGUCCAAACUCCGA | 2393 |
| AGACCCUCCGUCCAAACUCC | 2394 |
| CAGACCCUCCGUCCAAACUC | 2395 |
| UCCAGACCCUCCGUCCAAAC | 2396 |
| GUCCAGACCCUCCGUCCAAA | 2397 |
| AGACACGGAAAGGUCGCUGG | 2398 |
| CAGACACGGAAAGGUCGCUG | 2399 |
| ACAGACACGGAAAGGUCGCU | 2400 |
| CACAGACACGGAAAGGUCGC | 2401 |
| UCACAGACACGGAAAGGUCG | 2402 |
| AUCACAGACACGGAAAGGUC | 2403 |
| GAUCACAGACACGGAAAGGU | 2404 |
| UUGGCCUACUUACUUUGGCU | 2405 |
| CUUGGCCUACUUACUUUGGC | 2406 |
| ACUUGGCCUACUUACUUUGG | 2407 |
| GAGGAACUUGGCCUACUUAC | 2408 |
| CGAGGAACUUGGCCUACUUA | 2409 |
| CCGAGGAACUUGGCCUACUU | 2410 |
| ACCGAGGAACUUGGCCUACU | 2411 |
| AACCGAGGAACUUGGCCUAC | 2412 |
| GAACCGAGGAACUUGGCCUA | 2413 |
| GGAACCGAGGAACUUGGCCU | 2414 |
| AGGAACCGAGGAACUUGGCC | 2415 |
| UAGGAACCGAGGAACUUGGC | 2416 |
| AUAGGAACCGAGGAACUUGG | 2417 |
| UAUAGGAACCGAGGAACUUG | 2418 |
| AUCACAAGUUGCCACUGUUG | 2419 |
| CAUCACAAGUUGCCACUGUU | 2420 |
| AUCAUCACAAGUUGCCACUG | 2421 |
| CAUCAUCACAAGUUGCCACU | 2422 |
| CUGCUCCAUCAUCACAAGUU | 2423 |
| UCUGCUCCAUCAUCACAAGU | 2424 |
| CCCUCUGCUCCAUCAUCACA | 2425 |
| UCAGCCCUCUGCUCCAUCAU | 2426 |
| UGACUUCAGCCCUCUGCUCC | 2427 |
| GUGACUUCAGCCCUCUGCUC | 2428 |
| UGUGACUUCAGCCCUCUGCU | 2429 |
| GUGUGACUUCAGCCCUCUGC | 2430 |
| UGUGUGACUUCAGCCCUCUG | 2431 |

TABLE 4-continued

| Sequence | SEQ ID NO: |
|---|---|
| GCCCACUCCGCUGCUUUUAG | 2432 |
| GGCCCACUCCGCUGCUUUUA | 2433 |
| AGGCCCACUCCGCUGCUUUU | 2434 |
| UAGGCCCACUCCGCUGCUUU | 2435 |
| UUAGGCCCACUCCGCUGCUU | 2436 |
| AUUAGGCCCACUCCGCUGCU | 2437 |
| UCAUUAGGCCCACUCCGCUG | 2438 |
| CUCAUUAGGCCCACUCCGCU | 2439 |
| AGCUCAUUAGGCCCACUCCG | 2440 |
| CUCCCAUAGAAAAGCUCACU | 2441 |
| GCUCCCAUAGAAAAGCUCAC | 2442 |
| UGCUCCCAUAGAAAAGCUCA | 2443 |
| CUGCUCCCAUAGAAAAGCUC | 2444 |
| CCUGCUCCCAUAGAAAAGCU | 2445 |
| UCCCUAUCUCCUGCUAACCC | 2446 |
| CCUCGAACUCUCCCUAUCUC | 2447 |
| CCCUCGAACUCUCCCUAUCU | 2448 |
| UCCCUCGAACUCUCCCUAUC | 2449 |
| GUCCCUCGAACUCUCCCUAU | 2450 |
| CUUUCCAUACUAGCUUCUGA | 2451 |
| CCUUUCCAUACUAGCUUCUG | 2452 |
| ACCUUUCCAUACUAGCUUCU | 2453 |
| CACACAAAUCACCUUUCCAU | 2454 |
| GUCACACAAAUCACCUUUCC | 2455 |
| UGUCACACAAAUCACCUUUC | 2456 |
| UUUGACAGGCAGGAAGUGGC | 2457 |
| GGUUUGACAGGCAGGAAGUG | 2458 |
| AGGUUUGACAGGCAGGAAGU | 2459 |
| AAGGUUUGACAGGCAGGAAG | 2460 |
| AACUUCCCAAGGUUUGACAG | 2461 |
| CAACUUCCCAAGGUUUGACA | 2462 |
| GAACAACUUCCCAAGGUUUG | 2463 |
| UGAACAACUUCCCAAGGUUU | 2464 |
| GUAGGUUGAACAACUUCCCA | 2465 |
| GGUAGGUUGAACAACUUCCC | 2466 |
| UGGUAGGUUGAACAACUUCC | 2467 |
| GGUUUUGGUAGGUUGAACAA | 2468 |
| UGAGGUUUUGGUAGGUUGAA | 2469 |
| CUGAGGUUUUGGUAGGUUGA | 2470 |
| CCUACAUUAUCCUCUUACUC | 2471 |
| GGACUUUACCUACAUUAUCC | 2472 |
| GUAUGAGGACUUUACCUACA | 2473 |
| GCCAGGUAUGAGGACUUUAC | 2474 |
| UGCCAGGUAUGAGGACUUUA | 2475 |
| GUGCCAGGUAUGAGGACUUU | 2476 |
| CUGUGCCAGGUAUGAGGACU | 2477 |
| UCUGUGCCAGGUAUGAGGAC | 2478 |
| CCUCAAGAGUUCUCCAGAAG | 2479 |
| CCCUCAAGAGUUCUCCAGAA | 2480 |
| ACCCUCAAGAGUUCUCCAGA | 2481 |
| ACACCCUCAAGAGUUCUCCA | 2482 |
| CACACCCUCAAGAGUUCUCC | 2483 |
| CCACACCCUCAAGAGUUCUC | 2484 |
| CCCACACCCUCAAGAGUUCU | 2485 |
| UUCCCACACCCUCAAGAGUU | 2486 |
| CAAUGCUGCACCCACUUCC | 2487 |
| UACAAUGCUGCACCUCACUU | 2488 |
| CUACAAUGCUGCACCUCACU | 2489 |
| UCUACAAUGCUGCACCUCAC | 2490 |
| AUCUACAAUGCUGCACCUCA | 2491 |
| UAUCUACAAUGCUGCACCUC | 2492 |
| CUUAUCUACAAUGCUGCACC | 2493 |
| GUCUUAUCUACAAUGCUGCA | 2494 |
| UGUCUUAUCUACAAUGCUGC | 2495 |
| CUGUCUUAUCUACAAUGCUG | 2496 |
| CACCCUUCUGUCUUAUCUAC | 2497 |
| UCCACCCUUCUGUCUUAUCU | 2498 |
| GUCCACCCUUCUGUCUUAUC | 2499 |
| AGUCCACCCUUCUGUCUUAU | 2500 |
| AAGUCCACCCUUCUGUCUUA | 2501 |
| GAAAGCAAGCCAGGUUCUCA | 2502 |
| GGAAAGCAAGCCAGGUUCUC | 2503 |
| GGAAUUGGAAAGCAAGCCAG | 2504 |
| ACCAUGUCAUUGGCAUCUCC | 2505 |
| UACCAUGUCAUUGGCAUCUC | 2506 |
| CCUACCAUGUCAUUGGCAUC | 2507 |

TABLE 4-continued

| Sequence | SEQ ID NO: |
|---|---|
| UCCUACCAUGUCAUUGGCAU | 2508 |
| CUCCUACCAUGUCAUUGGCA | 2509 |
| GCUCCUACCAUGUCAUUGGC | 2510 |
| UGCUCCUACCAUGUCAUUGG | 2511 |
| UCUUUGCUCCUACCAUGUCA | 2512 |
| CCUCUUUGCUCCUACCAUGU | 2513 |
| UUCCUCUUUGCUCCUACCAU | 2514 |
| UCUCCGUGUUCUUCAGUUUU | 2515 |
| CUCUCCGUGUUCUUCAGUUU | 2516 |
| AGCUCUCCGUGUUCUUCAGU | 2517 |
| UGCAGCUCUCCGUGUUCUUC | 2518 |
| GGUUGCAGCUCUCCGUGUUC | 2519 |
| AGGUUGCAGCUCUCCGUGUU | 2520 |
| AAAGGUUGCAGCUCUCCGUG | 2521 |
| UAAAGGUUGCAGCUCUCCGU | 2522 |
| CUAAAGGUUGCAGCUCUCCG | 2523 |
| CCUAAAGGUUGCAGCUCUCC | 2524 |
| UCCUAAAGGUUGCAGCUCUC | 2525 |
| CUCCUAAAGGUUGCAGCUCU | 2526 |
| CCUCCUAAAGGUUGCAGCUC | 2527 |
| GCACUUUGAUACCUCCUAAA | 2528 |
| GGCACUUUGAUACCUCCUAA | 2529 |
| GAUGUCCCACUUUGACUUUC | 2530 |
| UCGAUGUCCCACUUUGACUU | 2531 |
| GUCGAUGUCCCACUUUGACU | 2532 |
| GGUCGAUGUCCCACUUUGAC | 2533 |
| UGGUCGAUGUCCCACUUUGA | 2534 |
| UUGGUCGAUGUCCCACUUUG | 2535 |
| AUUGGUCGAUGUCCCACUUU | 2536 |
| CAUUGGUCGAUGUCCCACUU | 2537 |
| AACAUCCAUCAGUUGGCUCU | 2538 |
| CUGCCCAACAUCCAUCAGUU | 2539 |
| AGCUGCCCAACAUCCAUCAG | 2540 |
| UAGCUGCCCAACAUCCAUCA | 2541 |
| UUAGCUGCCCAACAUCCAUC | 2542 |
| UUUAGCUGCCCAACAUCCAU | 2543 |
| CUUUAGCUGCCCAACAUCCA | 2544 |
| CCUCUUUAGCUGCCCAACAU | 2545 |
| CCCUCUUUAGCUGCCCAACA | 2546 |
| UCCCUCUUUAGCUGCCCAAC | 2547 |
| UUCCCUCUUUAGCUGCCCAA | 2548 |
| CCUUCCCUCUUUAGCUGCCC | 2549 |
| CCCUUCCCUCUUUAGCUGCC | 2550 |
| GCAGGUCUUAUCCCAUGCCC | 2551 |
| GGGCAGGUCUUAUCCCAUGC | 2552 |
| AGGGCAGGUCUUAUCCCAUG | 2553 |
| AAGGGCAGGUCUUAUCCCAU | 2554 |
| GAAGGGCAGGUCUUAUCCCA | 2555 |
| AGAAGGGCAGGUCUUAUCCC | 2556 |
| CCAAUGGCAAGAAGCAAGAA | 2557 |
| CCCAAUGGCAAGAAGCAAGA | 2558 |
| GCCCAAUGGCAAGAAGCAAG | 2559 |
| UCCAAUGCCUGCCCAAUGGC | 2560 |
| CUCCAAUGCCUGCCCAAUGG | 2561 |
| UCUCCAAUGCCUGCCCAAUG | 2562 |
| GGUCUCCAAUGCCUGCCCAA | 2563 |
| UAGGGUCUCCAAUGCCUGCC | 2564 |
| GUAGGGUCUCCAAUGCCUGC | 2565 |
| AGUAGGGUCUCCAAUGCCUG | 2566 |
| CAGUAGGGUCUCCAAUGCCU | 2567 |
| GCAGUAGGGUCUCCAAUGCC | 2568 |
| AGCAGUAGGGUCUCCAAUGC | 2569 |
| CAGCAGUAGGGUCUCCAAUG | 2570 |
| UCAGCAGUAGGGUCUCCAAU | 2571 |
| AUUCAGCAGUAGGGUCUCCA | 2572 |
| CAUUCAGCAGUAGGGUCUCC | 2573 |
| CCAUUCAGCAGUAGGGUCUC | 2574 |
| UCCAUUCAGCAGUAGGGUCU | 2575 |
| ACUCCAUUCAGCAGUAGGGU | 2576 |
| CACUCCAUUCAGCAGUAGGG | 2577 |
| GCACUCCAUUCAGCAGUAGG | 2578 |
| AGCACUCCAUUCAGCAGUAG | 2579 |
| UAGCACUCCAUUCAGCAGUA | 2580 |
| GGUUAGCACUCCAUUCAGCA | 2581 |
| GGUUAGCACUCCAUUCAGCA | 2582 |
| GGGUUAGCACUCCAUUCAGC | 2583 |

TABLE 4-continued

| Sequence | SEQ ID NO: |
|---|---|
| CAGGGUUAGCACUCCAUUCA | 2584 |
| CCAGGGUUAGCACUCCAUUC | 2585 |
| ACCAGGGUUAGCACUCCAUU | 2586 |
| CACCAGGGUUAGCACUCCAU | 2587 |
| GCACCAGGGUUAGCACUCCA | 2588 |
| AGCACCAGGGUUAGCACUCC | 2589 |
| UAGCACCAGGGUUAGCACUC | 2590 |
| CUAGCACCAGGGUUAGCACU | 2591 |
| UCUAGCACCAGGGUUAGCAC | 2592 |
| CUCUAGCACCAGGGUUAGCA | 2593 |
| CCUCUAGCACCAGGGUUAGC | 2594 |
| UCCUCUAGCACCAGGGUUAG | 2595 |
| CUCCUCUAGCACCAGGGUUA | 2596 |
| CCUCCUCUAGCACCAGGGUU | 2597 |
| UCCUCCUCUAGCACCAGGGU | 2598 |
| GUUCCAUCCUCCUCUAGCAC | 2599 |
| AAGUCCUCACUGUCCACUGC | 2600 |
| GAAGUCCUCACUGUCCACUG | 2601 |
| AGAAGUCCUCACUGUCCACU | 2602 |
| AAGAAGUCCUCACUGUCCAC | 2603 |
| GAAGAAGUCCUCACUGUCCA | 2604 |
| GGAAGAAGUCCUCACUGUCC | 2605 |
| UGGAAGAAGUCCUCACUGUC | 2606 |
| CUGGAAGAAGUCCUCACUGU | 2607 |
| AGCUGGAAGAAGUCCUCACU | 2608 |
| ACUGCAACACCAUCAGGCAC | 2609 |
| GACUGCAACACCAUCAGGCA | 2610 |
| AGACUGCAACACCAUCAGGC | 2611 |
| CAGACUGCAACACCAUCAGG | 2612 |
| CCAGACUGCAACACCAUCAG | 2613 |
| GACCAGACUGCAACACCAUC | 2614 |
| CUCUGACCAGACUGCAACAC | 2615 |
| AGCUCUGACCAGACUGCAAC | 2616 |
| CCAGCUCUGACCAGACUGCA | 2617 |
| UGUAGGGCUCCAGCUCUGAC | 2618 |
| CUUGUAGGGCUCCAGCUCUG | 2619 |
| CCUUGUAGGGCUCCAGCUCU | 2620 |
| ACAGGCAUUGGAAGCAGCCC | 2621 |
| GACAGGCAUUGGAAGCAGCC | 2622 |
| AAGGACAGGCAUUGGAAGCA | 2623 |
| AAAGGACAGGCAUUGGAAGC | 2624 |
| UAAAGGACAGGCAUUGGAAG | 2625 |
| CUAAAGGACAGGCAUUGGAA | 2626 |
| GCUCUAAAGGACAGGCAUUG | 2627 |
| AGCUCUAAAGGACAGGCAUU | 2628 |
| AAGCUCUAAAGGACAGGCAU | 2629 |
| AAAGCUCUAAAGGACAGGCA | 2630 |
| GAAAGCUCUAAAGGACAGGC | 2631 |
| CGGGAAAGCUCUAAAGGACA | 2632 |
| CCGGGAAAGCUCUAAAGGAC | 2633 |
| AGGGUUAAGCUAGAGAGGAA | 2634 |
| UCAGGGUUAAGCUAGAGAGG | 2635 |
| GAUCAGGGUUAAGCUAGAGA | 2636 |
| GGAUCAGGGUUAAGCUAGAG | 2637 |
| AGGAUCAGGGUUAAGCUAGA | 2638 |
| CCCAGGAUCAGGGUUAAGCU | 2639 |
| CAACUCCUCCUGCACCUGGU | 2640 |
| ACAACUCCUCCUGCACCUGG | 2641 |
| GACAAUUCCACAACUCCUCC | 2642 |
| UGACAAUUCCACAACUCCUC | 2643 |
| UUGACAAUUCCACAACUCCU | 2644 |
| CUUGACAAUUCCACAACUCC | 2645 |
| UCCUUGACAAUUCCACAACU | 2646 |
| AUCCUUGACAAUUCCACAAC | 2647 |
| CAUCCUUGACAAUUCCACAA | 2648 |
| ACAUCCUUGACAAUUCCACA | 2649 |
| GACAUCCUUGACAAUUCCAC | 2650 |
| UGACAUCCUUGACAAUUCCA | 2651 |
| UGUGUGACAUCCUUGACAAU | 2652 |
| ACUGUGUGACAUCCUUGACA | 2653 |
| ACUUUCUGUCCACUGUGUGA | 2654 |
| CCUCGCUUGGACUUUCUGUC | 2655 |
| CCCUCGCUUGGACUUUCUGU | 2656 |
| UCCCUCGCUUGGACUUUCUG | 2657 |
| CUCCCUCGCUUGGACUUUCU | 2658 |
| CCUCCCUCGCUUGGACUUUC | 2659 |

TABLE 4-continued

| Sequence | SEQ ID NO: |
|---|---|
| CCCUCCCUCGCUUGGACUUU | 2660 |
| UCCAUCAGCACUGGGUCAGA | 2661 |
| ACCACUAAUCUCCAUCAGCA | 2662 |
| CACCACUAAUCUCCAUCAGC | 2663 |
| CCACCACUAAUCUCCAUCAG | 2664 |
| CCCACCACUAAUCUCCAUCA | 2665 |
| ACCAGACACCCACCACUAAU | 2666 |
| UACCAGACACCCACCACUAA | 2667 |
| CUCAUACCAGACACCCACCA | 2668 |
| CCUCAUACCAGACACCCACC | 2669 |
| UCCUCAUACCAGACACCCAC | 2670 |
| AUCCUCAUACCAGACACCCA | 2671 |
| GAUCCUCAUACCAGACACCC | 2672 |
| AGAUCCUCAUACCAGACACC | 2673 |
| UAGAUCCUCAUACCAGACAC | 2674 |
| GUAGAUCCUCAUACCAGACA | 2675 |
| AGUAGAUCCUCAUACCAGAC | 2676 |
| CAGUAGAUCCUCAUACCAGA | 2677 |
| UGCAGUAGAUCCUCAUACCA | 2678 |
| GUGCAGUAGAUCCUCAUACC | 2679 |
| AGUGCAGUAGAUCCUCAUAC | 2680 |
| ACUCUGUAGGACACCCUUGU | 2681 |
| CACUCUGUAGGACACCCUUG | 2682 |
| CCACUCUGUAGGACACCCUU | 2683 |
| UCCACUCUGUAGGACACCCU | 2684 |
| CUCCACUCUGUAGGACACCC | 2685 |
| ACUCCACUCUGUAGGACACC | 2686 |
| CACUCCACUCUGUAGGACAC | 2687 |
| AGCACUCCACUCUGUAGGAC | 2688 |
| UAUGACAGCACUCCACUCUG | 2689 |
| AUAUGACAGCACUCCACUCU | 2690 |
| UUGCUGUGCUUGGGCCUCUC | 2691 |
| ACGUCAAAGGUGAAUCGGGC | 2692 |
| CACGUCAAAGGUGAAUCGGG | 2693 |
| ACACGUCAAAGGUGAAUCGG | 2694 |
| UACACGUCAAAGGUGAAUCG | 2695 |
| GUACACGUCAAAGGUGAAUC | 2696 |
| GGCUGCCAAAGAGGUCUCGA | 2697 |
| UCAGGCUGCCAAAGAGGUCU | 2698 |
| CAUUCAGGCUGCCAAAGAGG | 2699 |
| GACAUUCAGGCUGCCAAAGA | 2700 |
| UGACAUUCAGGCUGCCAAAG | 2701 |
| CUUUGACAUUCAGGCUGCCA | 2702 |
| GCUUUGACAUUCAGGCUGCC | 2703 |
| CCGUAGAAUGUGGCUUUGAC | 2704 |
| GCCCGUAGAAUGUGGCUUUG | 2705 |
| UAGAGCCCGUAGAAUGUGGC | 2706 |
| GUAGAGCCCGUAGAAUGUGG | 2707 |
| AGUAGAGCCCGUAGAAUGUG | 2708 |
| AGAGUAGAGCCCGUAGAAUG | 2709 |
| UAGAGUAGAGCCCGUAGAAU | 2710 |
| AUAGAGUAGAGCCCGUAGAA | 2711 |
| CAUAGAGUAGAGCCCGUAGA | 2712 |
| UCAUAGAGUAGAGCCCGUAG | 2713 |
| CUCAUAGAGUAGAGCCCGUA | 2714 |
| GAAAGUCACAACUCAUAGAG | 2715 |
| CCUUGAAAGUCACAACUCAU | 2716 |
| AAGUCCUUGAAAGUCACAAC | 2717 |
| CCAAGUCCUUGAAAGUCACA | 2718 |
| UUCUUUGGGCCAAGUCCUUG | 2719 |
| UUUCUUUGGGCCAAGUCCUU | 2720 |
| UUGAUUUCUGACCUGAGUAC | 2721 |
| GUUGAUUUCUGACCUGAGUA | 2722 |
| GGGACUAUCCAACUGUAGGG | 2723 |
| GCAAGAGGACGAAUUAUGGG | 2724 |
| UGCAAGAGGACGAAUUAUGG | 2725 |
| GUGCAAGAGGACGAAUUAUG | 2726 |
| GGUGCAAGAGGACGAAUUAU | 2727 |
| GGGUGCAAGAGGACGAAUUA | 2728 |
| UGGGUGCAAGAGGACGAAUU | 2729 |
| GUGGGUGCAAGAGGACGAAU | 2730 |
| GGUGGGUGCAAGAGGACGAA | 2731 |
| UAGGUGGGUGCAAGAGGACG | 2732 |
| GUAGGUGGGUGCAAGAGGAC | 2733 |
| GGUAGGUGGGUGCAAGAGGA | 2734 |
| CCACAAGCAAGAGCUAACUA | 2735 |

TABLE 4-continued

| Sequence | SEQ ID NO: |
|---|---|
| ACUUUCCACAAGCAAGAGCU | 2736 |
| GACUUUCCACAAGCAAGAGC | 2737 |
| GGACUUUCCACAAGCAAGAG | 2738 |
| AGGACUUUCCACAAGCAAGA | 2739 |
| GAGGACUUUCCACAAGCAAG | 2740 |
| UGAGGACUUUCCACAAGCAA | 2741 |
| AUGAGGACUUUCCACAAGCA | 2742 |
| GAUGAGGACUUUCCACAAGC | 2743 |
| AGAUGAGGACUUUCCACAAG | 2744 |
| GAGAUGAGGACUUUCCACAA | 2745 |
| GGAGAUGAGGACUUUCCACA | 2746 |
| UGGGAGAUGAGGACUUUCCA | 2747 |
| GCUGGGAGAUGAGGACUUUC | 2748 |
| UCAAGCUGGGAGAUGAGGAC | 2749 |
| AAGCCAUCAAGCUGGGAGAU | 2750 |
| GAAGCCAUCAAGCUGGGAGA | 2751 |
| GGAGGAAGCCAUCAAGCUGG | 2752 |
| GGGAGGAAGCCAUCAAGCUG | 2753 |
| AACUUGGGAGGAAGCCAUCA | 2754 |
| AAACUUGGGAGGAAGCCAUC | 2755 |
| CAGCAGUGUGGAGGUCCAAC | 2756 |
| GCAGCAGUGUGGAGGUCCAA | 2757 |
| UGCAGCAGUGUGGAGGUCCA | 2758 |
| UUGCAGCAGUGUGGAGGUCC | 2759 |
| GGUGGAGGAAAUUCCCAGCA | 2760 |
| ACGAAGGGUGGAGGAAAUUC | 2761 |
| GACGAAGGGUGGAGGAAAUU | 2762 |
| AUGACGAAGGGUGGAGGAAA | 2763 |
| CAUGACGAAGGGUGGAGGAA | 2764 |
| GCAUGACGAAGGGUGGAGGA | 2765 |
| UGCAUGACGAAGGGUGGAGG | 2766 |
| CUGCAUGACGAAGGGUGGAG | 2767 |
| ACUGCAUGACGAAGGGUGGA | 2768 |
| CACUGCAUGACGAAGGGUGG | 2769 |
| CCACUGCAUGACGAAGGGUG | 2770 |
| UCCACUGCAUGACGAAGGGU | 2771 |
| CUCCACUGCAUGACGAAGGG | 2772 |
| CCUCCACUGCAUGACGAAGG | 2773 |

TABLE 4-continued

| Sequence | SEQ ID NO: |
|---|---|
| CCCUCCACUGCAUGACGAAG | 2774 |
| CUUAGUAGGAAUGGAGGCGG | 2775 |
| CCUUAGUAGGAAUGGAGGCG | 2776 |
| CCCUUAGUAGGAAUGGAGGC | 2777 |
| UCGGUUGGAAUGAUUCUGGG | 2778 |
| GUCGGUUGGAAUGAUUCUGG | 2779 |
| GGUCGGUUGGAAUGAUUCUG | 2780 |
| GGGUCGGUUGGAAUGAUUCU | 2781 |
| UGGGUCGGUUGGAAUGAUUC | 2782 |
| GUGGGUCGGUUGGAAUGAUU | 2783 |
| AGUGGGUCGGUUGGAAUGAU | 2784 |
| CAGUGGGUCGGUUGGAAUGA | 2785 |
| GCAGUGGGUCGGUUGGAAUG | 2786 |
| UGCAGUGGGUCGGUUGGAAU | 2787 |
| UUGCAGUGGGUCGGUUGGAA | 2788 |
| UUUGCAGUGGGUCGGUUGGA | 2789 |
| CUUUGCAGUGGGUCGGUUGG | 2790 |
| UCUUUGCAGUGGGUCGGUUG | 2791 |
| UAGUCUUUGCAGUGGGUCGG | 2792 |
| AUAGUCUUUGCAGUGGGUCG | 2793 |
| CUGUCAUAGUCUUUGCAGUG | 2794 |
| UGCUGUCAUAGUCUUUGCAG | 2795 |
| UCUAGCCUGUACUGUCUGCA | 2796 |
| AUCUAGCCUGUACUGUCUGC | 2797 |
| UAUCUAGCCUGUACUGUCUG | 2798 |
| UUAUCUAGCCUGUACUGUCU | 2799 |
| GUUAUCUAGCCUGUACUGUC | 2800 |
| GGUUAUCUAGCCUGUACUGU | 2801 |
| GGGUUAUCUAGCCUGUACUG | 2802 |
| UGGGUUAUCUAGCCUGUACU | 2803 |
| GUGGGUUAUCUAGCCUGUAC | 2804 |
| GGUGGGUUAUCUAGCCUGUA | 2805 |
| GGGUGGGUUAUCUAGCCUGU | 2806 |
| UGGGUGGGUUAUCUAGCCUG | 2807 |
| UUGGGUGGGUUAUCUAGCCU | 2808 |
| AUUGGGUGGGUUAUCUAGCC | 2809 |
| AAUUGGGUGGGUUAUCUAGC | 2810 |
| AAAUUGGGUGGGUUAUCUAG | 2811 |

TABLE 4-continued

| Sequence | SEQ ID NO: |
|---|---|
| GGAAAUUGGGUGGGUUAUCU | 2812 |
| GGGAAAUUGGGUGGGUUAUC | 2813 |
| GAAAGGUUCUGUCACGAGGG | 2814 |
| GCUGAAAGGUUCUGUCACGA | 2815 |
| UGCUGAAAGGUUCUGUCACG | 2816 |
| GGCGUUAUGCUGAAAGGUUC | 2817 |
| AGGCGUUAUGCUGAAAGGUU | 2818 |
| GAGGCGUUAUGCUGAAAGGU | 2819 |
| UGAGGCGUUAUGCUGAAAGG | 2820 |
| GUGAGGCGUUAUGCUGAAAG | 2821 |
| AUGUGAGGCGUUAUGCUGAA | 2822 |
| GAUGUGAGGCGUUAUGCUGA | 2823 |
| GGAUGUGAGGCGUUAUGCUG | 2824 |
| GGGAUGUGAGGCGUUAUGCU | 2825 |
| CUUGGGAUGUGAGGCGUUAU | 2826 |
| AGACUUGGGAUGUGAGGCGU | 2827 |
| UAGACUUGGGAUGUGAGGCG | 2828 |
| AUAGACUUGGGAUGUGAGGC | 2829 |
| UAUAGACUUGGGAUGUGAGG | 2830 |
| GGGUAUAGACUUGGGAUGUG | 2831 |
| AGGGUAUAGACUUGGGAUGU | 2832 |
| AAGGUGGCUAGGAAAGAACA | 2833 |
| AAAGGUGGCUAGGAAAGAAC | 2834 |
| GAAAGGUGGCUAGGAAAGAA | 2835 |
| ACAUCUUGAUCUUGGCCUUU | 2836 |
| GGCUGGGAUCAAGAUGCCUG | 2837 |
| GUCAGGCUGGGAUCAAGAUG | 2838 |
| AGUCAGGCUGGGAUCAAGAU | 2839 |
| CAGUCAGGCUGGGAUCAAGA | 2840 |
| AGCAGUCAGGCUGGGAUCAA | 2841 |
| GAUGUAGCAGCAGUCAGGCU | 2842 |
| GGAUUAGAUGUAGCAGCAGU | 2843 |
| GGGAUUAGAUGUAGCAGCAG | 2844 |
| GACAGGAGGCAUUGGUAGGG | 2845 |
| UUAGGGACAGGAGGCAUUGG | 2846 |
| UUUAGGGACAGGAGGCAUUG | 2847 |
| GAGUUUAGGGACAGGAGGCA | 2848 |
| GGAGUUUAGGGACAGGAGGC | 2849 |

TABLE 4-continued

| Sequence | SEQ ID NO: |
|---|---|
| GCUGUCAUCAGUAUGCUGGG | 2850 |
| GGCUGUCAUCAGUAUGCUGG | 2851 |
| GGGCUGUCAUCAGUAUGCUG | 2852 |
| AGGGCUGUCAUCAGUAUGCU | 2853 |
| AGAGAGGGCUGUCAUCAGUA | 2854 |
| CAGAGAGGGCUGUCAUCAGU | 2855 |
| UCAGAGAGGGCUGUCAUCAG | 2856 |
| GUCAGAGAGGGCUGUCAUCA | 2857 |
| GGUAAAGUCAGAGAGGGCUG | 2858 |
| GGGAAGGGUAUGAAGACAGA | 2859 |
| GUCAGAAGUCUUAGUGGUAA | 2860 |
| AGUCAGAAGUCUUAGUGGUA | 2861 |
| GAGUCAGAAGUCUUAGUGGU | 2862 |
| CUGGGACUGGGUGUUGAUGG | 2863 |
| AUCUGGGACUGGGUGUUGAU | 2864 |
| GAUCUGGGACUGGGUGUUGA | 2865 |
| UGGAUCUGGGACUGGGUGUU | 2866 |
| UUUGGAUCUGGGACUGGGUG | 2867 |
| GCUUUGGAUCUGGGACUGGG | 2868 |

In some embodiments, the antisense nucleic acid molecules targeted to Transcript D comprise or consist of the nucleotide sequences shown in Table 5.

TABLE 5

| Sequence | SEQ ID NO: |
|---|---|
| ACACUGCUGAGCUGGAAGAC | 2869 |
| CGAGACACUGCUGAGCUGGA | 2870 |
| ACGAGACACUGCUGAGCUGG | 2871 |
| AACGAGACACUGCUGAGCUG | 2872 |
| GAACGAGACACUGCUGAGCU | 2873 |
| GGAACGAGACACUGCUGAGC | 2874 |
| GGGAACGAGACACUGCUGAG | 2875 |
| AGGGAACGAGACACUGCUGA | 2876 |
| CAGGGAACGAGACACUGCUG | 2877 |
| CCAGGGAACGAGACACUGCU | 2878 |
| AAGGAUGUCGGUCUGCUACC | 2879 |
| GAAGGAUGUCGGUCUGCUAC | 2880 |
| AGAAGGAUGUCGGUCUGCUA | 2881 |

TABLE 5-continued

| Sequence | SEQ ID NO: |
|---|---|
| UAGGCCCAGAAGGAUGUCGG | 2882 |
| GUAGGCCCAGAAGGAUGUCG | 2883 |
| UGUAGGCCCAGAAGGAUGUC | 2884 |
| CUGUAGGCCCAGAAGGAUGU | 2885 |
| CCUGUAGGCCCAGAAGGAUG | 2886 |
| ACCUGUAGGCCCAGAAGGAU | 2887 |
| CUUCUCAUCGGGCAUCACAG | 2888 |
| CCUUCUCAUCGGGCAUCACA | 2889 |
| ACCUUCUCAUCGGGCAUCAC | 2890 |
| CACCUUCUCAUCGGGCAUCA | 2891 |
| GCACCUUCUCAUCGGGCAUC | 2892 |
| GGCACCUUCUCAUCGGGCAU | 2893 |
| UGGCACCUUCUCAUCGGGCA | 2894 |
| AUGGCACCUUCUCAUCGGGC | 2895 |
| CAUGGCACCUUCUCAUCGGG | 2896 |
| GCAUGGCACCUUCUCAUCGG | 2897 |
| GGCAUGGCACCUUCUCAUCG | 2898 |
| GAGGCAUGGCACCUUCUCAU | 2899 |
| GGAGGCAUGGCACCUUCUCA | 2900 |
| GACUCCCAGGCAGAAAAGAG | 2901 |
| GGACUCCCAGGCAGAAAAGA | 2902 |
| AGGACUCCCAGGCAGAAAAG | 2903 |
| UCAGGACUCCCAGGCAGAAA | 2904 |
| GAAGUCAGGACUCCCAGGCA | 2905 |
| GUGGAAGUCAGGACUCCCAG | 2906 |
| UCGUGGAAGUCAGGACUCCC | 2907 |
| CUCGUGGAAGUCAGGACUCC | 2908 |
| CCUCGUGGAAGUCAGGACUC | 2909 |
| UGGGUCCUCGUGGAAGUCAG | 2910 |
| CUGGGUCCUCGUGGAAGUCA | 2911 |
| UCUGGGUCCUCGUGGAAGUC | 2912 |
| GUCUGGGUCCUCGUGGAAGU | 2913 |
| AAGAAGGAGUUGUGUUUGAG | 2914 |
| CCAAGAAGGAGUUGUGUUUG | 2915 |
| GUUCCAAGAAGGAGUUGUGU | 2916 |
| GGUUCCAAGAAGGAGUUGUG | 2917 |
| CAGGUCAACUGACUGGGAGC | 2918 |
| UGCCUGUUUACCACUGAGCU | 2919 |

TABLE 5-continued

| Sequence | SEQ ID NO: |
|---|---|
| AUGCCUGUUUACCACUGAGC | 2920 |
| UAUGCCUGUUUACCACUGAG | 2921 |
| UUAUGCCUGUUUACCACUGA | 2922 |
| UUUAUGCCUGUUUACCACUG | 2923 |
| CUUUAUGCCUGUUUACCACU | 2924 |
| ACUUUAUGCCUGUUUACCAC | 2925 |
| UAGAGAUAGUGACAGCCUGG | 2926 |
| GUAGAGAUAGUGACAGCCUG | 2927 |
| UGGUGGUAGAGAUAGUGACA | 2928 |
| GUGGUGGUAGAGAUAGUGAC | 2929 |
| UAGAGGAGUGGUGGUAGAGA | 2930 |
| ACUAGAGGAGUGGUGGUAGA | 2931 |
| AGACUAGAGGAGUGGUGGUA | 2932 |
| CAGACUAGAGGAGUGGUGGU | 2933 |
| CCAGACUAGAGGAGUGGUGG | 2934 |
| GCCAGACUAGAGGAGUGGUG | 2935 |
| GGCCAGACUAGAGGAGUGGU | 2936 |
| GCCCAGAUGUGCUAGAAUGG | 2937 |
| UGCCCAGAUGUGCUAGAAUG | 2938 |
| UUGCCCAGAUGUGCUAGAAU | 2939 |
| UUUGCCCAGAUGUGCUAGAA | 2940 |
| UUUUGCCCAGAUGUGCUAGA | 2941 |
| CCAGUUUUGCCCAGAUGUGC | 2942 |
| AUCCAGUUUUGCCCAGAUGU | 2943 |
| CCAUCCAGUUUUGCCCAGAU | 2944 |
| CACCAUCCAGUUUUGCCCAG | 2945 |
| CCACCAUCCAGUUUUGCCCA | 2946 |
| CCCACCAUCCAGUUUUGCCC | 2947 |
| UUGCUCCCAGCUUGGUAAGU | 2948 |
| GCUUGCUCCCAGCUUGGUAA | 2949 |
| AUCCUGCUUGCUCCCAGCUU | 2950 |
| AAUCCUGCUUGCUCCCAGCU | 2951 |
| CAAUCCUGCUUGCUCCCAGC | 2952 |
| CCAAUCCUGCUUGCUCCCAG | 2953 |
| AACCUUUCAGCUUCUCCAGG | 2954 |
| UAACCUUUCAGCUUCUCCAG | 2955 |
| UUAACCUUUCAGCUUCUCCA | 2956 |
| ACUGCUGCUUAACCUUUCAG | 2957 |

TABLE 5-continued

| Sequence | SEQ ID NO: |
|---|---|
| UACUGCUGCUUAACCUUUCA | 2958 |
| CUACUGCUGCUUAACCUUUC | 2959 |
| CCUACUGCUGCUUAACCUUU | 2960 |
| GCCUACUGCUGCUUAACCUU | 2961 |
| CAGGACAGGAGUAGGCACCU | 2962 |
| ACAGGACAGGAGUAGGCACC | 2963 |
| GCACAGGACAGGAGUAGGCA | 2964 |
| AUAGGCACAGGACAGGAGUA | 2965 |
| GAUAGGCACAGGACAGGAGU | 2966 |
| UGAUAGGCACAGGACAGGAG | 2967 |
| ACCCUCUGCAAAUGUGAUAG | 2968 |
| CUUACCCUCUGCAAAUGUGA | 2969 |
| GUCUUACCCUCUGCAAAUGU | 2970 |
| UGUCUUACCCUCUGCAAAUG | 2971 |
| UUGUCUUACCCUCUGCAAAU | 2972 |
| CUUGUCUUACCCUCUGCAAA | 2973 |
| UCUUGUCUUACCCUCUGCAA | 2974 |
| CAUUCUUGUCUUACCCUCUG | 2975 |
| CCCAUUCUUGUCUUACCCUC | 2976 |
| GAGCCUCAUCUUGUCCCUCC | 2977 |
| UGAGCCUCAUCUUGUCCCUC | 2978 |

In some embodiments, the antisense nucleic acid molecules targeted to Transcript E comprise or consist of the nucleotide sequences shown in Table 6.

TABLE 6

| Sequence | SEQ ID NO: |
|---|---|
| ACCACGCAGUCAACCUUCUG | 2979 |
| UACCACGCAGUCAACCUUCU | 2980 |
| CUACCACGCAGUCAACCUUC | 2981 |
| CCUACCACGCAGUCAACCUU | 2982 |
| CCCUACCACGCAGUCAACCU | 2983 |
| UUGCCUUCGGCUUGCUCUGG | 2984 |
| CUUGCCUUCGGCUUGCUCUG | 2985 |
| GCUUGCCUUCGGCUUGCUCU | 2986 |
| UGCUUGCCUUCGGCUUGCUC | 2987 |
| GUGCUUGCCUUCGGCUUGCU | 2988 |
| UCGUGCUUGCCUUCGGCUUG | 2989 |
| AUCGUGCUUGCCUUCGGCUU | 2990 |

TABLE 6-continued

| Sequence | SEQ ID NO: |
|---|---|
| CAUCGUGCUUGCCUUCGGCU | 2991 |
| AGCGCCAUCGUGCUUGCCUU | 2992 |
| UGGUGAGCGCCAUCGUGCUU | 2993 |
| CUGAUGCUCGGCUGCUACAG | 2994 |
| GCUGAUGCUCGGCUGCUACA | 2995 |
| UUUCGGGCUGAUGCUCGGCU | 2996 |
| UCCUUUCGGGCUGAUGCUCG | 2997 |
| UUCCUUUCGGGCUGAUGCUC | 2998 |
| CUUCCUUUCGGGCUGAUGCU | 2999 |
| GCUUCCUUUCGGGCUGAUGC | 3000 |
| UGCUUCCUUUCGGGCUGAUG | 3001 |
| GUGCUUCCUUUCGGGCUGAU | 3002 |
| CGUGCUUCCUUUCGGGCUGA | 3003 |
| UCGUGCUUCCUUUCGGGCUG | 3004 |
| UUCGUGCUUCCUUUCGGGCU | 3005 |
| UUUCGUGCUUCCUUUCGGGC | 3006 |
| CUUUCGUGCUUCCUUUCGGG | 3007 |
| GCUUUCGUGCUUCCUUUCGG | 3008 |
| AUGUACGCCAGCGUGCUGCU | 3009 |
| UCAGCAUGUACGCCAGCGUG | 3010 |
| AGGCGGUGUACUACGUGUGC | 3011 |
| AAGGCGGUGUACUACGUGUG | 3012 |
| CAAGGCGGUGUACUACGUGU | 3013 |
| GCAAGGCGGUGUACUACGUG | 3014 |
| UGCAAGGCGGUGUACUACGU | 3015 |
| CUGCAAGGCGGUGUACUACG | 3016 |
| GCUGCAAGGCGGUGUACUAC | 3017 |
| GGCUGCAAGGCGGUGUACUA | 3018 |
| GCUCUUUGUGGCCUUCCUGA | 3019 |
| CGCUCUUUGUGGCCUUCCUG | 3020 |

In some embodiments, the antisense nucleic acid molecules targeted to Transcript F comprise or consist of the nucleotide sequences shown in Table 7.

TABLE 7

| Sequence | SEQ ID NO: |
|---|---|
| AGAAGUCCUCACUGUCCACU | 3021 |
| AAGAAGUCCUCACUGUCCAC | 3022 |
| GAAGAAGUCCUCACUGUCCA | 3023 |
| GGAAGAAGUCCUCACUGUCC | 3024 |

TABLE 7-continued

| Sequence | SEQ ID NO: |
|---|---|
| UGGAAGAAGUCCUCACUGUC | 3025 |
| CUGGAAGAAGUCCUCACUGU | 3026 |
| AGCUGGAAGAAGUCCUCACU | 3027 |
| ACUGCAACACCAUCAGGCAC | 3028 |
| GACUGCAACACCAUCAGGCA | 3029 |
| AGACUGCAACACCAUCAGGC | 3030 |
| CAGACUGCAACACCAUCAGG | 3031 |
| CCAGACUGCAACACCAUCAG | 3032 |
| GACCAGACUGCAACACCAUC | 3033 |
| CUCUGACCAGACUGCAACAC | 3034 |
| AGCUCUGACCAGACUGCAAC | 3035 |
| CCAGCUCUGACCAGACUGCA | 3036 |
| UGUAGGGCUCCAGCUCUGAC | 3037 |
| CUUGUAGGGCUCCAGCUCUG | 3038 |
| CCUUGUAGGGCUCCAGCUCU | 3039 |
| ACAGGCAUUGGAAGCAGCCC | 3040 |
| GACAGGCAUUGGAAGCAGCC | 3041 |
| AAGGACAGGCAUUGGAAGCA | 3042 |
| AAAGGACAGGCAUUGGAAGC | 3043 |
| UAAAGGACAGGCAUUGGAAG | 3044 |
| CUAAAGGACAGGCAUUGGAA | 3045 |
| GCUCUAAAGGACAGGCAUUG | 3046 |
| AGCUCUAAAGGACAGGCAUU | 3047 |
| AAGCUCUAAAGGACAGGCAU | 3048 |
| AAAGCUCUAAAGGACAGGCA | 3049 |
| GAAAGCUCUAAAGGACAGGC | 3050 |
| CGGGAAAGCUCUAAAGGACA | 3051 |
| CCGGGAAAGCUCUAAAGGAC | 3052 |
| AGGGUUAAGCUAGAGAGGAA | 3053 |
| UCAGGGUUAAGCUAGAGAGG | 3054 |
| GAUCAGGGUUAAGCUAGAGA | 3055 |
| GGAUCAGGGUUAAGCUAGAG | 3056 |
| AGGAUCAGGGUUAAGCUAGA | 3057 |
| CCCAGGAUCAGGGUUAAGCU | 3058 |
| CAACUCCUCCUGCACCUGGU | 3059 |
| ACAACUCCUCCUGCACCUGG | 3060 |
| GACAAUUCCACAACUCCUCC | 3061 |
| UGACAAUUCCACAACUCCUC | 3062 |
| UUGACAAUUCCACAACUCCU | 3063 |

TABLE 7-continued

| Sequence | SEQ ID NO: |
|---|---|
| CUUGACAAUUCCACAACUCC | 3064 |
| UCCUUGACAAUUCCACAACU | 3065 |
| AUCCUUGACAAUUCCACAAC | 3066 |
| CAUCCUUGACAAUUCCACAA | 3067 |
| ACAUCCUUGACAAUUCCACA | 3068 |
| GACAUCCUUGACAAUUCCAC | 3069 |
| UGACAUCCUUGACAAUUCCA | 3070 |
| UGUGUGACAUCCUUGACAAU | 3071 |
| ACUGUGUGACAUCCUUGACA | 3072 |
| ACUUUCUGUCCACUGUGUGA | 3073 |
| CCUCGCUUGGACUUUCUGUC | 3074 |
| CCCUCGCUUGGACUUUCUGU | 3075 |
| UCCCUCGCUUGGACUUUCUG | 3076 |
| CUCCCUCGCUUGGACUUUCU | 3077 |
| CCUCCCUCGCUUGGACUUUC | 3078 |
| CCCUCCCUCGCUUGGACUUU | 3079 |
| UCCAUCAGCACUGGGUCAGA | 3080 |
| ACCACUAAUCUCCAUCAGCA | 3081 |
| CACCACUAAUCUCCAUCAGC | 3082 |
| CCACCACUAAUCUCCAUCAG | 3083 |
| CCCACCACUAAUCUCCAUCA | 3084 |
| ACCAGACACCCACCACUAAU | 3085 |
| UACCAGACACCCACCACUAA | 3086 |
| CUCAUACCAGACACCCACCA | 3087 |
| CCUCAUACCAGACACCCACC | 3088 |
| UCCUCAUACCAGACACCCAC | 3089 |
| AUCCUCAUACCAGACACCCA | 3090 |
| GAUCCUCAUACCAGACACCC | 3091 |
| AGAUCCUCAUACCAGACACC | 3092 |
| UAGAUCCUCAUACCAGACAC | 3093 |
| GUAGAUCCUCAUACCAGACA | 3094 |
| AGUAGAUCCUCAUACCAGAC | 3095 |
| CAGUAGAUCCUCAUACCAGA | 3096 |
| UGCAGUAGAUCCUCAUACCA | 3097 |
| GUGCAGUAGAUCCUCAUACC | 3098 |
| AGUGCAGUAGAUCCUCAUAC | 3099 |
| ACUCUGUAGGACACCCUUGU | 3100 |
| CACUCUGUAGGACACCCUUG | 3101 |
| CCACUCUGUAGGACACCCUU | 3102 |

TABLE 7-continued

| Sequence | SEQ ID NO: |
|---|---|
| UCCACUCUGUAGGACACCCU | 3103 |
| CUCCACUCUGUAGGACACCC | 3104 |
| ACUCCACUCUGUAGGACACC | 3105 |
| CACUCCACUCUGUAGGACAC | 3106 |
| AGCACUCCACUCUGUAGGAC | 3107 |
| UAUGACAGCACUCCACUCUG | 3108 |
| AUAUGACAGCACUCCACUCU | 3109 |
| UUGCUGUGCUUGGGCCUCUC | 3110 |
| ACGUCAAAGGUGAAUCGGGC | 3111 |
| CACGUCAAAGGUGAAUCGGG | 3112 |
| ACACGUCAAAGGUGAAUCGG | 3113 |
| UACACGUCAAAGGUGAAUCG | 3114 |
| GUACACGUCAAAGGUGAAUC | 3115 |
| GGCUGCCAAAGAGGUCUCGA | 3116 |
| UCAGGCUGCCAAAGAGGUCU | 3117 |
| CAUUCAGGCUGCCAAAGAGG | 3118 |
| GACAUUCAGGCUGCCAAAGA | 3119 |
| UGACAUUCAGGCUGCCAAAG | 3120 |
| CUUUGACAUUCAGGCUGCCA | 3121 |
| GCUUUGACAUUCAGGCUGCC | 3122 |
| CCGUAGAAUGUGGCUUUGAC | 3123 |
| GCCCGUAGAAUGUGGCUUUG | 3124 |
| UAGAGCCCGUAGAAUGUGGC | 3125 |
| GUAGAGCCCGUAGAAUGUGG | 3126 |
| AGUAGAGCCCGUAGAAUGUG | 3127 |
| AGAGUAGAGCCCGUAGAAUG | 3128 |
| UAGAGUAGAGCCCGUAGAAU | 3129 |
| AUAGAGUAGAGCCCGUAGAA | 3130 |
| CAUAGAGUAGAGCCCGUAGA | 3131 |
| UCAUAGAGUAGAGCCCGUAG | 3132 |
| CUCAUAGAGUAGAGCCCGUA | 3133 |
| GAAAGUCACAACUCAUAGAG | 3134 |
| CCUUGAAAGUCACAACUCAU | 3135 |
| AAGUCCUUGAAAGUCACAAC | 3136 |
| CCAAGUCCUUGAAAGUCACA | 3137 |
| UUCUUUGGGCCAAGUCCUUG | 3138 |
| UUUCUUUGGGCCAAGUCCUU | 3139 |
| UUGAUUUCUGACCUGAGUAC | 3140 |
| GUUGAUUUCUGACCUGAGUA | 3141 |

TABLE 7-continued

| Sequence | SEQ ID NO: |
|---|---|
| GGGACUAUCCAACUGUAGGG | 3142 |
| GCAAGAGGACGAAUUAUGGG | 3143 |
| UGCAAGAGGACGAAUUAUGG | 3144 |
| GUGCAAGAGGACGAAUUAUG | 3145 |
| GGUGCAAGAGGACGAAUUAU | 3146 |
| GGGUGCAAGAGGACGAAUUA | 3147 |
| UGGGUGCAAGAGGACGAAUU | 3148 |
| GUGGGUGCAAGAGGACGAAU | 3149 |
| GGUGGGUGCAAGAGGACGAA | 3150 |
| UAGGUGGGUGCAAGAGGACG | 3151 |
| GUAGGUGGGUGCAAGAGGAC | 3152 |
| GGUAGGUGGGUGCAAGAGGA | 3153 |
| CCACAAGCAAGAGCUAACUA | 3154 |
| ACUUUCCACAAGCAAGAGCU | 3155 |
| GACUUUCCACAAGCAAGAGC | 3156 |
| GGACUUUCCACAAGCAAGAG | 3157 |
| AGGACUUUCCACAAGCAAGA | 3158 |
| GAGGACUUUCCACAAGCAAG | 3159 |
| UGAGGACUUUCCACAAGCAA | 3160 |
| AUGAGGACUUUCCACAAGCA | 3161 |
| GAUGAGGACUUUCCACAAGC | 3162 |
| AGAUGAGGACUUUCCACAAG | 3163 |
| GAGAUGAGGACUUUCCACAA | 3164 |
| GGAGAUGAGGACUUUCCACA | 3165 |
| UGGGAGAUGAGGACUUUCCA | 3166 |
| GCUGGGAGAUGAGGACUUUC | 3167 |
| UCAAGCUGGGAGAUGAGGAC | 3168 |
| AAGCCAUCAAGCUGGGAGAU | 3169 |
| GAAGCCAUCAAGCUGGGAGA | 3170 |
| GGAGGAAGCCAUCAAGCUGG | 3171 |
| GGGAGGAAGCCAUCAAGCUG | 3172 |
| AACUUGGGAGGAAGCCAUCA | 3173 |
| AAACUUGGGAGGAAGCCAUC | 3174 |
| CAGCAGUGUGGAGGUCCAAC | 3175 |
| GCAGCAGUGUGGAGGUCCAA | 3176 |
| UGCAGCAGUGUGGAGGUCCA | 3177 |
| UUGCAGCAGUGUGGAGGUCC | 3178 |
| GGUGGAGGAAAUUCCCAGCA | 3179 |
| ACGAAGGGUGGAGGAAAUUC | 3180 |

TABLE 7-continued

| Sequence | SEQ ID NO: |
|---|---|
| GACGAAGGGUGGAGGAAAUU | 3181 |
| AUGACGAAGGGUGGAGGAAA | 3182 |
| CAUGACGAAGGGUGGAGGAA | 3183 |
| GCAUGACGAAGGGUGGAGGA | 3184 |
| UGCAUGACGAAGGGUGGAGG | 3185 |
| CUGCAUGACGAAGGGUGGAG | 3186 |
| ACUGCAUGACGAAGGGUGGA | 3187 |
| CACUGCAUGACGAAGGGUGG | 3188 |
| CCACUGCAUGACGAAGGGUG | 3189 |
| UCCACUGCAUGACGAAGGGU | 3190 |
| CUCCACUGCAUGACGAAGGG | 3191 |
| CCUCCACUGCAUGACGAAGG | 3192 |
| CCCUCCACUGCAUGACGAAG | 3193 |
| CUUAGUAGGAAUGGAGGCGG | 3194 |
| CCUUAGUAGGAAUGGAGGCG | 3195 |
| CCCUUAGUAGGAAUGGAGGC | 3196 |

In some embodiments, the siRNA molecules targeted to Transcript A comprise or consist of the nucleotide sequences (sense and antisense strands) shown in Table 8.

TABLE 8

| Sense Sequence | SEQ ID NO: | Antisense Sequence | SEQ ID NO: |
|---|---|---|---|
| GACCGCCUGCAGAAGGUUG | 3197 | CAACCUUCUGCAGGCGGUC | 3198 |
| ACCGCCUGCAGAAGGUUGA | 3199 | UCAACCUUCUGCAGGCGGU | 3200 |
| CCGCCUGCAGAAGGUUGAC | 3201 | GUCAACCUUCUGCAGGCGG | 3202 |
| CGCCUGCAGAAGGUUGACU | 3203 | AGUCAACCUUCUGCAGGCG | 3204 |
| GCCUGCAGAAGGUUGACUG | 3205 | CAGUCAACCUUCUGCAGGC | 3206 |
| CAGAAGGUUGACUGCGUGG | 3207 | CCACGCAGUCAACCUUCUG | 3208 |
| AGAAGGUUGACUGCGUGGU | 3209 | ACCACGCAGUCAACCUUCU | 3210 |
| GAAGGUUGACUGCGUGGUA | 3211 | UACCACGCAGUCAACCUUC | 3212 |
| AAGGUUGACUGCGUGGUAG | 3213 | CUACCACGCAGUCAACCUU | 3214 |
| AGGUUGACUGCGUGGUAGG | 3215 | CCUACCACGCAGUCAACCU | 3216 |
| GGUUGACUGCGUGGUAGGG | 3217 | CCCUACCACGCAGUCAACC | 3218 |
| CCAGAGCAAGCCGAAGGCA | 3219 | UGCCUUCGGCUUGCUCUGG | 3220 |
| CAGAGCAAGCCGAAGGCAA | 3221 | UUGCCUUCGGCUUGCUCUG | 3222 |
| AGAGCAAGCCGAAGGCAAG | 3223 | CUUGCCUUCGGCUUGCUCU | 3224 |
| GAGCAAGCCGAAGGCAAGC | 3225 | GCUUGCCUUCGGCUUGCUC | 3226 |
| AGCAAGCCGAAGGCAAGCA | 3227 | UGCUUGCCUUCGGCUUGCU | 3228 |
| GCAAGCCGAAGGCAAGCAC | 3229 | GUGCUUGCCUUCGGCUUGC | 3230 |
| CAAGCCGAAGGCAAGCACG | 3231 | CGUGCUUGCCUUCGGCUUG | 3232 |
| AAGCCGAAGGCAAGCACGA | 3233 | UCGUGCUUGCCUUCGGCUU | 3234 |
| AGCCGAAGGCAAGCACGAU | 3235 | AUCGUGCUUGCCUUCGGCU | 3236 |
| GCCGAAGGCAAGCACGAUG | 3237 | CAUCGUGCUUGCCUUCGGC | 3238 |
| AAGGCAAGCACGAUGGCGC | 3239 | GCGCCAUCGUGCUUGCCUU | 3240 |
| AGGCAAGCACGAUGGCGCU | 3241 | AGCGCCAUCGUGCUUGCCU | 3242 |
| AAGCACGAUGGCGCUCACC | 3243 | GGUGAGCGCCAUCGUGCUU | 3244 |
| AGCACGAUGGCGCUCACCA | 3245 | UGGUGAGCGCCAUCGUGCU | 3246 |
| CUGUAGCAGCCGAGCAUCA | 3247 | UGAUGCUCGGCUGCUACAG | 3248 |
| AGCCGAGCAUCAGCCCGAA | 3249 | UUCGGGCUGAUGCUCGGCU | 3250 |
| GUCAGAGUCUCCAGGCUCA | 3251 | UGAGCCUGGAGACUCUGAC | 3252 |
| UCAGAGUCUCCAGGCUCAG | 3253 | CUGAGCCUGGAGACUCUGA | 3254 |
| CAGAGUCUCCAGGCUCAGG | 3255 | CCUGAGCCUGGAGACUCUG | 3256 |
| AGAGUCUCCAGGCUCAGGU | 3257 | ACCUGAGCCUGGAGACUCU | 3258 |
| GAGUCUCCAGGCUCAGGUG | 3259 | CACCUGAGCCUGGAGACUC | 3260 |
| AGUCUCCAGGCUCAGGUGG | 3261 | CCACCUGAGCCUGGAGACU | 3262 |
| GGGUGGCACAGCUGGCAUA | 3263 | UAUGCCAGCUGUGCCACCC | 3264 |
| GUGGCACAGCUGGCAUACG | 3265 | CGUAUGCCAGCUGUGCCAC | 3266 |
| UGGCACAGCUGGCAUACGC | 3267 | GCGUAUGCCAGCUGUGCCA | 3268 |
| CUCCACAGGUGGCGGUAGA | 3269 | UCUACCGCCACCUGUGGAG | 3270 |
| UCCACAGGUGGCGGUAGAC | 3271 | GUCUACCGCCACCUGUGGA | 3272 |
| UGAGCAGCACGCUGGCGUA | 3273 | UACGCCAGCGUGCUGCUCA | 3274 |
| AGCAGCACGCUGGCGUACA | 3275 | UGUACGCCAGCGUGCUGCU | 3276 |
| GCAGCACGCUGGCGUACAU | 3277 | AUGUACGCCAGCGUGCUGC | 3278 |
| CAGCACGCUGGCGUACAUG | 3279 | CAUGUACGCCAGCGUGCUG | 3280 |
| AGCACGCUGGCGUACAUGC | 3281 | GCAUGUACGCCAGCGUGCU | 3282 |
| GCACGCUGGCGUACAUGCU | 3283 | AGCAUGUACGCCAGCGUGC | 3284 |
| CACGCUGGCGUACAUGCUG | 3285 | CAGCAUGUACGCCAGCGUG | 3286 |
| ACGCUGGCGUACAUGCUGA | 3287 | UCAGCAUGUACGCCAGCGU | 3288 |
| CUGGCGUACAUGCUGAGCG | 3289 | CGCUCAGCAUGUACGCCAG | 3290 |
| UGGCGUACAUGCUGAGCGC | 3291 | GCGCUCAGCAUGUACGCCA | 3292 |
| CGCGCACACGUAGUACACC | 3293 | GGUGUACUACGUGUGCGCG | 3294 |
| GCGCACACGUAGUACACCG | 3295 | CGGUGUACUACGUGUGCGC | 3296 |
| CGCACACGUAGUACACCGC | 3297 | GCGGUGUACUACGUGUGCG | 3298 |
| GCACACGUAGUACACCGCC | 3299 | GGCGGUGUACUACGUGUGC | 3300 |
| CACACGUAGUACACCGCCU | 3301 | AGGCGGUGUACUACGUGUG | 3302 |
| ACACGUAGUACACCGCCUU | 3303 | AAGGCGGUGUACUACGUGU | 3304 |
| CACGUAGUACACCGCCUUG | 3305 | CAAGGCGGUGUACUACGUG | 3306 |

TABLE 8-continued

| Sense Sequence | SEQ ID NO: | Antisense Sequence | SEQ ID NO: |
|---|---|---|---|
| UAGUACACCGCCUUGCAGC | 3307 | GCUGCAAGGCGGUGUACUA | 3308 |
| CCAAGCUCCACACCACGAA | 3309 | UUCGUGGUGUGGAGCUUGG | 3310 |
| CAAGCUCCACACCACGAAG | 3311 | CUUCGUGGUGUGGAGCUUG | 3312 |
| AAGCUCCACACCACGAAGC | 3313 | GCUUCGUGGUGUGGAGCUU | 3314 |
| AGCUCCACACCACGAAGCC | 3315 | GGCUUCGUGGUGUGGAGCU | 3316 |
| CUCCACACCACGAAGCCGU | 3317 | ACGGCUUCGUGGUGUGGAG | 3318 |
| UCCACACCACGAAGCCGUU | 3319 | AACGGCUUCGUGGUGUGGA | 3320 |
| CCACACCACGAAGCCGUUG | 3321 | CAACGGCUUCGUGGUGUGG | 3322 |
| CACACCACGAAGCCGUUGC | 3323 | GCAACGGCUUCGUGGUGUG | 3324 |
| ACACCACGAAGCCGUUGCC | 3325 | GGCAACGGCUUCGUGGUGU | 3326 |
| CACCACGAAGCCGUUGCCA | 3327 | UGGCAACGGCUUCGUGGUG | 3328 |
| ACCACGAAGCCGUUGCCAG | 3329 | CUGGCAACGGCUUCGUGGU | 3330 |
| CCGCGAAGUCUUCCAGCUC | 3331 | GAGCUGGAAGACUUCGCGG | 3332 |
| CGCGAAGUCUUCCAGCUCA | 3333 | UGAGCUGGAAGACUUCGCG | 3334 |
| GCGAAGUCUUCCAGCUCAG | 3335 | CUGAGCUGGAAGACUUCGC | 3336 |
| UUCCAGCUCAGCAGUGUCU | 3337 | AGACACUGCUGAGCUGGAA | 3338 |
| UCCAGCUCAGCAGUGUCUC | 3339 | GAGACACUGCUGAGCUGGA | 3340 |
| CCAGCUCAGCAGUGUCUCG | 3341 | CGAGACACUGCUGAGCUGG | 3342 |
| CAGCUCAGCAGUGUCUCGU | 3343 | ACGAGACACUGCUGAGCUG | 3344 |
| AGCUCAGCAGUGUCUCGUU | 3345 | AACGAGACACUGCUGAGCU | 3346 |
| GCUCAGCAGUGUCUCGUUC | 3347 | GAACGAGACACUGCUGAGC | 3348 |
| CUCAGCAGUGUCUCGUUCC | 3349 | GGAACGAGACACUGCUGAG | 3350 |
| GUAGCAGACCGACAUCCUU | 3351 | AAGGAUGUCGGUCUGCUAC | 3352 |
| UAGCAGACCGACAUCCUUC | 3353 | GAAGGAUGUCGGUCUGCUA | 3354 |
| AGCAGACCGACAUCCUUCU | 3355 | AGAAGGAUGUCGGUCUGCU | 3356 |
| AGACCGACAUCCUUCUGGG | 3357 | CCCAGAAGGAUGUCGGUCU | 3358 |
| GACCGACAUCCUUCUGGGC | 3359 | GCCCAGAAGGAUGUCGGUC | 3360 |
| CCGACAUCCUUCUGGGCCU | 3361 | AGGCCCAGAAGGAUGUCGG | 3362 |
| CGACAUCCUUCUGGGCCUA | 3363 | UAGGCCCAGAAGGAUGUCG | 3364 |
| GACAUCCUUCUGGGCCUAC | 3365 | GUAGGCCCAGAAGGAUGUC | 3366 |
| CUUCUGGGCCUACAGGUGG | 3367 | CCACCUGUAGGCCCAGAAG | 3368 |
| UUCUGGGCCUACAGGUGGG | 3369 | CCCACCUGUAGGCCCAGAA | 3370 |
| UCUGGGCCUACAGGUGGGU | 3371 | ACCCACCUGUAGGCCCAGA | 3372 |
| GGCCUACAGGUGGGUGGAA | 3373 | UUCCACCCACCUGUAGGCC | 3374 |
| CCUACAGGUGGGUGGAAGG | 3375 | CCUUCCACCCACCUGUAGG | 3376 |
| CUACAGGUGGGUGGAAGGC | 3377 | GCCUUCCACCCACCUGUAG | 3378 |
| UACAGGUGGGUGGAAGGCG | 3379 | CGCCUUCCACCCACCUGUA | 3380 |
| ACUUCCCUGCAGCCUGCCU | 3381 | AGGCAGGCUGCAGGGAAGU | 3382 |

| Sense Sequence | SEQ ID NO: | Antisense Sequence | SEQ ID NO: |
|---|---|---|---|
| CCUGCAGCCUGCCUCUUUU | 3383 | AAAAGAGGCAGGCUGCAGG | 3384 |
| CUGCAGCCUGCCUCUUUUC | 3385 | GAAAAGAGGCAGGCUGCAG | 3386 |
| GCAGCCUGCCUCUUUUCUG | 3387 | CAGAAAAGAGGCAGGCUGC | 3388 |
| CAGCCUGCCUCUUUUCUGC | 3389 | GCAGAAAAGAGGCAGGCUG | 3390 |
| AGCCUGCCUCUUUUCUGCC | 3391 | GGCAGAAAAGAGGCAGGCU | 3392 |
| GCCUCUUUUCUGCCUGGGA | 3393 | UCCCAGGCAGAAAAGAGGC | 3394 |
| CUUUUCUGCCUGGGAGUCC | 3395 | GGACUCCCAGGCAGAAAAG | 3396 |
| UUUUCUGCCUGGGAGUCCU | 3397 | AGGACUCCCAGGCAGAAAA | 3398 |
| UUCUGCCUGGGAGUCCUGA | 3399 | UCAGGACUCCCAGGCAGAA | 3400 |
| UCUGCCUGGGAGUCCUGAC | 3401 | GUCAGGACUCCCAGGCAGA | 3402 |
| UGCCUGGGAGUCCUGACUU | 3403 | AAGUCAGGACUCCCAGGCA | 3404 |
| GCCUGGGAGUCCUGACUUC | 3405 | GAAGUCAGGACUCCCAGGC | 3406 |
| CUGGGAGUCCUGACUUCCA | 3407 | UGGAAGUCAGGACUCCCAG | 3408 |
| UGGGAGUCCUGACUUCCAC | 3409 | GUGGAAGUCAGGACUCCCA | 3410 |
| GGGAGUCCUGACUUCCACG | 3411 | CGUGGAAGUCAGGACUCCC | 3412 |
| GGAGUCCUGACUUCCACGA | 3413 | UCGUGGAAGUCAGGACUCC | 3414 |
| GAGUCCUGACUUCCACGAG | 3415 | CUCGUGGAAGUCAGGACUC | 3416 |
| AGUCCUGACUUCCACGAGG | 3417 | CCUCGUGGAAGUCAGGACU | 3418 |
| CCUGACUUCCACGAGGACC | 3419 | GGUCCUCGUGGAAGUCAGG | 3420 |
| CUGACUUCCACGAGGACCC | 3421 | GGGUCCUCGUGGAAGUCAG | 3422 |
| UGACUUCCACGAGGACCCA | 3423 | UGGGUCCUCGUGGAAGUCA | 3424 |
| GACUUCCACGAGGACCCAG | 3425 | CUGGGUCCUCGUGGAAGUC | 3426 |
| ACUUCCACGAGGACCCAGA | 3427 | UCUGGGUCCUCGUGGAAGU | 3428 |
| CUUCCACGAGGACCCAGAC | 3429 | GUCUGGGUCCUCGUGGAAG | 3430 |
| UUCCACGAGGACCCAGACC | 3431 | GGUCUGGGUCCUCGUGGAA | 3432 |
| CCCUGCUCCCAGUCAGUUG | 3433 | CAACUGACUGGGAGCAGGG | 3434 |
| CCUGCUCCCAGUCAGUUGA | 3435 | UCAACUGACUGGGAGCAGG | 3436 |
| CUGCUCCCAGUCAGUUGAC | 3437 | GUCAACUGACUGGGAGCAG | 3438 |
| UGCUCCCAGUCAGUUGACC | 3439 | GGUCAACUGACUGGGAGCA | 3440 |
| CCCAGUCAGUUGACCUGCC | 3441 | GGCAGGUCAACUGACUGGG | 3442 |
| CCAGUCAGUUGACCUGCCC | 3443 | GGGCAGGUCAACUGACUGG | 3444 |
| GCCUCCUUCCCAGAGCUCA | 3445 | UGAGCUCUGGGAAGGAGGC | 3446 |
| CCUCCUUCCCAGAGCUCAG | 3447 | CUGAGCUCUGGGAAGGAGG | 3448 |
| CUCCUUCCCAGAGCUCAGU | 3449 | ACUGAGCUCUGGGAAGGAG | 3450 |
| UCCUUCCCAGAGCUCAGUG | 3451 | CACUGAGCUCUGGGAAGGA | 3452 |
| CCUUCCCAGAGCUCAGUGG | 3453 | CCACUGAGCUCUGGGAAGG | 3454 |
| UUCCCAGAGCUCAGUGGUA | 3455 | UACCACUGAGCUCUGGGAA | 3456 |
| UCCCAGAGCUCAGUGGUAA | 3457 | UUACCACUGAGCUCUGGGA | 3458 |

TABLE 8-continued

| Sense Sequence | SEQ ID NO: | Antisense Sequence | SEQ ID NO: |
|---|---|---|---|
| CAGGCUGUCACUAUCUCUA | 3459 | UAGAGAUAGUGACAGCCUG | 3460 |
| AGGCUGUCACUAUCUCUAC | 3461 | GUAGAGAUAGUGACAGCCU | 3462 |
| UCUCUACCACCACUCCUCU | 3463 | AGAGGAGUGGUGGUAGAGA | 3464 |
| CCACCACUCCUCUAGUCUG | 3465 | CAGACUAGAGGAGUGGUGG | 3466 |
| CACCACUCCUCUAGUCUGG | 3467 | CCAGACUAGAGGAGUGGUG | 3468 |
| ACCACUCCUCUAGUCUGGC | 3469 | GCCAGACUAGAGGAGUGGU | 3470 |
| CCACUCCUCUAGUCUGGCC | 3471 | GGCCAGACUAGAGGAGUGG | 3472 |
| CACUCCUCUAGUCUGGCCC | 3473 | GGGCCAGACUAGAGGAGUG | 3474 |
| AUUCUAGCACAUCUGGGCA | 3475 | UGCCCAGAUGUGCUAGAAU | 3476 |
| UUCUAGCACAUCUGGGCAA | 3477 | UUGCCCAGAUGUGCUAGAA | 3478 |
| UCUAGCACAUCUGGGCAAA | 3479 | UUUGCCCAGAUGUGCUAGA | 3480 |
| CUAGCACAUCUGGGCAAAA | 3481 | UUUUGCCCAGAUGUGCUAG | 3482 |
| GGGUGUAAAGGGACGUGCA | 3483 | UGCACGUCCCUUUACACCC | 3484 |
| GGUGUAAAGGGACGUGCAC | 3485 | GUGCACGUCCCUUUACACC | 3486 |
| GUGUAAAGGGACGUGCACA | 3487 | UGUGCACGUCCCUUUACAC | 3488 |
| UGUAAAGGGACGUGCACAG | 3489 | CUGUGCACGUCCCUUUACA | 3490 |
| GUAAAGGGACGUGCACAGA | 3491 | UCUGUGCACGUCCCUUUAC | 3492 |
| UAAAGGGACGUGCACAGAU | 3493 | AUCUGUGCACGUCCCUUUA | 3494 |
| AAAGGGACGUGCACAGAUC | 3495 | GAUCUGUGCACGUCCCUUU | 3496 |
| AAGGGACGUGCACAGAUCU | 3497 | AGAUCUGUGCACGUCCCUU | 3498 |
| AGGGACGUGCACAGAUCUA | 3499 | UAGAUCUGUGCACGUCCCU | 3500 |
| CGUGCACAGAUCUACUUAC | 3501 | GUAAGUAGAUCUGUGCACG | 3502 |
| GUGCACAGAUCUACUUACC | 3503 | GGUAAGUAGAUCUGUGCAC | 3504 |
| UGCACAGAUCUACUUACCA | 3505 | UGGUAAGUAGAUCUGUGCA | 3506 |
| GCACAGAUCUACUUACCAA | 3507 | UUGGUAAGUAGAUCUGUGC | 3508 |
| CACAGAUCUACUUACCAAG | 3509 | CUUGGUAAGUAGAUCUGUG | 3510 |
| ACAGAUCUACUUACCAAGC | 3511 | GCUUGGUAAGUAGAUCUGU | 3512 |
| CAGAUCUACUUACCAAGCU | 3513 | AGCUUGGUAAGUAGAUCUG | 3514 |
| AGAUCUACUUACCAAGCUG | 3515 | CAGCUUGGUAAGUAGAUCU | 3516 |
| AUCUACUUACCAAGCUGGG | 3517 | CCCAGCUUGGUAAGUAGAU | 3518 |
| UCUACUUACCAAGCUGGGA | 3519 | UCCCAGCUUGGUAAGUAGA | 3520 |
| CUUACCAAGCUGGGAGCAA | 3521 | UUGCUCCCAGCUUGGUAAG | 3522 |
| UUACCAAGCUGGGAGCAAG | 3523 | CUUGCUCCCAGCUUGGUAA | 3524 |
| UACCAAGCUGGGAGCAAGC | 3525 | GCUUGCUCCCAGCUUGGUA | 3526 |
| ACCAAGCUGGGAGCAAGCA | 3527 | UGCUUGCUCCCAGCUUGGU | 3528 |
| GCUGGGAGCAAGCAGGAUU | 3529 | AAUCCUGCUUGCUCCCAGC | 3530 |
| CUGGGAGCAAGCAGGAUUG | 3531 | CAAUCCUGCUUGCUCCCAG | 3532 |
| UGGGAGCAAGCAGGAUUGG | 3533 | CCAAUCCUGCUUGCUCCCA | 3534 |
| GGGAGCAAGCAGGAUUGGG | 3535 | CCCAAUCCUGCUUGCUCCC | 3536 |
| AAAGGUUAAGCAGCAGUAG | 3537 | CUACUGCUGCUUAACCUUU | 3538 |
| AAGGUUAAGCAGCAGUAGG | 3539 | CCUACUGCUGCUUAACCUU | 3540 |
| AGGUUAAGCAGCAGUAGGC | 3541 | GCCUACUGCUGCUUAACCU | 3542 |
| GGUGCCUACUCCUGUCCUG | 3543 | CAGGACAGGAGUAGGCACC | 3544 |
| GUGCCUACUCCUGUCCUGU | 3545 | ACAGGACAGGAGUAGGCAC | 3546 |
| UGCCUACUCCUGUCCUGUG | 3547 | CACAGGACAGGAGUAGGCA | 3548 |
| GCCUACUCCUGUCCUGUGC | 3549 | GCACAGGACAGGAGUAGGC | 3550 |
| CCUACUCCUGUCCUGUGCC | 3551 | GGCACAGGACAGGAGUAGG | 3552 |
| CUACUCCUGUCCUGUGCCU | 3553 | AGGCACAGGACAGGAGUAG | 3554 |
| UACUCCUGUCCUGUGCCUA | 3555 | UAGGCACAGGACAGGAGUA | 3556 |
| ACUCCUGUCCUGUGCCUAU | 3557 | AUAGGCACAGGACAGGAGU | 3558 |
| CUCCUGUCCUGUGCCUAUC | 3559 | GAUAGGCACAGGACAGGAG | 3560 |
| UCCUGUCCUGUGCCUAUCA | 3561 | UGAUAGGCACAGGACAGGA | 3562 |
| GUGCCUAUCACAUUUGCAG | 3563 | CUGCAAAUGUGAUAGGCAC | 3564 |
| CUAUCACAUUUGCAGAGGG | 3565 | CCCUCUGCAAAUGUGAUAG | 3566 |
| UAUCACAUUUGCAGAGGGU | 3567 | ACCCUCUGCAAAUGUGAUA | 3568 |
| AUCACAUUUGCAGAGGGUA | 3569 | UACCCUCUGCAAAUGUGAU | 3570 |
| UCACAUUUGCAGAGGGUAA | 3571 | UUACCCUCUGCAAAUGUGA | 3572 |
| CACAUUUGCAGAGGGUAAG | 3573 | CUUACCCUCUGCAAAUGUG | 3574 |
| ACAUUUGCAGAGGGUAAGA | 3575 | UCUUACCCUCUGCAAAUGU | 3576 |
| CUCACCCUGCUCCUUCCCA | 3577 | UGGGAAGGAGCAGGGUGAG | 3578 |
| CACCCUGCUCCUUCCCAUC | 3579 | GAUGGGAAGGAGCAGGGUG | 3580 |
| CCUGCUCCUUCCCAUCACC | 3581 | GGUGAUGGGAAGGAGCAGG | 3582 |
| UGCUCCUUCCCAUCACCAA | 3583 | UUGGUGAUGGGAAGGAGCA | 3584 |
| CAGUAAGAUUCCCUGGUGG | 3585 | CCACCAGGGAAUCUUACUG | 3586 |
| AGUAAGAUUCCCUGGUGGU | 3587 | ACCACCAGGGAAUCUUACU | 3588 |
| GUAAGAUUCCCUGGUGGUG | 3589 | CACCACCAGGGAAUCUUAC | 3590 |
| UAAGAUUCCCUGGUGGUGG | 3591 | CCACCACCAGGGAAUCUUA | 3592 |
| AAGAUUCCCUGGUGGUGGA | 3593 | UCCACCACCAGGGAAUCUU | 3594 |
| UCCCUGGUGGUGGAAGGAA | 3595 | UUCCUUCCACCACCAGGGA | 3596 |
| UCUGCUGAAUCCUGGUCCU | 3597 | AGGACCAGGAUUCAGCAGA | 3598 |
| CUGCUGAAUCCUGGUCCUG | 3599 | CAGGACCAGGAUUCAGCAG | 3600 |
| UGCUGAAUCCUGGUCCUGC | 3601 | GCAGGACCAGGAUUCAGCA | 3602 |
| GCUGAAUCCUGGUCCUGCU | 3603 | AGCAGGACCAGGAUUCAGC | 3604 |
| CUGAAUCCUGGUCCUGCUU | 3603 | GAAGCAGGACCAGGAUUCA | 3604 |
| GAAUCCUGGUCCUGCUUCU | 3605 | AGAAGCAGGACCAGGAUUC | 3606 |
| AAUCCUGGUCCUGCUUCUG | 3607 | CAGAAGCAGGACCAGGAUU | 3608 |
| AUCCUGGUCCUGCUUCUGU | 3609 | ACAGAAGCAGGACCAGGAU | 3610 |

TABLE 8-continued

| Sense Sequence | SEQ ID NO: | Antisense Sequence | SEQ ID NO: |
|---|---|---|---|
| UCCUGGUCCUGCUUCUGUU | 3611 | AACAGAAGCAGGACCAGGA | 3612 |
| CCUGGUCCUGCUUCUGUUC | 3613 | GAACAGAAGCAGGACCAGG | 3614 |
| CUGGUCCUGCUUCUGUUCU | 3615 | AGAACAGAAGCAGGACCAG | 3616 |
| UUCUGUUCUCAUCCCUCCC | 3617 | GGGAGGGAUGAGAACAGAA | 3618 |
| CUUCUGCAGUGUGUAUGUU | 3619 | AACAUACACACUGCAGAAG | 3620 |
| UUCUGCAGUGUGUAUGUUG | 3621 | CAACAUACACACUGCAGAA | 3622 |
| UCUGCAGUGUGUAUGUUGC | 3623 | GCAACAUACACACUGCAGA | 3624 |
| CUGCAGUGUGUAUGUUGCC | 3625 | GGCAACAUACACACUGCAG | 3626 |
| UGCAGUGUGUAUGUUGCCU | 3627 | AGGCAACAUACACACUGCA | 3628 |
| GCAGUGUGUAUGUUGCCUG | 3629 | CAGGCAACAUACACACUGC | 3630 |
| CAGUGUGUAUGUUGCCUGG | 3631 | CCAGGCAACAUACACACUG | 3632 |
| AGUGUGUAUGUUGCCUGGU | 3633 | ACCAGGCAACAUACACACU | 3634 |
| GUGUGUAUGUUGCCUGGUC | 3635 | GACCAGGCAACAUACACAC | 3636 |
| UGUGUAUGUUGCCUGGUCU | 3637 | AGACCAGGCAACAUACACA | 3638 |
| GUGUAUGUUGCCUGGUCUC | 3639 | GAGACCAGGCAACAUACAC | 3640 |
| UGUAUGUUGCCUGGUCUCU | 3641 | AGAGACCAGGCAACAUACA | 3642 |
| GUAUGUUGCCUGGUCUCUC | 3643 | GAGAGACCAGGCAACAUAC | 3644 |
| UAUGUUGCCUGGUCUCUCU | 3645 | AGAGAGACCAGGCAACAUA | 3646 |
| AUGUUGCCUGGUCUCUCUG | 3647 | CAGAGAGACCAGGCAACAU | 3648 |
| UGUUGCCUGGUCUCUCUGG | 3649 | CCAGAGAGACCAGGCAACA | 3650 |
| GUUGCCUGGUCUCUCUGGC | 3651 | GCCAGAGAGACCAGGCAAC | 3652 |
| UUGCCUGGUCUCUCUGGCC | 3653 | GGCCAGAGAGACCAGGCAA | 3654 |
| CUGGUCUCUCUGGCCUGCA | 3655 | UGCAGGCCAGAGAGACCAG | 3656 |
| CCUGCAGAGGUGACCCAAA | 3657 | UUUGGGUCACCUCUGCAGG | 3658 |
| CUGCCUUAUCCUUGCCUGU | 3659 | ACAGGCAAGGAUAAGGCAG | 3660 |
| UGCCUUAUCCUUGCCUGUU | 3661 | AACAGGCAAGGAUAAGGCA | 3662 |
| GCCUUAUCCUUGCCUGUUU | 3663 | AAACAGGCAAGGAUAAGGC | 3664 |
| AGUCUCCUGGUCCGGCUGA | 3665 | UCAGCCGGACCAGGAGACU | 3666 |
| GUCAAUGACAGCUUUUCCA | 3667 | UGGAAAAGCUGUCAUUGAC | 3668 |
| UGACAGCUUUUCCAUGUAA | 3669 | UUACAUGGAAAAGCUGUCA | 3670 |
| GACAGCUUUUCCAUGUAAG | 3671 | CUUACAUGGAAAAGCUGUC | 3672 |
| ACAGCUUUUCCAUGUAAGG | 3673 | CCUUACAUGGAAAAGCUGU | 3674 |
| CAGCUUUUCCAUGUAAGGC | 3675 | GCCUUACAUGGAAAAGCUG | 3676 |
| AGCUUUUCCAUGUAAGGCA | 3677 | UGCCUUACAUGGAAAAGCU | 3678 |
| UGUAAGGCAUGGUGCUAGG | 3679 | CCUAGCACCAUGCCUUACA | 3680 |
| GUAAGGCAUGGUGCUAGGU | 3681 | ACCUAGCACCAUGCCUUAC | 3682 |
| UAAGGCAUGGUGCUAGGUU | 3683 | AACCUAGCACCAUGCCUUA | 3684 |
| GCAUGGUGCUAGGUUCCAG | 3685 | CUGGAACCUAGCACCAUGC | 3686 |
| CAUGGUGCUAGGUUCCAGG | 3687 | CCUGGAACCUAGCACCAUG | 3688 |
| AUGGUGCUAGGUUCCAGGA | 3689 | UCCUGGAACCUAGCACCAU | 3690 |
| UGGUGCUAGGUUCCAGGAG | 3691 | CUCCUGGAACCUAGCACCA | 3692 |
| GGUGCUAGGUUCCAGGAGG | 3693 | CCUCCUGGAACCUAGCACC | 3694 |
| GUGCUAGGUUCCAGGAGGA | 3695 | UCCUCCUGGAACCUAGCAC | 3696 |
| UGCAUGGAGGCAUAAUGGU | 3697 | ACCAUUAUGCCUCCAUGCA | 3698 |
| GCAUGGAGGCAUAAUGGUU | 3699 | AACCAUUAUGCCUCCAUGC | 3700 |
| CAUGGAGGCAUAAUGGUUA | 3701 | UAACCAUUAUGCCUCCAUG | 3702 |
| AUGGAGGCAUAAUGGUUAG | 3703 | CUAACCAUUAUGCCUCCAU | 3704 |
| UGGAGGCAUAAUGGUUAGG | 3705 | CCUAACCAUUAUGCCUCCA | 3706 |
| GGAGGCAUAAUGGUUAGGG | 3707 | CCCUAACCAUUAUGCCUCC | 3708 |
| GAGGCAUAAUGGUUAGGGA | 3709 | UCCCUAACCAUUAUGCCUC | 3710 |
| CAUAAUGGUUAGGGAGUCA | 3711 | UGACUCCCUAACCAUUAUG | 3712 |
| AUAAUGGUUAGGGAGUCAU | 3713 | AUGACUCCCUAACCAUUAU | 3714 |
| UAAUGGUUAGGGAGUCAUG | 3715 | CAUGACUCCCUAACCAUUA | 3716 |
| GGUUAGGGAGUCAUGACAC | 3717 | GUGUCAUGACUCCCUAACC | 3718 |
| CAUUACCAGGCUGCACCAG | 3719 | CUGGUGCAGCCUGGUAAUG | 3720 |
| AUUACCAGGCUGCACCAGG | 3721 | CCUGGUGCAGCCUGGUAAU | 3722 |
| UACCAGGCUGCACCAGGAU | 3723 | AUCCUGGUGCAGCCUGGUA | 3724 |
| ACCAGGCUGCACCAGGAUA | 3725 | UAUCCUGGUGCAGCCUGGU | 3726 |
| CCAGGCUGCACCAGGAUAC | 3727 | GUAUCCUGGUGCAGCCUGG | 3728 |
| AAAGGAUGAGUAGGGACAU | 3729 | AUGUCCCUACUCAUCCUUU | 3730 |
| AAGGAUGAGUAGGGACAUA | 3731 | UAUGUCCCUACUCAUCCUU | 3732 |
| AGGAUGAGUAGGGACAUAC | 3733 | GUAUGUCCCUACUCAUCCU | 3734 |
| GUAGGGACAUACUAAGAAG | 3735 | CUUCUUAGUAUGUCCCUAC | 3736 |
| GGACAUACUAAGAAGCAGC | 3737 | GCUGCUUCUUAGUAUGUCC | 3738 |
| AUACUAAGAAGCAGCCCUC | 3739 | GAGGGCUGCUUCUUAGUAU | 3740 |
| UACUAAGAAGCAGCCCUCU | 3741 | AGAGGGCUGCUUCUUAGUA | 3742 |
| ACUAAGAAGCAGCCCUCUC | 3743 | GAGAGGGCUGCUUCUUAGU | 3744 |
| AGAAGCAGCCCUCUCCUCU | 3745 | AGAGGAGAGGGCUGCUUCU | 3746 |
| GAAGCAGCCCUCUCCUCUU | 3747 | AAGAGGAGAGGGCUGCUUC | 3748 |
| CAGCCCUCUCCUCUUGGAA | 3749 | UUCCAAGAGGAGAGGGCUG | 3750 |
| GCCUGGCAGAUGGAUAGAG | 3751 | CUCUAUCCAUCUGCCAGGC | 3752 |
| CCUGGCAGAUGGAUAGAGC | 3753 | GCUCUAUCCAUCUGCCAGG | 3754 |
| CUGGCAGAUGGAUAGAGCU | 3755 | AGCUCUAUCCAUCUGCCAG | 3756 |
| UGGCAGAUGGAUAGAGCUG | 3757 | CAGCUCUAUCCAUCUGCCA | 3758 |
| GGCAGAUGGAUAGAGCUGG | 3759 | CCAGCUCUAUCCAUCUGCC | 3760 |
| GCAGAUGGAUAGAGCUGGG | 3761 | CCCAGCUCUAUCCAUCUGC | 3762 |

TABLE 8-continued

| Sense Sequence | SEQ ID NO: | Antisense Sequence | SEQ ID NO: |
|---|---|---|---|
| AAAGGCCUCUGCUCAAGUA | 3763 | UACUUGAGCAGAGGCCUUU | 3764 |
| AAGGCCUCUGCUCAAGUAA | 3765 | UUACUUGAGCAGAGGCCUU | 3766 |
| AGGCCUCUGCUCAAGUAAC | 3767 | GUUACUUGAGCAGAGGCCU | 3768 |
| CAGGAGCACUGUCUUAGUU | 3769 | AACUAAGACAGUGCUCCUG | 3770 |
| AGGAGCACUGUCUUAGUUU | 3771 | AAACUAAGACAGUGCUCCU | 3772 |
| GGAGCACUGUCUUAGUUUG | 3773 | CAAACUAAGACAGUGCUCC | 3774 |
| GAGCACUGUCUUAGUUUGG | 3775 | CCAAACUAAGACAGUGCUC | 3776 |
| AGCACUGUCUUAGUUUGGG | 3777 | CCCAAACUAAGACAGUGCU | 3778 |
| GUUCUUCCAAAGCAGAGCU | 3779 | AGCUCUGCUUUGGAAGAAC | 3780 |
| AGCAGAGCUUGAGCUAAGG | 3781 | CCUUAGCUCAAGCUCUGCU | 3782 |
| GCAGAGCUUGAGCUAAGGG | 3783 | CCCUUAGCUCAAGCUCUGC | 3784 |
| CAGAGCUUGAGCUAAGGGC | 3785 | GCCCUUAGCUCAAGCUCUG | 3786 |
| GCUUGAGCUAAGGGCUUGG | 3787 | CCAAGCCCUUAGCUCAAGC | 3788 |
| UUGAGCUAAGGGCUUGGGU | 3789 | ACCCAAGCCCUUAGCUCAA | 3790 |
| UGAGCUAAGGGCUUGGGUA | 3791 | UACCCAAGCCCUUAGCUCA | 3792 |
| GAGCUAAGGGCUUGGGUAC | 3793 | GUACCCAAGCCCUUAGCUC | 3794 |
| AGCUAAGGGCUUGGGUACA | 3795 | UGUACCCAAGCCCUUAGCU | 3796 |
| GCUAAGGGCUUGGGUACAG | 3797 | CUGUACCCAAGCCCUUAGC | 3798 |
| AGGGCUUGGGUACAGGUGA | 3799 | UCACCUGUACCCAAGCCCU | 3800 |
| GGGCUUGGGUACAGGUGAU | 3801 | AUCACCUGUACCCAAGCCC | 3802 |
| GGCUUGGGUACAGGUGAUC | 3803 | GAUCACCUGUACCCAAGCC | 3804 |
| GCUUGGGUACAGGUGAUCC | 3805 | GGAUCACCUGUACCCAAGC | 3806 |
| AGGUGAUCCUGUAUUCUUG | 3807 | CAAGAAUACAGGAUCACCU | 3808 |
| GGUGAUCCUGUAUUCUUGA | 3809 | UCAAGAAUACAGGAUCACC | 3810 |
| GUGAUCCUGUAUUCUUGAG | 3811 | CUCAAGAAUACAGGAUCAC | 3812 |
| UGAUCCUGUAUUCUUGAGC | 3813 | GCUCAAGAAUACAGGAUCA | 3814 |
| UCCUGUAUUCUUGAGCUAA | 3815 | UUAGCUCAAGAAUACAGGA | 3816 |
| CCUGUAUUCUUGAGCUAAG | 3817 | CUUAGCUCAAGAAUACAGG | 3818 |
| UGUAUUCUUGAGCUAAGGG | 3819 | CCCUUAGCUCAAGAAUACA | 3820 |
| GUAUUCUUGAGCUAAGGGC | 3821 | GCCCUUAGCUCAAGAAUAC | 3822 |
| UCUUGAGCUAAGGGCUUGG | 3823 | CCAAGCCCUUAGCUCAAGA | 3824 |
| UUGAGCUAAGGGCUUGGGU | 3825 | ACCCAAGCCCUUAGCUCAA | 3826 |
| UGAGCUAAGGGCUUGGGUA | 3827 | UACCCAAGCCCUUAGCUCA | 3828 |
| GAGCUAAGGGCUUGGGUAC | 3829 | GUACCCAAGCCCUUAGCUC | 3830 |
| AGCUAAGGGCUUGGGUACA | 3831 | UGUACCCAAGCCCUUAGCU | 3832 |
| GCUAAGGGCUUGGGUACAG | 3833 | CUGUACCCAAGCCCUUAGC | 3834 |
| AGGGCUUGGGUACAGGUGA | 3835 | UCACCUGUACCCAAGCCCU | 3836 |
| GGGCUUGGGUACAGGUGAU | 3837 | AUCACCUGUACCCAAGCCC | 3838 |
| GGCUUGGGUACAGGUGAUC | 3839 | GAUCACCUGUACCCAAGCC | 3840 |
| GCUUGGGUACAGGUGAUCC | 3841 | GGAUCACCUGUACCCAAGC | 3842 |
| AGGUGAUCCUGUAUUGGG | 3843 | CCCAAAUACAGGAUCACCU | 3844 |
| GGUGAUCCUGUAUUGGGA | 3845 | UCCCAAAUACAGGAUCACC | 3846 |
| AUCCUGUAUUGGGAGGUU | 3847 | AACCUCCCAAAUACAGGAU | 3848 |
| UCCUGUAUUGGGAGGUUA | 3849 | UAACCUCCCAAAUACAGGA | 3850 |
| CCUGUAUUGGGAGGUUAA | 3851 | UUAACCUCCCAAAUACAGG | 3852 |
| CUGUAUUGGGAGGUUAAC | 3853 | GUUAACCUCCCAAAUACAG | 3854 |
| UGUAUUGGGAGGUUAACU | 3855 | AGUUAACCUCCCAAAUACA | 3856 |
| GUAUUGGGAGGUUAACUC | 3857 | GAGUUAACCUCCCAAAUAC | 3858 |
| UAUUGGGAGGUUAACUCA | 3859 | UGAGUUAACCUCCCAAAUA | 3860 |
| GGAGGUUAACUCAGGAAGU | 3861 | ACUUCCUGAGUUAACCUCC | 3862 |
| GAGGUUAACUCAGGAAGUG | 3863 | CACUUCCUGAGUUAACCUC | 3864 |
| AGGUUAACUCAGGAAGUGA | 3865 | UCACUUCCUGAGUUAACCU | 3866 |
| UCAGGAAGUGAGGGCAUAA | 3867 | UUAUGCCCUCACUUCCUGA | 3868 |
| CAGGAAGUGAGGGCAUAAG | 3869 | CUUAUGCCCUCACUUCCUG | 3870 |
| AGGAAGUGAGGGCAUAAGG | 3871 | CCUUAUGCCCUCACUUCCU | 3872 |
| GGAAGUGAGGGCAUAAGGU | 3873 | ACCUUAUGCCCUCACUUCC | 3874 |
| GAAGUGAGGGCAUAAGGUA | 3875 | UACCUUAUGCCCUCACUUC | 3876 |
| AAGUGAGGGCAUAAGGUAA | 3877 | UUACCUUAUGCCCUCACUU | 3878 |
| AGUGAGGGCAUAAGGUAAA | 3879 | UUUACCUUAUGCCCUCACU | 3880 |
| AAAGCCAUUAAGAGUAUGU | 3881 | ACAUACUCUUAAUGGCUUU | 3882 |
| AAGCCAUUAAGAGUAUGUU | 3883 | AACAUACUCUUAAUGGCUU | 3884 |
| AGCCAUUAAGAGUAUGUUA | 3885 | UAACAUACUCUUAAUGGCU | 3886 |
| UAAGAGUAUGUUAAGUCCC | 3887 | GGGACUUAACAUACUCUUA | 3888 |
| AAGAGUAUGUUAAGUCCCU | 3889 | AGGGACUUAACAUACUCUU | 3890 |
| AGAGUAUGUUAAGUCCCUU | 3891 | AAGGGACUUAACAUACUCU | 3892 |
| GAGUAUGUUAAGUCCCUUC | 3893 | GAAGGGACUUAACAUACUC | 3894 |
| AGUAUGUUAAGUCCCUUCA | 3895 | UGAAGGGACUUAACAUACU | 3896 |
| GUAUGUUAAGUCCCUUCAG | 3897 | CUGAAGGGACUUAACAUAC | 3898 |
| UAUGUUAAGUCCCUUCAGU | 3899 | ACUGAAGGGACUUAACAUA | 3900 |
| AUGUUAAGUCCCUUCAGUA | 3901 | UACUGAAGGGACUUAACAU | 3902 |
| UGUUAAGUCCCUUCAGUAG | 3903 | CUACUGAAGGGACUUAACA | 3904 |
| GUUAAGUCCCUUCAGUAGG | 3905 | CCUACUGAAGGGACUUAAC | 3906 |
| UUAAGUCCCUUCAGUAGGC | 3907 | GCCUACUGAAGGGACUUAA | 3908 |
| UAAGUCCCUUCAGUAGGCC | 3909 | GGCCUACUGAAGGGACUUA | 3910 |
| AAGUCCCUUCAGUAGGCCU | 3911 | AGGCCUACUGAAGGGACUU | 3912 |
| AGUCCCUUCAGUAGGCCUU | 3913 | AAGGCCUACUGAAGGGACU | 3914 |

TABLE 8-continued

| Sense Sequence | SEQ ID NO: | Antisense Sequence | SEQ ID NO: |
|---|---|---|---|
| GUCCCUUCAGUAGGCCUUG | 3915 | CAAGGCCUACUGAAGGGAC | 3916 |
| UCCCUUCAGUAGGCCUUGG | 3917 | CCAAGGCCUACUGAAGGGA | 3918 |
| CCCUUCAGUAGGCCUUGGG | 3919 | CCCAAGGCCUACUGAAGGG | 3920 |
| CCUUCAGUAGGCCUUGGGA | 3921 | UCCCAAGGCCUACUGAAGG | 3922 |
| CUUCAGUAGGCCUUGGGAA | 3923 | UUCCCAAGGCCUACUGAAG | 3924 |
| AAAAGUAUAGAUUGCCCAA | 3925 | UUGGGCAAUCUAUACUUUU | 3926 |
| AAAGUAUAGAUUGCCCAAG | 3927 | CUUGGGCAAUCUAUACUUU | 3928 |
| AAGUAUAGAUUGCCCAAGA | 3929 | UCUUGGGCAAUCUAUACUU | 3930 |
| AAAGACUGGCAGGGUGAUC | 3931 | GAUCACCCUGCCAGUCUUU | 3932 |
| AAGACUGGCAGGGUGAUCA | 3933 | UGAUCACCCUGCCAGUCUU | 3934 |
| CUGGCAGGGUGAUCAGUCC | 3935 | GGACUGAUCACCCUGCCAG | 3936 |
| GAAUGUACUUAAUGAGUGG | 3937 | CCACUCAUUAAGUACAUUC | 3938 |
| AAUGUACUUAAUGAGUGGG | 3939 | CCCACUCAUUAAGUACAUU | 3940 |
| UGUACUUAAUGAGUGGGCU | 3941 | AGCCCACUCAUUAAGUACA | 3942 |
| GUACUUAAUGAGUGGGCUA | 3943 | UAGCCCACUCAUUAAGUAC | 3944 |
| UACUUAAUGAGUGGGCUAC | 3945 | GUAGCCCACUCAUUAAGUA | 3946 |
| CUUAAUGAGUGGGCUACAG | 3947 | CUGUAGCCCACUCAUUAAG | 3948 |
| UAAUGAGUGGGCUACAGCG | 3949 | CGCUGUAGCCCACUCAUUA | 3950 |
| AAUGAGUGGGCUACAGCGU | 3951 | ACGCUGUAGCCCACUCAUU | 3952 |
| AUGAGUGGGCUACAGCGUA | 3953 | UACGCUGUAGCCCACUCAU | 3954 |
| UGAGUGGGCUACAGCGUAU | 3955 | AUACGCUGUAGCCCACUCA | 3956 |
| GAGUGGGCUACAGCGUAUC | 3957 | GAUACGCUGUAGCCCACUC | 3958 |
| AGUGGGCUACAGCGUAUCC | 3959 | GGAUACGCUGUAGCCCACU | 3960 |
| GUGGGCUACAGCGUAUCCU | 3961 | AGGAUACGCUGUAGCCCAC | 3962 |
| UGGGCUACAGCGUAUCCUC | 3963 | GAGGAUACGCUGUAGCCCA | 3964 |
| AGAGUUGUUCUACCUGGGU | 3965 | ACCCAGGUAGAACAACUCU | 3966 |
| GAGUUGUUCUACCUGGGUA | 3967 | UACCCAGGUAGAACAACUC | 3968 |
| AGUUGUUCUACCUGGGUAU | 3969 | AUACCCAGGUAGAACAACU | 3970 |
| GUUGUUCUACCUGGGUAUA | 3971 | UAUACCCAGGUAGAACAAC | 3972 |
| UUGUUCUACCUGGGUAUAU | 3973 | AUAUACCCAGGUAGAACAA | 3974 |
| UGUUCUACCUGGGUAUAUC | 3975 | GAUAUACCCAGGUAGAACA | 3976 |
| GUUCUACCUGGGUAUAUCC | 3977 | GGAUAUACCCAGGUAGAAC | 3978 |
| UACCUGGGUAUAUCCAAAA | 3979 | UUUUGGAUAUACCCAGGUA | 3980 |
| AGGGUAUGGAGUUUACGAG | 3981 | CUCGUAAACUCCAUACCCU | 3982 |
| GGGUAUGGAGUUUACGAGG | 3983 | CCUCGUAAACUCCAUACCC | 3984 |
| GGUAUGGAGUUUACGAGGG | 3985 | CCCUCGUAAACUCCAUACC | 3986 |
| GUAUGGAGUUUACGAGGGU | 3987 | ACCCUCGUAAACUCCAUAC | 3988 |
| UAUGGAGUUUACGAGGGUU | 3989 | AACCCUCGUAAACUCCAUA | 3990 |
| AUGGAGUUUACGAGGGUUC | 3991 | GAACCCUCGUAAACUCCAU | 3992 |
| UGGAGUUUACGAGGGUUCA | 3993 | UGAACCCUCGUAAACUCCA | 3994 |
| GGAGUUUACGAGGGUUCAA | 3995 | UUGAACCCUCGUAAACUCC | 3996 |
| GAGUUUACGAGGGUUCAAG | 3997 | CUUGAACCCUCGUAAACUC | 3998 |
| AGUUUACGAGGGUUCAAGG | 3999 | CCUUGAACCCUCGUAAACU | 4000 |
| GUUUACGAGGGUUCAAGGU | 4001 | ACCUUGAACCCUCGUAAAC | 4002 |
| UUUACGAGGGUUCAAGGUA | 4003 | UACCUUGAACCCUCGUAAA | 4004 |
| CGAGGGUUCAAGGUAUUUG | 4005 | CAAAUACCUUGAACCCUCG | 4006 |
| GAGGGUUCAAGGUAUUUGG | 4007 | CCAAAUACCUUGAACCCUC | 4008 |
| AGGGUUCAAGGUAUUUGGU | 4009 | ACCAAAUACCUUGAACCCU | 4010 |
| GGGUUCAAGGUAUUUGGUU | 4011 | AACCAAAUACCUUGAACCC | 4012 |
| GGUUCAAGGUAUUUGGUUC | 4013 | GAACCAAAUACCUUGAACC | 4014 |
| GUUCAAGGUAUUUGGUUCA | 4015 | UGAACCAAAUACCUUGAAC | 4016 |
| UUCAAGGUAUUUGGUUCAG | 4017 | CUGAACCAAAUACCUUGAA | 4018 |
| UCAAGGUAUUUGGUUCAGG | 4019 | CCUGAACCAAAUACCUUGA | 4020 |
| CAACUGGCCAGGUCACAGG | 4021 | CCUGUGACCUGGCCAGUUG | 4022 |
| GCCAGGUCACAGGGCAAUC | 4023 | GAUUGCCCUGUGACCUGGC | 4024 |
| CCAGGUCACAGGGCAAUCA | 4025 | UGAUUGCCCUGUGACCUGG | 4026 |
| AGGUCACAGGGCAAUCAAG | 4027 | CUUGAUUGCCCUGUGACCU | 4028 |
| GGUCACAGGGCAAUCAAGU | 4029 | ACUUGAUUGCCCUGUGACC | 4030 |
| GUCACAGGGCAAUCAAGUU | 4031 | AACUUGAUUGCCCUGUGAC | 4032 |
| UCAGGGCAAUCAAGUUA | 4033 | UAACUUGAUUGCCCUGUGA | 4034 |
| CACAGGGCAAUCAAGUUAC | 4035 | GUAACUUGAUUGCCCUGUG | 4036 |
| ACAGGGCAAUCAAGUUACU | 4037 | AGUAACUUGAUUGCCCUGU | 4038 |
| CAGGGCAAUCAAGUUACUC | 4039 | GAGUAACUUGAUUGCCCUG | 4040 |
| AGGGCAAUCAAGUUACUCU | 4041 | AGAGUAACUUGAUUGCCCU | 4042 |
| CAAUCAAGUUACUCUGUGU | 4043 | ACACAGAGUAACUUGAUUG | 4044 |
| AAUCAAGUUACUCUGUGUU | 4045 | AACACAGAGUAACUUGAUU | 4046 |
| AUCAAGUUACUCUGUGUUU | 4047 | AAACACAGAGUAACUUGAU | 4048 |
| ACUCUGUGUUUCUUUGUCA | 4049 | UGACAAAGAAACACAGAGU | 4050 |
| UCUGUGUUUCUUUGUCAGG | 4051 | CCUGACAAAGAAACACAGA | 4052 |
| UGUUUCUUUGUCAGGACAC | 4053 | GUGUCCUGACAAAGAAACA | 4054 |
| AAAGCAGGGAUUGUGUUCA | 4055 | UGAACACAAUCCCUGCUUU | 4056 |
| AAGCAGGGAUUGUGUUCAU | 4057 | AUGAACACAAUCCCUGCUU | 4058 |
| AGCAGGGAUUGUGUUCAUU | 4059 | AAUGAACACAAUCCCUGCU | 4060 |
| GCAGGGAUUGUGUUCAUUU | 4061 | AAAUGAACACAAUCCCUGC | 4062 |
| CAGGGAUUGUGUUCAUUUG | 4063 | CAAAUGAACACAAUCCCUG | 4064 |
| AGGGAUUGUGUUCAUUUGA | 4065 | UCAAAUGAACACAAUCCCU | 4066 |

TABLE 8-continued

| Sense Sequence | SEQ ID NO: | Antisense Sequence | SEQ ID NO: |
|---|---|---|---|
| GUGUUCAUUUGAGGGUUUC | 4067 | GAAACCCUCAAAUGAACAC | 4068 |
| UGUUCAUUUGAGGGUUUCA | 4069 | UGAAACCCUCAAAUGAACA | 4070 |
| GUUCAUUUGAGGGUUUCAC | 4071 | GUGAAACCCUCAAAUGAAC | 4072 |
| UUCAUUUGAGGGUUUCACU | 4073 | AGUGAAACCCUCAAAUGAA | 4074 |
| UCAUUUGAGGGUUUCACUG | 4075 | CAGUGAAACCCUCAAAUGA | 4076 |
| CAUUUGAGGGUUUCACUGU | 4077 | ACAGUGAAACCCUCAAAUG | 4078 |
| AGUCUCAGCUUCCAUGCAA | 4079 | UUGCAUGGAAGCUGAGACU | 4080 |
| UCUCAGCUUCCAUGCAACU | 4081 | AGUUGCAUGGAAGCUGAGA | 4082 |
| CUCAGCUUCCAUGCAACUG | 4083 | CAGUUGCAUGGAAGCUGAG | 4084 |
| UCAGCUUCCAUGCAACUGU | 4085 | ACAGUUGCAUGGAAGCUGA | 4086 |
| CAGCUUCCAUGCAACUGUC | 4087 | GACAGUUGCAUGGAAGCUG | 4088 |
| AGCUUCCAUGCAACUGUCC | 4089 | GGACAGUUGCAUGGAAGCU | 4090 |
| GCUUCCAUGCAACUGUCCA | 4091 | UGGACAGUUGCAUGGAAGC | 4092 |
| CUUCCAUGCAACUGUCCAU | 4093 | AUGGACAGUUGCAUGGAAG | 4094 |
| UUCCAUGCAACUGUCCAUC | 4095 | GAUGGACAGUUGCAUGGAA | 4096 |
| CCAUGCAACUGUCCAUCAC | 4097 | GUGAUGGACAGUUGCAUGG | 4098 |
| CAUGCAACUGUCCAUCACG | 4099 | CGUGAUGGACAGUUGCAUG | 4100 |
| AUGCAACUGUCCAUCACGG | 4101 | CCGUGAUGGACAGUUGCAU | 4102 |
| UGCAACUGUCCAUCACGGC | 4103 | GCCGUGAUGGACAGUUGCA | 4104 |
| GCAACUGUCCAUCACGGCU | 4105 | AGCCGUGAUGGACAGUUGC | 4106 |
| CAACUGUCCAUCACGGCUG | 4107 | CAGCCGUGAUGGACAGUUG | 4108 |
| AACUGUCCAUCACGGCUGC | 4109 | GCAGCCGUGAUGGACAGUU | 4110 |
| ACUGUCCAUCACGGCUGCA | 4111 | UGCAGCCGUGAUGGACAGU | 4112 |
| CUGUCCAUCACGGCUGCAA | 4113 | UUGCAGCCGUGAUGGACAG | 4114 |
| UGUCCAUCACGGCUGCAAC | 4115 | GUUGCAGCCGUGAUGGACA | 4116 |
| GUCCAUCACGGCUGCAACU | 4117 | AGUUGCAGCCGUGAUGGAC | 4118 |
| UCCAUCACGGCUGCAACUG | 4119 | CAGUUGCAGCCGUGAUGGA | 4120 |
| CCAUCACGGCUGCAACUGA | 4121 | UCAGUUGCAGCCGUGAUGG | 4122 |
| CAUCACGGCUGCAACUGAA | 4123 | UUCAGUUGCAGCCGUGAUG | 4124 |
| ACAGCGCACCAGAAGCUAA | 4125 | UUAGCUUCUGGUGCGCUGU | 4126 |
| CAGCGCACCAGAAGCUAAA | 4127 | UUUAGCUUCUGGUGCGCUG | 4128 |
| AGCGCACCAGAAGCUAAAG | 4129 | CUUUAGCUUCUGGUGCGCU | 4130 |
| GCGCACCAGAAGCUAAAGU | 4131 | ACUUUAGCUUCUGGUGCGC | 4132 |
| CGCACCAGAAGCUAAAGUC | 4133 | GACUUUAGCUUCUGGUGCG | 4134 |
| GCACCAGAAGCUAAAGUCU | 4135 | AGACUUUAGCUUCUGGUGC | 4136 |
| CACCAGAAGCUAAAGUCUU | 4137 | AAGACUUUAGCUUCUGGUG | 4138 |
| ACCAGAAGCUAAAGUCUUG | 4139 | CAAGACUUUAGCUUCUGGU | 4140 |
| CCAGAAGCUAAAGUCUUGA | 4141 | UCAAGACUUUAGCUUCUGG | 4142 |
| CAGAAGCUAAAGUCUUGAU | 4143 | AUCAAGACUUUAGCUUCUG | 4144 |
| AGAAGCUAAAGUCUUGAUG | 4145 | CAUCAAGACUUUAGCUUCU | 4146 |
| GAAGCUAAAGUCUUGAUGC | 4147 | GCAUCAAGACUUUAGCUUC | 4148 |
| AAGCUAAAGUCUUGAUGCC | 4149 | GGCAUCAAGACUUUAGCUU | 4150 |
| AGCUAAAGUCUUGAUGCCA | 4151 | UGGCAUCAAGACUUUAGCU | 4152 |
| CCCAUUCACAUCUCUGUCA | 4153 | UGACAGAGAUGUGAAUGGG | 4154 |
| UUCACAUCUCUGUCACGUC | 4155 | GACGUGACAGAGAUGUGAA | 4156 |
| UCACAUCUCUGUCACGUCC | 4157 | GGACGUGACAGAGAUGUGA | 4158 |
| CACAUCUCUGUCACGUCCA | 4159 | UGGACGUGACAGAGAUGUG | 4160 |
| UCUCUGUCACGUCCACUAA | 4161 | UUAGUGGACGUGACAGAGA | 4162 |
| CUCUGUCACGUCCACUAAU | 4163 | AUUAGUGGACGUGACAGAG | 4164 |
| UCUGUCACGUCCACUAAUC | 4165 | GAUUAGUGGACGUGACAGA | 4166 |
| CUGUCACGUCCACUAAUCG | 4167 | CGAUUAGUGGACGUGACAG | 4168 |
| UGUCACGUCCACUAAUCGG | 4169 | CCGAUUAGUGGACGUGACA | 4170 |
| GUCACGUCCACUAAUCGGC | 4171 | GCCGAUUAGUGGACGUGAC | 4172 |
| UCACGUCCACUAAUCGGCA | 4173 | UGCCGAUUAGUGGACGUGA | 4174 |
| CACGUCCACUAAUCGGCAA | 4175 | UUGCCGAUUAGUGGACGUG | 4176 |
| ACGUCCACUAAUCGGCAAA | 4177 | UUUGCCGAUUAGUGGACGU | 4178 |
| CGUCCACUAAUCGGCAAAA | 4179 | UUUUGCCGAUUAGUGGACG | 4180 |
| GUCCACUAAUCGGCAAAAG | 4181 | CUUUUGCCGAUUAGUGGAC | 4182 |
| UCCACUAAUCGGCAAAAGG | 4183 | CCUUUUGCCGAUUAGUGGA | 4184 |
| CCACUAAUCGGCAAAAGGA | 4185 | UCCUUUUGCCGAUUAGUGG | 4186 |
| CACUAAUCGGCAAAAGGAG | 4187 | CUCCUUUUGCCGAUUAGUG | 4188 |
| AGAAGAUGACCUAAGUGUG | 4189 | CACACUUAGGUCAUCUUCU | 4190 |
| GAAGAUGACCUAAGUGUGA | 4191 | UCACACUUAGGUCAUCUUC | 4192 |
| AAGAUGACCUAAGUGUGAC | 4193 | GUCACACUUAGGUCAUCUU | 4194 |
| AGAUGACCUAAGUGUGACU | 4195 | AGUCACACUUAGGUCAUCU | 4196 |
| GAUGACCUAAGUGUGACUG | 4197 | CAGUCACACUUAGGUCAUC | 4198 |
| AUGACCUAAGUGUGACUGC | 4199 | GCAGUCACACUUAGGUCAU | 4200 |
| UGACCUAAGUGUGACUGCA | 4201 | UGCAGUCACACUUAGGUCA | 4202 |
| AAAAUGAAGCCAGAGCAGU | 4203 | ACUGCUCUGGCUUCAUUUU | 4204 |
| UCCGACCAAGGAGGAAGGA | 4205 | UCCUUCCUCCUUGGUCGGA | 4206 |
| CCGACCAAGGAGGAAGGAA | 4207 | UUCCUUCCUCCUUGGUCGG | 4208 |
| AGAGCAGGUAAGCAGGAAG | 4209 | CUUCCUGCUUACCUGCUCU | 4210 |
| GAGCAGGUAAGCAGGAAGG | 4211 | CCUUCCUGCUUACCUGCUC | 4212 |
| AGGUAAGCAGGAAGGCCAG | 4213 | CUGGCCUUCCUGCUUACCU | 4214 |
| AGCAGGAAGGCCAGUGUCC | 4215 | GGACACUGGCCUUCCUGCU | 4216 |
| CAGGAAGGCCAGUGUCCCA | 4217 | UGGGACACUGGCCUUCCUG | 4218 |

TABLE 8-continued

| Sense Sequence | SEQ ID NO: | Antisense Sequence | SEQ ID NO: |
|---|---|---|---|
| UCCCAGACAGGACCCUAAU | 4219 | AUUAGGGUCCUGUCUGGGA | 4220 |
| CCCAGACAGGACCCUAAUG | 4221 | CAUUAGGGUCCUGUCUGGG | 4222 |
| CCAGACAGGACCCUAAUGA | 4223 | UCAUUAGGGUCCUGUCUGG | 4224 |
| CAGACAGGACCCUAAUGAU | 4225 | AUCAUUAGGGUCCUGUCUG | 4226 |
| AGACAGGACCCUAAUGAUC | 4227 | GAUCAUUAGGGUCCUGUCU | 4228 |
| GACAGGACCCUAAUGAUCC | 4229 | GGAUCAUUAGGGUCCUGUC | 4230 |
| GGACCCUAAUGAUCCUGAA | 4231 | UUCAGGAUCAUUAGGGUCC | 4232 |
| CCUAAUGAUCCUGAAUCCA | 4233 | UGGAUUCAGGAUCAUUAGG | 4234 |
| CUAAUGAUCCUGAAUCCAU | 4235 | AUGGAUUCAGGAUCAUUAG | 4236 |
| UGAUCCUGAAUCCAUGUAU | 4237 | AUACAUGGAUUCAGGAUCA | 4238 |
| GAUCCUGAAUCCAUGUAUC | 4239 | GAUACAUGGAUUCAGGAUC | 4240 |
| AUCCUGAAUCCAUGUAUCA | 4241 | UGAUACAUGGAUUCAGGAU | 4242 |
| UCCAUGUAUCAGGAUCCAU | 4243 | AUGGAUCCUGAUACAUGGA | 4244 |
| CCAUGUAUCAGGAUCCAUC | 4245 | GAUGGAUCCUGAUACAUGG | 4246 |
| CAUGUAUCAGGAUCCAUCC | 4247 | GGAUGGAUCCUGAUACAUG | 4248 |
| UCACCUCUCAUUUUCCAAA | 4249 | UUUGGAAAAUGAGAGGUGA | 4250 |
| UCCAAAGCCCUGCCAUGCU | 4251 | AGCAUGGCAGGGCUUUGGA | 4252 |
| CCAAAGCCCUGCCAUGCUG | 4253 | CAGCAUGGCAGGGCUUUGG | 4254 |
| CAUGCUGCCAUCCCACUUC | 4255 | GAAGUGGGAUGGCAGCAUG | 4256 |
| AUGCUGCCAUCCCACUUCC | 4257 | GGAAGUGGGAUGGCAGCAU | 4258 |
| UGCUGCCAUCCCACUUCCC | 4259 | GGGAAGUGGGAUGGCAGCA | 4260 |
| CGGGUUCCCUUUUCCUAAA | 4261 | UUUAGGAAAAGGGAACCCG | 4262 |
| AGCUGCAGCUUAUGGCUUC | 4263 | GAAGCCAUAAGCUGCAGCU | 4264 |
| GCUGCAGCUUAUGGCUUCU | 4265 | AGAAGCCAUAAGCUGCAGC | 4266 |
| CUGCAGCUUAUGGCUUCUC | 4267 | GAGAAGCCAUAAGCUGCAG | 4268 |
| UGCAGCUUAUGGCUUCUCC | 4269 | GGAGAAGCCAUAAGCUGCA | 4270 |
| GCAGCUUAUGGCUUCUCCA | 4271 | UGGAGAAGCCAUAAGCUGC | 4272 |
| CAGCUUAUGGCUUCUCCAG | 4273 | CUGGAGAAGCCAUAAGCUG | 4274 |
| AGCUUAUGGCUUCUCCAGU | 4275 | ACUGGAGAAGCCAUAAGCU | 4276 |
| GCUUAUGGCUUCUCCAGUA | 4277 | UACUGGAGAAGCCAUAAGC | 4278 |
| CUUAUGGCUUCUCCAGUAG | 4279 | CUACUGGAGAAGCCAUAAG | 4280 |
| UUAUGGCUUCUCCAGUAGG | 4281 | CCUACUGGAGAAGCCAUAA | 4282 |
| UAUGGCUUCUCCAGUAGGU | 4283 | ACCUACUGGAGAAGCCAUA | 4284 |
| AUGGCUUCUCCAGUAGGUG | 4285 | CACCUACUGGAGAAGCCAU | 4286 |
| UGGCUUCUCCAGUAGGUGG | 4287 | CCACCUACUGGAGAAGCCA | 4288 |
| GGCUUCUCCAGUAGGUGGC | 4289 | GCCACCUACUGGAGAAGCC | 4290 |
| GCUUCUCCAGUAGGUGGCA | 4291 | UGCCACCUACUGGAGAAGC | 4292 |
| CUUCUCCAGUAGGUGGCAG | 4293 | CUGCCACCUACUGGAGAAG | 4294 |
| UUCUCCAGUAGGUGGCAGC | 4295 | GCUGCCACCUACUGGAGAA | 4296 |
| UCUCCAGUAGGUGGCAGCA | 4297 | UGCUGCCACCUACUGGAGA | 4298 |
| CUCCAGUAGGUGGCAGCAC | 4299 | GUGCUGCCACCUACUGGAG | 4300 |
| ACACCAGAAGUCACAUUUC | 4301 | GAAAUGUGACUUCUGGUGU | 4302 |
| GAAGUCACAUUUCAUCCUU | 4303 | AAGGAUGAAAUGUGACUUC | 4304 |
| AAGUCACAUUUCAUCCUUU | 4305 | AAAGGAUGAAAUGUGACUU | 4306 |
| AGUCACAUUUCAUCCUUUU | 4307 | AAAAGGAUGAAAUGUGACU | 4308 |
| UUUCAUCCUUUUACAUGGU | 4309 | ACCAUGUAAAAGGAUGAAA | 4310 |
| UUCAUCCUUUUACAUGGUU | 4311 | AACCAUGUAAAAGGAUGAA | 4312 |
| UCAUCCUUUUACAUGGUUC | 4313 | GAACCAUGUAAAAGGAUGA | 4314 |
| CAUCCUUUUACAUGGUUCC | 4315 | GGAACCAUGUAAAAGGAUG | 4316 |
| UGGUUCCCAUCUACCCUCA | 4317 | UGAGGGUAGAUGGGAACCA | 4318 |
| GGUUCCCAUCUACCCUCAC | 4319 | GUGAGGGUAGAUGGGAACC | 4320 |
| GUUCCCAUCUACCCUCACA | 4321 | UGUGAGGGUAGAUGGGAAC | 4322 |
| GGCAAUUCUUCCUCCAGGA | 4323 | UCCUGGAGGAAGAAUUGCC | 4324 |
| GCAAUUCUUCCUCCAGGAC | 4325 | GUCCUGGAGGAAGAAUUGC | 4326 |
| CAAUUCUUCCUCCAGGACC | 4327 | GGUCCUGGAGGAAGAAUUG | 4328 |
| AAUUCUUCCUCCAGGACCC | 4329 | GGGUCCUGGAGGAAGAAUU | 4330 |
| CCCUUGGACUUUGCCCUUC | 4331 | GAAGGGCAAAGUCCAAGGG | 4332 |
| CCUUGGACUUUGCCCUUCU | 4333 | AGAAGGGCAAAGUCCAAGG | 4334 |
| CUUGGACUUUGCCCUUCUU | 4335 | AAGAAGGGCAAAGUCCAAG | 4336 |
| UUGGACUUUGCCCUUCUUA | 4337 | UAAGAAGGGCAAAGUCCAA | 4338 |
| UGGACUUUGCCCUUCUUAC | 4339 | GUAAGAAGGGCAAAGUCCA | 4340 |
| GGACUUUGCCCUUCUUACU | 4341 | AGUAAGAAGGGCAAAGUCC | 4342 |
| UUUGCCCUUCUUACUGGCC | 4343 | GGCCAGUAAGAAGGGCAAA | 4344 |
| UUGCCCUUCUUACUGGCCA | 4345 | UGGCCAGUAAGAAGGGCAA | 4346 |
| UGCCCUUCUUACUGGCCAG | 4347 | CUGGCCAGUAAGAAGGGCA | 4348 |
| UCUUACUGGCCAGGCAGGG | 4349 | CCCUGCCUGGCCAGUAAGA | 4350 |
| GGCCAGAGUCCAGGCUUGA | 4351 | UCAAGCCUGGACUCUGGCC | 4352 |
| GCCAGAGUCCAGGCUUGAC | 4353 | GUCAAGCCUGGACUCUGGC | 4354 |
| GUCCAGGCUUGACUCAUUC | 4355 | GAAUGAGUCAAGCCUGGAC | 4356 |
| AGGCUUGACUCAUUCCCAC | 4357 | GUGGGAAUGAGUCAAGCCU | 4358 |
| GACUCAUUCCCACCUUGUC | 4359 | GACAAGGUGGGAAUGAGUC | 4360 |
| ACUCAUUCCCACCUUGUCC | 4361 | GGACAAGGUGGGAAUGAGU | 4362 |
| UCAUUCCCACCUUGUCCUG | 4363 | CAGGACAAGGUGGGAAUGA | 4364 |
| CACCUUGUCCUGGGCUGAG | 4365 | CUCAGCCCAGGACAAGGUG | 4366 |
| ACCACCCAGCCCAGAAGUU | 4367 | AACUUCUGGGCUGGGUGGU | 4368 |
| CCACCCAGCCCAGAAGUUC | 4369 | GAACUUCUGGGCUGGGUGG | 4370 |

TABLE 8-continued

| Sense Sequence | SEQ ID NO: | Antisense Sequence | SEQ ID NO: |
|---|---|---|---|
| CACCCAGCCCAGAAGUUCC | 4371 | GGAACUUCUGGGCUGGGUG | 4372 |
| ACCCAGCCCAGAAGUUCCA | 4373 | UGGAACUUCUGGGCUGGGU | 4374 |
| CCAGAAGUUCCAGGGAAGG | 4375 | CCUUCCCUGGAACUUCUGG | 4376 |
| CAGAAGUUCCAGGGAAGGA | 4377 | UCCUUCCCUGGAACUUCUG | 4378 |
| AACUCUCCGGUCCACCAUG | 4379 | CAUGGUGGACCGGAGAGUU | 4380 |
| ACUCUCCGGUCCACCAUGG | 4381 | CCAUGGUGGACCGGAGAGU | 4382 |
| CACCAUGGAGUACCUCUCA | 4383 | UGAGAGGUACUCCAUGGUG | 4384 |
| ACCAUGGAGUACCUCUCAG | 4385 | CUGAGAGGUACUCCAUGGU | 4386 |
| UGGAGUACCUCUCAGCUCU | 4387 | AGAGCUGAGAGGUACUCCA | 4388 |
| GGAGUACCUCUCAGCUCUG | 4389 | CAGAGCUGAGAGGUACUCC | 4390 |
| GAGUACCUCUCAGCUCUGA | 4391 | UCAGAGCUGAGAGGUACUC | 4392 |
| AGUACCUCUCAGCUCUGAA | 4393 | UUCAGAGCUGAGAGGUACU | 4394 |
| CCAGUGACUUACUCAGGUG | 4395 | CACCUGAGUAAGUCACUGG | 4396 |
| CAGUGACUUACUCAGGUGA | 4397 | UCACCUGAGUAAGUCACUG | 4398 |
| AGUGACUUACUCAGGUGAC | 4399 | GUCACCUGAGUAAGUCACU | 4400 |
| GUGACUUACUCAGGUGACU | 4401 | AGUCACCUGAGUAAGUCAC | 4402 |
| UGACUUACUCAGGUGACUG | 4403 | CAGUCACCUGAGUAAGUCA | 4404 |
| GACUUACUCAGGUGACUGC | 4405 | GCAGUCACCUGAGUAAGUC | 4406 |
| ACUUACUCAGGUGACUGCU | 4407 | AGCAGUCACCUGAGUAAGU | 4408 |
| CUUACUCAGGUGACUGCUA | 4409 | UAGCAGUCACCUGAGUAAG | 4410 |
| UUACUCAGGUGACUGCUAA | 4411 | UUAGCAGUCACCUGAGUAA | 4412 |
| UACUCAGGUGACUGCUAAC | 4413 | GUUAGCAGUCACCUGAGUA | 4414 |
| ACUCAGGUGACUGCUAACC | 4415 | GGUUAGCAGUCACCUGAGU | 4416 |
| CUCAGGUGACUGCUAACCC | 4417 | GGGUUAGCAGUCACCUGAG | 4418 |
| GGUGACUGCUAACCCUCCG | 4419 | CGGAGGGUUAGCAGUCACC | 4420 |
| GUGACUGCUAACCCUCCGC | 4421 | GCGGAGGGUUAGCAGUCAC | 4422 |
| UGACUGCUAACCCUCCGCU | 4423 | AGCGGAGGGUUAGCAGUCA | 4424 |
| GACUGCUAACCCUCCGCUC | 4425 | GAGCGGAGGGUUAGCAGUC | 4426 |
| ACUGCUAACCCUCCGCUCU | 4427 | AGAGCGGAGGGUUAGCAGU | 4428 |
| CUGCUAACCCUCCGCUCUA | 4429 | UAGAGCGGAGGGUUAGCAG | 4430 |
| UGCUAACCCUCCGCUCUAC | 4431 | GUAGAGCGGAGGGUUAGCA | 4432 |
| AACCCUCCGCUCUACCCUC | 4433 | GAGGGUAGAGCGGAGGGUU | 4434 |
| ACUCCACAGUGGGCUUGUC | 4435 | GACAAGCCCACUGUGGAGU | 4436 |
| CUCCACAGUGGGCUUGUCA | 4437 | UGACAAGCCCACUGUGGAG | 4438 |
| UCCACAGUGGGCUUGUCAA | 4439 | UUGACAAGCCCACUGUGGA | 4440 |
| CCACAGUGGGCUUGUCAAG | 4441 | CUUGACAAGCCCACUGUGG | 4442 |
| GUCAAGCUCCUGAGCCACC | 4443 | GGUGGCUCAGGAGCUUGAC | 4444 |
| CCAUGGUCUCUCCCUCAUC | 4445 | GAUGAGGGAGAGACCAUGG | 4446 |
| CAUGGUCUCUCCCUCAUCC | 4447 | GGAUGAGGGAGAGACCAUG | 4448 |
| AUGGUCUCUCCCUCAUCCC | 4449 | GGGAUGAGGGAGAGACCAU | 4450 |
| UCUCUCCCUCAUCCCUAAU | 4451 | AUUAGGGAUGAGGGAGAGA | 4452 |
| CUCUCCCUCAUCCCUAAUC | 4453 | GAUUAGGGAUGAGGGAGAG | 4454 |
| UCUCCCUCAUCCCUAAUCG | 4455 | CGAUUAGGGAUGAGGGAGA | 4456 |
| CUCCCUCAUCCCUAAUCGA | 4457 | UCGAUUAGGGAUGAGGGAG | 4458 |
| UCCCUCAUCCCUAAUCGAU | 4459 | AUCGAUUAGGGAUGAGGGA | 4460 |
| CCCUCAUCCCUAAUCGAUA | 4461 | UAUCGAUUAGGGAUGAGGG | 4462 |
| CCUCAUCCCUAAUCGAUAA | 4463 | UUAUCGAUUAGGGAUGAGG | 4464 |
| CUCAUCCCUAAUCGAUAAA | 4465 | UUUAUCGAUUAGGGAUGAG | 4466 |
| AACCUAGAUCUCUCCCUCC | 4467 | GGAGGGAGAGAUCUAGGUU | 4468 |
| ACCUAGAUCUCUCCCUCCC | 4469 | GGGAGGGAGAGAUCUAGGU | 4470 |
| CUAGAUCUCUCCCUCCCUA | 4471 | UAGGGAGGGAGAGAUCUAG | 4472 |
| UAGAUCUCUCCCUCCCUAG | 4473 | CUAGGGAGGGAGAGAUCUA | 4474 |
| AGAUCUCUCCCUCCCUAGC | 4475 | GCUAGGGAGGGAGAGAUCU | 4476 |
| GAUCUCUCCCUCCCUAGCC | 4477 | GGCUAGGGAGGGAGAGAUC | 4478 |
| AUCUCUCCCUCCCUAGCCC | 4479 | GGGCUAGGGAGGGAGAGAU | 4480 |
| UAGCCCUCUAGCCACUCUA | 4481 | UAGAGUGGCUAGAGGGCUA | 4482 |
| AGCCCUCUAGCCACUCUAC | 4483 | GUAGAGUGGCUAGAGGGCU | 4484 |
| CUCUAGCCACUCUACCCUC | 4485 | GAGGGUAGAGUGGCUAGAG | 4486 |
| UCUAGCCACUCUACCCUCA | 4487 | UGAGGGUAGAGUGGCUAGA | 4488 |
| CUAGCCACUCUACCCUCAU | 4489 | AUGAGGGUAGAGUGGCUAG | 4490 |
| UAGCCACUCUACCCUCAUC | 4491 | GAUGAGGGUAGAGUGGCUA | 4492 |
| AGCCACUCUACCCUCAUCA | 4493 | UGAUGAGGGUAGAGUGGCU | 4494 |
| GCCACUCUACCCUCAUCAU | 4495 | AUGAUGAGGGUAGAGUGGC | 4496 |
| CCACUCUACCCUCAUCAUG | 4497 | CAUGAUGAGGGUAGAGUGG | 4498 |
| CACUCUACCCUCAUCAUGC | 4499 | GCAUGAUGAGGGUAGAGUG | 4500 |
| ACUCUACCCUCAUCAUGCC | 4501 | GGCAUGAUGAGGGUAGAGU | 4502 |
| CUCUACCCUCAUCAUGCCC | 4503 | GGGCAUGAUGAGGGUAGAG | 4504 |
| UCUACCCUCAUCAUGCCCU | 4505 | AGGGCAUGAUGAGGGUAGA | 4506 |
| CUACCCUCAUCAUGCCCUU | 4507 | AAGGGCAUGAUGAGGGUAG | 4508 |
| UACCCUCAUCAUGCCCUUU | 4509 | AAAGGGCAUGAUGAGGGUA | 4510 |
| ACCCUCAUCAUGCCCUUUA | 4511 | UAAAGGGCAUGAUGAGGGU | 4512 |
| CCCUCAUCAUGCCCUUUAC | 4513 | GUAAAGGGCAUGAUGAGGG | 4514 |
| CUCAUCAUGCCCUUUACAC | 4515 | GUGUAAAGGGCAUGAUGAG | 4516 |
| UCAUCAUGCCCUUUACACU | 4517 | AGUGUAAAGGGCAUGAUGA | 4518 |
| CCCUUCUUGACUUUUCUUC | 4519 | GAAGAAAAGUCAAGAAGGG | 4520 |
| CUUCUUGACUUUUCUUCUC | 4521 | GAGAAGAAAAGUCAAGAAG | 4522 |

TABLE 8-continued

| Sense Sequence | SEQ ID NO: | Antisense Sequence | SEQ ID NO: |
|---|---|---|---|
| GACUUUUCUUCUCAACUAC | 4523 | GUAGUUGAGAAGAAAAGUC | 4524 |
| ACUUUUCUUCUCAACUACC | 4525 | GGUAGUUGAGAAGAAAAGU | 4526 |
| CUUUUCUUCUCAACUACCA | 4527 | UGGUAGUUGAGAAGAAAAG | 4528 |
| UUUUCUUCUCAACUACCAG | 4529 | CUGGUAGUUGAGAAGAAAA | 4530 |
| UAUCUAAUAUAAGCUCGGA | 4531 | UCCGAGCUUAUAUUAGAUA | 4532 |
| AUCUAAUAUAAGCUCGGAG | 4533 | CUCCGAGCUUAUAUUAGAU | 4534 |
| UCUAAUAUAAGCUCGGAGU | 4535 | ACUCCGAGCUUAUAUUAGA | 4536 |
| CUAAUAUAAGCUCGGAGUU | 4537 | AACUCCGAGCUUAUAUUAG | 4538 |
| UAAUAUAAGCUCGGAGUUU | 4539 | AAACUCCGAGCUUAUAUUA | 4540 |
| AAUAUAAGCUCGGAGUUUG | 4541 | CAAACUCCGAGCUUAUAUU | 4542 |
| AUAUAAGCUCGGAGUUUGG | 4543 | CCAAACUCCGAGCUUAUAU | 4544 |
| UAUAAGCUCGGAGUUUGGA | 4545 | UCCAAACUCCGAGCUUAUA | 4546 |
| AUAAGCUCGGAGUUUGGAC | 4547 | GUCCAAACUCCGAGCUUAU | 4548 |
| UAAGCUCGGAGUUUGGACG | 4549 | CGUCCAAACUCCGAGCUUA | 4550 |
| AAGCUCGGAGUUUGGACGG | 4551 | CCGUCCAAACUCCGAGCUU | 4552 |
| AGCUCGGAGUUUGGACGGA | 4553 | UCCGUCCAAACUCCGAGCU | 4554 |
| GCUCGGAGUUUGGACGGAG | 4555 | CUCCGUCCAAACUCCGAGC | 4556 |
| CUCGGAGUUUGGACGGAGG | 4557 | CCUCCGUCCAAACUCCGAG | 4558 |
| UCGGAGUUUGGACGGAGGG | 4559 | CCCUCCGUCCAAACUCCGA | 4560 |
| CGGAGUUUGGACGGAGGGU | 4561 | ACCCUCCGUCCAAACUCCG | 4562 |
| UUUGGACGGAGGGUCUGGA | 4563 | UCCAGACCCUCCGUCCAAA | 4564 |
| CCCAGCGACCUUUCCGUGU | 4565 | ACACGGAAAGGUCGCUGGG | 4566 |
| CCAGCGACCUUUCCGUGUC | 4567 | GACACGGAAAGGUCGCUGG | 4568 |
| CAGCGACCUUUCCGUGUCU | 4569 | AGACACGGAAAGGUCGCUG | 4570 |
| AGCGACCUUUCCGUGUCUG | 4571 | CAGACACGGAAAGGUCGCU | 4572 |
| GCGACCUUUCCGUGUCUGU | 4573 | ACAGACACGGAAAGGUCGC | 4574 |
| CGACCUUUCCGUGUCUGUG | 4575 | CACAGACACGGAAAGGUCG | 4576 |
| CUUUCCGUGUCUGUGAUCA | 4577 | UGAUCACAGACACGGAAAG | 4578 |
| UUUCCGUGUCUGUGAUCAC | 4579 | GUGAUCACAGACACGGAAA | 4580 |
| UUCCGUGUCUGUGAUCACA | 4581 | UGUGAUCACAGACACGGAA | 4582 |
| AAGGCCUGACAGCUGCCAC | 4583 | GUGGCAGCUGUCAGGCCUU | 4584 |
| GCCAGGAGCUGCUAGCCAA | 4585 | UUGGCUAGCAGCUCCUGGC | 4586 |
| CCAGGAGCUGCUAGCCAAA | 4587 | UUUGGCUAGCAGCUCCUGG | 4588 |
| GAGCUGCUAGCCAAAGUAA | 4589 | UUACUUUGGCUAGCAGCUC | 4590 |
| AGCUGCUAGCCAAAGUAAG | 4591 | CUUACUUUGGCUAGCAGCU | 4592 |
| GCUGCUAGCCAAAGUAAGU | 4593 | ACUUACUUUGGCUAGCAGC | 4594 |
| CUGCUAGCCAAAGUAAGUA | 4595 | UACUUACUUUGGCUAGCAG | 4596 |
| UGCUAGCCAAAGUAAGUAG | 4597 | CUACUUACUUUGGCUAGCA | 4598 |
| GCUAGCCAAAGUAAGUAGG | 4599 | CCUACUUACUUUGGCUAGC | 4600 |
| UAGCCAAAGUAAGUAGGCC | 4601 | GGCCUACUUACUUUGGCUA | 4602 |
| AGCCAAAGUAAGUAGGCCA | 4603 | UGGCCUACUUACUUUGGCU | 4604 |
| GCCAAAGUAAGUAGGCCAA | 4605 | UUGGCCUACUUACUUUGGC | 4606 |
| CCAAAGUAAGUAGGCCAAG | 4607 | CUUGGCCUACUUACUUUGG | 4608 |
| CAAAGUAAGUAGGCCAAGU | 4609 | ACUUGGCCUACUUACUUUG | 4610 |
| AAAGUAAGUAGGCCAAGUU | 4611 | AACUUGGCCUACUUACUUU | 4612 |
| AAGUAAGUAGGCCAAGUUC | 4613 | GAACUUGGCCUACUUACUU | 4614 |
| AGUAAGUAGGCCAAGUUCC | 4615 | GGAACUUGGCCUACUUACU | 4616 |
| GUAAGUAGGCCAAGUUCCU | 4617 | AGGAACUUGGCCUACUUAC | 4618 |
| UAAGUAGGCCAAGUUCCUC | 4619 | GAGGAACUUGGCCUACUUA | 4620 |
| UAGGCCAAGUUCCUCGGUU | 4621 | AACCGAGGAACUUGGCCUA | 4622 |
| AGGCCAAGUUCCUCGGUUC | 4623 | GAACCGAGGAACUUGGCCU | 4624 |
| GGCCAAGUUCCUCGGUUCC | 4625 | GGAACCGAGGAACUUGGCC | 4626 |
| GCCAAGUUCCUCGGUUCCU | 4627 | AGGAACCGAGGAACUUGGC | 4628 |
| CCAAGUUCCUCGGUUCCUA | 4629 | UAGGAACCGAGGAACUUGG | 4630 |
| CAAGUUCCUCGGUUCCUAU | 4631 | AUAGGAACCGAGGAACUUG | 4632 |
| AAGUUCCUCGGUUCCUAUA | 4633 | UAUAGGAACCGAGGAACUU | 4634 |
| AGUUCCUCGGUUCCUAUAG | 4635 | CUAUAGGAACCGAGGAACU | 4636 |
| GUUCCUCGGUUCCUAUAGC | 4637 | GCUAUAGGAACCGAGGAAC | 4638 |
| UUCCUCGGUUCCUAUAGCA | 4639 | UGCUAUAGGAACCGAGGAA | 4640 |
| UCCUCGGUUCCUAUAGCAG | 4641 | CUGCUAUAGGAACCGAGGA | 4642 |
| CAGUGGCAACUUGUGAUGA | 4643 | UCAUCACAAGUUGCCACUG | 4644 |
| AGUGGCAACUUGUGAUGAU | 4645 | AUCAUCACAAGUUGCCACU | 4646 |
| GUGGCAACUUGUGAUGAUG | 4647 | CAUCAUCACAAGUUGCCAC | 4648 |
| GGCAACUUGUGAUGAUGGA | 4649 | UCCAUCAUCACAAGUUGCC | 4650 |
| ACUUGUGAUGAUGGAGCAG | 4651 | CUGCUCCAUCAUCACAAGU | 4652 |
| CUUGUGAUGAUGGAGCAGA | 4663 | UCUGCUCCAUCAUCACAAG | 4654 |
| GUGAUGAUGGAGCAGAGGG | 4666 | CCCUCUGCUCCAUCAUCAC | 4656 |
| UGAUGAUGGAGCAGAGGGC | 4667 | GCCCUCUGCUCCAUCAUCA | 4658 |
| UGGAGCAGAGGGCUGAAGU | 4659 | ACUUCAGCCCUCUGCUCCA | 4660 |
| GGAGCAGAGGGCUGAAGUC | 4661 | GACUUCAGCCCUCUGCUCC | 4662 |
| GAGCAGAGGGCUGAAGUCA | 4663 | UGACUUCAGCCCUCUGCUC | 4664 |
| CUAAAAGCAGCGGAGUGGG | 4665 | CCCACUCCGCUGCUUUUAG | 4666 |
| UAAAAGCAGCGGAGUGGGC | 4667 | GCCCACUCCGCUGCUUUUA | 4668 |
| AAAAGCAGCGGAGUGGGCC | 4669 | GGCCCACUCCGCUGCUUUU | 4670 |
| AAAGCAGCGGAGUGGGCCU | 4671 | AGGCCCACUCCGCUGCUUU | 4672 |
| AAGCAGCGGAGUGGGCCUA | 4673 | UAGGCCCACUCCGCUGCUU | 4674 |

TABLE 8-continued

| Sense Sequence | SEQ ID NO: | Antisense Sequence | SEQ ID NO: |
|---|---|---|---|
| AGCAGCGGAGUGGGCCUAA | 4675 | UUAGGCCCACUCCGCUGCU | 4676 |
| GCAGCGGAGUGGGCCUAAU | 4677 | AUUAGGCCCACUCCGCUGC | 4678 |
| CAGCGGAGUGGGCCUAAUG | 4679 | CAUUAGGCCCACUCCGCUG | 4680 |
| AGCGGAGUGGGCCUAAUGA | 4681 | UCAUUAGGCCCACUCCGCU | 4682 |
| GCGGAGUGGGCCUAAUGAG | 4683 | CUCAUUAGGCCCACUCCGC | 4684 |
| AGUGGGCCUAAUGAGCUCU | 4685 | AGAGCUCAUUAGGCCCACU | 4686 |
| GUGGGCCUAAUGAGCUCUG | 4687 | CAGAGCUCAUUAGGCCCAC | 4688 |
| UGGGCCUAAUGAGCUCUGG | 4689 | CCAGAGCUCAUUAGGCCCA | 4690 |
| GGGCCUAAUGAGCUCUGGU | 4691 | ACCAGAGCUCAUUAGGCCC | 4692 |
| GGCCUAAUGAGCUCUGGUC | 4693 | GACCAGAGCUCAUUAGGCC | 4694 |
| GCCUAAUGAGCUCUGGUCA | 4695 | UGACCAGAGCUCAUUAGGC | 4696 |
| CCUAAUGAGCUCUGGUCAA | 4697 | UUGACCAGAGCUCAUUAGG | 4698 |
| CUAAUGAGCUCUGGUCAAU | 4699 | AUUGACCAGAGCUCAUUAG | 4700 |
| UAAUGAGCUCUGGUCAAUU | 4701 | AAUUGACCAGAGCUCAUUA | 4702 |
| AAUGAGCUCUGGUCAAUUU | 4703 | AAAUUGACCAGAGCUCAUU | 4704 |
| AUGAGCUCUGGUCAAUUUG | 4705 | CAAAUUGACCAGAGCUCAU | 4706 |
| UGAGCUCUGGUCAAUUUGU | 4707 | ACAAAUUGACCAGAGCUCA | 4708 |
| CUGGUCAAUUUGUUCAUUU | 4709 | AAAUGAACAAAUUGACCAG | 4710 |
| CAAUUUGUUCAUUUCCAC | 4711 | GUGGAAAUGAACAAAUUG | 4712 |
| AGUGAGCUUUUCUAUGGGA | 4713 | UCCCAUAGAAAAGCUCACU | 4714 |
| AGCUUUUCUAUGGGAGCAG | 4715 | CUGCUCCCAUAGAAAAGCU | 4716 |
| GAAUUCAGAAGCUAGUAUG | 4717 | CAUACUAGCUUCUGAAUUC | 4718 |
| AUUCAGAAGCUAGUAUGGA | 4719 | UCCAUACUAGCUUCUGAAU | 4720 |
| UUCAGAAGCUAGUAUGGAA | 4721 | UUCCAUACUAGCUUCUGAA | 4722 |
| AAAGGUGAUUUGUGUGACA | 4728 | UGUCACACAAAUCACCUUU | 4724 |
| AUUCUGAUUCUGCCACUUC | 4725 | GAAGUGGCAGAAUCAGAAU | 4726 |
| AUUCUGCCACUUCCUGCCU | 4727 | AGGCAGGAAGUGGCAGAAU | 4728 |
| GCCACUUCCUGCCUGUCAA | 4729 | UUGACAGGCAGGAAGUGGC | 4730 |
| CCACUUCCUGCCUGUCAAA | 4731 | UUUGACAGGCAGGAAGUGG | 4732 |
| AACCUUGGGAAGUUGUUCA | 4733 | UGAACAACUUCCCAAGGUU | 4734 |
| ACCUUGGGAAGUUGUUCAA | 4735 | UUGAACAACUUCCCAAGGU | 4736 |
| CCUUGGGAAGUUGUUCAAC | 4737 | GUUGAACAACUUCCCAAGG | 4738 |
| GGGAAGUUGUUCAACCUAC | 4739 | GUAGGUUGAACAACUUCCC | 4740 |
| GGAAGUUGUUCAACCUACC | 4741 | GGUAGGUUGAACAACUUCC | 4742 |
| GAAGUUGUUCAACCUACCA | 4743 | UGGUAGGUUGAACAACUUC | 4744 |
| AAGUUGUUCAACCUACCAA | 4745 | UUGGUAGGUUGAACAACUU | 4746 |
| AGUUGUUCAACCUACCAAA | 4747 | UUUGGUAGGUUGAACAACU | 4748 |
| GUUGUUCAACCUACCAAAA | 4749 | UUUUGGUAGGUUGAACAAC | 4750 |
| GCAAUAAUAAUACAUCACC | 4751 | GGUGAUGUAUUAUUAUUGC | 4752 |
| AUAAUAAUACAUCACCUCC | 4753 | GGAGGUGAUGUAUUAUUAU | 4754 |
| UAAUACAUCACCUCCUAGG | 4755 | CCUAGGAGGUGAUGUAUUA | 4756 |
| AAUACAUCACCUCCUAGGG | 4757 | CCCUAGGAGGUGAUGUAUU | 4758 |
| AUACAUCACCUCCUAGGGU | 4759 | ACCCUAGGAGGUGAUGUAU | 4760 |
| UACAUCACCUCCUAGGGUU | 4761 | AACCCUAGGAGGUGAUGUA | 4762 |
| ACAUCACCUCCUAGGGUUG | 4763 | CAACCCUAGGAGGUGAUGU | 4764 |
| AAAGGAGUAAGAGGAUAAU | 4765 | AUUAUCCUCUUACUCCUUU | 4766 |
| AAGGAGUAAGAGGAUAAUG | 4767 | CAUUAUCCUCUUACUCCUU | 4768 |
| AGUAAGAGGAUAAUGUAGG | 4769 | CCUACAUUAUCCUCUUACU | 4770 |
| GUAAGAGGAUAAUGUAGGU | 4771 | ACCUACAUUAUCCUCUUAC | 4772 |
| UAAGAGGAUAAUGUAGGUA | 4778 | UACCUACAUUAUCCUCUUA | 4774 |
| AAGAGGAUAAUGUAGGUAA | 4776 | UUACCUACAUUAUCCUCUU | 4776 |
| AGAGGAUAAUGUAGGUAAA | 4777 | UUUACCUACAUUAUCCUCU | 4778 |
| GAGGAUAAUGUAGGUAAAG | 4779 | CUUUACCUACAUUAUCCUC | 4780 |
| GGAUAAUGUAGGUAAAGUC | 4781 | GACUUUACCUACAUUAUCC | 4782 |
| AUAAUGUAGGUAAAGUCCU | 4783 | AGGACUUUACCUACAUUAU | 4784 |
| GUAGGUAAAGUCCUCAUAC | 4785 | GUAUGAGGACUUUACCUAC | 4786 |
| GUAAAGUCCUCAUACCUGG | 4787 | CCAGGUAUGAGGACUUUAC | 4788 |
| UAAAGUCCUCAUACCUGGC | 4789 | GCCAGGUAUGAGGACUUUA | 4790 |
| AAAGUCCUCAUACCUGGCA | 4791 | UGCCAGGUAUGAGGACUUU | 4792 |
| AAGUCCUCAUACCUGGCAC | 4793 | GUGCCAGGUAUGAGGACUU | 4794 |
| AGUCCUCAUACCUGGCACA | 4795 | UGUGCCAGGUAUGAGGACU | 4796 |
| GUCCUCAUACCUGGCACAG | 4797 | CUGUGCCAGGUAUGAGGAC | 4798 |
| UCCUCAUACCUGGCACAGA | 4799 | UCUGUGCCAGGUAUGAGGA | 4800 |
| UCUUGAGGGUGUGGGAAGU | 4801 | ACUUCCCACACCCUCAAGA | 4802 |
| CUUGAGGGUGUGGGAAGUG | 4803 | CACUUCCCACACCCUCAAG | 4804 |
| UUGAGGGUGUGGGAAGUGA | 4805 | UCACUUCCCACACCCUCAA | 4806 |
| UGAGGGUGUGGGAAGUGAG | 4807 | CUCACUUCCCACACCCUCA | 4808 |
| AGGGUGUGGGAAGUGAGGU | 4809 | ACCUCACUUCCCACACCCU | 4810 |
| GGGUGUGGGAAGUGAGGUG | 4811 | CACCUCACUUCCCACACCC | 4812 |
| GGGAAGUGAGGUGCAGCAU | 4813 | AUGCUGCACCUCACUUCCC | 4814 |
| GGAAGUGAGGUGCAGCAUU | 4815 | AAUGCUGCACCUCACUUCC | 4816 |
| GAAGUGAGGUGCAGCAUUG | 4817 | CAAUGCUGCACCUCACUUC | 4818 |
| AAGUGAGGUGCAGCAUUGU | 4819 | ACAAUGCUGCACCUCACUU | 4820 |
| AGUGAGGUGCAGCAUUGUA | 4821 | UACAAUGCUGCACCUCACU | 4822 |
| GUGAGGUGCAGCAUUGUAG | 4823 | CUACAAUGCUGCACCUCAC | 4824 |
| UGAGGUGCAGCAUUGUAGA | 4825 | UCUACAAUGCUGCACCUCA | 4826 |

TABLE 8-continued

| Sense Sequence | SEQ ID NO: | Antisense Sequence | SEQ ID NO: |
|---|---|---|---|
| GAGGUGCAGCAUUGUAGAU | 4827 | AUCUACAAUGCUGCACCUC | 4828 |
| AGGUGCAGCAUUGUAGAUA | 4829 | UAUCUACAAUGCUGCACCU | 4830 |
| GGUGCAGCAUUGUAGAUAA | 4831 | UUAUCUACAAUGCUGCACC | 4832 |
| GUGCAGCAUUGUAGAUAAG | 4833 | CUUAUCUACAAUGCUGCAC | 4834 |
| UGCAGCAUUGUAGAUAAGA | 4835 | UCUUAUCUACAAUGCUGCA | 4836 |
| GCAUUGUAGAUAAGACAGA | 4837 | UCUGUCUUAUCUACAAUGC | 4838 |
| CAUUGUAGAUAAGACAGAA | 4839 | UUCUGUCUUAUCUACAAUG | 4840 |
| AUUGUAGAUAAGACAGAAG | 4841 | CUUCUGUCUUAUCUACAAU | 4842 |
| AUAAGACAGAAGGGUGGAC | 4843 | GUCCACCCUUCUGUCUUAU | 4844 |
| UAAGACAGAAGGGUGGACU | 4845 | AGUCCACCCUUCUGUCUUA | 4846 |
| AACCUGGCUUGCUUUCCAA | 4847 | UUGGAAAGCAAGCCAGGUU | 4848 |
| CCUGGCUUGCUUUCCAAUU | 4849 | AAUUGGAAAGCAAGCCAGG | 4850 |
| ACCAGAAGUGACUUGGAGG | 4851 | CCUCCAAGUCACUUCUGGU | 4852 |
| CCAGAAGUGACUUGGAGGG | 4853 | CCCUCCAAGUCACUUCUGG | 4854 |
| AGAUGCCAAUGACAUGGUA | 4855 | UACCAUGUCAUUGGCAUCU | 4856 |
| GAUGCCAAUGACAUGGUAG | 4857 | CUACCAUGUCAUUGGCAUC | 4858 |
| AUGCCAAUGACAUGGUAGG | 4859 | CCUACCAUGUCAUUGGCAU | 4860 |
| CAAUGACAUGGUAGGAGCA | 4861 | UGCUCCUACCAUGUCAUUG | 4862 |
| AAUGACAUGGUAGGAGCAA | 4863 | UUGCUCCUACCAUGUCAUU | 4864 |
| AUGACAUGGUAGGAGCAAA | 4865 | UUUGCUCCUACCAUGUCAU | 4866 |
| UGACAUGGUAGGAGCAAAG | 4867 | CUUUGCUCCUACCAUGUCA | 4868 |
| GACAUGGUAGGAGCAAAGA | 4869 | UCUUUGCUCCUACCAUGUC | 4870 |
| AAAAGGUCAGCCUCUAGCU | 4871 | AGCUAGAGGCUGACCUUUU | 4872 |
| AAAGGUCAGCCUCUAGCUA | 4873 | UAGCUAGAGGCUGACCUUU | 4874 |
| AGGUCAGCCUCUAGCUAGG | 4875 | CCUAGCUAGAGGCUGACCU | 4876 |
| GGUCAGCCUCUAGCUAGGA | 4877 | UCCUAGCUAGAGGCUGACC | 4878 |
| GUCAGCCUCUAGCUAGGAU | 4879 | AUCCUAGCUAGAGGCUGAC | 4880 |
| CAGCCUCUAGCUAGGAUCC | 4881 | GGAUCCUAGCUAGAGGCUG | 4882 |
| AGCCUCUAGCUAGGAUCCC | 4883 | GGGAUCCUAGCUAGAGGCU | 4884 |
| AGAGCUGCAACCUUUAGGA | 4885 | UCCUAAAGGUUGCAGCUCU | 4886 |
| GAGCUGCAACCUUUAGGAG | 4887 | CUCCUAAAGGUUGCAGCUC | 4888 |
| AGCUGCAACCUUUAGGAGG | 4889 | CCUCCUAAAGGUUGCAGCU | 4890 |
| UUUAGGAGGUAUCAAAGUG | 4891 | CACUUUGAUACCUCCUAAA | 4892 |
| UUAGGAGGUAUCAAAGUGC | 4893 | GCACUUUGAUACCUCCUAA | 4894 |
| UAGGAGGUAUCAAAGUGCC | 4895 | GGCACUUUGAUACCUCCUA | 4896 |
| GUCAAAGUGGGACAUCGAC | 4897 | GUCGAUGUCCCACUUUGAC | 4898 |
| CAUCGACCAAUGUCUAGAG | 4899 | CUCUAGACAUUGGUCGAUG | 4900 |
| AUCGACCAAUGUCUAGAGC | 4901 | GCUCUAGACAUUGGUCGAU | 4902 |
| ACCAAUGUCUAGAGCCAAC | 4903 | GUUGGCUCUAGACAUUGGU | 4904 |
| CAAUGUCUAGAGCCAACUG | 4905 | CAGUUGGCUCUAGACAUUG | 4906 |
| AAUGUCUAGAGCCAACUGA | 4907 | UCAGUUGGCUCUAGACAUU | 4908 |
| AUGUCUAGAGCCAACUGAU | 4909 | AUCAGUUGGCUCUAGACAU | 4910 |
| UGUCUAGAGCCAACUGAUG | 4911 | CAUCAGUUGGCUCUAGACA | 4912 |
| GUCUAGAGCCAACUGAUGG | 4913 | CCAUCAGUUGGCUCUAGAC | 4914 |
| UCUAGAGCCAACUGAUGGA | 4915 | UCCAUCAGUUGGCUCUAGA | 4916 |
| CUAGAGCCAACUGAUGGAU | 4917 | AUCCAUCAGUUGGCUCUAG | 4918 |
| UAGAGCCAACUGAUGGAUG | 4919 | CAUCCAUCAGUUGGCUCUA | 4920 |
| AGAGCCAACUGAUGGAUGU | 4921 | ACAUCCAUCAGUUGGCUCU | 4922 |
| GAGCCAACUGAUGGAUGUU | 4923 | AACAUCCAUCAGUUGGCUC | 4924 |
| AACUGAUGGAUGUUGGGCA | 4925 | UGCCCAACAUCCAUCAGUU | 4926 |
| UGGAUGUUGGGCAGCUAAA | 4927 | UUUAGCUGCCCAACAUCCA | 4928 |
| GGAUGUUGGGCAGCUAAAG | 4929 | CUUUAGCUGCCCAACAUCC | 4930 |
| GAUGUUGGGCAGCUAAAGA | 4931 | UCUUUAGCUGCCCAACAUC | 4932 |
| UUGGGCAGCUAAAGAGGGA | 4933 | UCCCUCUUUAGCUGCCCAA | 4934 |
| UGGGCAGCUAAAGAGGGAA | 4935 | UUCCCUCUUUAGCUGCCCA | 4936 |
| GGGCAGCUAAAGAGGGAAG | 4937 | CUUCCCUCUUUAGCUGCCC | 4938 |
| GGCAGCUAAAGAGGGAAGG | 4939 | CCUUCCCUCUUUAGCUGCC | 4940 |
| GCAGCUAAAGAGGGAAGGG | 4941 | CCCUUCCCUCUUUAGCUGC | 4942 |
| GGGCAUGGGAUAAGACCUG | 4943 | CAGGUCUUAUCCCAUGCCC | 4944 |
| GGCAUGGGAUAAGACCUGC | 4945 | GCAGGUCUUAUCCCAUGCC | 4946 |
| GCAUGGGAUAAGACCUGCC | 4947 | GGCAGGUCUUAUCCCAUGC | 4948 |
| CAUGGGAUAAGACCUGCCC | 4949 | GGGCAGGUCUUAUCCCAUG | 4950 |
| AUGGGAUAAGACCUGCCCU | 4951 | AGGGCAGGUCUUAUCCCAU | 4952 |
| UGGGAUAAGACCUGCCCUU | 4953 | AAGGGCAGGUCUUAUCCCA | 4954 |
| GGGAUAAGACCUGCCCUUC | 4955 | GAAGGGCAGGUCUUAUCCC | 4956 |
| GGAUAAGACCUGCCCUUCU | 4957 | AGAAGGGCAGGUCUUAUCC | 4958 |
| AGACCUGCCCUUCUUGCUU | 4959 | AAGCAAGAAGGGCAGGUCU | 4960 |
| GACCUGCCCUUCUUGCUUC | 4961 | GAAGCAAGAAGGGCAGGUC | 4962 |
| CCUGCCCUUCUUGCUUCUU | 4963 | AAGAAGCAAGAAGGGCAGG | 4964 |
| CUGCCCUUCUUGCUUCUUG | 4965 | CAAGAAGCAAGAAGGGCAG | 4966 |
| UGCCCUUCUUGCUUCUUGC | 4967 | GCAAGAAGCAAGAAGGGCA | 4968 |
| UCUUGCUUCUUGCCAUUGG | 4969 | CCAAUGGCAAGAAGCAAGA | 4970 |
| CUUGCUUCUUGCCAUUGGG | 4971 | CCCAAUGGCAAGAAGCAAG | 4972 |
| UUGCUUCUUGCCAUUGGGC | 4973 | GCCCAAUGGCAAGAAGCAA | 4974 |
| CCAUUGGGCAGGCAUUGGA | 4975 | UCCAAUGCCUGCCCAAUGG | 4976 |
| CAUUGGGCAGGCAUUGGAG | 4977 | CUCCAAUGCCUGCCCAAUG | 4978 |

TABLE 8-continued

| Sense Sequence | SEQ ID NO: | Antisense Sequence | SEQ ID NO: |
|---|---|---|---|
| GACCCUACUGCUGAAUGGA | 4979 | UCCAUUCAGCAGUAGGGUC | 4980 |
| UACUGCUGAAUGGAGUGCU | 4981 | AGCACUCCAUUCAGCAGUA | 4982 |
| ACUGCUGAAUGGAGUGCUA | 4983 | UAGCACUCCAUUCAGCAGU | 4984 |
| CUGCUGAAUGGAGUGCUAA | 4985 | UUAGCACUCCAUUCAGCAG | 4986 |
| UGCUGAAUGGAGUGCUAAC | 4987 | GUUAGCACUCCAUUCAGCA | 4988 |
| GCUGAAUGGAGUGCUAACC | 4989 | GGUUAGCACUCCAUUCAGC | 4990 |
| CUGAAUGGAGUGCUAACCC | 4991 | GGGUUAGCACUCCAUUCAG | 4992 |
| UAACCCUGGUGCUAGAGGA | 4993 | UCCUCUAGCACCAGGGUUA | 4994 |
| AACCCUGGUGCUAGAGGAG | 4995 | CUCCUCUAGCACCAGGGUU | 4996 |
| ACCCUGGUGCUAGAGGAGG | 4997 | CCUCCUCUAGCACCAGGGU | 4998 |
| CCCUGGUGCUAGAGGAGGA | 4999 | UCCUCCUCUAGCACCAGGG | 5000 |
| CCUGGUGCUAGAGGAGGAU | 5001 | AUCCUCCUCUAGCACCAGG | 5002 |
| CUGGUGCUAGAGGAGGAUG | 5003 | CAUCCUCCUCUAGCACCAG | 5004 |
| GGUGCUAGAGGAGGAUGGA | 5005 | UCCAUCCUCCUCUAGCACC | 5006 |
| GUGCUAGAGGAGGAUGGAA | 5007 | UUCCAUCCUCCUCUAGCAC | 5008 |
| CUGCAGUGGACAGUGAGGA | 5009 | UCCUCACUGUCCACUGCAG | 5010 |
| UGCAGUGGACAGUGAGGAC | 5011 | GUCCUCACUGUCCACUGCA | 5012 |
| GCAGUGGACAGUGAGGACU | 5013 | AGUCCUCACUGUCCACUGC | 5014 |
| CAGUGGACAGUGAGGACUU | 5015 | AAGUCCUCACUGUCCACUG | 5016 |
| AGUGGACAGUGAGGACUUC | 5017 | GAAGUCCUCACUGUCCACU | 5018 |
| GUGGACAGUGAGGACUUCU | 5019 | AGAAGUCCUCACUGUCCAC | 5020 |
| UGGACAGUGAGGACUUCUU | 5021 | AAGAAGUCCUCACUGUCCA | 5022 |
| GGACAGUGAGGACUUCUUC | 5023 | GAAGAAGUCCUCACUGUCC | 5024 |
| AGUGAGGACUUCUUCCAGC | 5025 | GCUGGAAGAAGUCCUCACU | 5026 |
| GUGAGGACUUCUUCCAGCU | 5027 | AGCUGGAAGAAGUCCUCAC | 5028 |
| UGAGGACUUCUUCCAGCUG | 5029 | CAGCUGGAAGAAGUCCUCA | 5030 |
| GAGGACUUCUUCCAGCUGC | 5031 | GCAGCUGGAAGAAGUCCUC | 5032 |
| GUGCCUGAUGGUGUUGCAG | 5033 | CUGCAACACCAUCAGGCAC | 5034 |
| GAUGGUGUUGCAGUCUGGU | 5035 | ACCAGACUGCAACACCAUC | 5036 |
| UGGUGUUGCAGUCUGGUCA | 5037 | UGACCAGACUGCAACACCA | 5038 |
| GGUGUUGCAGUCUGGUCAG | 5039 | CUGACCAGACUGCAACACC | 5040 |
| GUGUUGCAGUCUGGUCAGA | 5041 | UCUGACCAGACUGCAACAC | 5042 |
| UGCAGUCUGGUCAGAGCUG | 5043 | CAGCUCUGACCAGACUGCA | 5044 |
| GCAGUCUGGUCAGAGCUGG | 5045 | CCAGCUCUGACCAGACUGC | 5046 |
| CAGUCUGGUCAGAGCUGGA | 5047 | UCCAGCUCUGACCAGACUG | 5048 |
| AGUCUGGUCAGAGCUGGAG | 5049 | CUCCAGCUCUGACCAGACU | 5050 |
| GUCUGGUCAGAGCUGGAGC | 5051 | GCUCCAGCUCUGACCAGAC | 5052 |
| UCUGGUCAGAGCUGGAGCC | 5053 | GGCUCCAGCUCUGACCAGA | 5054 |
| UGGUCAGAGCUGGAGCCCU | 5055 | AGGGCUCCAGCUCUGACCA | 5056 |
| GGUCAGAGCUGGAGCCCUA | 5057 | UAGGGCUCCAGCUCUGACC | 5058 |
| GUCAGAGCUGGAGCCCUAC | 5059 | GUAGGGCUCCAGCUCUGAC | 5060 |
| CAAGGGUAAGAGGCCUAUA | 5061 | UAUAGGCCUCUUACCCUUG | 5062 |
| AAGGGUAAGAGGCCUAUAC | 5063 | GUAUAGGCCUCUUACCCUU | 5064 |
| AGGGUAAGAGGCCUAUACU | 5065 | AGUAUAGGCCUCUUACCCU | 5066 |
| GGGUAAGAGGCCUAUACUG | 5067 | CAGUAUAGGCCUCUUACCC | 5068 |
| GGUAAGAGGCCUAUACUGG | 5069 | CCAGUAUAGGCCUCUUACC | 5070 |
| GUAAGAGGCCUAUACUGGG | 5071 | CCCAGUAUAGGCCUCUUAC | 5072 |
| GGGCUGCUUCCAAUGCCUG | 5073 | CAGGCAUUGGAAGCAGCCC | 5074 |
| GGCUGCUUCCAAUGCCUGU | 5075 | ACAGGCAUUGGAAGCAGCC | 5076 |
| GCUGCUUCCAAUGCCUGUC | 5077 | GACAGGCAUUGGAAGCAGC | 5078 |
| CUGCUUCCAAUGCCUGUCC | 5079 | GGACAGGCAUUGGAAGCAG | 5080 |
| UGCUUCCAAUGCCUGUCCU | 5081 | AGGACAGGCAUUGGAAGCA | 5082 |
| GCUUCCAAUGCCUGUCCUU | 5083 | AAGGACAGGCAUUGGAAGC | 5084 |
| CUUCCAAUGCCUGUCCUUU | 5085 | AAAGGACAGGCAUUGGAAG | 5086 |
| UUCCAAUGCCUGUCCUUUA | 5087 | UAAAGGACAGGCAUUGGAA | 5088 |
| UCCAAUGCCUGUCCUUUAG | 5089 | CUAAAGGACAGGCAUUGGA | 5090 |
| CAAUGCCUGUCCUUUAGAG | 5091 | CUCUAAAGGACAGGCAUUG | 5092 |
| AAUGCCUGUCCUUUAGAGC | 5093 | GCUCUAAAGGACAGGCAUU | 5094 |
| AUGCCUGUCCUUUAGAGCU | 5095 | AGCUCUAAAGGACAGGCAU | 5096 |
| CUUCCUCUCUAGCUUAACC | 5097 | GGUUAAGCUAGAGAGGAAG | 5098 |
| UUCCUCUCUAGCUUAACCC | 5099 | GGGUUAAGCUAGAGAGGAA | 5100 |
| UCUCUAGCUUAACCCUGAU | 5101 | AUCAGGGUUAAGCUAGAGA | 5102 |
| UAGCUUAACCCUGAUCCUG | 5103 | CAGGAUCAGGGUUAAGCUA | 5104 |
| GACCAGGUGCAGGAGGAGU | 5105 | ACUCCUCCUGCACCUGGUC | 5106 |
| ACCAGGUGCAGGAGGAGUU | 5107 | AACUCCUCCUGCACCUGGU | 5108 |
| CCAGGUGCAGGAGGAGUUG | 5109 | CAACUCCUCCUGCACCUGG | 5110 |
| CAGGUGCAGGAGGAGUUGU | 5111 | ACAACUCCUCCUGCACCUG | 5112 |
| AGGUGCAGGAGGAGUUGUG | 5113 | CACAACUCCUCCUGCACCU | 5114 |
| UGCAGGAGGAGUUGUGGAA | 5115 | UUCCACAACUCCUCCUGCA | 5116 |
| GCAGGAGGAGUUGUGGAAU | 5117 | AUUCCACAACUCCUCCUGC | 5118 |
| AGGAGGAGUUGUGGAAUUG | 5119 | CAAUUCCACAACUCCUCCU | 5120 |
| GGAGGAGUUGUGGAAUUGU | 5121 | ACAAUUCCACAACUCCUCC | 5122 |
| GAGGAGUUGUGGAAUUGUC | 5123 | GACAAUUCCACAACUCCUC | 5124 |
| AGGAGUUGUGGAAUUGUCA | 5125 | UGACAAUUCCACAACUCCU | 5126 |
| GGAGUUGUGGAAUUGUCAA | 5127 | UUGACAAUUCCACAACUCC | 5128 |
| GAGUUGUGGAAUUGUCAAG | 5129 | CUUGACAAUUCCACAACUC | 5130 |

TABLE 8-continued

| Sense Sequence | SEQ ID NO: | Antisense Sequence | SEQ ID NO: |
|---|---|---|---|
| AGUUGUGGAAUUGUCAAGG | 5131 | CCUUGACAAUUCCACAACU | 5132 |
| GUUGUGGAAUUGUCAAGGA | 5133 | UCCUUGACAAUUCCACAAC | 5134 |
| UGGAAUUGUCAAGGAUGUC | 5135 | GACAUCCUUGACAAUUCCA | 5136 |
| GGAAUUGUCAAGGAUGUCA | 5137 | UGACAUCCUUGACAAUUCC | 5138 |
| AGUCCAAGCGAGGGAGGGU | 5139 | ACCCUCCCUCGCUUGGACU | 5140 |
| CAAGCGAGGGAGGGUCUGA | 5141 | UCAGACCCUCCCUCGCUUG | 5142 |
| AAGCGAGGGAGGGUCUGAC | 5143 | GUCAGACCCUCCCUCGCUU | 5144 |
| CUGACCCAGUGCUGAUGGA | 5145 | UCCAUCAGCACUGGGUCAG | 5146 |
| AGAUUAGUGGUGGGUGUCU | 5147 | AGACACCCACCACUAAUCU | 5148 |
| AUUAGUGGUGGGUGUCUGG | 5149 | CCAGACACCCACCACUAAU | 5150 |
| UUAGUGGUGGGUGUCUGGU | 5151 | ACCAGACACCCACCACUAA | 5152 |
| UAGUGGUGGGUGUCUGGUA | 5153 | UACCAGACACCCACCACUA | 5154 |
| AGUGGUGGGUGUCUGGUAU | 5155 | AUACCAGACACCCACCACU | 5156 |
| GUGGUGGGUGUCUGGUAUG | 5157 | CAUACCAGACACCCACCAC | 5158 |
| UGGUGGGUGUCUGGUAUGA | 5159 | UCAUACCAGACACCCACCA | 5160 |
| GGUGGGUGUCUGGUAUGAG | 5161 | CUCAUACCAGACACCCACC | 5162 |
| GUGGGUGUCUGGUAUGAGG | 5163 | CCUCAUACCAGACACCCAC | 5164 |
| UGGGUGUCUGGUAUGAGGA | 5165 | UCCUCAUACCAGACACCCA | 5166 |
| GGGUGUCUGGUAUGAGGAU | 5167 | AUCCUCAUACCAGACACCC | 5168 |
| GGUGUCUGGUAUGAGGAUC | 5169 | GAUCCUCAUACCAGACACC | 5170 |
| GUGUCUGGUAUGAGGAUCU | 5171 | AGAUCCUCAUACCAGACAC | 5172 |
| UGUCUGGUAUGAGGAUCUA | 5173 | UAGAUCCUCAUACCAGACA | 5174 |
| CAAGGGUGUCCUACAGAGU | 5175 | ACUCUGUAGGACACCCUUG | 5176 |
| AAGGGUGUCCUACAGAGUG | 5177 | CACUCUGUAGGACACCCUU | 5178 |
| AGGGUGUCCUACAGAGUGG | 5179 | CCACUCUGUAGGACACCCU | 5180 |
| GGGUGUCCUACAGAGUGGA | 5181 | UCCACUCUGUAGGACACCC | 5182 |
| GGUGUCCUACAGAGUGGAG | 5183 | CUCCACUCUGUAGGACACC | 5184 |
| UCCUACAGAGUGGAGUGCU | 5185 | AGCACUCCACUCUGUAGGA | 5186 |
| AGUGGAGUGCUGUCAUAUG | 5187 | CAUAUGACAGCACUCCACU | 5188 |
| GUGGAGUGCUGUCAUAUGG | 5189 | CCAUAUGACAGCACUCCAC | 5190 |
| UGGAGUGCUGUCAUAUGGC | 5191 | GCCAUAUGACAGCACUCCA | 5192 |
| GGAGUGCUGUCAUAUGGCC | 5193 | GGCCAUAUGACAGCACUCC | 5194 |
| GAGUGCUGUCAUAUGGCCU | 5195 | AGGCCAUAUGACAGCACUC | 5196 |
| AGUGCUGUCAUAUGGCCUG | 5197 | CAGGCCAUAUGACAGCACU | 5198 |
| GUGCUGUCAUAUGGCCUGG | 5199 | CCAGGCCAUAUGACAGCAC | 5200 |
| UGCUGUCAUAUGGCCUGGG | 5201 | CCCAGGCCAUAUGACAGCA | 5202 |
| GCUGUCAUAUGGCCUGGGA | 5203 | UCCCAGGCCAUAUGACAGC | 5204 |
| CUGUCAUAUGGCCUGGGAC | 5205 | GUCCCAGGCCAUAUGACAG | 5206 |
| UGUCAUAUGGCCUGGGACG | 5207 | CGUCCCAGGCCAUAUGACA | 5208 |
| GUCAUAUGGCCUGGGACGG | 5209 | CCGUCCCAGGCCAUAUGAC | 5210 |
| AGAGGCCCAAGCACAGCAA | 5211 | UUGCUGUGCUUGGGCCUCU | 5212 |
| GAGGCCCAAGCACAGCAAG | 5213 | CUUGCUGUGCUUGGGCCUC | 5214 |
| AGGCCCAAGCACAGCAAGG | 5215 | CCUUGCUGUGCUUGGGCCU | 5216 |
| GGCCCAAGCACAGCAAGGA | 5217 | UCCUUGCUGUGCUUGGGCC | 5218 |
| CCAAGCACAGCAAGGACAU | 5219 | AUGUCCUUGCUGUGCUUGG | 5220 |
| GCCCGAUUCACCUUUGACG | 5221 | CGUCAAAGGUGAAUCGGGC | 5222 |
| GAUUCACCUUUGACGUGUA | 5223 | UACACGUCAAAGGUGAAUC | 5224 |
| AUUCACCUUUGACGUGUAC | 5225 | GUACACGUCAAAGGUGAAU | 5226 |
| UUGGCAGCCUGAAUGUCAA | 5227 | UUGACAUUCAGGCUGCCAA | 5228 |
| UGGCAGCCUGAAUGUCAAA | 5229 | UUUGACAUUCAGGCUGCCA | 5230 |
| GGCAGCCUGAAUGUCAAAG | 5231 | CUUUGACAUUCAGGCUGCC | 5232 |
| GCAGCCUGAAUGUCAAAGC | 5233 | GCUUUGACAUUCAGGCUGC | 5234 |
| CAGCCUGAAUGUCAAAGCC | 5235 | GGCUUUGACAUUCAGGCUG | 5236 |
| AGCCUGAAUGUCAAAGCCA | 5237 | UGGCUUUGACAUUCAGGCU | 5238 |
| GCCUGAAUGUCAAAGCCAC | 5239 | GUGGCUUUGACAUUCAGGC | 5240 |
| GUCAAAGCCACAUUCUACG | 5241 | CGUAGAAUGUGGCUUUGAC | 5242 |
| UCAAAGCCACAUUCUACGG | 5243 | CCGUAGAAUGUGGCUUUGA | 5244 |
| CAAAGCCACAUUCUACGGG | 5245 | CCCGUAGAAUGUGGCUUUG | 5246 |
| AAAGCCACAUUCUACGGGC | 5247 | GCCCGUAGAAUGUGGCUUU | 5248 |
| GCCACAUUCUACGGGCUCU | 5249 | AGAGCCCGUAGAAUGUGGC | 5250 |
| CCACAUUCUACGGGCUCUA | 5251 | UAGAGCCCGUAGAAUGUGG | 5252 |
| CACAUUCUACGGGCUCUAC | 5253 | GUAGAGCCCGUAGAAUGUG | 5254 |
| UUCUACGGGCUCUACUCUA | 5255 | UAGAGUAGAGCCCGUAGAA | 5256 |
| UCUACGGGCUCUACUCUAU | 5257 | AUAGAGUAGAGCCCGUAGA | 5258 |
| CUACGGGCUCUACUCUAUG | 5259 | CAUAGAGUAGAGCCCGUAG | 5260 |
| CUCUAUGAGUUGUGACUUU | 5261 | AAAGUCACAACUCAUAGAG | 5262 |
| UCUAUGAGUUGUGACUUUC | 5263 | GAAAGUCACAACUCAUAGA | 5264 |
| UGAGUUGUGACUUUCAAGG | 5265 | CCUUGAAAGUCACAACUCA | 5266 |
| GAGUUGUGACUUUCAAGGA | 5267 | UCCUUGAAAGUCACAACUC | 5268 |
| AGUUGUGACUUUCAAGGAC | 5269 | GUCCUUGAAAGUCACAACU | 5270 |
| GUUGUGACUUUCAAGGACU | 5271 | AGUCCUUGAAAGUCACAAC | 5272 |
| GACUUUCAAGGACUUGGCC | 5273 | GGCCAAGUCCUUGAAAGUC | 5274 |
| UUUCAAGGACUUGGCCAA | 5275 | UUGGGCCAAGUCCUUGAAA | 5276 |
| UUCAAGGACUUGGCCCAAA | 5277 | UUUGGGCCAAGUCCUUGAA | 5278 |
| CCCUACAGUUGGAUAGUCC | 5279 | GGACUAUCCAACUGUAGGG | 5280 |
| CCUACAGUUGGAUAGUCCC | 5281 | GGGACUAUCCAACUGUAGG | 5282 |

TABLE 8-continued

| Sense Sequence | SEQ ID NO: | Antisense Sequence | SEQ ID NO: |
|---|---|---|---|
| AUUCGUCCUCUUGCACCCA | 5283 | UGGGUGCAAGAGGACGAAU | 5284 |
| UUCGUCCUCUUGCACCCAC | 5285 | GUGGGUGCAAGAGGACGAA | 5286 |
| UCCUCUUGCACCCACCUAC | 5287 | GUAGGUGGGUGCAAGAGGA | 5288 |
| CCUCUUGCACCCACCUACC | 5289 | GGUAGGUGGGUGCAAGAGG | 5290 |
| CUCUUGCACCCACCUACCC | 5291 | GGGUAGGUGGGUGCAAGAG | 5292 |
| CUAGUUAGCUCUUGCUUGU | 5293 | ACAAGCAAGAGCUAACUAG | 5294 |
| UAGUUAGCUCUUGCUUGUG | 5295 | CACAAGCAAGAGCUAACUA | 5296 |
| AGUUAGCUCUUGCUUGUGG | 5297 | CCACAAGCAAGAGCUAACU | 5298 |
| UUAGCUCUUGCUUGUGGAA | 5299 | UUCCACAAGCAAGAGCUAA | 5300 |
| UCCUCAUCUCCCAGCUUGA | 5301 | UCAAGCUGGGAGAUGAGGA | 5302 |
| AUCUCCCAGCUUGAUGGCU | 5303 | AGCCAUCAAGCUGGGAGAU | 5304 |
| UCUCCCAGCUUGAUGGCUU | 5305 | AAGCCAUCAAGCUGGGAGA | 5306 |
| CUCCCAGCUUGAUGGCUUC | 5307 | GAAGCCAUCAAGCUGGGAG | 5308 |
| UCCCAGCUUGAUGGCUUCC | 5309 | GGAAGCCAUCAAGCUGGGA | 5310 |
| CCCAGCUUGAUGGCUUCCU | 5311 | AGGAAGCCAUCAAGCUGGG | 5312 |
| CCAGCUUGAUGGCUUCCUC | 5313 | GAGGAAGCCAUCAAGCUGG | 5314 |
| UGAUGGCUUCCUCCCAAGU | 5315 | ACUUGGGAGGAAGCCAUCA | 5316 |
| GAUGGCUUCCUCCCAAGUU | 5317 | AACUUGGGAGGAAGCCAUC | 5318 |
| GGCUUCCUCCCAAGUUUUC | 5319 | GAAAACUUGGGAGGAAGCC | 5320 |
| CCUCCCAAGUUUUCCAAAU | 5321 | AUUUGGAAAACUUGGGAGG | 5322 |
| CCCAAGUUUUCCAAAUCAU | 5323 | AUGAUUUGGAAAACUUGGG | 5324 |
| CCAAGUUUUCCAAAUCAUC | 5325 | GAUGAUUUGGAAAACUUGG | 5326 |
| CAAGUUUUCCAAAUCAUCU | 5327 | AGAUGAUUUGGAAAACUUG | 5328 |
| AAGUUUUCCAAAUCAUCUG | 5329 | CAGAUGAUUUGGAAAACUU | 5330 |
| GUUUUCCAAAUCAUCUGAU | 5331 | AUCAGAUGAUUUGGAAAAC | 5332 |
| AUCUGAUUCCUCUUGUCU | 5333 | AGACAAGAGGAAAUCAGAU | 5334 |
| UCUGAUUUCCUCUUGUCUC | 5335 | GAGACAAGAGGAAAUCAGA | 5336 |
| CUGAUUUCCUCUUGUCUCU | 5337 | AGAGACAAGAGGAAAUCAG | 5338 |
| CUCUUGUCUCUGCCAUUCA | 5339 | UGAAUGGCAGAGACAAGAG | 5340 |
| GUUGGACCUCCACACUGCU | 5341 | AGCAGUGUGGAGGUCCAAC | 5342 |
| CCACACUGCUGCAAGGCCU | 5343 | AGGCCUUGCAGCAGUGUGG | 5344 |
| CACACUGCUGCAAGGCCUG | 5345 | CAGGCCUUGCAGCAGUGUG | 5346 |
| ACACUGCUGCAAGGCCUGG | 5347 | CCAGGCCUUGCAGCAGUGU | 5348 |
| UGCAAGGCCUGGGCCAUAU | 5349 | AUAUGGCCCAGGCCUUGCA | 5350 |
| GCAAGGCCUGGGCCAUAUG | 5351 | CAUAUGGCCCAGGCCUUGC | 5352 |
| CAAGGCCUGGGCCAUAUGU | 5353 | ACAUAUGGCCCAGGCCUUG | 5354 |
| AAGGCCUGGGCCAUAUGUU | 5355 | AACAUAUGGCCCAGGCCUU | 5356 |
| AGGCCUGGGCCAUAUGUUG | 5357 | CAACAUAUGGCCCAGGCCU | 5358 |
| GGCCUGGGCCAUAUGUUGC | 5359 | GCAACAUAUGGCCCAGGCC | 5360 |
| GCCUGGGCCAUAUGUUGCU | 5361 | AGCAACAUAUGGCCCAGGC | 5362 |
| CCUGGGCCAUAUGUUGCUG | 5363 | CAGCAACAUAUGGCCCAGG | 5364 |
| GGCCAUAUGUUGCUGGGAA | 5365 | UUCCCAGCAACAUAUGGCC | 5366 |
| CCAUAUGUUGCUGGGAAUU | 5367 | AAUUCCCAGCAACAUAUGG | 5368 |
| GGAAUUUCCUCCACCCUUC | 5369 | GAAGGGUGGAGGAAAUUCC | 5370 |
| GAAUUUCCUCCACCCUUCG | 5371 | CGAAGGGUGGAGGAAAUUC | 5372 |
| AAUUUCCUCCACCCUUCGU | 5373 | ACGAAGGGUGGAGGAAAUU | 5374 |
| AUUUCCUCCACCCUUCGUC | 5375 | GACGAAGGGUGGAGGAAAU | 5376 |
| UUUCCUCCACCCUUCGUCA | 5377 | UGACGAAGGGUGGAGGAAA | 5378 |
| UUCCUCCACCCUUCGUCAU | 5379 | AUGACGAAGGGUGGAGGAA | 5380 |
| UCCUCCACCCUUCGUCAUG | 5381 | CAUGACGAAGGGUGGAGGA | 5382 |
| CCUCCACCCUUCGUCAUGC | 5383 | GCAUGACGAAGGGUGGAGG | 5384 |
| CUCCACCCUUCGUCAUGCA | 5385 | UGCAUGACGAAGGGUGGAG | 5386 |
| CCUUCGUCAUGCAGUGGAG | 5387 | CUCCACUGCAUGACGAAGG | 5388 |
| CUUCGUCAUGCAGUGGAGG | 5389 | CCUCCACUGCAUGACGAAG | 5390 |
| UUCGUCAUGCAGUGGAGGG | 5391 | CCCUCCACUGCAUGACGAA | 5392 |
| CGCCUCCAUUCCUACUAAG | 5393 | CUUAGUAGGAAUGGAGGCG | 5394 |
| GCCUCCAUUCCUACUAAGG | 5395 | CCUUAGUAGGAAUGGAGGC | 5396 |
| CCUCCAUUCCUACUAAGGG | 5397 | CCCUUAGUAGGAAUGGAGG | 5398 |
| CAGAAUCAUUCCAACCGAC | 5399 | GUCGGUUGGAAUGAUUCUG | 5400 |
| AGAAUCAUUCCAACCGACC | 5401 | GGUCGGUUGGAAUGAUUCU | 5402 |
| GAAUCAUUCCAACCGACCC | 5403 | GGGUCGGUUGGAAUGAUUC | 5404 |
| AAUCAUUCCAACCGACCCA | 5405 | UGGGUCGGUUGGAAUGAUU | 5406 |
| AUCAUUCCAACCGACCCAC | 5407 | GUGGGUCGGUUGGAAUGAU | 5408 |
| UCAUUCCAACCGACCCACU | 5409 | AGUGGGUCGGUUGGAAUGA | 5410 |
| UCCAACCGACCCACUGCAA | 5411 | UUGCAGUGGGUCGGUUGGA | 5412 |
| CCAACCGACCCACUGCAAA | 5413 | UUUGCAGUGGGUCGGUUGG | 5414 |
| CAACCGACCCACUGCAAAG | 5415 | CUUUGCAGUGGGUCGGUUG | 5416 |
| AACCGACCCACUGCAAAGA | 5417 | UCUUUGCAGUGGGUCGGUU | 5418 |
| ACCGACCCACUGCAAAGAC | 5419 | GUCUUUGCAGUGGGUCGGU | 5420 |
| CCGACCCACUGCAAAGACU | 5421 | AGUCUUUGCAGUGGGUCGG | 5422 |
| CGACCCACUGCAAAGACUA | 5423 | UAGUCUUUGCAGUGGGUCG | 5424 |
| GACCCACUGCAAAGACUAU | 5425 | AUAGUCUUUGCAGUGGGUC | 5426 |
| ACCCACUGCAAAGACUAUG | 5427 | CAUAGUCUUUGCAGUGGGU | 5428 |
| ACUGCAAAGACUAUGACAG | 5429 | CUGUCAUAGUCUUUGCAGU | 5430 |
| CUGCAAAGACUAUGACAGC | 5431 | GCUGUCAUAGUCUUUGCAG | 5432 |
| UGCAAAGACUAUGACAGCA | 5433 | UGCUGUCAUAGUCUUUGCA | 5434 |

TABLE 8-continued

| Sense Sequence | SEQ ID NO: | Antisense Sequence | SEQ ID NO: |
|---|---|---|---|
| GCAAAGACUAUGACAGCAU | 5435 | AUGCUGUCAUAGUCUUUGC | 5436 |
| AAAGACUAUGACAGCAUCA | 5437 | UGAUGCUGUCAUAGUCUUU | 5438 |
| AAGACUAUGACAGCAUCAA | 5439 | UUGAUGCUGUCAUAGUCUU | 5440 |
| AGACUAUGACAGCAUCAAA | 5441 | UUUGAUGCUGUCAUAGUCU | 5442 |
| GACUAUGACAGCAUCAAAU | 5443 | AUUUGAUGCUGUCAUAGUC | 5444 |
| CUAUGACAGCAUCAAAUUU | 5445 | AAAUUUGAUGCUGUCAUAG | 5446 |
| UAUGACAGCAUCAAAUUUC | 5447 | GAAAUUUGAUGCUGUCAUA | 5448 |
| GCAUCAAAUUUCAGGACCU | 5449 | AGGUCCUGAAAUUUGAUGC | 5450 |
| AUCAAAUUUCAGGACCUGC | 5451 | GCAGGUCCUGAAAUUUGAU | 5452 |
| UCAAAUUUCAGGACCUGCA | 5453 | UGCAGGUCCUGAAAUUUGA | 5454 |
| UUCAGGACCUGCAGACAGU | 5455 | ACUGUCUGCAGGUCCUGAA | 5456 |
| UCAGGACCUGCAGACAGUA | 5457 | UACUGUCUGCAGGUCCUGA | 5458 |
| CAGGACCUGCAGACAGUAC | 5459 | GUACUGUCUGCAGGUCCUG | 5460 |
| AGGACCUGCAGACAGUACA | 5461 | UGUACUGUCUGCAGGUCCU | 5462 |
| GGACCUGCAGACAGUACAG | 5463 | CUGUACUGUCUGCAGGUCC | 5464 |
| CUGCAGACAGUACAGGCUA | 5465 | UAGCCUGUACUGUCUGCAG | 5466 |
| GACAGUACAGGCUAGAUAA | 5467 | UUAUCUAGCCUGUACUGUC | 5468 |
| ACAGUACAGGCUAGAUAAC | 5469 | GUUAUCUAGCCUGUACUGU | 5470 |
| CAGUACAGGCUAGAUAACC | 5471 | GGUUAUCUAGCCUGUACUG | 5472 |
| AGUACAGGCUAGAUAACCC | 5473 | GGGUUAUCUAGCCUGUACU | 5474 |
| GUACAGGCUAGAUAACCCA | 5475 | UGGGUUAUCUAGCCUGUAC | 5476 |
| UACAGGCUAGAUAACCCAC | 5477 | GUGGGUUAUCUAGCCUGUA | 5478 |
| GCUAGAUAACCCACCCAAU | 5479 | AUUGGGUGGGUUAUCUAGC | 5480 |
| CUAGAUAACCCACCCAAUU | 5481 | AAUUGGGUGGGUUAUCUAG | 5482 |
| AGAUAACCCACCCAAUUUC | 5483 | GAAAUUGGGUGGGUUAUCU | 5484 |
| GAUAACCCACCCAAUUUCC | 5485 | GGAAAUUGGGUGGGUUAUC | 5486 |
| AACCUUUCAGCAUAACGCC | 5487 | GGCGUUAUGCUGAAAGGUU | 5488 |
| ACCUUUCAGCAUAACGCCU | 5489 | AGGCGUUAUGCUGAAAGGU | 5490 |
| CCUUUCAGCAUAACGCCUC | 5491 | GAGGCGUUAUGCUGAAAGG | 5492 |
| CUUUCAGCAUAACGCCUCA | 5493 | UGAGGCGUUAUGCUGAAAG | 5494 |
| UUUCAGCAUAACGCCUCAC | 5495 | GUGAGGCGUUAUGCUGAAA | 5496 |
| UUCAGCAUAACGCCUCACA | 5497 | UGUGAGGCGUUAUGCUGAA | 5498 |
| UCAGCAUAACGCCUCACAU | 5499 | AUGUGAGGCGUUAUGCUGA | 5500 |
| CAGCAUAACGCCUCACAUC | 5501 | GAUGUGAGGCGUUAUGCUG | 5502 |
| AGCAUAACGCCUCACAUCC | 5503 | GGAUGUGAGGCGUUAUGCU | 5504 |
| GCAUAACGCCUCACAUCCC | 5505 | GGGAUGUGAGGCGUUAUGC | 5506 |
| AACGCCUCACAUCCCAAGU | 5507 | ACUUGGGAUGUGAGGCGUU | 5508 |
| ACGCCUCACAUCCCAAGUC | 5509 | GACUUGGGAUGUGAGGCGU | 5510 |
| CGCCUCACAUCCCAAGUCU | 5511 | AGACUUGGGAUGUGAGGCG | 5512 |
| UCACAUCCCAAGUCUAUAC | 5513 | GUAUAGACUUGGGAUGUGA | 5514 |
| CACAUCCCAAGUCUAUACC | 5515 | GGUAUAGACUUGGGAUGUG | 5516 |
| ACAUCCCAAGUCUAUACCC | 5517 | GGGUAUAGACUUGGGAUGU | 5518 |
| CAUCCCAAGUCUAUACCCU | 5519 | AGGGUAUAGACUUGGGAUG | 5520 |
| AAUGCUGUUCUUUCCUAGC | 5521 | GCUAGGAAAGAACAGCAUU | 5522 |
| AUGCUGUUCUUUCCUAGCC | 5523 | GGCUAGGAAAGAACAGCAU | 5524 |
| CUGUUCUUUCCUAGCCACC | 5525 | GGUGGCUAGGAAAGAACAG | 5526 |
| UGUUCUUUCCUAGCCACCU | 5527 | AGGUGGCUAGGAAAGAACA | 5528 |
| GCCAAGAUCAAGAUGUCCC | 5529 | GGGACAUCUUGAUCUUGGC | 5530 |
| UCUUGAUCCCAGCCUGACU | 5531 | AGUCAGGCUGGGAUCAAGA | 5532 |
| CUUGAUCCCAGCCUGACUG | 5533 | CAGUCAGGCUGGGAUCAAG | 5534 |
| UUGAUCCCAGCCUGACUGC | 5535 | GCAGUCAGGCUGGGAUCAA | 5536 |
| UGAUCCCAGCCUGACUGCU | 5537 | AGCAGUCAGGCUGGGAUCA | 5538 |
| CUGACUGCUGCUACAUCUA | 5539 | UAGAUGUAGCAGCAGUCAG | 5540 |
| GACUGCUGCUACAUCUAAU | 5541 | AUUAGAUGUAGCAGCAGUC | 5542 |
| ACUGCUGCUACAUCUAAUC | 5543 | GAUUAGAUGUAGCAGCAGU | 5544 |
| CUGCUGCUACAUCUAAUCC | 5545 | GGAUUAGAUGUAGCAGCAG | 5546 |
| UGCUGCUACAUCUAAUCCC | 5547 | GGGAUUAGAUGUAGCAGCA | 5548 |
| CCUACCAAUGCCUCCUGUC | 5549 | GACAGGAGGCAUUGGUAGG | 5550 |
| CUACCAAUGCCUCCUGUCC | 5551 | GGACAGGAGGCAUUGGUAG | 5552 |
| CCAAUGCCUCCUGUCCCUA | 5553 | UAGGGACAGGAGGCAUUGG | 5554 |
| CAAUGCCUCCUGUCCCUAA | 5555 | UUAGGGACAGGAGGCAUUG | 5556 |
| AAUGCCUCCUGUCCCUAAA | 5557 | UUUAGGGACAGGAGGCAUU | 5558 |
| CCCAGCAUACUGAUGACAG | 5559 | CUGUCAUCAGUAUGCUGGG | 5560 |
| CCAGCAUACUGAUGACAGC | 5561 | GCUGUCAUCAGUAUGCUGG | 5562 |
| CAUACUGAUGACAGCCCUC | 5563 | GAGGGCUGUCAUCAGUAUG | 5564 |
| AUACUGAUGACAGCCCUCU | 5565 | AGAGGGCUGUCAUCAGUAU | 5566 |
| UACUGAUGACAGCCCUCUC | 5567 | GAGAGGGCUGUCAUCAGUA | 5568 |
| ACUGAUGACAGCCCUCUCU | 5569 | AGAGAGGGCUGUCAUCAGU | 5570 |
| CUGAUGACAGCCCUCUCUG | 5571 | CAGAGAGGGCUGUCAUCAG | 5572 |
| UGAUGACAGCCCUCUCUGA | 5573 | UCAGAGAGGGCUGUCAUCA | 5574 |
| GAUGACAGCCCUCUCUGAC | 5575 | GUCAGAGAGGGCUGUCAUC | 5576 |
| AUGACAGCCCUCUCUGACU | 5577 | AGUCAGAGAGGGCUGUCAU | 5578 |
| UGACAGCCCUCUCUGACUU | 5579 | AAGUCAGAGAGGGCUGUCA | 5580 |
| GACAGCCCUCUCUGACUUU | 5581 | AAAGUCAGAGAGGGCUGUC | 5582 |
| ACAGCCCUCUCUGACUUUA | 5583 | UAAAGUCAGAGAGGGCUGU | 5584 |
| CAGCCCUCUCUGACUUUAC | 5585 | GUAAAGUCAGAGAGGGCUG | 5586 |

TABLE 8-continued

| Sense Sequence | SEQ ID NO: | Antisense Sequence | SEQ ID NO: |
|---|---|---|---|
| AGCCCUCUCUGACUUUACC | 5587 | GGUAAAGUCAGAGAGGGCU | 5588 |
| GCCCUCUCUGACUUUACCU | 5589 | AGGUAAAGUCAGAGAGGGC | 5590 |
| CCCUCUCUGACUUUACCUU | 5591 | AAGGUAAAGUCAGAGAGGG | 5592 |
| CCUCUCUGACUUUACCUUG | 5593 | CAAGGUAAAGUCAGAGAGG | 5594 |
| CUCUCUGACUUUACCUUGA | 5595 | UCAAGGUAAAGUCAGAGAG | 5596 |
| AGAUCUGUCUUCAUACCCU | 5597 | AGGGUAUGAAGACAGAUCU | 5598 |
| GAUCUGUCUUCAUACCCUU | 5599 | AAGGGUAUGAAGACAGAUC | 5600 |
| CUGUCUUCAUACCCUUCCC | 5601 | GGGAAGGGUAUGAAGACAG | 5602 |

In some embodiments, the siRNA molecules targeted to Transcript B comprise or consist of the nucleotide sequences (sense and antisense strands) shown in Table 9.

TABLE 9

| Sense Sequence | SEQ ID NO: | Antisense Sequence | SEQ ID NO: |
|---|---|---|---|
| CCAGAGCAAGCCGAAGGCA | 5603 | UGCCUUCGGCUUGCUCUGG | 5604 |
| CAGAGCAAGCCGAAGGCAA | 5605 | UUGCCUUCGGCUUGCUCUG | 5606 |
| AGAGCAAGCCGAAGGCAAG | 5607 | CUUGCCUUCGGCUUGCUCU | 5608 |
| GAGCAAGCCGAAGGCAAGC | 5609 | GCUUGCCUUCGGCUUGCUC | 5610 |
| AGCAAGCCGAAGGCAAGCA | 5611 | UGCUUGCCUUCGGCUUGCU | 5612 |
| GCAAGCCGAAGGCAAGCAC | 5613 | GUGCUUGCCUUCGGCUUGC | 5614 |
| CAAGCCGAAGGCAAGCACG | 5615 | CGUGCUUGCCUUCGGCUUG | 5616 |
| AAGCCGAAGGCAAGCACGA | 5617 | UCGUGCUUGCCUUCGGCUU | 5618 |
| AGCCGAAGGCAAGCACGAU | 5619 | AUCGUGCUUGCCUUCGGCU | 5620 |
| GCCGAAGGCAAGCACGAUG | 5621 | CAUCGUGCUUGCCUUCGGC | 5622 |
| AAGGCAAGCACGAUGGCGC | 5623 | GCGCCAUCGUGCUUGCCUU | 5624 |
| AGGCAAGCACGAUGGCGCU | 5625 | AGCGCCAUCGUGCUUGCCU | 5626 |
| AAGCACGAUGGCGCUCACC | 5627 | GGUGAGCGCCAUCGUGCUU | 5628 |
| AGCACGAUGGCGCUCACCA | 5629 | UGGUGAGCGCCAUCGUGCU | 5630 |
| CUGUAGCAGCCGAGCAUCA | 5631 | UGAUGCUCGGCUGCUACAG | 5632 |
| AGCCGAGCAUCAGCCCGAA | 5633 | UUCGGGCUGAUGCUCGGCU | 5634 |
| GUCAGAGUCUCCAGGCUCA | 5635 | UGAGCCUGGAGACUCUGAC | 5636 |
| UCAGAGUCUCCAGGCUCAG | 5637 | CUGAGCCUGGAGACUCUGA | 5638 |
| CAGAGUCUCCAGGCUCAGG | 5639 | CCUGAGCCUGGAGACUCUG | 5640 |
| AGAGUCUCCAGGCUCAGGU | 5641 | ACCUGAGCCUGGAGACUCU | 5642 |
| GAGUCUCCAGGCUCAGGUG | 5643 | CACCUGAGCCUGGAGACUC | 5644 |
| AGUCUCCAGGCUCAGGUGG | 5645 | CCACCUGAGCCUGGAGACU | 5646 |
| GGGUGGCACAGCUGGCAUA | 5647 | UAUGCCAGCUGUGCCACCC | 5648 |
| GUGGCACAGCUGGCAUACG | 5649 | CGUAUGCCAGCUGUGCCAC | 5650 |

TABLE 9-continued

| Sense Sequence | SEQ ID NO: | Antisense Sequence | SEQ ID NO: |
|---|---|---|---|
| UGGCACAGCUGGCAUACGC | 5651 | GCGUAUGCCAGCUGUGCCA | 5652 |
| CUCCACAGGUGGCGGUAGA | 5653 | UCUACCGCCACCUGUGGAG | 5654 |
| UCCACAGGUGGCGGUAGAC | 5655 | GUCUACCGCCACCUGUGGA | 5656 |
| UGAGCAGCACGCUGGCGUA | 5657 | UACGCCAGCGUGCUGCUCA | 5658 |
| AGCAGCACGCUGGCGUACA | 5659 | UGUACGCCAGCGUGCUGCU | 5660 |
| GCAGCACGCUGGCGUACAU | 5661 | AUGUACGCCAGCGUGCUGC | 5662 |
| CAGCACGCUGGCGUACAUG | 5663 | CAUGUACGCCAGCGUGCUG | 5664 |
| AGCACGCUGGCGUACAUGC | 5665 | GCAUGUACGCCAGCGUGCU | 5666 |
| GCACGCUGGCGUACAUGCU | 5667 | AGCAUGUACGCCAGCGUGC | 5668 |
| CACGCUGGCGUACAUGCUG | 5669 | CAGCAUGUACGCCAGCGUG | 5670 |
| ACGCUGGCGUACAUGCUGA | 5671 | UCAGCAUGUACGCCAGCGU | 5672 |
| CUGGCGUACAUGCUGAGCG | 5673 | CGCUCAGCAUGUACGCCAG | 5674 |
| UGGCGUACAUGCUGAGCGC | 5675 | GCGCUCAGCAUGUACGCCA | 5676 |
| CGCGCACACGUAGUACACC | 5677 | GGUGUACUACGUGUGCGCG | 5678 |
| GCGCACACGUAGUACACCG | 5679 | CGGUGUACUACGUGUGCGC | 5680 |
| CGCACACGUAGUACACCGC | 5681 | GCGGUGUACUACGUGUGCG | 5682 |
| GCACACGUAGUACACCGCC | 5683 | GGCGGUGUACUACGUGUGC | 5684 |
| CACACGUAGUACACCGCCU | 5685 | AGGCGGUGUACUACGUGUG | 5686 |
| ACACGUAGUACACCGCCUU | 5687 | AAGGCGGUGUACUACGUGU | 5688 |
| CACGUAGUACACCGCCUUG | 5689 | CAAGGCGGUGUACUACGUG | 5690 |
| UAGUACACCGCCUUGCAGC | 5691 | GCUGCAAGGCGGUGUACUA | 5692 |
| CCAAGCUCCACACCACGAA | 5693 | UUCGUGGUGUGGAGCUUGG | 5694 |
| CAAGCUCCACACCACGAAG | 5695 | CUUCGUGGUGUGGAGCUUG | 5696 |
| AAGCUCCACACCACGAAGC | 5697 | GCUUCGUGGUGUGGAGCUU | 5698 |
| AGCUCCACACCACGAAGCC | 5699 | GGCUUCGUGGUGUGGAGCU | 5700 |
| CUCCACACCACGAAGCCGU | 5701 | ACGGCUUCGUGGUGUGGAG | 5702 |
| UCCACACCACGAAGCCGUU | 5703 | AACGGCUUCGUGGUGUGGA | 5704 |
| CCACACCACGAAGCCGUUG | 5705 | CAACGGCUUCGUGGUGUGG | 5706 |
| CACACCACGAAGCCGUUGC | 5707 | GCAACGGCUUCGUGGUGUG | 5708 |
| ACACCACGAAGCCGUUGCC | 5709 | GGCAACGGCUUCGUGGUGU | 5710 |
| CACCACGAAGCCGUUGCCA | 5711 | UGGCAACGGCUUCGUGGUG | 5712 |
| ACCACGAAGCCGUUGCCAG | 5713 | CUGGCAACGGCUUCGUGGU | 5714 |
| CCGCGAAGUCUUCCAGCUC | 5715 | GAGCUGGAAGACUUCGCGG | 5716 |
| CGCGAAGUCUUCCAGCUCA | 5717 | UGAGCUGGAAGACUUCGCG | 5718 |
| GCGAAGUCUUCCAGCUCAG | 5719 | CUGAGCUGGAAGACUUCGC | 5720 |
| UUCCAGCUCAGCAGUGUCU | 5721 | AGACACUGCUGAGCUGGAA | 5722 |
| UCCAGCUCAGCAGUGUCUC | 5723 | GAGACACUGCUGAGCUGGA | 5724 |
| CCAGCUCAGCAGUGUCUCG | 5725 | CGAGACACUGCUGAGCUGG | 5726 |

TABLE 9-continued

| Sense Sequence | SEQ ID NO: | Antisense Sequence | SEQ ID NO: |
|---|---|---|---|
| CAGCUCAGCAGUGUCUCGU | 5727 | ACGAGACACUGCUGAGCUG | 5728 |
| AGCUCAGCAGUGUCUCGUU | 5729 | AACGAGACACUGCUGAGCU | 5730 |
| GCUCAGCAGUGUCUCGUUC | 5731 | GAACGAGACACUGCUGAGC | 5732 |
| CUCAGCAGUGUCUCGUUCC | 5733 | GGAACGAGACACUGCUGAG | 5734 |
| GUAGCAGACCGACAUCCUU | 5735 | AAGGAUGUCGGUCUGCUAC | 5736 |
| UAGCAGACCGACAUCCUUC | 5737 | GAAGGAUGUCGGUCUGCUA | 5738 |
| AGCAGACCGACAUCCUUCU | 5739 | AGAAGGAUGUCGGUCUGCU | 5740 |
| AGACCGACAUCCUUCUGGG | 5741 | CCCAGAAGGAUGUCGGUCU | 5742 |
| GACCGACAUCCUUCUGGGC | 5743 | GCCCAGAAGGAUGUCGGUC | 5744 |
| CCGACAUCCUUCUGGGCCU | 5745 | AGGCCCAGAAGGAUGUCGG | 5746 |
| CGACAUCCUUCUGGGCCUA | 5747 | UAGGCCCAGAAGGAUGUCG | 5748 |
| GACAUCCUUCUGGGCCUAC | 5749 | GUAGGCCCAGAAGGAUGUC | 5750 |
| CUUCUGGGCCUACAGGUGG | 5751 | CCACCUGUAGGCCCAGAAG | 5752 |
| UUCUGGGCCUACAGGUGGG | 5753 | CCCACCUGUAGGCCCAGAA | 5754 |
| UCUGGGCCUACAGGUGGGU | 5755 | ACCCACCUGUAGGCCCAGA | 5756 |
| GGCCUACAGGUGGGUGGAA | 5757 | UUCCACCCACCUGUAGGCC | 5758 |
| CCUACAGGUGGGUGGAAGG | 5759 | CCUUCCACCCACCUGUAGG | 5760 |
| CUACAGGUGGGUGGAAGGC | 5761 | GCCUUCCACCCACCUGUAG | 5762 |
| UACAGGUGGGUGGAAGGCG | 5763 | CGCCUUCCACCCACCUGUA | 5764 |
| ACUUCCUGCAGCCUGCCU | 5765 | AGGCAGGCUGCAGGGAAGU | 5766 |
| CCUGCAGCCUGCCUCUUUU | 5767 | AAAAGAGGCAGGCUGCAGG | 5768 |
| CUGCAGCCUGCCUCUUUUC | 5769 | GAAAAGAGGCAGGCUGCAG | 5770 |
| GCAGCCUGCCUCUUUUCUG | 5771 | CAGAAAAGAGGCAGGCUGC | 5772 |
| CAGCCUGCCUCUUUUCUGC | 5773 | GCAGAAAAGAGGCAGGCUG | 5774 |
| AGCCUGCCUCUUUUCUGCC | 5775 | GGCAGAAAAGAGGCAGGCU | 5776 |
| GCCUCUUUUCUGCCUGGGA | 5777 | UCCCAGGCAGAAAAGAGGC | 5778 |
| CUUUUCUGCCUGGGAGUCC | 5779 | GGACUCCCAGGCAGAAAAG | 5780 |
| UUUUCUGCCUGGGAGUCCU | 5781 | AGGACUCCCAGGCAGAAAA | 5782 |
| UUCUGCCUGGGAGUCCUGA | 5783 | UCAGGACUCCCAGGCAGAA | 5784 |
| UCUGCCUGGGAGUCCUGAC | 5785 | GUCAGGACUCCCAGGCAGA | 5786 |
| UGCCUGGGAGUCCUGACUU | 5787 | AAGUCAGGACUCCCAGGCA | 5788 |
| GCCUGGGAGUCCUGACUUC | 5789 | GAAGUCAGGACUCCCAGGC | 5790 |
| CUGGGAGUCCUGACUUCCA | 5791 | UGGAAGUCAGGACUCCCAG | 5792 |
| UGGGAGUCCUGACUUCCAC | 5793 | GUGGAAGUCAGGACUCCCA | 5794 |
| GGGAGUCCUGACUUCCACG | 5795 | CGUGGAAGUCAGGACUCCC | 5796 |
| GGAGUCCUGACUUCCACGA | 5797 | UCGUGGAAGUCAGGACUCC | 5798 |
| GAGUCCUGACUUCCACGAG | 5799 | CUCGUGGAAGUCAGGACUC | 5800 |
| AGUCCUGACUUCCACGAGG | 5801 | CCUCGUGGAAGUCAGGACU | 5802 |
| CCUGACUUCCACGAGGACC | 5803 | GGUCCUCGUGGAAGUCAGG | 5804 |
| CUGACUUCCACGAGGACCC | 5805 | GGGUCCUCGUGGAAGUCAG | 5806 |
| UGACUUCCACGAGGACCCA | 5807 | UGGGUCCUCGUGGAAGUCA | 5808 |
| GACUUCCACGAGGACCCAG | 5809 | CUGGGUCCUCGUGGAAGUC | 5810 |
| ACUUCCACGAGGACCCAGA | 5811 | UCUGGGUCCUCGUGGAAGU | 5812 |
| CuUCCACGAGGACCCAGAC | 5813 | GUCUGGGUCCUCGUGGAAG | 5814 |
| UUCCACGAGGACCCAGACC | 5815 | GGUCUGGGUCCUCGUGGAA | 5816 |
| CCCUGCUCCCAGUCAGUUG | 5817 | CAACUGACUGGGAGCAGGG | 5818 |
| CCUGCUCCCAGUCAGUUGA | 5819 | UCAACUGACUGGGAGCAGG | 5820 |
| CUGCUCCCAGUCAGUUGAC | 5821 | GUCAACUGACUGGGAGCAG | 5822 |
| UGCUCCCAGUCAGUUGACC | 5823 | GGUCAACUGACUGGGAGCA | 5824 |
| CCCAGUCAGUUGACCUGCC | 5825 | GGCAGGUCAACUGACUGGG | 5826 |
| CCAGUCAGUUGACCUGCCC | 5827 | GGGCAGGUCAACUGACUGG | 5828 |
| GCCUCCUUCCCAGAGCUCA | 5829 | UGAGCUCUGGGAAGGAGGC | 5830 |
| CCUCCUUCCCAGAGCUCAG | 5831 | CUGAGCUCUGGGAAGGAGG | 5832 |
| CUCCUUCCCAGAGCUCAGU | 5833 | ACUGAGCUCUGGGAAGGAG | 5834 |
| UCCUUCCCAGAGCUCAGUG | 5835 | CACUGAGCUCUGGGAAGGA | 5836 |
| CCUUCCCAGAGCUCAGUGG | 5837 | CCACUGAGCUCUGGGAAGG | 5838 |
| UUCCCAGAGCUCAGUGGUA | 5839 | UACCACUGAGCUCUGGGAA | 5840 |
| UCCCAGAGCUCAGUGGUAA | 5841 | UUACCACUGAGCUCUGGGA | 5842 |
| CAGGCUGUCACUAUCUCUA | 5843 | UAGAGAUAGUGACAGCCUG | 5844 |
| AGGCUGUCACUAUCUCUAC | 5845 | GUAGAGAUAGUGACAGCCU | 5846 |
| UCUCUACCACCACUCCUCU | 5847 | AGAGGAGUGGUGGUAGAGA | 5848 |
| CCACCACUCCUCUAGUCUG | 5849 | CAGACUAGAGGAGUGGUGG | 5850 |
| CACCACUCCUCUAGUCUGG | 5851 | CCAGACUAGAGGAGUGGUG | 5852 |
| ACCACUCCUCUAGUCUGGC | 5853 | GCCAGACUAGAGGAGUGGU | 5854 |
| CCACUCCUCUAGUCUGGCC | 5855 | GGCCAGACUAGAGGAGUGG | 5856 |
| CACUCCUCUAGUCUGGCCC | 5857 | GGGCCAGACUAGAGGAGUG | 5858 |
| AUUCUAGCACAUCUGGGCA | 5859 | UGCCCAGAUGUGCUAGAAU | 5860 |
| UUCUAGCACAUCUGGGCAA | 5861 | UUGCCCAGAUGUGCUAGAA | 5862 |
| UCUAGCACAUCUGGGCAAA | 5863 | UUUGCCCAGAUGUGCUAGA | 5864 |
| CUAGCACAUCUGGGCAAAA | 5865 | UUUUGCCCAGAUGUGCUAG | 5866 |
| GGGUGUAAAGGGACGUGCA | 5867 | UGCACGUCCCUUUACACCC | 5868 |
| GGUGUAAAGGGACGUGCAC | 5869 | GUGCACGUCCCUUUACACC | 5870 |
| GUGUAAAGGGACGUGCACA | 5871 | UGUGCACGUCCCUUUACAC | 5872 |
| UGUAAAGGGACGUGCACAG | 5873 | CUGUGCACGUCCCUUUACA | 5874 |
| GUAAAGGGACGUGCACAGA | 5875 | UCUGUGCACGUCCCUUUAC | 5876 |
| UAAAGGGACGUGCACAGAU | 5877 | AUCUGUGCACGUCCCUUUA | 5878 |

TABLE 9-continued

| Sense Sequence | SEQ ID NO: | Antisense Sequence | SEQ ID NO: |
|---|---|---|---|
| AAAGGGACGUGCACAGAUC | 5879 | GAUCUGUGCACGUCCCUUU | 5880 |
| AAGGGACGUGCACAGAUCU | 5881 | AGAUCUGUGCACGUCCCUU | 5882 |
| AGGGACGUGCACAGAUCUA | 5883 | UAGAUCUGUGCACGUCCU | 5884 |
| CGUGCACAGAUCUACUUAC | 5885 | GUAAGUAGAUCUGUGCACG | 5886 |
| GUGCACAGAUCUACUUACC | 5887 | GGUAAGUAGAUCUGUGCAC | 5888 |
| UGCACAGAUCUACUUACCA | 5889 | UGGUAAGUAGAUCUGUGCA | 5890 |
| GCACAGAUCUACUUACCAA | 5891 | UUGGUAAGUAGAUCUGUGC | 5892 |
| CACAGAUCUACUUACCAAG | 5893 | CUUGGUAAGUAGAUCUGUG | 5894 |
| ACAGAUCUACUUACCAAGC | 5895 | GCUUGGUAAGUAGAUCUGU | 5896 |
| CAGAUCUACUUACCAAGCU | 5897 | AGCUUGGUAAGUAGAUCUG | 5898 |
| AGAUCUACUUACCAAGCUG | 5899 | CAGCUUGGUAAGUAGAUCU | 5900 |
| AUCUACUUACCAAGCUGGG | 5901 | CCCAGCUUGGUAAGUAGAU | 5902 |
| UCUACUUACCAAGCUGGGA | 5903 | UCCCAGCUUGGUAAGUAGA | 5904 |
| CUUACCAAGCUGGGAGCAA | 5905 | UUGCUCCCAGCUUGGUAAG | 5906 |
| UUACCAAGCUGGGAGCAAG | 5907 | CUUGCUCCCAGCUUGGUAA | 5908 |
| UACCAAGCUGGGAGCAAGC | 5909 | GCUUGCUCCCAGCUUGGUA | 5910 |
| ACCAAGCUGGGAGCAAGCA | 5911 | UGCUUGCUCCCAGCUUGGU | 5912 |
| GCUGGGAGCAAGCAGGAUU | 5913 | AAUCCUGCUUGCUCCCAGC | 5914 |
| CUGGGAGCAAGCAGGAUUG | 5915 | CAAUCCUGCUUGCUCCCAG | 5916 |
| UGGGAGCAAGCAGGAUUGG | 5917 | CCAAUCCUGCUUGCUCCCA | 5918 |
| GGGAGCAAGCAGGAUUGGG | 5919 | CCCAAUCCUGCUUGCUCCC | 5920 |
| AAAGGUUAAGCAGCAGUAG | 5921 | CUACUGCUGCUUAACCUUU | 5922 |
| AAGGUUAAGCAGCAGUAGG | 5923 | CCUACUGCUGCUUAACCUU | 5924 |
| AGGUUAAGCAGCAGUAGGC | 5925 | GCCUACUGCUGCUUAACCU | 5926 |
| GGUGCCUACUCCUGUCCUG | 5927 | CAGGACAGGAGUAGGCACC | 5928 |
| GUGCCUACUCCUGUCCUGU | 5929 | ACAGGACAGGAGUAGGCAC | 5930 |
| UGCCUACUCCUGUCCUGUG | 5931 | CACAGGACAGGAGUAGGCA | 5932 |
| GCCUACUCCUGUCCUGUGC | 5933 | GCACAGGACAGGAGUAGGC | 5934 |
| CCUACUCCUGUCCUGUGCC | 5935 | GGCACAGGACAGGAGUAGG | 5936 |
| CUACUCCUGUCCUGUGCCU | 5937 | AGGCACAGGACAGGAGUAG | 5938 |
| UACUCCUGUCCUGUGCCUA | 5939 | UAGGCACAGGACAGGAGUA | 5940 |
| ACUCCUGUCCUGUGCCUAU | 5941 | AUAGGCACAGGACAGGAGU | 5942 |
| CUCCUGUCCUGUGCCUAUC | 5943 | GAUAGGCACAGGACAGGAG | 5944 |
| UCCUGUCCUGUGCCUAUCA | 5945 | UGAUAGGCACAGGACAGGA | 5946 |
| GUGCCUAUCACAUUUGCAG | 5947 | CUGCAAAUGUGAUAGGCAC | 5948 |
| CUAUCACAUUUGCAGAGGG | 5949 | CCCUCUGCAAAUGUGAUAG | 5950 |
| UAUCACAUUUGCAGAGGGU | 5951 | ACCCUCUGCAAAUGUGAUA | 5952 |
| AUCACAUUUGCAGAGGGUA | 5953 | UACCCUCUGCAAAUGUGAU | 5954 |
| UCACAUUUGCAGAGGGUAA | 5955 | UUACCCUCUGCAAAUGUGA | 5956 |
| CACAUUUGCAGAGGGUAAG | 5957 | CUUACCCUCUGCAAAUGUG | 5958 |
| ACAUUUGCAGAGGGUAAGA | 5959 | UCUUACCCUCUGCAAAUGU | 5960 |
| CUCACCCUGCUCCUUCCCA | 5961 | UGGGAAGGAGCAGGGUGAG | 5962 |
| CACCCUGCUCCUUCCCAUC | 5963 | GAUGGGAAGGAGCAGGGUG | 5964 |
| CCUGCUCCUUCCCAUCACC | 5965 | GGUGAUGGGAAGGAGCAGG | 5966 |
| UGCUCCUUCCCAUCACCAA | 5967 | UUGGUGAUGGGAAGGAGCA | 5968 |
| CAGUAAGAUUCCCUGGUGG | 5969 | CCACCAGGGAAUCUUACUG | 5970 |
| AGUAAGAUUCCCUGGUGGU | 5971 | ACCACCAGGGAAUCUUACU | 5972 |
| GUAAGAUUCCCUGGUGGUG | 5973 | CACCACCAGGGAAUCUUAC | 5974 |
| UAAGAUUCCCUGGUGGUGG | 5975 | CCACCACCAGGGAAUCUUA | 5976 |
| AAGAUUCCCUGGUGGUGGA | 5977 | UCCACCACCAGGGAAUCUU | 5978 |
| UCCCUGGUGGUGGAAGGAA | 5979 | UUCCUUCCACCACCAGGGA | 5980 |
| UCUGCUGAAUCCUGGUCCU | 5981 | AGGACCAGGAUUCAGCAGA | 5982 |
| CUGCUGAAUCCUGGUCCUG | 5983 | CAGGACCAGGAUUCAGCAG | 5984 |
| UGCUGAAUCCUGGUCCUGC | 5985 | GCAGGACCAGGAUUCAGCA | 5986 |
| GCUGAAUCCUGGUCCUGCUUC | 5987 | GAAGCAGGACCAGGAUUCA | 5988 |
| GAAUCCUGGUCCUGCUUCU | 5989 | AGAAGCAGGACCAGGAUUC | 5990 |
| AAUCCUGGUCCUGCUUCUG | 5991 | CAGAAGCAGGACCAGGAUU | 5992 |
| AUCCUGGUCCUGCUUCUGU | 5993 | ACAGAAGCAGGACCAGGAU | 5994 |
| UCCUGGUCCUGCUUCUGUU | 5995 | AACAGAAGCAGGACCAGGA | 5996 |
| CCUGGUCCUGCUUCUGUUC | 5997 | GAACAGAAGCAGGACCAGG | 5998 |
| CUGGUCCUGCUUCUGUUCU | 5999 | AGAACAGAAGCAGGACCAG | 6000 |
| UUCUGUUCUCAUCCCUCCC | 6001 | GGGAGGGAUGAGAACAGAA | 6002 |
| CUUCUGCAGUGUGUAUGUU | 6003 | AACAUACACACUGCAGAAG | 6004 |
| UUCUGCAGUGUGUAUGUUG | 6005 | CAACAUACACACUGCAGAA | 6006 |
| UCUGCAGUGUGUAUGUUGC | 6007 | GCAACAUACACACUGCAGA | 6008 |
| CUGCAGUGUGUAUGUUGCC | 6009 | GGCAACAUACACACUGCAG | 6010 |
| UGCAGUGUGUAUGUUGCCU | 6011 | AGGCAACAUACACACUGCA | 6012 |
| GCAGUGUGUAUGUUGCCUG | 6013 | CAGGCAACAUACACACUGC | 6014 |
| CAGUGUGUAUGUUGCCUGG | 6015 | CCAGGCAACAUACACACUG | 6016 |
| AGUGUGUAUGUUGCCUGGU | 6017 | ACCAGGCAACAUACACACU | 6018 |
| GUGUGUAUGUUGCCUGGUC | 6019 | GACCAGGCAACAUACACAC | 6020 |
| UGUGUAUGUUGCCUGGUCU | 6021 | AGACCAGGCAACAUACACA | 6022 |
| GUGUAUGUUGCCUGGUCUC | 6023 | GAGACCAGGCAACAUACAC | 6024 |
| UGUAUGUUGCCUGGUCUCU | 6025 | AGAGACCAGGCAACAUACA | 6026 |
| GUAUGUUGCCUGGUCUCUC | 6027 | GAGAGACCAGGCAACAUAC | 6028 |
| UAUGUUGCCUGGUCUCUCU | 6029 | AGAGAGACCAGGCAACAUA | 6030 |

TABLE 9-continued

| Sense Sequence | SEQ ID NO: | Antisense Sequence | SEQ ID NO: |
|---|---|---|---|
| AUGUUGCCUGGUCUCUCUG | 6031 | CAGAGAGACCAGGCAACAU | 6032 |
| UGUUGCCUGGUCUCUCUGG | 6033 | CCAGAGAGACCAGGCAACA | 6034 |
| GUUGCCUGGUCUCUCUGGC | 6035 | GCCAGAGAGACCAGGCAAC | 6036 |
| UUGCCUGGUCUCUCUGGCC | 6037 | GGCCAGAGAGACCAGGCAA | 6038 |
| CUGGUCUCUCUGGCCUGCA | 6039 | UGCAGGCCAGAGAGACCAG | 6040 |
| CCUGCAGAGGUGACCCAAA | 6041 | UUUGGGUCACCUCUGCAGG | 6042 |
| CUGCCUUAUCCUUGCCUGU | 6043 | ACAGGCAAGGAUAAGGCAG | 6044 |
| UGCCUUAUCCUUGCCUGUU | 6045 | AACAGGCAAGGAUAAGGCA | 6046 |
| GCCUUAUCCUUGCCUGUUU | 6047 | AAACAGGCAAGGAUAAGGC | 6048 |
| AGUCUCCUGGUCCGGCUGA | 6049 | UCAGCCGGACCAGGAGACU | 6050 |
| GUCAAUGACAGCUUUUCCA | 6051 | UGGAAAAGCUGUCAUUGAC | 6052 |
| UGACAGCUUUUCCAUGUAA | 6053 | UUACAUGGAAAAGCUGUCA | 6054 |
| GACAGCUUUUCCAUGUAAG | 6055 | CUUACAUGGAAAAGCUGUC | 6056 |
| ACAGCUUUUCCAUGUAAGG | 6057 | CCUUACAUGGAAAAGCUGU | 6058 |
| CAGCUUUUCCAUGUAAGGC | 6059 | GCCUUACAUGGAAAAGCUG | 6060 |
| AGCUUUUCCAUGUAAGGCA | 6061 | UGCCUUACAUGGAAAAGCU | 6062 |
| UGUAAGGCAUGGUGCUAGG | 6063 | CCUAGCACCAUGCCUUACA | 6064 |
| GUAAGGCAUGGUGCUAGGU | 6066 | ACCUAGCACCAUGCCUUAC | 6066 |
| UAAGGCAUGGUGCUAGGUU | 6067 | AACCUAGCACCAUGCCUUA | 6068 |
| GCAUGGUGCUAGGUUCCAG | 6069 | CUGGAACCUAGCACCAUGC | 6070 |
| CAUGGUGCUAGGUUCCAGG | 6071 | CCUGGAACCUAGCACCAUG | 6072 |
| AUGGUGCUAGGUUCCAGGA | 6073 | UCCUGGAACCUAGCACCAU | 6074 |
| UGGUGCUAGGUUCCAGGAG | 6076 | CUCCUGGAACCUAGCACCA | 6076 |
| GGUGCUAGGUUCCAGGAGG | 6077 | CCUCCUGGAACCUAGCACC | 6078 |
| GUGCUAGGUUCCAGGAGGA | 6079 | UCCUCCUGGAACCUAGCAC | 6080 |
| UGCAUGGAGGCAUAAUGGU | 6081 | ACCAUUAUGCCUCCAUGCA | 6082 |
| GCAUGGAGGCAUAAUGGUU | 6083 | AACCAUUAUGCCUCCAUGC | 6084 |
| CAUGGAGGCAUAAUGGUUA | 6086 | UAACCAUUAUGCCUCCAUG | 6086 |
| AUGGAGGCAUAAUGGUUAG | 6087 | CUAACCAUUAUGCCUCCAU | 6088 |
| UGGAGGCAUAAUGGUUAGG | 6089 | CCUAACCAUUAUGCCUCCA | 6090 |
| GGAGGCAUAAUGGUUAGGG | 6091 | CCCUAACCAUUAUGCCUCC | 6092 |
| GAGGCAUAAUGGUUAGGGA | 6093 | UCCCUAACCAUUAUGCCUC | 6094 |
| CAUAAUGGUUAGGGAGUCA | 6096 | UGACUCCCUAACCAUUAUG | 6096 |
| AUAAUGGUUAGGGAGUCAU | 6097 | AUGACUCCCUAACCAUUAU | 6098 |
| UAAUGGUUAGGGAGUCAUG | 6099 | CAUGACUCCCUAACCAUUA | 6100 |
| GGUUAGGGAGUCAUGACAC | 6101 | GUGUCAUGACUCCCUAACC | 6102 |
| CAUUACCAGGCUGCACCAG | 6103 | CUGGUGCAGCCUGGUAAUG | 6104 |
| AUUACCAGGCUGCACCAGG | 6105 | CCUGGUGCAGCCUGGUAAU | 6106 |
| UACCAGGCUGCACCAGGAU | 6107 | AUCCUGGUGCAGCCUGGUA | 6108 |
| ACCAGGCUGCACCAGGAUA | 6109 | UAUCCUGGUGCAGCCUGGU | 6110 |
| CCAGGCUGCACCAGGAUAC | 6111 | GUAUCCUGGUGCAGCCUGG | 6112 |
| AAAGGAUGAGUAGGGACAU | 6113 | AUGUCCCUACUCAUCCUUU | 6114 |
| AAGGAUGAGUAGGGACAUA | 6116 | UAUGUCCCUACUCAUCCUU | 6116 |
| AGGAUGAGUAGGGACAUAC | 6117 | GUAUGUCCCUACUCAUCCU | 6118 |
| GUAGGGACAUACUAAGAAG | 6119 | CUUCUUAGUAUGUCCCUAC | 6120 |
| GGACAUACUAAGAAGCAGC | 6121 | GCUGCUUCUUAGUAUGUCC | 6122 |
| AUACUAAGAAGCAGCCCUC | 6123 | GAGGGCUGCUUCUUAGUAU | 6124 |
| UACUAAGAAGCAGCCCUCU | 6125 | AGAGGGCUGCUUCUUAGUA | 6126 |
| ACUAAGAAGCAGCCCUCUC | 6127 | GAGAGGGCUGCUUCUUAGU | 6128 |
| AGAAGCAGCCCUCUCCUCU | 6129 | AGAGGAGAGGGCUGCUUCU | 6130 |
| GAAGCAGCCCUCUCCUCUU | 6131 | AAGAGGAGAGGGCUGCUUC | 6132 |
| CAGCCCUCUCCUCUUGGAA | 6133 | UUCCAAGAGGAGAGGGCUG | 6134 |
| GCCUGGCAGAUGGAUAGAG | 6136 | CUCUAUCCAUCUGCCAGGC | 6136 |
| CCUGGCAGAUGGAUAGAGC | 6137 | GCUCUAUCCAUCUGCCAGG | 6138 |
| CUGGCAGAUGGAUAGAGCU | 6139 | AGCUCUAUCCAUCUGCCAG | 6140 |
| UGGCAGAUGGAUAGAGCUG | 6141 | CAGCUCUAUCCAUCUGCCA | 6142 |
| GGCAGAUGGAUAGAGCUGG | 6143 | CCAGCUCUAUCCAUCUGCC | 6144 |
| GCAGAUGGAUAGAGCUGGG | 6145 | CCCAGCUCUAUCCAUCUGC | 6146 |
| AAAGGCCUCUGCUCAAGUA | 6147 | UACUUGAGCAGAGGCCUUU | 6148 |
| AAGGCCUCUGCUCAAGUAA | 6149 | UUACUUGAGCAGAGGCCUU | 6150 |
| AGGCCUCUGCUCAAGUAAC | 6151 | GUUACUUGAGCAGAGGCCU | 6152 |
| CAGGAGCACUGUCUUAGUU | 6153 | AACUAAGACAGUGCUCCUG | 6154 |
| AGGAGCACUGUCUUAGUUU | 6155 | AAACUAAGACAGUGCUCCU | 6156 |
| GGAGCACUGUCUUAGUUUG | 6157 | CAAACUAAGACAGUGCUCC | 6158 |
| GAGCACUGUCUUAGUUUGG | 6159 | CCAAACUAAGACAGUGCUC | 6160 |
| AGCACUGUCUUAGUUUGGG | 6161 | CCCAAACUAAGACAGUGCU | 6162 |
| GUUCUUCCAAAGCAGAGCU | 6163 | AGCUCUGCUUUGGAAGAAC | 6164 |
| AGCAGAGCUUGAGCUAAGG | 6165 | CCUUAGCUCAAGCUCUGCU | 6166 |
| GCAGAGCUUGAGCUAAGGG | 6167 | CCCUUAGCUCAAGCUCUGC | 6168 |
| CAGAGCUUGAGCUAAGGGC | 6169 | GCCCUUAGCUCAAGCUCUG | 6170 |
| GCUUGAGCUAAGGGCUUGG | 6171 | CCAAGCCCUUAGCUCAAGC | 6172 |
| UUGAGCUAAGGGCUUGGGU | 6173 | ACCCAAGCCCUUAGCUCAA | 6174 |
| UGAGCUAAGGGCUUGGGUA | 6175 | UACCCAAGCCCUUAGCUCA | 6176 |
| GAGCUAAGGGCUUGGGUAC | 6177 | GUACCCAAGCCCUUAGCUC | 6178 |
| AGCUAAGGGCUUGGGUACA | 6179 | UGUACCCAAGCCCUUAGCU | 6180 |
| GCUAAGGGCUUGGGUACAG | 6181 | CUGUACCCAAGCCCUUAGC | 6182 |

TABLE 9-continued

| Sense Sequence | SEQ ID NO: | Antisense Sequence | SEQ ID NO: |
|---|---|---|---|
| AGGGCUUGGGUACAGGUGA | 6183 | UCACCUGUACCCAAGCCCU | 6184 |
| GGGCUUGGGUACAGGUGAU | 6185 | AUCACCUGUACCCAAGCCC | 6186 |
| GGCUUGGGUACAGGUGAUC | 6187 | GAUCACCUGUACCCAAGCC | 6188 |
| GCUUGGGUACAGGUGAUCC | 6189 | GGAUCACCUGUACCCAAGC | 6190 |
| AGGUGAUCCUGUAUUCUUG | 6191 | CAAGAAUACAGGAUCACCU | 6192 |
| GGUGAUCCUGUAUUCUUGA | 6193 | UCAAGAAUACAGGAUCACC | 6194 |
| GUGAUCCUGUAUUCUUGAG | 6195 | CUCAAGAAUACAGGAUCAC | 6196 |
| UGAUCCUGUAUUCUUGAGC | 6197 | GCUCAAGAAUACAGGAUCA | 6198 |
| UCCUGUAUUCUUGAGCUAA | 6199 | UUAGCUCAAGAAUACAGGA | 6200 |
| CCUGUAUUCUUGAGCUAAG | 6201 | CUUAGCUCAAGAAUACAGG | 6202 |
| UGUAUUCUUGAGCUAAGGG | 6203 | CCCUUAGCUCAAGAAUACA | 6204 |
| GUAUUCUUGAGCUAAGGGC | 6205 | GCCCUUAGCUCAAGAAUAC | 6206 |
| UCUUGAGCUAAGGGCUUGG | 6207 | CCAAGCCCUUAGCUCAAGA | 6208 |
| UUGAGCUAAGGGCUUGGGU | 6209 | ACCCAAGCCCUUAGCUCAA | 6210 |
| UGAGCUAAGGGCUUGGGUA | 6211 | UACCCAAGCCCUUAGCUCA | 6212 |
| GAGCUAAGGGCUUGGGUAC | 6213 | GUACCCAAGCCCUUAGCUC | 6214 |
| AGCUAAGGGCUUGGGUACA | 6215 | UGUACCCAAGCCCUUAGCU | 6216 |
| GCUAAGGGCUUGGGUACAG | 6217 | CUGUACCCAAGCCCUUAGC | 6218 |
| AGGGCUUGGGUACAGGUGA | 6219 | UCACCUGUACCCAAGCCCU | 6220 |
| GGGCUUGGGUACAGGUGAU | 6221 | AUCACCUGUACCCAAGCCC | 6222 |
| GGCUUGGGUACAGGUGAUC | 6223 | GAUCACCUGUACCCAAGCC | 6224 |
| GCUUGGGUACAGGUGAUCC | 6225 | GGAUCACCUGUACCCAAGC | 6226 |
| AGGUGAUCCUGUAUUUGGG | 6227 | CCCAAAUACAGGAUCACCU | 6228 |
| GGUGAUCCUGUAUUUGGGA | 6229 | UCCCAAAUACAGGAUCACC | 6230 |
| AUCCUGUAUUUGGGAGGUU | 6231 | AACCUCCCAAAUACAGGAU | 6232 |
| UCCUGUAUUUGGGAGGUUA | 6233 | UAACCUCCCAAAUACAGGA | 6234 |
| CCUGUAUUUGGGAGGUUAA | 6235 | UUAACCUCCCAAAUACAGG | 6236 |
| CUGUAUUUGGGAGGUUAAC | 6237 | GUUAACCUCCCAAAUACAG | 6238 |
| UGUAUUUGGGAGGUUAACU | 6239 | AGUUAACCUCCCAAAUACA | 6240 |
| GUAUUUGGGAGGUUAACUC | 6241 | GAGUUAACCUCCCAAAUAC | 6242 |
| UAUUUGGGAGGUUAACUCA | 6243 | UGAGUUAACCUCCCAAAUA | 6244 |
| GGAGGUUAACUCAGGAAGU | 6245 | ACUUCCUGAGUUAACCUCC | 6246 |
| GAGGUUAACUCAGGAAGUG | 6247 | CACUUCCUGAGUUAACCUC | 6248 |
| AGGUUAACUCAGGAAGUGA | 6249 | UCACUUCCUGAGUUAACCU | 6250 |
| UCAGGAAGUGAGGGCAUAA | 6251 | UUAUGCCCUCACUUCCUGA | 6252 |
| CAGGAAGUGAGGGCAUAAG | 6253 | CUUAUGCCCUCACUUCCUG | 6254 |
| AGGAAGUGAGGGCAUAAGG | 6255 | CCUUAUGCCCUCACUUCCU | 6256 |
| GGAAGUGAGGGCAUAAGGU | 6257 | ACCUUAUGCCCUCACUUCC | 6258 |
| GAAGUGAGGGCAUAAGGUA | 6259 | UACCUUAUGCCCUCACUUC | 6260 |
| AAGUGAGGGCAUAAGGUAA | 6261 | UUACCUUAUGCCCUCACUU | 6262 |
| AGUGAGGGCAUAAGGUAAA | 6263 | UUUACCUUAUGCCCUCACU | 6264 |
| AAAGCCAUUAAGAGUAUGU | 6265 | ACAUACUCUUAAUGGCUUU | 6266 |
| AAGCCAUUAAGAGUAUGUU | 6267 | AACAUACUCUUAAUGGCUU | 6268 |
| AGCCAUUAAGAGUAUGUUA | 6269 | UAACAUACUCUUAAUGGCU | 6270 |
| UAAGAGUAUGUUAAGUCCC | 6271 | GGGACUUAACAUACUCUUA | 6272 |
| AAGAGUAUGUUAAGUCCCU | 6273 | AGGGACUUAACAUACUCUU | 6274 |
| AGAGUAUGUUAAGUCCCUU | 6275 | AAGGGACUUAACAUACUCU | 6276 |
| GAGUAUGUUAAGUCCCUUC | 6277 | GAAGGGACUUAACAUACUC | 6278 |
| AGUAUGUUAAGUCCCUUCA | 6279 | UGAAGGGACUUAACAUACU | 6280 |
| GUAUGUUAAGUCCCUUCAG | 6281 | CUGAAGGGACUUAACAUAC | 6282 |
| UAUGUUAAGUCCCUUCAGU | 6283 | ACUGAAGGGACUUAACAUA | 6284 |
| AUGUUAAGUCCCUUCAGUA | 6285 | UACUGAAGGGACUUAACAU | 6286 |
| UGUUAAGUCCCUUCAGUAG | 6287 | CUACUGAAGGGACUUAACA | 6288 |
| GUUAAGUCCCUUCAGUAGG | 6289 | CCUACUGAAGGGACUUAAC | 6290 |
| UUAAGUCCCUUCAGUAGGC | 6291 | GCCUACUGAAGGGACUUAA | 6292 |
| UAAGUCCCUUCAGUAGGCC | 6293 | GGCCUACUGAAGGGACUUA | 6294 |
| AAGUCCCUUCAGUAGGCCU | 6295 | AGGCCUACUGAAGGGACUU | 6296 |
| AGUCCCUUCAGUAGGCCUU | 6297 | AAGGCCUACUGAAGGGACU | 6298 |
| GUCCCUUCAGUAGGCCUUG | 6299 | CAAGGCCUACUGAAGGGAC | 6300 |
| UCCCUUCAGUAGGCCUUGG | 6301 | CCAAGGCCUACUGAAGGGA | 6302 |
| CCCUUCAGUAGGCCUUGGG | 6303 | CCCAAGGCCUACUGAAGGG | 6304 |
| CCUUCAGUAGGCCUUGGGA | 6305 | UCCCAAGGCCUACUGAAGG | 6306 |
| CUUCAGUAGGCCUUGGGAA | 6307 | UUCCCAAGGCCUACUGAAG | 6308 |
| AAAAGUAUAGAUUGCCCAA | 6309 | UUGGGCAAUCUAUACUUUU | 6310 |
| AAAGUAUAGAUUGCCCAAG | 6311 | CUUGGGCAAUCUAUACUUU | 6312 |
| AAGUAUAGAUUGCCCAAGA | 6313 | UCUUGGGCAAUCUAUACUU | 6314 |
| AAAGACUGGCAGGGUGAUC | 6315 | GAUCACCCUGCCAGUCUUU | 6316 |
| AAGACUGGCAGGGUGAUCA | 6317 | UGAUCACCCUGCCAGUCUU | 6318 |
| CUGGCAGGGUGAUCAGUCC | 6319 | GGACUGAUCACCCUGCCAG | 6320 |
| GAAUGUACUUAAUGAGUGG | 6321 | CCACUCAUUAAGUACAUUC | 6322 |
| AAUGUACUUAAUGAGUGGG | 6323 | CCCACUCAUUAAGUACAUU | 6324 |
| UGUACUUAAUGAGUGGGCU | 6325 | AGCCCACUCAUUAAGUACA | 6326 |
| GUACUUAAUGAGUGGGCUA | 6327 | UAGCCCACUCAUUAAGUAC | 6328 |
| UACUUAAUGAGUGGGCUAC | 6329 | GUAGCCCACUCAUUAAGUA | 6330 |
| CUUAAUGAGUGGGCUACAG | 6331 | CUGUAGCCCACUCAUUAAG | 6332 |
| UAAUGAGUGGGCUACAGCG | 6333 | CGCUGUAGCCCACUCAUUA | 6334 |

TABLE 9-continued

| Sense Sequence | SEQ ID NO: | Antisense Sequence | SEQ ID NO: |
|---|---|---|---|
| AAUGAGUGGGCUACAGCGU | 6335 | ACGCUGUAGCCCACUCAUU | 6336 |
| AUGAGUGGGCUACAGCGUA | 6337 | UACGCUGUAGCCCACUCAU | 6338 |
| UGAGUGGGCUACAGCGUAU | 6339 | AUACGCUGUAGCCCACUCA | 6340 |
| GAGUGGGCUACAGCGUAUC | 6341 | GAUACGCUGUAGCCCACUC | 6342 |
| AGUGGGCUACAGCGUAUCC | 6343 | GGAUACGCUGUAGCCCACU | 6344 |
| GUGGGCUACAGCGUAUCCU | 6345 | AGGAUACGCUGUAGCCCAC | 6346 |
| UGGGCUACAGCGUAUCCUC | 6347 | GAGGAUACGCUGUAGCCCA | 6348 |
| AGAGUUGUUCUACCUGGGU | 6349 | ACCCAGGUAGAACAACUCU | 6350 |
| GAGUUGUUCUACCUGGGUA | 6351 | UACCCAGGUAGAACAACUC | 6352 |
| AGUUGUUCUACCUGGGUAU | 6353 | AUACCCAGGUAGAACAACU | 6354 |
| GUUGUUCUACCUGGGUAUA | 6355 | UAUACCCAGGUAGAACAAC | 6356 |
| UUGUUCUACCUGGGUAUAU | 6357 | AUAUACCCAGGUAGAACAA | 6358 |
| UGUUCUACCUGGGUAUAUC | 6359 | GAUAUACCCAGGUAGAACA | 6360 |
| GUUCUACCUGGGUAUAUCC | 6361 | GGAUAUACCCAGGUAGAAC | 6362 |
| UACCUGGGUAUAUCCAAAA | 6363 | UUUUGGAUAUACCCAGGUA | 6364 |
| AGGGUAUGGAGUUUACGAG | 6365 | CUCGUAAACUCCAUACCCU | 6366 |
| GGGUAUGGAGUUUACGAGG | 6367 | CCUCGUAAACUCCAUACCC | 6368 |
| GGUAUGGAGUUUACGAGGG | 6369 | CCCUCGUAAACUCCAUACC | 6370 |
| GUAUGGAGUUUACGAGGGU | 6371 | ACCCUCGUAAACUCCAUAC | 6372 |
| UAUGGAGUUUACGAGGGUU | 6373 | AACCCUCGUAAACUCCAUA | 6374 |
| AUGGAGUUUACGAGGGUUC | 6375 | GAACCCUCGUAAACUCCAU | 6376 |
| UGGAGUUUACGAGGGUUCA | 6377 | UGAACCCUCGUAAACUCCA | 6378 |
| GGAGUUUACGAGGGUUCAA | 6379 | UUGAACCCUCGUAAACUCC | 6380 |
| GAGUUUACGAGGGUUCAAG | 6381 | CUUGAACCCUCGUAAACUC | 6382 |
| AGUUUACGAGGGUUCAAGG | 6383 | CCUUGAACCCUCGUAAACU | 6384 |
| GUUUACGAGGGUUCAAGGU | 6385 | ACCUUGAACCCUCGUAAAC | 6386 |
| UUUACGAGGGUUCAAGGUA | 6387 | UACCUUGAACCCUCGUAAA | 6388 |
| CGAGGGUUCAAGGUAUUUG | 6389 | CAAAUACCUUGAACCCUCG | 6390 |
| GAGGGUUCAAGGUAUUUGG | 6391 | CCAAAUACCUUGAACCCUC | 6392 |
| AGGGUUCAAGGUAUUUGGU | 6393 | ACCAAAUACCUUGAACCCU | 6394 |
| GGGUUCAAGGUAUUUGGUU | 6395 | AACCAAAUACCUUGAACCC | 6396 |
| GGUUCAAGGUAUUUGGUUC | 6397 | GAACCAAAUACCUUGAACC | 6398 |
| GUUCAAGGUAUUUGGUUCA | 6399 | UGAACCAAAUACCUUGAAC | 6400 |
| UUCAAGGUAUUUGGUUCAG | 6401 | CUGAACCAAAUACCUUGAA | 6402 |
| UCAAGGUAUUUGGUUCAGG | 6403 | CCUGAACCAAAUACCUUGA | 6404 |
| CAACUGGCCAGGUCACAGG | 6405 | CCUGUGACCUGGCCAGUUG | 6406 |
| GCCAGGUCACAGGGCAAUC | 6407 | GAUUGCCCUGUGACCUGGC | 6408 |
| CCAGGUCACAGGGCAAUCA | 6409 | UGAUUGCCCUGUGACCUGG | 6410 |
| AGGUCACAGGGCAAUCAAG | 6411 | CUUGAUUGCCCUGUGACCU | 6412 |
| GGUCACAGGGCAAUCAAGU | 6413 | ACUUGAUUGCCCUGUGACC | 6414 |
| GUCACAGGGCAAUCAAGUU | 6415 | AACUUGAUUGCCCUGUGAC | 6416 |
| UCACAGGGCAAUCAAGUUA | 6417 | UAACUUGAUUGCCCUGUGA | 6418 |
| CACAGGGCAAUCAAGUUAC | 6419 | GUAACUUGAUUGCCCUGUG | 6420 |
| ACAGGGCAAUCAAGUUACU | 6421 | AGUAACUUGAUUGCCCUGU | 6422 |
| CAGGGCAAUCAAGUUACUC | 6423 | GAGUAACUUGAUUGCCCUG | 6424 |
| AGGGCAAUCAAGUUACUCU | 6425 | AGAGUAACUUGAUUGCCCU | 6426 |
| CAAUCAAGUUACUCUGUGU | 6427 | ACACAGAGUAACUUGAUUG | 6428 |
| AAUCAAGUUACUCUGUGUU | 6429 | AACACAGAGUAACUUGAUU | 6430 |
| AUCAAGUUACUCUGUGUUU | 6431 | AAACACAGAGUAACUUGAU | 6432 |
| ACUCUGUGUUUCUUUGUCA | 6433 | UGACAAAGAAACACAGAGU | 6434 |
| UCUGUGUUUCUUUGUCAGG | 6435 | CCUGACAAAGAAACACAGA | 6436 |
| UGUUUCUUUGUCAGGACAC | 6437 | GUGUCCUGACAAAGAAACA | 6438 |
| AAAGCAGGGAUUGUGUUCA | 6439 | UGAACACAAUCCCUGCUUU | 6440 |
| AAGCAGGGAUUGUGUUCAU | 6441 | AUGAACACAAUCCCUGCUU | 6442 |
| AGCAGGGAUUGUGUUCAUU | 6443 | AAUGAACACAAUCCCUGCU | 6444 |
| GCAGGGAUUGUGUUCAUUU | 6445 | AAAUGAACACAAUCCCUGC | 6446 |
| CAGGGAUUGUGUUCAUUUG | 6447 | CAAAUGAACACAAUCCCUG | 6448 |
| AGGGAUUGUGUUCAUUUGA | 6449 | UCAAAUGAACACAAUCCCU | 6450 |
| GUGUUCAUUUGAGGGUUUC | 6451 | GAAACCCUCAAAUGAACAC | 6452 |
| UGUUCAUUUGAGGGUUUCA | 6453 | UGAAACCCUCAAAUGAACA | 6454 |
| GUUCAUUUGAGGGUUUCAC | 6455 | GUGAAACCCUCAAAUGAAC | 6456 |
| UUCAUUUGAGGGUUUCACU | 6457 | AGUGAAACCCUCAAAUGAA | 6458 |
| UCAUUUGAGGGUUUCACUG | 6459 | CAGUGAAACCCUCAAAUGA | 6460 |
| CAUUUGAGGGUUUCACUGU | 6461 | ACAGUGAAACCCUCAAAUG | 6462 |
| AGUCUCAGCUUCCAUGCAA | 6463 | UUGCAUGGAAGCUGAGACU | 6464 |
| UCUCAGCUUCCAUGCAACU | 6465 | AGUUGCAUGGAAGCUGAGA | 6466 |
| CUCAGCUUCCAUGCAACUG | 6467 | CAGUUGCAUGGAAGCUGAG | 6468 |
| UCAGCUUCCAUGCAACUGU | 6469 | ACAGUUGCAUGGAAGCUGA | 6470 |
| CAGCUUCCAUGCAACUGUC | 6471 | GACAGUUGCAUGGAAGCUG | 6472 |
| AGCUUCCAUGCAACUGUCC | 6473 | GGACAGUUGCAUGGAAGCU | 6474 |
| GCUUCCAUGCAACUGUCCA | 6475 | UGGACAGUUGCAUGGAAGC | 6476 |
| CUUCCAUGCAACUGUCCAU | 6477 | AUGGACAGUUGCAUGGAAG | 6478 |
| UUCCAUGCAACUGUCCAUC | 6479 | GAUGGACAGUUGCAUGGAA | 6480 |
| CCAUGCAACUGUCCAUCAC | 6481 | GUGAUGGACAGUUGCAUGG | 6482 |
| CAUGCAACUGUCCAUCACG | 6483 | CGUGAUGGACAGUUGCAUG | 6484 |
| AUGCAACUGUCCAUCACGG | 6485 | CCGUGAUGGACAGUUGCAU | 6486 |

TABLE 9-continued

| Sense Sequence | SEQ ID NO: | Antisense Sequence | SEQ ID NO: |
|---|---|---|---|
| UGCAACUGUCCAUCACGGC | 6487 | GCCGUGAUGGACAGUUGCA | 6488 |
| GCAACUGUCCAUCACGGCU | 6489 | AGCCGUGAUGGACAGUUGC | 6490 |
| CAACUGUCCAUCACGGCUG | 6491 | CAGCCGUGAUGGACAGUUG | 6492 |
| AACUGUCCAUCACGGCUGC | 6493 | GCAGCCGUGAUGGACAGUU | 6494 |
| ACUGUCCAUCACGGCUGCA | 6495 | UGCAGCCGUGAUGGACAGU | 6496 |
| CUGUCCAUCACGGCUGCAA | 6497 | UUGCAGCCGUGAUGGACAG | 6498 |
| UGUCCAUCACGGCUGCAAC | 6499 | GUUGCAGCCGUGAUGGACA | 6500 |
| GUCCAUCACGGCUGCAACU | 6501 | AGUUGCAGCCGUGAUGGAC | 6502 |
| UCCAUCACGGCUGCAACUG | 6503 | CAGUUGCAGCCGUGAUGGA | 6504 |
| CCAUCACGGCUGCAACUGA | 6505 | UCAGUUGCAGCCGUGAUGG | 6506 |
| CAUCACGGCUGCAACUGAA | 6507 | UUCAGUUGCAGCCGUGAUG | 6508 |
| ACAGCGCACCAGAAGCUAA | 6509 | UUAGCUUCUGGUGCGCUGU | 6510 |
| CAGCGCACCAGAAGCUAAA | 6511 | UUUAGCUUCUGGUGCGCUG | 6512 |
| AGCGCACCAGAAGCUAAAG | 6513 | CUUUAGCUUCUGGUGCGCU | 6514 |
| GCGCACCAGAAGCUAAAGU | 6515 | ACUUUAGCUUCUGGUGCGC | 6516 |
| CGCACCAGAAGCUAAAGUC | 6517 | GACUUUAGCUUCUGGUGCG | 6518 |
| GCACCAGAAGCUAAAGUCU | 6519 | AGACUUUAGCUUCUGGUGC | 6520 |
| CACCAGAAGCUAAAGUCUU | 6521 | AAGACUUUAGCUUCUGGUG | 6522 |
| ACCAGAAGCUAAAGUCUUG | 6523 | CAAGACUUUAGCUUCUGGU | 6524 |
| CCAGAAGCUAAAGUCUUGA | 6525 | UCAAGACUUUAGCUUCUGG | 6526 |
| CAGAAGCUAAAGUCUUGAU | 6527 | AUCAAGACUUUAGCUUCUG | 6528 |
| AGAAGCUAAAGUCUUGAUG | 6529 | CAUCAAGACUUUAGCUUCU | 6530 |
| GAAGCUAAAGUCUUGAUGC | 6531 | GCAUCAAGACUUUAGCUUC | 6532 |
| AAGCUAAAGUCUUGAUGCC | 6533 | GGCAUCAAGACUUUAGCUU | 6534 |
| AGCUAAAGUCUUGAUGCCA | 6535 | UGGCAUCAAGACUUUAGCU | 6536 |
| CCCAUUCACAUCUCUGUCA | 6537 | UGACAGAGAUGUGAAUGGG | 6538 |
| UUCACAUCUCUGUCACGUC | 6539 | GACGUGACAGAGAUGUGAA | 6540 |
| UCACAUCUCUGUCACGUCC | 6541 | GGACGUGACAGAGAUGUGA | 6542 |
| CACAUCUCUGUCACGUCCA | 6543 | UGGACGUGACAGAGAUGUG | 6544 |
| UCUCUGUCACGUCCACUAA | 6545 | UUAGUGGACGUGACAGAGA | 6546 |
| CUCUGUCACGUCCACUAAU | 6547 | AUUAGUGGACGUGACAGAG | 6548 |
| UCUGUCACGUCCACUAAUC | 6549 | GAUUAGUGGACGUGACAGA | 6550 |
| CUGUCACGUCCACUAAUCG | 6551 | CGAUUAGUGGACGUGACAG | 6552 |
| UGUCACGUCCACUAAUCGG | 6553 | CCGAUUAGUGGACGUGACA | 6554 |
| GUCACGUCCACUAAUCGGC | 6555 | GCCGAUUAGUGGACGUGAC | 6556 |
| UCACGUCCACUAAUCGGCA | 6557 | UGCCGAUUAGUGGACGUGA | 6558 |
| CACGUCCACUAAUCGGCAA | 6559 | UUGCCGAUUAGUGGACGUG | 6560 |
| ACGUCCACUAAUCGGCAAA | 6561 | UUUGCCGAUUAGUGGACGU | 6562 |
| CGUCCACUAAUCGGCAAAA | 6563 | UUUUGCCGAUUAGUGGACG | 6564 |
| GUCCACUAAUCGGCAAAAG | 6565 | CUUUUGCCGAUUAGUGGAC | 6566 |
| UCCACUAAUCGGCAAAAGG | 6567 | CCUUUUGCCGAUUAGUGGA | 6568 |
| CCACUAAUCGGCAAAAGGA | 6569 | UCCUUUUGCCGAUUAGUGG | 6570 |
| CACUAAUCGGCAAAAGGAG | 6571 | CUCCUUUUGCCGAUUAGUG | 6572 |
| AGAAGAUGACCUAAGUGUG | 6573 | CACACUUAGGUCAUCUUCU | 6574 |
| GAAGAUGACCUAAGUGUGA | 6575 | UCACACUUAGGUCAUCUUC | 6576 |
| AAGAUGACCUAAGUGUGAC | 6577 | GUCACACUUAGGUCAUCUU | 6578 |
| AGAUGACCUAAGUGUGACU | 6579 | AGUCACACUUAGGUCAUCU | 6580 |
| GAUGACCUAAGUGUGACUG | 6581 | CAGUCACACUUAGGUCAUC | 6582 |
| AUGACCUAAGUGUGACUGC | 6583 | GCAGUCACACUUAGGUCAU | 6584 |
| UGACCUAAGUGUGACUGCA | 6585 | UGCAGUCACACUUAGGUCA | 6586 |
| AAAAUGAAGCCAGAGCAGU | 6587 | ACUGCUCUGGCUUCAUUUU | 6588 |
| UCCGACCAAGGAGGAAGGA | 6589 | UCCUUCCUCCUUGGUCGGA | 6590 |
| CCGACCAAGGAGGAAGGAA | 6591 | UUCCUUCCUCCUUGGUCGG | 6592 |
| AGAGCAGGUAAGCAGGAAG | 6593 | CUUCCUGCUUACCUGCUCU | 6594 |
| GAGCAGGUAAGCAGGAAGG | 6595 | CCUUCCUGCUUACCUGCUC | 6596 |
| AGGUAAGCAGGAAGGCCAG | 6597 | CUGGCCUUCCUGCUUACCU | 6598 |
| AGCAGGAAGGCCAGUGUCC | 6599 | GGACACUGGCCUUCCUGCU | 6600 |
| CAGGAAGGCCAGUGUCCCA | 6601 | UGGGACACUGGCCUUCCUG | 6602 |
| UCCCAGACAGGACCCUAAU | 6603 | AUUAGGGUCCUGUCUGGGA | 6604 |
| CCCAGACAGGACCCUAAUG | 6605 | CAUUAGGGUCCUGUCUGGG | 6606 |
| CCAGACAGGACCCUAAUGA | 6607 | UCAUUAGGGUCCUGUCUGG | 6608 |
| CAGACAGGACCCUAAUGAU | 6609 | AUCAUUAGGGUCCUGUCUG | 6610 |
| AGACAGGACCCUAAUGAUC | 6611 | GAUCAUUAGGGUCCUGUCU | 6612 |
| GACAGGACCCUAAUGAUCC | 6613 | GGAUCAUUAGGGUCCUGUC | 6614 |
| GGACCCUAAUGAUCCUGAA | 6615 | UUCAGGAUCAUUAGGGUCC | 6616 |
| CCUAAUGAUCCUGAAUCCA | 6617 | UGGAUUCAGGAUCAUUAGG | 6618 |
| CUAAUGAUCCUGAAUCCAU | 6619 | AUGGAUUCAGGAUCAUUAG | 6620 |
| UGAUCCUGAAUCCAUGUAU | 6621 | AUACAUGGAUUCAGGAUCA | 6622 |
| GAUCCUGAAUCCAUGUAUC | 6623 | GAUACAUGGAUUCAGGAUC | 6624 |
| AUCCUGAAUCCAUGUAUCA | 6625 | UGAUACAUGGAUUCAGGAU | 6626 |
| UCCUGAAUCCAUGUAUCAG | 6627 | AUGGAUCCUGAUACAUGGA | 6628 |
| CCAUGUAUCAGGAUCCAUC | 6629 | GAUGGAUCCUGAUACAUGG | 6630 |
| CAUGUAUCAGGAUCCAUCC | 6631 | GGAUGGAUCCUGAUACAUG | 6632 |
| UCACCUCUCAUUUUCCAAA | 6633 | UUUGGAAAAUGAGAGGUGA | 6634 |
| UCCAAAGCCCUGCCAUGCU | 6635 | AGCAUGGCAGGGCUUUGGA | 6636 |
| CCAAAGCCCUGCCAUGCUG | 6637 | CAGCAUGGCAGGGCUUUGG | 6638 |

TABLE 9-continued

| Sense Sequence | SEQ ID NO: | Antisense Sequence | SEQ ID NO: |
|---|---|---|---|
| CAUGCUGCCAUCCCACUUC | 6639 | GAAGUGGGAUGGCAGCAUG | 6640 |
| AUGCUGCCAUCCCACUUCC | 6641 | GGAAGUGGGAUGGCAGCAU | 6642 |
| UGCUGCCAUCCCACUUCCC | 6643 | GGGAAGUGGGAUGGCAGCA | 6644 |
| CGGGUUCCCUUUUCCUAAA | 6645 | UUUAGGAAAAGGGAACCCG | 6646 |
| AGCUGCAGCUUAUGGCUUC | 6647 | GAAGCCAUAAGCUGCAGCU | 6648 |
| GCUGCAGCUUAUGGCUUCU | 6649 | AGAAGCCAUAAGCUGCAGC | 6650 |
| CUGCAGCUUAUGGCUUCUC | 6651 | GAGAAGCCAUAAGCUGCAG | 6652 |
| UGCAGCUUAUGGCUUCUCC | 6653 | GGAGAAGCCAUAAGCUGCA | 6654 |
| GCAGCUUAUGGCUUCUCCA | 6655 | UGGAGAAGCCAUAAGCUGC | 6656 |
| CAGCUUAUGGCUUCUCCAG | 6657 | CUGGAGAAGCCAUAAGCUG | 6658 |
| AGCUUAUGGCUUCUCCAGU | 6659 | ACUGGAGAAGCCAUAAGCU | 6660 |
| GCUUAUGGCUUCUCCAGUA | 6661 | UACUGGAGAAGCCAUAAGC | 6662 |
| CUUAUGGCUUCUCCAGUAG | 6663 | CUACUGGAGAAGCCAUAAG | 6664 |
| UUAUGGCUUCUCCAGUAGG | 6665 | CCUACUGGAGAAGCCAUAA | 6666 |
| UAUGGCUUCUCCAGUAGGU | 6667 | ACCUACUGGAGAAGCCAUA | 6668 |
| AUGGCUUCUCCAGUAGGUG | 6669 | CACCUACUGGAGAAGCCAU | 6670 |
| UGGCUUCUCCAGUAGGUGG | 6671 | CCACCUACUGGAGAAGCCA | 6672 |
| GGCUUCUCCAGUAGGUGGC | 6673 | GCCACCUACUGGAGAAGCC | 6674 |
| GCUUCUCCAGUAGGUGGCA | 6675 | UGCCACCUACUGGAGAAGC | 6676 |
| CUUCUCCAGUAGGUGGCAG | 6677 | CUGCCACCUACUGGAGAAG | 6678 |
| UUCUCCAGUAGGUGGCAGC | 6679 | GCUGCCACCUACUGGAGAA | 6680 |
| UCUCCAGUAGGUGGCAGCA | 6681 | UGCUGCCACCUACUGGAGA | 6682 |
| CUCCAGUAGGUGGCAGCAC | 6683 | GUGCUGCCACCUACUGGAG | 6684 |
| ACACCAGAAGUCACAUUUC | 6685 | GAAAUGUGACUUCUGGUGU | 6686 |
| GAAGUCACAUUUCAUCCUU | 6687 | AAGGAUGAAAUGUGACUUC | 6688 |
| AAGUCACAUUUCAUCCUUU | 6689 | AAAGGAUGAAAUGUGACUU | 6690 |
| AGUCACAUUUCAUCCUUUU | 6691 | AAAAGGAUGAAAUGUGACU | 6692 |
| UUUCAUCCUUUUACAUGGU | 6693 | ACCAUGUAAAAGGAUGAAA | 6694 |
| UUCAUCCUUUUACAUGGUU | 6695 | AACCAUGUAAAAGGAUGAA | 6696 |
| UCAUCCUUUUACAUGGUUC | 6697 | GAACCAUGUAAAAGGAUGA | 6698 |
| CAUCCUUUUACAUGGUUCC | 6699 | GGAACCAUGUAAAAGGAUG | 6700 |
| UGGUUCCCAUCUACCCUCA | 6701 | UGAGGGUAGAUGGGAACCA | 6702 |
| GGUUCCCAUCUACCCUCAC | 6703 | GUGAGGGUAGAUGGGAACC | 6704 |
| GUUCCCAUCUACCCUCACA | 6705 | UGUGAGGGUAGAUGGGAAC | 6706 |
| GGCAAUUCUUCCUCCAGGA | 6707 | UCCUGGAGGAAGAAUUGCC | 6708 |
| GCAAUUCUUCCUCCAGGAC | 6709 | GUCCUGGAGGAAGAAUUGC | 6710 |
| CAAUUCUUCCUCCAGGACC | 6711 | GGUCCUGGAGGAAGAAUUG | 6712 |
| AAUUCUUCCUCCAGGACCC | 6713 | GGGUCCUGGAGGAAGAAUU | 6714 |
| CCCUUGGACUUUGCCCUUC | 6715 | GAAGGGCAAAGUCCAAGGG | 6716 |
| CCUUGGACUUUGCCCUUCU | 6717 | AGAAGGGCAAAGUCCAAGG | 6718 |
| CUUGGACUUUGCCCUUCUU | 6719 | AAGAAGGGCAAAGUCCAAG | 6720 |
| UUGGACUUUGCCCUUCUUA | 6721 | UAAGAAGGGCAAAGUCCAA | 6722 |
| UGGACUUUGCCCUUCUUAC | 6723 | GUAAGAAGGGCAAAGUCCA | 6724 |
| GGACUUUGCCCUUCUUACU | 6725 | AGUAAGAAGGGCAAAGUCC | 6726 |
| UUUGCCCUUCUUACUGGCC | 6727 | GGCCAGUAAGAAGGGCAAA | 6728 |
| UUGCCCUUCUUACUGGCCA | 6729 | UGGCCAGUAAGAAGGGCAA | 6730 |
| UGCCCUUCUUACUGGCCAG | 6731 | CUGGCCAGUAAGAAGGGCA | 6732 |
| UCUUACUGGCCAGGCAGGG | 6733 | CCCUGCCUGGCCAGUAAGA | 6734 |
| GGCCAGAGUCCAGGCUUGA | 6735 | UCAAGCCUGGACUCUGGCC | 6736 |
| GCCAGAGUCCAGGCUUGAC | 6737 | GUCAAGCCUGGACUCUGGC | 6738 |
| GUCCAGGCUUGACUCAUUC | 6739 | GAAUGAGUCAAGCCUGGAC | 6740 |
| AGGCUUGACUCAUUCCCAC | 6741 | GUGGGAAUGAGUCAAGCCU | 6742 |
| GACUCAUUCCCACCUUGUC | 6743 | GACAAGGUGGGAAUGAGUC | 6744 |
| ACUCAUUCCCACCUUGUCC | 6745 | GGACAAGGUGGGAAUGAGU | 6746 |
| UCAUUCCCACCUUGUCCUG | 6747 | CAGGACAAGGUGGGAAUGA | 6748 |
| CACCUUGUCCUGGGCUGAG | 6749 | CUCAGCCCAGGACAAGGUG | 6750 |
| ACCACCCAGCCCAGAAGUU | 6751 | AACUUCUGGGCUGGGUGGU | 6752 |
| CCACCCAGCCCAGAAGUUC | 6753 | GAACUUCUGGGCUGGGUGG | 6754 |
| CACCCAGCCCAGAAGUUCC | 6755 | GGAACUUCUGGGCUGGGUG | 6756 |
| ACCCAGCCCAGAAGUUCCA | 6757 | UGGAACUUCUGGGCUGGGU | 6758 |
| CCAGAAGUUCCAGGGAAGG | 6759 | CCUUCCCUGGAACUUCUGG | 6760 |
| CAGAAGUUCCAGGGAAGGA | 6761 | UCCUUCCCUGGAACUUCUG | 6762 |
| AACUCUCCGGUCCACCAUG | 6763 | CAUGGUGGACCGGAGAGUU | 6764 |
| ACUCUCCGGUCCACCAUGG | 6765 | CCAUGGUGGACCGGAGAGU | 6766 |
| CACCAUGGAGUACCUCUCA | 6767 | UGAGAGGUACUCCAUGGUG | 6768 |
| ACCAUGGAGUACCUCUCAG | 6769 | CUGAGAGGUACUCCAUGGU | 6770 |
| UGGAGUACCUCUCAGCUCU | 6771 | AGAGCUGAGAGGUACUCCA | 6772 |
| GGAGUACCUCUCAGCUCUG | 6773 | CAGAGCUGAGAGGUACUCC | 6774 |
| GAGUACCUCUCAGCUCUGA | 6775 | UCAGAGCUGAGAGGUACUC | 6776 |
| AGUACCUCUCAGCUCUGAA | 6777 | UUCAGAGCUGAGAGGUACU | 6778 |
| CCAGUGACUUACUCAGGUG | 6779 | CACCUGAGUAAGUCACUGG | 6780 |
| CAGUGACUUACUCAGGUGA | 6781 | UCACCUGAGUAAGUCACUG | 6782 |
| AGUGACUUACUCAGGUGAC | 6783 | GUCACCUGAGUAAGUCACU | 6784 |
| GUGACUUACUCAGGUGACU | 6785 | AGUCACCUGAGUAAGUCAC | 6786 |
| UGACUUACUCAGGUGACUG | 6787 | CAGUCACCUGAGUAAGUCA | 6788 |
| GACUUACUCAGGUGACUGC | 6789 | GCAGUCACCUGAGUAAGUC | 6790 |

TABLE 9-continued

| Sense Sequence | SEQ ID NO: | Antisense Sequence | SEQ ID NO: |
|---|---|---|---|
| ACUUACUCAGGUGACUGCU | 6791 | AGCAGUCACCUGAGUAAGU | 6792 |
| CUUACUCAGGUGACUGCUA | 6793 | UAGCAGUCACCUGAGUAAG | 6794 |
| UUACUCAGGUGACUGCUAA | 6795 | UUAGCAGUCACCUGAGUAA | 6796 |
| UACUCAGGUGACUGCUAAC | 6797 | GUUAGCAGUCACCUGAGUA | 6798 |
| ACUCAGGUGACUGCUAACC | 6799 | GGUUAGCAGUCACCUGAGU | 6800 |
| CUCAGGUGACUGCUAACCC | 6801 | GGGUUAGCAGUCACCUGAG | 6802 |
| GGUGACUGCUAACCCUCCG | 6803 | CGGAGGGUUAGCAGUCACC | 6804 |
| GUGACUGCUAACCCUCCGC | 6805 | GCGGAGGGUUAGCAGUCAC | 6806 |
| UGACUGCUAACCCUCCGCU | 6807 | AGCGGAGGGUUAGCAGUCA | 6808 |
| GACUGCUAACCCUCCGCUC | 6809 | GAGCGGAGGGUUAGCAGUC | 6810 |
| ACUGCUAACCCUCCGCUCU | 6811 | AGAGCGGAGGGUUAGCAGU | 6812 |
| CUGCUAACCCUCCGCUCUA | 6813 | UAGAGCGGAGGGUUAGCAG | 6814 |
| UGCUAACCCUCCGCUCUAC | 6815 | GUAGAGCGGAGGGUUAGCA | 6816 |
| AACCCUCCGCUCUACCCUC | 6817 | GAGGGUAGAGCGGAGGGUU | 6818 |
| ACUCCACAGUGGGCUUGUC | 6819 | GACAAGCCCACUGUGGAGU | 6820 |
| CUCCACAGUGGGCUUGUCA | 6821 | UGACAAGCCCACUGUGGAG | 6822 |
| UCCACAGUGGGCUUGUCAA | 6823 | UUGACAAGCCCACUGUGGA | 6824 |
| CCACAGUGGGCUUGUCAAG | 6825 | CUUGACAAGCCCACUGUGG | 6826 |
| GUCAAGCUCCUGAGCCACC | 6827 | GGUGGCUCAGGAGCUUGAC | 6828 |
| CCAUGGUCUCUCCCUCAUC | 6829 | GAUGAGGGAGAGACCAUGG | 6830 |
| CAUGGUCUCUCCCUCAUCC | 6831 | GGAUGAGGGAGAGACCAUG | 6832 |
| AUGGUCUCUCCCUCAUCCC | 6833 | GGGAUGAGGGAGAGACCAU | 6834 |
| UCUCUCCCUCAUCCCUAAU | 6835 | AUUAGGGAUGAGGGAGAGA | 6836 |
| CUCUCCCUCAUCCCUAAUC | 6837 | GAUUAGGGAUGAGGGAGAG | 6838 |
| UCUCCCUCAUCCCUAAUCG | 6839 | CGAUUAGGGAUGAGGGAGA | 6840 |
| CUCCCUCAUCCCUAAUCGA | 6841 | UCGAUUAGGGAUGAGGGAG | 6842 |
| UCCCUCAUCCCUAAUCGAU | 6843 | AUCGAUUAGGGAUGAGGGA | 6844 |
| CCCUCAUCCCUAAUCGAUA | 6845 | UAUCGAUUAGGGAUGAGGG | 6846 |
| CCUCAUCCCUAAUCGAUAA | 6847 | UUAUCGAUUAGGGAUGAGG | 6848 |
| CUCAUCCCUAAUCGAUAAA | 6849 | UUUAUCGAUUAGGGAUGAG | 6850 |
| AACCUAGAUCUCUCCCUCC | 6851 | GGAGGGAGAGAUCUAGGUU | 6852 |
| ACCUAGAUCUCUCCCUCCC | 6853 | GGGAGGGAGAGAUCUAGGU | 6854 |
| CUAGAUCUCUCCCUCCCUA | 6855 | UAGGGAGGGAGAGAUCUAG | 6856 |
| UAGAUCUCUCCCUCCCUAG | 6857 | CUAGGGAGGGAGAGAUCUA | 6858 |
| AGAUCUCUCCCUCCCUAGC | 6859 | GCUAGGGAGGGAGAGAUCU | 6860 |
| GAUCUCUCCCUCCCUAGCC | 6861 | GGCUAGGGAGGGAGAGAUC | 6862 |
| AUCUCUCCCUCCCUAGCCC | 6863 | GGGCUAGGGAGGGAGAGAU | 6864 |
| UAGCCCUCUAGCCACUCUA | 6865 | UAGAGUGGCUAGAGGGCUA | 6866 |
| AGCCCUCUAGCCACUCUAC | 6867 | GUAGAGUGGCUAGAGGGCU | 6868 |
| CUCUAGCCACUCUACCCUC | 6869 | GAGGGUAGAGUGGCUAGAG | 6870 |
| UCUAGCCACUCUACCCUCA | 6871 | UGAGGGUAGAGUGGCUAGA | 6872 |
| CUAGCCACUCUACCCUCAU | 6873 | AUGAGGGUAGAGUGGCUAG | 6874 |
| UAGCCACUCUACCCUCAUC | 6875 | GAUGAGGGUAGAGUGGCUA | 6876 |
| AGCCACUCUACCCUCAUCA | 6877 | UGAUGAGGGUAGAGUGGCU | 6878 |
| GCCACUCUACCCUCAUCAU | 6879 | AUGAUGAGGGUAGAGUGGC | 6880 |
| CCACUCUACCCUCAUCAUG | 6881 | CAUGAUGAGGGUAGAGUGG | 6882 |
| CACUCUACCCUCAUCAUGC | 6883 | GCAUGAUGAGGGUAGAGUG | 6884 |
| ACUCUACCCUCAUCAUGCC | 6885 | GGCAUGAUGAGGGUAGAGU | 6886 |
| CUCUACCCUCAUCAUGCCC | 6887 | GGGCAUGAUGAGGGUAGAG | 6888 |
| UCUACCCUCAUCAUGCCCU | 6889 | AGGGCAUGAUGAGGGUAGA | 6890 |
| CUACCCUCAUCAUGCCCUU | 6891 | AAGGGCAUGAUGAGGGUAG | 6892 |
| UACCCUCAUCAUGCCCUUU | 6893 | AAAGGGCAUGAUGAGGGUA | 6894 |
| ACCCUCAUCAUGCCCUUUA | 6895 | UAAAGGGCAUGAUGAGGGU | 6896 |
| CCCUCAUCAUGCCCUUUAC | 6897 | GUAAAGGGCAUGAUGAGGG | 6898 |
| CUCAUCAUGCCCUUUACAC | 6899 | GUGUAAAGGGCAUGAUGAG | 6900 |
| UCAUCAUGCCCUUUACACU | 6901 | AGUGUAAAGGGCAUGAUGA | 6902 |
| CCCUUCUUGACUUUUCUUC | 6903 | GAAGAAAAGUCAAGAAGGG | 6904 |
| CUUCUUGACUUUUCUUCUC | 6905 | GAGAAGAAAAGUCAAGAAG | 6906 |
| GACUUUUCUUCUCAACUAC | 6907 | GUAGUUGAGAAGAAAAGUC | 6908 |
| ACUUUUCUUCUCAACUACC | 6909 | GGUAGUUGAGAAGAAAAGU | 6910 |
| CUUUUCUUCUCAACUACCA | 6911 | UGGUAGUUGAGAAGAAAAG | 6912 |
| UUUUCUUCUCAACUACCAG | 6913 | CUGGUAGUUGAGAAGAAAA | 6914 |
| UAUCUAAUAUAAGCUCGGA | 6915 | UCCGAGCUUAUAUUAGAUA | 6916 |
| AUCUAAUAUAAGCUCGGAG | 6917 | CUCCGAGCUUAUAUUAGAU | 6918 |
| UCUAAUAUAAGCUCGGAGU | 6919 | ACUCCGAGCUUAUAUUAGA | 6920 |
| CUAAUAUAAGCUCGGAGUU | 6921 | AACUCCGAGCUUAUAUUAG | 6922 |
| UAAUAUAAGCUCGGAGUUU | 6923 | AAACUCCGAGCUUAUAUUA | 6924 |
| AAUAUAAGCUCGGAGUUUG | 6925 | CAAACUCCGAGCUUAUAUU | 6926 |
| AUAUAAGCUCGGAGUUUGG | 6927 | CCAAACUCCGAGCUUAUAU | 6928 |
| UAUAAGCUCGGAGUUUGGA | 6929 | UCCAAACUCCGAGCUUAUA | 6930 |
| AUAAGCUCGGAGUUUGGAC | 6931 | GUCCAAACUCCGAGCUUAU | 6932 |
| UAAGCUCGGAGUUUGGACG | 6933 | CGUCCAAACUCCGAGCUUA | 6934 |
| AAGCUCGGAGUUUGGACGG | 6935 | CCGUCCAAACUCCGAGCUU | 6936 |
| AGCUCGGAGUUUGGACGGA | 6937 | UCCGUCCAAACUCCGAGCU | 6938 |
| GCUCGGAGUUUGGACGGAG | 6939 | CUCCGUCCAAACUCCGAGC | 6940 |
| CUCGGAGUUUGGACGGAGG | 6941 | CCUCCGUCCAAACUCCGAG | 6942 |

TABLE 9-continued

| Sense Sequence | SEQ ID NO: | Antisense Sequence | SEQ ID NO: |
|---|---|---|---|
| UCGGAGUUUGGACGGAGGG | 6943 | CCCUCCGUCCAAACUCCGA | 6944 |
| CGGAGUUUGGACGGAGGGU | 6945 | ACCCUCCGUCCAAACUCCG | 6946 |
| UUUGGACGGAGGGUCUGGA | 6947 | UCCAGACCCUCCGUCCAAA | 6948 |
| CCCAGCGACCUUUCCGUGU | 6949 | ACACGGAAAGGUCGCUGGG | 6950 |
| CCAGCGACCUUUCCGUGUC | 6951 | GACACGGAAAGGUCGCUGG | 6952 |
| CAGCGACCUUUCCGUGUCU | 6953 | AGACACGGAAAGGUCGCUG | 6954 |
| AGCGACCUUUCCGUGUCUG | 6955 | CAGACACGGAAAGGUCGCU | 6956 |
| GCGACCUUUCCGUGUCUGU | 6957 | ACAGACACGGAAAGGUCGC | 6958 |
| CGACCUUUCCGUGUCUGUG | 6959 | CACAGACACGGAAAGGUCG | 6960 |
| CUUUCCGUGUCUGUGAUCA | 6961 | UGAUCACAGACACGGAAAG | 6962 |
| UUUCCGUGUCUGUGAUCAC | 6963 | GUGAUCACAGACACGGAAA | 6964 |
| UUCCGUGUCUGUGAUCACA | 6965 | UGUGAUCACAGACACGGAA | 6966 |
| AAGGCCUGACAGCUGCCAC | 6967 | GUGGCAGCUGUCAGGCCUU | 6968 |
| GCCAGGAGCUGCUAGCCAA | 6969 | UUGGCUAGCAGCUCCUGGC | 6970 |
| CCAGGAGCUGCUAGCCAAA | 6971 | UUUGGCUAGCAGCUCCUGG | 6972 |
| GAGCUGCUAGCCAAAGUAA | 6973 | UUACUUUGGCUAGCAGCUC | 6974 |
| AGCUGCUAGCCAAAGUAAG | 6975 | CUUACUUUGGCUAGCAGCU | 6976 |
| GCUGCUAGCCAAAGUAAGU | 6977 | ACUUACUUUGGCUAGCAGC | 6978 |
| CUGCUAGCCAAAGUAAGUA | 6979 | UACUUACUUUGGCUAGCAG | 6980 |
| UGCUAGCCAAAGUAAGUAG | 6981 | CUACUUACUUUGGCUAGCA | 6982 |
| GCUAGCCAAAGUAAGUAGG | 6983 | CCUACUUACUUUGGCUAGC | 6984 |
| UAGCCAAAGUAAGUAGGCC | 6985 | GGCCUACUUACUUUGGCUA | 6986 |
| AGCCAAAGUAAGUAGGCCA | 6987 | UGGCCUACUUACUUUGGCU | 6988 |
| GCCAAAGUAAGUAGGCCAA | 6989 | UUGGCCUACUUACUUUGGC | 6990 |
| CCAAAGUAAGUAGGCCAAG | 6991 | CUUGGCCUACUUACUUUGG | 6992 |
| CAAAGUAAGUAGGCCAAGU | 6993 | ACUUGGCCUACUUACUUUG | 6994 |
| AAAGUAAGUAGGCCAAGUU | 6995 | AACUUGGCCUACUUACUUU | 6996 |
| AAGUAAGUAGGCCAAGUUC | 6997 | GAACUUGGCCUACUUACUU | 6998 |
| AGUAAGUAGGCCAAGUUCC | 6999 | GGAACUUGGCCUACUUACU | 7000 |
| GUAAGUAGGCCAAGUUCCU | 7001 | AGGAACUUGGCCUACUUAC | 7002 |
| UAAGUAGGCCAAGUUCCUC | 7003 | GAGGAACUUGGCCUACUUA | 7004 |
| UAGGCCAAGUUCCUCGGUU | 7005 | AACCGAGGAACUUGGCCUA | 7006 |
| AGGCCAAGUUCCUCGGUUC | 7007 | GAACCGAGGAACUUGGCCU | 7008 |
| GGCCAAGUUCCUCGGUUCC | 7009 | GGAACCGAGGAACUUGGCC | 7010 |
| GCCAAGUUCCUCGGUUCCU | 7011 | AGGAACCGAGGAACUUGGC | 7012 |
| CCAAGUUCCUCGGUUCCUA | 7013 | UAGGAACCGAGGAACUUGG | 7014 |
| CAAGUUCCUCGGUUCCUAU | 7015 | AUAGGAACCGAGGAACUUG | 7016 |
| AAGUUCCUCGGUUCCUAUA | 7017 | UAUAGGAACCGAGGAACUU | 7018 |
| AGUUCCUCGGUUCCUAUAG | 7019 | CUAUAGGAACCGAGGAACU | 7020 |
| GUUCCUCGGUUCCUAUAGC | 7021 | GCUAUAGGAACCGAGGAAC | 7022 |
| UUCCUCGGUUCCUAUAGCA | 7023 | UGCUAUAGGAACCGAGGAA | 7024 |
| UCCUCGGUUCCUAUAGCAG | 7025 | CUGCUAUAGGAACCGAGGA | 7026 |
| CAGUGGCAACUUGUGAUGA | 7027 | UCAUCACAAGUUGCCACUG | 7028 |
| AGUGGCAACUUGUGAUGAU | 7029 | AUCAUCACAAGUUGCCACU | 7030 |
| GUGGCAACUUGUGAUGAUG | 7031 | CAUCAUCACAAGUUGCCAC | 7032 |
| GGCAACUUGUGAUGAUGGA | 7033 | UCCAUCAUCACAAGUUGCC | 7034 |
| ACUUGUGAUGAUGGAGCAG | 7035 | CUGCUCCAUCAUCACAAGU | 7036 |
| CUUGUGAUGAUGGAGCAGA | 7037 | UCUGCUCCAUCAUCACAAG | 7038 |
| GUGAUGAUGGAGCAGAGGG | 7039 | CCCUCUGCUCCAUCAUCAC | 7040 |
| UGAUGAUGGAGCAGAGGGC | 7041 | GCCCUCUGCUCCAUCAUCA | 7042 |
| UGGAGCAGAGGGCUGAAGU | 7043 | ACUUCAGCCCUCUGCUCCA | 7044 |
| GGAGCAGAGGGCUGAAGUC | 7045 | GACUUCAGCCCUCUGCUCC | 7046 |
| GAGCAGAGGGCUGAAGUCA | 7047 | UGACUUCAGCCCUCUGCUC | 7048 |
| CUAAAAGCAGCGGAGUGGG | 7049 | CCCACUCCGCUGCUUUUAG | 7050 |
| UAAAAGCAGCGGAGUGGGC | 7051 | GCCCACUCCGCUGCUUUUA | 7052 |
| AAAAGCAGCGGAGUGGGCC | 7053 | GGCCCACUCCGCUGCUUUU | 7054 |
| AAAGCAGCGGAGUGGGCCU | 7055 | AGGCCCACUCCGCUGCUUU | 7056 |
| AAGCAGCGGAGUGGGCCUA | 7057 | UAGGCCCACUCCGCUGCUU | 7058 |
| AGCAGCGGAGUGGGCCUAA | 7059 | UUAGGCCCACUCCGCUGCU | 7060 |
| GCAGCGGAGUGGGCCUAAU | 7061 | AUUAGGCCCACUCCGCUGC | 7062 |
| CAGCGGAGUGGGCCUAAUG | 7063 | CAUUAGGCCCACUCCGCUG | 7064 |
| AGCGGAGUGGGCCUAAUGA | 7065 | UCAUUAGGCCCACUCCGCU | 7066 |
| GCGGAGUGGGCCUAAUGAG | 7067 | CUCAUUAGGCCCACUCCGC | 7068 |
| AGUGGGCCUAAUGAGCUCU | 7069 | AGAGCUCAUUAGGCCCACU | 7070 |
| GUGGGCCUAAUGAGCUCUG | 7071 | CAGAGCUCAUUAGGCCCAC | 7072 |
| UGGGCCUAAUGAGCUCUGG | 7073 | CCAGAGCUCAUUAGGCCCA | 7074 |
| GGGCCUAAUGAGCUCUGGU | 7075 | ACCAGAGCUCAUUAGGCCC | 7076 |
| GGCCUAAUGAGCUCUGGUC | 7077 | GACCAGAGCUCAUUAGGCC | 7078 |
| GCCUAAUGAGCUCUGGUCA | 7079 | UGACCAGAGCUCAUUAGGC | 7080 |
| CCUAAUGAGCUCUGGUCAA | 7081 | UUGACCAGAGCUCAUUAGG | 7082 |
| CUAAUGAGCUCUGGUCAAU | 7083 | AUUGACCAGAGCUCAUUAG | 7084 |
| UAAUGAGCUCUGGUCAAUU | 7085 | AAUUGACCAGAGCUCAUUA | 7086 |
| AAUGAGCUCUGGUCAAUUU | 7087 | AAAUUGACCAGAGCUCAUU | 7088 |
| AUGAGCUCUGGUCAAUUUG | 7089 | CAAAUUGACCAGAGCUCAU | 7090 |
| UGAGCUCUGGUCAAUUUGU | 7091 | ACAAAUUGACCAGAGCUCA | 7092 |
| CUGGUCAAUUUGUUCAUUU | 7093 | AAAUGAACAAAUUGACCAG | 7094 |

TABLE 9-continued

| Sense Sequence | SEQ ID NO: | Antisense Sequence | SEQ ID NO: |
|---|---|---|---|
| CAAUUUGUUCAUUUUCCAC | 7095 | GUGGAAAAUGAACAAAUUG | 7096 |
| AGUGAGCUUUUCUAUGGGA | 7097 | UCCCAUAGAAAAGCUCACU | 7098 |
| AGCUUUUCUAUGGGAGCAG | 7099 | CUGCUCCCAUAGAAAAGCU | 7100 |
| GAAUUCAGAAGCUAGUAUG | 7101 | CAUACUAGCUUCUGAAUUC | 7102 |
| AUUCAGAAGCUAGUAUGGA | 7103 | UCCAUACUAGCUUCUGAAU | 7104 |
| UUCAGAAGCUAGUAUGGAA | 7105 | UUCCAUACUAGCUUCUGAA | 7106 |
| AAAGGUGAUUUGUGUGACA | 7107 | UGUCACACAAAUCACCUUU | 7108 |
| AUUCUGAUUCUGCCACUUC | 7109 | GAAGUGGCAGAAUCAGAAU | 7110 |
| AUUCUGCCACUUCCUGCCU | 7111 | AGGCAGGAAGUGGCAGAAU | 7112 |
| GCCACUUCCUGCCUGUCAA | 7113 | UUGACAGGCAGGAAGUGGC | 7114 |
| CCACUUCCUGCCUGUCAAA | 7115 | UUUGACAGGCAGGAAGUGG | 7116 |
| AACCUUGGGAAGUUGUUCA | 7117 | UGAACAACUUCCCAAGGUU | 7118 |
| ACCUUGGGAAGUUGUUCAA | 7119 | UUGAACAACUUCCCAAGGU | 7120 |
| CCUUGGGAAGUUGUUCAAC | 7121 | GUUGAACAACUUCCCAAGG | 7122 |
| GGGAAGUUGUUCAACCUAC | 7123 | GUAGGUUGAACAACUUCCC | 7124 |
| GGAAGUUGUUCAACCUACC | 7125 | GGUAGGUUGAACAACUUCC | 7126 |
| GAAGUUGUUCAACCUACCA | 7127 | UGGUAGGUUGAACAACUUC | 7128 |
| AAGUUGUUCAACCUACCAA | 7129 | UUGGUAGGUUGAACAACUU | 7130 |
| AGUUGUUCAACCUACCAAA | 7131 | UUUGGUAGGUUGAACAACU | 7132 |
| GUUGUUCAACCUACCAAAA | 7133 | UUUUGGUAGGUUGAACAAC | 7134 |
| GCAAUAAUAAUACAUCACC | 7135 | GGUGAUGUAUUAUUAUUGC | 7136 |
| AUAAUAAUACAUCACCUCC | 7137 | GGAGGUGAUGUAUUAUUAU | 7138 |
| UAAUACAUCACCUCCUAGG | 7139 | CCUAGGAGGUGAUGUAUUA | 7140 |
| AAUACAUCACCUCCUAGGG | 7141 | CCCUAGGAGGUGAUGUAUU | 7142 |
| AUACAUCACCUCCUAGGGU | 7143 | ACCCUAGGAGGUGAUGUAU | 7144 |
| UACAUCACCUCCUAGGGUU | 7145 | AACCCUAGGAGGUGAUGUA | 7146 |
| ACAUCACCUCCUAGGGUUG | 7147 | CAACCCUAGGAGGUGAUGU | 7148 |
| AAAGGAGUAAGAGGAUAAU | 7149 | AUUAUCCUCUUACUCCUUU | 7150 |
| AAGGAGUAAGAGGAUAAUG | 7151 | CAUUAUCCUCUUACUCCUU | 7152 |
| AGUAAGAGGAUAAUGUAGG | 7153 | CCUACAUUAUCCUCUUACU | 7154 |
| GUAAGAGGAUAAUGUAGGU | 7155 | ACCUACAUUAUCCUCUUAC | 7156 |
| UAAGAGGAUAAUGUAGGUA | 7157 | UACCUACAUUAUCCUCUUA | 7158 |
| AAGAGGAUAAUGUAGGUAA | 7159 | UUACCUACAUUAUCCUCUU | 7160 |
| AGAGGAUAAUGUAGGUAAA | 7161 | UUUACCUACAUUAUCCUCU | 7162 |
| GAGGAUAAUGUAGGUAAAG | 7163 | CUUUACCUACAUUAUCCUC | 7164 |
| GGAUAAUGUAGGUAAAGUC | 7165 | GACUUUACCUACAUUAUCC | 7166 |
| AUAAUGUAGGUAAAGUCCU | 7167 | AGGACUUUACCUACAUUAU | 7168 |
| GUAGGUAAAGUCCUCAUAC | 7169 | GUAUGAGGACUUUACCUAC | 7170 |
| GUAAAGUCCUCAUACCUGG | 7171 | CCAGGUAUGAGGACUUUAC | 7172 |
| UAAAGUCCUCAUACCUGGC | 7173 | GCCAGGUAUGAGGACUUUA | 7174 |
| AAAGUCCUCAUACCUGGCA | 7175 | UGCCAGGUAUGAGGACUUU | 7176 |
| AAGUCCUCAUACCUGGCAC | 7177 | GUGCCAGGUAUGAGGACUU | 7178 |
| AGUCCUCAUACCUGGCACA | 7179 | UGUGCCAGGUAUGAGGACU | 7180 |
| GUCCUCAUACCUGGCACAG | 7181 | CUGUGCCAGGUAUGAGGAC | 7182 |
| UCCUCAUACCUGGCACAGA | 7183 | UCUGUGCCAGGUAUGAGGA | 7184 |
| UCUUGAGGGUGUGGGAAGU | 7185 | ACUUCCCACACCCUCAAGA | 7186 |
| CUUGAGGGUGUGGGAAGUG | 7187 | CACUUCCCACACCCUCAAG | 7188 |
| UUGAGGGUGUGGGAAGUGA | 7189 | UCACUUCCCACACCCUCAA | 7190 |
| UGAGGGUGUGGGAAGUGAG | 7191 | CUCACUUCCCACACCCUCA | 7192 |
| AGGGUGUGGGAAGUGAGGU | 7193 | ACCUCACUUCCCACACCCU | 7194 |
| GGGUGUGGGAAGUGAGGUG | 7195 | CACCUCACUUCCCACACCC | 7196 |
| GGAAGUGAGGUGCAGCAU | 7197 | AUGCUGCACCUCACUUCCC | 7198 |
| GGAAGUGAGGUGCAGCAUU | 7199 | AAUGCUGCACCUCACUUCC | 7200 |
| GAAGUGAGGUGCAGCAUUG | 7201 | CAAUGCUGCACCUCACUUC | 7202 |
| AAGUGAGGUGCAGCAUUGU | 7203 | ACAAUGCUGCACCUCACUU | 7204 |
| AGUGAGGUGCAGCAUUGUA | 7205 | UACAAUGCUGCACCUCACU | 7206 |
| GUGAGGUGCAGCAUUGUAG | 7207 | CUACAAUGCUGCACCUCAC | 7208 |
| UGAGGUGCAGCAUUGUAGA | 7209 | UCUACAAUGCUGCACCUCA | 7210 |
| GAGGUGCAGCAUUGUAGAU | 7211 | AUCUACAAUGCUGCACCUC | 7212 |
| AGGUGCAGCAUUGUAGAUA | 7213 | UAUCUACAAUGCUGCACCU | 7214 |
| GGUGCAGCAUUGUAGAUAA | 7215 | UUAUCUACAAUGCUGCACC | 7216 |
| GUGCAGCAUUGUAGAUAAG | 7217 | CUUAUCUACAAUGCUGCAC | 7218 |
| UGCAGCAUUGUAGAUAAGA | 7219 | UCUUAUCUACAAUGCUGCA | 7220 |
| GCAUUGUAGAUAAGACAGA | 7221 | UCUGUCUUAUCUACAAUGC | 7222 |
| CAUUGUAGAUAAGACAGAA | 7223 | UUCUGUCUUAUCUACAAUG | 7224 |
| AUUGUAGAUAAGACAGAAG | 7225 | CUUCUGUCUUAUCUACAAU | 7226 |
| AUAAGACAGAAGGGUGGAC | 7227 | GUCCACCCUUCUGUCUUAU | 7228 |
| UAAGACAGAAGGGUGGACU | 7229 | AGUCCACCCUUCUGUCUUA | 7230 |
| AACCUGGCUUGCUUUCCAA | 7231 | UUGGAAAGCAAGCCAGGUU | 7232 |
| CCUGGCUUGCUUUCCAAUU | 7233 | AAUUGGAAAGCAAGCCAGG | 7234 |
| ACCAGAAGUGACUUGGAGG | 7235 | CCUCCAAGUCACUUCUGGU | 7236 |
| CCAGAAGUGACUUGGAGGG | 7237 | CCCUCCAAGUCACUUCUGG | 7238 |
| AGAUGCCAAUGACAUGGUA | 7239 | UACCAUGUCAUUGGCAUCU | 7240 |
| GAUGCCAAUGACAUGGUAG | 7241 | CUACCAUGUCAUUGGCAUC | 7242 |
| AUGCCAAUGACAUGGUAGG | 7243 | CCUACCAUGUCAUUGGCAU | 7244 |
| CAAUGACAUGGUAGGAGCA | 7245 | UGCUCCUACCAUGUCAUUG | 7246 |

TABLE 9-continued

| Sense Sequence | SEQ ID NO: | Antisense Sequence | SEQ ID NO: |
|---|---|---|---|
| AAUGACAUGGUAGGAGCAA | 7247 | UUGCUCCUACCAUGUCAUU | 7248 |
| AUGACAUGGUAGGAGCAAA | 7249 | UUUGCUCCUACCAUGUCAU | 7250 |
| UGACAUGGUAGGAGCAAAG | 7251 | CUUUGCUCCUACCAUGUCA | 7252 |
| GACAUGGUAGGAGCAAAGA | 7253 | UCUUUGCUCCUACCAUGUC | 7254 |
| AAAAGGUCAGCCUCUAGCU | 7255 | AGCUAGAGGCUGACCUUUU | 7256 |
| AAAGGUCAGCCUCUAGCUA | 7257 | UAGCUAGAGGCUGACCUUU | 7258 |
| AGGUCAGCCUCUAGCUAGG | 7259 | CCUAGCUAGAGGCUGACCU | 7260 |
| GGUCAGCCUCUAGCUAGGA | 7261 | UCCUAGCUAGAGGCUGACC | 7262 |
| GUCAGCCUCUAGCUAGGAU | 7263 | AUCCUAGCUAGAGGCUGAC | 7264 |
| CAGCCUCUAGCUAGGAUCC | 7265 | GGAUCCUAGCUAGAGGCUG | 7266 |
| AGCCUCUAGCUAGGAUCCC | 7267 | GGGAUCCUAGCUAGAGGCU | 7268 |
| AGAGCUGCAACCUUUAGGA | 7269 | UCCUAAAGGUUGCAGCUCU | 7270 |
| GAGCUGCAACCUUUAGGAG | 7271 | CUCCUAAAGGUUGCAGCUC | 7272 |
| AGCUGCAACCUUUAGGAGG | 7273 | CCUCCUAAAGGUUGCAGCU | 7274 |
| UUUAGGAGGUAUCAAAGUG | 7275 | CACUUUGAUACCUCCUAAA | 7276 |
| UUAGGAGGUAUCAAAGUGC | 7277 | GCACUUUGAUACCUCCUAA | 7278 |
| UAGGAGGUAUCAAAGUGCC | 7279 | GGCACUUUGAUACCUCCUA | 7280 |
| GUCAAAGUGGGACAUCGAC | 7281 | GUCGAUGUCCCACUUUGAC | 7282 |
| CAUCGACCAAUGUCUAGAG | 7283 | CUCUAGACAUUGGUCGAUG | 7284 |
| AUCGACCAAUGUCUAGAGC | 7285 | GCUCUAGACAUUGGUCGAU | 7286 |
| ACCAAUGUCUAGAGCCAAC | 7287 | GUUGGCUCUAGACAUUGGU | 7288 |
| CAAUGUCUAGAGCCAACUG | 7289 | CAGUUGGCUCUAGACAUUG | 7290 |
| AAUGUCUAGAGCCAACUGA | 7291 | UCAGUUGGCUCUAGACAUU | 7292 |
| AUGUCUAGAGCCAACUGAU | 7293 | AUCAGUUGGCUCUAGACAU | 7294 |
| UGUCUAGAGCCAACUGAUG | 7295 | CAUCAGUUGGCUCUAGACA | 7296 |
| GUCUAGAGCCAACUGAUGG | 7297 | CCAUCAGUUGGCUCUAGAC | 7298 |
| UCUAGAGCCAACUGAUGGA | 7299 | UCCAUCAGUUGGCUCUAGA | 7300 |
| CUAGAGCCAACUGAUGGAU | 7301 | AUCCAUCAGUUGGCUCUAG | 7302 |
| UAGAGCCAACUGAUGGAUG | 7303 | CAUCCAUCAGUUGGCUCUA | 7304 |
| AGAGCCAACUGAUGGAUGU | 7305 | ACAUCCAUCAGUUGGCUCU | 7306 |
| GAGCCAACUGAUGGAUGUU | 7307 | AACAUCCAUCAGUUGGCUC | 7308 |
| AACUGAUGGAUGUUGGGCA | 7309 | UGCCCAACAUCCAUCAGUU | 7310 |
| UGGAUGUUGGGCAGCUAAA | 7311 | UUUAGCUGCCCAACAUCCA | 7312 |
| GGAUGUUGGGCAGCUAAAG | 7313 | CUUUAGCUGCCCAACAUCC | 7314 |
| GAUGUUGGGCAGCUAAAGA | 7315 | UCUUUAGCUGCCCAACAUC | 7316 |
| UUGGGCAGCUAAAGAGGGA | 7317 | UCCCUCUUUAGCUGCCCAA | 7318 |
| UGGGCAGCUAAAGAGGGAA | 7319 | UUCCCUCUUUAGCUGCCCA | 7320 |
| GGGCAGCUAAAGAGGGAAG | 7321 | CUUCCCUCUUUAGCUGCCC | 7322 |
| GGCAGCUAAAGAGGGAAGG | 7323 | CCUUCCCUCUUUAGCUGCC | 7324 |
| GCAGCUAAAGAGGGAAGGG | 7325 | CCCUUCCCUCUUUAGCUGC | 7326 |
| GGGCAUGGGAUAAGACCUG | 7327 | CAGGUCUUAUCCCAUGCCC | 7328 |
| GGCAUGGGAUAAGACCUGC | 7329 | GCAGGUCUUAUCCCAUGCC | 7330 |
| GCAUGGGAUAAGACCUGCC | 7331 | GGCAGGUCUUAUCCCAUGC | 7332 |
| CAUGGGAUAAGACCUGCCC | 7333 | GGGCAGGUCUUAUCCCAUG | 7334 |
| AUGGGAUAAGACCUGCCCU | 7335 | AGGGCAGGUCUUAUCCCAU | 7336 |
| UGGGAUAAGACCUGCCCUU | 7337 | AAGGGCAGGUCUUAUCCCA | 7338 |
| GGGAUAAGACCUGCCCUUC | 7339 | GAAGGGCAGGUCUUAUCCC | 7340 |
| GGAUAAGACCUGCCCUUCU | 7341 | AGAAGGGCAGGUCUUAUCC | 7342 |
| AGACCUGCCCUUCUUGCUU | 7343 | AAGCAAGAAGGGCAGGUCU | 7344 |
| GACCUGCCCUUCUUGCUUC | 7345 | GAAGCAAGAAGGGCAGGUC | 7346 |
| CCUGCCCUUCUUGCUUCUU | 7347 | AAGAAGCAAGAAGGGCAGG | 7348 |
| CUGCCCUUCUUGCUUCUUG | 7349 | CAAGAAGCAAGAAGGGCAG | 7350 |
| UGCCCUUCUUGCUUCUUGC | 7351 | GCAAGAAGCAAGAAGGGCA | 7352 |
| UCUUGCUUCUUGCCAUUGG | 7353 | CCAAUGGCAAGAAGCAAGA | 7354 |
| CUUGCUUCUUGCCAUUGGG | 7355 | CCCAAUGGCAAGAAGCAAG | 7356 |
| UUGCUUCUUGCCAUUGGGC | 7357 | GCCCAAUGGCAAGAAGCAA | 7358 |
| CCAUUGGGCAGGCAUUGGA | 7359 | UCCAAUGCCUGCCCAAUGG | 7360 |
| CAUUGGGCAGGCAUUGGAG | 7361 | CUCCAAUGCCUGCCCAAUG | 7362 |
| GACCCUACUGCUGAAUGGA | 7363 | UCCAUUCAGCAGUAGGGUC | 7364 |
| UACUGCUGAAUGGAGUGCU | 7365 | AGCACUCCAUUCAGCAGUA | 7366 |
| ACUGCUGAAUGGAGUGCUA | 7367 | UAGCACUCCAUUCAGCAGU | 7368 |
| CUGCUGAAUGGAGUGCUAA | 7369 | UUAGCACUCCAUUCAGCAG | 7370 |
| UGCUGAAUGGAGUGCUAAC | 7371 | GUUAGCACUCCAUUCAGCA | 7372 |
| GCUGAAUGGAGUGCUAACC | 7373 | GGUUAGCACUCCAUUCAGC | 7374 |
| CUGAAUGGAGUGCUAACCC | 7375 | GGGUUAGCACUCCAUUCAG | 7376 |
| UAACCUGGUGCUAGAGGA | 7377 | UCCUCUAGCACCAGGGUUA | 7378 |
| AACCCUGGUGCUAGAGGAG | 7379 | CUCCUCUAGCACCAGGGUU | 7380 |
| ACCCUGGUGCUAGAGGAGG | 7381 | CCUCCUCUAGCACCAGGGU | 7382 |
| CCCUGGUGCUAGAGGAGGA | 7383 | UCCUCCUCUAGCACCAGGG | 7384 |
| CCUGGUGCUAGAGGAGGAU | 7385 | AUCCUCCUCUAGCACCAGG | 7386 |
| CUGGUGCUAGAGGAGGAUG | 7387 | CAUCCUCCUCUAGCACCAG | 7388 |
| GGUGCUAGAGGAGGAUGGA | 7389 | UCCAUCCUCCUCUAGCACC | 7390 |
| GUGCUAGAGGAGGAUGGAA | 7391 | UUCCAUCCUCCUCUAGCAC | 7392 |
| CUGCAGUGGACAGUGAGGA | 7393 | UCCUCACUGUCCACUGCAG | 7394 |
| UGCAGUGGACAGUGAGGAC | 7395 | GUCCUCACUGUCCACUGCA | 7396 |
| GCAGUGGACAGUGAGGACU | 7397 | AGUCCUCACUGUCCACUGC | 7398 |

TABLE 9-continued

| Sense Sequence | SEQ ID NO: | Antisense Sequence | SEQ ID NO: |
|---|---|---|---|
| CAGUGGACAGUGAGGACUU | 7399 | AAGUCCUCACUGUCCACUG | 7400 |
| AGUGGACAGUGAGGACUUC | 7401 | GAAGUCCUCACUGUCCACU | 7402 |
| GUGGACAGUGAGGACUUCU | 7403 | AGAAGUCCUCACUGUCCAC | 7404 |
| UGGACAGUGAGGACUUCUU | 7405 | AAGAAGUCCUCACUGUCCA | 7406 |
| GGACAGUGAGGACUUCUUC | 7407 | GAAGAAGUCCUCACUGUCC | 7408 |
| AGUGAGGACUUCUUCCAGC | 7409 | GCUGGAAGAAGUCCUCACU | 7410 |
| GUGAGGACUUCUUCCAGCU | 7411 | AGCUGGAAGAAGUCCUCAC | 7412 |
| UGAGGACUUCUUCCAGCUG | 7413 | CAGCUGGAAGAAGUCCUCA | 7414 |
| GAGGACUUCUUCCAGCUGC | 7415 | GCAGCUGGAAGAAGUCCUC | 7416 |
| GUGCCUGAUGGUGUUGCAG | 7417 | CUGCAACACCAUCAGGCAC | 7418 |
| GAUGGUGUUGCAGUCUGGU | 7419 | ACCAGACUGCAACACCAUC | 7420 |
| UGGUGUUGCAGUCUGGUCA | 7421 | UGACCAGACUGCAACACCA | 7422 |
| GGUGUUGCAGUCUGGUCAG | 7423 | CUGACCAGACUGCAACACC | 7424 |
| GUGUUGCAGUCUGGUCAGA | 7425 | UCUGACCAGACUGCAACAC | 7426 |
| UGCAGUCUGGUCAGAGCUG | 7427 | CAGCUCUGACCAGACUGCA | 7428 |
| GCAGUCUGGUCAGAGCUGG | 7429 | CCAGCUCUGACCAGACUGC | 7430 |
| CAGUCUGGUCAGAGCUGGA | 7431 | UCCAGCUCUGACCAGACUG | 7432 |
| AGUCUGGUCAGAGCUGGAG | 7433 | CUCCAGCUCUGACCAGACU | 7434 |
| GUCUGGUCAGAGCUGGAGC | 7435 | GCUCCAGCUCUGACCAGAC | 7436 |
| UCUGGUCAGAGCUGGAGCC | 7437 | GGCUCCAGCUCUGACCAGA | 7438 |
| UGGUCAGAGCUGGAGCCCU | 7439 | AGGGCUCCAGCUCUGACCA | 7440 |
| GGUCAGAGCUGGAGCCCUA | 7441 | UAGGGCUCCAGCUCUGACC | 7442 |
| GUCAGAGCUGGAGCCCUAC | 7443 | GUAGGGCUCCAGCUCUGAC | 7444 |
| CAAGGGUAAGAGGCCUAUA | 7445 | UAUAGGCCUCUUACCCUUG | 7446 |
| AAGGGUAAGAGGCCUAUAC | 7447 | GUAUAGGCCUCUUACCCUU | 7448 |
| AGGGUAAGAGGCCUAUACU | 7449 | AGUAUAGGCCUCUUACCCU | 7450 |
| GGGUAAGAGGCCUAUACUG | 7451 | CAGUAUAGGCCUCUUACCC | 7452 |
| GGUAAGAGGCCUAUACUGG | 7453 | CCAGUAUAGGCCUCUUACC | 7454 |
| GUAAGAGGCCUAUACUGGG | 7455 | CCCAGUAUAGGCCUCUUAC | 7456 |
| GGGCUGCUUCCAAUGCCUG | 7457 | CAGGCAUUGGAAGCAGCCC | 7458 |
| GGCUGCUUCCAAUGCCUGU | 7459 | ACAGGCAUUGGAAGCAGCC | 7460 |
| GCUGCUUCCAAUGCCUGUC | 7461 | GACAGGCAUUGGAAGCAGC | 7462 |
| CUGCUUCCAAUGCCUGUCC | 7463 | GGACAGGCAUUGGAAGCAG | 7464 |
| UGCUUCCAAUGCCUGUCCU | 7465 | AGGACAGGCAUUGGAAGCA | 7466 |
| GCUUCCAAUGCCUGUCCUU | 7467 | AAGGACAGGCAUUGGAAGC | 7468 |
| CUUCCAAUGCCUGUCCUUU | 7469 | AAAGGACAGGCAUUGGAAG | 7470 |
| UUCCAAUGCCUGUCCUUUA | 7471 | UAAAGGACAGGCAUUGGAA | 7472 |
| UCCAAUGCCUGUCCUUUAG | 7473 | CUAAAGGACAGGCAUUGGA | 7474 |
| CAAUGCCUGUCCUUUAGAG | 7475 | CUCUAAAGGACAGGCAUUG | 7476 |
| AAUGCCUGUCCUUUAGAGC | 7477 | GCUCUAAAGGACAGGCAUU | 7478 |
| AUGCCUGUCCUUUAGAGCU | 7479 | AGCUCUAAAGGACAGGCAU | 7480 |
| CUUCCUCUCUAGCUUAACC | 7481 | GGUUAAGCUAGAGAGGAAG | 7482 |
| UUCCUCUCUAGCUUAACCC | 7483 | GGGUUAAGCUAGAGAGGAA | 7484 |
| UCUCUAGCUUAACCCUGAU | 7485 | AUCAGGGUUAAGCUAGAGA | 7486 |
| UAGCUUAACCCUGAUCCUG | 7487 | CAGGAUCAGGGUUAAGCUA | 7488 |
| GACCAGGUGCAGGAGGAGU | 7489 | ACUCCUCCUGCACCUGGUC | 7490 |
| ACCAGGUGCAGGAGGAGUU | 7491 | AACUCCUCCUGCACCUGGU | 7492 |
| CCAGGUGCAGGAGGAGUUG | 7493 | CAACUCCUCCUGCACCUGG | 7494 |
| CAGGUGCAGGAGGAGUUGU | 7495 | ACAACUCCUCCUGCACCUG | 7496 |
| AGGUGCAGGAGGAGUUGUG | 7497 | CACAACUCCUCCUGCACCU | 7498 |
| UGCAGGAGGAGUUGUGGAA | 7499 | UUCCACAACUCCUCCUGCA | 7500 |
| GCAGGAGGAGUUGUGGAAU | 7501 | AUUCCACAACUCCUCCUGC | 7502 |
| AGGAGGAGUUGUGGAAUUG | 7503 | CAAUUCCACAACUCCUCCU | 7504 |
| GGAGGAGUUGUGGAAUUGU | 7505 | ACAAUUCCACAACUCCUCC | 7506 |
| GAGGAGUUGUGGAAUUGUC | 7507 | GACAAUUCCACAACUCCUC | 7508 |
| AGGAGUUGUGGAAUUGUCA | 7509 | UGACAAUUCCACAACUCCU | 7510 |
| GGAGUUGUGGAAUUGUCAA | 7511 | UUGACAAUUCCACAACUCC | 7512 |
| GAGUUGUGGAAUUGUCAAG | 7513 | CUUGACAAUUCCACAACUC | 7514 |
| AGUUGUGGAAUUGUCAAGG | 7515 | CCUUGACAAUUCCACAACU | 7516 |
| GUUGUGGAAUUGUCAAGGA | 7517 | UCCUUGACAAUUCCACAAC | 7518 |
| UGGAAUUGUCAAGGAUGUC | 7519 | GACAUCCUUGACAAUUCCA | 7520 |
| GGAAUUGUCAAGGAUGUCA | 7521 | UGACAUCCUUGACAAUUCC | 7522 |
| AGUCCAAGCGAGGGAGGGU | 7523 | ACCCUCCCUCGCUUGGACU | 7524 |
| CAAGCGAGGGAGGGUCUGA | 7525 | UCAGACCCUCCCUCGCUUG | 7526 |
| AAGCGAGGGAGGGUCUGAC | 7527 | GUCAGACCCUCCCUCGCUU | 7528 |
| CUGACCCAGUGCUGAUGGA | 7529 | UCCAUCAGCACUGGGUCAG | 7530 |
| AGAUUAGUGGUGGGUGUCU | 7531 | AGACACCCACCACUAAUCU | 7532 |
| AUUAGUGGUGGGUGUCUGG | 7533 | CCAGACACCCACCACUAAU | 7534 |
| UUAGUGGUGGGUGUCUGGU | 7535 | ACCAGACACCCACCACUAA | 7536 |
| UAGUGGUGGGUGUCUGGUA | 7537 | UACCAGACACCCACCACUA | 7538 |
| AGUGGUGGGUGUCUGGUAU | 7539 | AUACCAGACACCCACCACU | 7540 |
| GUGGUGGGUGUCUGGUAUG | 7541 | CAUACCAGACACCCACCAC | 7542 |
| UGGUGGGUGUCUGGUAUGA | 7543 | UCAUACCAGACACCCACCA | 7544 |
| GGUGGGUGUCUGGUAUGAG | 7545 | CUCAUACCAGACACCCACC | 7546 |
| GUGGGUGUCUGGUAUGAGG | 7547 | CCUCAUACCAGACACCCAC | 7548 |
| UGGGUGUCUGGUAUGAGGA | 7549 | UCCUCAUACCAGACACCCA | 7550 |

TABLE 9-continued

| Sense Sequence | SEQ ID NO: | Antisense Sequence | SEQ ID NO: |
|---|---|---|---|
| GGGUGUCUGGUAUGAGGAU | 7551 | AUCCUCAUACCAGACACCC | 7552 |
| GGUGUCUGGUAUGAGGAUC | 7553 | GAUCCUCAUACCAGACACC | 7554 |
| GUGUCUGGUAUGAGGAUCU | 7555 | AGAUCCUCAUACCAGACAC | 7556 |
| UGUCUGGUAUGAGGAUCUA | 7557 | UAGAUCCUCAUACCAGACA | 7558 |
| CAAGGGUGUCCUACAGAGU | 7559 | ACUCUGUAGGACACCCUUG | 7560 |
| AAGGGUGUCCUACAGAGUG | 7561 | CACUCUGUAGGACACCCUU | 7562 |
| AGGGUGUCCUACAGAGUGG | 7563 | CCACUCUGUAGGACACCCU | 7564 |
| GGGUGUCCUACAGAGUGGA | 7565 | UCCACUCUGUAGGACACCC | 7566 |
| GGUGUCCUACAGAGUGGAG | 7567 | CUCCACUCUGUAGGACACC | 7568 |
| UCCUACAGAGUGGAGUGCU | 7569 | AGCACUCCACUCUGUAGGA | 7570 |
| AGUGGAGUGCUGUCAUAUG | 7571 | CAUAUGACAGCACUCCACU | 7572 |
| GUGGAGUGCUGUCAUAUGG | 7573 | CCAUAUGACAGCACUCCAC | 7574 |
| UGGAGUGCUGUCAUAUGGC | 7575 | GCCAUAUGACAGCACUCCA | 7576 |
| GGAGUGCUGUCAUAUGGCC | 7577 | GGCCAUAUGACAGCACUCC | 7578 |
| GAGUGCUGUCAUAUGGCCU | 7579 | AGGCCAUAUGACAGCACUC | 7580 |
| AGUGCUGUCAUAUGGCCUG | 7581 | CAGGCCAUAUGACAGCACU | 7582 |
| GUGCUGUCAUAUGGCCUGG | 7583 | CCAGGCCAUAUGACAGCAC | 7584 |
| UGCUGUCAUAUGGCCUGGG | 7585 | CCCAGGCCAUAUGACAGCA | 7586 |
| GCUGUCAUAUGGCCUGGGA | 7587 | UCCCAGGCCAUAUGACAGC | 7588 |
| CUGUCAUAUGGCCUGGGAC | 7589 | GUCCCAGGCCAUAUGACAG | 7590 |
| UGUCAUAUGGCCUGGGACG | 7591 | CGUCCCAGGCCAUAUGACA | 7592 |
| GUCAUAUGGCCUGGGACGG | 7593 | CCGUCCCAGGCCAUAUGAC | 7594 |
| AGAGGCCCAAGCACAGCAA | 7595 | UUGCUGUGCUUGGGCCUCU | 7596 |
| GAGGCCCAAGCACAGCAAG | 7597 | CUUGCUGUGCUUGGGCCUC | 7598 |
| AGGCCCAAGCACAGCAAGG | 7599 | CCUUGCUGUGCUUGGGCCU | 7600 |
| GGCCCAAGCACAGCAAGGA | 7601 | UCCUUGCUGUGCUUGGGCC | 7602 |
| CCAAGCACAGCAAGGACAU | 7603 | AUGUCCUUGCUGUGCUUGG | 7604 |
| GCCCGAUUCACCUUUGACG | 7605 | CGUCAAAGGUGAAUCGGGC | 7606 |
| GAUUCACCUUUGACGUGUA | 7607 | UACACGUCAAAGGUGAAUC | 7608 |
| AUUCACCUUUGACGUGUAC | 7609 | GUACACGUCAAAGGUGAAU | 7610 |
| UUGGCAGCCUGAAUGUCAA | 7611 | UUGACAUUCAGGCUGCCAA | 7612 |
| UGGCAGCCUGAAUGUCAAA | 7613 | UUUGACAUUCAGGCUGCCA | 7614 |
| GGCAGCCUGAAUGUCAAAG | 7615 | CUUUGACAUUCAGGCUGCC | 7616 |
| GCAGCCUGAAUGUCAAAGC | 7617 | GCUUUGACAUUCAGGCUGC | 7618 |
| CAGCCUGAAUGUCAAAGCC | 7619 | GGCUUUGACAUUCAGGCUG | 7620 |
| AGCCUGAAUGUCAAAGCCA | 7621 | UGGCUUUGACAUUCAGGCU | 7622 |
| GCCUGAAUGUCAAAGCCAC | 7623 | GUGGCUUUGACAUUCAGGC | 7624 |
| GUCAAAGCCACAUUCUACG | 7625 | CGUAGAAUGUGGCUUUGAC | 7626 |
| UCAAAGCCACAUUCUACGG | 7627 | CCGUAGAAUGUGGCUUUGA | 7628 |
| CAAAGCCACAUUCUACGGG | 7629 | CCCGUAGAAUGUGGCUUUG | 7630 |
| AAAGCCACAUUCUACGGGC | 7631 | GCCCGUAGAAUGUGGCUUU | 7632 |
| GCCACAUUCUACGGGCUCU | 7633 | AGAGCCCGUAGAAUGUGGC | 7634 |
| CCACAUUCUACGGGCUCUA | 7635 | UAGAGCCCGUAGAAUGUGG | 7636 |
| CACAUUCUACGGGCUCUAC | 7637 | GUAGAGCCCGUAGAAUGUG | 7638 |
| UUCUACGGGCUCUACUCUA | 7639 | UAGAGUAGAGCCCGUAGAA | 7640 |
| UCUACGGGCUCUACUCUAU | 7641 | AUAGAGUAGAGCCCGUAGA | 7642 |
| CUACGGGCUCUACUCUAUG | 7643 | CAUAGAGUAGAGCCCGUAG | 7644 |
| CUCUAUGAGUUGUGACUUU | 7645 | AAAGUCACAACUCAUAGAG | 7646 |
| UCUAUGAGUUGUGACUUUC | 7647 | GAAAGUCACAACUCAUAGA | 7648 |
| UGAGUUGUGACUUUCAAGG | 7649 | CCUUGAAAGUCACAACUCA | 7650 |
| GAGUUGUGACUUUCAAGGA | 7651 | UCCUUGAAAGUCACAACUC | 7652 |
| AGUUGUGACUUUCAAGGAC | 7653 | GUCCUUGAAAGUCACAACU | 7654 |
| GUUGUGACUUUCAAGGACU | 7655 | AGUCCUUGAAAGUCACAAC | 7656 |
| GACUUUCAAGGACUUGGCC | 7657 | GGCCAAGUCCUUGAAAGUC | 7658 |
| UUUCAAGGACUUGGCCCAA | 7659 | UUGGGCCAAGUCCUUGAAA | 7660 |
| UUCAAGGACUUGGCCCAAA | 7661 | UUUGGGCCAAGUCCUUGAA | 7662 |
| CCCUACAGUUGGAUAGUCC | 7663 | GGACUAUCCAACUGUAGGG | 7664 |
| CCUACAGUUGGAUAGUCCC | 7665 | GGGACUAUCCAACUGUAGG | 7666 |
| AUUCGUCCUCUUGCACCCA | 7667 | UGGGUGCAAGAGGACGAAU | 7668 |
| UUCGUCCUCUUGCACCCAC | 7669 | GUGGGUGCAAGAGGACGAA | 7670 |
| UCCUCUUGCACCCACCUAC | 7671 | GUAGGUGGGUGCAAGAGGA | 7672 |
| CCUCUUGCACCCACCUACC | 7673 | GGUAGGUGGGUGCAAGAGG | 7674 |
| CUCUUGCACCCACCUACCC | 7675 | GGGUAGGUGGGUGCAAGAG | 7676 |
| CUAGUUAGCUCUUGCUUGU | 7677 | ACAAGCAAGAGCUAACUAG | 7678 |
| UAGUUAGCUCUUGCUUGUG | 7679 | CACAAGCAAGAGCUAACUA | 7680 |
| AGUUAGCUCUUGCUUGUGG | 7681 | CCACAAGCAAGAGCUAACU | 7682 |
| UUAGCUCUUGCUUGUGGAA | 7683 | UUCCACAAGCAAGAGCUAA | 7684 |
| UCCUCAUCUCCCAGCUUGA | 7685 | UCAAGCUGGGAGAUGAGGA | 7686 |
| AUCUCCCAGCUUGAUGGCU | 7687 | AGCCAUCAAGCUGGGAGAU | 7688 |
| UCUCCCAGCUUGAUGGCUU | 7689 | AAGCCAUCAAGCUGGGAGA | 7690 |
| CUCCCAGCUUGAUGGCUUC | 7691 | GAAGCCAUCAAGCUGGGAG | 7692 |
| UCCCAGCUUGAUGGCUUCC | 7693 | GGAAGCCAUCAAGCUGGGA | 7694 |
| CCCAGCUUGAUGGCUUCCU | 7695 | AGGAAGCCAUCAAGCUGGG | 7696 |
| CCAGCUUGAUGGCUUCCUC | 7697 | GAGGAAGCCAUCAAGCUGG | 7698 |
| UGAUGGCUUCCUCCCAAGU | 7699 | ACUUGGGAGGAAGCCAUCA | 7700 |
| GAUGGCUUCCUCCCAAGUU | 7701 | AACUUGGGAGGAAGCCAUC | 7702 |

TABLE 9-continued

| Sense Sequence | SEQ ID NO: | Antisense Sequence | SEQ ID NO: |
|---|---|---|---|
| GGCUUCCUCCCAAGUUUUC | 7703 | GAAAACUUGGGAGGAAGCC | 7704 |
| CCUCCCAAGUUUUCCAAAU | 7705 | AUUUGGAAAACUUGGGAGG | 7706 |
| CCCAAGUUUUCCAAAUCAU | 7707 | AUGAUUUGGAAAACUUGGG | 7708 |
| CCAAGUUUUCCAAAUCAUC | 7709 | GAUGAUUUGGAAAACUUGG | 7710 |
| CAAGUUUUCCAAAUCAUCU | 7711 | AGAUGAUUUGGAAAACUUG | 7712 |
| AAGUUUUCCAAAUCAUCUG | 7713 | CAGAUGAUUUGGAAAACUU | 7714 |
| GUUUUCCAAAUCAUCUGAU | 7715 | AUCAGAUGAUUUGGAAAAC | 7716 |
| AUCUGAUUCCUCUUGUCU | 7717 | AGACAAGAGGAAAUCAGAU | 7718 |
| UCUGAUUCCUCUUGUCUC | 7719 | GAGACAAGAGGAAAUCAGA | 7720 |
| CUGAUUUCCUCUUGUCUCU | 7721 | AGAGACAAGAGGAAAUCAG | 7722 |
| CUCUUGUCUCUGCCAUUCA | 7723 | UGAAUGGCAGAGACAAGAG | 7724 |
| GUUGGACCUCCACACUGCU | 7725 | AGCAGUGUGGAGGUCCAAC | 7726 |
| CCACACUGCUGCAAGGCCU | 7727 | AGGCCUUGCAGCAGUGUGG | 7728 |
| CACACUGCUGCAAGGCCUG | 7729 | CAGGCCUUGCAGCAGUGUG | 7730 |
| ACACUGCUGCAAGGCCUGG | 7731 | CCAGGCCUUGCAGCAGUGU | 7732 |
| UGCAAGGCCUGGGCCAUAU | 7733 | AUAUGGCCCAGGCCUUGCA | 7734 |
| GCAAGGCCUGGGCCAUAUG | 7735 | CAUAUGGCCCAGGCCUUGC | 7736 |
| CAAGGCCUGGGCCAUAUGU | 7737 | ACAUAUGGCCCAGGCCUUG | 7738 |
| AAGGCCUGGGCCAUAUGUU | 7739 | AACAUAUGGCCCAGGCCUU | 7740 |
| AGGCCUGGGCCAUAUGUUG | 7741 | CAACAUAUGGCCCAGGCCU | 7742 |
| GGCCUGGGCCAUAUGUUGC | 7743 | GCAACAUAUGGCCCAGGCC | 7744 |
| GCCUGGGCCAUAUGUUGCU | 7745 | AGCAACAUAUGGCCCAGGC | 7746 |
| CCUGGGCCAUAUGUUGCUG | 7747 | CAGCAACAUAUGGCCCAGG | 7748 |
| GGCCAUAUGUUGCUGGGAA | 7749 | UUCCCAGCAACAUAUGGCC | 7750 |
| CCAUAUGUUGCUGGGAAUU | 7751 | AAUUCCCAGCAACAUAUGG | 7752 |
| GGAAUUCCUCCACCCUUC | 7753 | GAAGGGUGGAGGAAUUCC | 7754 |
| GAAUUCCUCCACCCUUCG | 7755 | CGAAGGGUGGAGGAAUUC | 7756 |
| AAUUCCUCCACCCUUCGU | 7757 | ACGAAGGGUGGAGGAAUU | 7758 |
| AUUCCUCCACCCUUCGUC | 7759 | GACGAAGGGUGGAGGAAU | 7760 |
| UUCCUCCACCCUUCGUCA | 7761 | UGACGAAGGGUGGAGGAA | 7762 |
| UCCUCCACCCUUCGUCAU | 7763 | AUGACGAAGGGUGGAGGAA | 7764 |
| CCUCCACCCUUCGUCAUG | 7765 | CAUGACGAAGGGUGGAGGA | 7766 |
| CUCCACCCUUCGUCAUGC | 7767 | GCAUGACGAAGGGUGGAGG | 7768 |
| UCCACCCUUCGUCAUGCA | 7769 | UGCAUGACGAAGGGUGGAG | 7770 |
| CCUUCGUCAUGCAGUGGAG | 7771 | CUCCACUGCAUGACGAAGG | 7772 |
| CUUCGUCAUGCAGUGGAGG | 7773 | CCUCCACUGCAUGACGAAG | 7774 |
| UUCGUCAUGCAGUGGAGGG | 7775 | CCCUCCACUGCAUGACGAA | 7776 |
| CGCCUCCAUUCCUACUAAG | 7777 | CUUAGUAGGAAUGGAGGCG | 7778 |
| GCCUCCAUUCCUACUAAGG | 7779 | CCUUAGUAGGAAUGGAGGC | 7780 |
| CCUCCAUUCCUACUAAGGG | 7781 | CCCUUAGUAGGAAUGGAGG | 7782 |
| CAGAAUCAUUCCAACCGAC | 7783 | GUCGGUUGGAAUGAUUCUG | 7784 |
| AGAAUCAUUCCAACCGACC | 7785 | GGUCGGUUGGAAUGAUUCU | 7786 |
| GAAUCAUUCCAACCGACCC | 7787 | GGGUCGGUUGGAAUGAUUC | 7788 |
| AAUCAUUCCAACCGACCCA | 7789 | UGGGUCGGUUGGAAUGAUU | 7790 |
| AUCAUUCCAACCGACCCAC | 7791 | GUGGGUCGGUUGGAAUGAU | 7792 |
| UCAUUCCAACCGACCCACU | 7793 | AGUGGGUCGGUUGGAAUGA | 7794 |
| UCCAACCGACCCACUGCAA | 7795 | UUGCAGUGGGUCGGUUGGA | 7796 |
| CCAACCGACCCACUGCAAA | 7797 | UUUGCAGUGGGUCGGUUGG | 7798 |
| CAACCGACCCACUGCAAAG | 7799 | CUUUGCAGUGGGUCGGUUG | 7800 |
| AACCGACCCACUGCAAAGA | 7801 | UCUUUGCAGUGGGUCGGUU | 7802 |
| ACCGACCCACUGCAAAGAC | 7803 | GUCUUUGCAGUGGGUCGGU | 7804 |
| CCGACCCACUGCAAAGACU | 7805 | AGUCUUUGCAGUGGGUCGG | 7806 |
| CGACCCACUGCAAAGACUA | 7807 | UAGUCUUUGCAGUGGGUCG | 7808 |
| GACCCACUGCAAAGACUAU | 7809 | AUAGUCUUUGCAGUGGGUC | 7810 |
| ACCCACUGCAAAGACUAUG | 7811 | CAUAGUCUUUGCAGUGGGU | 7812 |
| ACUGCAAAGACUAUGACAG | 7813 | CUGUCAUAGUCUUUGCAGU | 7814 |
| CUGCAAAGACUAUGACAGC | 7815 | GCUGUCAUAGUCUUUGCAG | 7816 |
| UGCAAAGACUAUGACAGCA | 7817 | UGCUGUCAUAGUCUUUGCA | 7818 |
| GCAAAGACUAUGACAGCAU | 7819 | AUGCUGUCAUAGUCUUUGC | 7820 |
| AAAGACUAUGACAGCAUCA | 7821 | UGAUGCUGUCAUAGUCUUU | 7822 |
| AAGACUAUGACAGCAUCAA | 7823 | UUGAUGCUGUCAUAGUCUU | 7824 |
| AGACUAUGACAGCAUCAAA | 7825 | UUUGAUGCUGUCAUAGUCU | 7826 |
| GACUAUGACAGCAUCAAAU | 7827 | AUUUGAUGCUGUCAUAGUC | 7828 |
| CUAUGACAGCAUCAAAUUU | 7829 | AAAUUUGAUGCUGUCAUAG | 7830 |
| UAUGACAGCAUCAAAUUUC | 7831 | GAAAUUUGAUGCUGUCAUA | 7832 |
| GCAUCAAAUUUCAGGACCU | 7833 | AGGUCCUGAAAUUUGAUGC | 7834 |
| AUCAAAUUUCAGGACCUGC | 7835 | GCAGGUCCUGAAAUUUGAU | 7836 |
| UCAAAUUUCAGGACCUGCA | 7837 | UGCAGGUCCUGAAAUUUGA | 7838 |
| UUCAGGACCUGCAGACAGU | 7839 | ACUGUCUGCAGGUCCUGAA | 7840 |
| UCAGGACCUGCAGACAGUA | 7841 | UACUGUCUGCAGGUCCUGA | 7842 |
| CAGGACCUGCAGACAGUAC | 7843 | GUACUGUCUGCAGGUCCUG | 7844 |
| AGGACCUGCAGACAGUACA | 7845 | UGUACUGUCUGCAGGUCCU | 7846 |
| GGACCUGCAGACAGUACAG | 7847 | CUGUACUGUCUGCAGGUCC | 7848 |
| CUGCAGACAGUACAGGCUA | 7849 | UAGCCUGUACUGUCUGCAG | 7850 |
| GACAGUACAGGCUAGAUAA | 7851 | UUAUCUAGCCUGUACUGUC | 7852 |
| ACAGUACAGGCUAGAUAAC | 7853 | GUUAUCUAGCCUGUACUGU | 7854 |

TABLE 9-continued

| Sense Sequence | SEQ ID NO: | Antisense Sequence | SEQ ID NO: |
|---|---|---|---|
| CAGUACAGGCUAGAUAACC | 7855 | GGUUAUCUAGCCUGUACUG | 7856 |
| AGUACAGGCUAGAUAACCC | 7857 | GGGUUAUCUAGCCUGUACU | 7858 |
| GUACAGGCUAGAUAACCCA | 7859 | UGGGUUAUCUAGCCUGUAC | 7860 |
| UACAGGCUAGAUAACCCAC | 7861 | GUGGGUUAUCUAGCCUGUA | 7862 |
| GCUAGAUAACCCACCCAAU | 7863 | AUUGGGUGGGUUAUCUAGC | 7864 |
| CUAGAUAACCCACCCAAUU | 7865 | AAUUGGGUGGGUUAUCUAG | 7866 |
| AGAUAACCCACCCAAUUUC | 7867 | GAAAUUGGGUGGGUUAUCU | 7868 |
| GAUAACCCACCCAAUUUCC | 7869 | GGAAAUUGGGUGGGUUAUC | 7870 |
| AACCUUUCAGCAUAACGCC | 7871 | GGCGUUAUGCUGAAAGGUU | 7872 |
| ACCUUUCAGCAUAACGCCU | 7873 | AGGCGUUAUGCUGAAAGGU | 7874 |
| CCUUUCAGCAUAACGCCUC | 7875 | GAGGCGUUAUGCUGAAAGG | 7876 |
| CUUUCAGCAUAACGCCUCA | 7877 | UGAGGCGUUAUGCUGAAAG | 7878 |
| UUUCAGCAUAACGCCUCAC | 7879 | GUGAGGCGUUAUGCUGAAA | 7880 |
| UUCAGCAUAACGCCUCACA | 7881 | UGUGAGGCGUUAUGCUGAA | 7882 |
| UCAGCAUAACGCCUCACAU | 7883 | AUGUGAGGCGUUAUGCUGA | 7884 |
| CAGCAUAACGCCUCACAUC | 7885 | GAUGUGAGGCGUUAUGCUG | 7886 |
| AGCAUAACGCCUCACAUCC | 7887 | GGAUGUGAGGCGUUAUGCU | 7888 |
| GCAUAACGCCUCACAUCCC | 7889 | GGGAUGUGAGGCGUUAUGC | 7890 |
| AACGCCUCACAUCCCAAGU | 7891 | ACUUGGGAUGUGAGGCGUU | 7892 |
| ACGCCUCACAUCCCAAGUC | 7893 | GACUUGGGAUGUGAGGCGU | 7894 |
| CGCCUCACAUCCCAAGUCU | 7895 | AGACUUGGGAUGUGAGGCG | 7896 |
| UCACAUCCCAAGUCUAUAC | 7897 | GUAUAGACUUGGGAUGUGA | 7898 |
| CACAUCCCAAGUCUAUACC | 7899 | GGUAUAGACUUGGGAUGUG | 7900 |
| ACAUCCCAAGUCUAUACCC | 7901 | GGGUAUAGACUUGGGAUGU | 7902 |
| CAUCCCAAGUCUAUACCCU | 7903 | AGGGUAUAGACUUGGGAUG | 7904 |
| AAUGCUGUUCUUUCCUAGC | 7905 | GCUAGGAAAGAACAGCAUU | 7906 |
| AUGCUGUUCUUUCCUAGCC | 7907 | GGCUAGGAAAGAACAGCAU | 7908 |
| CUGUUCUUUCCUAGCCACC | 7909 | GGUGGCUAGGAAAGAACAG | 7910 |
| UGUUCUUUCCUAGCCACCU | 7911 | AGGUGGCUAGGAAAGAACA | 7912 |
| GCCAAGAUCAAGAUGUCCC | 7913 | GGGACAUCUUGAUCUUGGC | 7914 |
| UCUUGAUCCCAGCCUGACU | 7915 | AGUCAGGCUGGGAUCAAGA | 7916 |
| CUUGAUCCCAGCCUGACUG | 7917 | CAGUCAGGCUGGGAUCAAG | 7918 |
| UUGAUCCCAGCCUGACUGC | 7919 | GCAGUCAGGCUGGGAUCAA | 7920 |
| UGAUCCCAGCCUGACUGCU | 7921 | AGCAGUCAGGCUGGGAUCA | 7922 |
| CUGACUGCUGCUACAUCUA | 7923 | UAGAUGUAGCAGCAGUCAG | 7924 |
| GACUGCUGCUACAUCUAAU | 7925 | AUUAGAUGUAGCAGCAGUC | 7926 |
| ACUGCUGCUACAUCUAAUC | 7927 | GAUUAGAUGUAGCAGCAGU | 7928 |
| CUGCUGCUACAUCUAAUCC | 7929 | GGAUUAGAUGUAGCAGCAG | 7930 |
| UGCUGCUACAUCUAAUCCC | 7931 | GGGAUUAGAUGUAGCAGCA | 7932 |
| CCUACCAAUGCCUCCUGUC | 7933 | GACAGGAGGCAUUGGUAGG | 7934 |
| CUACCAAUGCCUCCUGUCC | 7935 | GGACAGGAGGCAUUGGUAG | 7936 |
| CCAAUGCCUCCUGUCCCUA | 7937 | UAGGGACAGGAGGCAUUGG | 7938 |
| CAAUGCCUCCUGUCCCUAA | 7939 | UUAGGGACAGGAGGCAUUG | 7940 |
| AAUGCCUCCUGUCCCUAAA | 7941 | UUUAGGGACAGGAGGCAUU | 7942 |
| CCCAGCAUACUGAUGACAG | 7943 | CUGUCAUCAGUAUGCUGGG | 7944 |
| CCAGCAUACUGAUGACAGC | 7945 | GCUGUCAUCAGUAUGCUGG | 7946 |
| CAUACUGAUGACAGCCCUC | 7947 | GAGGGCUGUCAUCAGUAUG | 7948 |
| AUACUGAUGACAGCCCUCU | 7949 | AGAGGGCUGUCAUCAGUAU | 7950 |
| UACUGAUGACAGCCCUCUC | 7951 | GAGAGGGCUGUCAUCAGUA | 7952 |
| ACUGAUGACAGCCCUCUCU | 7953 | AGAGAGGGCUGUCAUCAGU | 7954 |
| CUGAUGACAGCCCUCUCUG | 7955 | CAGAGAGGGCUGUCAUCAG | 7956 |
| UGAUGACAGCCCUCUCUGA | 7957 | UCAGAGAGGGCUGUCAUCA | 7958 |
| GAUGACAGCCCUCUCUGAC | 7959 | GUCAGAGAGGGCUGUCAUC | 7960 |
| AUGACAGCCCUCUCUGACU | 7961 | AGUCAGAGAGGGCUGUCAU | 7962 |
| UGACAGCCCUCUCUGACUU | 7963 | AAGUCAGAGAGGGCUGUCA | 7964 |
| GACAGCCCUCUCUGACUUU | 7965 | AAAGUCAGAGAGGGCUGUC | 7966 |
| ACAGCCCUCUCUGACUUUA | 7967 | UAAAGUCAGAGAGGGCUGU | 7968 |
| CAGCCCUCUCUGACUUUAC | 7969 | GUAAAGUCAGAGAGGGCUG | 7970 |
| AGCCCUCUCUGACUUUACC | 7971 | GGUAAAGUCAGAGAGGGCU | 7972 |
| GCCCUCUCUGACUUUACCU | 7973 | AGGUAAAGUCAGAGAGGGC | 7974 |
| CCCUCUCUGACUUUACCUU | 7975 | AAGGUAAAGUCAGAGAGGG | 7976 |
| CCUCUCUGACUUUACCUUG | 7977 | CAAGGUAAAGUCAGAGAGG | 7978 |
| CUCUCUGACUUUACCUUGA | 7979 | UCAAGGUAAAGUCAGAGAG | 7980 |
| AGAUCUGUCUUCAUACCCU | 7981 | AGGGUAUGAAGACAGAUCU | 7982 |
| GAUCUGUCUUCAUACCCUU | 7983 | AAGGGUAUGAAGACAGAUC | 7984 |
| CUGUCUUCAUACCCUUCCC | 7985 | GGGAAGGGUAUGAAGACAG | 7986 |

In some embodiments, the siRNA molecules targeted to Transcript C comprise or consist of the nucleotide sequences (sense and antisense strands) shown in Table 10.

TABLE 10

| Sense Sequence | SEQ ID NO: | Antisense Sequence | SEQ ID NO: |
|---|---|---|---|
| ACACCAGAAGUCACAUUUC | 7987 | GAAAUGUGACUUCUGGUGU | 7988 |
| GAAGUCACAUUUCAUCCUU | 7989 | AAGGAUGAAAUGUGACUUC | 7990 |
| AAGUCACAUUUCAUCCUUU | 7991 | AAAGGAUGAAAUGUGACUU | 7992 |
| AGUCACAUUUCAUCCUUUU | 7993 | AAAAGGAUGAAAUGUGACU | 7994 |

TABLE 10-continued

| Sense Sequence | SEQ ID NO: | Antisense Sequence | SEQ ID NO: |
|---|---|---|---|
| UUUCAUCCUUUUACAUGGU | 7995 | ACCAUGUAAAAGGAUGAAA | 7996 |
| UUCAUCCUUUUACAUGGUU | 7997 | AACCAUGUAAAAGGAUGAA | 7998 |
| UCAUCCUUUUACAUGGUUC | 7999 | GAACCAUGUAAAAGGAUGA | 8000 |
| CAUCCUUUUACAUGGUUCC | 8001 | GGAACCAUGUAAAAGGAUG | 8002 |
| UGGUUCCCAUCUACCCUCA | 8003 | UGAGGGUAGAUGGGAACCA | 8004 |
| GGUUCCCAUCUACCCUCAC | 8005 | GUGAGGGUAGAUGGGAACC | 8006 |
| GUUCCCAUCUACCCUCACA | 8007 | UGUGAGGGUAGAUGGGAAC | 8008 |
| GGCAAUUCUUCCUCCAGGA | 8009 | UCCUGGAGGAAGAAUUGCC | 8010 |
| GCAAUUCUUCCUCCAGGAC | 8011 | GUCCUGGAGGAAGAAUUGC | 8012 |
| CAAUUCUUCCUCCAGGACC | 8013 | GGUCCUGGAGGAAGAAUUG | 8014 |
| AAUUCUUCCUCCAGGACCC | 8015 | GGGUCCUGGAGGAAGAAUU | 8016 |
| CCCUUGGACUUUGCCCUUC | 8017 | GAAGGGCAAAGUCCAAGGG | 8018 |
| CCUUGGACUUUGCCCUUCU | 8019 | AGAAGGGCAAAGUCCAAGG | 8020 |
| CUUGGACUUUGCCCUUCUU | 8021 | AAGAAGGGCAAAGUCCAAG | 8022 |
| UUGGACUUUGCCCUUCUUA | 8023 | UAAGAAGGGCAAAGUCCAA | 8024 |
| UGGACUUUGCCCUUCUUAC | 8025 | GUAAGAAGGGCAAAGUCCA | 8026 |
| GGACUUUGCCCUUCUUACU | 8027 | AGUAAGAAGGGCAAAGUCC | 8028 |
| UUUGCCCUUCUUACUGGCC | 8029 | GGCCAGUAAGAAGGGCAAA | 8030 |
| UUGCCCUUCUUACUGGCCA | 8031 | UGGCCAGUAAGAAGGGCAA | 8032 |
| UGCCCUUCUUACUGGCCAG | 8033 | CUGGCCAGUAAGAAGGGCA | 8034 |
| UCUUACUGGCCAGGCAGGG | 8035 | CCCUGCCUGGCCAGUAAGA | 8036 |
| GGCCAGAGUCCAGGCUUGA | 8037 | UCAAGCCUGGACUCUGGCC | 8038 |
| GCCAGAGUCCAGGCUUGAC | 8039 | GUCAAGCCUGGACUCUGGC | 8040 |
| GUCCAGGCUUGACUCAUUC | 8041 | GAAUGAGUCAAGCCUGGAC | 8042 |
| AGGCUUGACUCAUUCCCAC | 8043 | GUGGGAAUGAGUCAAGCCU | 8044 |
| GACUCAUUCCCACCUUGUC | 8045 | GACAAGGUGGGAAUGAGUC | 8046 |
| ACUCAUUCCCACCUUGUCC | 8047 | GGACAAGGUGGGAAUGAGU | 8048 |
| UCAUUCCCACCUUGUCCUG | 8049 | CAGGACAAGGUGGGAAUGA | 8050 |
| CACCUUGUCCUGGGCUGAG | 8051 | CUCAGCCCAGGACAAGGUG | 8052 |
| ACCACCCAGCCCAGAAGUU | 8053 | AACUUCUGGGCUGGGUGGU | 8054 |
| CCACCCAGCCCAGAAGUUC | 8055 | GAACUUCUGGGCUGGGUGG | 8056 |
| CACCCAGCCCAGAAGUUCC | 8057 | GGAACUUCUGGGCUGGGUG | 8058 |
| ACCCAGCCCAGAAGUUCCA | 8059 | UGGAACUUCUGGGCUGGGU | 8060 |
| CCAGAAGUUCCAGGGAAGG | 8061 | CCUUCCCUGGAACUUCUGG | 8062 |
| CAGAAGUUCCAGGGAAGGA | 8063 | UCCUUCCCUGGAACUUCUG | 8064 |
| AACUCUCCGGUCCACCAUG | 8065 | CAUGGUGGACCGGAGAGUU | 8066 |
| ACUCUCCGGUCCACCAUGG | 8067 | CCAUGGUGGACCGGAGAGU | 8068 |
| CACCAUGGAGUACCUCUCA | 8069 | UGAGAGGUACUCCAUGGUG | 8070 |
| ACCAUGGAGUACCUCUCAG | 8071 | CUGAGAGGUACUCCAUGGU | 8072 |
| UGGAGUACCUCUCAGCUCU | 8073 | AGAGCUGAGAGGUACUCCA | 8074 |
| GGAGUACCUCUCAGCUCUG | 8075 | CAGAGCUGAGAGGUACUCC | 8076 |
| GAGUACCUCUCAGCUCUGA | 8077 | UCAGAGCUGAGAGGUACUC | 8078 |
| AGUACCUCUCAGCUCUGAA | 8079 | UUCAGAGCUGAGAGGUACU | 8080 |
| CCAGUGACUUACUCAGGUG | 8081 | CACCUGAGUAAGUCACUGG | 8082 |
| CAGUGACUUACUCAGGUGA | 8083 | UCACCUGAGUAAGUCACUG | 8084 |
| AGUGACUUACUCAGGUGAC | 8085 | GUCACCUGAGUAAGUCACU | 8086 |
| GUGACUUACUCAGGUGACU | 8087 | AGUCACCUGAGUAAGUCAC | 8088 |
| UGACUUACUCAGGUGACUG | 8089 | CAGUCACCUGAGUAAGUCA | 8090 |
| GACUUACUCAGGUGACUGC | 8091 | GCAGUCACCUGAGUAAGUC | 8092 |
| ACUUACUCAGGUGACUGCU | 8093 | AGCAGUCACCUGAGUAAGU | 8094 |
| CUUACUCAGGUGACUGCUA | 8095 | UAGCAGUCACCUGAGUAAG | 8096 |
| UUACUCAGGUGACUGCUAA | 8097 | UUAGCAGUCACCUGAGUAA | 8098 |
| UACUCAGGUGACUGCUAAC | 8099 | GUUAGCAGUCACCUGAGUA | 8100 |
| ACUCAGGUGACUGCUAACC | 8101 | GGUUAGCAGUCACCUGAGU | 8102 |
| CUCAGGUGACUGCUAACCC | 8103 | GGGUUAGCAGUCACCUGAG | 8104 |
| GGUGACUGCUAACCCUCCG | 8105 | CGGAGGGUUAGCAGUCACC | 8106 |
| GUGACUGCUAACCCUCCGC | 8107 | GCGGAGGGUUAGCAGUCAC | 8108 |
| UGACUGCUAACCCUCCGCU | 8109 | AGCGGAGGGUUAGCAGUCA | 8110 |
| GACUGCUAACCCUCCGCUC | 8111 | GAGCGGAGGGUUAGCAGUC | 8112 |
| ACUGCUAACCCUCCGCUCU | 8113 | AGAGCGGAGGGUUAGCAGU | 8114 |
| CUGCUAACCCUCCGCUCUA | 8115 | UAGAGCGGAGGGUUAGCAG | 8116 |
| UGCUAACCCUCCGCUCUAC | 8117 | GUAGAGCGGAGGGUUAGCA | 8118 |
| AACCCUCCGCUCUACCCUC | 8119 | GAGGGUAGAGCGGAGGGUU | 8120 |
| ACUCCACAGUGGGCUUGUC | 8121 | GACAAGCCCACUGUGGAGU | 8122 |
| CUCCACAGUGGGCUUGUCA | 8123 | UGACAAGCCCACUGUGGAG | 8124 |
| UCCACAGUGGGCUUGUCAA | 8125 | UUGACAAGCCCACUGUGGA | 8126 |
| CCACAGUGGGCUUGUCAAG | 8127 | CUUGACAAGCCCACUGUGG | 8128 |
| GUCAAGCUCCUGAGCCACC | 8129 | GGUGGCUCAGGAGCUUGAC | 8130 |
| CCAUGGUCUCUCCCUCAUC | 8131 | GAUGAGGGAGAGACCAUGG | 8132 |
| CAUGGUCUCUCCCUCAUCC | 8133 | GGAUGAGGGAGAGACCAUG | 8134 |
| AUGGUCUCUCCCUCAUCCC | 8135 | GGGAUGAGGGAGAGACCAU | 8136 |
| UCUCUCCCUCAUCCCUAAU | 8137 | UCGAUUAGGGAUGAGGGAG | 8144 |
| CUCUCCCUCAUCCCUAAUC | 8139 | GAUUAGGGAUGAGGGAGAG | 8140 |
| UCUCCCUCAUCCCUAAUCG | 8141 | CGAUUAGGGAUGAGGGAGA | 8142 |
| CUCCCUCAUCCCUAAUCGA | 8143 | UCGAUUAGGGAUGAGGGAG | 8144 |
| UCCCUCAUCCCUAAUCGAU | 8145 | AUCGAUUAGGGAUGAGGGA | 8146 |

TABLE 10-continued

| Sense Sequence | SEQ ID NO: | Antisense Sequence | SEQ ID NO: |
|---|---|---|---|
| CCCUCAUCCCUAAUCGAUA | 8147 | UAUCGAUUAGGGAUGAGGG | 8148 |
| CCUCAUCCCUAAUCGAUAA | 8149 | UUAUCGAUUAGGGAUGAGG | 8150 |
| CUCAUCCCUAAUCGAUAAA | 8151 | UUUAUCGAUUAGGGAUGAG | 8152 |
| AACCUAGAUCUCUCCCUCC | 8153 | GGAGGGAGAGAUCUAGGUU | 8154 |
| ACCUAGAUCUCUCCCUCCC | 8155 | GGGAGGGAGAGAUCUAGGU | 8156 |
| CUAGAUCUCUCCCUCCCUA | 8157 | UAGGGAGGGAGAGAUCUAG | 8158 |
| UAGAUCUCUCCCUCCCUAG | 8159 | CUAGGGAGGGAGAGAUCUA | 8160 |
| AGAUCUCUCCCUCCCUAGC | 8161 | GCUAGGGAGGGAGAGAUCU | 8162 |
| GAUCUCUCCCUCCCUAGCC | 8163 | GGCUAGGGAGGGAGAGAUC | 8164 |
| AUCUCUCCCUCCCUAGCCC | 8165 | GGGCUAGGGAGGGAGAGAU | 8166 |
| UAGCCCUCUAGCCACUCUA | 8167 | UAGAGUGGCUAGAGGGCUA | 8168 |
| AGCCCUCUAGCCACUCUAC | 8169 | GUAGAGUGGCUAGAGGGCU | 8170 |
| CUCUAGCCACUCUACCCUC | 8171 | GAGGGUAGAGUGGCUAGAG | 8172 |
| UCUAGCCACUCUACCCUCA | 8173 | UGAGGGUAGAGUGGCUAGA | 8174 |
| CUAGCCACUCUACCCUCAU | 8175 | AUGAGGGUAGAGUGGCUAG | 8176 |
| UAGCCACUCUACCCUCAUC | 8177 | GAUGAGGGUAGAGUGGCUA | 8178 |
| AGCCACUCUACCCUCAUCA | 8179 | UGAUGAGGGUAGAGUGGCU | 8180 |
| GCCACUCUACCCUCAUCAU | 8181 | AUGAUGAGGGUAGAGUGGC | 8182 |
| CCACUCUACCCUCAUCAUG | 8183 | CAUGAUGAGGGUAGAGUGG | 8184 |
| CACUCUACCCUCAUCAUGC | 8185 | GCAUGAUGAGGGUAGAGUG | 8186 |
| ACUCUACCCUCAUCAUGCC | 8187 | GGCAUGAUGAGGGUAGAGU | 8188 |
| CUCUACCCUCAUCAUGCCC | 8189 | GGGCAUGAUGAGGGUAGAG | 8190 |
| UCUACCCUCAUCAUGCCCU | 8191 | AGGGCAUGAUGAGGGUAGA | 8192 |
| CUACCCUCAUCAUGCCCUU | 8193 | AAGGGCAUGAUGAGGGUAG | 8194 |
| UACCCUCAUCAUGCCCUUU | 8195 | AAAGGGCAUGAUGAGGGUA | 8196 |
| ACCCUCAUCAUGCCCUUUA | 8197 | UAAAGGGCAUGAUGAGGGU | 8198 |
| CCCUCAUCAUGCCCUUUAC | 8199 | GUAAAGGGCAUGAUGAGGG | 8200 |
| CUCAUCAUGCCCUUUACAC | 8201 | GUGUAAAGGGCAUGAUGAG | 8202 |
| UCAUCAUGCCCUUUACACU | 8203 | AGUGUAAAGGGCAUGAUGA | 8204 |
| CCCUUCUUGACUUUUCUUC | 8205 | GAAGAAAAGUCAAGAAGGG | 8206 |
| CUUCUUGACUUUUCUUCUC | 8207 | GAGAAGAAAAGUCAAGAAG | 8208 |
| GACUUUUCUUCUCAACUAC | 8209 | GUAGUUGAGAAGAAAAGUC | 8210 |
| ACUUUUCUUCUCAACUACC | 8211 | GGUAGUUGAGAAGAAAAGU | 8212 |
| CUUUUCUUCUCAACUACCA | 8213 | UGGUAGUUGAGAAGAAAAG | 8214 |
| UUUUCUUCUCAACUACCAG | 8215 | CUGGUAGUUGAGAAGAAAA | 8216 |
| UAUCUAAUAUAAGCUCGGA | 8217 | UCCGAGCUUAUAUUAGAUA | 8218 |
| AUCUAAUAUAAGCUCGGAG | 8219 | CUCCGAGCUUAUAUUAGAU | 8220 |
| UCUAAUAUAAGCUCGGAGU | 8221 | ACUCCGAGCUUAUAUUAGA | 8222 |
| CUAAUAUAAGCUCGGAGUU | 8223 | AACUCCGAGCUUAUAUUAG | 8224 |
| UAAUAUAAGCUCGGAGUUU | 8225 | AAACUCCGAGCUUAUAUUA | 8226 |
| AAUAUAAGCUCGGAGUUUG | 8227 | CAAACUCCGAGCUUAUAUU | 8228 |
| AUAUAAGCUCGGAGUUUGG | 8229 | CCAAACUCCGAGCUUAUAU | 8230 |
| UAUAAGCUCGGAGUUUGGA | 8231 | UCCAAACUCCGAGCUUAUA | 8232 |
| AUAAGCUCGGAGUUUGGAC | 8233 | GUCCAAACUCCGAGCUUAU | 8234 |
| UAAGCUCGGAGUUUGGACG | 8235 | CGUCCAAACUCCGAGCUUA | 8236 |
| AAGCUCGGAGUUUGGACGG | 8237 | CCGUCCAAACUCCGAGCUU | 8238 |
| AGCUCGGAGUUUGGACGGA | 8239 | UCCGUCCAAACUCCGAGCU | 8240 |
| GCUCGGAGUUUGGACGGAG | 8241 | CUCCGUCCAAACUCCGAGC | 8242 |
| CUCGGAGUUUGGACGGAGG | 8243 | CCUCCGUCCAAACUCCGAG | 8244 |
| UCGGAGUUUGGACGGAGGG | 8245 | CCCUCCGUCCAAACUCCGA | 8246 |
| CGGAGUUUGGACGGAGGGU | 8247 | ACCCUCCGUCCAAACUCCG | 8248 |
| UUUGGACGAGGGUCUGGA | 8249 | UCCAGACCCUCCGUCCAAA | 8250 |
| CCCAGCGACCUUUCCGUGU | 8251 | ACACGGAAAGGUCGCUGGG | 8252 |
| CCAGCGACCUUUCCGUGUC | 8253 | GACACGGAAAGGUCGCUGG | 8254 |
| CAGCGACCUUUCCGUGUCU | 8255 | AGACACGGAAAGGUCGCUG | 8256 |
| AGCGACCUUUCCGUGUCUG | 8257 | CAGACACGGAAAGGUCGCU | 8258 |
| GCGACCUUUCCGUGUCUGU | 8259 | ACAGACACGGAAAGGUCGC | 8260 |
| CGACCUUUCCGUGUCUGUG | 8261 | CACAGACACGGAAAGGUCG | 8262 |
| CUUUCCGUGUCUGUGAUCA | 8263 | UGAUCACAGACACGGAAAG | 8264 |
| UUUCCGUGUCUGUGAUCAC | 8265 | GUGAUCACAGACACGGAAA | 8266 |
| UUCCGUGUCUGUGAUCACA | 8267 | UGUGAUCACAGACACGGAA | 8268 |
| AAGGCCUGACAGCUGCCAC | 8269 | GUGGCAGCUGUCAGGCCUU | 8270 |
| GCCAGGAGCUGCUAGCCAA | 8271 | UUGGCUAGCAGCUCCUGGC | 8272 |
| CCAGGAGCUGCUAGCCAAA | 8273 | UUUGGCUAGCAGCUCCUGG | 8274 |
| GAGCUGCUAGCCAAAGUAA | 8275 | UUACUUUGGCUAGCAGCUC | 8276 |
| AGCUGCUAGCCAAAGUAAG | 8277 | CUUACUUUGGCUAGCAGCU | 8278 |
| GCUGCUAGCCAAAGUAAGU | 8279 | ACUUACUUUGGCUAGCAGC | 8280 |
| CUGCUAGCCAAAGUAAGUA | 8281 | UACUUACUUUGGCUAGCAG | 8282 |
| UGCUAGCCAAAGUAAGUAG | 8283 | CUACUUACUUUGGCUAGCA | 8284 |
| GCUAGCCAAAGUAAGUAGG | 8285 | CCUACUUACUUUGGCUAGC | 8286 |
| UAGCCAAAGUAAGUAGGCC | 8287 | GGCCUACUUACUUUGGCUA | 8288 |
| AGCCAAAGUAAGUAGGCCA | 8289 | UGGCCUACUUACUUUGGCU | 8290 |
| GCCAAAGUAAGUAGGCCAA | 8291 | UUGGCCUACUUACUUUGGC | 8292 |
| CCAAAGUAAGUAGGCCAAG | 8293 | CUUGGCCUACUUACUUUGG | 8294 |
| CAAAGUAAGUAGGCCAAGU | 8295 | ACUUGGCCUACUUACUUUG | 8296 |
| AAAGUAAGUAGGCCAAGUU | 8297 | AACUUGGCCUACUUACUUU | 8298 |

TABLE 10-continued

| Sense Sequence | SEQ ID NO: | Antisense Sequence | SEQ ID NO: |
|---|---|---|---|
| AAGUAAGUAGGCCAAGUUC | 8299 | GAACUUGGCCUACUUACUU | 8300 |
| AGUAAGUAGGCCAAGUUCC | 8301 | GGAACUUGGCCUACUUACU | 8302 |
| GUAAGUAGGCCAAGUUCCU | 8303 | AGGAACUUGGCCUACUUAC | 8304 |
| UAAGUAGGCCAAGUUCCUC | 8305 | GAGGAACUUGGCCUACUUA | 8306 |
| UAGGCCAAGUUCCUCGGUU | 8307 | AACCGAGGAACUUGGCCUA | 8308 |
| AGGCCAAGUUCCUCGGUUC | 8309 | GAACCGAGGAACUUGGCCU | 8310 |
| GGCCAAGUUCCUCGGUUCC | 8311 | GGAACCGAGGAACUUGGCC | 8312 |
| GCCAAGUUCCUCGGUUCCU | 8313 | AGGAACCGAGGAACUUGGC | 8314 |
| CCAAGUUCCUCGGUUCCUA | 8315 | UAGGAACCGAGGAACUUGG | 8316 |
| CAAGUUCCUCGGUUCCUAU | 8317 | AUAGGAACCGAGGAACUUG | 8318 |
| AAGUUCCUCGGUUCCUAUA | 8319 | UAUAGGAACCGAGGAACUU | 8320 |
| AGUUCCUCGGUUCCUAUAG | 8321 | CUAUAGGAACCGAGGAACU | 8322 |
| GUUCCUCGGUUCCUAUAGC | 8323 | GCUAUAGGAACCGAGGAAC | 8324 |
| UUCCUCGGUUCCUAUAGCA | 8325 | UGCUAUAGGAACCGAGGAA | 8326 |
| UCCUCGGUUCCUAUAGCAG | 8327 | CUGCUAUAGGAACCGAGGA | 8328 |
| CAGUGGCAACUUGUGAUGA | 8329 | UCAUCACAAGUUGCCACUG | 8330 |
| AGUGGCAACUUGUGAUGAU | 8331 | AUCAUCACAAGUUGCCACU | 8332 |
| GUGGCAACUUGUGAUGAUG | 8333 | CAUCAUCACAAGUUGCCAC | 8334 |
| GGCAACUUGUGAUGAUGGA | 8335 | UCCAUCAUCACAAGUUGCC | 8336 |
| ACUUGUGAUGAUGGAGCAG | 8337 | CUGCUCCAUCAUCACAAGU | 8338 |
| CUUGUGAUGAUGGAGCAGA | 8339 | UCUGCUCCAUCAUCACAAG | 8340 |
| GUGAUGAUGGAGCAGAGGG | 8341 | CCCUCUGCUCCAUCAUCAC | 8342 |
| UGAUGAUGGAGCAGAGGGC | 8343 | GCCCUCUGCUCCAUCAUCA | 8344 |
| UGGAGCAGAGGGCUGAAGU | 8345 | ACUUCAGCCCUCUGCUCCA | 8346 |
| GGAGCAGAGGGCUGAAGUC | 8347 | GACUUCAGCCCUCUGCUCC | 8348 |
| GAGCAGAGGGCUGAAGUCA | 8349 | UGACUUCAGCCCUCUGCUC | 8350 |
| CUAAAAGCAGCGGAGUGGG | 8351 | CCCACUCCGCUGCUUUUAG | 8352 |
| UAAAAGCAGCGGAGUGGGC | 8353 | GCCCACUCCGCUGCUUUUA | 8354 |
| AAAAGCAGCGGAGUGGGCC | 8355 | GGCCCACUCCGCUGCUUUU | 8356 |
| AAAGCAGCGGAGUGGGCCU | 8357 | AGGCCCACUCCGCUGCUUU | 8358 |
| AAGCAGCGGAGUGGGCCUA | 8359 | UAGGCCCACUCCGCUGCUU | 8360 |
| AGCAGCGGAGUGGGCCUAA | 8361 | UUAGGCCCACUCCGCUGCU | 8362 |
| GCAGCGGAGUGGGCCUAAU | 8363 | AUUAGGCCCACUCCGCUGC | 8364 |
| CAGCGGAGUGGGCCUAAUG | 8365 | CAUUAGGCCCACUCCGCUG | 8366 |
| AGCGGAGUGGGCCUAAUGA | 8367 | UCAUUAGGCCCACUCCGCU | 8368 |
| GCGGAGUGGGCCUAAUGAG | 8369 | CUCAUUAGGCCCACUCCGC | 8370 |
| AGUGGGCCUAAUGAGCUCU | 8371 | AGAGCUCAUUAGGCCCACU | 8372 |
| GUGGGCCUAAUGAGCUCUG | 8373 | CAGAGCUCAUUAGGCCCAC | 8374 |
| UGGGCCUAAUGAGCUCUGG | 8375 | CCAGAGCUCAUUAGGCCCA | 8376 |
| GGGCCUAAUGAGCUCUGGU | 8377 | ACCAGAGCUCAUUAGGCCC | 8378 |
| GGCCUAAUGAGCUCUGGUC | 8379 | GACCAGAGCUCAUUAGGCC | 8380 |
| GCCUAAUGAGCUCUGGUCA | 8381 | UGACCAGAGCUCAUUAGGC | 8382 |
| CCUAAUGAGCUCUGGUCAA | 8383 | UUGACCAGAGCUCAUUAGG | 8384 |
| CUAAUGAGCUCUGGUCAAU | 8385 | AUUGACCAGAGCUCAUUAG | 8386 |
| UAAUGAGCUCUGGUCAAUU | 8387 | AAUUGACCAGAGCUCAUUA | 8388 |
| AAUGAGCUCUGGUCAAUUU | 8389 | AAAUUGACCAGAGCUCAUU | 8390 |
| AUGAGCUCUGGUCAAUUUG | 8391 | CAAAUUGACCAGAGCUCAU | 8392 |
| UGAGCUCUGGUCAAUUUGU | 8393 | ACAAAUUGACCAGAGCUCA | 8394 |
| CUGGUCAAUUUGUUCAUUU | 8395 | AAAUGAACAAAUUGACCAG | 8396 |
| CAAUUUGUUCAUUUUCCAC | 8397 | GUGGAAAAUGAACAAAUUG | 8398 |
| AGUGAGCUUUUCUAUGGGA | 8399 | UCCCAUAGAAAAGCUCACU | 8400 |
| AGCUUUUCUAUGGGAGCAG | 8401 | CUGCUCCCAUAGAAAAGCU | 8402 |
| GAAUUCAGAAGCUAGUAUG | 8403 | CAUACUAGCUUCUGAAUUC | 8404 |
| AUUCAGAAGCUAGUAUGGA | 8405 | UCCAUACUAGCUUCUGAAU | 8406 |
| UUCAGAAGCUAGUAUGGAA | 8407 | UUCCAUACUAGCUUCUGAA | 8408 |
| AAAGGUGAUUUGUGUGACA | 8409 | UGUCACACAAAUCACCUUU | 8410 |
| AUUCUGAUUCUGCCACUUC | 8411 | GAAGUGGCAGAAUCAGAAU | 8412 |
| AUUCUGCCACUUCCUGCCU | 8413 | AGGCAGGAAGUGGCAGAAU | 8414 |
| GCCACUUCCUGCCUGUCAA | 8415 | UUGACAGGCAGGAAGUGGC | 8416 |
| CCACUUCCUGCCUGUCAAA | 8417 | UUUGACAGGCAGGAAGUGG | 8418 |
| AACCUUGGGAAGUUGUUCA | 8419 | UGAACAACUUCCCAAGGUU | 8420 |
| ACCUUGGGAAGUUGUUCAA | 8421 | UUGAACAACUUCCCAAGGU | 8422 |
| CCUUGGGAAGUUGUUCAAC | 8423 | GUUGAACAACUUCCCAAGG | 8424 |
| GGGAAGUUGUUCAACCUAC | 8425 | GUAGGUUGAACAACUUCCC | 8426 |
| GGAAGUUGUUCAACCUACC | 8427 | GGUAGGUUGAACAACUUCC | 8428 |
| GAAGUUGUUCAACCUACCA | 8429 | UGGUAGGUUGAACAACUUC | 8430 |
| AAGUUGUUCAACCUACCAA | 8431 | UUGGUAGGUUGAACAACUU | 8432 |
| AGUUGUUCAACCUACCAAA | 8433 | UUUGGUAGGUUGAACAACU | 8434 |
| GUUGUUCAACCUACCAAAA | 8435 | UUUUGGUAGGUUGAACAAC | 8436 |
| GCAAUAAUAUACAUCACC | 8437 | GGUGAUGUAUUAUUAUGC | 8438 |
| AUAAUAUACAUCACCUCC | 8439 | GGAGGUGAUGUAUUAUUAU | 8440 |
| UAAUACAUCACCUCCUAGG | 8441 | CCUAGGAGGUGAUGUAUUA | 8442 |
| AAUACAUCACCUCCUAGGG | 8443 | CCCUAGGAGGUGAUGUAUU | 8444 |
| AUACAUCACCUCCUAGGGU | 8445 | ACCCUAGGAGGUGAUGUAU | 8446 |
| UACAUCACCUCCUAGGGUU | 8447 | AACCCUAGGAGGUGAUGUA | 8448 |
| ACAUCACCUCCUAGGGUUG | 8449 | CAACCCUAGGAGGUGAUGU | 8450 |

TABLE 10-continued

| Sense Sequence | SEQ ID NO: | Antisense Sequence | SEQ ID NO: |
|---|---|---|---|
| AAAGGAGUAAGAGGAUAAU | 8451 | AUUAUCCUCUUACUCCUUU | 8452 |
| AAGGAGUAAGAGGAUAAUG | 8453 | CAUUAUCCUCUUACUCCUU | 8454 |
| AGUAAGAGGAUAAUGUAGG | 8455 | CCUACAUUAUCCUCUUACU | 8456 |
| GUAAGAGGAUAAUGUAGGU | 8457 | ACCUACAUUAUCCUCUUAC | 8458 |
| UAAGAGGAUAAUGUAGGUA | 8459 | UACCUACAUUAUCCUCUUA | 8460 |
| AAGAGGAUAAUGUAGGUAA | 8461 | UUACCUACAUUAUCCUCUU | 8462 |
| AGAGGAUAAUGUAGGUAAA | 8463 | UUUACCUACAUUAUCCUCU | 8464 |
| GAGGAUAAUGUAGGUAAAG | 8465 | CUUUACCUACAUUAUCCUC | 8466 |
| GGAUAAUGUAGGUAAAGUC | 8467 | GACUUUACCUACAUUAUCC | 8468 |
| AUAAUGUAGGUAAAGUCCU | 8469 | AGGACUUUACCUACAUUAU | 8470 |
| GUAGGUAAAGUCCUCAUAC | 8471 | GUAUGAGGACUUUACCUAC | 8472 |
| GUAAAGUCCUCAUACCUGG | 8473 | CCAGGUAUGAGGACUUUAC | 8474 |
| UAAAGUCCUCAUACCUGGC | 8475 | GCCAGGUAUGAGGACUUUA | 8476 |
| AAAGUCCUCAUACCUGGCA | 8477 | UGCCAGGUAUGAGGACUUU | 8478 |
| AAGUCCUCAUACCUGGCAC | 8479 | GUGCCAGGUAUGAGGACUU | 8480 |
| AGUCCUCAUACCUGGCACA | 8481 | UGUGCCAGGUAUGAGGACU | 8482 |
| GUCCUCAUACCUGGCACAG | 8483 | CUGUGCCAGGUAUGAGGAC | 8484 |
| UCCUCAUACCUGGCACAGA | 8485 | UCUGUGCCAGGUAUGAGGA | 8486 |
| UCUUGAGGGUGUGGGAAGU | 8487 | ACUUCCCACACCCUCAAGA | 8488 |
| CUUGAGGGUGUGGGAAGUG | 8489 | CACUUCCCACACCCUCAAG | 8490 |
| UUGAGGGUGUGGGAAGUGA | 8491 | UCACUUCCCACACCCUCAA | 8492 |
| UGAGGGUGUGGGAAGUGAG | 8493 | CUCACUUCCCACACCCUCA | 8494 |
| AGGGUGUGGGAAGUGAGGU | 8495 | ACCUCACUUCCCACACCCU | 8496 |
| GGGUGUGGGAAGUGAGGUG | 8497 | CACCUCACUUCCCACACCC | 8498 |
| GGGAAGUGAGGUGCAGCAU | 8499 | AUGCUGCACCUCACUUCCC | 8500 |
| GGAAGUGAGGUGCAGCAUU | 8501 | AAUGCUGCACCUCACUUCC | 8502 |
| GAAGUGAGGUGCAGCAUUG | 8503 | CAAUGCUGCACCUCACUUC | 8504 |
| AAGUGAGGUGCAGCAUUGU | 8505 | ACAAUGCUGCACCUCACUU | 8506 |
| AGUGAGGUGCAGCAUUGUA | 8507 | UACAAUGCUGCACCUCACU | 8508 |
| GUGAGGUGCAGCAUUGUAG | 8509 | CUACAAUGCUGCACCUCAC | 8510 |
| UGAGGUGCAGCAUUGUAGA | 8511 | UCUACAAUGCUGCACCUCA | 8512 |
| GAGGUGCAGCAUUGUAGAU | 8513 | AUCUACAAUGCUGCACCUC | 8514 |
| AGGUGCAGCAUUGUAGAUA | 8515 | UAUCUACAAUGCUGCACCU | 8516 |
| GGUGCAGCAUUGUAGAUAA | 8517 | UUAUCUACAAUGCUGCACC | 8518 |
| GUGCAGCAUUGUAGAUAAG | 8519 | CUUAUCUACAAUGCUGCAC | 8520 |
| UGCAGCAUUGUAGAUAAGA | 8521 | UCUUAUCUACAAUGCUGCA | 8522 |
| GCAUUGUAGAUAAGACAGA | 8523 | UCUGUCUUAUCUACAAUGC | 8524 |
| CAUUGUAGAUAAGACAGAA | 8525 | UUCUGUCUUAUCUACAAUG | 8526 |
| AUUGUAGAUAAGACAGAAG | 8527 | CUUCUGUCUUAUCUACAAU | 8528 |
| AUAAGACAGAAGGGUGGAC | 8529 | GUCCACCCUUCUGUCUUAU | 8530 |
| UAAGACAGAAGGGUGGACU | 8531 | AGUCCACCCUUCUGUCUUA | 8532 |
| AACCUGGCUUGCUUUCCAA | 8533 | UUGGAAAGCAAGCCAGGUU | 8534 |
| CCUGGCUUGCUUUCCAAUU | 8535 | AAUUGGAAAGCAAGCCAGG | 8536 |
| ACCAGAAGUGACUUGGAGG | 8537 | CCUCCAAGUCACUUCUGGU | 8538 |
| CCAGAAGUGACUUGGAGGG | 8539 | CCCUCCAAGUCACUUCUGG | 8540 |
| AGAUGCCAAUGACAUGGUA | 8541 | UACCAUGUCAUUGGCAUCU | 8542 |
| GAUGCCAAUGACAUGGUAG | 8543 | CUACCAUGUCAUUGGCAUC | 8544 |
| AUGCCAAUGACAUGGUAGG | 8545 | CCUACCAUGUCAUUGGCAU | 8546 |
| CAAUGACAUGGUAGGAGCA | 8547 | UGCUCCUACCAUGUCAUUG | 8548 |
| AAUGACAUGGUAGGAGCAA | 8549 | UUGCUCCUACCAUGUCAUU | 8550 |
| AUGACAUGGUAGGAGCAAA | 8551 | UUUGCUCCUACCAUGUCAU | 8552 |
| UGACAUGGUAGGAGCAAAG | 8553 | CUUUGCUCCUACCAUGUCA | 8554 |
| GACAUGGUAGGAGCAAAGA | 8555 | UCUUUGCUCCUACCAUGUC | 8556 |
| AAAAGGUCAGCCUCUAGCU | 8557 | AGCUAGAGGCUGACCUUUU | 8558 |
| AAAGGUCAGCCUCUAGCUA | 8559 | UAGCUAGAGGCUGACCUUU | 8560 |
| AGGUCAGCCUCUAGCUAGG | 8561 | CCUAGCUAGAGGCUGACCU | 8562 |
| GGUCAGCCUCUAGCUAGGA | 8563 | UCCUAGCUAGAGGCUGACC | 8564 |
| GUCAGCCUCUAGCUAGGAU | 8565 | AUCCUAGCUAGAGGCUGAC | 8566 |
| CAGCCUCUAGCUAGGAUCC | 8567 | GGAUCCUAGCUAGAGGCUG | 8568 |
| AGCCUCUAGCUAGGAUCCC | 8569 | GGGAUCCUAGCUAGAGGCU | 8570 |
| AGAGCUGCAACCUUUAGGA | 8571 | UCCUAAAGGUUGCAGCUCU | 8572 |
| GAGCUGCAACCUUUAGGAG | 8573 | CUCCUAAAGGUUGCAGCUC | 8574 |
| AGCUGCAACCUUUAGGAGG | 8575 | CCUCCUAAAGGUUGCAGCU | 8576 |
| UUUAGGAGGUAUCAAAGUG | 8577 | CACUUUGAUACCUCCUAAA | 8578 |
| UUAGGAGGUAUCAAAGUGC | 8579 | GCACUUUGAUACCUCCUAA | 8580 |
| UAGGAGGUAUCAAAGUGCC | 8581 | GGCACUUUGAUACCUCCUA | 8582 |
| GUCAAAGUGGGACAUCGAC | 8583 | GUCGAUGUCCCACUUUGAC | 8584 |
| CAUCGACCAAUGUCUAGAG | 8585 | CUCUAGACAUUGGUCGAUG | 8586 |
| AUCGACCAAUGUCUAGAGC | 8587 | GCUCUAGACAUUGGUCGAU | 8588 |
| ACCAAUGUCUAGAGCCAAC | 8589 | GUUGGCUCUAGACAUUGGU | 8590 |
| CAAUGUCUAGAGCCAACUG | 8591 | CAGUUGGCUCUAGACAUUG | 8592 |
| AAUGUCUAGAGCCAACUGA | 8593 | UCAGUUGGCUCUAGACAUU | 8594 |
| AUGUCUAGAGCCAACUGAU | 8595 | AUCAGUUGGCUCUAGACAU | 8596 |
| UGUCUAGAGCCAACUGAUG | 8597 | CAUCAGUUGGCUCUAGACA | 8598 |
| GUCUAGAGCCAACUGAUGG | 8599 | CCAUCAGUUGGCUCUAGAC | 8600 |
| UCUAGAGCCAACUGAUGGA | 8601 | UCCAUCAGUUGGCUCUAGA | 8602 |

TABLE 10-continued

| Sense Sequence | SEQ ID NO: | Antisense Sequence | SEQ ID NO: |
|---|---|---|---|
| CUAGAGCCAACUGAUGGAU | 8603 | AUCCAUCAGUUGGCUCUAG | 8604 |
| UAGAGCCAACUGAUGGAUG | 8605 | CAUCCAUCAGUUGGCUCUA | 8606 |
| AGAGCCAACUGAUGGAUGU | 8607 | ACAUCCAUCAGUUGGCUCU | 8608 |
| GAGCCAACUGAUGGAUGUU | 8609 | AACAUCCAUCAGUUGGCUC | 8610 |
| AACUGAUGGAUGUUGGGCA | 8611 | UGCCCAACAUCCAUCAGUU | 8612 |
| UGGAUGUUGGGCAGCUAAA | 8613 | UUUAGCUGCCCAACAUCCA | 8614 |
| GGAUGUUGGGCAGCUAAAG | 8615 | CUUUAGCUGCCCAACAUCC | 8616 |
| GAUGUUGGGCAGCUAAAGA | 8617 | UCUUUAGCUGCCCAACAUC | 8618 |
| UUGGGCAGCUAAAGAGGGA | 8619 | UCCCUCUUUAGCUGCCCAA | 8620 |
| UGGGCAGCUAAAGAGGGAA | 8621 | UUCCCUCUUUAGCUGCCCA | 8622 |
| GGGCAGCUAAAGAGGGAAG | 8623 | CUUCCCUCUUUAGCUGCCC | 8624 |
| GGCAGCUAAAGAGGGAAGG | 8625 | CCUUCCCUCUUUAGCUGCC | 8626 |
| GCAGCUAAAGAGGGAAGGG | 8627 | CCCUUCCCUCUUUAGCUGC | 8628 |
| GGGCAUGGGAUAAGACCUG | 8629 | CAGGUCUUAUCCCAUGCCC | 8630 |
| GGCAUGGGAUAAGACCUGC | 8631 | GCAGGUCUUAUCCCAUGCC | 8632 |
| GCAUGGGAUAAGACCUGCC | 8633 | GGCAGGUCUUAUCCCAUGC | 8634 |
| CAUGGGAUAAGACCUGCCC | 8635 | GGGCAGGUCUUAUCCCAUG | 8636 |
| AUGGGAUAAGACCUGCCCU | 8637 | AGGGCAGGUCUUAUCCCAU | 8638 |
| UGGGAUAAGACCUGCCCUU | 8639 | AAGGGCAGGUCUUAUCCCA | 8640 |
| GGGAUAAGACCUGCCCUUC | 8641 | GAAGGGCAGGUCUUAUCCC | 8642 |
| GGAUAAGACCUGCCCUUCU | 8643 | AGAAGGGCAGGUCUUAUCC | 8644 |
| AGACCUGCCCUUCUUGCUU | 8645 | AAGCAAGAAGGGCAGGUCU | 8646 |
| GACCUGCCCUUCUUGCUUC | 8647 | GAAGCAAGAAGGGCAGGUC | 8648 |
| CCUGCCCUUCUUGCUUCUU | 8649 | AAGAAGCAAGAAGGGCAGG | 8650 |
| CUGCCCUUCUUGCUUCUUG | 8651 | CAAGAAGCAAGAAGGGCAG | 8652 |
| UGCCCUUCUUGCUUCUUGC | 8653 | GCAAGAAGCAAGAAGGGCA | 8654 |
| UCUUGCUUCUUGCCAUUGG | 8655 | CCAAUGGCAAGAAGCAAGA | 8656 |
| CUUGCUUCUUGCCAUUGGG | 8657 | CCCAAUGGCAAGAAGCAAG | 8658 |
| UUGCUUCUUGCCAUUGGGC | 8659 | GCCCAAUGGCAAGAAGCAA | 8660 |
| CCAUUGGGCAGGCAUUGGA | 8661 | UCCAAUGCCUGCCCAAUGG | 8662 |
| CAUUGGGCAGGCAUUGGAG | 8663 | CUCCAAUGCCUGCCCAAUG | 8664 |
| GACCCUACUGCUGAAUGGA | 8665 | UCCAUUCAGCAGUAGGGUC | 8666 |
| UACUGCUGAAUGGAGUGCU | 8667 | AGCACUCCAUUCAGCAGUA | 8668 |
| ACUGCUGAAUGGAGUGCUA | 8669 | UAGCACUCCAUUCAGCAGU | 8670 |
| CUGCUGAAUGGAGUGCUAA | 8671 | UUAGCACUCCAUUCAGCAG | 8672 |
| UGCUGAAUGGAGUGCUAAC | 8673 | GUUAGCACUCCAUUCAGCA | 8674 |
| GCUGAAUGGAGUGCUAACC | 8675 | GGUUAGCACUCCAUUCAGC | 8676 |
| CUGAAUGGAGUGCUAACCC | 8677 | GGGUUAGCACUCCAUUCAG | 8678 |
| UAACCCUGGUGCUAGAGGA | 8679 | UCCUCUAGCACCAGGGUUA | 8680 |
| AACCCUGGUGCUAGAGGAG | 8681 | CUCCUCUAGCACCAGGGUU | 8682 |
| ACCCUGGUGCUAGAGGAGG | 8683 | CCUCCUCUAGCACCAGGGU | 8684 |
| CCCUGGUGCUAGAGGAGGA | 8685 | UCCUCCUCUAGCACCAGGG | 8686 |
| CCUGGUGCUAGAGGAGGAU | 8687 | AUCCUCCUCUAGCACCAGG | 8688 |
| CUGGUGCUAGAGGAGGAUG | 8689 | CAUCCUCCUCUAGCACCAG | 8690 |
| GGUGCUAGAGGAGGAUGGA | 8691 | UCCAUCCUCCUCUAGCACC | 8692 |
| GUGCUAGAGGAGGAUGGAA | 8693 | UUCCAUCCUCCUCUAGCAC | 8694 |
| CUGCAGUGGACAGUGAGGA | 8695 | UCCUCACUGUCCACUGCAG | 8696 |
| UGCAGUGGACAGUGAGGAC | 8697 | GUCCUCACUGUCCACUGCA | 8698 |
| GCAGUGGACAGUGAGGACU | 8699 | AGUCCUCACUGUCCACUGC | 8700 |
| CAGUGGACAGUGAGGACUU | 8701 | AAGUCCUCACUGUCCACUG | 8702 |
| AGUGGACAGUGAGGACUUC | 8703 | GAAGUCCUCACUGUCCACU | 8704 |
| GUGGACAGUGAGGACUUCU | 8705 | AGAAGUCCUCACUGUCCAC | 8706 |
| UGGACAGUGAGGACUUCUU | 8707 | AAGAAGUCCUCACUGUCCA | 8708 |
| GGACAGUGAGGACUUCUUC | 8709 | GAAGAAGUCCUCACUGUCC | 8710 |
| AGUGAGGACUUCUUCCAGC | 8711 | GCUGGAAGAAGUCCUCACU | 8712 |
| GUGAGGACUUCUUCCAGCU | 8713 | AGCUGGAAGAAGUCCUCAC | 8714 |
| UGAGGACUUCUUCCAGCUG | 8715 | CAGCUGGAAGAAGUCCUCA | 8716 |
| GAGGACUUCUUCCAGCUGC | 8717 | GCAGCUGGAAGAAGUCCUC | 8718 |
| GUGCCUGAUGGUGUUGCAG | 8719 | CUGCAACACCAUCAGGCAC | 8720 |
| GAUGGUGUUGCAGUCUGGU | 8721 | ACCAGACUGCAACACCAUC | 8722 |
| UGGUGUUGCAGUCUGGUCA | 8723 | UGACCAGACUGCAACACCA | 8724 |
| GGUGUUGCAGUCUGGUCAG | 8725 | CUGACCAGACUGCAACACC | 8726 |
| GUGUUGCAGUCUGGUCAGA | 8727 | UCUGACCAGACUGCAACAC | 8728 |
| UGCAGUCUGGUCAGAGCUG | 8729 | CAGCUCUGACCAGACUGCA | 8730 |
| GCAGUCUGGUCAGAGCUGG | 8731 | CCAGCUCUGACCAGACUGC | 8732 |
| CAGUCUGGUCAGAGCUGGA | 8733 | UCCAGCUCUGACCAGACUG | 8734 |
| AGUCUGGUCAGAGCUGGAG | 8735 | CUCCAGCUCUGACCAGACU | 8736 |
| GUCUGGUCAGAGCUGGAGC | 8737 | GCUCCAGCUCUGACCAGAC | 8738 |
| UCUGGUCAGAGCUGGAGCC | 8739 | GGCUCCAGCUCUGACCAGA | 8740 |
| UGGUCAGAGCUGGAGCCCU | 8741 | AGGGCUCCAGCUCUGACCA | 8742 |
| GGUCAGAGCUGGAGCCCUA | 8743 | UAGGGCUCCAGCUCUGACC | 8744 |
| GUCAGAGCUGGAGCCCUAC | 8745 | GUAGGGCUCCAGCUCUGAC | 8746 |
| CAAGGGUAAGAGGCCUAUA | 8747 | UAUAGGCCUCUUACCCUUG | 8748 |
| AAGGGUAAGAGGCCUAUAC | 8749 | GUAUAGGCCUCUUACCCUU | 8750 |
| AGGGUAAGAGGCCUAUACU | 8751 | AGUAUAGGCCUCUUACCCU | 8752 |
| GGGUAAGAGGCCUAUACUG | 8753 | CAGUAUAGGCCUCUUACCC | 8754 |

TABLE 10-continued

| Sense Sequence | SEQ ID NO: | Antisense Sequence | SEQ ID NO: |
|---|---|---|---|
| GGUAAGAGGCCUAUACUGG | 8755 | CCAGUAUAGGCCUCUUACC | 8756 |
| GUAAGAGGCCUAUACUGGG | 8757 | CCCAGUAUAGGCCUCUUAC | 8758 |
| GGGCUGCUUCCAAUGCCUG | 8759 | CAGGCAUUGGAAGCAGCCC | 8760 |
| GGCUGCUUCCAAUGCCUGU | 8761 | ACAGGCAUUGGAAGCAGCC | 8762 |
| GCUGCUUCCAAUGCCUGUC | 8763 | GACAGGCAUUGGAAGCAGC | 8764 |
| CUGCUUCCAAUGCCUGUCC | 8765 | GGACAGGCAUUGGAAGCAG | 8766 |
| UGCUUCCAAUGCCUGUCCU | 8767 | AGGACAGGCAUUGGAAGCA | 8768 |
| GCUUCCAAUGCCUGUCCUU | 8769 | AAGGACAGGCAUUGGAAGC | 8770 |
| CUUCCAAUGCCUGUCCUUU | 8771 | AAAGGACAGGCAUUGGAAG | 8772 |
| UUCCAAUGCCUGUCCUUUA | 8773 | UAAAGGACAGGCAUUGGAA | 8774 |
| UCCAAUGCCUGUCCUUUAG | 8775 | CUAAAGGACAGGCAUUGGA | 8776 |
| CAAUGCCUGUCCUUUAGAG | 8777 | CUCUAAAGGACAGGCAUUG | 8778 |
| AAUGCCUGUCCUUUAGAGC | 8779 | GCUCUAAAGGACAGGCAUU | 8780 |
| AUGCCUGUCCUUUAGAGCU | 8781 | AGCUCUAAAGGACAGGCAU | 8782 |
| CUUCCUCUCUAGCUUAACC | 8783 | GGUUAAGCUAGAGAGGAAG | 8784 |
| UUCCUCUCUAGCUUAACCC | 8785 | GGGUUAAGCUAGAGAGGAA | 8786 |
| UCUCUAGCUUAACCCUGAU | 8787 | AUCAGGGUUAAGCUAGAGA | 8788 |
| UAGCUUAACCCUGAUCCUG | 8789 | CAGGAUCAGGGUUAAGCUA | 8790 |
| GACCAGGUGCAGGAGGAGU | 8791 | ACUCCUCCUGCACCUGGUC | 8792 |
| ACCAGGUGCAGGAGGAGUU | 8793 | AACUCCUCCUGCACCUGGU | 8794 |
| CCAGGUGCAGGAGGAGUUG | 8795 | CAACUCCUCCUGCACCUGG | 8796 |
| CAGGUGCAGGAGGAGUUGU | 8797 | ACAACUCCUCCUGCACCUG | 8798 |
| AGGUGCAGGAGGAGUUGUG | 8799 | CACAACUCCUCCUGCACCU | 8800 |
| UGCAGGAGGAGUUGUGGAA | 8801 | UUCCACAACUCCUCCUGCA | 8802 |
| GCAGGAGGAGUUGUGGAAU | 8803 | AUUCCACAACUCCUCCUGC | 8804 |
| AGGAGGAGUUGUGGAAUUG | 8805 | CAAUUCCACAACUCCUCCU | 8806 |
| GGAGGAGUUGUGGAAUUGU | 8807 | ACAAUUCCACAACUCCUCC | 8808 |
| GAGGAGUUGUGGAAUUGUC | 8809 | GACAAUUCCACAACUCCUC | 8810 |
| AGGAGUUGUGGAAUUGUCA | 8811 | UGACAAUUCCACAACUCCU | 8812 |
| GGAGUUGUGGAAUUGUCAA | 8813 | UUGACAAUUCCACAACUCC | 8814 |
| GAGUUGUGGAAUUGUCAAG | 8815 | CUUGACAAUUCCACAACUC | 8816 |
| AGUUGUGGAAUUGUCAAGG | 8817 | CCUUGACAAUUCCACAACU | 8818 |
| GUUGUGGAAUUGUCAAGGA | 8819 | UCCUUGACAAUUCCACAAC | 8820 |
| UGGAAUUGUCAAGGAUGUC | 8821 | GACAUCCUUGACAAUUCCA | 8822 |
| GGAAUUGUCAAGGAUGUCA | 8823 | UGACAUCCUUGACAAUUCC | 8824 |
| AGUCCAAGCGAGGGAGGGU | 8825 | ACCCUCCCUCGCUUGGACU | 8826 |
| CAAGCGAGGGAGGGUCUGA | 8827 | UCAGACCCUCCCUCGCUUG | 8828 |
| AAGCGAGGGAGGGUCUGAC | 8829 | GUCAGACCCUCCCUCGCUU | 8830 |
| CUGACCCAGUGCUGAUGGA | 8831 | UCCAUCAGCACUGGGUCAG | 8832 |
| AGAUUAGUGGUGGGUGUCU | 8833 | AGACACCCACCACUAAUCU | 8834 |
| AUUAGUGGUGGGUGUCUGG | 8835 | CCAGACACCCACCACUAAU | 8836 |
| UUAGUGGUGGGUGUCUGGU | 8837 | ACCAGACACCCACCACUAA | 8838 |
| UAGUGGUGGGUGUCUGGUA | 8839 | UACCAGACACCCACCACUA | 8840 |
| AGUGGUGGGUGUCUGGUAU | 8841 | AUACCAGACACCCACCACU | 8842 |
| GUGGUGGGUGUCUGGUAUG | 8843 | CAUACCAGACACCCACCAC | 8844 |
| UGGUGGGUGUCUGGUAUGA | 8845 | UCAUACCAGACACCCACCA | 8846 |
| GGUGGGUGUCUGGUAUGAG | 8847 | CUCAUACCAGACACCCACC | 8848 |
| GUGGGUGUCUGGUAUGAGG | 8849 | CCUCAUACCAGACACCCAC | 8850 |
| UGGGUGUCUGGUAUGAGGA | 8851 | UCCUCAUACCAGACACCCA | 8852 |
| GGGUGUCUGGUAUGAGGAU | 8853 | AUCCUCAUACCAGACACCC | 8854 |
| GGUGUCUGGUAUGAGGAUC | 8855 | GAUCCUCAUACCAGACACC | 8856 |
| GUGUCUGGUAUGAGGAUCU | 8857 | AGAUCCUCAUACCAGACAC | 8858 |
| UGUCUGGUAUGAGGAUCUA | 8859 | UAGAUCCUCAUACCAGACA | 8860 |
| CAAGGGUGUCCUACAGAGU | 8861 | ACUCUGUAGGACACCCUUG | 8862 |
| AAGGGUGUCCUACAGAGUG | 8863 | CACUCUGUAGGACACCCUU | 8864 |
| AGGGUGUCCUACAGAGUGG | 8865 | CCACUCUGUAGGACACCCU | 8866 |
| GGGUGUCCUACAGAGUGGA | 8867 | UCCACUCUGUAGGACACCC | 8868 |
| GGUGUCCUACAGAGUGGAG | 8869 | CUCCACUCUGUAGGACACC | 8870 |
| UCCUACAGAGUGGAGUGCU | 8871 | AGCACUCCACUCUGUAGGA | 8872 |
| AGUGGAGUGCUGUCAUAUG | 8873 | CAUAUGACAGCACUCCACU | 8874 |
| GUGGAGUGCUGUCAUAUGG | 8875 | CCAUAUGACAGCACUCCAC | 8876 |
| UGGAGUGCUGUCAUAUGGC | 8877 | GCCAUAUGACAGCACUCCA | 8878 |
| GGAGUGCUGUCAUAUGGCC | 8879 | GGCCAUAUGACAGCACUCC | 8880 |
| GAGUGCUGUCAUAUGGCCU | 8881 | AGGCCAUAUGACAGCACUC | 8882 |
| AGUGCUGUCAUAUGGCCUG | 8883 | CAGGCCAUAUGACAGCACU | 8884 |
| GUGCUGUCAUAUGGCCUGG | 8885 | CCAGGCCAUAUGACAGCAC | 8886 |
| UGCUGUCAUAUGGCCUGGG | 8887 | CCCAGGCCAUAUGACAGCA | 8888 |
| GCUGUCAUAUGGCCUGGGA | 8889 | UCCCAGGCCAUAUGACAGC | 8890 |
| CUGUCAUAUGGCCUGGGAC | 8891 | GUCCCAGGCCAUAUGACAG | 8892 |
| UGUCAUAUGGCCUGGGACG | 8893 | CGUCCCAGGCCAUAUGACA | 8894 |
| GUCAUAUGGCCUGGGACGG | 8895 | CCGUCCCAGGCCAUAUGAC | 8896 |
| AGAGGCCCAAGCACAGCAA | 8897 | UUGCUGUGCUUGGGCCUCU | 8898 |
| GAGGCCCAAGCACAGCAAG | 8899 | CUUGCUGUGCUUGGGCCUC | 8900 |
| AGGCCCAAGCACAGCAAGG | 8901 | CCUUGCUGUGCUUGGGCCU | 8902 |
| GGCCCAAGCACAGCAAGGA | 8903 | UCCUUGCUGUGCUUGGGCC | 8904 |
| CCAAGCACAGCAAGGACAU | 8905 | AUGUCCUUGCUGUGCUUGG | 8906 |

TABLE 10-continued

| Sense Sequence | SEQ ID NO: | Antisense Sequence | SEQ ID NO: |
|---|---|---|---|
| GCCCGAUUCACCUUUGACG | 8907 | CGUCAAAGGUGAAUCGGGC | 8908 |
| GAUUCACCUUUGACGUGUA | 8909 | UACACGUCAAAGGUGAAUC | 8910 |
| AUUCACCUUUGACGUGUAC | 8911 | GUACACGUCAAAGGUGAAU | 8912 |
| UUGGCAGCCUGAAUGUCAA | 8913 | UUGACAUUCAGGCUGCCAA | 8914 |
| UGGCAGCCUGAAUGUCAAA | 8915 | UUUGACAUUCAGGCUGCCA | 8916 |
| GGCAGCCUGAAUGUCAAAG | 8917 | CUUUGACAUUCAGGCUGCC | 8918 |
| GCAGCCUGAAUGUCAAAGC | 8919 | GCUUUGACAUUCAGGCUGC | 8920 |
| CAGCCUGAAUGUCAAAGCC | 8921 | GGCUUUGACAUUCAGGCUG | 8922 |
| AGCCUGAAUGUCAAAGCCA | 8923 | UGGCUUUGACAUUCAGGCU | 8924 |
| GCCUGAAUGUCAAAGCCAC | 8925 | GUGGCUUUGACAUUCAGGC | 8926 |
| GUCAAAGCCACAUUCUACG | 8927 | CGUAGAAUGUGGCUUUGAC | 8928 |
| UCAAAGCCACAUUCUACGG | 8929 | CCGUAGAAUGUGGCUUUGA | 8930 |
| CAAAGCCACAUUCUACGGG | 8931 | CCCGUAGAAUGUGGCUUUG | 8932 |
| AAAGCCACAUUCUACGGGC | 8933 | GCCCGUAGAAUGUGGCUUU | 8934 |
| GCCACAUUCUACGGGCUCU | 8935 | AGAGCCCGUAGAAUGUGGC | 8936 |
| CCACAUUCUACGGGCUCUA | 8937 | UAGAGCCCGUAGAAUGUGG | 8938 |
| CACAUUCUACGGGCUCUAC | 8939 | GUAGAGCCCGUAGAAUGUG | 8940 |
| UUCUACGGGCUCUACUCUA | 8941 | UAGAGUAGAGCCCGUAGAA | 8942 |
| UCUACGGGCUCUACUCUAU | 8943 | AUAGAGUAGAGCCCGUAGA | 8944 |
| CUACGGGCUCUACUCUAUG | 8945 | CAUAGAGUAGAGCCCGUAG | 8946 |
| CUCUAUGAGUUGUGACUUU | 8947 | AAAGUCACAACUCAUAGAG | 8948 |
| UCUAUGAGUUGUGACUUUC | 8949 | GAAAGUCACAACUCAUAGA | 8950 |
| UGAGUUGUGACUUUCAAGG | 8951 | CCUUGAAAGUCACAACUCA | 8952 |
| GAGUUGUGACUUUCAAGGA | 8953 | UCCUUGAAAGUCACAACUC | 8954 |
| AGUUGUGACUUUCAAGGAC | 8955 | GUCCUUGAAAGUCACAACU | 8956 |
| GUUGUGACUUUCAAGGACU | 8957 | AGUCCUUGAAAGUCACAAC | 8958 |
| GACUUUCAAGGACUUGGCC | 8959 | GGCCAAGUCCUUGAAAGUC | 8960 |
| UUUCAAGGACUUGGCCCAA | 8961 | UUGGGCCAAGUCCUUGAAA | 8962 |
| UUCAAGGACUUGGCCCAAA | 8963 | UUUGGGCCAAGUCCUUGAA | 8964 |
| CCCUACAGUUGGAUAGUCC | 8965 | GGACUAUCCAACUGUAGGG | 8966 |
| CCUACAGUUGGAUAGUCCC | 8967 | GGGACUAUCCAACUGUAGG | 8968 |
| AUUCGUCCUCUUGCACCCA | 8969 | UGGGUGCAAGAGGACGAAU | 8970 |
| UUCGUCCUCUUGCACCCAC | 8971 | GUGGGUGCAAGAGGACGAA | 8972 |
| UCCUCUUGCACCCACCUAC | 8973 | GUAGGUGGGUGCAAGAGGA | 8974 |
| CCUCUUGCACCCACCUACC | 8975 | GGUAGGUGGGUGCAAGAGG | 8976 |
| CUCUUGCACCCACCUACCC | 8977 | GGGUAGGUGGGUGCAAGAG | 8978 |
| CUAGUUAGCUCUUGCUUGU | 8979 | ACAAGCAAGAGCUAACUAG | 8980 |
| UAGUUAGCUCUUGCUUGUG | 8981 | CACAAGCAAGAGCUAACUA | 8982 |
| AGUUAGCUCUUGCUUGUGG | 8983 | CCACAAGCAAGAGCUAACU | 8984 |
| UUAGCUCUUGCUUGUGGAA | 8985 | UUCCACAAGCAAGAGCUAA | 8986 |
| UCCUCAUCUCCCAGCUUGA | 8987 | UCAAGCUGGGAGAUGAGGA | 8988 |
| AUCUCCCAGCUUGAUGGCU | 8989 | AGCCAUCAAGCUGGGAGAU | 8990 |
| UCUCCCAGCUUGAUGGCUU | 8991 | AAGCCAUCAAGCUGGGAGA | 8992 |
| CUCCCAGCUUGAUGGCUUC | 8993 | GAAGCCAUCAAGCUGGGAG | 8994 |
| UCCCAGCUUGAUGGCUUCC | 8995 | GGAAGCCAUCAAGCUGGGA | 8996 |
| CCCAGCUUGAUGGCUUCCU | 8997 | AGGAAGCCAUCAAGCUGGG | 8998 |
| CCAGCUUGAUGGCUUCCUC | 8999 | GAGGAAGCCAUCAAGCUGG | 9000 |
| UGAUGGCUUCCUCCCAAGU | 9001 | ACUUGGGAGGAAGCCAUCA | 9002 |
| GAUGGCUUCCUCCCAAGUU | 9003 | AACUUGGGAGGAAGCCAUC | 9004 |
| GGCUUCCUCCCAAGUUUUC | 9005 | GAAAACUUGGGAGGAAGCC | 9006 |
| CCUCCCAAGUUUUCCAAAU | 9007 | AUUUGGAAAACUUGGGAGG | 9008 |
| CCCAAGUUUUCCAAAUCAU | 9009 | AUGAUUUGGAAAACUUGGG | 9010 |
| CCAAGUUUUCCAAAUCAUC | 9011 | GAUGAUUUGGAAAACUUGG | 9012 |
| CAAGUUUUCCAAAUCAUCU | 9013 | AGAUGAUUUGGAAAACUUG | 9014 |
| AAGUUUUCCAAAUCAUCUG | 9015 | CAGAUGAUUUGGAAAACUU | 9016 |
| GUUUUCCAAAUCAUCUGAU | 9017 | AUCAGAUGAUUUGGAAAAC | 9018 |
| AUCUGAUUUCCUCUUGUCU | 9019 | AGACAAGAGGAAAUCAGAU | 9020 |
| UCUGAUUUCCUCUUGUCUC | 9021 | GAGACAAGAGGAAAUCAGA | 9022 |
| CUGAUUUCCUCUUGUCUCU | 9023 | AGAGACAAGAGGAAAUCAG | 9024 |
| CUCUUGUCUCUGCCAUUCA | 9025 | UGAAUGGCAGAGACAAGAG | 9026 |
| GUUGGACCUCCACACUGCU | 9027 | AGCAGUGUGGAGGUCCAAC | 9028 |
| CCACACUGCUGCAAGGCCU | 9029 | AGGCCUUGCAGCAGUGUGG | 9030 |
| CACACUGCUGCAAGGCCUG | 9031 | CAGGCCUUGCAGCAGUGUG | 9032 |
| ACACUGCUGCAAGGCCUGG | 9033 | CCAGGCCUUGCAGCAGUGU | 9034 |
| UGCAAGGCCUGGGCCAUAU | 9035 | AUAUGGCCCAGGCCUUGCA | 9036 |
| GCAAGGCCUGGGCCAUAUG | 9037 | CAUAUGGCCCAGGCCUUGC | 9038 |
| CAAGGCCUGGGCCAUAUGU | 9039 | ACAUAUGGCCCAGGCCUUG | 9040 |
| AAGGCCUGGGCCAUAUGUU | 9041 | AACAUAUGGCCCAGGCCUU | 9042 |
| AGGCCUGGGCCAUAUGUUG | 9043 | CAACAUAUGGCCCAGGCCU | 9044 |
| GGCCUGGGCCAUAUGUUGC | 9045 | GCAACAUAUGGCCCAGGCC | 9046 |
| GCCUGGGCCAUAUGUUGCU | 9047 | AGCAACAUAUGGCCCAGGC | 9048 |
| CCUGGGCCAUAUGUUGCUG | 9049 | CAGCAACAUAUGGCCCAGG | 9050 |
| GGCCAUAUGUUGCUGGGAA | 9051 | UUCCCAGCAACAUAUGGCC | 9052 |
| CCAUAUGUUGCUGGGAAUU | 9053 | AAUUCCCAGCAACAUAUGG | 9054 |
| GGAAUUCCUCCACCCUUC | 9055 | GAAGGGUGGAGGAAUUCC | 9056 |
| GAAUUCCUCCACCCUUCG | 9057 | CGAAGGGUGGAGGAAUUC | 9058 |

TABLE 10-continued

| Sense Sequence | SEQ ID NO: | Antisense Sequence | SEQ ID NO: |
|---|---|---|---|
| AAUUCCUCCACCCUUCGU | 9059 | ACGAAGGGUGGAGGAAAUU | 9060 |
| AUUCCUCCACCCUUCGUC | 9061 | GACGAAGGGUGGAGGAAAU | 9062 |
| UUCCUCCACCCUUCGUCA | 9063 | UGACGAAGGGUGGAGGAAA | 9064 |
| UCCUCCACCCUUCGUCAU | 9065 | AUGACGAAGGGUGGAGGAA | 9066 |
| CCUCCACCCUUCGUCAUG | 9067 | CAUGACGAAGGGUGGAGGA | 9068 |
| CUCCACCCUUCGUCAUGC | 9069 | GCAUGACGAAGGGUGGAGG | 9070 |
| CUCCACCCUUCGUCAUGCA | 9071 | UGCAUGACGAAGGGUGGAG | 9072 |
| CCUUCGUCAUGCAGUGGAG | 9073 | CUCCACUGCAUGACGAAGG | 9074 |
| CUUCGUCAUGCAGUGGAGG | 9075 | CCUCCACUGCAUGACGAAG | 9076 |
| UUCGUCAUGCAGUGGAGGG | 9077 | CCCUCCACUGCAUGACGAA | 9078 |
| CGCCUCCAUUCCUACUAAG | 9079 | CUUAGUAGGAAUGGAGGCG | 9080 |
| GCCUCCAUUCCUACUAAGG | 9081 | CCUUAGUAGGAAUGGAGGC | 9082 |
| CCUCCAUUCCUACUAAGGG | 9083 | CCCUUAGUAGGAAUGGAGG | 9084 |
| CAGAAUCAUUCCAACCGAC | 9085 | GUCGGUUGGAAUGAUUCUG | 9086 |
| AGAAUCAUUCCAACCGACC | 9087 | GGUCGGUUGGAAUGAUUCU | 9088 |
| GAAUCAUUCCAACCGACCC | 9089 | GGGUCGGUUGGAAUGAUUC | 9090 |
| AAUCAUUCCAACCGACCCA | 9091 | UGGGUCGGUUGGAAUGAUU | 9092 |
| AUCAUUCCAACCGACCCAC | 9093 | GUGGGUCGGUUGGAAUGAU | 9094 |
| UCAUUCCAACCGACCCACU | 9095 | AGUGGGUCGGUUGGAAUGA | 9096 |
| UCCAACCGACCCACUGCAA | 9097 | UUGCAGUGGGUCGGUUGGA | 9098 |
| CCAACCGACCCACUGCAAA | 9099 | UUUGCAGUGGGUCGGUUGG | 9100 |
| CAACCGACCCACUGCAAAG | 9101 | CUUUGCAGUGGGUCGGUUG | 9102 |
| AACCGACCCACUGCAAAGA | 9103 | UCUUUGCAGUGGGUCGGUU | 9104 |
| ACCGACCCACUGCAAAGAC | 9105 | GUCUUUGCAGUGGGUCGGU | 9106 |
| CCGACCCACUGCAAAGACU | 9107 | AGUCUUUGCAGUGGGUCGG | 9108 |
| CGACCCACUGCAAAGACUA | 9109 | UAGUCUUUGCAGUGGGUCG | 9110 |
| GACCCACUGCAAAGACUAU | 9111 | AUAGUCUUUGCAGUGGGUC | 9112 |
| ACCCACUGCAAAGACUAUG | 9113 | CAUAGUCUUUGCAGUGGGU | 9114 |
| ACUGCAAAGACUAUGACAG | 9115 | CUGUCAUAGUCUUUGCAGU | 9116 |
| CUGCAAAGACUAUGACAGC | 9117 | GCUGUCAUAGUCUUUGCAG | 9118 |
| UGCAAAGACUAUGACAGCA | 9119 | UGCUGUCAUAGUCUUUGCA | 9120 |
| GCAAAGACUAUGACAGCAU | 9121 | AUGCUGUCAUAGUCUUUGC | 9122 |
| AAAGACUAUGACAGCAUCA | 9123 | UGAUGCUGUCAUAGUCUUU | 9124 |
| AAGACUAUGACAGCAUCAA | 9125 | UUGAUGCUGUCAUAGUCUU | 9126 |
| AGACUAUGACAGCAUCAAA | 9127 | UUUGAUGCUGUCAUAGUCU | 9128 |
| GACUAUGACAGCAUCAAAU | 9129 | AUUUGAUGCUGUCAUAGUC | 9130 |
| CUAUGACAGCAUCAAAUUU | 9131 | AAAUUUGAUGCUGUCAUAG | 9132 |
| UAUGACAGCAUCAAAUUUC | 9133 | GAAAUUUGAUGCUGUCAUA | 9134 |
| GCAUCAAAUUUCAGGACCU | 9135 | AGGUCCUGAAAUUUGAUGC | 9136 |
| AUCAAAUUUCAGGACCUGC | 9137 | GCAGGUCCUGAAAUUUGAU | 9138 |
| UCAAAUUUCAGGACCUGCA | 9139 | UGCAGGUCCUGAAAUUUGA | 9140 |
| UUCAGGACCUGCAGACAGU | 9141 | ACUGUCUGCAGGUCCUGAA | 9142 |
| UCAGGACCUGCAGACAGUA | 9143 | UACUGUCUGCAGGUCCUGA | 9144 |
| CAGGACCUGCAGACAGUAC | 9145 | GUACUGUCUGCAGGUCCUG | 9146 |
| AGGACCUGCAGACAGUACA | 9147 | UGUACUGUCUGCAGGUCCU | 9148 |
| GGACCUGCAGACAGUACAG | 9149 | CUGUACUGUCUGCAGGUCC | 9150 |
| CUGCAGACAGUACAGGCUA | 9151 | UAGCCUGUACUGUCUGCAG | 9152 |
| GACAGUACAGGCUAGAUAA | 9153 | UUAUCUAGCCUGUACUGUC | 9154 |
| ACAGUACAGGCUAGAUAAC | 9155 | GUUAUCUAGCCUGUACUGU | 9156 |
| CAGUACAGGCUAGAUAACC | 9157 | GGUUAUCUAGCCUGUACUG | 9158 |
| AGUACAGGCUAGAUAACCC | 9159 | GGGUUAUCUAGCCUGUACU | 9160 |
| GUACAGGCUAGAUAACCCA | 9161 | UGGGUUAUCUAGCCUGUAC | 9162 |
| UACAGGCUAGAUAACCCAC | 9163 | GUGGGUUAUCUAGCCUGUA | 9164 |
| GCUAGAUAACCCACCCAAU | 9165 | AUGGGUGGGUUAUCUAGC | 9166 |
| CUAGAUAACCCACCCAAUU | 9167 | AAUUGGGUGGGUUAUCUAG | 9168 |
| AGAUAACCCACCCAAUUUC | 9169 | GAAAUUGGGUGGGUUAUCU | 9170 |
| GAUAACCCACCCAAUUUCC | 9171 | GGAAAUUGGGUGGGUUAUC | 9172 |
| AACCUUUCAGCAUAACGCC | 9173 | GGCGUUAUGCUGAAAGGUU | 9174 |
| ACCUUUCAGCAUAACGCCU | 9175 | AGGCGUUAUGCUGAAAGGU | 9176 |
| CCUUUCAGCAUAACGCCUC | 9177 | GAGGCGUUAUGCUGAAAGG | 9178 |
| CUUUCAGCAUAACGCCUCA | 9179 | UGAGGCGUUAUGCUGAAAG | 9180 |
| UUUCAGCAUAACGCCUCAC | 9181 | GUGAGGCGUUAUGCUGAAA | 9182 |
| UUCAGCAUAACGCCUCACA | 9183 | UGUGAGGCGUUAUGCUGAA | 9184 |
| UCAGCAUAACGCCUCACAU | 9185 | AUGUGAGGCGUUAUGCUGA | 9186 |
| CAGCAUAACGCCUCACAUC | 9187 | GAUGUGAGGCGUUAUGCUG | 9188 |
| AGCAUAACGCCUCACAUCC | 9189 | GGAUGUGAGGCGUUAUGCU | 9190 |
| GCAUAACGCCUCACAUCCC | 9191 | GGGAUGUGAGGCGUUAUGC | 9192 |
| AACGCCUCACAUCCCAAGU | 9193 | ACUUGGGAUGUGAGGCGUU | 9194 |
| ACGCCUCACAUCCCAAGUC | 9195 | GACUUGGGAUGUGAGGCGU | 9196 |
| CGCCUCACAUCCCAAGUCU | 9197 | AGACUUGGGAUGUGAGGCG | 9198 |
| UCACAUCCCAAGUCUAUAC | 9199 | GUAUAGACUUGGGAUGUGA | 9200 |
| CACAUCCCAAGUCUAUACC | 9201 | GGUAUAGACUUGGGAUGUG | 9202 |
| ACAUCCCAAGUCUAUACCC | 9203 | GGGUAUAGACUUGGGAUGU | 9204 |
| CAUCCCAAGUCUAUACCCU | 9205 | AGGGUAUAGACUUGGGAUG | 9206 |
| AAUGCUGUUCUUUCCUAGC | 9207 | GCUAGGAAAGAACAGCAUU | 9208 |
| AUGCUGUUCUUUCCUAGCC | 9209 | GGCUAGGAAAGAACAGCAU | 9210 |

TABLE 10-continued

| Sense Sequence | SEQ ID NO: | Antisense Sequence | SEQ ID NO: |
|---|---|---|---|
| CUGUUCUUUCCUAGCCACC | 9211 | GGUGGCUAGGAAAGAACAG | 9212 |
| UGUUCUUUCCUAGCCACCU | 9213 | AGGUGGCUAGGAAAGAACA | 9214 |
| GCCAAGAUCAAGAUGUCCC | 9215 | GGGACAUCUUGAUCUUGGC | 9216 |
| UCUUGAUCCCAGCCUGACU | 9217 | AGUCAGGCUGGGAUCAAGA | 9218 |
| CUUGAUCCCAGCCUGACUG | 9219 | CAGUCAGGCUGGGAUCAAG | 9220 |
| UUGAUCCCAGCCUGACUGC | 9221 | GCAGUCAGGCUGGGAUCAA | 9222 |
| UGAUCCCAGCCUGACUGCU | 9223 | AGCAGUCAGGCUGGGAUCA | 9224 |
| CUGACUGCUGCUACAUCUA | 9225 | UAGAUGUAGCAGCAGUCAG | 9226 |
| GACUGCUGCUACAUCUAAU | 9227 | AUUAGAUGUAGCAGCAGUC | 9228 |
| ACUGCUGCUACAUCUAAUC | 9229 | GAUUAGAUGUAGCAGCAGU | 9230 |
| CUGCUGCUACAUCUAAUCC | 9231 | GGAUUAGAUGUAGCAGCAG | 9232 |
| UGCUGCUACAUCUAAUCCC | 9233 | GGGAUUAGAUGUAGCAGCA | 9234 |
| CCUACCAAUGCCUCCUGUC | 9235 | GACAGGAGGCAUUGGUAGG | 9236 |
| CUACCAAUGCCUCCUGUCC | 9237 | GGACAGGAGGCAUUGGUAG | 9238 |
| CCAAUGCCUCCUGUCCCUA | 9239 | UAGGGACAGGAGGCAUUGG | 9240 |
| CAAUGCCUCCUGUCCCUAA | 9241 | UUAGGGACAGGAGGCAUUG | 9242 |
| AAUGCCUCCUGUCCCUAAA | 9243 | UUUAGGGACAGGAGGCAUU | 9244 |
| CCCAGCAUACUGAUGACAG | 9245 | CUGUCAUCAGUAUGCUGGG | 9246 |
| CCAGCAUACUGAUGACAGC | 9247 | GCUGUCAUCAGUAUGCUGG | 9248 |
| CAUACUGAUGACAGCCCUC | 9249 | GAGGGCUGUCAUCAGUAUG | 9250 |
| AUACUGAUGACAGCCCUCU | 9251 | AGAGGGCUGUCAUCAGUAU | 9252 |
| UACUGAUGACAGCCCUCUC | 9253 | GAGAGGGCUGUCAUCAGUA | 9254 |
| ACUGAUGACAGCCCUCUCU | 9255 | AGAGAGGGCUGUCAUCAGU | 9256 |
| CUGAUGACAGCCCUCUCUG | 9257 | CAGAGAGGGCUGUCAUCAG | 9258 |
| UGAUGACAGCCCUCUCUGA | 9259 | UCAGAGAGGGCUGUCAUCA | 9260 |
| GAUGACAGCCCUCUCUGAC | 9261 | GUCAGAGAGGGCUGUCAUC | 9262 |
| AUGACAGCCCUCUCUGACU | 9263 | AGUCAGAGAGGGCUGUCAU | 9264 |
| UGACAGCCCUCUCUGACUU | 9265 | AAGUCAGAGAGGGCUGUCA | 9266 |
| GACAGCCCUCUCUGACUUU | 9267 | AAAGUCAGAGAGGGCUGUC | 9268 |
| ACAGCCCUCUCUGACUUUA | 9269 | UAAAGUCAGAGAGGGCUGU | 9270 |
| CAGCCCUCUCUGACUUUAC | 9271 | GUAAAGUCAGAGAGGGCUG | 9272 |
| AGCCCUCUCUGACUUUACC | 9273 | GGUAAAGUCAGAGAGGGCU | 9274 |
| GCCCUCUCUGACUUUACCU | 9275 | AGGUAAAGUCAGAGAGGGC | 9276 |
| CCCUCUCUGACUUUACCUU | 9277 | AAGGUAAAGUCAGAGAGGG | 9278 |
| CCUCUCUGACUUUACCUUG | 9279 | CAAGGUAAAGUCAGAGAGG | 9280 |
| CUCUCUGACUUUACCUUGA | 9281 | UCAAGGUAAAGUCAGAGAG | 9282 |
| AGAUCUGUCUUCAUACCCU | 9283 | AGGGUAUGAAGACAGAUCU | 9284 |
| GAUCUGUCUUCAUACCCUU | 9285 | AAGGGUAUGAAGACAGAUC | 9286 |
| CUGUCUUCAUACCCUUCCC | 9287 | GGGAAGGGUAUGAAGACAG | 9288 |
| UAUUUACCACUAAGACUUC | 9289 | GAAGUCUUAGUGGUAAAUA | 9290 |
| AUUUACCACUAAGACUUCU | 9291 | AGAAGUCUUAGUGGUAAAU | 9292 |
| UUUACCACUAAGACUUCUG | 9293 | CAGAAGUCUUAGUGGUAAA | 9294 |
| UUACCACUAAGACUUCUGA | 9295 | UCAGAAGUCUUAGUGGUAA | 9296 |
| UACCACUAAGACUUCUGAC | 9297 | GUCAGAAGUCUUAGUGGUA | 9298 |
| ACCACUAAGACUUCUGACU | 9299 | AGUCAGAAGUCUUAGUGGU | 9300 |
| ACUUCUGACUCCAAUUUAA | 9301 | UUAAAUUGGAGUCAGAAGU | 9302 |
| CUUCUGACUCCAAUUUAAA | 9303 | UUUAAAUUGGAGUCAGAAG | 9304 |
| ACACCCAGUCCCAGAUCCA | 9305 | UGGAUCUGGGACUGGGUGU | 9306 |
| CACCCAGUCCCAGAUCCAA | 9307 | UUGGAUCUGGGACUGGGUG | 9308 |
| ACCCAGUCCCAGAUCCAAA | 9309 | UUUGGAUCUGGGACUGGGU | 9310 |

In some embodiments, the siRNA molecules targeted to Transcript D comprise or consist of the nucleotide sequences (sense and antisense strands) shown in Table 11.

TABLE 11

| Sense Sequence | SEQ ID NO: | Antisense Sequence | SEQ ID NO: |
|---|---|---|---|
| UUCCAGCUCAGCAGUGUCU | 9311 | AGACACUGCUGAGCUGGAA | 9312 |
| UCCAGCUCAGCAGUGUCUC | 9313 | GAGACACUGCUGAGCUGGA | 9314 |
| CCAGCUCAGCAGUGUCUCG | 9315 | CGAGACACUGCUGAGCUGG | 9316 |
| CAGCUCAGCAGUGUCUCGU | 9317 | ACGAGACACUGCUGAGCUG | 9318 |
| AGCUCAGCAGUGUCUCGUU | 9319 | AACGAGACACUGCUGAGCU | 9320 |
| GCUCAGCAGUGUCUCGUUC | 9321 | GAACGAGACACUGCUGAGC | 9322 |
| CUCAGCAGUGUCUCGUUCC | 9323 | GGAACGAGACACUGCUGAG | 9324 |
| GUAGCAGACCGACAUCCUU | 9325 | AAGGAUGUCGGUCUGCUAC | 9326 |
| UAGCAGACCGACAUCCUUC | 9327 | GAAGGAUGUCGGUCUGCUA | 9328 |
| AGCAGACCGACAUCCUUCU | 9329 | AGAAGGAUGUCGGUCUGCU | 9330 |
| AGACCGACAUCCUUCUGGG | 9331 | CCCAGAAGGAUGUCGGUCU | 9332 |
| GACCGACAUCCUUCUGGGC | 9333 | GCCCAGAAGGAUGUCGGUC | 9334 |
| CCGACAUCCUUCUGGGCCU | 9335 | AGGCCCAGAAGGAUGUCGG | 9336 |
| CGACAUCCUUCUGGGCCUA | 9337 | UAGGCCCAGAAGGAUGUCG | 9338 |
| GACAUCCUUCUGGGCCUAC | 9339 | GUAGGCCCAGAAGGAUGUC | 9340 |
| CUUCUGGGCCUACAGGUGG | 9341 | CCACCUGUAGGCCCAGAAG | 9342 |
| UUCUGGGCCUACAGGUGGG | 9343 | CCCACCUGUAGGCCCAGAA | 9344 |
| UCUGGGCCUACAGGUGGGU | 9345 | ACCCACCUGUAGGCCCAGA | 9346 |
| GGCCUACAGGUGGGUGGAA | 9347 | UUCCACCCACCUGUAGGCC | 9348 |
| CCUACAGGUGGGUGGAAGG | 9349 | CCUUCCACCCACCUGUAGG | 9350 |

TABLE 11-continued

| Sense Sequence | SEQ ID NO: | Antisense Sequence | SEQ ID NO: |
|---|---|---|---|
| CUACAGGUGGGUGGAAGGC | 9351 | GCCUUCCACCCACCUGUAG | 9352 |
| UACAGGUGGGUGGAAGGCU | 9353 | CGCCUUCCACCCACCUGUA | 9354 |
| ACUUCCCUGCAGCCUGCCU | 9355 | AGGCAGGCUGCAGGGAAGU | 9356 |
| CCUGCAGCCUGCCUCUUUU | 9357 | AAAAGAGGCAGGCUGCAGG | 9358 |
| CUGCAGCCUGCCUCUUUUC | 9359 | GAAAAGAGGCAGGCUGCAG | 9360 |
| GCAGCCUGCCUCUUUUCUG | 9361 | CAGAAAAGAGGCAGGCUGC | 9362 |
| CAGCCUGCCUCUUUUCUGC | 9363 | GCAGAAAAGAGGCAGGCUG | 9364 |
| AGCCUGCCUCUUUUCUGCC | 9365 | GGCAGAAAAGAGGCAGGCU | 9366 |
| GCCUCUUUUCUGCCUGGGA | 9367 | UCCCAGGCAGAAAAGAGGC | 9368 |
| CUUUUCUGCCUGGGAGUCC | 9369 | GGACUCCCAGGCAGAAAAG | 9370 |
| UUUUCUGCCUGGGAGUCCU | 9371 | AGGACUCCCAGGCAGAAAA | 9372 |
| UUCUGCCUGGGAGUCCUGA | 9373 | UCAGGACUCCCAGGCAGAA | 9374 |
| UCUGCCUGGGAGUCCUGAC | 9375 | GUCAGGACUCCCAGGCAGA | 9376 |
| UGCCUGGGAGUCCUGACUU | 9377 | AAGUCAGGACUCCCAGGCA | 9378 |
| GCCUGGGAGUCCUGACUUC | 9379 | GAAGUCAGGACUCCCAGGC | 9380 |
| CUGGGAGUCCUGACUUCCA | 9381 | UGGAAGUCAGGACUCCCAG | 9382 |
| UGGGAGUCCUGACUUCCAC | 9383 | GUGGAAGUCAGGACUCCCA | 9384 |
| GGGAGUCCUGACUUCCACG | 9385 | CGUGGAAGUCAGGACUCCC | 9386 |
| GGAGUCCUGACUUCCACGA | 9387 | UCGUGGAAGUCAGGACUCC | 9388 |
| GAGUCCUGACUUCCACGAG | 9389 | CUCGUGGAAGUCAGGACUC | 9390 |
| AGUCCUGACUUCCACGAGG | 9391 | CCUCGUGGAAGUCAGGACU | 9392 |
| CCUGACUUCCACGAGGACC | 9393 | GGUCCUCGUGGAAGUCAGG | 9394 |
| CUGACUUCCACGAGGACCC | 9395 | GGGUCCUCGUGGAAGUCAG | 9396 |
| UGACUUCCACGAGGACCCA | 9397 | UGGGUCCUCGUGGAAGUCA | 9398 |
| GACUUCCACGAGGACCCAG | 9399 | CUGGGUCCUCGUGGAAGUC | 9400 |
| ACUUCCACGAGGACCCAGA | 9401 | UCUGGGUCCUCGUGGAAGU | 9402 |
| CUUCCACGAGGACCCAGAC | 9403 | GUCUGGGUCCUCGUGGAAG | 9404 |
| UUCCACGAGGACCCAGACC | 9405 | GGUCUGGGUCCUCGUGGAA | 9406 |
| CCCUGCUCCCAGUCAGUUG | 9407 | CAACUGACUGGGAGCAGGG | 9408 |
| CCUGCUCCCAGUCAGUUGA | 9409 | UCAACUGACUGGGAGCAGG | 9410 |
| CUGCUCCCAGUCAGUUGAC | 9411 | GUCAACUGACUGGGAGCAG | 9412 |
| UGCUCCCAGUCAGUUGACC | 9413 | GGUCAACUGACUGGGAGCA | 9414 |
| CCCAGUCAGUUGACCUGCC | 9415 | GGCAGGUCAACUGACUGGG | 9416 |
| CCAGUCAGUUGACCUGCCC | 9417 | GGGCAGGUCAACUGACUGG | 9418 |
| GCCUCCUUCCCAGAGCUCA | 9419 | UGAGCUCUGGGAAGGAGGC | 9420 |
| CCUCCUUCCCAGAGCUCAG | 9421 | CUGAGCUCUGGGAAGGAGG | 9422 |
| CUCCUUCCCAGAGCUCAGU | 9423 | ACUGAGCUCUGGGAAGGAG | 9424 |
| UCCUUCCCAGAGCUCAGUG | 9425 | CACUGAGCUCUGGGAAGGA | 9426 |
| CCUUCCCAGAGCUCAGUGG | 9427 | CCACUGAGCUCUGGGAAGG | 9428 |
| UUCCCAGAGCUCAGUGGUA | 9429 | UACCACUGAGCUCUGGGAA | 9430 |
| UCCCAGAGCUCAGUGGUAA | 9431 | UUACCACUGAGCUCUGGGA | 9432 |
| CAGGCUGUCACUAUCUCUA | 9433 | UAGAGAUAGUGACAGCCUG | 9434 |
| AGGCUGUCACUAUCUCUAC | 9435 | GUAGAGAUAGUGACAGCCU | 9436 |
| UCUCUACCACCACUCCUCU | 9437 | AGAGGAGUGGUGGUAGAGA | 9438 |
| CCACCACUCCUCUAGUCUG | 9439 | CAGACUAGAGGAGUGGUGG | 9440 |
| CACCACUCCUCUAGUCUGG | 9441 | CCAGACUAGAGGAGUGGUG | 9442 |
| ACCACUCCUCUAGUCUGGC | 9443 | GCCAGACUAGAGGAGUGGU | 9444 |
| CCACUCCUCUAGUCUGGCC | 9445 | GGCCAGACUAGAGGAGUGG | 9446 |
| CACUCCUCUAGUCUGGCCC | 9447 | GGGCCAGACUAGAGGAGUG | 9448 |
| AUUCUAGCACAUCUGGGCA | 9449 | UGCCCAGAUGUGCUAGAAU | 9450 |
| UUCUAGCACAUCUGGGCAA | 9451 | UUGCCCAGAUGUGCUAGAA | 9452 |
| UCUAGCACAUCUGGGCAAA | 9453 | UUUGCCCAGAUGUGCUAGA | 9454 |
| CUAGCACAUCUGGGCAAAA | 9455 | UUUUGCCCAGAUGUGCUAG | 9456 |
| GGGUGUAAAGGGACGUGCA | 9457 | UGCACGUCCCUUUACACCC | 9458 |
| GGUGUAAAGGGACGUGCAC | 9459 | GUGCACGUCCCUUUACACC | 9460 |
| GUGUAAAGGGACGUGCACA | 9461 | UGUGCACGUCCCUUUACAC | 9462 |
| UGUAAAGGGACGUGCACAG | 9463 | CUGUGCACGUCCCUUUACA | 9464 |
| GUAAAGGGACGUGCACAGA | 9465 | UCUGUGCACGUCCCUUUAC | 9466 |
| UAAAGGGACGUGCACAGAU | 9467 | AUCUGUGCACGUCCCUUUA | 9468 |
| AAAGGGACGUGCACAGAUC | 9469 | GAUCUGUGCACGUCCCUUU | 9470 |
| AAGGGACGUGCACAGAUCU | 9471 | AGAUCUGUGCACGUCCCUU | 9472 |
| AGGGACGUGCACAGAUCUA | 9473 | UAGAUCUGUGCACGUCCCU | 9474 |
| CGUGCACAGAUCUACUUAC | 9475 | GUAAGUAGAUCUGUGCACG | 9476 |
| GUGCACAGAUCUACUUACC | 9477 | GGUAAGUAGAUCUGUGCAC | 9478 |
| UGCACAGAUCUACUUACCA | 9479 | UGGUAAGUAGAUCUGUGCA | 9480 |
| GCACAGAUCUACUUACCAA | 9481 | UUGGUAAGUAGAUCUGUGC | 9482 |
| CACAGAUCUACUUACCAAG | 9483 | CUUGGUAAGUAGAUCUGUG | 9484 |
| ACAGAUCUACUUACCAAGC | 9485 | GCUUGGUAAGUAGAUCUGU | 9486 |
| CAGAUCUACUUACCAAGCU | 9487 | AGCUUGGUAAGUAGAUCUG | 9488 |
| AGAUCUACUUACCAAGCUG | 9489 | CAGCUUGGUAAGUAGAUCU | 9490 |
| AUCUACUUACCAAGCUGGG | 9491 | CCCAGCUUGGUAAGUAGAU | 9492 |
| UCUACUUACCAAGCUGGGA | 9493 | UCCCAGCUUGGUAAGUAGA | 9494 |
| CUUACCAAGCUGGGAGCAA | 9495 | UUGCUCCCAGCUUGGUAAG | 9496 |
| UUACCAAGCUGGGAGCAAG | 9497 | CUUGCUCCCAGCUUGGUAA | 9498 |
| UACCAAGCUGGGAGCAAGC | 9499 | GCUUGCUCCCAGCUUGGUA | 9500 |
| ACCAAGCUGGGAGCAAGCA | 9501 | UGCUUGCUCCCAGCUUGGU | 9502 |

TABLE 11-continued

| Sense Sequence | SEQ ID NO: | Antisense Sequence | SEQ ID NO: |
| --- | --- | --- | --- |
| GCUGGGAGCAAGCAGGAUU | 9503 | AAUCCUGCUUGCUCCCAGC | 9504 |
| CUGGGAGCAAGCAGGAUUG | 9505 | CAAUCCUGCUUGCUCCCAG | 9506 |
| UGGGAGCAAGCAGGAUUGG | 9507 | CCAAUCCUGCUUGCUCCCA | 9508 |
| GGGAGCAAGCAGGAUUGGG | 9509 | CCCAAUCCUGCUUGCUCCC | 9510 |
| AAAGGUUAAGCAGCAGUAG | 9511 | CUACUGCUGCUUAACCUUU | 9512 |
| AAGGUUAAGCAGCAGUAGG | 9513 | CCUACUGCUGCUUAACCUU | 9514 |
| AGGUUAAGCAGCAGUAGGC | 9515 | GCCUACUGCUGCUUAACCU | 9516 |
| GGUGCCUACUCCUGUCCUG | 9517 | CAGGACAGGAGUAGGCACC | 9518 |
| GUGCCUACUCCUGUCCUGU | 9519 | ACAGGACAGGAGUAGGCAC | 9520 |
| UGCCUACUCCUGUCCUGUG | 9521 | CACAGGACAGGAGUAGGCA | 9522 |
| GCCUACUCCUGUCCUGUGC | 9523 | GCACAGGACAGGAGUAGGC | 9524 |
| CCUACUCCUGUCCUGUGCC | 9525 | GGCACAGGACAGGAGUAGG | 9526 |
| CUACUCCUGUCCUGUGCCU | 9527 | AGGCACAGGACAGGAGUAG | 9528 |
| UACUCCUGUCCUGUGCCUA | 9529 | UAGGCACAGGACAGGAGUA | 9530 |
| ACUCCUGUCCUGUGCCUAU | 9531 | AUAGGCACAGGACAGGAGU | 9532 |
| CUCCUGUCCUGUGCCUAUC | 9533 | GAUAGGCACAGGACAGGAG | 9534 |
| UCCUGUCCUGUGCCUAUCA | 9535 | UGAUAGGCACAGGACAGGA | 9536 |
| GUGCCUAUCACAUUUGCAG | 9537 | CUGCAAAUGUGAUAGGCAC | 9538 |
| CUAUCACAUUUGCAGAGGG | 9539 | CCCUCUGCAAAUGUGAUAG | 9540 |
| UAUCACAUUUGCAGAGGGU | 9541 | ACCCUCUGCAAAUGUGAUA | 9542 |
| AUCACAUUUGCAGAGGGUA | 9543 | UACCCUCUGCAAAUGUGAU | 9544 |
| UCACAUUUGCAGAGGGUAA | 9545 | UUACCCUCUGCAAAUGUGA | 9546 |
| CACAUUUGCAGAGGGUAAG | 9547 | CUUACCCUCUGCAAAUGUG | 9548 |
| ACAUUUGCAGAGGGUAAGA | 9549 | UCUUACCCUCUGCAAAUGU | 9550 |

In some embodiments, the siRNA molecules targeted to Transcript E comprise or consist of the nucleotide sequences (sense and antisense strands) shown in Table 12.

TABLE 12

| Sense Sequence | SEQ ID NO: | Antisense Sequence | SEQ ID NO: |
| --- | --- | --- | --- |
| GACCGCCUGCAGAAGGUUG | 9551 | CAACCUUCUGCAGGCGGUC | 9552 |
| ACCGCCUGCAGAAGGUUGA | 9553 | UCAACCUUCUGCAGGCGGU | 9554 |
| CCGCCUGCAGAAGGUUGAC | 9555 | GUCAACCUUCUGCAGGCGG | 9556 |
| CGCCUGCAGAAGGUUGACU | 9557 | AG UCAACCU UCUGCAGGCG | 9558 |
| GCCUGCAGAAGGUUGACUG | 9559 | CAGUCAACCUUCUGCAGGC | 9560 |
| CAGAAGGUUGACUGCGUGG | 9561 | CCACGCAGUCAACCUUCUG | 9562 |
| AGAAGGUUGACUGCGUGGU | 9563 | ACCACGCAGUCAACCUUCU | 9564 |
| GAAGGUUGACUGCGUGGUA | 9565 | UACCACGCAGUCAACCUU | 9566 |
| AAGGUUGACUGCGUGGUAG | 9567 | CUACCACGCAGUCAACCUU | 9568 |
| AGGUUGACUGCGUGGUAGG | 9569 | CCUACCACGCAGUCAACCU | 9570 |
| GGUUGACUGCGUGGUAGGC | 9571 | CCCUACCACGCAGUCAACC | 9572 |
| CCAGAGCAAGCCGAAGGCA | 9573 | UGCCUUCGGCUUGCUCUGG | 9574 |
| CAGAGCAAGCCGAAGGCAA | 9575 | UUGCCUUCGGCUUGCUCUG | 9576 |
| AGAGCAAGCCGAAGGCAAG | 9577 | CUUGCCUUCGGCUUGCUCU | 9578 |
| GAGCAAGCCGAAGGCAAGC | 9579 | GCUUGCCUUCGGCUUGCUC | 9580 |
| AGCAAGCCGAAGGCAAGCA | 9581 | UGCUUGCCUUCGGCUUGCU | 9582 |
| GCAAGCCGAAGGCAAGCAC | 9583 | GUGCUUGCCUUCGGCUUGC | 9584 |
| CAAGCCGAAGGCAAGCACG | 9585 | CGUGCUUGCCUUCGGCUUG | 9586 |
| AAGCCGAAGGCAAGCACGA | 9587 | UCGUGCUUGCCUUCGGCUU | 9588 |
| AGCCGAAGGCAAGCACGAU | 9589 | AUCGUGCUUGCCUUCGGCU | 9590 |
| GCCGAAGGCAAGCACGAUG | 9591 | CAUCGUGCUUGCCUUCGGC | 9592 |
| AAGGCAAGCACGAUGGCGC | 9593 | GCGCCAUCGUGCUUGCCUU | 9594 |
| AGGCAAGCACGAUGGCGCU | 9595 | AGCGCCAUCGUGCUUGCCU | 9596 |
| AAGCACGAUGGCGCUCACC | 9597 | GGUGAGCGCCAUCGUGCUU | 9598 |
| AGCACGAUGGCGCUCACCA | 9599 | UGGUGAGCGCCAUCGUGCU | 9600 |
| CUGUAGCAGCCGAGCAUCA | 9601 | UGAUGCUCGGCUGCUACAG | 9602 |
| AGCCGAGCAUCAGCCCGAA | 9603 | UUCGGGCUGAUGCUCGGCU | 9604 |
| GUCAGAGUCUCCAGGCUCA | 9605 | UGAGCCUGGAGACUCUGAC | 9606 |
| UCAGAGUCUCCAGGCUCAG | 9607 | CUGAGCCUGGAGACUCUGA | 9608 |
| CAGAGUCUCCAGGCUCAGG | 9609 | CCUGAGCCUGGAGACUCUG | 9610 |
| AGAGUCUCCAGGCUCAGGU | 9611 | ACCUGAGCCUGGAGACUCU | 9612 |
| GAGUCUCCAGGCUCAGGUG | 9613 | CACCUGAGCCUGGAGACUC | 9614 |
| AGUCUCCAGGCUCAGGUGG | 9615 | CCACCUGAGCCUGGAGACU | 9616 |
| GGGUGGCACAGCUGGCAUA | 9617 | UAUGCCAGCUGUGCCACCC | 9618 |
| GUGGCACAGCUGGCAUACG | 9619 | CGUAUGCCAGCUGUGCCAC | 9620 |
| UGGCACAGCUGGCAUACGC | 9621 | GCGUAUGCCAGCUGUGCCA | 9622 |
| CUCCACAGGUGGCGGUAGA | 9623 | UCUACCGCCACCUGUGGAG | 9624 |
| UCCACAGGUGGCGGUAGAC | 9625 | GUCUACCGCCACCUGUGGA | 9626 |
| UGAGCAGCACGCUGGCGUA | 9627 | UACGCCAGCGUGCUGCUCA | 9628 |
| AGCAGCACGCUGGCGUACA | 9629 | UGUACGCCAGCGUGCUGCU | 9630 |
| GCAGCACGCUGGCGUACAU | 9631 | AUGUACGCCAGCGUGCUGC | 9632 |
| CAGCACGCUGGCGUACAUG | 9633 | CAUGUACGCCAGCGUGCUG | 9634 |
| AGCACGCUGGCGUACAUGC | 9635 | GCAUGUACGCCAGCGUGCU | 9636 |
| GCACGCUGGCGUACAUGCU | 9637 | AGCAUGUACGCCAGCGUGC | 9638 |
| CACGCUGGCGUACAUGCUG | 9639 | CAGCAUGUACGCCAGCGUG | 9640 |
| ACGCUGGCGUACAUGCUGA | 9641 | UCAGCAUGUACGCCAGCGU | 9642 |

TABLE 12-continued

| Sense Sequence | SEQ ID NO: | Antisense Sequence | SEQ ID NO: |
|---|---|---|---|
| CUGGCGUACAUGCUGAGCG | 9643 | CGCUCAGCAUGUACGCCAG | 9644 |
| UGGCGUACAUGCUGAGCGC | 9645 | GCGCUCAGCAUGUACGCCA | 9646 |
| CGCGCACACGUAGUACACC | 9647 | GGUGUACUACGUGUGCGCG | 9648 |
| GCGCACACGUAGUACACCG | 9649 | CGGUGUACUACGUGUGCGC | 9650 |
| CGCACACGUAGUACACCGC | 9651 | GCGGUGUACUACGUGUGCG | 9652 |
| GCACACGUAGUACACCGCC | 9653 | GGCGGUGUACUACGUGUGC | 9654 |
| CACACGUAGUACACCGCCU | 9655 | AGGCGGUGUACUACGUGUG | 9656 |
| ACACGUAGUACACCGCCUU | 9657 | AAGGCGGUGUACUACGUGU | 9658 |
| CACGUAGUACACCGCCUUG | 9659 | CAAGGCGGUGUACUACGUG | 9660 |
| UAGUACACCGCCUUGCAGC | 9661 | GCUGCAAGGCGGUGUACUA | 9662 |

In some embodiments, the siRNA molecules targeted to Transcript F comprise or consist of the nucleotide sequences (sense and antisense strands) shown in Table 13.

| Sense Sequence | SEQ ID NO: | Antisense Sequence | SEQ ID NO: |
|---|---|---|---|
| AGUGGACAGUGAGGACUUC | 9663 | GAAGUCCUCACUGUCCACU | 9664 |
| GUGGACAGUGAGGACUUCU | 9665 | AGAAGUCCUCACUGUCCAC | 9666 |
| UGGACAGUGAGGACUUCUU | 9667 | AAGAAGUCCUCACUGUCCA | 9668 |
| GGACAGUGAGGACUUCUUC | 9669 | GAAGAAGUCCUCACUGUCC | 9670 |
| AGUGAGGACUUCUUCCAGC | 9671 | GCUGGAAGAAGUCCUCACU | 9672 |
| GUGAGGACUUCUUCCAGCU | 9673 | AGCUGGAAGAAGUCCUCAC | 9674 |
| UGAGGACUUCUUCCAGCUG | 9675 | CAGCUGGAAGAAGUCCUCA | 9676 |
| GAGGACUUCUUCCAGCUGC | 9677 | GCAGCUGGAAGAAGUCCUC | 9678 |
| GUGCCUGAUGGUGUUGCAG | 9679 | CUGCAACACCAUCAGGCAC | 9680 |
| GAUGGUGUUGCAGUCUGGU | 9681 | ACCAGACUGCAACACCAUC | 9682 |
| UGGUGUUGCAGUCUGGUCA | 9683 | UGACCAGACUGCAACACCA | 9684 |
| GGUGUUGCAGUCUGGUCAG | 9685 | CUGACCAGACUGCAACACC | 9686 |
| GUGUUGCAGUCUGGUCAGA | 9687 | UCUGACCAGACUGCAACAC | 9688 |
| UGCAGUCUGGUCAGAGCUG | 9689 | CAGCUCUGACCAGACUGCA | 9690 |
| GCAGUCUGGUCAGAGCUGG | 9691 | CCAGCUCUGACCAGACUGC | 9692 |
| CAGUCUGGUCAGAGCUGGA | 9693 | UCCAGCUCUGACCAGACUG | 9694 |
| AGUCUGGUCAGAGCUGGAG | 9695 | CUCCAGCUCUGACCAGACU | 9696 |
| GUCUGGUCAGAGCUGGAGC | 9697 | GCUCCAGCUCUGACCAGAC | 9698 |
| UCUGGUCAGAGCUGGAGCC | 9699 | GGCUCCAGCUCUGACCAGA | 9700 |
| UGGUCAGAGCUGGAGCCCU | 9701 | AGGGCUCCAGCUCUGACCA | 9702 |
| GGUCAGAGCUGGAGCCCUA | 9703 | UAGGGCUCCAGCUCUGACC | 9704 |
| GUCAGAGCUGGAGCCCUAC | 9705 | GUAGGGCUCCAGCUCUGAC | 9706 |
| CAAGGGUAAGAGGCCUAUA | 9707 | UAUAGGCCUCUUACCCUUG | 9708 |
| AAGGGUAAGAGGCCUAUAC | 9709 | GUAUAGGCCUCUUACCCUU | 9710 |
| AGGGUAAGAGGCCUAUACU | 9711 | AGUAUAGGCCUCUUACCCU | 9712 |
| GGGUAAGAGGCCUAUACUG | 9713 | CAGUAUAGGCCUCUUACCC | 9714 |
| GGUAAGAGGCCUAUACUGG | 9715 | CCAGUAUAGGCCUCUUACC | 9716 |
| GUAAGAGGCCUAUACUGGG | 9717 | CCCAGUAUAGGCCUCUUAC | 9718 |
| GGGCUGCUUCCAAUGCCUG | 9719 | CAGGCAUUGGAAGCAGCCC | 9720 |
| GGCUGCUUCCAAUGCCUGU | 9721 | ACAGGCAUUGGAAGCAGCC | 9722 |
| GCUGCUUCCAAUGCCUGUC | 9723 | GACAGGCAUUGGAAGCAGC | 9724 |
| CUGCUUCCAAUGCCUGUCC | 9725 | GGACAGGCAUUGGAAGCAG | 9726 |
| UGCUUCCAAUGCCUGUCCU | 9727 | AGGACAGGCAUUGGAAGCA | 9728 |
| GCUUCCAAUGCCUGUCCUU | 9729 | AAGGACAGGCAUUGGAAGC | 9730 |
| CUUCCAAUGCCUGUCCUUU | 9731 | AAAGGACAGGCAUUGGAAG | 9732 |
| UUCCAAUGCCUGUCCUUUA | 9733 | UAAAGGACAGGCAUUGGAA | 9734 |
| UCCAAUGCCUGUCCUUUAG | 9735 | CUAAAGGACAGGCAUUGGA | 9736 |
| CAAUGCCUGUCCUUUAGAG | 9737 | CUCUAAAGGACAGGCAUUG | 9738 |
| AAUGCCUGUCCUUUAGAGC | 9739 | GCUCUAAAGGACAGGCAUU | 9740 |
| AUGCCUGUCCUUUAGAGCU | 9741 | AGCUCUAAAGGACAGGCAU | 9742 |
| CUUCCUCUCUAGCUUAACC | 9743 | GGUUAAGCUAGAGAGGAAG | 9744 |
| UUCCUCUCUAGCUUAACCC | 9745 | GGGUUAAGCUAGAGAGGAA | 9746 |
| UCUCUAGCUUAACCCUGAU | 9747 | AUCAGGGUUAAGCUAGAGA | 9748 |
| UAGCUUAACCCUGAUCCUG | 9749 | CAGGAUCAGGGUUAAGCUA | 9750 |
| GACCAGGUGCAGGAGGAGU | 9751 | ACUCCUCCUGCACCUGGUC | 9752 |
| ACCAGGUGCAGGAGGAGUU | 9753 | AACUCCUCCUGCACCUGGU | 9754 |
| CCAGGUGCAGGAGGAGUUG | 9755 | CAACUCCUCCUGCACCUGG | 9756 |
| CAGGUGCAGGAGGAGUUGU | 9757 | ACAACUCCUCCUGCACCUG | 9758 |
| AGGUGCAGGAGGAGUUGUG | 9759 | CACAACUCCUCCUGCACCU | 9760 |
| UGCAGGAGGAGUUGUGGAA | 9761 | UUCCACAACUCCUCCUGCA | 9762 |
| GCAGGAGGAGUUGUGGAAU | 9763 | AUUCCACAACUCCUCCUGC | 9764 |
| AGGAGGAGUUGUGGAAUUG | 9765 | CAAUUCCACAACUCCUCCU | 9766 |
| GGAGGAGUUGUGGAAUUGU | 9767 | ACAAUUCCACAACUCCUCC | 9768 |
| GAGGAGUUGUGGAAUUGUC | 9769 | GACAAUUCCACAACUCCUC | 9770 |
| AGGAGUUGUGGAAUUGUCA | 9771 | UGACAAUUCCACAACUCCU | 9772 |
| GGAGUUGUGGAAUUGUCAA | 9773 | UUGACAAUUCCACAACUCC | 9774 |
| GAGUUGUGGAAUUGUCAAG | 9775 | CUUGACAAUUCCACAACUC | 9776 |
| AGUUGUGGAAUUGUCAAGG | 9777 | CCUUGACAAUUCCACAACU | 9778 |
| GUUGUGGAAUUGUCAAGGA | 9779 | UCCUUGACAAUUCCACAAC | 9780 |
| UGGAAUUGUCAAGGAUGUC | 9781 | GACAUCCUUGACAAUUCCA | 9782 |

| Sense Sequence | SEQ ID NO: | Antisense Sequence | SEQ ID NO: |
|---|---|---|---|
| GGAAUUGUCAAGGAUGUCA | 9783 | UGACAUCCUUGACAAUUCC | 9784 |
| AGUCCAAGCGAGGGAGGGU | 9785 | ACCCUCCCUCGCUUGGACU | 9786 |
| CAAGCGAGGGAGGGUCUGA | 9787 | UCAGACCCUCCCUCGCUUG | 9788 |
| AAGCGAGGGAGGGUCUGAC | 9789 | GUCAGACCCUCCCUCGCUU | 9790 |
| CUGACCCAGUGCUGAUGGA | 9791 | UCCAUCAGCACUGGGUCAG | 9792 |
| AGAUUAGUGGUGGGUGUCU | 9793 | AGACACCCACCACUAAUCU | 9794 |
| AUUAGUGGUGGGUGUCUGG | 9795 | CCAGACACCCACCACUAAU | 9796 |
| UUAGUGGUGGGUGUCUGGU | 9797 | ACCAGACACCCACCACUAA | 9798 |
| UAGUGGUGGGUGUCUGGUA | 9799 | UACCAGACACCCACCACUA | 9800 |
| AGUGGUGGGUGUCUGGUAU | 9801 | AUACCAGACACCCACCACU | 9802 |
| GUGGUGGGUGUCUGGUAUG | 9803 | CAUACCAGACACCCACCAC | 9804 |
| UGGUGGGUGUCUGGUAUGA | 9805 | UCAUACCAGACACCCACCA | 9806 |
| GGUGGGUGUCUGGUAUGAG | 9807 | CUCAUACCAGACACCCACC | 9808 |
| GUGGGUGUCUGGUAUGAGG | 9809 | CCUCAUACCAGACACCCAC | 9810 |
| UGGGUGUCUGGUAUGAGGA | 9811 | UCCUCAUACCAGACACCCA | 9812 |
| GGGUGUCUGGUAUGAGGAU | 9813 | AUCCUCAUACCAGACACCC | 9814 |
| GGUGUCUGGUAUGAGGAUC | 9815 | GAUCCUCAUACCAGACACC | 9816 |
| GUGUCUGGUAUGAGGAUCU | 9817 | AGAUCCUCAUACCAGACAC | 9818 |
| UGUCUGGUAUGAGGAUCUA | 9819 | UAGAUCCUCAUACCAGACA | 9820 |
| CAAGGGUGUCCUACAGAGU | 9821 | ACUCUGUAGGACACCCUUG | 9822 |
| AAGGGUGUCCUACAGAGUG | 9823 | CACUCUGUAGGACACCCUU | 9824 |
| AGGGUGUCCUACAGAGUGG | 9825 | CCACUCUGUAGGACACCCU | 9826 |
| GGGUGUCCUACAGAGUGGA | 9827 | UCCACUCUGUAGGACACCC | 9828 |
| GGUGUCCUACAGAGUGGAG | 9829 | CUCCACUCUGUAGGACACC | 9830 |
| UCCUACAGAGUGGAGUGCU | 9831 | AGCACUCCACUCUGUAGGA | 9832 |
| AGUGGAGUGCUGUCAUAUG | 9833 | CAUAUGACAGCACUCCACU | 9834 |
| GUGGAGUGCUGUCAUAUGG | 9835 | CCAUAUGACAGCACUCCAC | 9836 |
| UGGAGUGCUGUCAUAUGGC | 9837 | GCCAUAUGACAGCACUCCA | 9838 |
| GGAGUGCUGUCAUAUGGCC | 9839 | GGCCAUAUGACAGCACUCC | 9840 |
| GAGUGCUGUCAUAUGGCCU | 9841 | AGGCCAUAUGACAGCACUC | 9842 |
| AGUGCUGUCAUAUGGCCUG | 9843 | CAGGCCAUAUGACAGCACU | 9844 |
| GUGCUGUCAUAUGGCCUGG | 9845 | CCAGGCCAUAUGACAGCAC | 9846 |
| UGCUGUCAUAUGGCCUGGG | 9847 | CCCAGGCCAUAUGACAGCA | 9848 |
| GCUGUCAUAUGGCCUGGGA | 9849 | UCCCAGGCCAUAUGACAGC | 9850 |
| CUGUCAUAUGGCCUGGGAC | 9851 | GUCCCAGGCCAUAUGACAG | 9852 |
| UGUCAUAUGGCCUGGGACG | 9853 | CGUCCCAGGCCAUAUGACA | 9854 |
| GUCAUAUGGCCUGGGACGG | 9855 | CCGUCCCAGGCCAUAUGAC | 9856 |
| AGAGGCCCAAGCACAGCAA | 9857 | UUGCUGUGCUUGGGCCUCU | 9858 |
| GAGGCCCAAGCACAGCAAG | 9859 | CUUGCUGUGCUUGGGCCUC | 9860 |
| AGGCCCAAGCACAGCAAGG | 9861 | CCUUGCUGUGCUUGGGCCU | 9862 |
| GGCCCAAGCACAGCAAGGA | 9863 | UCCUUGCUGUGCUUGGGCC | 9864 |
| CCAAGCACAGCAAGGACAU | 9865 | AUGUCCUUGCUGUGCUUGG | 9866 |
| GCCCGAUUCACCUUUGACG | 9867 | CGUCAAAGGUGAAUCGGGC | 9868 |
| GAUUCACCUUUGACGUGUA | 9869 | UACACGUCAAAGGUGAAUC | 9870 |
| AUUCACCUUUGACGUGUAC | 9871 | GUACACGUCAAAGGUGAAU | 9872 |
| UUGGCAGCCUGAAUGUCAA | 9873 | UUGACAUUCAGGCUGCCAA | 9874 |
| UGGCAGCCUGAAUGUCAAA | 9875 | UUUGACAUUCAGGCUGCCA | 9876 |
| GGCAGCCUGAAUGUCAAAG | 9877 | CUUUGACAUUCAGGCUGCC | 9878 |
| GCAGCCUGAAUGUCAAAGC | 9879 | GCUUUGACAUUCAGGCUGC | 9880 |
| CAGCCUGAAUGUCAAAGCC | 9881 | GGCUUUGACAUUCAGGCUG | 9882 |
| AGCCUGAAUGUCAAAGCCA | 9883 | UGGCUUUGACAUUCAGGCU | 9884 |
| GCCUGAAUGUCAAAGCCAC | 9885 | GUGGCUUUGACAUUCAGGC | 9886 |
| GUCAAAGCCACAUUCUACG | 9887 | CGUAGAAUGUGGCUUUGAC | 9888 |
| UCAAAGCCACAUUCUACGG | 9889 | CCGUAGAAUGUGGCUUUGA | 9890 |
| CAAAGCCACAUUCUACGGG | 9891 | CCCGUAGAAUGUGGCUUUG | 9892 |
| AAAGCCACAUUCUACGGGC | 9893 | GCCCGUAGAAUGUGGCUUU | 9894 |
| GCCACAUUCUACGGGCUCU | 9895 | AGAGCCCGUAGAAUGUGGC | 9896 |
| CCACAUUCUACGGGCUCUA | 9897 | UAGAGCCCGUAGAAUGUGG | 9898 |
| CACAUUCUACGGGCUCUAC | 9899 | GUAGAGCCCGUAGAAUGUG | 9900 |
| UUCUACGGGCUCUACUCUA | 9901 | UAGAGUAGAGCCCGUAGAA | 9902 |
| UCUACGGGCUCUACUCUAU | 9903 | AUAGAGUAGAGCCCGUAGA | 9904 |
| CUACGGGCUCUACUCUAUG | 9905 | CAUAGAGUAGAGCCCGUAG | 9906 |
| CUCUAUGAGUUGUGACUUU | 9907 | AAAGUCACAACUCAUAGAG | 9908 |
| UCUAUGAGUUGUGACUUUC | 9909 | GAAAGUCACAACUCAUAGA | 9910 |
| UGAGUUGUGACUUUCAAGG | 9911 | CCUUGAAAGUCACAACUCA | 9912 |
| GAGUUGUGACUUUCAAGGA | 9913 | UCCUUGAAAGUCACAACUC | 9914 |
| AGUUGUGACUUUCAAGGAC | 9915 | GUCCUUGAAAGUCACAACU | 9916 |
| GUUGUGACUUUCAAGGACU | 9917 | AGUCCUUGAAAGUCACAAC | 9918 |
| GACUUUCAAGGACUUGGCC | 9919 | GGCCAAGUCCUUGAAAGUC | 9920 |
| UUUCAAGGACUUGGCCCAA | 9921 | UUGGGCCAAGUCCUUGAAA | 9922 |
| UUCAAGGACUUGGCCCAAA | 9923 | UUUGGGCCAAGUCCUUGAA | 9924 |
| CCCUACAGUUGGAUAGUCC | 9925 | GGACUAUCCAACUGUAGGG | 9926 |
| CCUACAGUUGGAUAGUCCC | 9927 | GGGACUAUCCAACUGUAGG | 9928 |
| AUUCGUCCUCUUGCACCCA | 9929 | UGGGUGCAAGAGGACGAAU | 9930 |
| UUCGUCCUCUUGCACCCAC | 9931 | GUGGGUGCAAGAGGACGAA | 9932 |

| Sense Sequence | SEQ ID NO: | Antisense Sequence | SEQ ID NO: |
|---|---|---|---|
| UCCUCUUGCACCCACCUAC | 9933 | GUAGGUGGGUGCAAGAGGA | 9934 |
| CCUCUUGCACCCACCUACC | 9935 | GGUAGGUGGGUGCAAGAGG | 9936 |
| CUCUUGCACCCACCUACCC | 9937 | GGGUAGGUGGGUGCAAGAG | 9938 |
| CUAGUUAGCUCUUGCUUGU | 9939 | ACAAGCAAGAGCUAACUAG | 9940 |
| UAGUUAGCUCUUGCUUGUG | 9941 | CACAAGCAAGAGCUAACUA | 9942 |
| AGUUAGCUCUUGCUUGUGG | 9943 | CCACAAGCAAGAGCUAACU | 9944 |
| UUAGCUCUUGCUUGUGGAA | 9945 | UUCCACAAGCAAGAGCUAA | 9946 |
| UCCUCAUCUCCCAGCUUGA | 9947 | UCAAGCUGGGAGAUGAGGA | 9948 |
| AUCUCCCAGCUUGAUGGCU | 9949 | AGCCAUCAAGCUGGGAGAU | 9950 |
| UCUCCCAGCUUGAUGGCUU | 9951 | AAGCCAUCAAGCUGGGAGA | 9952 |
| CUCCCAGCUUGAUGGCUUC | 9953 | GAAGCCAUCAAGCUGGGAG | 9954 |
| UCCCAGCUUGAUGGCUUCC | 9955 | GGAAGCCAUCAAGCUGGGA | 9956 |
| CCCAGCUUGAUGGCUUCCU | 9957 | AGGAAGCCAUCAAGCUGGG | 9958 |
| CCAGCUUGAUGGCUUCCUC | 9959 | GAGGAAGCCAUCAAGCUGG | 9960 |
| UGAUGGCUUCCUCCCAAGU | 9961 | ACUUGGGAGGAAGCCAUCA | 9962 |
| GAUGGCUUCCUCCCAAGUU | 9963 | AACUUGGGAGGAAGCCAUC | 9964 |
| GGCUUCCUCCCAAGUUUUC | 9965 | GAAAACUUGGGAGGAAGCC | 9966 |
| CCUCCCAAGUUUUCCAAAU | 9967 | AUUUGGAAAACUUGGGAGG | 9968 |
| CCCAAGUUUUCCAAAUCAU | 9969 | AUGAUUUGGAAAACUUGGG | 9970 |
| CCAAGUUUUCCAAAUCAUC | 9971 | GAUGAUUUGGAAAACUUGG | 9972 |
| CAAGUUUUCCAAAUCAUCU | 9973 | AGAUGAUUUGGAAAACUUG | 9974 |
| AAGUUUUCCAAAUCAUCUG | 9975 | CAGAUGAUUUGGAAAACUU | 9976 |
| GUUUUCCAAAUCAUCUGAU | 9977 | AUCAGAUGAUUUGGAAAAC | 9978 |
| AUCUGAUUUCCUCUUGUCU | 9979 | AGACAAGAGGAAAUCAGAU | 9980 |
| UCUGAUUUCCUCUUGUCUC | 9981 | GAGACAAGAGGAAAUCAGA | 9982 |
| CUGAUUUCCUCUUGUCUCU | 9983 | AGAGACAAGAGGAAAUCAG | 9984 |
| CUCUUGUCUCUGCCAUUCA | 9985 | UGAAUGGCAGAGACAAGAG | 9986 |
| GUUGGACCUCCACACUGCU | 9987 | AGCAGUGUGGAGGUCCAAC | 9988 |
| CCACACUGCUGCAAGGCCU | 9989 | AGGCCUUGCAGCAGUGUGG | 9990 |
| CACACUGCUGCAAGGCCUG | 9991 | CAGGCCUUGCAGCAGUGUG | 9992 |
| ACACUGCUGCAAGGCCUGG | 9993 | CCAGGCCUUGCAGCAGUGU | 9994 |
| UGCAAGGCCUGGGCCAUAU | 9995 | AUAUGGCCCAGGCCUUGCA | 9996 |
| GCAAGGCCUGGGCCAUAUG | 9997 | CAUAUGGCCCAGGCCUUGC | 9998 |
| CAAGGCCUGGGCCAUAUGU | 9999 | ACAUAUGGCCCAGGCCUUG | 10000 |
| AAGGCCUGGGCCAUAUGUU | 10001 | AACAUAUGGCCCAGGCCUU | 10002 |
| AGGCCUGGGCCAUAUGUUG | 10003 | CAACAUAUGGCCCAGGCCU | 10004 |
| GGCCUGGGCCAUAUGUUGC | 10005 | GCAACAUAUGGCCCAGGCC | 10006 |
| GCCUGGGCCAUAUGUUGCU | 10007 | AGCAACAUAUGGCCCAGGC | 10008 |
| CCUGGGCCAUAUGUUGCUG | 10009 | CAGCAACAUAUGGCCCAGG | 10010 |
| GGCCAUAUGUUGCUGGGAA | 10011 | UUCCCAGCAACAUAUGGCC | 10012 |
| CCAUAUGUUGCUGGGAAUU | 10013 | AAUUCCCAGCAACAUAUGG | 10014 |
| GGAAUUCCUCCACCCUUC | 10015 | GAAGGGUGGAGGAAAUUCC | 10016 |
| GAAUUCCUCCACCCUUCG | 10017 | CGAAGGGUGGAGGAAAUUC | 10018 |
| AAUUCCUCCACCCUUCGU | 10019 | ACGAAGGGUGGAGGAAAUU | 10020 |
| AUUCCUCCACCCUUCGUC | 10021 | GACGAAGGGUGGAGGAAAU | 10022 |
| UUUCCUCCACCCUUCGUCA | 10023 | UGACGAAGGGUGGAGGAAA | 10024 |
| UUCCUCCACCCUUCGUCAU | 10025 | AUGACGAAGGGUGGAGGAA | 10026 |
| UCCUCCACCCUUCGUCAUG | 10027 | CAUGACGAAGGGUGGAGGA | 10028 |
| CCUCCACCCUUCGUCAUGC | 10029 | GCAUGACGAAGGGUGGAGG | 10030 |
| CUCCACCCUUCGUCAUGCA | 10031 | UGCAUGACGAAGGGUGGAG | 10032 |
| CCUUCGUCAUGCAGUGGAG | 10033 | CUCCACUGCAUGACGAAGG | 10034 |
| CUUCGUCAUGCAGUGGAGG | 10035 | CCUCCACUGCAUGACGAAG | 10036 |
| UUCGUCAUGCAGUGGAGGG | 10037 | CCCUCCACUGCAUGACGAA | 10038 |
| CGCCUCCAUUCCUACUAAG | 10039 | CUUAGUAGGAAUGGAGGCG | 10040 |
| GCCUCCAUUCCUACUAAGG | 10041 | CCUUAGUAGGAAUGGAGGC | 10042 |
| CCUCCAUUCCUACUAAGGG | 10043 | CCCUUAGUAGGAAUGGAGG | 10044 |

In some embodiments, the PNPLA3 inhibitor comprises an inhibitory nucleic acid molecule. Examples of inhibitory nucleic acid molecules include, but are not limited to, antisense nucleic acid molecules, siRNAs, and shRNAs. Such inhibitory nucleic acid molecules can be designed to target any region of a PNPLA3 mRNA. In some embodiments, the antisense RNA, siRNA, or shRNA hybridizes to a sequence within a PNPLA3 genomic nucleic acid molecule or mRNA molecule and decreases expression of the PNPLA3 polypeptide in a cell in the subject. In some embodiments, the PNPLA3 inhibitor comprises an antisense RNA that hybridizes to a PNPLA3 genomic nucleic acid molecule or mRNA molecule and decreases expression of the PNPLA3 polypeptide in a cell in the subject. In some embodiments, the PNPLA3 inhibitor comprises an siRNA that hybridizes to a PNPLA3 genomic nucleic acid molecule or mRNA molecule and decreases expression of the PNPLA3 polypeptide in a cell in the subject. In some embodiments, the PNPLA3 inhibitor comprises an shRNA that hybridizes to a PNPLA3 genomic nucleic acid molecule or mRNA molecule and decreases expression of the PNPLA3 polypeptide in a cell in the subject.

The inhibitory nucleic acid molecules described herein can be targeted to various PNPLA3 transcripts. For example, the inhibitory nucleic acid molecules described herein can be targeted to the PNPLA3 transcripts (derived from chromosome 22; Ensembl Gene ID=ENSG00000100344.11; hgnc symbol=PNPLA3).

In some embodiments, the HSD17B13 inhibitor comprises an inhibitory nucleic acid molecule. Examples of inhibitory nucleic acid molecules include, but are not limited to, antisense nucleic acid molecules, siRNAs, and shRNAs. Such inhibitory nucleic acid molecules can be designed to target any region of a HSD17B13 mRNA. In some embodiments, the antisense RNA, siRNA, or shRNA hybridizes to a sequence within a HSD17B13 genomic nucleic acid molecule or mRNA molecule and decreases expression of the HSD17B13 polypeptide in a cell in the subject. In some embodiments, the HSD17B13 inhibitor comprises an antisense RNA that hybridizes to a HSD17B13 genomic nucleic acid molecule or mRNA molecule and decreases expression of the HSD17B13 polypeptide in a cell in the subject. In some embodiments, the HSD17B13 inhibitor comprises an siRNA that hybridizes to a HSD17B13 genomic nucleic acid molecule or mRNA molecule and decreases expression of the HSD17B13 polypeptide in a cell in the subject. In some embodiments, the HSD17B13 inhibitor comprises an shRNA that hybridizes to a HSD17B13 genomic nucleic acid molecule or mRNA molecule and decreases expression of the HSD17B13 polypeptide in a cell in the subject.

The inhibitory nucleic acid molecules described herein can be targeted to various HSD17B13 transcripts. For example, the inhibitory nucleic acid molecules described herein can be targeted to the HSD17B13 transcripts (derived from chromosome 4; Ensembl Gene ID=ENSG00000170509.8; hgnc symbol=HSD17B13).

The inhibitory nucleic acid molecules disclosed herein can comprise RNA, DNA, or both RNA and DNA. The inhibitory nucleic acid molecules can also be linked or fused to a heterologous nucleic acid sequence, such as in a vector, or a heterologous label. For example, the inhibitory nucleic acid molecules disclosed herein can be within a vector or as an exogenous donor sequence comprising the inhibitory nucleic acid molecule and a heterologous nucleic acid sequence. The inhibitory nucleic acid molecules can also be linked or fused to a heterologous label. The label can be directly detectable (such as, for example, fluorophore) or indirectly detectable (such as, for example, hapten, enzyme, or fluorophore quencher). Such labels can be detectable by spectroscopic, photochemical, biochemical, immunochemical, or chemical means. Such labels include, for example, radiolabels, pigments, dyes, chromogens, spin labels, and fluorescent labels. The label can also be, for example, a chemiluminescent substance; a metal-containing substance; or an enzyme, where there occurs an enzyme-dependent secondary generation of signal. The term "label" can also refer to a "tag" or hapten that can bind selectively to a conjugated molecule such that the conjugated molecule, when added subsequently along with a substrate, is used to generate a detectable signal. For example, biotin can be used as a tag along with an avidin or streptavidin conjugate of horseradish peroxidate (HRP) to bind to the tag, and examined using a calorimetric substrate (such as, for example, tetramethylbenzidine (TMB)) or a fluorogenic substrate to detect the presence of HRP. Exemplary labels that can be used as tags to facilitate purification include, but are not limited to, myc, HA, FLAG or 3×FLAG, 6×His (SEQ ID NO:10045) or polyhistidine, glutathione-S-transferase (GST), maltose binding protein, an epitope tag, or the Fc portion of immunoglobulin. Numerous labels include, for example, particles, fluorophores, haptens, enzymes and their calorimetric, fluorogenic and chemiluminescent substrates and other labels.

The inhibitory nucleic acid molecules disclosed herein can comprise, for example, nucleotides or non-natural or modified nucleotides, such as nucleotide analogs or nucleotide substitutes. Such nucleotides include a nucleotide that contains a modified base, sugar, or phosphate group, or that incorporates a non-natural moiety in its structure. Examples of non-natural nucleotides include, but are not limited to, dideoxynucleotides, biotinylated, aminated, deaminated, alkylated, benzylated, and fluorophor-labeled nucleotides.

The inhibitory nucleic acid molecules disclosed herein can also comprise one or more nucleotide analogs or substitutions. A nucleotide analog is a nucleotide which contains a modification to either the base, sugar, or phosphate moieties. Modifications to the base moiety include, but are not limited to, natural and synthetic modifications of A, C, G, and T/U, as well as different purine or pyrimidine bases such as, for example, pseudouridine, uracil-5-yl, hypoxanthin-9-yl (I), and 2-aminoadenin-9-yl. Modified bases include, but are not limited to, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo (such as, for example, 5-bromo), 5-trifluoromethyl and other 5-substituted uracils and cytosines, 7-methylguanine, 7-methyladenine, 8-azaguanine, 8-azaadenine, 7-deazaguanine, 7-deazaadenine, 3-deazaguanine, and 3-deazaadenine.

Nucleotide analogs can also include modifications of the sugar moiety. Modifications to the sugar moiety include, but are not limited to, natural modifications of the ribose and deoxy ribose as well as synthetic modifications. Sugar modifications include, but are not limited to, the following modifications at the 2' position: OH; F; O-, S-, or N-alkyl; O-, S-, or N-alkenyl; O-, S- or N-alkynyl; or O-alkyl-O-alkyl, wherein the alkyl, alkenyl, and alkynyl may be substituted or unsubstituted $C_{1-10}$alkyl or $C_{2-10}$alkenyl, and $C_{2-10}$alkynyl. Exemplary 2' sugar modifications also include, but are not limited to, $-O[(CH_2)_nO]_mCH_3$, $-O(CH_2)_nOCH_3$, $-O(CH_2)_nNH_2$, $-O(CH_2)_nCH_3$, $-O(CH_2)_n-ONH_2$, and $-O(CH_2)_nON[(CH_2)_nCH_3)]_2$, where n and m, independently, are from 1 to about 10. Other modifications at the 2' position include, but are not limited to, $C_{1-10}$alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars can also include those that contain modifications at the bridging ring oxygen, such as $CH_2$ and S. Nucleotide sugar analogs can also have sugar mimetics, such as cyclobutyl moieties in place of the pentofuranosyl sugar.

Nucleotide analogs can also be modified at the phosphate moiety. Modified phosphate moieties include, but are not limited to, those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. These phosphate or modified phosphate linkage between two nucleotides can be through a 3'-5' linkage or a 2'-5' linkage, and the linkage can contain inverted polarity such as 3'-5' to 5'-3' or 2'-5' to 5'-2'. Various salts, mixed salts, and free acid forms are also included. Nucleotide substitutes also include peptide nucleic acids (PNAs).

In some embodiments, the antisense nucleic acid molecules are gapmers, whereby the first one to seven nucleotides at the 5' and 3' ends each have 2'-methoxyethyl (2'-MOE) modifications. In some embodiments, the first five nucleotides at the 5' and 3' ends each have 2'-MOE modifications. In some embodiments, the first one to seven nucleotides at the 5' and 3' ends are RNA nucleotides. In some embodiments, the first five nucleotides at the 5' and 3' ends are RNA nucleotides. In some embodiments, each of the backbone linkages between the nucleotides is a phosphorothioate linkage.

In some embodiments, the siRNA molecules have termini modifications. In some embodiments, the 5' end of the antisense strand is phosphorylated. In some embodiments, 5'-phosphate analogs that cannot be hydrolyzed, such as 5'-(E)-vinyl-phosphonate are used.

In some embodiments, the siRNA molecules have backbone modifications. In some embodiments, the modified phosphodiester groups that link consecutive ribose nucleosides have been shown to enhance the stability and in vivo bioavailability of siRNAs The non-ester groups (—OH, =O) of the phosphodiester linkage can be replaced with sulfur, boron, or acetate to give phosphorothioate, boranophosphate, and phosphonoacetate linkages. In addition, substituting the phosphodiester group with a phosphotriester can facilitate cellular uptake of siRNAs and retention on serum components by eliminating their negative charge. In some embodiments, the siRNA molecules have sugar modifications. In some embodiments, the sugars are deprotonated (reaction catalyzed by exo- and endonucleases) whereby the 2'-hydroxyl can act as a nucleophile and attack the adjacent phosphorous in the phosphodiester bond. Such alternatives include 2'-O-methyl, 2'-O-methoxyethyl, and 2'-fluoro modifications.

In some embodiments, the siRNA molecules have base modifications. In some embodiments, the bases can be substituted with modified bases such as pseudouridine, 5'-methylcytidine, N6-methyladenosine, inosine, and N7-methylguanosine.

In some embodiments, the siRNA molecules are conjugated to lipids. Lipids can be conjugated to the 5' or 3' termini of siRNA to improve their in vivo bioavailability by allowing them to associate with serum lipoproteins. Representative lipids include, but are not limited to, cholesterol and vitamin E, and fatty acids, such as palmitate and tocopherol.

In some embodiments, a representative siRNA has the following formula:
Sense: mN*mN*/i2FN/mN/i2FN/mN/i2FN/mN/i2FN/mN/i2FN/mN/i2FN/mN/i2FN/mN/i2FN/*mN*/32FN/
Antisense: /52FN/*/i2FN/*mN/i2FN/mN/i2FN/mN/i2FN/mN/i2FN/mN/i2FN/mN/i2FN/mN/i2FN/mN/i2FN/mN*N*N
wherein: "N" is the base; "2F" is a 2'-F modification; "m" is a 2'-O-methyl modification, "I" is an internal base; and "*" is a phosphorothioate backbone linkage.

The present disclosure also provides vectors comprising any one or more of the inhibitory nucleic acid molecules disclosed herein. In some embodiments, the vectors comprise any one or more of the inhibitory nucleic acid molecules disclosed herein and a heterologous nucleic acid. The vectors can be viral or nonviral vectors capable of transporting a nucleic acid molecule. In some embodiments, the vector is a plasmid or cosmid (such as, for example, a circular double-stranded DNA into which additional DNA segments can be ligated). In some embodiments, the vector is a viral vector, wherein additional DNA segments can be ligated into the viral genome. Expression vectors include, but are not limited to, plasmids, cosmids, retroviruses, adenoviruses, adeno-associated viruses (AAV), plant viruses such as cauliflower mosaic virus and tobacco mosaic virus, yeast artificial chromosomes (YACs), Epstein-Barr (EBV)-derived episomes, and other expression vectors known in the art.

The present disclosure also provides compositions comprising any one or more of the inhibitory nucleic acid molecules disclosed herein. In some embodiments, the composition is a pharmaceutical composition. In some embodiments, the compositions comprise a carrier and/or excipient. Examples of carriers include, but are not limited to, poly (lactic acid) (PLA) microspheres, poly(D,L-lactic-coglycolic-acid) (PLGA) microspheres, liposomes, micelles, inverse micelles, lipid cochleates, and lipid microtubules. A carrier may comprise a buffered salt solution such as PBS, HBSS, etc.

In some embodiments, the CIDEB inhibitor comprises a nuclease agent that induces one or more nicks or double-strand breaks at a recognition sequence(s) or a DNA-binding protein that binds to a recognition sequence within a CIDEB genomic nucleic acid molecule. The recognition sequence can be located within a coding region of the CIDEB gene, or within regulatory regions that influence the expression of the gene. A recognition sequence of the DNA-binding protein or nuclease agent can be located in an intron, an exon, a promoter, an enhancer, a regulatory region, or any non-protein coding region. The recognition sequence can include or be proximate to the start codon of the CIDEB gene. For example, the recognition sequence can be located about 10, about 20, about 30, about 40, about 50, about 100, about 200, about 300, about 400, about 500, or about 1,000 nucleotides from the start codon.

In some embodiments, the PNPLA3 inhibitor comprises a nuclease agent that induces one or more nicks or double-strand breaks at a recognition sequence(s) or a DNA-binding protein that binds to a recognition sequence within a PNPLA3 genomic nucleic acid molecule. The recognition sequence can be located within a coding region of the PNPLA3 gene, or within regulatory regions that influence the expression of the gene. A recognition sequence of the DNA-binding protein or nuclease agent can be located in an intron, an exon, a promoter, an enhancer, a regulatory region, or any non-protein coding region. The recognition sequence can include or be proximate to the start codon of the PNPLA3 gene. For example, the recognition sequence can be located about 10, about 20, about 30, about 40, about 50, about 100, about 200, about 300, about 400, about 500, or about 1,000 nucleotides from the start codon.

In some embodiments, the HSD17B13 inhibitor comprises a nuclease agent that induces one or more nicks or double-strand breaks at a recognition sequence(s) or a DNA-binding protein that binds to a recognition sequence within an HSD17B13 genomic nucleic acid molecule. The recognition sequence can be located within a coding region of the HSD17B13 gene, or within regulatory regions that influence the expression of the gene. A recognition sequence of the DNA-binding protein or nuclease agent can be located in an intron, an exon, a promoter, an enhancer, a regulatory region, or any non-protein coding region. The recognition sequence can include or be proximate to the start codon of the HSD17B13 gene. For example, the recognition sequence can be located about 10, about 20, about 30, about 40, about 50, about 100, about 200, about 300, about 400, about 500, or about 1,000 nucleotides from the start codon.

As another example, two or more nuclease agents can be used, each targeting a nuclease recognition sequence including or proximate to the start codon. As another example, two nuclease agents can be used, one targeting a nuclease recognition sequence including or proximate to the start codon, and one targeting a nuclease recognition sequence including or proximate to the stop codon, wherein cleavage by the nuclease agents can result in deletion of the coding region between the two nuclease recognition sequences. Any nuclease agent that induces a nick or double-strand break into a desired recognition sequence can be used in the methods and compositions disclosed herein. Any DNA-binding protein that binds to a desired recognition sequence can be used in the methods and compositions disclosed herein.

Suitable nuclease agents and DNA-binding proteins for use herein include, but are not limited to, zinc finger protein or zinc finger nuclease (ZFN) pair, Transcription Activator-Like Effector (TALE) protein or Transcription Activator-Like Effector Nuclease (TALEN), or Clustered Regularly Interspersed Short Palindromic Repeats (CRISPR)/CRISPR-associated (Cas) systems. The length of the recognition sequence can vary, and includes, for example, recognition sequences that are about 30-36 bp for a zinc finger protein or ZFN pair, about 15-18 bp for each ZFN, about 36 bp for a TALE protein or TALEN, and about 20 bp for a CRISPR/Cas guide RNA.

In some embodiments, CRISPR/Cas systems can be used to modify a CIDEB genomic nucleic acid molecule, a PNPLA3 genomic nucleic acid molecule, or an HSD17B13 genomic nucleic acid molecule within a cell. The methods and compositions disclosed herein can employ CRISPR-Cas systems by utilizing CRISPR complexes (comprising a guide RNA (gRNA) complexed with a Cas protein) for site-directed cleavage of CIDEB nucleic acid molecules, PNPLA3 nucleic acid molecules, or HSD17B13 nucleic acid molecules.

Cas proteins generally comprise at least one RNA recognition or binding domain that can interact with gRNAs. Cas proteins can also comprise nuclease domains (such as, for example, DNase or RNase domains), DNA binding domains, helicase domains, protein-protein interaction domains, dimerization domains, and other domains. Suitable Cas proteins include, for example, a wild type Cas9 protein and a wild type Cpf1 protein (such as, for example, FnCpf1). A Cas protein can have full cleavage activity to create a double-strand break in a CIDEB genomic nucleic acid molecule, a PNPLA3 genomic nucleic acid molecule, or an HSD17B13 genomic nucleic acid molecule, or it can be a nickase that creates a single-strand break in a CIDEB genomic nucleic acid molecule, a PNPLA3 genomic nucleic acid molecule, or an HSD17B13 genomic nucleic acid molecule. Additional examples of Cas proteins include, but are not limited to, Cas1, Cas1B, Cast, Cas3, Cas4, Cas5, Cas5e (CasD), Cas6, Cas6e, Cas6f, Cas7, Cas8a1, Cas8a2, Cas8b, Cas8c, Cas9 (Csn1 or Csx12), Cas10, Cas10d, Cas12a, CasF, CasG, CasH, Csy1, Csy2, Csy3, Cse1 (CasA), Cse2 (CasB), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cu1966, and homologs or modified versions thereof. In some embodiments, a Cas system, such as Cas12a, can have multiple gRNAs encoded into a single crRNA. Cas proteins can also be operably linked to heterologous polypeptides as fusion proteins. For example, a Cas protein can be fused to a cleavage domain, an epigenetic modification domain, a transcriptional activation domain, or a transcriptional repressor domain. Cas proteins can be provided in any form. For example, a Cas protein can be provided in the form of a protein, such as a Cas protein complexed with a gRNA. Alternately, a Cas protein can be provided in the form of a nucleic acid molecule encoding the Cas protein, such as an RNA or DNA.

In some embodiments, targeted genetic modifications of CIDEB genomic nucleic acid molecules can be generated by contacting a cell with a Cas protein and one or more gRNAs that hybridize to one or more gRNA recognition sequences within a target genomic locus in the CIDEB genomic nucleic acid molecule. For example, a gRNA recognition sequence can be located within a region of SEQ ID NO:1. For example, the gRNA recognition sequence can be located from about 1000, from about 500, from about 400, from about 300, from about 200, from about 100, from about 50, from about 45, from about 40, from about 35, from about 30, from about 25, from about 20, from about 15, from about 10, or from about 5 nucleotides of a position corresponding to any one or more of positions: 14:24305635, 14:24305641, 14:24305650, 14:24305657, 14:24305662, 14:24305667, 14:24305671, 14:24305701, 14:24305709, 14:24305718, 14:24305721, 14:24305728, 14:24305743, 14:24305948, 14:24305966, 14:24305974, 14:24305980, 14:24305988, 14:24306014, 14:24306034, 14:24306041, 14:24306044, 14:24306047, 14:24306051, 14:24306064, 14:24306074, 14:24306077, 14:24306082, 14:24306083, 14:24306095, 14:24306122, 14:24306134, 14:24306373, 14:24306379, 14:24306382, 14:24306383, 14:24306426, 14:24306437, 14:24306439, 14:24306442, 14:24306444, 14:24306457, 14:24306463, 14:24306469, 14:24306480, 14:24306486, 14:24306504, 14:24306519, 14:24307382, 14:24307405, 14:24307417, 14:24307421, 14:24307441, 14:24307444, 14:24307444, 14:24307450, 14:24307461, 14:24307469, 14:24307474, 14:24307475, 14:24307833, 14:24307851, 14:24306426, 14:24307849, 14:24307448, 14:24305671, 14:24305663, 14:24305686, 14:24307829, 14:24307818, 14:24307856, 14:24306423, 14:24306061, 14:24307390, 14:24306382, 14:24306373, 14:24305733, 14:24307858, 14:24306387, 14:24305637, 14:24306062, 14:24307853, 14:24307450, 14:24306052, 14:24305673, 14:24306043, 14:24307834, 14:24306417, 14:24307451, 14:24307436, 14:24305953, 14:24306489, 14:24307441, 14:24306375, 14:24305657, 14:24306427, 14:24306524, 14:24307516, 14:24307840, 14:24307501, 14:24305968, 14:24305986, 14:24307441, 14:24307459, 14:24306017, 14:24307424, 14:24306072, 14:24307423, 14:24307450, 14:24306420, 14:24307454, 14:24305653, 14:24307442, 14:24306002, 14:24306076, 14:24305664, 14:24305961, 14:24305706, 14:24305946, 14:24306455, 14:24307468, 14:24307825, 14:24306110, 14:24305710, 14:24307483, 14:24306459, 14:24305754, 14:24305650, 14:24305691, 14:24306508, 14:24306039, 14:24306139, 14:24306391, 14:24306373, 14:24307498, 14:24307451, 14:24306138, 14:24307453, 14:24305692, 14:24305683, 14:24307484, 14:24307385, 14:24306519, 14:24307839, 14:24305965, 14:24305988, 14:24306087, 14:24307439, 14:24307477, 14:24306436, 14:24306507, 14:24307397, 14:24307495, 14:24306034, 14:24306013, 14:24307381, 14:24306383, 14:24305638, 14:24307420, 14:24306020, 14:24306470, 14:24307435, 14:24306469, 14:24306451, 14:24306403, 14:24307515, 14:24307489, 14:24307414, 14:24306483, 14:24305755, 14:24305766, 14:24306064, 14:24307516, 14:24305766, 14:24306489, 14:24306097, 14:24305763, 14:24307447, 14:24307402, 14:24305972, 14:24306423, 14:24305974, 14:24307411, 14:24306121, 14:24307516, 14:24306424, 14:24306039, 14:24307853, 14:24306388, 14:24305990, 14:24307822, 14:24305640, 14:24307418, 14:24305758, 14:24306131, 14:24305953, 14:24305730, 14:24306418, 14:24306059, 14:24307842, 14:24307837, 14:24306095, 14:24306109, 14:24307822, 14:24306077, 14:24307824, 14:24306080, 14:24305649, 14:24306433, 14:24306420, 14:24305658, 14:24306472, 14:24307412, 14:24306062, 14:24306044, 14:24306047, 14:24306126, 14:24306449, 14:24307391, or 14:24307857 (according to GRCh38/hg38 human genome assembly coordinates). The gRNA recognition sequence can include or be proximate to the start codon of a CIDEB genomic nucleic acid molecule or the stop codon of a CIDEB genomic nucleic acid molecule. For example, the gRNA recognition sequence can be located from about 10, from about 20, from about 30, from about 40, from about 50, from about 100, from about 200, from about 300, from about 400, from about 500, or from about 1,000 nucleotides of the start codon or the stop codon.

The gRNA recognition sequences within a target genomic locus in a CIDEB genomic nucleic acid molecule can be located near a Protospacer Adjacent Motif (PAM) sequence, which is a 2-6 base pair DNA sequence immediately following the DNA sequence targeted by the Cas9 nuclease. The canonical PAM is the sequence 5'-NGG-3' where "N" is any nucleobase followed by two guanine ("G") nucleobases. gRNAs can transport Cas9 to anywhere in the genome for gene editing, but no editing can occur at any site other than one at which Cas9 recognizes PAM. In addition, 5'-NGA-3' can be a highly efficient non-canonical PAM for human cells. Generally, the PAM is about 2-6 nucleotides downstream of the DNA sequence targeted by the gRNA. The PAM can flank the gRNA recognition sequence. In some embodiments, the gRNA recognition sequence can be flanked on the 3' end by the PAM. In some embodiments, the gRNA recognition sequence can be flanked on the 5' end by the PAM. For example, the cleavage site of Cas proteins can be about 1 to about 10, about 2 to about 5 base pairs, or three base pairs upstream or downstream of the PAM sequence. In some embodiments (such as when Cas9 from *S. pyogenes* or a closely related Cas9 is used), the PAM sequence of the non-complementary strand can be 5'-NGG-3', where N is any DNA nucleotide and is immediately 3' of the gRNA recognition sequence of the non-complementary strand of the target DNA. As such, the PAM sequence of the complementary strand would be 5'-CCN-3', where N is any DNA nucleotide and is immediately 5' of the gRNA recognition sequence of the complementary strand of the target DNA.

A gRNA is an RNA molecule that binds to a Cas protein and targets the Cas protein to a specific location within a CIDEB genomic nucleic acid molecule. An exemplary gRNA is a gRNA effective to direct a Cas enzyme to bind to or cleave a CIDEB genomic nucleic acid molecule, wherein the gRNA comprises a DNA-targeting segment that hybridizes to a gRNA recognition sequence within the CIDEB genomic nucleic acid molecule that includes or is proximate to a position corresponding to positions: 14:24305635, 14:24305641, 14:24305650, 14:24305657, 14:24305662, 14:24305667, 14:24305671, 14:24305701, 14:24305709, 14:24305718, 14:24305721, 14:24305728, 14:24305743, 14:24305948, 14:24305966, 14:24305974, 14:24305980, 14:24305988, 14:24306014, 14:24306034, 14:24306041, 14:24306044, 14:24306047, 14:24306051, 14:24306064, 14:24306074, 14:24306077, 14:24306082, 14:24306083, 14:24306095, 14:24306122, 14:24306134, 14:24306373, 14:24306379, 14:24306382, 14:24306383, 14:24306426, 14:24306437, 14:24306439, 14:24306442, 14:24306444, 14:24306457, 14:24306463, 14:24306469, 14:24306480, 14:24306486, 14:24306504, 14:24306519, 14:24307382, 14:24307405, 14:24307417, 14:24307421, 14:24307441, 14:24307444, 14:24307444, 14:24307450, 14:24307461, 14:24307469, 14:24307474, 14:24307475, 14:24307833, 14:24307851, 14:24306426, 14:24307849, 14:24307448, 14:24305663, 14:24305686, 14:24307829, 14:24307818, 14:24307856, 14:24306423, 14:24306061, 14:24307390, 14:24306382, 14:24306373, 14:24305733, 14:24307858, 14:24306387, 14:24305637, 14:24306062, 14:24307853, 14:24307450, 14:24306052, 14:24305673, 14:24306043, 14:24307834, 14:24306417, 14:24307451, 14:24307436, 14:24305953, 14:24306489, 14:24307441, 14:24306375, 14:24305657, 14:24306427, 14:24306524, 14:24307516, 14:24307840, 14:24307501, 14:24305968, 14:24305986, 14:24307441, 14:24307459, 14:24306017, 14:24307424, 14:24306072, 14:24307423, 14:24307450, 14:24306420, 14:24307454, 14:24305653, 14:24307442, 14:24306002, 14:24306076, 14:24305664, 14:24305961, 14:24305706, 14:24305946, 14:24306455, 14:24307468, 14:24307825, 14:24306110, 14:24305710, 14:24307483, 14:24306459, 14:24305754, 14:24305650, 14:24305691, 14:24306508, 14:24306039, 14:24306139, 14:24306391, 14:24306373, 14:24307498, 14:24307415, 14:24306138, 14:24307453, 14:24305692, 14:24305683, 14:24307484, 14:24307385, 14:24306519, 14:24307839, 14:24305965, 14:24305988, 14:24306087, 14:24307439, 14:24307477, 14:24306436, 14:24306507, 14:24307397, 14:24307495, 14:24306034, 14:24306013, 14:24307381, 14:24306383, 14:24305638, 14:24307420, 14:24306020, 14:24306470, 14:24307435, 14:24306469, 14:24306451, 14:24306403, 14:24307515, 14:24307489, 14:24307414, 14:24306483, 14:24305755, 14:24305766, 14:24306064, 14:24307516, 14:24305766, 14:24306489, 14:24306097, 14:24305763, 14:24307447, 14:24307402, 14:24305972, 14:24306423, 14:24305974, 14:24307411, 14:24306121, 14:24307516, 14:24306424, 14:24306039, 14:24307853, 14:24306388, 14:24305990, 14:24307822, 14:24305640, 14:24307418, 14:24305758, 14:24306131, 14:24305953, 14:24305730, 14:24306418, 14:24306059, 14:24307842, 14:24307837, 14:24306095, 14:24306109, 14:24307822, 14:24306077, 14:24307824, 14:24306080, 14:24305649, 14:24306433, 14:24306420, 14:24305658, 14:24306472, 14:24307412, 14:24306062, 14:24306044, 14:24306047, 14:24306126, 14:24306449, 14:24307391, or 14:24307857 (according to GRCh38/hg38 human genome assembly coordinates). For example, a gRNA can be selected such that it hybridizes to a gRNA recognition sequence that is located from about 5, from about 10, from about 15, from about 20, from about 25, from about 30, from about 35, from about 40, from about 45, from about 50, from about 100, from about 200, from about 300, from about 400, from about 500, or from about 1,000 nucleotides of a position corresponding to: 14:24305635, 14:24305641, 14:24305650, 14:24305657, 14:24305662, 14:24305667, 14:24305671, 14:24305701, 14:24305709, 14:24305718, 14:24305721, 14:24305728, 14:24305743, 14:24305948, 14:24305966, 14:24305974, 14:24305980, 14:24305988, 14:24306014, 14:24306034, 14:24306041, 14:24306044, 14:24306047, 14:24306051, 14:24306064, 14:24306074, 14:24306077, 14:24306082, 14:24306083, 14:24306095, 14:24306122, 14:24306134, 14:24306373, 14:24306379, 14:24306382, 14:24306383, 14:24306426, 14:24306437, 14:24306439, 14:24306442, 14:24306444, 14:24306457, 14:24306463, 14:24306469, 14:24306480, 14:24306486, 14:24306504, 14:24306519, 14:24307382, 14:24307405, 14:24307417, 14:24307421, 14:24307441, 14:24307444, 14:24307444, 14:24307450, 14:24307461, 14:24307469, 14:24307474, 14:24307475, 14:24307833, 14:24307851, 14:24306426, 14:24307849, 14:24307448, 14:24305663, 14:24305686, 14:24307829, 14:24307818, 14:24307856, 14:24306423, 14:24306061, 14:24307390, 14:24306382, 14:24306373, 14:24305733, 14:24307858, 14:24306387, 14:24305637, 14:24306062, 14:24307853, 14:24307450, 14:24306052, 14:24305673, 14:24306043, 14:24307834, 14:24306417, 14:24307451, 14:24307436, 14:24305953, 14:24306489, 14:24307441, 14:24306375, 14:24305657, 14:24306427, 14:24306524, 14:24307516, 14:24307840, 14:24307501, 14:24305968, 14:24305986, 14:24307441, 14:24307459, 14:24306017, 14:24307424, 14:24306072, 14:24307423, 14:24307450, 14:24306420, 14:24307454, 14:24305653, 14:24307442, 14:24306002, 14:24306076, 14:24305664, 14:24305961, 14:24305706, 14:24305946, 14:24306455, 14:24307468, 14:24307825, 14:24306110, 14:24305710, 14:24307483, 14:24306459, 14:24305754, 14:24305650, 14:24305691, 14:24306508, 14:24306039, 14:24306139, 14:24306391, 14:24306373, 14:24307498, 14:24307415, 14:24306138, 14:24307453, 14:24305692, 14:24305683, 14:24307484, 14:24307385, 14:24306519, 14:24307839, 14:24305965, 14:24305988, 14:24306087, 14:24307439, 14:24307477, 14:24306436, 14:24306507, 14:24307397, 14:24307495, 14:24306034, 14:24306013, 14:24307381, 14:24306383, 14:24305638, 14:24307420, 14:24306020, 14:24306470, 14:24307435, 14:24306469, 14:24306451, 14:24306403, 14:24307515, 14:24307489, 14:24307414, 14:24306483, 14:24305755, 14:24305766, 14:24306064, 14:24307516, 14:24305766, 14:24306489, 14:24306097, 14:24305763, 14:24307447, 14:24307402, 14:24305972, 14:24306423, 14:24305974, 14:24307411, 14:24306121, 14:24307516, 14:24306424, 14:24306039, 14:24307853, 14:24306388, 14:24305990, 14:24307822, 14:24305640, 14:24307418, 14:24305758, 14:24306131, 14:24305953, 14:24305730, 14:24306418, 14:24306059, 14:24307842, 14:24307837, 14:24306095, 14:24306109, 14:24307822, 14:24306077, 14:24307824, 14:24306080, 14:24305649, 14:24306433, 14:24306420, 14:24305658, 14:24306472, 14:24307412, 14:24306062, 14:24306044, 14:24306047, 14:24306126, 14:24306449, 14:24307391, or 14:24307857 (according to GRCh38/hg38 human genome assembly coordinates). Other exemplary gRNAs comprise a DNA-targeting segment that hybridizes to a gRNA recognition sequence present within a CIDEB genomic nucleic acid molecule that includes or is proximate to the start codon or the stop codon. For example, a gRNA can be selected such that it hybridizes to a gRNA recognition sequence that is located from about 5, from about 10, from about 15, from about 20, from about 25, from about 30, from about 35, from about 40, from about 45, from about 50, from about 100, from about 200, from about 300, from about 400, from about 500, or from about 1,000 nucleotides of the start codon or located from about 5, from about 10, from about 15, from about 20, from about 25, from about 30, from about 35, from about 40, from about 45, from about 50, from about 100, from about 200, from about 300, from about 400, from about 500, or from about 1,000 nucleotides of the stop codon. Suitable gRNAs can comprise from about 17 to about 25 nucleotides, from about 17 to about 23 nucleotides, from about 18 to about 22 nucleotides, or from about 19 to about 21 nucleotides. In some embodiments, the gRNAs can comprise 20 nucleotides.

Examples of suitable gRNA recognition sequences located within the human CIDEB reference gene are set forth in Table 14 as SEQ ID NOs:25-37.

TABLE 14

Guide RNA Recognition Sequences Near CIDEB Variation(s)

| Strand | gRNA Recognition Sequence | SEQ ID NO: |
|---|---|---|
| + | AGCTGAGAGGTACTCCATGGTGG | 25 |
| + | CAGAGCTGAGAGGTACTCCATGG | 26 |
| + | GTCACCTGAGTAAGTCACTGGGG | 27 |
| + | AGTCACCTGAGTAAGTCACTGGG | 28 |
| + | CAGTCACCTGAGTAAGTCACTGG | 29 |
| + | GCTTATATTAGATACTGACCTGG | 30 |
| − | GTCAGTATCTAATATAAGCTCGG | 31 |
| − | ATATAAGCTCGGAGTTTGGACGG | 32 |
| + | CAGACACGGAAAGGTCGCTGGGG | 33 |
| + | TTGTGATCACAGACACGGAAAGG | 34 |
| − | TCCGTGTCTGTGATCACAAGCGG | 35 |
| − | TCCGCTTGTGATCACAGACACGG | 36 |
| + | AGCTGTCAGGCCTTTCCGGATGG | 37 |

The Cas protein and the gRNA form a complex, and the Cas protein cleaves the target CIDEB genomic nucleic acid molecule. The Cas protein can cleave the nucleic acid molecule at a site within or outside of the nucleic acid sequence present in the target CIDEB, genomic nucleic acid sequence to which the DNA-targeting segment of a gRNA will bind. For example, formation of a CRISPR complex (comprising a gRNA hybridized to a gRNA recognition sequence and complexed with a Cas protein) can result in cleavage of one or both strands in or near (such as, for example, within 1, 2, 3, 4, 5, 6, 7, 8, 9, 10, 20, 50, or more base pairs from) the nucleic acid sequence present in the CIDEB genomic nucleic acid molecule to which a DNA-targeting segment of a gRNA will bind.

Such methods can result, for example, in a CIDEB genomic nucleic acid molecule in which a region of SEQ ID NO:1 is disrupted, the start codon is disrupted, the stop codon is disrupted, or the coding sequence is disrupted or deleted. Optionally, the cell can be further contacted with one or more additional gRNAs that hybridize to additional gRNA recognition sequences within the target genomic locus in the CIDEB genomic nucleic acid molecule. By contacting the cell with one or more additional gRNAs (such as, for example, a second gRNA that hybridizes to a second gRNA recognition sequence), cleavage by the Cas protein can create two or more double-strand breaks or two or more single-strand breaks.

In some embodiments, targeted genetic modifications of PNPLA3 genomic nucleic acid molecules can be generated by contacting a cell with a Cas protein and one or more gRNAs that hybridize to one or more gRNA recognition sequences within a target genomic locus in the PHPLA3 genomic nucleic acid molecule. For example, a gRNA recognition sequence can be located within a region of SEQ ID NO:43. For example, the gRNA recognition sequence can be located from about 1000, from about 500, from about 400, from about 300, from about 200, from about 100, from about 50, from about 45, from about 40, from about 35, from about 30, from about 25, from about 20, from about 15, from about 10, or from about 5 nucleotides of a position corresponding to position 5109 according to SEQ ID NO:43. Other exemplary gRNAs comprise a DNA-targeting segment that hybridizes to a gRNA recognition sequence present within a PNPLA3 genomic nucleic acid molecule that includes or is proximate to the start codon or the stop codon. For example, a gRNA can be selected such that it hybridizes to a gRNA recognition sequence that is located about 5, about 10, about 15, about 20, about 25, about 30, about 35, about 40, about 45, about 50, about 100, about 200, about 300, about 400, about 500, or about 1,000 nucleotides from the start codon or located about 5, about 10, about 15, about 20, about 25, about 30, about 35, about 40, about 45, about 50, about 100, about 200, about 300, about 400, about 500, or about 1,000 nucleotides from the stop codon. Suitable gRNAs can comprise from about 17 to about 25 nucleotides, from about 17 to about 23 nucleotides, from about 18 to about 22 nucleotides, or from about 19 to about 21 nucleotides. In some embodiments, the gRNAs comprise 20 nucleotides.

Examples of suitable gRNA recognition sequences located within the PNPLA3 reference gene are set forth in Table 15 as SEQ ID NOs:75-94.

TABLE 15

PNPLA3 Guide RNA Recognition Sequences

| Strand | gRNA Recognition Sequence | SEQ ID NO: |
|---|---|---|
| + | TCGGTCCAAAGACGAAGTCG | 75 |
| − | CCTTCCGCACAAGATCTGAG | 76 |
| − | TGTCGTACTCCCCATAGAAG | 77 |
| − | ATGCATCCAAATATCCTCGA | 78 |
| − | ACAACATGCGCGCGTCGCGG | 79 |
| − | GGCATTTGCAGAGACCCTGT | 80 |
| + | TTAAGCAAGTTCCTCCGACA | 81 |
| − | GCGTCCCCAGACGCACCCAG | 82 |
| − | CTCAGGATCCATCCCTTCTG | 83 |
| + | TCTTACCAGAGTGTCTGATG | 84 |
| − | AAGCTCTCGAGAGAAGGTAG | 85 |
| − | GCAGAGGCGTAGACTGAGCT | 86 |
| + | TAAAAGCGATATGTGGATGG | 87 |
| − | CGAACAACATGCGCGCGTCG | 88 |
| + | CTGGGAGAGATATGCCTTCG | 89 |
| + | AGGTCCTCTCAGATCTTGTG | 90 |
| − | CCAACTCACCTTGAGATCCG | 91 |
| − | GGAGATGAGCTGGTGGACAT | 92 |

TABLE 15-continued

PNPLA3 Guide RNA Recognition Sequences

| Strand | gRNA Recognition Sequence | SEQ ID NO: |
|---|---|---|
| + | TCAGTCTACGCCTCTGCACA | 93 |
| − | TCCAGGATGCTCTCATCCCA | 94 |

The Cas protein and the gRNA form a complex, and the Cas protein cleaves the target PNPLA3 genomic nucleic acid molecule. The Cas protein can cleave the nucleic acid molecule at a site within or outside of the nucleic acid sequence present in the target PNPLA3, genomic nucleic acid molecule to which the DNA-targeting segment of a gRNA will bind. For example, formation of a CRISPR complex (comprising a gRNA hybridized to a gRNA recognition sequence and complexed with a Cas protein) can result in cleavage of one or both strands in or near (such as, for example, within 1, 2, 3, 4, 5, 6, 7, 8, 9, 10, 20, 50, or more base pairs from) the nucleic acid sequence present in the PNPLA3 genomic nucleic acid molecule to which a DNA-targeting segment of a gRNA will bind.

Such methods can result, for example, in a PNPLA3 genomic nucleic acid molecule in which a region of SEQ ID NO:43 is disrupted, the start codon is disrupted, the stop codon is disrupted, or the coding sequence is disrupted or deleted. Optionally, the cell can be further contacted with one or more additional gRNAs that hybridize to additional gRNA recognition sequences within the target genomic locus in the PNPLA3 genomic nucleic acid molecule. By contacting the cell with one or more additional gRNAs (such as, for example, a second gRNA that hybridizes to a second gRNA recognition sequence), cleavage by the Cas protein can create two or more double-strand breaks or two or more single-strand breaks.

In some embodiments, targeted genetic modifications of HSD17B13 genomic nucleic acid molecules can be generated by contacting a cell with a Cas protein and one or more gRNAs that hybridize to one or more gRNA recognition sequences within a target genomic locus in the PHPLA3 genomic nucleic acid molecule. For example, a gRNA recognition sequence can a DNA-targeting segment that hybridizes to a gRNA recognition sequence present within an HSD17B13 genomic nucleic acid molecule that includes or is proximate to the start codon or the stop codon. For example, a gRNA can be selected such that it hybridizes to a gRNA recognition sequence that is located about 5, about 10, about 15, about 20, about 25, about 30, about 35, about 40, about 45, about 50, about 100, about 200, about 300, about 400, about 500, or about 1,000 nucleotides from the start codon or located about 5, about 10, about 15, about 20, about 25, about 30, about 35, about 40, about 45, about 50, about 100, about 200, about 300, about 400, about 500, or about 1,000 nucleotides from the stop codon. Suitable gRNAs can comprise from about 17 to about 25 nucleotides, from about 17 to about 23 nucleotides, from about 18 to about 22 nucleotides, or from about 19 to about 21 nucleotides. In some embodiments, the gRNAs comprise 20 nucleotides.

Examples of suitable gRNA recognition sequences located within the HSD17B13 reference gene are set forth in Table 16 as SEQ ID NOs:95-114.

TABLE 16

HSD17B13 Guide RNA Recognition Sequences

| Strand | gRNA Recognition Sequence | SEQ ID NO: |
|---|---|---|
| − | AGTGGGTGATGTAACAATCG | 95 |
| + | TGAGGTAAGGAATCCCTTCG | 96 |
| + | ACCTCTGTGAAAGCCAACAG | 97 |
| − | TTCCTAATTACAGCGCGGTG | 98 |
| − | ACATTTGAGGTCAACATCCT | 99 |
| + | CACTCACCCAAAAATGTCCT | 100 |
| − | CAATCGTGGTGAATAATGCT | 101 |
| + | CTTCACCAACGACTCCAAGT | 102 |
| + | ATACTTACCAATATGGGATG | 103 |
| − | CGTCACTGCGCATGCGTATG | 104 |
| − | AGCCGATCTTCTCAGCACCA | 105 |
| − | ACAGAGCATATTGGTTCTGT | 106 |
| − | GAGCTGGGCATGGAATAGGC | 107 |
| + | CTGAAGCCACTGTGACGATG | 108 |
| − | GCAGCTGAGTGCCGAAAACT | 109 |
| − | AGCACTTCTTCCATCGATGA | 110 |
| − | CTTCAGTGTGCGGCCACGAA | 111 |
| − | AGAGGAGAAAATCTGTGGCT | 112 |
| − | TCCTCAGAGGAGAAAATCTG | 113 |
| + | GATGTTGACCTCAAATGTCT | 114 |

The Cas protein and the gRNA form a complex, and the Cas protein cleaves the target HSD17B13 genomic nucleic acid molecule. The Cas protein can cleave the nucleic acid molecule at a site within or outside of the nucleic acid sequence present in the target HSD17B13, genomic nucleic acid molecule to which the DNA-targeting segment of a gRNA will bind. For example, formation of a CRISPR complex (comprising a gRNA hybridized to a gRNA recognition sequence and complexed with a Cas protein) can result in cleavage of one or both strands in or near (such as, for example, within 1, 2, 3, 4, 5, 6, 7, 8, 9, 10, 20, 50, or more base pairs from) the nucleic acid sequence present in the HSD17B13 genomic nucleic acid molecule to which a DNA-targeting segment of a gRNA will bind.

Such methods can also result, for example, in an HSD17B13 genomic nucleic acid molecule in which a region of SEQ ID NO:52 is disrupted, the start codon is disrupted, the stop codon is disrupted, or the coding sequence is disrupted or deleted. Optionally, the cell can be further contacted with one or more additional gRNAs that hybridize to additional gRNA recognition sequences within the target genomic locus in the HSD17B13 genomic nucleic acid molecule. By contacting the cell with one or more additional gRNAs (such as, for example, a second gRNA that hybridizes to a second gRNA recognition sequence), cleavage by the Cas protein can create two or more double-strand breaks or two or more single-strand breaks.

In some embodiments, the CIDEB inhibitor is a small molecule. In some embodiments, the CIDEB inhibitor is an antibody. In some embodiments, the CIDEB inhibitor comprises an inhibitory nucleic acid molecule, such as, for example an antisense nucleic acid molecule, an siRNA, or an shRNA.

In some embodiments, the PNPLA3 inhibitor is a small molecule. In some embodiments, the PNPLA3 inhibitor is an antibody. In some embodiments, the PNPLA3 inhibitor comprises an inhibitory nucleic acid molecule, such as, for example an antisense nucleic acid molecule, an siRNA, or an shRNA. An exemplary PNPLA3 inhibitor is AZD2693.

In some embodiments, the HSD17B13 inhibitor is a small molecule. Numerous HSD17B13 inhibitors are described in, for example, PCT Publications WO2019/183329, WO2019/183164, and WO2020/061177. In some embodiments, the HSD17B13 inhibitor is an antibody. In some embodiments, the HSD17B13 inhibitor comprises an inhibitory nucleic acid molecule, such as, for example an antisense nucleic acid molecule, an siRNA, or an shRNA. Additional examples of HSD17B13 inhibitors include, but are not limited to ARO-HSD or ALN-HSD.

In some embodiments, the dose of the CIDEB inhibitor can be reduced by about 10%, by about 20%, by about 30%, by about 40%, by about 50%, by about 60%, by about 70%, by about 80%, or by about 90% for subjects that are heterozygous for one or more CIDEB variant nucleic acid molecules compared to subjects that are CIDEB reference (who may receive a standard dosage amount). In some embodiments, the dose of the CIDEB inhibitor can be reduced by about 10%, by about 20%, by about 30%, by about 40%, or by about 50%. In addition, the dose of the CIDEB inhibitor in subjects that are heterozygous for one or more CIDEB variant nucleic acid molecules can be administered less frequently compared to subjects that are CIDEB reference. The dose can also be changed based on BMI, % liver fat, liver span, age, sex, etc.

In some embodiments, the dose of the PNPLA3 inhibitor can be increased by about 10%, by about 20%, by about 30%, by about 40%, by about 50%, by about 60%, by about 70%, by about 80%, or by about 90% for subjects that are heterozygous for one or more PNPLA3 variant nucleic acid molecules compared to subjects that are PNPLA3 reference (who may receive a standard dosage amount). In some embodiments, the dose of the PNPLA3 inhibitor can be increased by about 10%, by about 20%, by about 30%, by about 40%, or by about 50%. In addition, the dose of the PNPLA3 inhibitor in subjects that are heterozygous for one or more PNPLA3 variant nucleic acid molecules can be administered more frequently compared to subjects that are PNPLA3 reference.

In some embodiments, the dose of the HSD17B13 inhibitor can be reduced by about 10%, by about 20%, by about 30%, by about 40%, by about 50%, by about 60%, by about 70%, by about 80%, or by about 90% for subjects that are heterozygous for one or more HSD17B13 variant nucleic acid molecules compared to subjects that are HSD17B13 reference (who may receive a standard dosage amount). In some embodiments, the dose of the HSD17B13 inhibitor can be reduced by about 10%, by about 20%, by about 30%, by about 40%, or by about 50%. In addition, the dose of the HSD17B13 inhibitor in subjects that are heterozygous for one or more HSD17B13 variant nucleic acid molecules can be administered less frequently compared to subjects that are HSD17B13 reference.

In some embodiments, the methods further comprise detecting the presence or absence of a CIDEB variant nucleic acid molecule and/or a CIDEB predicted loss-of-function polypeptide in a biological sample from the subject.

In some embodiments, the CIDEB variant nucleic acid molecule is a genomic nucleic acid molecule. In some embodiments, the CIDEB variant nucleic acid molecule is an mRNA molecule. In some embodiments, the CIDEB variant nucleic acid molecule is a cDNA molecule produced from an mRNA molecule. In some embodiments, the CIDEB variant nucleic acid molecule is a missense variant, a splice-site variant, a stop-gain variant, a start-loss variant, a stop-loss variant, a frameshift variant, or an in-frame indel variant, or a variant that encodes a truncated or mutated CIDEB polypeptide. In some embodiments, the CIDEB variant nucleic acid molecule comprises 14:24305635:A: AGTAG, 14:24305641:A:C, 14:24305650:G:A, 14:24305657:C:A, 14:24305662:G:T, 14:24305667:T:C, 14:24305671:C:A, 14:24305671:C:G, 14:24305701:A:T, 14:24305709:C:T, 14:24305718:A:G, 14:24305721:T:C, 14:24305728:G:GGCCTT, 14:24305743:T:C, 14:24305948: T:C, 14:24305966:C:T, 14:24305974:T:C, 14:24305980: TCA:T, 14:24305988:C:T, 14:24306014:C:T, 14:24306034: A:C, 14:24306041:C:G, 14:24306044:G:A, 14:24306047: G:A, 14:24306051:T:G, 14:24306064:T:C, 14:24306074:A: G, 14:24306077:G:C, 14:24306082:A:G, 14:24306083:T:A, 14:24306095:G:A, 14:24306122:A:G, 14:24306134:C:G, 14:24306373:C:G, 14:24306379:T:C, 14:24306382:G:A, 14:24306383:G:T, 14:24306426:T:G, 14:24306437:C:G, 14:24306439:G:C, 14:24306442:A:G, 14:24306444:A:G, 14:24306457:C:T, 14:24306463:C:T, 14:24306469:C:T, 14:24306480:A:G, 14:24306486:A:C, 14:24306504:A:G, 14:24306519:A:G, 14:24307382:G:C, 14:24307405:A:G, 14:24307417:A:T, 14:24307421:T:A, 14:24307441:C:A, 14:24307444:A:C, 14:24307444:A:G, 14:24307450:C: CGCTG, 14:24307461:TG:T, 14:24307469:AG:A, 14:24307474:C:T, 14:24307475:A:G, 14:24307833:G:C, 14:24307851:T:TAC, 14:24306426:T:C, 14:24307849:G:C, 14:24307448:G:T, 14:24305671:C:T, 14:24305663:C:T, 14:24305686:C:G, 14:24307829:A:C, 14:24307818:CT-GAG:C, 14:24307856:C:T, 14:24306423:T:C, 14:24306061:AC:A, 14:24307390:C:T, 14:24306382:G:T, 14:24306373:C:T, 14:24305733:T:C, 14:24307858:T:C, 14:24306387:C:T, 14:24305637:T:C, 14:24306062:C:T, 14:24307853:C:G, 14:24307450:C:G, 14:24306052:TG:T, 14:24305673:G:A, 14:24306043:C:T, 14:24307834:G:A, 14:24306417:C:T, 14:24307451:G:A, 14:24307436:A:C, 14:24305953:ACTTT:A, 14:24306489:G:T, 14:24307441: C:T, 14:24306375:C:T, 14:24305657:C:G, 14:24306427:C: T, 14:24306524:C:T, 14:24307516:C:A, 14:24307840:G:C, 14:24307501:A:G, 14:24305968:A:C, 14:24305986:C:T, 14:24307441:C:G, 14:24307459:G:T, 14:24306017:T:A, 14:24307424:G:A, 14:24306072:G:T, 14:24307423:C:T, 14:24307450:C:T, 14:24306420:G:A, 14:24307454:G:A, 14:24305653:C:T, 14:24307442:G:A, 14:24306002:C:T, 14:24306076:C:T, 14:24305664:C:T, 14:24305961:TG:T, 14:24305706:A:G, 14:24305946:C:T, 14:24306455:G:C, 14:24307468:G:A, 14:24307825:A:C, 14:24306110:G:A, 14:24305710:C:T, 14:24307483:C:T, 14:24306459:A:G, 14:24305754:C:T, 14:24305650:G:C, 14:24305691:C:T, 14:24306508:G:C, 14:24306039:G:T, 14:24306139:T:C, 14:24306391:T:C, 14:24306373:C:A, 14:24307498:C:T, 14:24307415:G:A, 14:24306138:CTG:C, 14:24307453:T:C, 14:24305692:G:A, 14:24305683:C:G, 14:24307484:G:A, 14:24307385:C:T, 14:24306519:A:T, 14:24307839:A:C, 14:24305965:C:T, 14:24305988:CAT:C, 14:24306087:C:G, 14:24307439:C:T, 14:24307477:A:C, 14:24306436:G:T, 14:24306507:A:G, 14:24307397:C:T, 14:24307495:G:A, 14:24306034:A:T, 14:24306013:G:A, 14:24307381:A:G, 14:24306383:G:C, 14:24305638:A:G, 14:24307420:G:A, 14:24306020:C:T, 14:24306470:A:C, 14:24307435:C:T, 14:24306469:C:G, 14:24306451:C:T, 14:24306403:G:A, 14:24307515:C:G, 14:24307489:A:G, 14:24307414:C:T, 14:24306483:A:G, 14:24305755:G:A, 14:24305766:C:T, 14:24306064:T:G, 14:24307516:C:G, 14:24305766:C:G, 14:24306489:G:A, 14:24306097:T:C, 14:24305763:T:G, 14:24307447:G:A, 14:24307402:G:A, 14:24305972:C:G, 14:24306423:T:G, 14:24305974:T:TG, 14:24307411:T:C, 14:24306121:T:C, 14:24307516:C:T, 14:24306424:C:T, 14:24306039:G:C, 14:24307853:C:A, 14:24306388:A:G, 14:24305990:T:C, 14:24307822:G:GT, 14:24305640:G:A, 14:24307418:T:C, 14:24305758:G:C, 14:24306131:C:T, 14:24305953:A:G, 14:24305730:C:A, 14:24306418:A:G, 14:24306059:AC:A, 14:24307842:G:A, 14:24307837:T:G, 14:24306095:G:T, 14:24306109:C:T, 14:24307822:G:A, 14:24306077:G:A, 14:24307824:A:T, 14:24306080:C:T, 14:24305649:C:T, 14:24306433:G:GA, 14:24306420:G:C, 14:24305658:T:G, 14:24306472:C:T, 14:24307412:TC:T, 14:24306062:C:A, 14:24306044:G:C, 14:24306047:G:T, 14:24306126:CAG:C, 14:24306449:C:G, 14:24307391:G: A, or 14:24307857:A:C (according to GRCh38/hg38 human genome assembly coordinates).

Detecting the presence or absence of a CIDEB variant nucleic acid molecule in a biological sample from a subject and/or determining whether a subject has a CIDEB variant nucleic acid molecule can be carried out by any of the methods described herein. In some embodiments, these methods can be carried out in vitro. In some embodiments, these methods can be carried out in situ. In some embodiments, these methods can be carried out in vivo. In any of these embodiments, the nucleic acid molecule can be present within a cell obtained from the subject.

In some embodiments, the detecting step comprises obtaining or having obtained a biological sample from the subject, and performing or having performed an assay on the biological sample to determine whether the subject has the CIDEB variant nucleic acid molecule, and/or a CIDEB predicted loss-of-function polypeptide. In some embodiments, the assay is a sequence analysis that comprises sequencing at least a portion of the nucleotide sequence of the CIDEB genomic nucleic acid molecule in the biological sample. In some embodiments, the assay is a sequence analysis that comprises sequencing at least a portion of the nucleotide sequence of the CIDEB mRNA molecule in the biological sample. In some embodiments, the assay is a sequence analysis that comprises sequencing at least a portion of the nucleotide sequence of the CIDEB cDNA molecule produced from an mRNA molecule in the biological sample.

In some embodiments, the sequence analysis comprises: a) contacting the biological sample with a primer hybridizing to a portion of the nucleotide sequence of the CIDEB nucleic acid molecule that is proximate to a CIDEB variant nucleic acid molecule position; b) extending the primer at least through the CIDEB variant nucleic acid molecule position; and c) determining whether the extension product of the primer comprises a variant nucleotide at the CIDEB variant nucleic acid molecule position. In some embodiments, the sequence analysis comprises sequencing the entire nucleic acid molecule in the biological sample.

In some embodiments, the assay is a sequence analysis that comprises: a) amplifying at least a portion of the CIDEB nucleic acid molecule in the biological sample, wherein the portion comprises a CIDEB variant nucleic acid molecule position; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the CIDEB variant nucleic acid molecule position; and d) detecting the detectable label. In some embodiments, the CIDEB nucleic acid molecule in the biological sample is mRNA and the mRNA is reverse-transcribed into cDNA prior to the amplifying step.

In some embodiments, the assay is a sequence analysis that comprises contacting the CIDEB nucleic acid molecule in the biological sample with an alteration-specific probe comprising a detectable label, wherein the alteration-specific probe comprises a nucleotide sequence which hybridizes under stringent conditions to a CIDEB variant nucleic acid molecule position, and detecting the detectable label.

In some embodiments, the assay is an immunoassay for detecting the presence of a CIDEB predicted loss-of-function polypeptide. In some embodiments, mass spectrometry is used for detecting the presence of a CIDEB predicted loss-of-function polypeptide.

In some embodiments, the methods further comprise determining the subject's gene burden of having a CIDEB variant nucleic acid molecule and/or a CIDEB predicted loss-of-function polypeptide. When the subject has a lower gene burden, the subject is administered or continued to be administered the CIDEB inhibitor in a standard dosage amount. When the subject has a greater gene burden, the subject is administered or continued to be administered the CIDEB inhibitor in an amount that is the same as or less than the standard dosage amount. In some embodiments, the subject's gene burden represents a weighted sum of a plurality of genetic variants associated with protection against developing a liver disease. In some embodiments, the gene burden is calculated using at least about 2, at least about 3, at least about 4, at least about 5, at least about 10, at least about 20, at least about 30, at least about 40, at least about 50, at least about 60, at least about 70, at least about 80, at least about 100, at least about 120, at least about 150, at least about 200, at least about 250, at least about 300, at least about 400, at least about 500, or at least about 1,000 genetic variants associated with liver disease. In some embodiments, the gene burden may be divided into quintiles, e.g., top quintile, intermediate quintile, and bottom quintile, wherein the top quintile of gene burden corresponds to the lowest risk group and the bottom quintile of gene burden corresponds to the highest risk group.

The sequence analysis to determine whether a subject has a CIDEB variant nucleic acid molecule can be carried out by any of the methods described herein. In some embodiments, these methods can be carried out in vitro. In some embodiments, these methods can be carried out in situ. In some embodiments, these methods can be carried out in vivo. In any of these embodiments, the nucleic acid molecule can be present within a cell obtained from the subject.

In some embodiments, the methods further comprise detecting the presence or absence of a PNPLA3 variant nucleic acid molecule encoding PNPLA3 Ile148Met or PNPLA3 Ile144Met polypeptide and/or a PNPLA3 Ile148Met or a PNPLA3 Ile144Met polypeptide in a biological sample from the subject. In some embodiments, the PNPLA3 variant nucleic acid molecule is a genomic DNA molecule comprising a guanine at a position corresponding to position 5109 according to SEQ ID NO:43; an mRNA molecule comprising a guanine at a position corresponding to position 444 according to SEQ ID NO:46, or a guanine at a position corresponding to position 432 according to SEQ ID NO:47; a cDNA molecule produced from an mRNA molecule, wherein the cDNA molecule has a nucleotide sequence comprising: a guanine at a position corresponding to position 444 according to SEQ ID NO: 50, or a guanine at a position corresponding to position 432 according to SEQ ID NO:51.

Detecting the presence or absence of a PNPLA3 variant nucleic acid molecule encoding PNPLA3 Ile148Met or PNPLA3 Ile144Met polypeptide in a biological sample from a subject and/or determining whether a subject has a PNPLA3 variant nucleic acid molecule encoding PNPLA3 Ile148Met or PNPLA3 Ile144Met polypeptide can be carried out by any of the methods described herein. In some embodiments, these methods can be carried out in vitro. In some embodiments, these methods can be carried out in situ. In some embodiments, these methods can be carried out in vivo. In any of these embodiments, the nucleic acid molecule can be present within a cell obtained from the subject.

In some embodiments, the detecting step comprises obtaining or having obtained a biological sample from the subject, and performing or having performed an assay on the biological sample to determine whether the subject has: i) a PNPLA3 genomic nucleic acid molecule comprising a guanine at a position corresponding to position 5109 according to SEQ ID NO:43, or a complement thereof; ii) a PNPLA3 mRNA molecule comprising: a guanine at a position corresponding to position 444 according to SEQ ID NO:46, or a guanine at a position corresponding to position 432 according to SEQ ID NO:47, or a complement thereof; or iii) a PNPLA3 cDNA molecule comprising: a guanine at a position corresponding to position 444 according to SEQ ID NO: 50, or a guanine at a position corresponding to position 432 according to SEQ ID NO:51, or a complement thereof.

In some embodiments, the sequence analysis comprises: a) contacting the biological sample with a primer hybridizing to: i) a portion of the nucleotide sequence of the PNPLA3 genomic nucleic acid molecule, or a complement thereof, that is proximate to a position corresponding to position 5109 according to SEQ ID NO:43; ii) a portion of the nucleotide sequence of the PNPLA3 mRNA molecule, or the complement thereof, that is proximate to a position corresponding to position 444 according to SEQ ID NO:46, or position 432 according to SEQ ID NO:47; or iii) a portion of the nucleotide sequence of the PNPLA3 cDNA molecule, or the complement thereof, that is proximate to a position corresponding to position 444 according to SEQ ID NO:50, or position 432 according to SEQ ID NO:51; b) extending the primer at least through: i) position of the nucleotide sequence of PNPLA3 genomic nucleic acid molecule, or a complement thereof corresponding to position corresponding to position 5109 according to SEQ ID NO:43; ii) position of the nucleotide sequence of PNPLA3 mRNA molecule, or a complement thereof corresponding to a position corresponding to position 444 according to SEQ ID NO:46, or position 432 according to SEQ ID NO:47; or iii) position of the nucleotide sequence of PNPLA3 cDNA molecule, or a complement thereof corresponding to a position corresponding to position 444 according to SEQ ID NO:50, or position 432 according to SEQ ID NO:51; and c) determining whether the extension product of the primer comprises: a guanine at a position corresponding to position 5109 according to SEQ ID NO:43, or a complement thereof; a guanine at a position corresponding to position 444 according to SEQ ID NO:46, or a guanine at a position corresponding to position 432 according to SEQ ID NO:47, or a complement thereof; or a guanine at a position corresponding to position 444 according to SEQ ID NO:50, or a guanine at a position corresponding to position 432 according to SEQ ID NO:51, or a complement thereof.

In some embodiments, the assay is a sequence analysis that comprises a) amplifying at least a portion of: i) a PNPLA3 genomic nucleic acid molecule comprising a guanine at a position corresponding to position 5109 according to SEQ ID NO:43, or a complement thereof; ii) a PNPLA3 mRNA molecule comprising: a guanine at a position corresponding to position 444 according to SEQ ID NO:46, or a guanine at a position corresponding to position 432 according to SEQ ID NO:47, or a complement thereof; or iii) a PNPLA3 cDNA molecule comprising: a guanine at a position corresponding to position 444 according to SEQ ID NO: 50, or a guanine at a position corresponding to position 432 according to SEQ ID NO:51; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleotide sequence of the amplified nucleic acid molecule comprising: i) a guanine at a position corresponding to position 5109 according to SEQ ID NO:43, or a complement thereof; ii) a guanine at a position corresponding to position 444 according to SEQ ID NO:46, or a guanine at a position corresponding to position 432 according to SEQ ID NO:47, or a complement thereof; or iii) a guanine at a position corresponding to position 444 according to SEQ ID NO:50, or a guanine at a position corresponding to position 432 according to SEQ ID NO:51, or a complement thereof; and d) detecting the detectable label.

In some embodiments, the assay is a sequence analysis that comprises contacting the PNPLA3 nucleic acid molecule in the biological sample with an alteration-specific probe comprising a detectable label, wherein the alteration-specific probe comprises a nucleotide sequence which hybridizes under stringent conditions to: i) a PNPLA3 genomic nucleic acid molecule comprising a guanine at a position corresponding to position 5109 according to SEQ ID NO:43, or a complement thereof; ii) a PNPLA3 mRNA molecule comprising: a guanine at a position corresponding to position 444 according to SEQ ID NO:46, or a guanine at a position corresponding to position 432 according to SEQ ID NO:47, or a complement thereof; or iii) a PNPLA3 cDNA molecule comprising: a guanine at a position corresponding to position 444 according to SEQ ID NO: 50, or a guanine at a position corresponding to position 432 according to SEQ ID NO:51; and detecting the detectable label.

The sequence analysis to determine whether a subject has a PNPLA3 variant nucleic acid molecule encoding a PNPLA3 predicted loss-of-function polypeptide can be carried out by any of the methods described herein. In some embodiments, these methods can be carried out in vitro. In some embodiments, these methods can be carried out in situ. In some embodiments, these methods can be carried out in vivo. In any of these embodiments, the nucleic acid molecule can be present within a cell obtained from the subject.

In some embodiments, the assay is an immunoassay for detecting the presence of a PNPLA3 Ile148Met or Ile144Met variant polypeptide. In some embodiments, mass spectrometry is used for detecting the presence of a PNPLA3 Ile148Met or Ile144Met variant polypeptide.

In some embodiments, the methods further comprise detecting the presence or absence of a nucleic acid molecule encoding a reference HSD17B13 polypeptide or a functional HSD17B13 polypeptide and/or a reference HSD17B13 polypeptide or a functional HSD17B13 polypeptide in a biological sample from the subject. In some embodiments, the nucleic acid molecule encoding the reference HSD17B13 polypeptide or a functional HSD17B13 polypeptide comprises: a genomic nucleic acid molecule comprising the nucleotide sequence according to SEQ ID NO:52, or a nucleotide sequence having at least 90% sequence identity to SEQ ID NO:52 and encoding a reference HSD17B13 polypeptide or a functional HSD17B13 polypeptide; an mRNA molecule comprising the nucleotide sequence according to any one of SEQ ID NOs:53-62 or a nucleotide sequence having at least 90% sequence identity to SEQ ID NOs:53-62 and encoding a reference HSD17B13 polypeptide or a functional HSD17B13 polypeptide; or a cDNA molecule comprising the nucleotide sequence according to any one of SEQ ID NOs:63-72 or a nucleotide sequence having at least 90% sequence identity to SEQ ID NOs:63-72 and encoding a reference HSD17B13 polypeptide or a functional HSD17B13 polypeptide.

Detecting the presence or absence of a nucleic acid molecule encoding a reference HSD17B13 polypeptide or a functional HSD17B13 polypeptide and/or determining whether a subject has a nucleic acid molecule encoding a reference HSD17B13 polypeptide or a functional HSD17B13 polypeptide can be carried out by any of the methods described herein. In some embodiments, these methods can be carried out in vitro. In some embodiments, these methods can be carried out in situ. In some embodiments, these methods can be carried out in vivo. In any of these embodiments, the nucleic acid molecule can be present within a cell obtained from the subject.

In some embodiments, the detecting step comprises obtaining or having obtained a biological sample from the subject; and performing or having performed an assay on the biological sample to determine whether the subject has: i) an HSD17B13 genomic nucleic acid molecule comprising SEQ ID NO:52, or a nucleotide sequence having at least 90% sequence identity to SEQ ID NO:52 and encoding a reference HSD17B13 polypeptide or a functional HSD17B13 polypeptide; ii) an HSD17B13 mRNA molecule comprising any one of SEQ ID NOs:53-62, or a nucleotide sequence having at least 90% sequence identity to any one of SEQ ID NOs:53-62 and encoding a reference HSD17B13 polypeptide or a functional HSD17B13 polypeptide; or iii) an HSD17B13 cDNA molecule comprising any one of SEQ ID NOs:63-72, or a nucleotide sequence having at least 90% sequence identity to any one of SEQ ID NOs:63-72 and encoding a reference HSD17B13 polypeptide or a functional HSD17B13 polypeptide.

In some embodiments, the sequence analysis comprises sequencing at least a portion of the nucleotide sequence of the HSD17B13 genomic nucleic acid molecule, mRNA molecule, or cDNA molecule produced from mRNA molecule in the biological sample.

In some embodiments, the assay is an immunoassay for detecting the presence of an HSD17B13 wild type or reference polypeptide. In some embodiments, mass spectrometry is used for detecting the presence of an HSD17B13 wild type or reference polypeptide.

In any of the embodiments described herein, when the subject is CIDEB reference, the subject can be administered the CIDEB inhibitor in a standard dosage amount. When the subject is heterozygous for a CIDEB variant nucleic acid molecule encoding a CIDEB predicted loss-of-function polypeptide, the subject can be administered the CIDEB inhibitor in a dosage amount that is the same as or less than a standard dosage amount. The CIDEB inhibitor can also be administered in combination with one or more PNPLA3 inhibitors and/or one or more HSD17B13 inhibitors.

In any of the embodiments described herein, when the subject is CIDEB reference or is heterozygous for a CIDEB variant nucleic acid molecule and is also a carrier for a nucleic acid molecule encoding a PNPLA3 Ile148Met or an Ile144Met polypeptide, such a subject can be treated with a combination of one or more CIDEB inhibitors, one or more PNPLA3 inhibitors and/or one or more HSD17B13 inhibitors.

In any of the embodiments described herein, when the subject is homozygous for a nucleic acid molecule encoding a reference HSD17B13 polypeptide or a functional HSD17B13 polypeptide, the subject is administered a CIDEB inhibitor in an amount that is the same as or greater than a standard dosage amount, or is administered a combination of a CIDEB inhibitor in an amount that is the same as or greater than a standard dosage amount, an HSD17B13 inhibitor, and/or a PNPLA3 inhibitor. When the subject is not homozygous for a nucleic acid molecule encoding a reference HSD17B13 polypeptide or a functional HSD17B13 polypeptide (i.e., is a carrier for a loss-of-function HSD17B13), the subject is administered a CIDEB inhibitor in an amount that is less than a standard dosage amount, or is administered a combination of a CIDEB inhibitor in an amount that is less than a standard dosage amount, an HSD17B13 inhibitor, and/or a PNPLA3 inhibitor.

In some embodiments, when the subject is CIDEB reference, the subject is also administered a therapeutic agent that treats or inhibits liver disease in a standard dosage amount. In some embodiments, when the subject is heterozygous for a CIDEB variant nucleic acid molecule, the subject is also administered a therapeutic agent that treats or inhibits liver disease in a dosage amount that is the same as or less than a standard dosage amount.

In some embodiments, the treatment methods further comprise detecting the presence or absence of a CIDEB predicted loss-of-function polypeptide in a biological sample from the subject. In some embodiments, when the subject does not have a CIDEB predicted loss-of-function or polypeptide, the subject is also administered a therapeutic agent that treats or inhibits liver disease in a standard dosage amount. In some embodiments, when the subject has a CIDEB predicted loss-of-function polypeptide, the subject is also administered a therapeutic agent that treats or inhibits liver disease in a dosage amount that is the same as or less than a standard dosage amount.

In some embodiments, the treatment methods further comprise detecting the presence or absence of a PNPLA3 Ile148Met or an Ile144Met polypeptide in a biological sample from the subject. In some embodiments, when the subject has a CIDEB predicted loss-of-function polypeptide and a PNPLA3 Ile148Met or an Ile144Met polypeptide, the subject is also administered a therapeutic agent that treats or inhibits liver disease in a dosage amount that is the same as or greater than a standard dosage amount.

In some embodiments, the treatment methods further comprise detecting the presence or absence of a reference HSD17B13 polypeptide or a functional HSD17B13 polypeptide in a biological sample from the subject. In some embodiments, when the subject is homozygous for a nucleic acid molecule encoding a reference HSD17B13 polypeptide or a functional HSD17B13 polypeptide, the subject is administered a CIDEB inhibitor in an amount that is the same as or greater than a standard dosage amount, or is administered a combination of a CIDEB inhibitor in an amount that is the same as or greater than a standard dosage amount, an HSD17B13 inhibitor, and/or a PNPLA3 inhibitor. When the subject is not homozygous for a nucleic acid molecule encoding a reference HSD17B13 polypeptide or a functional HSD17B13 polypeptide (i.e., is a carrier for a loss-of-function HSD17B13), the subject is administered a CIDEB inhibitor in an amount that is less than a standard dosage amount, or is administered a combination of a CIDEB inhibitor in an amount that is less than a standard dosage amount, an HSD17B13 inhibitor, and/or a PNPLA3 inhibitor.

The present disclosure also provides methods of treating a subject with a CIDEB inhibitor, wherein the subject has a liver disease or is at risk of developing a liver disease. The methods comprise determining whether the subject has a CIDEB variant nucleic acid molecule by obtaining or having obtained a biological sample from the subject, and performing or having performed a sequence analysis on the biological sample to determine if the subject has a genotype comprising the CIDEB variant nucleic acid molecule. When the subject is CIDEB reference, the method further comprises administering or continuing to administer to the subject the CIDEB inhibitor in a standard dosage amount. When the subject is heterozygous for the CIDEB variant nucleic acid molecule, the method further comprises administering or continuing to administer to the subject the CIDEB inhibitor in a dosage amount that is the same as or less than a standard dosage amount. The presence of a genotype having the CIDEB variant nucleic acid molecule indicates the subject has a decreased risk of developing the liver disease or has a decreased risk of developing a more severe form of the liver disease. Determining whether the subject has a genotype comprising the CIDEB variant nucleic acid molecule can be carried out as described herein.

In some embodiments, the subject is CIDEB reference, and the subject is administered or continued to be administered the CIDEB inhibitor in a standard dosage amount. In some embodiments, the subject is heterozygous for the CIDEB variant nucleic acid molecule, and the subject is administered or continued to be administered the CIDEB inhibitor in a dosage amount that is the same as or less than a standard dosage amount.

In some embodiments, the subject is CIDEB reference or is heterozygous for the CIDEB variant nucleic acid molecule and the subject is a carrier of a nucleic acid molecule encoding a PNPLA3 Ile148Met or an Ile144Met polypeptide, the subject is administered or continued to be administered the CIDEB inhibitor and is also administered a PNPLA3 inhibitor and/or an HSD17B13 inhibitor.

In some embodiments, the subject is CIDEB reference or heterozygous for the CIDEB variant nucleic acid molecule and the subject is a carrier of a nucleic acid molecule encoding a reference HSD17B13 polypeptide or a functional HSD17B13 polypeptide, the subject is administered or continued to be administered the CIDEB inhibitor and is also administered an HSD17B13 inhibitor and/or a PNPLA3 inhibitor.

In any of the embodiments described herein, the method can further comprise administering a therapeutic agent for treating a liver disease to the subject.

In some embodiments, the subject being treated with the CIDEB inhibitor, the PNPLA3 inhibitor, or the HSD17B13 inhibitor, or any combination thereof, has excessive weight, has elevated BMI, is obese, has elevated body fat mass, has elevated percentage of liver fat, has elevated body fat percentage, has elevated body fat volume, and/or has excessive food intake. In some embodiments, the subject is obese. In some embodiments, the subject has excessive weight. In some embodiments, the subject has elevated BMI. In some embodiments, the subject has elevated body fat mass. In some embodiments, the subject has elevated body fat percentage. In some embodiments, the subject has elevated percentage of liver fat. In some embodiments, the subject has elevated body fat volume. In some embodiments, the subject has excessive food intake. In such subjects, the CIDEB inhibitor, the PNPLA3 inhibitor, or the HSD17B13 inhibitor, or any combination thereof, is administered to treat or prevent the complications of liver injury, liver fat accumulation, liver inflammation, fibrosis, liver cirrhosis or its comorbidities. In some embodiments, the CIDEB inhibitor, the PNPLA3 inhibitor, or the HSD17B13 inhibitor, or any combination thereof, is administered to treat or prevent the complications of liver injury, liver fat accumulation, liver inflammation, fibrosis, liver cirrhosis, or its comorbidities. In some embodiments, the CIDEB inhibitor, the PNPLA3 inhibitor, the HSD17B13 inhibitor, or any combination thereof, is administered to treat or prevent the complications of liver injury. In some embodiments, the CIDEB inhibitor, the PNPLA3 inhibitor, or the HSD17B13 inhibitor, or any combination thereof, is administered to treat or prevent the complications of liver fat accumulation. In some embodiments, the CIDEB inhibitor, the PNPLA3 inhibitor, or the HSD17B13 inhibitor, or any combination thereof, is administered to treat or prevent the complications of liver inflammation. In some embodiments, the CIDEB inhibitor, the PNPLA3 inhibitor, or the HSD17B13 inhibitor, or any combination thereof, is administered to treat or prevent the complications of fibrosis. In some embodiments, the CIDEB inhibitor, the PNPLA3 inhibitor, or the HSD17B13 inhibitor, or any combination thereof, is administered to treat or prevent the complications of liver cirrhosis or its comorbidities. In some embodiments, BMI is measured, body fat is determined, or fat distribution is determined to determine if the CIDEB inhibitor, the PNPLA3 inhibitor, or the HSD17B13 inhibitor, or any combination thereof, has to be used or used in different doses or patterns of administration. In some embodiments, BMI is measured. In some embodiments, body fat is determined. In some embodiments, fat distribution is determined. In some embodiments, the dosage of the CIDEB inhibitor, the PNPLA3 inhibitor, or the HSD17B13 inhibitor, or any combination thereof, can be increased upon an increase in any one or more of weight, BMI, obesity, body fat mass, liver fat percentage, body fat percentage, body fat volume, and/or food intake.

In some embodiments, the subject being treated with a CIDEB inhibitor, HSD17B13 inhibitor, and/or a PNPLA3 inhibitor is heterozygous or homozygous for a nucleic acid molecule encoding a PNPLA3 Ile148Met or Ile144Met polypeptide. In some embodiments, the subject being treated and having the PNPLA3 Ile148Met or Ile144Met polypeptide is administered the CIDEB inhibitor, the HSD17B13 inhibitor, and/or the PNPLA3 inhibitor to treat or prevent the complications of liver injury, liver fat accumulation, liver inflammation, fibrosis, liver cirrhosis or its comorbidities. In some embodiments, the CIDEB inhibitor, the HSD17B13 inhibitor, and/or the PNPLA3 inhibitor is administered to treat or prevent the complications of liver injury, liver fat accumulation, liver inflammation, fibrosis, liver cirrhosis or its comorbidities. In some embodiments, the CIDEB inhibitor, the HSD17B13 inhibitor, and/or the PNPLA3 inhibitor is administered to treat or prevent the complications of liver injury. In some embodiments, the CIDEB inhibitor, the HSD17B13 inhibitor, and/or the PNPLA3 inhibitor is administered to treat or prevent the complications of liver fat accumulation. In some embodiments, the CIDEB inhibitor, the HSD17B13 inhibitor, and/or the PNPLA3 inhibitor is administered to treat or prevent the complications of liver inflammation. In some embodiments, the CIDEB inhibitor, the HSD17B13 inhibitor, and/or the PNPLA3 inhibitor is administered to treat or prevent the complications of fibrosis. In some embodiments, the CIDEB inhibitor, the HSD17B13 inhibitor, and/or the PNPLA3 inhibitor is administered to treat or prevent the complications of liver cirrhosis or its comorbidities. In some embodiments, the methods further comprise genetic testing for the PNPLA3 Ile148Met or Ile144Met polypeptide to determine if the PNPLA3 inhibitor has to be used or used in a different dose or pattern of administration.

The present disclosure also provides methods of treating a subject having a liver disease or is at risk of developing a liver disease and who is heterozygous or homozygous for a nucleic acid molecule encoding a PNPLA3 Ile148Met or Ile144Met polypeptide, the methods comprising administering a CIDEB inhibitor, an HSD17B13 inhibitor, and/or a PNPLA3 inhibitor to the subject.

The amino acid sequences for two reference PNPLA3 polypeptides are set forth in SEQ ID NO:38 and SEQ ID NO:39. The reference PNPLA3 polypeptide having SEQ ID NO:38 is 481 amino acids in length, whereas the reference PNPLA3 polypeptide having SEQ ID NO:39 is 477 amino acids in length. The reference PNPLA3 polypeptide having SEQ ID NO:38 has an isoleucine at position 148. The reference PNPLA3 polypeptide having SEQ ID NO:39 has an isoleucine at position 144.

The PNPLA3 Ile148Met polypeptide comprises an amino acid sequence set forth in SEQ ID NO:40, where the isoleucine at position 148 is replaced with a methionine. The PNPLA3 Ile144Met polypeptide comprises an amino acid sequence set forth in SEQ ID NO:41, where the isoleucine at position 144 is replaced with a methionine.

The nucleotide sequence of a PNPLA3 genomic nucleic acid molecule encoding a reference PNPLA3 polypeptide is set forth in SEQ ID NO:42. The reference PNPLA3 genomic nucleic acid molecule having SEQ ID NO:42 comprises a cytosine at position 5109. The reference PNPLA3 genomic nucleic acid molecule having SEQ ID NO:42 comprises an ATC codon at positions 5107 to 5109.

The nucleotide sequence of a PNPLA3 variant genomic nucleic acid molecule encoding the PNPLA3 Ile148Met and Ile144Met polypeptide is set forth in SEQ ID NO:43, wherein the cytosine at the position corresponding to position 5109 of the reference PNPLA3 genomic nucleic acid molecule (according to SEQ ID NO:42) is replaced with a guanine, and the ATC codon at the positions corresponding to positions 5107 to 5109 of the reference PNPLA3 genomic DNA molecule (according to SEQ ID NO:42) is replaced by an ATG codon.

The nucleotide sequence of a PNPLA3 mRNA molecule encoding a PNPLA3 reference polypeptide having SEQ ID NO:38 is set forth in SEQ ID NO:44. The mRNA molecule encoding the PNPLA3 reference polypeptide having SEQ ID NO:38 comprises a cytosine at position 444. The mRNA molecule encoding the PNPLA3 reference polypeptide having SEQ ID NO:38 comprises an AUC codon at the positions 442 to 444. The nucleotide sequence of a PNPLA3 mRNA molecule encoding a PNPLA3 reference polypeptide having SEQ ID NO:39 is set forth in SEQ ID NO:45. The mRNA molecule encoding the PNPLA3 reference polypeptide having SEQ ID NO:39 comprises a cytosine at position 432. The mRNA molecule encoding the PNPLA3 reference polypeptide having SEQ ID NO:39 comprises an AUC codon at positions 430 to 432.

The nucleotide sequence of a PNPLA3 mRNA molecule encoding a PNPLA3 Ile148Met polypeptide is set forth in SEQ ID NO:46, wherein the cytosine at the position corresponding to position 444 of the PNPLA3 reference mRNA molecule (according to SEQ ID NO:44) is replaced with a guanine, and the AUC codon at positions corresponding to positions 442 to 444 of the PNPLA3 reference mRNA molecule (according to SEQ ID NO:44) is replaced by an AUG codon. The nucleotide sequence of a PNPLA3 mRNA molecule encoding a PNPLA3 Ile144Met polypeptide is set forth in SEQ ID NO:47, wherein the cytosine at the position corresponding to position 432 of the PNPLA3 reference mRNA molecule (according to SEQ ID NO:45) is replaced with a guanine, and the AUC codon at the positions corresponding to positions 430 to 432 of the PNPLA3 reference mRNA molecule (according to SEQ ID NO:45) is replaced by an AUG codon.

The nucleotide sequence of a PNPLA3 cDNA molecule encoding a PNPLA3 reference polypeptide having SEQ ID NO:38 is set forth in SEQ ID NO:48. The cDNA molecule encoding the PNPLA3 reference polypeptide having SEQ ID NO:38 comprises a cytosine at position 444. The cDNA molecule encoding the PNPLA3 reference polypeptide having SEQ ID NO:38 comprises an ATC codon at positions 442 to 444. The nucleotide sequence of a PNPLA3 cDNA molecule encoding a PNPLA3 reference polypeptide having SEQ ID NO:39 is set forth in SEQ ID NO:49. The cDNA molecule encoding the PNPLA3 reference polypeptide having SEQ ID NO:39 comprises a cytosine at position 432. The cDNA molecule encoding the PNPLA3 reference polypeptide having SEQ ID NO:39 comprises an ATC codon at positions 430 to 432.

The nucleotide sequence of a PNPLA3 cDNA molecule encoding PNPLA3 Ile148Met polypeptide is set forth in SEQ ID NO:50, wherein the cytosine at the position corresponding to position 444 of the PNPLA3 reference cDNA molecule (according to SEQ ID NO:48) is replaced with a guanine, and the ATC codon at positions corresponding to positions 442 to 444 of the PNPLA3 reference cDNA molecule (according to SEQ ID NO:48) is replaced by an ATG codon. The nucleotide sequence of a PNPLA3 cDNA molecule encoding PNPLA3 Ile144Met polypeptide is set forth in SEQ ID NO:51, wherein the cytosine at the position corresponding to position 432 of the PNPLA3 reference cDNA molecule (according to SEQ ID NO:49) is replaced with a guanine, and the ATC codon at positions corresponding to positions 430 to 432 of the PNPLA3 reference cDNA molecule (according to SEQ ID NO:49) is replaced by an ATG codon.

The present disclosure also provides methods of treating a subject with a CIDEB inhibitor and/or a PNPLA3 inhibitor and/or an HSD17B13 inhibitor, wherein the subject has a liver disease or is at risk of developing a liver disease, the methods comprising: determining whether the subject has a nucleic acid molecule encoding a PNPLA3 Ile148Met or Ile144Met polypeptide by: obtaining or having obtained a biological sample from the subject; and performing or having performed a sequence analysis on the biological sample to determine if the subject has a genotype comprising the nucleic acid molecule encoding the PNPLA3 Ile148Met or Ile144Met polypeptide; and administering or continuing to administer the CIDEB inhibitor and/or a PNPLA3 inhibitor and/or an HSD17B13 inhibitor to a subject that is heterozygous or homozygous for the nucleic acid molecule encoding the PNPLA3 Ile148Met or Ile144Met polypeptide; wherein the presence of a genotype having the PNPLA3 nucleic acid molecule encoding the Ile148Met or Ile144Met polypeptide indicates the subject is a candidate for treatment with the CIDEB inhibitor and/or the HSD17B13 inhibitor and/or the PNPLA3 inhibitor. In some embodiments, the PNPLA3 nucleic acid molecule encodes PNPLA3 Ile148Met. In some embodiments, the PNPLA3 nucleic acid molecule encodes PNPLA3 Ile144Met. In some embodiments, the subject is also administered a therapeutic agent that treats or inhibits liver disease.

In some embodiments, the PNPLA3 nucleic acid molecule encoding the Ile148Met or Ile144Met polypeptide is: a genomic nucleic acid molecule having a nucleotide sequence comprising a guanine at a position corresponding to position 5109 according to SEQ ID NO:43; an mRNA molecule having a nucleotide sequence comprising a guanine at a position corresponding to position 444 according to SEQ ID NO:46, or a guanine at a position corresponding to position 432 according to SEQ ID NO:47; or a cDNA molecule produced from an mRNA molecule, wherein the cDNA molecule has a nucleotide sequence comprising a guanine at a position corresponding to position 444 according to SEQ ID NO: 50, or a guanine at a position corresponding to position 432 according to SEQ ID NO:51.

Methods of detection of any of the PNPLA3 genomic nucleic acid molecules, mRNA molecules, cDNA molecules, or polypeptides can be carried out by gene chip assays, bead assays, sequencing, or immunoassays.

In some embodiments, the sequence analysis comprises sequencing at least a portion of the nucleotide sequence of the PNPLA3 genomic nucleic acid molecule in the biological sample, wherein the sequenced portion comprises a position corresponding to position 5109 according to SEQ ID NO:43, or the complement thereof. In some embodiments, the sequence analysis comprises sequencing at least a portion of the nucleotide sequence of the PNPLA3 mRNA molecule in the biological sample, wherein the sequenced portion comprises a position corresponding to position 444 according to SEQ ID NO:46, or the complement thereof, or position 432 according to SEQ ID NO:47, or the complement thereof. In some embodiments, the sequence analysis comprises sequencing at least a portion of the nucleotide sequence of the PNPLA3 cDNA molecule in the biological sample, wherein the sequenced portion comprises a position corresponding to position 444 according to SEQ ID NO:50, or the complement thereof, or position 432 according to SEQ ID NO:51, or the complement thereof.

In some embodiments, the sequence analysis comprises: a) contacting the biological sample with a primer hybridizing to a portion of the nucleotide sequence of the PNPLA3 genomic nucleic acid molecule that is proximate to a position corresponding to position 5109 according to SEQ ID NO:43; b) extending the primer at least through the position of the nucleotide sequence of the PNPLA3 genomic nucleic acid molecule corresponding to position 5109 according to SEQ ID NO:43; and c) determining whether the extension product of the primer comprises a guanine at a position corresponding to position 5109 according to SEQ ID NO:43.

In some embodiments, the sequence analysis comprises: a) contacting the biological sample with a primer hybridizing to a portion of the nucleotide sequence of the PNPLA3 mRNA molecule that is proximate to a position corresponding to position 444 according to SEQ ID NO:46, or position 432 according to SEQ ID NO:47; b) extending the primer at least through the position of the nucleotide sequence of the PNPLA3 mRNA molecule corresponding to position 444 according to SEQ ID NO:46, or position 432 according to SEQ ID NO:47; and c) determining whether the extension product of the primer comprises a guanine at a position corresponding to position 444 according to SEQ ID NO:46, or a guanine at a position corresponding to position 432 according to SEQ ID NO:47.

In some embodiments, the sequence analysis comprises: a) contacting the biological sample with a primer hybridizing to a portion of the nucleotide sequence of the PNPLA3 cDNA molecule that is proximate to a position corresponding to position 444 according to SEQ ID NO:50, or position 432 according to SEQ ID NO:51; b) extending the primer at least through the position of the nucleotide sequence of the PNPLA3 cDNA molecule corresponding to position 444 according to SEQ ID NO:50, or position 432 according to SEQ ID NO:51; and c) determining whether the extension product of the primer comprises a guanine at a position corresponding to position 444 according to SEQ ID NO:50, or a guanine at a position corresponding to position 432 according to SEQ ID NO:51.

In some embodiments, the sequence analysis comprises sequencing the entire nucleic acid molecule.

In some embodiments, the sequence analysis comprises: a) amplifying at least a portion of the nucleic acid molecule that encodes the PNPLA3 polypeptide, wherein the portion comprises a guanine at a position corresponding to position 5109 according to SEQ ID NO:43, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising a guanine at a position corresponding to position 5109 according to SEQ ID NO:43, or the complement thereof; and d) detecting the detectable label.

In some embodiments, the sequence analysis comprises: a) amplifying at least a portion of the nucleic acid molecule that encodes the PNPLA3 polypeptide, wherein the portion comprises a guanine at a position corresponding to position 444 according to SEQ ID NO:46, or the complement thereof; or a guanine at a position corresponding to position 432 according to SEQ ID NO:47, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising a guanine at a position corresponding to position 444 according to SEQ ID NO:46, or the complement thereof; or a guanine at a position corresponding to position 432 according to SEQ ID NO:47, or the complement thereof; and d) detecting the detectable label.

In some embodiments, the sequence analysis comprises: a) amplifying at least a portion of the nucleic acid molecule that encodes the PNPLA3 polypeptide, wherein the portion comprises a guanine at a position corresponding to position 444 according to SEQ ID NO:50, or the complement thereof; or a guanine at a position corresponding to position 432 according to SEQ ID NO:51, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising a guanine at a position corresponding to position 444 according to SEQ ID NO:50, or the complement thereof; or a guanine at a position corresponding to position 432 according to SEQ ID NO:51, or the complement thereof; and d) detecting the detectable label. In some embodiments, the nucleic acid molecule in the sample is mRNA and the mRNA is reverse-transcribed into cDNA prior to the amplifying step.

In some embodiments, the sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising a guanine at a position corresponding to position 5109 according to SEQ ID NO:43, or the complement thereof; and detecting the detectable label. In some embodiments, the sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising a guanine at a position corresponding to position 444 according to SEQ ID NO:46, or the complement thereof; or a guanine at a position corresponding to position 432 according to SEQ ID NO:47, or the complement thereof; and detecting the detectable label. In some embodiments, the sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising a guanine at a position corresponding to position 444 according to SEQ ID NO:50, or the complement thereof; or a guanine at a position corresponding to position 432 according to SEQ ID NO:51, or the complement thereof; and detecting the detectable label.

In some embodiments, the subject being treated with a CIDEB inhibitor, an HSD17B13 inhibitor, and/or a PNPLA3 inhibitor is heterozygous or homozygous for a nucleic acid molecule encoding a reference HSD17B13 polypeptide or a functional HSD17B13 polypeptide. In some embodiments, the subject being treated and having a nucleic acid molecule encoding a reference HSD17B13 polypeptide or a functional HSD17B13 polypeptide is administered the CIDEB inhibitor, the HSD17B13 inhibitor, and/or the PNPLA3 inhibitor to treat or prevent the complications of liver injury, liver fat accumulation, liver inflammation, fibrosis, liver cirrhosis or its comorbidities. In some embodiments, the CIDEB inhibitor, the HSD17B13 inhibitor, and/or the PNPLA3 inhibitor is administered to treat or prevent the complications of liver injury, liver fat accumulation, liver inflammation, fibrosis, liver cirrhosis or its comorbidities. In some embodiments, the CIDEB inhibitor, the HSD17B13 inhibitor, and/or the PNPLA3 inhibitor is administered to treat or prevent the complications of liver injury. In some embodiments, the CIDEB inhibitor, the HSD17B13 inhibitor, and/or the PNPLA3 inhibitor is administered to treat or prevent the complications of liver fat accumulation. In some embodiments, the CIDEB inhibitor, the HSD17B13 inhibitor, and/or the PNPLA3 inhibitor is administered to treat or prevent the complications of liver inflammation. In some embodiments, the CIDEB inhibitor, the HSD17B13 inhibitor, and/or the PNPLA3 inhibitor is administered to treat or prevent the complications of fibrosis. In some embodiments, the CIDEB inhibitor, the HSD17B13 inhibitor, and/or the PNPLA3 inhibitor is administered to treat or prevent the complications of liver cirrhosis or its comorbidities. In some embodiments, the methods further comprise genetic testing for the reference HSD17B13 polypeptide or a functional HSD17B13 polypeptide to determine if the CIDEB inhibitor, the HSD17B13 inhibitor, and/or the PNPLA3 inhibitor has to be used or used in different doses or patterns of administration.

The present disclosure also provides methods of treating a subject having a liver disease or at risk of developing a liver disease and who is heterozygous or homozygous for a nucleic acid encoding a reference HSD17B13 polypeptide or a functional HSD17B13 polypeptide, the methods comprising administering a CIDEB inhibitor, an HSD17B13 inhibitor, and/or a PNPLA3 inhibitor to the subject.

The amino acid sequences of two reference HSD17B13 polypeptides are set forth in SEQ ID NO:73 and SEQ ID NO:74. The reference HSD17B13 polypeptide having SEQ ID NO:73 is 264 amino acids in length, whereas the reference HSD17B13 polypeptide having SEQ ID NO:74 is 300 amino acids in length.

The nucleotide sequence of a genomic nucleic acid molecule encoding a reference HSD17B13 polypeptide is set forth in SEQ ID NO:52 (corresponding to ENSG00000170509.8 located at chr4:87,303,789-87,322,906 according to GRCh38/hg38 Human Genome Assembly).

The nucleotide sequence of an mRNA molecule encoding a reference HSD17B13 polypeptide is set forth in SEQ ID NO:53. The nucleotide sequence of another mRNA molecule encoding a reference HSD17B13 polypeptide is set forth in SEQ ID NO:54. The nucleotide sequence of another mRNA molecule encoding a reference HSD17B13 polypeptide is set forth in SEQ ID NO:55. The nucleotide sequence of another mRNA molecule encoding a reference HSD17B13 polypeptide is set forth in SEQ ID NO:56. The nucleotide sequence of another mRNA molecule encoding a reference HSD17B13 polypeptide is set forth in SEQ ID NO:57. The nucleotide sequence of another mRNA molecule encoding a reference HSD17B13 polypeptide is set forth in SEQ ID NO:58. The nucleotide sequence of another mRNA molecule encoding a reference HSD17B13 polypeptide is set forth in SEQ ID NO:59. The nucleotide sequence of another mRNA molecule encoding a reference HSD17B13 polypeptide is set forth in SEQ ID NO:60. The nucleotide sequence of another mRNA molecule encoding a reference HSD17B13 polypeptide is set forth in SEQ ID NO:61. The nucleotide sequence of another mRNA molecule encoding a reference HSD17B13 polypeptide is set forth in SEQ ID NO:62.

The nucleotide sequence of a cDNA molecule encoding a reference HSD17B13 polypeptide is set forth in SEQ ID NO:63. The nucleotide sequence of another cDNA molecule encoding a reference HSD17B13 polypeptide is set forth in SEQ ID NO:64. The nucleotide sequence of another cDNA molecule encoding a reference HSD17B13 polypeptide is set forth in SEQ ID NO:65. The nucleotide sequence of another cDNA molecule encoding a reference HSD17B13 polypeptide is set forth in SEQ ID NO:66. The nucleotide sequence of another cDNA molecule encoding a reference HSD17B13 polypeptide is set forth in SEQ ID NO:67. The nucleotide sequence of another cDNA molecule encoding a reference HSD17B13 polypeptide is set forth in SEQ ID NO:68. The nucleotide sequence of another cDNA molecule encoding a reference HSD17B13 polypeptide is set forth in SEQ ID NO:69. The nucleotide sequence of another cDNA molecule encoding a reference HSD17B13 polypeptide is set forth in SEQ ID NO:70. The nucleotide sequence of another cDNA molecule encoding a reference HSD17B13 polypeptide is set forth in SEQ ID NO:71. The nucleotide sequence of another cDNA molecule encoding a reference HSD17B13 polypeptide is set forth in SEQ ID NO:72.

The present disclosure also provides methods of treating a subject with a CIDEB inhibitor, an HSD17B13 inhibitor, and/or a PNPLA3 inhibitor, wherein the subject has a liver disease or is at risk of developing a liver disease, the methods comprising: determining whether the subject has a nucleic acid molecule encoding a reference HSD17B13 polypeptide or a functional HSD17B13 polypeptide by: obtaining or having obtained a biological sample from the subject; and performing or having performed an assay on the biological sample to determine whether the subject has: i) an HSD17B13 genomic nucleic acid molecule comprising SEQ ID NO:52, or a nucleotide sequence having at least 90% sequence identity to SEQ ID NO:52 and encoding a reference HSD17B13 polypeptide or a functional HSD17B13 polypeptide; ii) an HSD17B13 mRNA molecule comprising any one of SEQ ID NOs:53-62 or a nucleotide sequence having at least 90% sequence identity to any one of SEQ ID NOs:53-62 and encoding a reference HSD17B13 polypeptide or a functional HSD17B13 polypeptide; or iii) an HSD17B13 cDNA molecule comprising any one of SEQ ID NOs:63-72 or a nucleotide sequence having at least 90% sequence identity to any one of SEQ ID NOs:63-72 and encoding a reference HSD17B13 polypeptide or a functional HSD17B13 polypeptide, wherein the presence of a genotype having a nucleic acid molecule encoding a reference HSD17B13 polypeptide or a functional HSD17B13 polypeptide indicates the subject is a candidate for treatment with the CIDEB inhibitor, the HSD17B13 inhibitor, and/or the PNPLA3 inhibitor. In some embodiments, the subject is also administered a therapeutic agent that treats or inhibits liver disease.

In some embodiments, the nucleic acid molecule encoding the reference HSD17B13 polypeptide or a functional HSD17B13 polypeptide is: a genomic nucleic acid molecule comprising the nucleotide sequence according to SEQ ID NO:52, or a nucleotide sequence having at least 90% sequence identity to SEQ ID NO:52 and encoding a reference HSD17B13 polypeptide or a functional HSD17B13 polypeptide; an mRNA comprising the nucleotide sequence according to any one of SEQ ID NOs:53-62, or a nucleotide sequence having at least 90% sequence identity to any one of SEQ ID NOs:53-62 and encoding a reference HSD17B13 polypeptide or a functional HSD17B13 polypeptide; or a cDNA comprising the nucleotide sequence according to any one of SEQ ID NOs:63-72 or a nucleotide sequence having at least 90% sequence identity to any one of SEQ ID NOs:63-72 and encoding a reference HSD17B13 polypeptide or a functional HSD17B13 polypeptide.

Methods of detection of any of the HSD17B13 genomic nucleic acid molecules, mRNA molecules, cDNA molecules, or polypeptides can be carried out by gene chip assays, bead assays, sequencing, or immunoassays.

In some embodiments, the sequence analysis comprises sequencing at least a portion of the nucleotide sequence of the HSD17B13 genomic DNA, mRNA or cDNA produced from mRNA molecule in the biological sample.

In some embodiments, the sequence analysis comprises sequencing the entire nucleic acid molecule.

In some embodiments, the nucleic acid molecule is present within a cell obtained from the subject.

In some embodiments, the CIDEB inhibitor comprises an inhibitory nucleic acid molecule. In some embodiments, the inhibitory nucleic acid molecule comprises an antisense nucleic acid molecule, an siRNA, or an shRNA that hybridizes to a CIDEB nucleic acid molecule.

Examples of therapeutic agents that treat or inhibit liver disease include, but are not limited to: disulfiram, naltrexone, acamprosate, prednisone, azathioprine, penicillamine, trientine, deferoxamine, ciprofloxacin, norofloxacin, ceftriaxone, ofloxacin, amoxicillin-clavulanate, phytonadione, bumetanide, furosemide, hydrochlorothiazide, chlorothiazide, amiloride, triamterene, spironolactone, octreotide, atenolol, metoprolol, nadolol, propranolol, timolol, and carvedilol, or any combination thereof.

Additional examples of liver disease therapeutic agents (e.g., for use in chronic hepatitis C treatment) include, but are not limited to, ribavirin, paritaprevir, OLYSIO® (simeprevir), grazoprevir, ledipasvir, ombitasvir, elbasvir, DAKLINZA® (daclatasvir), dasabuvir, ritonavir, sofosbuvir, velpatasvir, voxilaprevir, glecaprevir, pibrentasvir, peginterferon alfa-2a, peginterferon alfa-2b, and interferon alfa-2b, or any combination thereof.

Additional examples of liver disease therapeutic agents (e.g., for use in nonalcoholic fatty liver disease) include, but are not limited to, weight loss inducing agents such as orlistat or sibutramine; insulin sensitizing agents such as thiazolidinediones (TZDs), metformin, and meglitinides; lipid lowering agents such as statins, fibrates, and omega-3 fatty acids; antioxidants such as, vitamin E, betaine, N-Acetyl-cysteine, lecithin, silymarin, and beta-carotene; anti TNF agents such as pentoxifylline; probiotics, such as VSL #3; and cytoprotective agents such as ursodeoxycholic acid (UDCA), or any combination thereof. Other suitable treatments include ACE inhibitors/ARBs, oligofructose, and Incretin analogs.

Additional examples of liver disease therapeutic agents (e.g., for use in NASH) include, but are not limited to, OCALIVA® (obeticholic acid), Selonsertib, Elafibranor, Cenicriviroc, GR_MD_02, MGL_3196, IMM124E, ARAMCHOL™ (arachidyl amido cholanoic acid), GS0976, Emricasan, Volixibat, NGM282, GS9674, Tropifexor, MN_001, LMB763, BI_1467335, MSDC_0602, PF_05221304, DF102, Saroglitazar, BMS986036, Lanifibranor, Semaglutide, Nitazoxanide, GRI_0621, EYP001, VK2809, Nalmefene, LIK066, MT_3995, Elobixibat, Namodenoson, Foralumab, SAR425899, Sotagliflozin, EDP_305, Isosabutate, Gemcabene, TERN_101, KBP_042, PF_06865571, DUR928, PF_06835919, NGM313, BMS_986171, Namacizumab, CER_209, ND_L02_s0201, RTU_1096, DRX_065, IONIS_DGAT2Rx, INT_767, NC_001, Seladepar, PXL770, TERN_201, NV556, AZD2693, SP_1373, VK0214, Hepastem, TGFTX4, RLBN1127, GKT_137831, RYI_018, CB4209-CB4211, and JH_0920, or any combination thereof.

Administration of the CIDEB inhibitor, PNPLA3 inhibitor, or HSD17B13 inhibitor, or any combination thereof, and/or therapeutic agents that treat or inhibit a liver disease can be repeated, for example, after one day, two days, three days, five days, one week, two weeks, three weeks, one month, five weeks, six weeks, seven weeks, eight weeks, two months, or three months. The repeated administration can be at the same dose or at a different dose. The administration can be repeated once, twice, three times, four times, five times, six times, seven times, eight times, nine times, ten times, or more. For example, according to certain dosage regimens a subject can receive therapy for a prolonged period of time such as, for example, 6 months, 1 year, or more.

Administration of the CIDEB inhibitor, PNPLA3 inhibitor, or HSD17B13 inhibitor, or any combination thereof, and/or therapeutic agents that treat or inhibit a liver disease can occur by any suitable route including, but not limited to, parenteral, intravenous, oral, subcutaneous, intra-arterial, intracranial, intrathecal, intraperitoneal, topical, intranasal, or intramuscular. Pharmaceutical compositions for administration are desirably sterile and substantially isotonic and manufactured under GMP conditions. Pharmaceutical compositions can be provided in unit dosage form (i.e., the dosage for a single administration). Pharmaceutical compositions can be formulated using one or more physiologically and pharmaceutically acceptable carriers, diluents, excipients or auxiliaries. The formulation depends on the route of administration chosen. The term "pharmaceutically acceptable" means that the carrier, diluent, excipient, or auxiliary is compatible with the other ingredients of the formulation and not substantially deleterious to the recipient thereof.

In any of the embodiments described herein, the subject can have or be at risk of developing any one or more of the liver diseases described herein. In some embodiments, the subject is CIDEB reference. In some embodiments, the subject is heterozygous for a CIDEB variant nucleic acid molecule. In some embodiments, the subject is homozygous for a CIDEB variant nucleic acid molecule.

The present disclosure also provides methods of treating a subject, wherein the subject is overweight, obese, has increased body mass index (BMI), has high liver fat percentage, or has high adiposity, the methods comprising administering to the subject a CIDEB inhibitor in an amount that is the same as or greater than a standard dosage amount, or a CIDEB inhibitor in combination with a PNPLA3 inhibitor and/or an HSD17B13 inhibitor. In some embodiments, the subject is obese. In some embodiments, the subject is overweight. In some embodiments, the subject has increased BMI. In some embodiments, the subject has high adiposity.

The terms "treat", "treating", and "treatment" and "prevent", "preventing", and "prevention" as used herein, refer to eliciting the desired biological response, such as a therapeutic and prophylactic effect, respectively. In some embodiments, a therapeutic effect comprises one or more of a decrease and/or reduction in a liver disease, a decrease and/or reduction in the severity of a liver disease, a decrease and/or reduction in symptoms and liver disease-related effects, delaying the onset of symptoms and liver disease-related effects, reducing the severity of symptoms of liver disease-related effects, reducing the number of symptoms and liver disease-related effects, reducing the latency of symptoms and liver disease-related effects, an amelioration of symptoms and liver disease-related effects, reducing secondary symptoms, reducing secondary infections, preventing relapse to a liver disease, decreasing the number or frequency of relapse episodes, increasing latency between symptomatic episodes, increasing time to sustained progression, speeding recovery, or increasing efficacy of or decreasing resistance to alternative therapeutics, and/or an increased survival time of the affected host animal, following administration of the agent or composition comprising the agent. A prophylactic effect may comprise a complete or partial avoidance and/or inhibition or a delay of liver disease development and/or progression (such as, for example, a complete or partial avoidance/inhibition or a delay), and an increased survival time of the affected host animal, following administration of a therapeutic protocol. Treatment of liver disease encompasses the treatment of subjects already diagnosed as having any form of liver disease at any clinical stage or manifestation, the delay of the onset or evolution or aggravation or deterioration of the symptoms or signs of liver disease, and/or preventing and/or reducing the severity of a liver disease.

The present disclosure also provides methods of identifying a subject having an increased risk of developing a liver disease. In some embodiments, the methods comprise determining or having determined in a biological sample obtained from the subject the presence or absence of a CIDEB variant nucleic acid molecule (such as a genomic nucleic acid molecule, mRNA molecule, and/or cDNA molecule). When the subject lacks a CIDEB variant nucleic acid molecule (i.e., the subject is genotypically categorized as a CIDEB reference), then the subject has an increased risk of developing a liver disease. When the subject has a CIDEB variant nucleic acid molecule (i.e., the subject is heterozygous or homozygous for a CIDEB variant nucleic acid molecule), then the subject has a decreased risk of developing a liver disease compared to a subject who is CIDEB reference.

Having a single copy of a CIDEB variant nucleic acid molecule is more protective of a subject from developing a liver disease than having no copies of a CIDEB variant nucleic acid molecule. Without intending to be limited to any particular theory or mechanism of action, it is believed that a single copy of a CIDEB variant nucleic acid molecule (i.e., heterozygous for a CIDEB variant nucleic acid molecule) is protective of a subject from developing a liver disease, and it is also believed that having two copies of a CIDEB variant nucleic acid molecule (i.e., homozygous for a CIDEB variant nucleic acid molecule) may be more protective of a subject from developing a liver disease, relative to a subject with a single copy. Thus, in some embodiments, a single copy of a CIDEB variant nucleic acid molecule may not be completely protective, but instead, may be partially or incompletely protective of a subject from developing a liver disease. While not desiring to be bound by any particular theory, there may be additional factors or molecules involved in the development of a liver disease that are still present in a subject having a single copy of a CIDEB variant nucleic acid molecule, thus resulting in less than complete protection from the development of a liver disease.

Determining whether a subject has a CIDEB variant nucleic acid molecule in a biological sample from a subject and/or determining whether a subject has a CIDEB variant nucleic acid molecule can be carried out by any of the methods described herein. In some embodiments, these methods can be carried out in vitro. In some embodiments, these methods can be carried out in situ. In some embodiments, these methods can be carried out in vivo. In any of these embodiments, the nucleic acid molecule can be present within a cell obtained from the subject.

The present disclosure also provides methods of identifying a subject having an increased risk of developing a liver disease, such as fatty liver disease, parenchymal liver disease, liver cirrhosis, and/or fibrosis, wherein the methods comprise determining or having determined the subject's gene burden of having one or more CIDEB variant genomic nucleic acid molecules described herein, one or more CIDEB variant mRNA molecules described herein, or one or more variant cDNA molecules described herein, and/or one or more CIDEB predicted loss-of-function polypeptides or missense polypeptides described herein. The greater the gene burden the subject has, the lower the risk of developing a liver disease. The lower the gene burden the subject has, the greater the risk of developing a liver disease.

In some embodiments, the subject's gene burden of having a plurality of (or all) CIDEB variant nucleic acid molecules represents a weighted sum of a plurality of genetic variants associated with protection against developing a liver disease. In some embodiments, the gene burden is calculated using at least about 2, at least about 3, at least about 4, at least about 5, at least about 10, at least about 20, at least about 30, at least about 40, at least about 50, at least about 60, at least about 70, at least about 80, at least about 100, at least about 120, at least about 150, at least about 200, at least about 250, at least about 300, at least about 400, at least about 500, or at least about 1,000 genetic variants associated with liver disease. In some embodiments, when the subject has a gene burden greater than a threshold score, the subject has a decreased risk of developing a liver disease. In some embodiments, when the subject has a gene burden below a threshold score, the subject has an increased risk of developing a liver disease.

In some embodiments, the gene burden is determined by consideration of one or more, or each, of the following variants: 14:24305635:A:AGTAG, 14:24305641:A:C, 14:24305650:G:A, 14:24305657:C:A, 14:24305662:G:T, 14:24305667:T:C, 14:24305671:C:A, 14:24305671:C:G, 14:24305701:A:T, 14:24305709:C:T, 14:24305718:A:G, 14:24305721:T:C, 14:24305728:G:GGCCTT, 14:24305743:T:C, 14:24305948:T:C, 14:24305966:C:T, 14:24305974:T:C, 14:24305980:TCA:T, 14:24305988:C:T, 14:24306014:C:T, 14:24306034:A:C, 14:24306041:C:G, 14:24306044:G:A, 14:24306047:G:A, 14:24306051:T:G, 14:24306064:T:C, 14:24306074:A:G, 14:24306077:G:C, 14:24306082:A:G, 14:24306083:T:A, 14:24306095:G:A, 14:24306122:A:G, 14:24306134:C:G, 14:24306373:C:G, 14:24306379:T:C, 14:24306382:G:A, 14:24306383:G:T, 14:24306426:T:G, 14:24306437:C:G, 14:24306439:G:C, 14:24306442:A:G, 14:24306444:A:G, 14:24306457:C:T, 14:24306463:C:T, 14:24306469:C:T, 14:24306480:A:G, 14:24306486:A:C, 14:24306504:A:G, 14:24306519:A:G, 14:24307382:G:C, 14:24307405:A:G, 14:24307417:A:T, 14:24307421:T:A, 14:24307441:C:A, 14:24307444:A:C, 14:24307444:A:G, 14:24307450:C:CGCTG, 14:24307461:TG:T, 14:24307469:AG:A, 14:24307474:C:T, 14:24307475:A:G, 14:24307833:G:C, 14:24307851:T:TAC, 14:24306426:T:C, 14:24307849:G:C, 14:24307448:G:T, 14:24305671:C:T, 14:24305663:C:T, 14:24305686:C:G, 14:24307829:A:C, 14:24307818:CTGAG:C, 14:24307856:C:T, 14:24306423:T:C, 14:24306061:AC:A, 14:24307390:C:T, 14:24306382:G:T, 14:24306373:C:T, 14:24305733:T:C, 14:24307858:T:C, 14:24306387:C:T, 14:24305637:T:C, 14:24306062:C:T, 14:24307853:C:G, 14:24307450:C:G, 14:24306052:TG:T, 14:24305673:G:A, 14:24306043:C:T, 14:24307834:G:A, 14:24306417:C:T, 14:24307451:G:A, 14:24307436:A:C, 14:24305953:ACTTT:A, 14:24306489:G:T, 14:24307441:C:T, 14:24306375:C:T, 14:24305657:C:G, 14:24306427:C:T, 14:24306524:C:T, 14:24307516:C:A, 14:24307840:G:C, 14:24307501:A:G, 14:24305968:A:C, 14:24305986:C:T, 14:24307441:C:G, 14:24307459:G:T, 14:24306017:T:A, 14:24307424:G:A, 14:24306072:G:T, 14:24307423:C:T, 14:24307450:C:T, 14:24306420:G:A, 14:24307454:G:A, 14:24305653:C:T, 14:24307442:G:A, 14:24306002:C:T, 14:24306076:C:T, 14:24305664:C:T, 14:24305961:TG:T, 14:24305706:A:G, 14:24305946:C:T, 14:24306455:G:C, 14:24307468:G:A, 14:24307825:A:C, 14:24306110:G:A, 14:24305710:C:T, 14:24307483:C:T, 14:24306459:A:G, 14:24305754:C:T, 14:24305650:G:C, 14:24305691:C:T, 14:24306508:G:C, 14:24306039:G:T, 14:24306139:T:C, 14:24306391:T:C, 14:24306373:C:A, 14:24307498:C:T, 14:24307415:G:A, 14:24306138:CTG:C, 14:24307453:T:C, 14:24305692:G:A, 14:24305683:C:G, 14:24307484:G:A, 14:24307385:C:T, 14:24306519:A:T, 14:24307839:A:C, 14:24305965:C:T, 14:24305988:CAT:C, 14:24306087:C:G, 14:24307439:C:T, 14:24307477:A:C, 14:24306436:G:T, 14:24306507:A:G, 14:24307397:C:T, 14:24307495:G:A, 14:24306034:A:T, 14:24306013:G:A, 14:24307381:A:G, 14:24306383:G:C, 14:24305638:A:G, 14:24307420:G:A, 14:24306020:C:T, 14:24306470:A:C, 14:24307435:C:T, 14:24306469:C:G, 14:24306451:C:T, 14:24306403:G:A, 14:24307515:C:G, 14:24307489:A:G, 14:24307414:C:T, 14:24306483:A:G, 14:24305755:G:A, 14:24305766:C:T, 14:24306064:T:G, 14:24307516:C:G, 14:24305766:C:G, 14:24306489:G:A, 14:24306097:T:C, 14:24305763:T:G, 14:24307447:G:A, 14:24307402:G:A, 14:24305972:C:G, 14:24306423:T:G, 14:24305974:T:TG, 14:24307411:T:C, 14:24306121:T:C, 14:24307516:C:T, 14:24306424:C:T, 14:24306039:G:C, 14:24307853:C:A, 14:24306388:A:G, 14:24305990:T:C, 14:24307822:G:GT, 14:24305640:G:A, 14:24307418:T:C, 14:24305758:G:C, 14:24306131:C:T, 14:24305953:A:G, 14:24305730:C:A, 14:24306418:A:G, 14:24306059:AC:A, 14:24307842:G:A, 14:24307837:T:G, 14:24306095:G:T, 14:24306109:C:T, 14:24307822:G:A, 14:24306077:G:A, 14:24307824:A:T, 14:24306080:C:T, 14:24305649:C:T, 14:24306433:G:GA, 14:24306420:G:C, 14:24305658:T:G, 14:24306472:C:T, 14:24307412:TC:T, 14:24306062:C:A, 14:24306044:G:C, 14:24306047:G:T, 14:24306126:CAG:C, 14:24306449:C:G, 14:24307391:G:A, or 14:24307857:A:C (according to GRCh38/hg38 human genome assembly coordinates).

In some embodiments, the gene burden may be divided into quintiles, e.g., top quintile, intermediate quintile, and bottom quintile, wherein the top quintile of gene burden corresponds to the lowest risk group and the bottom quintile of gene burden corresponds to the highest risk group.

In some embodiments, when a subject is identified as having an increased risk of developing a liver disease, the subject is further treated with a therapeutic agent that treats or inhibits liver disease and/or a CIDEB inhibitor, as described herein. For example, when the subject is CIDEB reference, and therefore has an increased risk of developing a liver disease, the subject can be administered a CIDEB inhibitor in a standard dosage amount. In some embodiments, such a subject is also administered a therapeutic agent that treats or inhibits a liver disease. In some embodiments, when the subject is heterozygous for a CIDEB variant nucleic acid molecule, the subject is administered the CIDEB inhibitor in a dosage amount that is the same as or less than a standard dosage amount, and can also be administered a therapeutic agent that treats or inhibits a liver disease. In some embodiments, the subject is CIDEB reference. In some embodiments, the subject is heterozygous for a CIDEB variant nucleic acid molecule.

The present disclosure also provides, in any of the methods described herein, the detection or determination of the presence of a CIDEB variant genomic nucleic acid molecule, a CIDEB variant mRNA molecule, and/or a CIDEB variant cDNA molecule produced from an mRNA molecule in a biological sample from a subject. It is understood that gene sequences within a population and mRNA molecules encoded by such genes can vary due to polymorphisms such as single-nucleotide polymorphisms. The sequences provided herein for the CIDEB variant nucleic acid molecules disclosed herein are only exemplary sequences. Other sequences for the CIDEB variant nucleic acid molecules are also possible.

The present disclosure also provides, in any of the methods described herein, the detection or determination of the presence of a genomic nucleic acid molecule encoding a PNPLA3 Ile148Met polypeptide or a PNPLA3 Ile144Met polypeptide, an mRNA molecule encoding a PNPLA3 Ile148Met polypeptide or a PNPLA3 Ile144Met polypeptide, a cDNA molecule encoding a PNPLA3 Ile148Met polypeptide or a PNPLA3 Ile144Met polypeptide, and/or a PNPLA3 Ile148Met polypeptide or a PNPLA3 Ile144Met polypeptide in a biological sample from the subject. It is understood that gene sequences within a population and mRNA molecules encoded by such genes can vary due to polymorphisms such as single-nucleotide polymorphisms. The sequences provided herein for the PNPLA3 variant nucleic acid molecules disclosed herein are only exemplary sequences. Other sequences for the PNPLA3 variant nucleic acid molecules are also possible. The detection or determination of the presence of PNPLA3 variant nucleic acid molecules is described in, for example, U.S. Pat. No. 10,961,583.

The present disclosure also provides, in any of the methods described herein, the detection or determination of the presence of a genomic nucleic acid molecule encoding a reference HSD17B13 polypeptide or a functional HSD17B13 polypeptide, an mRNA molecule encoding a reference HSD17B13 polypeptide or a functional HSD17B13 polypeptide, a cDNA molecule encoding a reference HSD17B13 polypeptide or a functional HSD17B13 polypeptide, and/or a reference HSD17B13 polypeptide or a functional HSD17B13 polypeptide in a biological sample from the subject. It is understood that gene sequences within a population and mRNA molecules encoded by such genes can vary due to polymorphisms such as single-nucleotide polymorphisms. The sequences provided herein for the HSD17B13 variant nucleic acid molecules disclosed herein are only exemplary sequences. Other sequences for the HSD17B13 nucleic acid molecules are also possible. The detection or determination of the presence of HSD17B13 nucleic acid molecules is described in, for example, U.S. Pat. No. 10,961,583.

The biological sample can be derived from any cell, tissue, or biological fluid from the subject. The sample may comprise any clinically relevant tissue, such as a bone marrow sample, a tumor biopsy, a fine needle aspirate, or a sample of bodily fluid, such as blood, gingival crevicular fluid, plasma, serum, lymph, ascitic fluid, cystic fluid, or urine. In some cases, the sample comprises a buccal swab. The sample used in the methods disclosed herein will vary based on the assay format, nature of the detection method, and the tissues, cells, or extracts that are used as the sample. A biological sample can be processed differently depending on the assay being employed. For example, when detecting any of the nucleic acid molecules, preliminary processing designed to isolate or enrich the sample for the genomic DNA can be employed. A variety of known techniques may be used for this purpose. When detecting the presence of or level of any CIDEB, PNPLA3, and/or HSD17B13 mRNA molecule, different techniques can be used enrich the biological sample with mRNA. Various methods to detect the presence or level of a mRNA or the presence of a particular variant genomic DNA locus can be used.

In some embodiments, detecting a CIDEB variant nucleic acid molecule in a subject comprises assaying or performing a sequence analysis on a biological sample obtained from the subject to determine whether a CIDEB genomic nucleic acid molecule, a CIDEB mRNA molecule, or a CIDEB cDNA molecule produced from an mRNA molecule in the biological sample is a CIDEB variant nucleic acid molecule.

In some embodiments, the methods of detecting the presence or absence of a CIDEB variant nucleic acid molecule (such as, for example, a genomic nucleic acid molecule, an mRNA molecule, and/or a cDNA molecule) in a subject, comprise performing an assay on a biological sample obtained from the subject, which assay determines whether a nucleic acid molecule in the biological sample comprises a particular nucleotide sequence.

In some embodiments, detecting a nucleic acid molecule encoding a PNPLA3 Ile148Met or Ile144Met polypeptide in a subject comprises assaying or performing a sequence analysis on a biological sample obtained from the subject to determine whether a PNPLA3 genomic nucleic acid molecule, a PNPLA3 mRNA molecule, or a PNPLA3 cDNA molecule produced from an mRNA molecule in the biological sample encodes an Ile148Met or Ile144Met polypeptide.

In some embodiments, the methods of detecting the presence or absence of a nucleic acid molecule encoding a PNPLA3 Ile148Met or Ile144Met polypeptide (such as, for example, a genomic nucleic acid molecule, an mRNA molecule, and/or a cDNA molecule) in a subject, comprise performing an assay on a biological sample obtained from the subject, which assay determines whether a nucleic acid molecule in the biological sample comprises a particular nucleotide sequence.

In some embodiments, detecting a nucleic acid molecule encoding a reference HSD17B13 polypeptide or a functional HSD17B13 polypeptide comprises assaying or performing a sequence analysis on a biological sample obtained from the subject to determine whether a HSD17B13 genomic nucleic acid molecule, a HSD17B13 mRNA molecule, or a HSD17B13 cDNA molecule produced from an mRNA molecule in the biological sample encodes a reference HSD17B13 polypeptide or a functional HSD17B13 polypeptide.

In some embodiments, the methods of detecting the presence or absence of a nucleic acid molecule encoding a reference HSD17B13 polypeptide or a functional HSD17B13 polypeptide (such as, for example, a genomic nucleic acid molecule, an mRNA molecule, and/or a cDNA molecule) in a subject, comprise performing an assay on a biological sample obtained from the subject, which assay determines whether a nucleic acid molecule in the biological sample comprises a particular nucleotide sequence.

In some embodiments, the biological sample comprises a cell or cell lysate. Such methods can further comprise, for example, obtaining a biological sample from the subject comprising a CIDEB, PNPLA3, and/or HSD17B13 genomic nucleic acid molecule or mRNA molecule, and if mRNA, optionally reverse transcribing the mRNA into cDNA. Such assays can comprise, for example determining the identity of these positions of the particular, CIDEB, PNPLA3, and/or HSD17B13 nucleic acid molecule. In some embodiments, the method is an in vitro method.

In some embodiments, the determining step, detecting step, or sequence analysis comprises sequencing at least a portion of the nucleotide sequence of the CIDEB, PNPLA3, and/or HSD17B13 genomic nucleic acid molecule, the CIDEB, PNPLA3, and/or HSD17B13 mRNA molecule, or the CIDEB, PNPLA3, and/or HSD17B13 cDNA molecule produced from the mRNA molecule in the biological sample, wherein the sequenced portion comprises one or more variations that cause a loss-of-function or missense (partial or complete) or are predicted to cause a loss-of-function or missense (partial or complete), such as any one or more of the CIDEB, PNPLA3, and/or HSD17B13 nucleic acid molecules described herein.

In any of the methods described herein, the determining step, detecting step, or sequence analysis comprises sequencing at least a portion of the nucleotide sequence of the CIDEB or PNPLA3 nucleic acid molecule in the biological sample, wherein the sequenced portion comprises a position corresponding to a variant nucleic acid molecule position, wherein when a variant nucleotide at the variant nucleic acid molecule position is detected, the CIDEB or PNPLA3 nucleic acid molecule in the biological sample is a CIDEB or PNPLA3 variant nucleic acid molecule.

In some embodiments, the determining step, detecting step, or sequence analysis comprises: a) contacting the biological sample with a primer hybridizing to a portion of the nucleotide sequence of the CIDEB nucleic acid molecule that is proximate to a variant nucleic acid molecule position; b) extending the primer at least through the variant nucleic acid molecule position; and c) determining whether the extension product of the primer comprises a variant nucleotide at the variant nucleic acid molecule position.

In some embodiments, the assay comprises sequencing the entire nucleic acid molecule. In some embodiments, only a CIDEB genomic nucleic acid molecule is analyzed. In some embodiments, only a CIDEB mRNA is analyzed. In some embodiments, only a CIDEB cDNA obtained from CIDEB mRNA is analyzed.

In some embodiments, the determining step, detecting step, or sequence analysis comprises: a) amplifying at least a portion of the CIDEB nucleic acid molecule that encodes the CIDEB polypeptide, wherein the portion comprises a variant nucleic acid molecule position; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the variant nucleic acid molecule position; and d) detecting the detectable label.

In any of the methods described herein, the determining step, detecting step, or sequence analysis comprises sequencing at least a portion of the nucleotide sequence of the nucleotide sequence of the PNPLA3 genomic nucleic acid molecule in the biological sample, wherein the sequenced portion comprises a position corresponding to position 5109 according to SEQ ID NO:43 (i.e., the variant nucleic acid molecule position), or the complement thereof. In some embodiments, the sequence analysis comprises sequencing at least a portion of the nucleotide sequence of the PNPLA3 mRNA molecule in the biological sample, wherein the sequenced portion comprises a position corresponding to position 444 according to SEQ ID NO:46 (i.e., the variant nucleic acid molecule position), or the complement thereof; or position 432 according to SEQ ID NO:47 (i.e., the variant nucleic acid molecule position), or the complement thereof. In some embodiments, the sequence analysis comprises sequencing at least a portion of the nucleotide sequence of the PNPLA3 cDNA molecule in the biological sample, wherein the sequenced portion comprises a position corresponding to position 444 according to SEQ ID NO:50 (i.e., the variant nucleic acid molecule position), or the complement thereof; or position 432 according to SEQ ID NO:51 (i.e., the variant nucleic acid molecule position), or the complement thereof.

In some embodiments, the sequence analysis comprises: a) contacting the biological sample with a primer hybridizing to a portion of the nucleotide sequence of the PNPLA3 genomic nucleic acid molecule that is proximate to a position corresponding to position 5109 according to SEQ ID NO:43; b) extending the primer at least through the position of the nucleotide sequence of the PNPLA3 genomic nucleic acid molecule corresponding to position 5109 according to SEQ ID NO:43; and c) determining whether the extension product of the primer comprises a guanine at a position corresponding to position 5109 according to SEQ ID NO:43.

In some embodiments, the sequence analysis comprises: a) contacting the biological sample with a primer hybridizing to a portion of the nucleotide sequence of the PNPLA3 mRNA molecule that is proximate to a position corresponding to position 444 according to SEQ ID NO:46, or position 432 according to SEQ ID NO:47; b) extending the primer at least through the position of the nucleotide sequence of the PNPLA3 mRNA molecule corresponding to position 444 according to SEQ ID NO:46, or position 432 according to SEQ ID NO:47; and c) determining whether the extension product of the primer comprises a guanine at a position corresponding to position 444 according to SEQ ID NO:46, or a guanine at a position corresponding to position 432 according to SEQ ID NO:47.

In some embodiments, the sequence analysis comprises: a) contacting the biological sample with a primer hybridizing to a portion of the nucleotide sequence of the PNPLA3 cDNA molecule that is proximate to a position corresponding to position 444 according to SEQ ID NO:50, or position 432 according to SEQ ID NO:51; b) extending the primer at least through the position of the nucleotide sequence of the PNPLA3 cDNA molecule corresponding to position 444 according to SEQ ID NO:50, or position 432 according to SEQ ID NO:51; and c) determining whether the extension product of the primer comprises a guanine at a position corresponding to position 444 according to SEQ ID NO:50, or a guanine at a position corresponding to position 432 according to SEQ ID NO:51.

In some embodiments, the assay comprises sequencing the entire nucleic acid molecule. In some embodiments, only a PNPLA3 genomic nucleic acid molecule is analyzed. In some embodiments, only a PNPLA3 mRNA is analyzed. In some embodiments, only a PNPLA3 cDNA obtained from PNPLA3 mRNA is analyzed.

In some embodiments, the sequence analysis comprises: a) amplifying at least a portion of the nucleic acid molecule that encodes the PNPLA3 polypeptide, wherein the portion comprises a guanine at a position corresponding to position 5109 according to SEQ ID NO:43, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising a guanine at a position corresponding to position 5109 according to SEQ ID NO:43, or the complement thereof; and d) detecting the detectable label.

In some embodiments, the sequence analysis comprises: a) amplifying at least a portion of the nucleic acid molecule that encodes the PNPLA3 polypeptide, wherein the portion comprises a guanine at a position corresponding to position 444 according to SEQ ID NO:46, or the complement thereof; or a guanine at a position corresponding to position 432 according to SEQ ID NO:47, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising a guanine at a position corresponding to position 444 according to SEQ ID NO:46, or the complement thereof; or a guanine at a position corresponding to position 432 according to SEQ ID NO:47, or the complement thereof; and d) detecting the detectable label.

In some embodiments, the sequence analysis comprises: a) amplifying at least a portion of the nucleic acid molecule that encodes the PNPLA3 polypeptide, wherein the portion comprises a guanine at a position corresponding to position 444 according to SEQ ID NO:50, or the complement thereof; or a guanine at a position corresponding to position 432 according to SEQ ID NO:51, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising a guanine at a position corresponding to position 444 according to SEQ ID NO:50, or the complement thereof; or a guanine at a position corresponding to position 432 according to SEQ ID NO:51, or the complement thereof; and d) detecting the detectable label.

In any of the methods described herein, the determining step, detecting step, or sequence analysis comprises obtaining or having obtained a biological sample from the subject; and performing or having performed an assay on the biological sample to determine whether the subject has: i) an HSD17B13 genomic DNA comprising SEQ ID NO:52; or a nucleotide sequence having at least 90% sequence identity to SEQ ID NO:52 and encoding a reference HSD17B13 polypeptide or a functional HSD17B13 polypeptide; ii) an HSD17B13 mRNA comprising any one of SEQ ID NOs: 53-62, or a nucleotide sequence having at least 90% sequence identity to any one of SEQ ID NOs:53-62 and encoding a reference HSD17B13 polypeptide or a functional HSD17B13 polypeptide; or iii) an HSD17B13 cDNA comprising any one of SEQ ID NOs:63-72, or a nucleotide sequence having at least 90% sequence identity to any one SEQ ID NOs:63-72 and encoding a reference HSD17B13 polypeptide or a functional HSD17B13 polypeptide.

In some embodiments, the sequence analysis comprises sequencing at least a portion of the nucleotide sequence of the HSD17B13 genomic DNA, mRNA or cDNA produced from mRNA molecule in the biological sample.

In some embodiments, the nucleic acid molecule is mRNA and the determining step further comprises reverse-transcribing the mRNA into a cDNA prior to the amplifying step.

In some embodiments, the determining step, detecting step, or sequence analysis comprises: contacting the nucleic acid molecule in the biological sample with an alteration-specific probe comprising a detectable label, wherein the alteration-specific probe comprises a nucleotide sequence which hybridizes under stringent conditions to a variant nucleic acid molecule position; and detecting the detectable label.

The alteration-specific probes or alteration-specific primers described herein comprise a nucleic acid sequence which is complementary to and/or hybridizes, or specifically hybridizes, to a CIDEB variant nucleic acid molecule, or the complement thereof. In some embodiments, the alteration-specific probes or alteration-specific primers comprise or consist of at least about 1, at least about 5, at least about 8, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 30, at least about 35, at least about 40, at least about 45, or at least about 50 nucleotides. In some embodiments, the alteration-specific probes or alteration-specific primers comprise or consist of at least 15 nucleotides. In some embodiments, the alteration-specific probes or alteration-specific primers comprise or consist of at least 15 nucleotides to at least about 35 nucleotides. In some embodiments, alteration-specific probes or alteration-specific primers hybridize to CIDEB variant genomic nucleic acid molecules, CIDEB variant mRNA molecules, and/or CIDEB variant cDNA molecules under stringent conditions.

The alteration-specific probes or alteration-specific primers described herein comprise a nucleic acid sequence which is complementary to and/or hybridizes, or specifically hybridizes, to a nucleic acid molecule encoding a PNPLA3 Ile148Met or Ile144Met polypeptide, or the complement thereof. In some embodiments, the alteration-specific probes or alteration-specific primers comprise or consist of at least about 1, at least about 5, at least about 8, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 30, at least about 35, at least about 40, at least about 45, or at least about 50 nucleotides. In some embodiments, the alteration-specific probes or alteration-specific primers comprise or consist of at least 15 nucleotides. In some embodiments, the alteration-specific probes or alteration-specific primers comprise or consist of at least 15 nucleotides to at least about 35 nucleotides. In some embodiments, alteration-specific probes or alteration-specific primers hybridize to genomic nucleic acid molecules encoding a PNPLA3 Ile148Met or Ile144Met polypeptide, mRNA molecules encoding a PNPLA3 Ile148Met or Ile144Met polypeptide, and/or cDNA molecules encoding a PNPLA3 Ile148Met or Ile144Met polypeptide under stringent conditions.

Alteration-specific polymerase chain reaction techniques can be used to detect mutations such as SNPs in a nucleic acid sequence. Alteration-specific primers can be used because the DNA polymerase will not extend when a mismatch with the template is present.

In some embodiments, the nucleic acid molecule in the sample is mRNA and the mRNA is reverse-transcribed into a cDNA prior to the amplifying step. In some embodiments, the nucleic acid molecule is present within a cell obtained from the subject.

In some embodiments, the assay comprises contacting the biological sample with a primer or probe, such as an alteration-specific primer or alteration-specific probe, that specifically hybridizes to a CIDEB variant genomic sequence, variant mRNA sequence, or variant cDNA sequence and not the corresponding CIDEB reference sequence under stringent conditions, and determining whether hybridization has occurred.

In some embodiments, the assay comprises contacting the biological sample with a primer or probe, such as an alteration-specific primer or alteration-specific probe, that specifically hybridizes to genomic nucleic acid molecules encoding a PNPLA3 Ile148Met or Ile144Met polypeptide, mRNA molecules encoding a PNPLA3 Ile148Met or Ile144Met polypeptide, and/or cDNA molecules encoding a PNPLA3 Ile148Met or Ile144Met polypeptide under stringent conditions, and determining whether hybridization has occurred.

In some embodiments, the assay comprises RNA sequencing (RNA-Seq). In some embodiments, the assays also comprise reverse transcribing mRNA into cDNA, such as by the reverse transcriptase polymerase chain reaction (RT-PCR).

In some embodiments, the methods utilize probes and primers of sufficient nucleotide length to bind to the target nucleotide sequence and specifically detect and/or identify a polynucleotide comprising a CIDEB variant genomic nucleic acid molecule, a variant mRNA molecule, or a variant cDNA molecule, and/or a nucleic acid molecule encoding a PNPLA3 Ile148Met or Ile144Met polypeptide, an mRNA molecule encoding a PNPLA3 Ile148Met or Ile144Met polypeptide, and/or a cDNA molecule encoding a PNPLA3 Ile148Met or Ile144Met polypeptide. The hybridization conditions or reaction conditions can be determined by the operator to achieve this result. The nucleotide length may be any length that is sufficient for use in a detection method of choice, including any assay described or exemplified herein. Such probes and primers can hybridize specifically to a target nucleotide sequence under high stringency hybridization conditions. Probes and primers may have complete nucleotide sequence identity of contiguous nucleotides within the target nucleotide sequence, although probes differing from the target nucleotide sequence and that retain the ability to specifically detect and/or identify a target nucleotide sequence may be designed by conventional methods. Probes and primers can have about 80%, about 85%, about 90%, about 91%, about 92%, about 93%, about 94%, about 95%, about 96%, about 97%, about 98%, about 99%, or 100% sequence identity or complementarity with the nucleotide sequence of the target nucleic acid molecule.

Illustrative examples of nucleic acid sequencing techniques include, but are not limited to, chain terminator (Sanger) sequencing and dye terminator sequencing. Other methods involve nucleic acid hybridization methods other than sequencing, including using labeled primers or probes directed against purified DNA, amplified DNA, and fixed cell preparations (fluorescence in situ hybridization (FISH)). In some methods, a target nucleic acid molecule may be amplified prior to or simultaneous with detection. Illustrative examples of nucleic acid amplification techniques include, but are not limited to, polymerase chain reaction (PCR), ligase chain reaction (LCR), strand displacement amplification (SDA), and nucleic acid sequence based amplification (NASBA). Other methods include, but are not limited to, ligase chain reaction, strand displacement amplification, and thermophilic SDA (tSDA).

In hybridization techniques, stringent conditions can be employed such that a probe or primer will specifically hybridize to its target. In some embodiments, a polynucleotide primer or probe under stringent conditions will hybridize to its target sequence to a detectably greater degree than to other non-target sequences, such as, at least 2-fold, at least 3-fold, at least 4-fold, or more over background, including over 10-fold over background. Stringent conditions are sequence-dependent and will be different in different circumstances.

Appropriate stringency conditions which promote DNA hybridization, for example, 6× sodium chloride/sodium citrate (SSC) at about 45° C., followed by a wash of 2×SSC at 50° C., are known or can be found in *Current Protocols in Molecular Biology*, John Wiley & Sons, N.Y. (1989), 6.3.1-6.3.6. Typically, stringent conditions for hybridization and detection will be those in which the salt concentration is less than about 1.5 M $Na^+$ ion, typically about 0.01 to 1.0 M $Na^+$ ion concentration (or other salts) at pH 7.0 to 8.3 and the temperature is at least about 30° C. for short probes (such as, for example, 10 to 50 nucleotides) and at least about 60° C. for longer probes (such as, for example, greater than 50 nucleotides). Stringent conditions may also be achieved with the addition of destabilizing agents such as formamide. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

In some embodiments, detecting the presence of a predicted loss-of-function polypeptide or missense polypeptide comprises performing an assay on a sample obtained from a subject to determine whether a CIDEB polypeptide in the subject contains one or more variations that causes the polypeptide to have a loss-of-function (partial or complete) or predicted loss-of-function (partial or complete) or missense variant. In some embodiments, the assay comprises sequencing at least a portion of the CIDEB polypeptide that comprises a variant position. In some embodiments, the detecting step comprises sequencing the entire polypeptide. Identification of a variant amino acid at the variant position of the CIDEB polypeptide indicates that the CIDEB polypeptide is a predicted loss-of-function or missense CIDEB polypeptide. In some embodiments, the assay comprises an immunoassay for detecting the presence of a polypeptide that comprises a variant. Detection of a variant amino acid at the variant position of the CIDEB polypeptide indicates that the CIDEB polypeptide is a CIDEB predicted loss-of-function or missense polypeptide.

In some embodiments, detecting the presence of a PNPLA3 Ile148Met or Ile144Met polypeptide comprises performing an assay on a sample obtained from a subject to determine whether a PNPLA3 polypeptide in the subject contains the Ile148Met or Ile144Met variation. In some embodiments, the assay comprises sequencing at least a portion of the PNPLA3 polypeptide that comprises a variant position. In some embodiments, the detecting step comprises sequencing the entire polypeptide. In some embodiments, the assay comprises an immunoassay for detecting the presence of a polypeptide that comprises a variant.

In some embodiments, isolated nucleic acid molecules hybridize to CIDEB variant nucleic acid molecules, nucleic acid molecules encoding a PNPLA3 Ile148Met or Ile144Met polypeptide, or nucleic acid molecules encoding a reference HSD17B13 polypeptide or a functional HSD17B13 polypeptide (such as genomic nucleic acid molecules, mRNA molecules, and/or cDNA molecules) under stringent conditions. Such nucleic acid molecules can be used, for example, as probes, primers, alteration-specific probes, or alteration-specific primers as described or exemplified herein, and include, without limitation primers, probes, antisense RNAs, shRNAs, and siRNAs, each of which is described in more detail elsewhere herein, and can be used in any of the methods described herein.

In some embodiments, the isolated nucleic acid molecules hybridize to at least about 15 contiguous nucleotides of a nucleic acid molecule that is at least about 70%, at least about 75%, at least about 80%, at least about 85%, at least about 90%, at least about 95%, at least about 96%, at least about 97%, at least about 98%, at least about 99%, or 100% identical to CIDEB variant genomic nucleic acid molecules, CIDEB variant mRNA molecules, and/or CIDEB variant cDNA molecules.

In some embodiments, the isolated nucleic acid molecules hybridize to at least about 15 contiguous nucleotides of a nucleic acid molecule that is at least about 70%, at least about 75%, at least about 80%, at least about 85%, at least about 90%, at least about 95%, at least about 96%, at least about 97%, at least about 98%, at least about 99%, or 100% identical to PNPLA3 genomic nucleic acid molecules encoding a PNPLA3 Ile148Met or Ile144Met polypeptide, PNPLA3 mRNA molecules encoding a PNPLA3 Ile148Met or Ile144Met polypeptide, and/or PNPLA3 cDNA molecules encoding a PNPLA3 Ile148Met or Ile144Met polypeptide.

In some embodiments, the isolated nucleic acid molecules hybridize to at least about 15 contiguous nucleotides of a nucleic acid molecule that is at least about 70%, at least about 75%, at least about 80%, at least about 85%, at least about 90%, at least about 95%, at least about 96%, at least about 97%, at least about 98%, at least about 99%, or 100% identical to HSD17B13 genomic nucleic acid molecules encoding a reference HSD17B13 polypeptide or a functional HSD17B13 polypeptide, HSD17B13 mRNA molecules encoding a reference HSD17B13 polypeptide or a functional HSD17B13 polypeptide, and/or HSD17B13 cDNA molecules encoding a reference HSD17B13 polypeptide or a functional HSD17B13 polypeptide. In some embodiments, the isolated nucleic acid molecules consist of or comprise from about 15 to about 100 nucleotides, or from about 15 to about 35 nucleotides. In some embodiments, the isolated nucleic acid molecules consist of or comprise from about 15 to about 100 nucleotides. In some embodiments, the isolated nucleic acid molecules consist of or comprise from about 15 to about 35 nucleotides.

In some embodiments, the alteration-specific probes and alteration-specific primers comprise DNA. In some embodiments, the alteration-specific probes and alteration-specific primers comprise RNA.

In some embodiments, the probes and primers described herein (including alteration-specific probes and alteration-specific primers) have a nucleotide sequence that specifically hybridizes to any of the nucleic acid molecules disclosed herein, or the complement thereof. In some embodiments, the probes and primers specifically hybridize to any of the nucleic acid molecules disclosed herein under stringent conditions.

In some embodiments, the primers, including alteration-specific primers, can be used in second generation sequencing or high throughput sequencing. In some instances, the primers, including alteration-specific primers, can be modified. In particular, the primers can comprise various modifications that are used at different steps of, for example, Massive Parallel Signature Sequencing (MPSS), Polony sequencing, and 454 Pyrosequencing. Modified primers can be used at several steps of the process, including biotinylated primers in the cloning step and fluorescently labeled primers used at the bead loading step and detection step. Polony sequencing is generally performed using a paired-end tags library wherein each molecule of DNA template is about 135 bp in length. Biotinylated primers are used at the bead loading step and emulsion PCR. Fluorescently labeled degenerate nonamer oligonucleotides are used at the detection step. An adaptor can contain a 5'-biotin tag for immobilization of the DNA library onto streptavidin-coated beads.

The probes and primers described herein can also be used to detect a nucleotide variation within any of the CIDEB variant genomic nucleic acid molecules, CIDEB variant mRNA molecules, and/or CIDEB variant cDNA molecules disclosed herein. The primers described herein can be used to amplify CIDEB variant genomic nucleic acid molecules, CIDEB variant mRNA molecules, or CIDEB variant cDNA molecules, or a fragment thereof.

In some embodiments, the probes (such as, for example, an alteration-specific probe) comprise a label. In some embodiments, the label is a fluorescent label, a radiolabel, or biotin.

The present disclosure also provides supports comprising a substrate to which any one or more of the probes disclosed herein is attached. Solid supports are solid-state substrates or supports with which molecules, such as any of the probes disclosed herein, can be associated. A form of solid support is an array. Another form of solid support is an array detector. An array detector is a solid support to which multiple different probes have been coupled in an array, grid, or other organized pattern. A form for a solid-state substrate is a microtiter dish, such as a standard 96-well type. In some embodiments, a multiwell glass slide can be employed that normally contains one array per well.

The present disclosure also provides therapeutic compositions that treat or inhibit a liver disease for use in the treatment of a liver disease in a subject having one or more CIDEB variant nucleic acid molecules comprising: 14:24305635:A:AGTAG, 14:24305641:A:C, 14:24305650:G:A, 14:24305657:C:A, 14:24305662:G:T, 14:24305667:T:C, 14:24305671:C:A, 14:24305671:C:G, 14:24305701:A:T, 14:24305709:C:T, 14:24305718:A:G, 14:24305721:T:C, 14:24305728:G:GGCCTT, 14:24305743:T:C, 14:24305948:T:C, 14:24305966:C:T, 14:24305974:T:C, 14:24305980:TCA:T, 14:24305988:C:T, 14:24306014:C:T, 14:24306034:A:C, 14:24306041:C:G, 14:24306044:G:A, 14:24306047:G:A, 14:24306051:T:G, 14:24306064:T:C, 14:24306074:A:G, 14:24306077:G:C, 14:24306082:A:G, 14:24306083:T:A, 14:24306095:G:A, 14:24306122:A:G, 14:24306134:C:G, 14:24306373:C:G, 14:24306379:T:C, 14:24306382:G:A, 14:24306383:G:T, 14:24306426:T:G, 14:24306437:C:G, 14:24306439:G:C, 14:24306442:A:G, 14:24306444:A:G, 14:24306457:C:T, 14:24306463:C:T, 14:24306469:C:T, 14:24306480:A:G, 14:24306486:A:C, 14:24306504:A:G, 14:24306519:A:G, 14:24307382:G:C, 14:24307405:A:G, 14:24307417:A:T, 14:24307421:T:A, 14:24307441:C:A, 14:24307444:A:C, 14:24307444:A:G, 14:24307450:C:CGCTG, 14:24307461:TG:T, 14:24307469:AG:A, 14:24307474:C:T, 14:24307475:A:G, 14:24307833:G:C, 14:24307851:T:TAC, 14:24306426:T:C, 14:24307849:G:C, 14:24307448:G:T, 14:24305671:C:T, 14:24305663:C:T, 14:24305686:C:G, 14:24307829:A:C, 14:24307818:CTGAG:C, 14:24307856:C:T, 14:24306423:T:C, 14:24306061:AC:A, 14:24307390:C:T, 14:24306382:G:T, 14:24306373:C:T, 14:24305733:T:C, 14:24307858:T:C, 14:24306387:C:T, 14:24305637:T:C, 14:24306062:C:T, 14:24307853:C:G, 14:24307450:C:G, 14:24306052:TG:T, 14:24305673:G:A, 14:24306043:C:T, 14:24307834:G:A, 14:24306417:C:T, 14:24307451:G:A, 14:24307436:A:C, 14:24305953:ACTTT:A, 14:24306489:G:T, 14:24307441:C:T, 14:24306375:C:T, 14:24305657:C:G, 14:24306427:C:T, 14:24306524:C:T, 14:24307516:C:A, 14:24307840:G:C, 14:24307501:A:G, 14:24305968:A:C, 14:24305986:C:T, 14:24307441:C:G, 14:24307459:G:T, 14:24306017:T:A, 14:24307424:G:A, 14:24306072:G:T, 14:24307423:C:T, 14:24307450:C:T, 14:24306420:G:A, 14:24307454:G:A, 14:24305653:C:T, 14:24307442:G:A, 14:24306002:C:T, 14:24306076:C:T, 14:24305664:C:T, 14:24305961:TG:T, 14:24305706:A:G, 14:24305946:C:T, 14:24306455:G:C, 14:24305468:G:A, 14:24307825:A:C, 14:24306110:G:A, 14:24305710:C:T, 14:24307483:C:T, 14:24306459:A:G, 14:24305754:C:T, 14:24305650:G:C, 14:24305691:C:T, 14:24306508:G:C, 14:24306039:G:T, 14:24306139:T:C, 14:24306391:T:C, 14:24306373:C:A, 14:24307498:C:T, 14:24307415:G:A, 14:24306138:CTG:C, 14:24307453:T:C, 14:24305692:G:A, 14:24305683:C:G, 14:24307484:G:A, 14:24307385:C:T, 14:24306519:A:T, 14:24307839:A:C, 14:24305965:C:T, 14:24305988:CAT:C, 14:24306087:C:G, 14:24307439:C:T, 14:24307477:A:C, 14:24306436:G:T, 14:24306507:A:G, 14:24307397:C:T, 14:24307495:G:A, 14:24306034:A:T, 14:24306013:G:A, 14:24307381:A:G, 14:24306383:G:C, 14:24305638:A:G, 14:24307420:G:A, 14:24306020:C:T, 14:24306470:A:C, 14:24307435:C:T, 14:24306469:C:G, 14:24306451:C:T, 14:24306403:G:A, 14:24307515:C:G, 14:24307489:A:G, 14:24307414:C:T, 14:24306483:A:G, 14:24305755:G:A, 14:24305766:C:T, 14:24306064:T:G, 14:24307516:C:G, 14:24305766:C:G, 14:24306489:G:A, 14:24306097:T:C, 14:24305763:T:G, 14:24307447:G:A, 14:24307402:G:A, 14:24305972:C:G, 14:24306423:T:G, 14:24305974:T:TG, 14:24307411:T:C, 14:24306121:T:C, 14:24307516:C:T, 14:24306424:C:T, 14:24306039:G:C, 14:24307853:C:A, 14:24306388:A:G, 14:24305990:T:C, 14:24307822:G:GT, 14:24305640:G:A, 14:24307418:T:C, 14:24305758:G:C, 14:24306131:C:T, 14:24305953:A:G, 14:24305730:C:A, 14:24306418:A:G, 14:24306059:AC:A, 14:24307842:G:A, 14:24307837:T:G, 14:24306095:G:T, 14:24306109:C:T, 14:24307822:G:A, 14:24306077:G:A, 14:24307824:A:T, 14:24306080:C:T, 14:24305649:C:T, 14:24306433:G:GA, 14:24306420:G:C, 14:24305658:T:G, 14:24306472:C:T, 14:24307412:TC:T, 14:24306062:C:A, 14:24306044:G:C, 14:24306047:G:T, 14:24306126:CAG:C, 14:24306449:C:G, 14:24307391:G:A, or 14:24307857:A:C (according to GRCh38/hg38 human genome assembly coordinates).

The present disclosure also provides compositions comprising therapeutic agents that treat or inhibit a liver disease for use in the preparation of a medicament for treatment of a liver disease in a subject having one or more CIDEB variant nucleic acid molecules comprising: 14:24305635:A:AGTAG, 14:24305641:A:C, 14:24305650:G:A, 14:24305657:C:A, 14:24305662:G:T, 14:24305667:T:C, 14:24305671:C:A, 14:24305671:C:G, 14:24305701:A:T, 14:24305709:C:T, 14:24305718:A:G, 14:24305721:T:C, 14:24305728:G:GGCCTT, 14:24305743:T:C, 14:24305948:T:C, 14:24305966:C:T, 14:24305974:T:C, 14:24305980:TCA:T, 14:24305988:C:T, 14:24306014:C:T, 14:24306034:A:C, 14:24306041:C:G, 14:24306044:G:A, 14:24306047:G:A, 14:24306051:T:G, 14:24306064:T:C, 14:24306074:A:G, 14:24306077:G:C, 14:24306082:A:G, 14:24306083:T:A, 14:24306095:G:A, 14:24306122:A:G, 14:24306134:C:G, 14:24306373:C:G, 14:24306379:T:C, 14:24306382:G:A, 14:24306383:G:T, 14:24306426:T:G, 14:24306437:C:G, 14:24306439:G:C, 14:24306442:A:G, 14:24306444:A:G, 14:24306457:C:T, 14:24306463:C:T, 14:24306469:C:T, 14:24306480:A:G, 14:24306486:A:C, 14:24306504:A:G, 14:24306519:A:G, 14:24307382:G:C, 14:24307405:A:G, 14:24307417:A:T, 14:24307421:T:A, 14:24307441:C:A, 14:24307444:A:C, 14:24307444:A:G, 14:24307450:C:CGCTG, 14:24307461:TG:T, 14:24307469:AG:A, 14:24307474:C:T, 14:24307475:A:G, 14:24307833:G:C, 14:24307851:T:TAC, 14:24306426:T:C, 14:24307849:G:C, 14:24307448:G:T, 14:24305671:C:T, 14:24305663:C:T, 14:24305686:C:G, 14:24307829:A:C, 14:24307818:CTGAG:C, 14:24307856:C:T, 14:24306423:T:C, 14:24306061:AC:A, 14:24307390:C:T, 14:24306382:G:T, 14:24306373:C:T, 14:24305733:T:C, 14:24307858:T:C, 14:24306387:C:T, 14:24305637:T:C, 14:24306062:C:T, 14:24307853:C:G, 14:24307450:C:G, 14:24306052:TG:T, 14:24305673:G:A, 14:24306043:C:T, 14:24307834:G:A, 14:24306417:C:T, 14:24307451:G:A, 14:24307436:A:C, 14:24305953:ACTTT:A, 14:24306489:G:T, 14:24307441:C:T, 14:24306375:C:T, 14:24305657:C:G, 14:24306427:C:

T, 14:24306524:C:T, 14:24307516:C:A, 14:24307840:G:C, 14:24307501:A:G, 14:24305968:A:C, 14:24305986:C:T, 14:24307441:C:G, 14:24307459:G:T, 14:24306017:T:A, 14:24307424:G:A, 14:24306072:G:T, 14:24307423:C:T, 14:24307450:C:T, 14:24306420:G:A, 14:24307454:G:A, 14:24305653:C:T, 14:24307442:G:A, 14:24306002:C:T, 14:24306076:C:T, 14:24305664:C:T, 14:24305961:TG:T, 14:24305706:A:G, 14:24305946:C:T, 14:24306455:G:C, 14:24307468:G:A, 14:24307825:A:C, 14:24306110:G:A, 14:24305710:C:T, 14:24307483:C:T, 14:24306459:A:G, 14:24305754:C:T, 14:24305650:G:C, 14:24305691:C:T, 14:24306508:G:C, 14:24306039:G:T, 14:24306139:T:C, 14:24306391:T:C, 14:24306373:C:A, 14:24307498:C:T, 14:24307415:G:A, 14:24306138:CTG:C, 14:24307453:T:C, 14:24305692:G:A, 14:24305683:C:G, 14:24307484:G:A, 14:24307385:C:T, 14:24306519:A:T, 14:24307839:A:C, 14:24305965:C:T, 14:24305988:CAT:C, 14:24306087:C:G, 14:24307439:C:T, 14:24307477:A:C, 14:24306436:G:T, 14:24306507:A:G, 14:24307397:C:T, 14:24307495:G:A, 14:24306034:A:T, 14:24306013:G:A, 14:24307381:A:G, 14:24306383:G:C, 14:24305638:A:G, 14:24307420:G:A, 14:24306020:C:T, 14:24306470:A:C, 14:24307435:C:T, 14:24306469:C:G, 14:24306451:C:T, 14:24306403:G:A, 14:24307515:C:G, 14:24307489:A:G, 14:24307414:C:T, 14:24306483:A:G, 14:24305755:G:A, 14:24305766:C:T, 14:24306064:T:G, 14:24307516:C:G, 14:24305766:C:G, 14:24306489:G:A, 14:24306097:T:C, 14:24305763:T:G, 14:24307447:G:A, 14:24307402:G:A, 14:24305972:C:G, 14:24306423:T:G, 14:24305974:T:TG, 14:24307411:T:C, 14:24306121:T:C, 14:24307516:C:T, 14:24306424:C:T, 14:24306039:G:C, 14:24307853:C:A, 14:24306388:A:G, 14:24305990:T:C, 14:24307822:G:GT, 14:24305640:G:A, 14:24307418:T:C, 14:24305758:G:C, 14:24306131:C:T, 14:24305953:A:G, 14:24305730:C:A, 14:24306418:A:G, 14:24306059:AC:A, 14:24307842:G:A, 14:24307837:T:G, 14:24306095:G:T, 14:24306109:C:T, 14:24307822:G:A, 14:24306077:G:A, 14:24307824:A:T, 14:24306080:C:T, 14:24305649:C:T, 14:24306433:G:GA, 14:24306420:G:C, 14:24305658:T:G, 14:24306472:C:T, 14:24307412:TC:T, 14:24306062:C:A, 14:24306044:G:C, 14:24306047:G:T, 14:24306126:CAG:C, 14:24306449:C:G, 14:24307391:G:A, or 14:24307857:A:C (according to GRCh38/hg38 human genome assembly coordinates).

The present disclosure also provides compositions comprising one or more CIDEB inhibitors, one or more PNPLA3 inhibitors, or one or more HSD17B13 inhibitors, or any combination thereof, for use in the treatment of a liver disease in a subject having one or more CIDEB variant nucleic acid molecules comprising: 14:24305635:A:AGTAG, 14:24305641:A:C, 14:24305650:G:A, 14:24305657:C:A, 14:24305662:G:T, 14:24305667:T:C, 14:24305671:C:A, 14:24305671:C:G, 14:24305701:A:T, 14:24305709:C:T, 14:24305718:A:G, 14:24305721:T:C, 14:24305728:G:GGCCTT, 14:24305743:T:C, 14:24305948:T:C, 14:24305966:C:T, 14:24305974:T:C, 14:24305980:TCA:T, 14:24305988:C:T, 14:24306014:C:T, 14:24306034:A:C, 14:24306041:C:G, 14:24306044:G:A, 14:24306047:G:A, 14:24306051:T:G, 14:24306064:T:C, 14:24306074:A:G, 14:24306077:G:C, 14:24306082:A:G, 14:24306083:T:A, 14:24306095:G:A, 14:24306122:A:G, 14:24306134:C:G, 14:24306373:C:G, 14:24306379:T:C, 14:24306382:G:A, 14:24306383:G:T, 14:24306426:T:G, 14:24306437:C:G, 14:24306439:G:C, 14:24306442:A:G, 14:24306444:A:G, 14:24306457:C:T, 14:24306463:C:T, 14:24306469:C:T, 14:24306480:A:G, 14:24306486:A:C, 14:24306504:A:G, 14:24306519:A:G, 14:24307382:G:C, 14:24307405:A:G, 14:24307417:A:T, 14:24307421:T:A, 14:24307441:C:A, 14:24307444:A:C, 14:24307444:A:G, 14:24307450:C:CGCTG, 14:24307461:TG:T, 14:24307469:AG:A, 14:24307474:C:T, 14:24307475:A:G, 14:24307833:G:C, 14:24307851:T:TAC, 14:24306426:T:C, 14:24307849:G:C, 14:24307448:G:T, 14:24305671:C:T, 14:24305663:C:T, 14:24305686:C:G, 14:24307829:A:C, 14:24307818:CTGAG:C, 14:24307856:C:T, 14:24306423:T:C, 14:24306061:AC:A, 14:24307390:C:T, 14:24306382:G:T, 14:24306373:C:T, 14:24305733:T:C, 14:24307858:T:C, 14:24306387:C:T, 14:24305637:T:C, 14:24306062:C:T, 14:24307853:C:G, 14:24307450:C:G, 14:24306052:TG:T, 14:24305673:G:A, 14:24306043:C:T, 14:24307834:G:A, 14:24306417:C:T, 14:24307451:G:A, 14:24307436:A:C, 14:24305953:ACTTT:A, 14:24306489:G:T, 14:24307441:C:T, 14:24306375:C:T, 14:24305657:C:G, 14:24306427:C:T, 14:24306524:C:T, 14:24307516:C:A, 14:24307840:G:C, 14:24307501:A:G, 14:24305968:A:C, 14:24305986:C:T, 14:24307441:C:G, 14:24307459:G:T, 14:24306017:T:A, 14:24307424:G:A, 14:24306072:G:T, 14:24307423:C:T, 14:24307450:C:T, 14:24306420:G:A, 14:24307454:G:A, 14:24305653:C:T, 14:24307442:G:A, 14:24306002:C:T, 14:24306076:C:T, 14:24305664:C:T, 14:24305961:TG:T, 14:24305706:A:G, 14:24305946:C:T, 14:24306455:G:C, 14:24307468:G:A, 14:24307825:A:C, 14:24306110:G:A, 14:24305710:C:T, 14:24307483:C:T, 14:24306459:A:G, 14:24305754:C:T, 14:24305650:G:C, 14:24305691:C:T, 14:24306508:G:C, 14:24306039:G:T, 14:24306139:T:C, 14:24306391:T:C, 14:24306373:C:A, 14:24307498:C:T, 14:24307415:G:A, 14:24306138:CTG:C, 14:24307453:T:C, 14:24305692:G:A, 14:24305683:C:G, 14:24307484:G:A, 14:24307385:C:T, 14:24306519:A:T, 14:24307839:A:C, 14:24305965:C:T, 14:24305988:CAT:C, 14:24306087:C:G, 14:24307439:C:T, 14:24307477:A:C, 14:24306436:G:T, 14:24306507:A:G, 14:24307397:C:T, 14:24307495:G:A, 14:24306034:A:T, 14:24306013:G:A, 14:24307381:A:G, 14:24306383:G:C, 14:24305638:A:G, 14:24307420:G:A, 14:24306020:C:T, 14:24306470:A:C, 14:24307435:C:T, 14:24306469:C:G, 14:24306451:C:T, 14:24306403:G:A, 14:24307515:C:G, 14:24307489:A:G, 14:24307414:C:T, 14:24306483:A:G, 14:24305755:G:A, 14:24305766:C:T, 14:24306064:T:G, 14:24307516:C:G, 14:24305766:C:G, 14:24306489:G:A, 14:24306097:T:C, 14:24305763:T:G, 14:24307447:G:A, 14:24307402:G:A, 14:24305972:C:G, 14:24306423:T:G, 14:24305974:T:TG, 14:24307411:T:C, 14:24306121:T:C, 14:24307516:C:T, 14:24306424:C:T, 14:24306039:G:C, 14:24307853:C:A, 14:24306388:A:G, 14:24305990:T:C, 14:24307822:G:GT, 14:24305640:G:A, 14:24307418:T:C, 14:24305758:G:C, 14:24306131:C:T, 14:24305953:A:G, 14:24305730:C:A, 14:24306418:A:G, 14:24306059:AC:A, 14:24307842:G:A, 14:24307837:T:G, 14:24306095:G:T, 14:24306109:C:T, 14:24307822:G:A, 14:24306077:G:A, 14:24307824:A:T, 14:24306080:C:T, 14:24305649:C:T, 14:24306433:G:GA, 14:24306420:G:C, 14:24305658:T:G, 14:24306472:C:T, 14:24307412:TC:T, 14:24306062:C:A, 14:24306044:G:C, 14:24306047:G:T, 14:24306126:CAG:C, 14:24306449:C:G, 14:24307391:G:A, or 14:24307857:A:C (according to GRCh38/hg38 human genome assembly coordinates). The CIDEB inhibitors, PNPLA3 inhibitors, and/or HSD17B13 inhibitors can be any of the CIDEB inhibitors, PNPLA3 inhibitors, and/or HSD17B13 inhibitors described herein.

The present disclosure also provides one or more CIDEB inhibitors, one or more PNPLA3 inhibitors, and/or one or more HSD17B13 inhibitors for use in the preparation of a medicament for treatment of a liver disease in a subject having one or more CIDEB variant nucleic acid molecules comprising: 14:24305635:A:AGTAG, 14:24305641:A:C, 14:24305650:G:A, 14:24305657:C:A, 14:24305662:G:T, 14:24305667:T:C, 14:24305671:C:A, 14:24305671:C:G, 14:24305701:A:T, 14:24305709:C:T, 14:24305718:A:G, 14:24305721:T:C, 14:24305728:G:GGCCTT, 14:24305743: T:C, 14:24305948:T:C, 14:24305966:C:T, 14:24305974:T: C, 14:24305980:TCA:T, 14:24305988:C:T, 14:24306014:C: T, 14:24306034:A:C, 14:24306041:C:G, 14:24306044:G:A, 14:24306047:G:A, 14:24306051:T:G, 14:24306064:T:C, 14:24306074:A:G, 14:24306077:G:C, 14:24306082:A:G, 14:24306083:T:A, 14:24306095:G:A, 14:24306122:A:G, 14:24306134:C:G, 14:24306373:C:G, 14:24306379:T:C, 14:24306382:G:A, 14:24306383:G:T, 14:24306426:T:G, 14:24306437:C:G, 14:24306439:G:C, 14:24306442:A:G, 14:24306444:A:G, 14:24306457:C:T, 14:24306463:C:T, 14:24306469:C:T, 14:24306480:A:G, 14:24306486:A:C, 14:24306504:A:G, 14:24306519:A:G, 14:24307382:G:C, 14:24307405:A:G, 14:24307417:A:T, 14:24307421:T:A, 14:24307441:C:A, 14:24307444:A:C, 14:24307444:A:G, 14:24307450:C:CGCTG, 14:24307461:TG:T, 14:24307469:AG:A, 14:24307474:C:T, 14:24307475:A:G, 14:24307833:G:C, 14:24307851:T:TAC, 14:24306426:T:C, 14:24307849:G:C, 14:24307448:G:T, 14:24305671:C:T, 14:24305663:C:T, 14:24305686:C:G, 14:24307829:A:C, 14:24307818:CTGAG:C, 14:24307856:C:T, 14:24306423: T:C, 14:24306061:AC:A, 14:24307390:C:T, 14:24306382: G:T, 14:24306373:C:T, 14:24305733:T:C, 14:24307858:T: C, 14:24306387:C:T, 14:24305637:T:C, 14:24306062:C:T, 14:24307853:C:G, 14:24307450:C:G, 14:24306052:TG:T, 14:24305673:G:A, 14:24306043:C:T, 14:24307834:G:A, 14:24306417:C:T, 14:24307451:G:A, 14:24307436:A:C, 14:24305953:ACTTT:A, 14:24306489:G:T, 14:24307441: C:T, 14:24306375:C:T, 14:24305657:C:G, 14:24306427:C: T, 14:24306524:C:T, 14:24307516:C:A, 14:24307840:G:C, 14:24307501:A:G, 14:24305968:A:C, 14:24305986:C:T, 14:24307441:C:G, 14:24307459:G:T, 14:24306017:T:A, 14:24307424:G:A, 14:24306072:G:T, 14:24307423:C:T, 14:24307450:C:T, 14:24306420:G:A, 14:24307454:G:A, 14:24305653:C:T, 14:24307442:G:A, 14:24306002:C:T, 14:24306076:C:T, 14:24305664:C:T, 14:24305961:TG:T, 14:24305706:A:G, 14:24305946:C:T, 14:24306455:G:C, 14:24307468:G:A, 14:24307825:A:C, 14:24306110:G:A, 14:24305710:C:T, 14:24307483:C:T, 14:24306459:A:G, 14:24305754:C:T, 14:24305650:G:C, 14:24305691:C:T, 14:24306508:G:C, 14:24306039:G:T, 14:24306139:T:C, 14:24306391:T:C, 14:24306373:C:A, 14:24307498:C:T, 14:24307415:G:A, 14:24306138:CTG:C, 14:24307453:T:C, 14:24305692:G:A, 14:24305683:C:G, 14:24307484:G:A, 14:24307385:C:T, 14:24306519:A:T, 14:24307839:A:C, 14:24305965:C:T, 14:24305988:CAT:C, 14:24306087:C:G, 14:24307439:C:T, 14:24307477:A:C, 14:24306436:G:T, 14:24306507:A:G, 14:24307397:C:T, 14:24307495:G:A, 14:24306034:A:T, 14:24306013:G:A, 14:24307381:A:G, 14:24306383:G:C, 14:24305638:A:G, 14:24307420:G:A, 14:24306020:C:T, 14:24306470:A:C, 14:24307435:C:T, 14:24306469:C:G, 14:24306451:C:T, 14:24306403:G:A, 14:24307515:C:G, 14:24307489:A:G, 14:24307414:C:T, 14:24306483:A:G, 14:24305755:G:A, 14:24305766:C:T, 14:24306064:T:G, 14:24307516:C:G, 14:24305766:C:G, 14:24306489:G:A, 14:24306097:T:C, 14:24305763:T:G, 14:24307447:G:A, 14:24307402:G:A, 14:24305972:C:G, 14:24306423:T:G, 14:24305974:T:TG, 14:24307411:T:C, 14:24306121:T:C, 14:24307516:C:T, 14:24306424:C:T, 14:24306039:G:C, 14:24307853:C:A, 14:24306388:A:G, 14:24305990:T:C, 14:24307822:G:GT, 14:24305640:G:A, 14:24307418:T:C, 14:24305758:G:C, 14:24306131:C:T, 14:24305953:A:G, 14:24305730:C:A, 14:24306418:A:G, 14:24306059:AC:A, 14:24307842:G:A, 14:24307837:T:G, 14:24306095:G:T, 14:24306109:C:T, 14:24307822:G:A, 14:24306077:G:A, 14:24307824:A:T, 14:24306080:C:T, 14:24305649:C:T, 14:24306433:G:GA, 14:24306420:G:C, 14:24305658:T:G, 14:24306472:C:T, 14:24307412:TC:T, 14:24306062:C:A, 14:24306044:G:C, 14:24306047:G:T, 14:24306126:CAG:C, 14:24306449:C:G, 14:24307391:G: A, or 14:24307857:A:C (according to GRCh38/hg38 human genome assembly coordinates). The CIDEB inhibitors, PNPLA3 inhibitors, and/or HSD17B13 inhibitors can be any of the CIDEB inhibitors, PNPLA3 inhibitors, and/or HSD17B13 inhibitors described herein.

The present disclosure also provides methods of treating a subject having a liver disease or at risk of developing a liver disease, wherein: when the subject is homozygous for a nucleic acid molecule encoding a reference HSD17B13 polypeptide or a functional HSD17B13 polypeptide, the subject is administered a CIDEB inhibitor in an amount that is the same as or greater than a standard dosage amount, or is administered a combination of a CIDEB inhibitor in an amount that is the same as or greater than a standard dosage amount and an HSD17B13 inhibitor and/or a PNPLA3 inhibitor; and when the subject is not homozygous for a nucleic acid molecule encoding a reference HSD17B13 polypeptide or a functional HSD17B13 polypeptide (i.e., is a carrier for a loss-of-function HSD17B13), the subject is administered a CIDEB inhibitor in an amount that is less than a standard dosage amount. The CIDEB inhibitors, PNPLA3 inhibitors, and/or HSD17B13 inhibitors can be any of the CIDEB inhibitors and/or HSD17B13 inhibitors described herein.

The present disclosure also provides methods of treating a subject with a CIDEB inhibitor, wherein the subject has a liver disease or is at risk of developing a liver disease, the methods comprising: determining whether the subject has a nucleic acid molecule encoding a reference HSD17B13 polypeptide or a functional HSD17B13 polypeptide by: obtaining or having obtained a biological sample from the subject; and performing or having performed a sequence analysis on the biological sample to determine if the subject has a genotype comprising the nucleic acid molecule encoding the reference HSD17B13 polypeptide or a functional HSD17B13 polypeptide; and when the subject is homozygous for a nucleic acid molecule encoding a reference HSD17B13 polypeptide or a functional HSD17B13 polypeptide, the subject is administered a CIDEB inhibitor in an amount that is the same as or greater than a standard dosage amount, or is administered a combination of a CIDEB inhibitor and an HSD17B13 inhibitor and/or a PNPLA3 inhibitor; and when the subject is not homozygous for a nucleic acid molecule encoding a reference HSD17B13 polypeptide or a functional HSD17B13 polypeptide (i.e., is a carrier for a loss-of-function HSD17B13), the subject is administered a CIDEB inhibitor in an amount that is less than a standard dosage amount; wherein the presence of a genotype having the nucleic acid molecule encoding the reference HSD17B13 polypeptide or a functional HSD17B13 polypeptide indicates the subject is a candidate for treatment with the CIDEB inhibitor.

All patent documents, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the present disclosure can be used in combination with any other feature, step, element, embodiment, or aspect unless specifically indicated otherwise. Although the present disclosure has been described in some detail by way of illustration and example for purposes of clarity and understanding, it will be apparent that certain changes and modifications may be practiced within the scope of the appended claims.

The following examples are provided to describe the embodiments in greater detail. They are intended to illustrate, not to limit, the claimed embodiments. The following examples provide those of ordinary skill in the art with a disclosure and description of how the compounds, compositions, articles, devices and/or methods described herein are made and evaluated, and are intended to be purely exemplary and are not intended to limit the scope of any claims. Efforts have been made to ensure accuracy with respect to numbers (such as, for example, amounts, temperature, etc.), but some errors and deviations may be accounted for. Unless indicated otherwise, parts are parts by weight, temperature is in ° C. or is at ambient temperature, and pressure is at or near atmospheric.

EXAMPLES

Example 1: General Methodology and Frequency of Rare Coding Variants in CIDEB Across Populations Study Participants Discovery exome-wide association analyses were performed in the UK Biobank (UKB) cohort and in the MyCode Community Health Initiative from Geisinger Health System (GHS). The UKB is a population-based cohort including individuals 40-69 years of age recruited at 22 testing sites in the UK between 2006-2010. 411,926 European ancestry, 9,830 South Asian ancestry, 8,544 African ancestry, 2,108 East Asian ancestry, and 587 American ancestry participants with available whole-exome sequencing and transaminase data were included. MyCode is a health system-based cohort of patients from rural Pennsylvania (USA) recruited in 2007-2021. 109,909 European ancestry participants with available whole-exome sequencing and transaminase data were included. Liver disease outcome association analyses further included up to 28,948 participants from the Malmö Diet and Cancer Study (MDCS). 13,418 participants from the University of Pennsylvania PennMedicine BioBank (UPENN-PMBB) and 23,849 participants from the Mount Sinai BioMe BioBank cohort (BioMe). Liver-histopathology association analyses were also performed in 3,599 bariatric surgery patients from GHS who were not included in the primary discovery analyses.

DNA Exome Sequencing

NimbleGen VCRome probes (for part of GHS) or a modified version of the xGen design available from Integrated DNA Technologies (IDT; for the rest of GHS and for other cohorts) were used to capture exome sequences. Following capture, balanced pools were sequenced using 75 bp paired-end reads on Illumina v4 HiSeq 2500 (for part of the GHS cohort) or NovaSeq (for the rest of GHS and for other cohorts) instruments. Sequencing achieved greater than 20× coverage over 85% of targeted bases in 96% of VCRome samples and 20× coverage over 90% of targeted bases in 99% of IDT samples. Following sequencing, pooled samples were demultiplexed using Illumina software, aligned sequenced reads to the GRCh38 Human Genome reference sequence using BWA-mem, and generated cohort-level genotype files with GLnexus.

Variants were annotated using the snpEff software and Ensembl v85 gene definitions. Annotations were prioritized for protein-coding transcripts based on the most deleterious functional effect for each gene based with the following hierarchy (from most to least deleterious): frameshift, stop-gain, stop-loss, splice acceptor, splice donor, in-frame indel, missense, other annotations. Predicted LOF genetic variants included: a) insertions or deletions resulting in a frameshift, b) insertions, deletions or single nucleotide variants resulting in the introduction of a premature stop codon or in the loss of the transcription start site or stop site, and c) variants in donor or acceptor splice sites. Missense variants were classified for likely functional impact according to the number of in silico prediction algorithms that predicted deleteriousness using SIFT, Polyphen2_HDIV and Polyphen2_HVAR, LRT and MutationTaster. For each gene, the alternative allele frequency (AAF) and functional annotation of each variant determined inclusion into these 7 gene burden exposures: 1) pLOF variants with AAF<1%; 2) pLOF or missense variants predicted deleterious by 5/5 algorithms with AAF<1%; 3) pLOF or missense variants predicted deleterious by 5/5 algorithms with AAF<0.1%; 4) pLOF or missense variants predicted deleterious by at least 1/5 algorithms with AAF<1%; 5) pLOF or missense variants predicted deleterious by at least 1/5 algorithms with AAF<0.1%; 6) pLOF or any missense with AAF<1%; 7) pLOF or any missense variants with AAF<0.1%.

Phenotype Definitions

For continuous traits, data cleaning was performed by removing non-physiologic lab values, or results stemming from invalid or contaminated specimens. In Geisinger Health System (GHS), the median transaminase values for each individual were extracted from electronic health records. In the UK Biobank (UKB), transaminases were measured using a Beckman Coulter AU5800 at the baseline study visit.

Cases of binary liver disease outcomes were defined based on one or more of the following criteria: i) self-reported disease obtained from digital questionnaire or interview with a trained nurse, ii) in-patient hospitalization for the disease or clinical-problem list entries of the disease according to International Classification of Diseases, Ninth (ICD-9) or Tenth (ICD-10) Revision diagnosis code, iii) medical procedures or surgery due to the disease, iv) death due to the disease, and v) a disease diagnosis code entered for two or more outpatient visits in separate calendar days. The specific entries used to define different types of liver disease are described in detail in Table 17. Controls were defined as individuals who did not meet any of the criteria for case status. To minimize misclassification, the following were excluded from the control group: i) non-cases diagnosed with any type of liver disease (not restricted to the type of liver disease in question), ii) non-cases with only one out-patient encounter related to the type of liver disease in question, iii) non-cases diagnosed with ascites presumably related to liver failure, and iv) non-cases with elevated alanine aminotransferase (ALT) levels (>33 IU/L for men, >25 IU/L for women).

TABLE 17

Definition of liver disease outcomes based on health surveys and electronic health records

| Liver disease outcome | Case definition |
| --- | --- |
| Liver disease (any) | ICD10: K70(Alcoholic liver disease), K71(Toxic liver disease), K72(Hepatic failure, not elsewhere classified), K73(Chronic hepatitis, not elsewhere classified), K74(Fibrosis and cirrhosis of liver), K75(Other inflammatory liver diseases), K76(Other diseases of liver), K77(Liver disorders in diseases classified elsewhere), I81(Portal vein thrombosis), I85(Secondary esophageal varices without bleeding), I982(Esophageal varices without bleeding in diseases classified elsewhere), I983(Esophageal varices with bleeding in diseases classified elsewhere), I864(Gastric varices), T864(Complications of liver transplant), Z944(Liver transplant status), C220(Liver cell carcinoma). Procedure codes according to OPCS4 classification: G10(Open operations on varices of esophagus), G144(Fiberoptic endoscopic injection sclerotherapy to varices of esophagus), J01(Transplantation of liver). Procedure codes according to NOMESCO classification version 1: JJC(liver transplant), JCA20(ligature of esophageal varices), JCA22(endoscopic ligature of esophageal varices), JDA22(endoscopic ligature of varices of stomach), TJC00(insertion of balloon tube for tamponade of esophageal varices [sengstaken-blakemore]). Procedure codes according to NOMESCO classification version 6: 5200(liver transplant), 5201(exploration of transplanted liver), 5212(resection of transplanted liver), 5214(extracorporeal resection of liver prior to transplant), 5219(other types of resection of transplanted liver), 5280(biopsy from transplanted liver), 5282(percutaneous liver biopsy from transplanted liver). Self-report: alcoholic liver disease, alcoholic cirrhosis, liver failure cirrhosis, esophageal varices. |
| Alcoholic liver disease | ICD10: K70(Alcoholic liver disease) |
| Non-alcoholic liver disease | ICD10: K721(Chronic hepatic failure), K740(Hepatic fibrosis), K741(Hepatic sclerosis), K742(Hepatic fibrosis with hepatic sclerosis), K746(Other and unspecified cirrhosis of liver), K758(Other specified inflammatory liver diseases), K760(Fatty [change of] liver, not elsewhere classified) |
| Liver cirrhosis (any) | ICD10: K703(Cirrhosis), K704(Alcoholic hepatic failure), K717(Toxic liver disease with fibrosis and cirrhosis of liver), K721(Chronic hepatic failure), K746(Other and unspecified cirrhosis of liver) |
| Alcoholic liver cirrhosis | ICD10: K703(Cirrhosis), K704(Alcoholic hepatic failure) |
| Non-alcoholic liver cirrhosis | ICD10: K746(Other and unspecified cirrhosis of liver) |
| Viral hepatitis | ICD10: B15(Acute hepatitis A), B16(Acute hepatitis B), B17(Other acute viral hepatitis), B18(Chronic viral hepatitis), B19(Unspecified viral hepatitis) |

ICD10 indicates the 10th revision of the International Statistical Classification of Diseases and Related Health Problems; OPCS4 indicates Office of Population Censuses and Surveys (OPCS) Classification of Interventions and Procedures version 4; NOMESCO indicates Nordic Medico-Statistical Committee procedure codes. Participants were excluded from the control population if they were: i) diagnosed with the "any liver disease" outcome codes (as defined in the table), ii) ascites presumably related to liver failure (ICD10 R18 (Ascites), excluding individuals with other potential causes of ascites; C16 (Malignant neoplasm of stomach), C17 (Malignant neoplasm of small intestine), C18 (Malignant neoplasm of colon), C20 (Malignant neoplasm of rectum), 142 (Cardiomyopathy),I50 (Heart failure)) or iii) if they had elevated ALT>33 U/L for men and >25 U/L for women.

Liver Histopathologic Phenotype Definitions in the GHS Bariatric Surgery Cohort

The GHS bariatric cohort consists of 3,599 individuals of European descent who underwent bariatric surgery and were enrolled in GHS's MyCode and GHS-Regeneron Genetics Center (RGC) DiscovEHR collaboration. Surgeons took wedge biopsies of the liver 10 cm to the left of falciform ligament prior to any liver retraction or surgery on the stomach, following a standardized protocol. The biopsy was divided into sections, with the primary section delivered to the clinical pathologists for liver histology (fixed in 10% neutral buffered formalin and stained with hematoxylin and eosin for routine histology and Masson's trichrome for assessment of fibrosis) and remaining sections stored within a research biobank (stabilized with the RNAlater tissue collection system (ThermoFisher Scientific) or frozen in liquid nitrogen). An experienced pathologist conducted histological examinations, which were subsequently re-reviewed by a second pathologist, and scored based on the NASH Clinical Research Network system: steatosis Grade 0 (<5% parenchymal involvement), Grade 1 (5 to <34%), Grade 2 (34 to <67%), and Grade 3 (>67%); lobular inflammation Grade 0 (no foci), Grade 1 (mild, <2 foci per 200× field), Grade 2 (moderate, 2-4 foci per 200× field), Grade 3 (severe, >4 foci per 200× field); ballooning Grade 0 (none), Grade 1 (few balloon cells), Grade 2 (many cells/prominent ballooning); fibrosis Stage 0 (none), Stage 1 (perisinusoidal or periportal fibrosis), Stage 2 (perisinusoidal and periportal fibrosis), Stage 3 (bridging fibrosis), and Stage 4 (liver cirrhosis). These histologic diagnoses were used to define the following phenotypes: 1) Normal liver: no evidence of steatosis, nonalcoholic steatohepatitis (NASH), or fibrosis; 2) Simple steatosis: Steatosis (regardless of grade) with no evidence of NASH or fibrosis; 3) NASH: Any presence of lobular inflammation or hepatocyte ballooning (regardless of grade), or any presence of fibrosis (regardless of stage); 4) Fibrosis: Any presence of fibrosis (regardless of stage); 5) Nonalcoholic fatty liver disease (NAFLD) activity score (NAS) defined as the unweighted sum of the scores for steatosis (0-3), lobular inflammation (0-3) and ballooning (0-2), thus ranging from 0-8.

Statistical Analysis

Associations between genotypes and phenotypes were estimated by fitting linear (for quantitative traits) or Firth bias-corrected logistic (for binary traits) regression models using REGENIE v2+(10.1038/s41588-021-00870-7) or the logistf function in R. Analyses were stratified by cohort and ancestry and adjusted for age, age$^2$, sex, age-by-sex and age$^2$-by-sex interaction terms, experimental batch-related covariates, the first 10 common variant-derived genetic principal components (PCs), the first 20 rare variant-derived PCs, and a polygenic score generated by REGENIE that accounts for relatedness, population structure, and polygenicity (10.1038/ng.257). To ensure independence between rare and common variants signals, discovery exome-wide analyses for common variant signals identified by fine-mapping were additionally adjusted as previously described. Results across studies were combined by fixed-effect inverse variance-weighted meta-analysis.

Frequency of CIDEB Coding Variants Identified by Exome Sequencing Across Ancestries Using exome sequencing across ancestry groups as described above, the frequency of homozygous reference genotype (reference-reference, RR), heterozygous alternative allele carrier genotype (reference-alternative, RA) and homozygous alternative allele carrier genotype (alternative-alternative, AA) were determined in sequenced individuals across ancestry groups. In each ancestry group, the RR genotype, which in the genetic analyses were associated with higher liver fat, injury and liver disease risk was the most common genotype (Table 18).

TABLE 18

Genotype frequencies for CIDEB predicted loss-of-function or missense variants identified by exome sequencing across ancestries

| Ancestry | RR genotype, % | RA genotype, % | AA genotype, % |
|---|---|---|---|
| African | 98.6% | 1.4% | 0.001% |
| American | 98.7% | 1.3% | 0.01% |
| European | 99.3% | 0.7% | 0.001% |

TABLE 18-continued

Genotype frequencies for CIDEB predicted loss-of-function or missense variants identified by exome sequencing across ancestries

| Ancestry | RR genotype, % | RA genotype, % | AA genotype, % |
|---|---|---|---|
| East Asian | 98.8% | 1.2% | 0% |
| South Asian | 97.8% | 2.2% | 0.02% |

Abbreviations:
RR, reference-reference genotype;
RA, reference-alternative genotype;
AA, alternative-alternative genotype for predicted loss-of-function or missense variants in CIDEB.
The sum of percentages may differ from 100% due to rounding.

GTEx RNA-seq

TMM normalized gene expression matrices per tissue were obtained using GTEx v8 raw expression matrices download from the GTEx portal. Within each tissue, we subset to samples included in the GTEx v8 analysis freeze and filter to genes using the same quality control filters described below.

Liver RNA-Seq in Bariatric Cohort Samples

Liver RNA-seq was performed in 2,304 patients from GHS who underwent a perioperative wedge biopsy of the liver as part of bariatric surgery.

RNA concentration was determined by UV absorbance and 500 ng of total RNA was used for processing. Samples were processed with the NEBNext Poly(A) mRNA Magnetic Isolation Module and NEB NEBNext Ultra II Directional RNA Library Prep Kit for Illumina (New England Biolabs), according to the manufacturer recommendations. Samples were amplified with 10 cycles of PCR with Kapa HiFi polymerase (Roche) and custom barcoded primers (IDT). Samples were sequenced on the Illumina NovaSeq 6000 platform on S2 flow cells with paired-end 75 bp reads. The mean number of reads per sample was 72 million and the median was 68 million; 93% of the samples had at least 50 million reads and 99% of the samples had more than 45 million reads, reflecting high coverage sequencing. The gene expression values for all samples were then normalized across samples using the trimmed mean of m-values approach (TMM) as implemented in edgeR.

RNA-seq data were processed broadly following the GTEx v8 analysis protocol (world wide web at gtexportal.ordhonne/documentationPage #staticTextAnalysisMethods). Briefly, sequenced samples were aligned to the human reference genome GRCh38/hg38 with STAR v2.5.3a. Duplicate marking was applied to optical duplicates only with Picard using the pixel distance setting OPTICAL_DUPLICATE_PIXEL_DISTANCE=15000.

The quantification of mRNA was based on the GENCODE Release 32 annotation (world wide web at gencodegenes.org/human/release_32.html), collapsed to a single transcript model for each gene. Gene-level expression quantification was performed using RNA-SeQC. Gene-level read counts and TPM values were produced using the following read-level filters: 1) reads were uniquely mapped; 2) reads were aligned in proper pairs; 3) the read alignment distance was 6; 4) reads were fully contained within exon boundaries.

Gene expression values for all samples were normalized: 1) read counts were normalized between samples using TMM; 2) genes were selected based on expression thresholds of ≥0.1 TPM in ≥20% of samples and reads (unnormalized) in ≥20% of samples.

Allele Specific Read Counts and Analyses

Read counts per allele generated by counting the number of reads overlapping the variant's position and carrying the allele of interest (reference or alternative). P-values for the observed degree of imbalance in read counts per allele were based on an exact binomial test as implemented in binom.test function in R version 4.0.5 assuming a 50% probability of success under the null.

CIDEB Knockdown in HepG2 Cells

HepG2 (ATCC) cells were cultured in MEM with Earle's salt supplemented with 10% FBS, 1% Penicillin-Streptomycin, and 1% L-glutamine. For siRNA knockdown, cells were transfected with CIDEB siRNA (Smartpool, Dharmacon L-004410-00-0050) or control siRNA (Non-targeting pool, Dharmacon D-001810-10-50) for 48 hours. For OA treatment, cells were treated with 400 μM OA for 24 hours, beginning 24 hours after transfection.

For localization of CIDEB with lipid droplets, cells were fixed in 3% PFA for 20 minutes then permeabilized in 0.1% saponin, blocked in 1% BSA and incubated overnight with primary antibody against CIDEB (1:1000, Abnova H00027141-M01). Alexa Fluor 594 goat anti-mouse IgG (Thermo) was used during the secondary antibody incubation. BODIPY493/503 was incubated for 1 hour during the secondary antibody incubation step followed by a 10-minute incubation with DAPI to stain nuclei. After washing, PBS was replaced with mounting medium for fluorescence microscopy (Ibidi 50001) then imaged using a Zeiss LSM 880 confocal microscope.

For western blotting, cells were lysed in RIPA lysis buffer plus protease and phosphatase inhibitors. Lysate was cleared, quantified, electrophoresed, and transferred to PVDF membranes. Membranes were blocked in Superblock T20 TBS buffer (Thermo 37536) then incubated in primary antibodies (CIDEB: Abnova H00027141-M01 1:1000; GAPDH: HRP-conjugated Sigma G9295). For CIDEB, bound antibody was detected via incubation with anti-mouse IgG, HRP secondary antibody (Cell Signaling 7076, 1:10000 dilution. Supersignal West Pico Plus Chemiluminescent Substrate (Thermo 4579) and Supersignal West Femto Maximum Sensitivity Substrate (Thermo 34094) were used for the development of chemiluminescent signal. Relative protein expression was determined by quantification of CIDEB and GAPDH bands on ImageJ. Data was normalized using GAPDH and control cells.

RNA isolation was performed using the RNeasy mini kit (QIAGEN 74104) with DNase I digestion (QIAGEN 79254) as per manufacturer's instructions. Total of 1 μg of RNA was used for cDNA synthesis using the SuperScript IV VILO cDNA synthesis kit (Thermo 11754050). Gene expression levels were determined using Taqman gene expression assays (Applied Biosystems assay IDs: CIDEB (Hs00205339_m1), GAPDH (Hs02786624_g1)) using the Taqman Fast Advanced Master Mix (Thermo 4444963) with the QuantStudio 6 instrument. The data was normalized using GAPDH and the control cells.

For lipid droplet visualization, cells were incubated with AdipoRed (Lonza PT-7009) for 10 minutes then fixed for 10 minutes in 4% paraformaldehyde (PFA). Cells were washed then incubated with 4',6-diamidino-2-phenylindole (DAPI) for 10 minutes to stain nuclei. After washing, PBS was replaced with mounting medium for fluorescence microscopy (Ibidi 50001) then imaged using a Zeiss LSM 880 confocal microscope.

For quantification of lipid droplets, lipid droplets were detected in the red channel (excitation at 485 nm and emission at 572 nm) using Laplacian-of-Gaussian blob detection, as implemented in the Scikit-Image Python package. To tune the detection threshold parameter of the blob detection algorithm, lipid droplets were manually marked for six random small regions (250×250 pixels) from three images per experimental group. The number of cells in each field was estimated from the DAPI channel. For each experimental group, the following quantitative endpoints were derived: average lipid droplet size (quantified as lipid droplet volumes), average number of lipid droplets per nucleus, and average cell lipid droplet staining (quantified as total lipid droplet areas per nucleus).

Levels of intracellular triglyceride content was measured using the Triglyceride Assay Kit (Abcam ab65336) according to manufacturer's instructions. Triglyceride content was normalized to total protein content as determined by the DC Protein assay (BioRad 5000111). IL8 protein concentrations in cell media were measured using a Meso Scale Diagnostics Proinflammatory Panel and were normalized to total protein content.

Two-way analysis of variation (ANOVA) was used to determine if an interaction between the effects of oleic acid and CIDEB siRNA was present, with Tukey's multiple comparisons tests with Sidak correction used to determine the pairwise effects of 1) 0 μM vs 400 μM oleic acid in the presence of control siRNA; 2) 0 μM vs 400 μM oleic acid in the presence of CIDEB siRNA; 3) control vs CIDEB siRNA in the presence of 0 μM oleic acid; 4) control vs CIDEB siRNA in the presence of 400 μM oleic acid. Welch's t-test was used to compare effects of control siRNA vs CIDEB siRNA on CIDEB expression via western blot and Taqman analysis since no oleic acid treatment was present. Statistical testing was performed using Prism 9.

Example 2: Loss-of-Function in CIDEB is Associated with Lower Liver Transaminases and Protection Against Liver Disease To identify genetic factors contributing to predisposition for or protection against chronic liver disease, an exome-sequencing analysis of alanine aminotransferase (ALT), a widely used biomarker of liver damage, was performed in over 500,000 people from the UK Biobank (UKB) cohort and the MyCode Community Health Initiative from Geisinger Health System (GHS). The UKB is a population-based cohort including individuals 40-69 years of age recruited at 22 testing sites in the UK between 2006-2010 (PLoS Med 2015; 12:e1001779). 411,926 European ancestry, 9,830 South Asian ancestry, 8,544 African ancestry, 2,108 East Asian ancestry and 587 American ancestry participants with available whole-exome sequencing and transaminase data were included (Table 19). MyCode is a health system-based cohort of patients from rural Pennsylvania (USA) recruited in 2007-2021 (Genet Med 2016; 18:906-13). 109,909 European ancestry participants with available whole-exome sequencing and transaminase data were included (Table 19).

TABLE 19

Baseline characteristics of individuals included in exome-wide association analyses

| Variable | UKB study (N = 432,995) | GHS study (N = 109,909) |
|---|---|---|
| Age, mean (SD) in years | 57 (8) | 59 (17) |
| Women, N (%) | 234,632 (54) | 66,739 (61) |
| Participant ancestry (%) | | |
| European | 411,926 (95.1) | 109,909 (100) |
| African | 8,544 (2) | |
| East Asian | 2,108 (0.5) | |
| South Asian | 9,830 (2.3) | |
| Admixed American | 587 (0.1) | |
| Body mass index, mean (SD) in kg/m$^2$ | 27.4 (4.8) | 31.3 (7.3) |
| Alanine Aminotransferase mean (SD) U/L | 23.5 (14.1) | 24.8 (11.6) |
| Aspartate Aminotransferase mean (SD) U/L | 26.2 (10.2) | 23.7 (6.4) |
| Body weight, mean (SD) in kg | 78 (16) | 89 (24) |
| Body mass index WHO categories, N (%) | | |
| Underweight (<18.5 kg/m$^2$) | 2,111 (0.5) | 813 (0.7) |
| Healthy weight (18.5 to <25 kg/m$^2$) | 140,560 (32.5) | 20,097 (18.3) |
| Overweight (25 to <30 kg/m$^2$) | 183,668 (42.4) | 31,725 (28.9) |
| Obesity, non-severe (30 to <40 kg/m$^2$) | 96,834 (22.4) | 41,918 (38.1) |
| Severe obesity (40 kg/m$^2$) | 8,105 (1.9) | 13,377 (12.2) |
| Blood pressure, mean (SD) in mmHg | | |
| Systolic | 137 (16) | 125 (10) |
| Diastolic | 82 (8) | 74 (6) |
| Low-density lipoprotein cholesterol, mean (SD) in mg/dL | 137 (34) | 106 (29) |
| Triglycerides, median (IQR) in mg/dL | 131 (98) | 125 (82) |

Abbreviations:
UKB, UK Biobank;
GHS, Geisinger Health System;
SD, standard deviation;
N, number of participants;
WHO, World Health Organization;
kg/m$^2$, kilograms per square meter;
mg/dL, milligrams per deciliter;
mmHg, millimeters of mercury;
IQR, inter-quartile range.

For each gene in the genome, associations with ALT were estimated for the burden of rare predicted loss-of-function (pLOF) and missense variants identified by exome sequencing (see Methods in Example 1). Statistically significant findings for a novel association in the CIDEB gene were subsequently evaluated for their association with: 1) aspartate aminotransferase (AST), another transaminase often associated with liver damage, 2) liver disease clinical outcomes, and 3) liver histopathology (see Methods in Example 1).

In the exome-wide analysis, the burden of rare (alternative allele frequency (AAF)<1%) predicted loss-of-function (pLOF) or missense genetic variants in the CIDEB gene was strongly associated with lower ALT at the exome-wide level of statistical significance (p<3.6×10$^{-7}$, a Bonferroni correction for 20,000 genes and seven variant selection models, Table 20), a novel association. Rare pLOF or missense variants in CIDEB were also associated with lower AST levels (Table 20).

TABLE 20

Associations with lower transaminase levels for the burden of rare pLOF plus missense variants in the CIDEB gene (gene = CIDEB; genetic exposure = pLOF plus any missense, AAF <1%)

| Outcome | Beta (95% CI), per allele | p | AAF, fraction of 1 | Genotype counts, RR\|RA\|AA genotypes |
|---|---|---|---|---|
| ALT | −0.09 (−0.12, −0.06) SD, −1.24 (−1.66, −0.83) U/L | 4.8 × 10$^{-09}$ | 0.00333 | 539,292\|3,609\|3 |

TABLE 20-continued

Associations with lower transaminase levels for the burden of rare pLOF plus missense variants in the CIDEB gene (gene = CIDEB; genetic exposure = pLOF plus any missense, AAF <1%)

| Outcome | Beta (95% CI), per allele | p | AAF, fraction of 1 | Genotype counts, RR\|RA\|AA genotypes |
|---|---|---|---|---|
| AST | −0.10 (−0.13, −0.07) SD, −0.95 (−1.26, −0.65) U/L | $1.0 \times 10^{-09}$ | 0.00333 | 536,658\|3,589\|3 |

Abbreviations:
CI, confidence interval;
SD, standard deviation;
U/L, unit liter;
AAF, alternative allele frequency;
RR, reference-reference genotype;
RA, reference-alternative heterozygous genotype;
AA, alternative-alternative homozygous genotype;
pLOF, predicted loss of function.

An association for rare CIDEB pLOF variants alone (excluding missense variants) with lower transaminases was also observed (Table 21), indicating that the association for rare pLOF plus missense variants reflects a loss-of-function in CIDEB.

TABLE 21

Associations with lower transaminase levels for the burden of rare pLOF variants in the CIDEB gene (gene = CIDEB; genetic exposure = pLOF, AAF <1%)

| Outcome | Beta (95% CI), per allele | p | AAF, fraction of 1 | Genotype counts, RR\|RA\|AA genotypes |
|---|---|---|---|---|
| ALT | −0.12 (−0.18, −0.05) SD, −1.57 (−2.48, −0.67) U/L | $6.6 \times 10^{-04}$ | 0.0007 | 542,144\|760\|0 |
| AST | −0.12 (−0.19, −0.06) SD, −1.25 (−1.91, −0.58) U/L | $2.8 \times 10^{-04}$ | 0.0007 | 539,495\|755\|0 |

Abbreviations:
CI, confidence interval;
SD, standard deviation;
U/L, unit liter;
AAF, alternative allele frequency;
RR, reference-reference genotype;
RA, reference-alternative heterozygous genotype;
AA, alternative-alternative homozygous genotype;
pLOF, predicted loss of function.

The associations of CIDEB rare coding variants with risk of liver disease outcomes across etiologies and severity spectrum we estimated. Rare coding variants in CIDEB were associated with: 1) lower risk of any-cause, alcoholic and nonalcoholic liver disease, 2) lower risk of any-cause, alcoholic and nonalcoholic cirrhosis, and 3) lower risk of viral hepatitis. Heterozygous carriers of rare coding variants had 29-53% lower odds of these outcomes compared with non-carriers (FIG. 1). On the log-linear scale and in the same set of individuals, the protective associations for rare coding variants in CIDEB were 3- to 7-fold larger than the rs72613567 splice LOF variant in the HSD17B13 gene previously reported to be associated with protection against liver disease (N. Engl. J. Med., 2018, 378, 1096-106) (FIG. 1).

Figure 2:
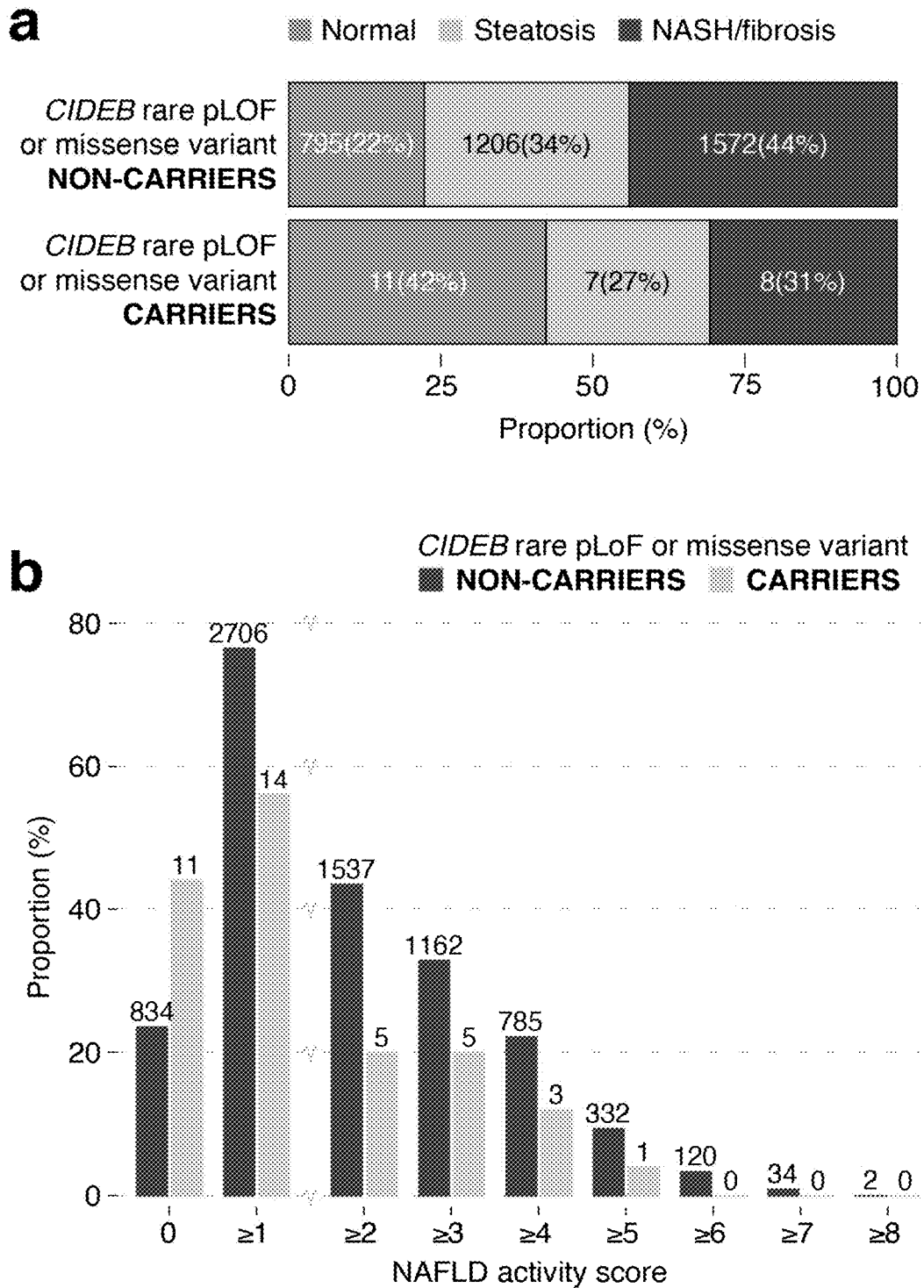
FIG. 2 shows an association of rare coding variants in CIDEB with liver histopathology phenotypes in bariatric surgery patients. Panel a shows the breakdown of liver histopathology categories (i.e., normal liver, simple steatosis, NASH or fibrosis) among carriers and non-carriers of rare coding (i.e., pLOF and missense) variants in CIDEB. Panel b shows the distribution of nonalcoholic fatty liver disease activity score at liver histopathology among carriers and non-carriers of rare coding (i.e., pLOF plus missense) variants in CIDEB. Data are from perioperative liver biopsies of participants in the GHS bariatric surgery cohort. Abbreviations: pLOF, predicted loss of function; NASH, nonalcoholic steatohepatitis; NALD, nonalcoholic fatty liver disease.

Associations with liver histopathology phenotypes in 3,599 bariatric surgery patients who underwent a perioperative liver biopsy (see Methods in Example 1) were estimated. Individuals carrying rare pLOF or missense variants in CIDEB had lower odds of biopsy-defined hepatic steatosis, NASH or fibrosis compared to non-carriers (per-allele odds ratio (OR), 0.34; 95% confidence interval, 0.14 to 0.79; p=0.012; FIG. 2, panel a). This association was driven by both a lower proportion of bariatric patients with simple steatosis and a lower proportion of patients with NASH or fibrosis among carriers (Table 22). Rare pLOF or missense variants in CIDEB were also associated with a lower NASH-CRN nonalcoholic fatty-liver disease activity score (NAS) at biopsy (per-allele beta in standard deviation units of the score, −0.56, 95% CI −0.88 to −0.24; per-allele beta in untransformed score units, −0.98; 95% CI −1.54 to −0.41; p=$7\times10^{-4}$, FIG. 2, panel b and Table 22).

TABLE 22

Association between rare pLOF or rare missense variants in CIDEB and liver histopathology phenotypes

| Outcome | OR or beta$_{SD}$ (95% CI) | P-value | CIDEB genotype counts (Ref/Het/Hom) |
|---|---|---|---|
| Steatosis/NASH/ fibrosis vs. normal liver | 0.34 (0.14 to 0.79) | 0.012 | Cases: 2778/15/0; Controls: 795/11/0 |
| Simple steatosis vs. normal liver | 0.37 (0.14 to 1.00) | 0.05 | Cases: 1206/7/0; Controls: 795/11/0 |
| NASH/fibrosis vs. normal liver | 0.25 (0.09 to 0.69) | 0.007 | Cases: 1572/8/0; Controls: 795/11/0 |

TABLE 22-continued

Association between rare pLOF or rare missense variants in CIDEB and liver histopathology phenotypes

| Outcome | OR or beta$_{SD}$ (95% CI) | P-value | CIDEB genotype counts (Ref/Het/Hom) |
|---|---|---|---|
| NAFLD activity score | −0.56 (−0.88 to −0.24) | 0.0007 | Participants: 3540/25/0 |

Abbreviations:
OR, odds ratio;
SD, standard deviation;
CI, confidence interval;
Ref, homozygous reference genotype;
Het, heterozygous carrier of rare pLOF or missense variant in CIDEB;
Hom, homozygous carrier of rare pLOF or missense variant in CIDEB;
NASH; nonalcoholic steatohepatitis;
NAFLD, nonalcoholic fatty liver disease.

Figure 3:
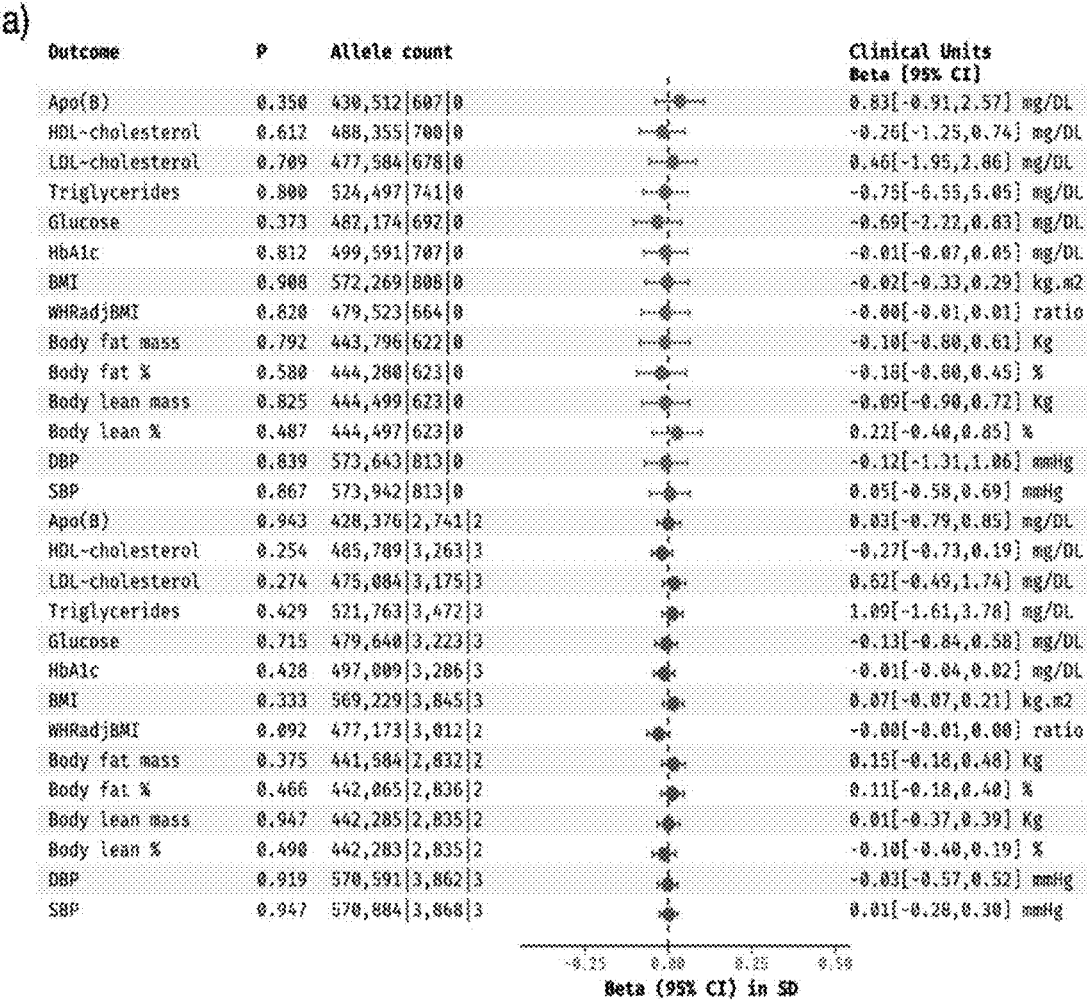
FIG. 3 shows associations with metabolic traits of rare coding variants in CIDEB. Associations estimates in blue are for rare coding (pLOF and missense) variants, while association estimates in red are for rare pLOF variants only. Panel a shows associations with continuous traits, while Panel b shows associations with binary outcomes traits. Abbreviations: HDL, high-density lipoprotein; LDL, low-density lipoprotein; BMI, Body mass index; WHRadjBMI, Waist-hip ratio adjusted for BMI; DBP, Diastolic blood pressure; SBP, Systolic blood pressure; pLOF, predicted loss of function; CI, Confidence interval; $kg/m^2$, kilograms per square meter; mg/DL, milligrams per deciliter; and mmHg, millimeter of mercury.

Associations with lipid, glycemic, and anthropometric traits for rare coding variants in CIDEB in over 500,000 people (FIG. 3) were estimated. Statistically significant associations for CIDEB pLOF or missense variants were not found with these traits, except for a nominally significant association with lower risk of type 2 diabetes (per-allele odds ratio, 0.87; 95% CI, 0.79 to 0.97; p=0.011).

Furthermore, whether rare pLOF or missense variants in CIDEB were associated with any of 6,040 clinical phenotypes was explored in a phenome-wide wide analysis in the GHS, UKB, or a meta-analysis of these two cohorts. In this analysis, no statistically significant associations were observed with clinical phenotypes other than the associations with lower liver enzymes and outcomes described above, after correction for the number of statistical tests performed ($p<8.3\times10^{-6}$).

The associations between CIDEB and liver phenotypes were driven by multiple rare pLOF or missense variants in the CIDEB gene (Table 23).

TABLE 23

Missense or pLOF variants of CIDEB that were identified by exome sequencing and included in the gene burden association analyses

| Genomic coordinates for the genetic variant, C:P:R:A | Coding DNA change | Protein change | Variant classified as pLOF | AAF, fraction of 1 |
|---|---|---|---|---|
| 14:24305640:G:A | c.653C > T, c.653C > T, c.653C > T | p.Ser218Phe, p.Ser218Phe, p.Ser218Phe | No | 4.0E−05 |
| 14:24305643:T:C | c.650A > G, c.650A > G, c.650A > G | p.His217Arg, p.His217Arg, p.His217Arg | No | 1.7E−05 |
| 14:24305649:C:T | c.644G > A, c.644G > A, c.644G > A | p.Arg215His, p.Arg215His, p.Arg215His | No | 1.2E−05 |
| 14:24305650:G:A | c.643C > T, c.643C > T, c.643C > T | p.Arg215Cys, p.Arg215Cys, p.Arg215Cys | No | 1.1E−05 |
| 14:24305650:G:C | c.643C > G, c.643C > G, c.643C > G | p.Arg215Gly, p.Arg215Gly, p.Arg215Gly | No | 3.8E−05 |
| 14:24305658:T:G | c.635A > C, c.635A > C, c.635A > C | p.Gln212Pro, p.Gln212Pro, p.Gln212Pro | No | 1.1E−05 |
| 14:24305664:C:T | c.629G > A, c.629G > A, c.629G > A | p.Trp210*, p.Trp210*, p.Trp210* | Yes | 1.1E−05 |
| 14:24305667:T:C | c.626A > G, c.626A > G, c.626A > G | p.Gln209Arg, p.Gln209Arg, p.Gln209Arg | No | 4.3E−06 |
| 14:24305671:C:T | c.622G > A, c.622G > A, c.622G > A | p.Glu208Lys, p.Glu208Lys, p.Glu208Lys | No | 5.8E−04 |
| 14:24305683:C:G | c.610G > C, c.610G > C, c.610G > C | p.Val204Leu, p.Val204Leu, p.Val204Leu | No | 5.8E−06 |
| 14:24305686:C:G | c.607G > C, c.607G > C, c.607G > C | p.Ala203Pro, p.Ala203Pro, p.Ala203Pro | No | 1.1E−04 |
| 14:24305691:C:T | c.602G > A, c.602G > A, c.602G > A | p.Arg201His, p.Arg201His, p.Arg201His | No | 2.9E−05 |
| 14:24305718:A:G | c.575T > C, c.575T > C, c.575T > C | p.Met192Thr, p.Met192Thr, p.Met192Thr | No | 1.4E−05 |
| 14:24305721:T:C | c.572A > G, c.572A > G, c.572A > G | p.His191Arg, p.His191Arg, p.His191Arg | No | 3.3E−05 |
| 14:24305733:T:C | c.560A > G, c.560A > G, c.560A > G | p.Gln187Arg, p.Gln187Arg, p.Gln187Arg | No | 2.0E−05 |
| 14:24305755:G:A | c.538C > T, c.538C > T, c.538C > T | p.Arg180Cys, p.Arg180Cys, p.Arg180Cys | No | 9.7E−05 |
| 14:24305766:C:T | c.528 − 1G > A, c.528 − 1G > A, c.528 − 1G > A | | Yes | 9.3E−06 |
| 14:24305946:C:T | c.527 + 1G > A, c.527 + 1G > A, c.527 + 1G > A | | Yes | 5.8E−05 |
| 14:24305953:A:G | c.521T > C, c.521T > C, c.521T > C | p.Val174Ala, p.Val174Ala, p.Val174Ala | No | 1.5E−05 |
| 14:24305963:G:A | c.511C > T, c.511C > T, c.511C > T | p.Pro171Ser, p.Pro171Ser, p.Pro171Ser | No | 4.5E−06 |
| 14:24305966:C:T | c.508G > A, c.508G > A, c.508G > A | p.Gly170Ser, p.Gly170Ser, p.Gly170Ser | No | 4.5E−06 |
| 14:24305972:C:G | c.502G > C, c.502G > C, c.502G > C | p.Gly168Arg, p.Gly168Arg, p.Gly168Arg | No | 7.8E−06 |
| 14:24305988:CAT:C | c.484_485delAT, c.484_485delAT, c.484_485delAT | p.Met162fs, p.Met162fs, p.Met162fs | Yes | 2.8E−05 |
| 14:24305990:T:C | c.484A > G, c.484A > G, c.484A > G | p.Met162Val, p.Met162Val, p.Met162Val | No | 5.8E−06 |
| 14:24306002:C:T | c.472G > A, c.472G > A, c.472G > A | p.Gly158Arg, p.Gly158Arg, p.Gly158Arg | No | 1.7E−05 |
| 14:24306017:T:A | c.457A > T, c.457A > T, c.457A > T | p.Lys153*, p.Lys153*, p.Lys153* | Yes | 5.5E−05 |
| 14:24306041:C:G | c.433G > C, c.433G > C, c.433G > C | p.Asp145His, p.Asp145His, p.Asp145His | No | 4.3E−06 |
| 14:24306047:G:A | c.427C > T, c.427C > T, c.427C > T | p.Pro143Ser, p.Pro143Ser, p.Pro143Ser | No | 4.7E−05 |
| 14:24306052:TG:T | c.421delC, c.421delC, c.421delC | p.Gln141fs, p.Gln141fs, p.Gln141fs | Yes | 2.3E−05 |
| 14:24306062:C:A | c.412G > T, c.412G > T, c.412G > T | p.Val138Leu, p.Val138Leu, p.Val138Leu | No | 3.5E−06 |
| 14:24306062:C:T | c.412G > A, c.412G > A, c.412G > A | p.Val138Met, p.Val138Met, p.Val138Met | No | 4.9E−05 |
| 14:24306076:C:T | c.398G > A, c.398G > A, c.398G > A | p.Arg133Gln, p.Arg133Gln, p.Arg133Gln | No | 1.7E−05 |
| 14:24306077:G:A | c.397C > T, c.397C > T, c.397C > T | p.Arg133*, p.Arg133*, p.Arg133* | Yes | 2.7E−05 |
| 14:24306082:A:G | c.392T > C, c.392T > C, c.392T > C | p.Ile131Thr, p.Ile131Thr, p.Ile131Thr | No | 8.9E−06 |
| 14:24306095:G:A | c.379C > T, c.379C > T, c.379C > T | p.His127Tyr, p.His127Tyr, p.His127Tyr | No | 7.2E−06 |
| 14:24306109:C:T | c.365G > A, c.365G > A, c.365G > A | p.Arg122Gln, p.Arg122Gln, p.Arg122Gln | No | 7.5E−05 |
| 14:24306110:G:A | c.364C > T, c.364C > T, c.364C > T | p.Arg122Trp, p.Arg122Trp, p.Arg122Trp | No | 4.0E−04 |
| 14:24306131:C:T | c.343G > A, c.343G > A, c.343G > A | p.Val115Met, p.Val115Met, p.Val115Met | No | 2.1E−05 |
| 14:24306373:C:T | c.336 + 1G > A, c.336 + 1G > A, c.336 + 1G > A | | Yes | 4.1E−04 |

TABLE 23-continued

Missense or pLOF variants of CIDEB that were identified by exome sequencing and included in the gene burden association analyses

| Genomic coordinates for the genetic variant, C:P:R:A | Coding DNA change | Protein change | Variant classified as pLOF | AAF, fraction of 1 |
|---|---|---|---|---|
| 14:24306379:T:C | c.331A > G, c.331A > G, c.331A > G | p.Thr111Ala, p.Thr111Ala, p.Thr111Ala | No | 3.6E-05 |
| 14:24306383:G:C | c.327C > G, c.327C > G, c.327C > G | p.Ser109Arg, p.Ser109Arg, p.Ser109Arg | No | 1.3E-05 |
| 14:24306403:G:A | c.307C > T, c.307C > T, c.307C > T | p.Gln103*, p.Gln103*, p.Gln103* | Yes | 1.4E-05 |
| 14:24306410:C:T | c.300G > A, c.300G > A, c.300G > A | p.Met100Ile, p.Met100Ile, p.Met100Ile | No | 3.2E-05 |
| 14:24306417:C:T | c.293G > A, c.293G > A, c.293G > A | p.Cys98Tyr, p.Cys98Tyr, p.Cys98Tyr | No | 1.8E-05 |
| 14:24306420:G:C | c.290C > G, c.290C > G, c.290C > G | p.Thr97Arg, p.Thr97Arg, p.Thr97Arg | No | 1.1E-05 |
| 14:24306420:G:A | c.290C > T, c.290C > T, c.290C > T | p.Thr97Met, p.Thr97Met, p.Thr97Met | No | 6.4E-04 |
| 14:24306423:T:G | c.287A > C, c.287A > C, c.287A > C | p.Asp96Ala, p.Asp96Ala, p.Asp96Ala | No | 5.2E-05 |
| 14:24306437:C:G | c.273G > C, c.273G > C, c.273G > C | p.Gln91His, p.Gln91His, p.Gln91His | No | 5.2E-06 |
| 14:24306442:A:G | c.268T > C, c.268T > C, c.268T > C | p.Phe90Leu, p.Phe90Leu, p.Phe90Leu | No | 4.7E-06 |
| 14:24306451:C:T | c.259G > A, c.259G > A, c.259G > A | p.Glu87Lys, p.Glu87Lys, p.Glu87Lys | No | 5.6E-05 |
| 14:24306463:C:T | c.247G > A, c.247G > A, c.247G > A | p.Ala83Thr, p.Ala83Thr, p.Ala83Thr | No | 1.2E-04 |
| 14:24306483:A:G | c.227T > C, c.227T > C, c.227T > C | p.Val76Ala, p.Val76Ala, p.Val76Ala | No | 2.2E-05 |
| 14:24306486:A:C | c.224T > G, c.224T > G, c.224T > G | p.Leu75Arg, p.Leu75Arg, p.Leu75Arg | No | 1.5E-05 |
| 14:24306504:A:G | c.206T > C, c.206T > C, c.206T > C | p.Leu69Pro, p.Leu69Pro, p.Leu69Pro | No | 5.3E-06 |
| 14:24307385:C:T | c.172G > A, c.172G > A, c.172G > A | p.Glu58Lys, p.Glu58Lys, p.Glu58Lys | No | 3.1E-05 |
| 14:24307390:C:T | c.167G > A, c.167G > A, c.167G > A | p.Arg56His, p.Arg56His, p.Arg56His | No | 1.0E-05 |
| 14:24307411:T:C | c.146A > G, c.146A > G, c.146A > G | p.Lys49Arg, p.Lys49Arg, p.Lys49Arg | No | 2.8E-05 |
| 14:24307423:C:T | c.134G > A, c.134G > A, c.134G > A | p.Arg45Gln, p.Arg45Gln, p.Arg45Gln | No | 1.1E-05 |
| 14:24307424:G:A | c.133C > T, c.133C > T, c.133C > T | p.Arg45Trp, p.Arg45Trp, p.Arg45Trp | No | 6.1E-05 |
| 14:24307442:G:A | c.115C > T, c.115C > T, c.115C > T | p.Arg39Cys, p.Arg39Cys, p.Arg39Cys | No | 1.0E-04 |
| 14:24307447:G:A | c.110C > T, c.110C > T, c.110C > T | p.Pro37Leu, p.Pro37Leu, p.Pro37Leu | No | 8.3E-06 |
| 14:24307451:G:A | c.106C > T, c.106C > T, c.106C > T | p.Arg36*, p.Arg36*, p.Arg36* | Yes | 3.4E-05 |
| 14:24307461:TG:T | c.95delC, c.95delC, c.95delC | p.Pro32fs, p.Pro32fs, p.Pro32fs | Yes | 1.3E-05 |
| 14:24307469:AG:A | c.87delC, c.87delC, c.87delC | p.Ser30fs, p.Ser30fs, p.Ser30fs | Yes | 1.7E-05 |
| 14:24307474:T:A | c.83G > A, c.83G > A, c.83G > A | p.Trp28*, p.Trp28*, p.Trp28* | Yes | 5.3E-06 |
| 14:24307483:C:T | c.74G > A, c.74G > A, c.74G > A | p.Arg25Gln, p.Arg25Gln, p.Arg25Gln | No | 3.4E-05 |
| 14:24307484:G:A | c.73C > T, c.73C > T, c.73C > T | p.Arg25Trp, p.Arg25Trp, p.Arg25Trp | No | 2.9E-05 |
| 14:24307495:G:A | c.62C > T, c.62C > T, c.62C > T | p.Ser21Leu, p.Ser21Leu, p.Ser21Leu | No | 1.3E-05 |
| 14:24307498:C:T | c.59G > A, c.59G > A, c.59G > A | p.Ser20Asn, p.Ser20Asn, p.Ser20Asn | No | 7.6E-05 |
| 14:24307825:A:C | c.34T > G, c.34T > G, c.34T > G | p.Leu12Val, p.Leu12Val, p.Leu12Val | No | 7.1E-05 |
| 14:24307829:A:C | c.30T > G, c.30T > G, c.30T > G | p.Ser10Arg, p.Ser10Arg, p.Ser10Arg | No | 4.7E-06 |
| 14:24307839:A:C | c.20T > G, c.20T > G, c.20T > G | p.Leu7Arg, p.Leu7Arg, p.Leu7Arg | No | 7.6E-06 |
| 14:24305635:A:AGTAG | c.654_657dupCTAC, c.654_657dupCTAC, c.654_657dupCTAC | p.Ter220fs, p.Ter220fs, p.Ter220fs | Yes | 3.2E-06 |
| 14:24305641:A:C | c.652T > G, c.652T > G, c.652T > G | p.Ser218Ala, p.Ser218Ala, p.Ser218Ala | No | 1.2E-05 |
| 14:24305662:G:T | c.631C > A, c.631C > A, c.631C > A | p.Gln211Lys, p.Gln211Lys, p.Gln211Lys | No | 3.9E-06 |
| 14:24305677:C:G | c.616G > C, c.616G > C, c.616G > C | p.Gly206Arg, p.Gly206Arg, p.Gly206Arg | No | 6.7E-06 |
| 14:24305692:G:A | c.601C > T, c.601C > T, c.601C > T | p.Arg201Cys, p.Arg201Cys, p.Arg201Cys | No | 6.0E-06 |
| 14:24305701:A:T | c.592T > A, c.592T > A, c.592T > A | p.Ser198Thr, p.Ser198Thr, p.Ser198Thr | No | 3.2E-06 |
| 14:24305728:G:GGCCTT | c.560_564dupAAGGC, c.560_564dupAAGGC, c.560_564dupAAGGC | p.Leu189fs, p.Leu189fs, p.Leu189fs | Yes | 3.7E-06 |
| 14:24305743:T:C | c.550A > G, c.550A > G, c.550A > G | p.Thr184Ala, p.Thr184Ala, p.Thr184Ala | No | 3.2E-06 |
| 14:24305754:C:T | c.539G > A, c.539G > A, c.539G > A | p.Arg180His, p.Arg180His, p.Arg180His | No | 8.6E-06 |
| 14:24305948:T:C | c.526A > G, c.526A > G, c.526A > G | p.Arg176Gly, p.Arg176Gly, p.Arg176Gly | No | 3.2E-06 |
| 14:24305953:ACTTT:A | c.517_520delAAAG, c.517_520delAAAG, c.517_520delAAAG | p.Lys173fs, p.Lys173fs, p.Lys173fs | Yes | 1.5E-05 |
| 14:24306014:C:T | c.460G > A, c.460G > A, c.460G > A | p.Ala154Thr, p.Ala154Thr, p.Ala154Thr | No | 3.4E-06 |
| 14:24306044:G:A | c.430C > T, c.430C > T, c.430C > T | p.Arg144*, p.Arg144*, p.Arg144* | Yes | 2.3E-05 |
| 14:24306064:T:C | c.410A > G, c.410A > G, c.410A > G | p.Asp137Gly, p.Asp137Gly, p.Asp137Gly | No | 3.2E-06 |
| 14:24306080:C:T | c.394G > A, c.394G > A, c.394G > A | p.Ala132Thr, p.Ala132Thr, p.Ala132Thr | No | 4.3E-05 |
| 14:24306083:T:A | c.391A > T, c.391A > T, c.391A > T | p.Ile131Phe, p.Ile131Phe, p.Ile131Phe | No | 3.2E-06 |
| 14:24306087:C:G | c.387G > C, c.387G > C, c.387G > C | p.Lys129Asn, p.Lys129Asn, p.Lys129Asn | No | 4.5E-06 |
| 14:24306095:G:T | c.379C > A, c.379C > A, c.379C > A | p.His127Asn, p.His127Asn, p.His127Asn | No | 1.5E-05 |
| 14:24306134:C:G | c.340G > C, c.340G > C, c.340G > C | p.Gly114Arg, p.Gly114Arg, p.Gly114Arg | No | 3.4E-06 |
| 14:24306138:CTG:C | c.337 − 3_337 − 2delCA, c.337 − 3_337 − 2delCA, c.337 − 3_337 − 2delCA | | Yes | 8.0E-06 |
| 14:24306139:T:C | c.337 − 2A > G, c.337 − 2A > G, c.337 − 2A > G | | Yes | 2.1E-05 |
| 14:24306373:C:A | c.336 + 1G > T, c.336 + 1G > T, c.336 + 1G > T | | Yes | 1.3E-05 |
| 14:24306382:G:A | c.328C > T, c.328C > T, c.328C > T | p.Pro110Ser, p.Pro110Ser, p.Pro110Ser | No | 3.2E-06 |
| 14:24306387:C:T | c.323G > A, c.323G > A, c.323G > A | p.Trp108*, p.Trp108*, p.Trp108* | Yes | 4.5E-06 |
| 14:24306418:A:G | c.292T > C, c.292T > C, c.292T > C | p.Cys98Arg, p.Cys98Arg, p.Cys98Arg | No | 8.4E-06 |
| 14:24306433:G:GA | c.276_277insT, c.276_277insT, c.276_277insT | p.Leu93fs, p.Leu93fs, p.Leu93fs | Yes | 5.4E-06 |

TABLE 23-continued

Missense or pLOF variants of CIDEB that were identified by exome sequencing and included in the gene burden association analyses

| Genomic coordinates for the genetic variant, C:P:R:A | Coding DNA change | Protein change | Variant classified as pLOF | AAF, fraction of 1 |
|---|---|---|---|---|
| 14:24306439:G:C | c.271C > G, c.271C > G, c.271C > G | p.Gln91Glu, p.Gln91Glu, p.Gln91Glu | No | 3.2E−06 |
| 14:24306444:A:G | c.266T > C, c.266T > C, c.266T > C | p.Phe89Ser, p.Phe89Ser, p.Phe89Ser | No | 3.2E−06 |
| 14:24306469:C:T | c.241G > A, c.241G > A, c.241G > A | p.Gly81Arg, p.Gly81Arg, p.Gly81Arg | No | 3.7E−06 |
| 14:24306480:A:G | c.230T > C, c.230T > C, c.230T > C | p.Leu77Pro, p.Leu77Pro, p.Leu77Pro | No | 3.2E−06 |
| 14:24306508:G:C | c.202C > G, c.202C > G, c.202C > G | p.Leu68Val, p.Leu68Val, p.Leu68Val | No | 5.6E−06 |
| 14:24306511:G:T | c.199C > A, c.199C > A, c.199C > A | p.Leu67Ile, p.Leu67Ile, p.Leu67Ile | No | 3.2E−06 |
| 14:24307382:G:C | c.175C > G, c.175C > G, c.175C > G | p.Leu59Val, p.Leu59Val, p.Leu59Val | No | 3.2E−06 |
| 14:24307391:G:A | c.166C > T, c.166C > T, c.166C > T | p.Arg56Cys, p.Arg56Cys, p.Arg56Cys | No | 5.2E−06 |
| 14:24307402:G:A | c.155C > T, c.155C > T, c.155C > T | p.Thr52Ile, p.Thr52Ile, p.Thr52Ile | No | 1.4E−05 |
| 14:24307405:A:G | c.152T > C, c.152T > C, c.152T > C | p.Leu51Pro, p.Leu51Pro, p.Leu51Pro | No | 6.2E−06 |
| 14:24307421:T:A | c.136A > T, c.136A > T, c.136A > T | p.Thr46Ser, p.Thr46Ser, p.Thr46Ser | No | 3.2E−06 |
| 14:24307441:C:A | c.116G > T, c.116G > T, c.116G > T | p.Arg39Leu, p.Arg39Leu, p.Arg39Leu | No | 3.2E−06 |
| 14:24307441:C:T | c.116G > A, c.116G > A, c.116G > A | p.Arg39His, p.Arg39His, p.Arg39His | No | 3.9E−05 |
| 14:24307448:G:T | c.109C > A, c.109C > A, c.109C > A | p.Pro37Thr, p.Pro37Thr, p.Pro37Thr | No | 3.3E−05 |
| 14:24307450:C:T | c.107G > A, c.107G > A, c.107G > A | p.Arg36Gln, p.Arg36Gln, p.Arg36Gln | No | 1.9E−05 |
| 14:24307475:A:G | c.82T > C, c.82T > C, c.82T > C | p.Trp28Arg, p.Trp28Arg, p.Trp28Arg | No | 6.4E−06 |
| 14:24307510:A:T | c.47T > A, c.47T > A, c.47T > A | p.Val16Glu, p.Val16Glu, p.Val16Glu | No | 4.1E−06 |
| 14:24307516:C:G | c.42 − 1G > C, c.42 − 1G > C, c.42 − 1G > C |  | Yes | 1.2E−05 |
| 14:24307822:G:GT | c.36dupA, c.36dupA, c.36dupA | p.Leu13fs, p.Leu13fs, p.Leu13fs | Yes | 4.1E−06 |
| 14:24307824:A:T | c.35T > A, c.35T > A, c.35T > A | p.Leu12*, p.Leu12*, p.Leu12* | Yes | 3.9E−06 |
| 14:24307833:G:C | c.26C > G, c.26C > G, c.26C > G | p.Pro9Arg, p.Pro9Arg, p.Pro9Arg | No | 3.2E−06 |
| 14:24307851:T:TAC | c.6_7dupGT, c.6_7dupGT, c.6_7dupGT | p.Tyr3fs, p.Tyr3fs, p.Tyr3fs | Yes | 7.5E−06 |
| 14:24307857:A:C | c.2T > G, c.2T > G, c.2T > G | p.Met1?, p.Met1?, p.Met1? | Yes | 2.0E−05 |
| 14:24305635:A:C | c.658T > G, c.658T > G, c.658T > G | p.Ter220Gluext*?, p.Ter220Gluext*?, p.Ter220Gluext*? | Yes | 8.7E−07 |
| 14:24305637:T:C | c.656A > G, c.656A > G, c.656A > G | p.Tyr219Cys, p.Tyr219Cys, p.Tyr219Cys | No | 6.1E−06 |
| 14:24305638:A:G | c.655T > C, c.655T > C, c.655T > C | p.Tyr219His, p.Tyr219His, p.Tyr219His | No | 8.7E−07 |
| 14:24305652:C:T | c.641G > A, c.641G > A, c.641G > A | p.Gly214Asp, p.Gly214Asp, p.Gly214Asp | No | 4.3E−07 |
| 14:24305653:C:T | c.640G > A, c.640G > A, c.640G > A | p.Gly214Ser, p.Gly214Ser, p.Gly214Ser | No | 1.3E−06 |
| 14:24305657:C:A | c.636G > T, c.636G > T, c.636G > T | p.Gln212His, p.Gln212His, p.Gln212His | No | 4.3E−07 |
| 14:24305657:C:G | c.636G > C, c.636G > C, c.636G > C | p.Gln212His, p.Gln212His, p.Gln212His | No | 8.7E−07 |
| 14:24305660:C:G | c.633G > C, c.633G > C, c.633G > C | p.Gln211His, p.Gln211His, p.Gln211His | No | 4.3E−07 |
| 14:24305661:T:G | c.632A > C, c.632A > C, c.632A > C | p.Gln211Pro, p.Gln211Pro, p.Gln211Pro | No | 4.3E−07 |
| 14:24305661:T:C | c.632A > G, c.632A > G, c.632A > G | p.Gln211Arg, p.Gln211Arg, p.Gln211Arg | No | 4.3E−07 |
| 14:24305663:C:G | c.630G > C, c.630G > C, c.630G > C | p.Trp210Cys, p.Trp210Cys, p.Trp210Cys | No | 1.7E−06 |
| 14:24305663:C:T | c.630G > A, c.630G > A, c.630G > A | p.Trp210*, p.Trp210*, p.Trp210* | Yes | 8.7E−07 |
| 14:24305668:G:A | c.625C > T, c.625C > T, c.625C > T | p.Gln209*, p.Gln209*, p.Gln209* | Yes | 4.3E−07 |
| 14:24305671:C:A | c.622G > T, c.622G > T, c.622G > T | p.Glu208*, p.Glu208*, p.Glu208* | Yes | 4.3E−07 |
| 14:24305671:C:G | c.622G > C, c.622G > C, c.622G > C | p.Glu208Gln, p.Glu208Gln, p.Glu208Gln | No | 4.3E−07 |
| 14:24305673:G:A | c.620C > T, c.620C > T, c.620C > T | p.Ala207Val, p.Ala207Val, p.Ala207Val | No | 1.7E−06 |
| 14:24305674:C:T | c.619G > A, c.619G > A, c.619G > A | p.Ala207Thr, p.Ala207Thr, p.Ala207Thr | No | 4.3E−07 |
| 14:24305676:C:T | c.617G > A, c.617G > A, c.617G > A | p.Gly206Glu, p.Gly206Glu, p.Gly206Glu | No | 4.3E−07 |
| 14:24305678:C:G | c.615G > C, c.615G > C, c.615G > C | p.Glu205Asp, p.Glu205Asp, p.Glu205Asp | No | 4.3E−07 |
| 14:24305678:C:A | c.615G > T, c.615G > T, c.615G > T | p.Glu205Asp, p.Glu205Asp, p.Glu205Asp | No | 4.3E−07 |
| 14:24305679:T:C | c.614A > G, c.614A > G, c.614A > G | p.Glu205Gly, p.Glu205Gly, p.Glu205Gly | No | 4.3E−07 |
| 14:24305680:C:G | c.613G > C, c.613G > C, c.613G > C | p.Glu205Gln, p.Glu205Gln, p.Glu205Gln | No | 4.3E−07 |
| 14:24305682:A:C | c.611T > G, c.611T > G, c.611T > G | p.Val204Gly, p.Val204Gly, p.Val204Gly | No | 8.7E−07 |
| 14:24305685:G:T | c.608C > A, c.608C > A, c.608C > A | p.Ala203Glu, p.Ala203Glu, p.Ala203Glu | No | 4.3E−07 |
| 14:24305685:G:C | c.608C > G, c.608C > G, c.608C > G | p.Ala203Gly, p.Ala203Gly, p.Ala203Gly | No | 2.6E−06 |
| 14:24305688:T:G | c.605A > C, c.605A > C, c.605A > C | p.His202Pro, p.His202Pro, p.His202Pro | No | 4.3E−07 |
| 14:24305695:G:C | c.598C > G, c.598C > G, c.598C > G | p.Leu200Val, p.Leu200Val, p.Leu200Val | No | 4.3E−07 |
| 14:24305695:G:T | c.598C > A, c.598C > A, c.598C > A | p.Leu200Ile, p.Leu200Ile, p.Leu200Ile | No | 1.3E−06 |
| 14:24305697:G:C | c.596C > G, c.596C > G, c.596C > G | p.Thr199Ser, p.Thr199Ser, p.Thr199Ser | No | 4.3E−07 |
| 14:24305706:A:G | c.587T > C, c.587T > C, c.587T > C | p.Ile196Thr, p.Ile196Thr, p.Ile196Thr | No | 4.3E−07 |
| 14:24305709:C:T | c.584G > A, c.584G > A, c.584G > A | p.Gly195Glu, p.Gly195Glu, p.Gly195Glu | No | 4.3E−07 |
| 14:24305710:C:T | c.583G > A, c.583G > A, c.583G > A | p.Gly195Arg, p.Gly195Arg, p.Gly195Arg | No | 1.7E−06 |
| 14:24305721:T:A | c.572A > T, c.572A > T, c.572A > T | p.His191Leu, p.His191Leu, p.His191Leu | No | 8.7E−07 |
| 14:24305722:G:C | c.571C > G, c.571C > G, c.571C > G | p.His191Asp, p.His191Asp, p.His191Asp | No | 4.3E−07 |
| 14:24305727:A:C | c.566T > G, c.566T > G, c.566T > G | p.Leu189Arg, p.Leu189Arg, p.Leu189Arg | No | 4.3E−07 |
| 14:24305730:C:A | c.563G > T, c.563G > T, c.563G > T | p.Gly188Val, p.Gly188Val, p.Gly188Val | No | 4.3E−07 |
| 14:24305748:G:T | c.545C > A, c.545C > A, c.545C > A | p.Thr182Asn, p.Thr182Asn, p.Thr182Asn | No | 4.3E−07 |
| 14:24305748:G:C | c.545C > G, c.545C > G, c.545C > G | p.Thr182Ser, p.Thr182Ser, p.Thr182Ser | No | 4.3E−07 |
| 14:24305749:T:C | c.544A > G, c.544A > G, c.544A > G | p.Thr182Ala, p.Thr182Ala, p.Thr182Ala | No | 4.3E−07 |
| 14:24305752:A:G | c.541T > C, c.541T > C, c.541T > C | p.Trp181Arg, p.Trp181Arg, p.Trp181Arg | No | 4.3E−07 |
| 14:24305754:C:A | c.539G > T, c.539G > T, c.539G > T | p.Arg180Leu, p.Arg180Leu, p.Arg180Leu | No | 8.7E−07 |
| 14:24305758:G:C | c.535C > G, c.535C > G, c.535C > G | p.Leu179Val, p.Leu179Val, p.Leu179Val | No | 4.3E−07 |
| 14:24305761:G:A | c.532C > T, c.532C > T, c.532C > T | p.Leu178Phe, p.Leu178Phe, p.Leu178Phe | No | 4.3E−07 |
| 14:24305763:T:G | c.530A > C, c.530A > C, c.530A > C | p.Glu177Ala, p.Glu177Ala, p.Glu177Ala | No | 4.3E−07 |

TABLE 23-continued

Missense or pLOF variants of CIDEB that were identified by exome sequencing and included in the gene burden association analyses

| Genomic coordinates for the genetic variant, C:P:R:A | Coding DNA change | Protein change | Variant classified as pLOF | AAF, fraction of 1 |
|---|---|---|---|---|
| 14:24305766:C:A | c.528 − 1G > T, c.528 − 1G > T, c.528 − 1G > T | | Yes | 4.3E−07 |
| 14:24305766:C:G | c.528 − 1G > C, c.528 − 1G > C, c.528 − 1G > C | | Yes | 7.8E−06 |
| 14:24305767:T:G | c.528 − 2A > C, c.528 − 2A > C, c.528 − 2A > C | | Yes | 4.3E−07 |
| 14:24305946:C:A | c.527 + 1G > T, c.527 + 1G > T, c.527 + 1G > T | | Yes | 7.4E−06 |
| 14:24305950:A:C | c.524T > G, c.524T > G, c.524T > G | p.Leu175Arg, p.Leu175Arg, p.Leu175Arg | No | 8.7E−07 |
| 14:24305951:G:A | c.523C > T, c.523C > T, c.523C > T | p.Leu175Phe, p.Leu175Phe, p.Leu175Phe | No | 4.3E−07 |
| 14:24305953:AC:A | c.520delG, c.520delG, c.520delG | p.Val174fs, p.Val174fs, p.Val174fs | Yes | 8.7E−07 |
| 14:24305954:C:CT | c.519dupA, c.519dupA, c.519dupA | p.Val174fs, p.Val174fs, p.Val174fs | Yes | 4.3E−07 |
| 14:24305957:T:A | c.517A > T, c.517A > T, c.517A > T | p.Lys173*, p.Lys173*, p.Lys173* | Yes | 4.3E−07 |
| 14:24305958:C:A | c.516G > T, c.516G > T, c.516G > T | p.Lys172Asn, p.Lys172Asn, p.Lys172Asn | No | 4.3E−07 |
| 14:24305958:C:G | c.516G > C, c.516G > C, c.516G > C | p.Lys172Asn, p.Lys172Asn, p.Lys172Asn | No | 4.3E−07 |
| 14:24305961:TG:T | c.512delC, c.512delC, c.512delC | p.Pro171fs, p.Pro171fs, p.Pro171fs | Yes | 4.3E−07 |
| 14:24305963:G:T | c.511C > A, c.511C > A, c.511C > A | p.Pro171Thr, p.Pro171Thr, p.Pro171Thr | No | 4.3E−07 |
| 14:24305965:C:T | c.509G > A, c.509G > A, c.509G > A | p.Gly170Asp, p.Gly170Asp, p.Gly170Asp | No | 1.7E−06 |
| 14:24305966:C:A | c.508G > T, c.508G > T, c.508G > T | p.Gly170Cys, p.Gly170Cys, p.Gly170Cys | No | 4.3E−07 |
| 14:24305968:A:C | c.506T > G, c.506T > G, c.506T > G | p.Leu169Arg, p.Leu169Arg, p.Leu169Arg | No | 1.4E−05 |
| 14:24305968:A:T | c.506T > A, c.506T > A, c.506T > A | p.Leu169His, p.Leu169His, p.Leu169His | No | 4.3E−07 |
| 14:24305968:A:G | c.506T > C, c.506T > C, c.506T > C | p.Leu169Pro, p.Leu169Pro, p.Leu169Pro | No | 4.3E−07 |
| 14:24305971:C:G | c.503G > C, c.503G > C, c.503G > C | p.Gly168Ala, p.Gly168Ala, p.Gly168Ala | No | 4.3E−07 |
| 14:24305974:T:TG | c.499dupC, c.499dupC, c.499dupC | p.Gln167fs, p.Gln167fs, p.Gln167fs | Yes | 6.5E−06 |
| 14:24305974:T:C | c.500A > G, c.500A > G, c.500A > G | p.Gln167Arg, p.Gln167Arg, p.Gln167Arg | No | 8.7E−07 |
| 14:24305980:T:A | c.494A > T, c.494A > T, c.494A > T | p.Asp165Val, p.Asp165Val, p.Asp165Val | No | 4.3E−07 |
| 14:24305980:TCA:T | c.492_493delTG, c.492_493delTG, c.492_493delTG | p.Cys164fs, p.Cys164fs, p.Cys164fs | Yes | 1.3E−06 |
| 14:24305982:A:C | c.492T > G, c.492T > G, c.492T > G | p.Cys164Trp, p.Cys164Trp, p.Cys164Trp | No | 1.3E−06 |
| 14:24305986:C:G | c.488G > C, c.488G > C, c.488G > C | p.Ser163Thr, p.Ser163Thr, p.Ser163Thr | No | 4.3E−07 |
| 14:24305986:C:T | c.488G > A, c.488G > A, c.488G > A | p.Ser163Asn, p.Ser163Asn, p.Ser163Asn | No | 8.7E−07 |
| 14:24305988:CATAGA:C | c.481_485delTCTAT, c.481_485delTCTAT, c.481_485delTCTAT | p.Ser161fs, p.Ser161fs, p.Ser161fs | Yes | 4.3E−07 |
| 14:24305988:C:T | c.486G > A, c.486G > A, c.486G > A | p.Met162Ile, p.Met162Ile, p.Met162Ile | No | 1.3E−06 |
| 14:24305989:A:G | c.485T > C, c.485T > C, c.485T > C | p.Met162Thr, p.Met162Thr, p.Met162Thr | No | 2.6E−06 |
| 14:24305990:T:A | c.484A > T, c.484A > T, c.484A > T | p.Met162Leu, p.Met162Leu, p.Met162Leu | No | 4.3E−07 |
| 14:24305992:G:A | c.482C > T, c.482C > T, c.482C > T | p.Ser161Phe, p.Ser161Phe, p.Ser161Phe | No | 4.3E−07 |
| 14:24305995:T:C | c.479A > G, c.479A > G, c.479A > G | p.Tyr160Cys, p.Tyr160Cys, p.Tyr160Cys | No | 1.3E−06 |
| 14:24305998:A:G | c.476T > C, c.476T > C, c.476T > C | p.Leu159Pro, p.Leu159Pro, p.Leu159Pro | No | 8.7E−07 |
| 14:24305999:G:A | c.475C > T, c.475C > T, c.475C > T | p.Leu159Phe, p.Leu159Phe, p.Leu159Phe | No | 8.7E−07 |
| 14:24306001:C:T | c.473G > A, c.473G > A, c.473G > A | p.Gly158Glu, p.Gly158Glu, p.Gly158Glu | No | 8.7E−07 |
| 14:24306003:G:T | c.471C > A, c.471C > A, c.471C > A | p.Tyr157*, p.Tyr157*, p.Tyr157* | Yes | 1.3E−06 |
| 14:24306005:A:C | c.469T > G, c.469T > G, c.469T > G | p.Tyr157Asp, p.Tyr157Asp, p.Tyr157Asp | No | 4.3E−07 |
| 14:24306006:G:C | c.468C > G, c.468C > G, c.468C > G | p.Phe156Leu, p.Phe156Leu, p.Phe156Leu | No | 4.3E−07 |
| 14:24306008:A:G | c.466T > C, c.466T > C, c.466T > C | p.Phe156Leu, p.Phe156Leu, p.Phe156Leu | No | 4.3E−07 |
| 14:24306010:G:A | c.464C > T, c.464C > T, c.464C > T | p.Thr155Ile, p.Thr155Ile, p.Thr155Ile | No | 4.3E−07 |
| 14:24306013:G:A | c.461C > T, c.461C > T, c.461C > T | p.Ala154Val, p.Ala154Val, p.Ala154Val | No | 4.3E−07 |
| 14:24306016:T:C | c.458A > G, c.458A > G, c.458A > G | p.Lys153Arg, p.Lys153Arg, p.Lys153Arg | No | 2.6E−06 |
| 14:24306020:C:T | c.454G > A, c.454G > A, c.454G > A | p.Val152Ile, p.Val152Ile, p.Val152Ile | No | 8.7E−07 |
| 14:24306027:G:C | c.447C > G, c.447C > G, c.447C > G | p.Ser149Arg, p.Ser149Arg, p.Ser149Arg | No | 4.3E−07 |
| 14:24306028:CT:C | c.445delA, c.445delA, c.445delA | p.Ser149fs, p.Ser149fs, p.Ser149fs | Yes | 4.3E−07 |
| 14:24306031:C:T | c.443G > A, c.443G > A, c.443G > A | p.Gly148Asp, p.Gly148Asp, p.Gly148Asp | No | 4.3E−07 |
| 14:24306032:C:T | c.442G > A, c.442G > A, c.442G > A | p.Gly148Ser, p.Gly148Ser, p.Gly148Ser | No | 2.2E−06 |
| 14:24306034:A:C | c.440T > G, c.440T > G, c.440T > G | p.Phe147Cys, p.Phe147Cys, p.Phe147Cys | No | 4.3E−07 |
| 14:24306034:A:T | c.440T > A, c.440T > A, c.440T > A | p.Phe147Tyr, p.Phe147Tyr, p.Phe147Tyr | No | 4.3E−07 |
| 14:24306034:A:G | c.440T > C, c.440T > C, c.440T > C | p.Phe147Ser, p.Phe147Ser, p.Phe147Ser | No | 4.3E−07 |
| 14:24306039:G:C | c.435C > G, c.435C > G, c.435C > G | p.Asp145Glu, p.Asp145Glu, p.Asp145Glu | No | 2.2E−06 |
| 14:24306039:G:T | c.435C > A, c.435C > A, c.435C > A | p.Asp145Glu, p.Asp145Glu, p.Asp145Glu | No | 8.7E−07 |
| 14:24306041:C:T | c.433G > A, c.433G > A, c.433G > A | p.Asp145Asn, p.Asp145Asn, p.Asp145Asn | No | 8.7E−07 |
| 14:24306043:C:A | c.431G > T, c.431G > T, c.431G > T | p.Arg144Leu, p.Arg144Leu, p.Arg144Leu | No | 8.7E−07 |
| 14:24306043:C:T | c.431G > A, c.431G > A, c.431G > A | p.Arg144Gln, p.Arg144Gln, p.Arg144Gln | No | 4.3E−06 |
| 14:24306043:C:G | c.431G > C, c.431G > C, c.431G > C | p.Arg144Pro, p.Arg144Pro, p.Arg144Pro | No | 1.7E−06 |
| 14:24306044:G:C | c.430C > G, c.430C > G, c.430C > G | p.Arg144Gly, p.Arg144Gly, p.Arg144Gly | No | 2.6E−06 |
| 14:24306046:G:A | c.428C > T, c.428C > T, c.428C > T | p.Pro143Leu, p.Pro143Leu, p.Pro143Leu | No | 4.3E−07 |
| 14:24306047:G:T | c.427C > A, c.427C > A, c.427C > A | p.Pro143Thr, p.Pro143Thr, p.Pro143Thr | No | 4.3E−07 |
| 14:24306051:T:G | c.423A > C, c.423A > C, c.423A > C | p.Gln141His, p.Gln141His, p.Gln141His | No | 4.3E−07 |
| 14:24306057:G:C | c.417C > G, c.417C > G, c.417C > G | p.Tyr139*, p.Tyr139*, p.Tyr139* | Yes | 4.3E−07 |

TABLE 23-continued

Missense or pLOF variants of CIDEB that were identified by exome sequencing and included in the gene burden association analyses

| Genomic coordinates for the genetic variant, C:P:R:A | Coding DNA change | Protein change | Variant classified as pLOF | AAF, fraction of 1 |
|---|---|---|---|---|
| 14:24306057:G:T | c.417C > A, c.417C > A, c.417C > A | p.Tyr139*, p.Tyr139*, p.Tyr139* | Yes | 4.3E−07 |
| 14:24306058:T:C | c.416A > G, c.416A > G, c.416A > G | p.Tyr139Cys, p.Tyr139Cys, p.Tyr139Cys | No | 1.3E−06 |
| 14:24306059:AC:A | c.414delG, c.414delG, c.414delG | p.Tyr139fs, p.Tyr139fs, p.Tyr139fs | Yes | 4.3E−07 |
| 14:24306061:AC:A | c.412delG, c.412delG, c.412delG | p.Val138fs, p.Val138fs, p.Val138fs | Yes | 4.3E−07 |
| 14:24306062:CGTCAAAG:C | c.405_411delCTTTGAC, c.405_411delCTTTGAC, c.405_411delCTTTGAC | p.Phe136fs, p.Phe136fs, p.Phe136fs | Yes | 8.7E−07 |
| 14:24306063:G:T | c.411C > A, c.411C > A, c.411C > A | p.Asp137Glu, p.Asp137Glu, p.Asp137Glu | No | 2.2E−06 |
| 14:24306064:T:G | c.410A > C, c.410A > C, c.410A > C | p.Asp137Ala, p.Asp137Ala, p.Asp137Ala | No | 4.3E−07 |
| 14:24306065:C:G | c.409G > C, c.409G > C, c.409G > C | p.Asp137His, p.Asp137His, p.Asp137His | No | 8.7E−07 |
| 14:24306066:A:C | c.408T > G, c.408T > G, c.408T > G | p.Phe136Leu, p.Phe136Leu, p.Phe136Leu | No | 4.3E−07 |
| 14:24306070:G:A | c.404C > T, c.404C > T, c.404C > T | p.Thr135Ile, p.Thr135Ile, p.Thr135Ile | No | 1.3E−06 |
| 14:24306072:G:T | c.402C > A, c.402C > A, c.402C > A | p.Phe134Leu, p.Phe134Leu, p.Phe134Leu | No | 4.3E−07 |
| 14:24306074:A:T | c.400T > A, c.400T > A, c.400T > A | p.Phe134Ile, p.Phe134Ile, p.Phe134Ile | No | 8.7E−07 |
| 14:24306074:A:G | c.400T > C, c.400T > C, c.400T > C | p.Phe134Leu, p.Phe134Leu, p.Phe134Leu | No | 4.3E−07 |
| 14:24306077:G:C | c.397C > G, c.397C > G, c.397C > G | p.Arg133Gly, p.Arg133Gly, p.Arg133Gly | No | 4.3E−07 |
| 14:24306083:T:C | c.391A > G, c.391A > G, c.391A > G | p.Ile131Val, p.Ile131Val, p.Ile131Val | No | 4.3E−07 |
| 14:24306086:C:T | c.388G > A, c.388G > A, c.388G > A | p.Asp130Asn, p.Asp130Asn, p.Asp130Asn | No | 1.3E−06 |
| 14:24306089:T:G | c.385A > C, c.385A > C, c.385A > C | p.Lys129Gln, p.Lys129Gln, p.Lys129Gln | No | 4.3E−07 |
| 14:24306092:T:A | c.382A > T, c.382A > T, c.382A > T | p.Ser128Cys, p.Ser128Cys, p.Ser128Cys | No | 4.3E−07 |
| 14:24306092:T:C | c.382A > G, c.382A > G, c.382A > G | p.Ser128Gly, p.Ser128Gly, p.Ser128Gly | No | 1.3E−06 |
| 14:24306092:T:G | c.382A > C, c.382A > C, c.382A > C | p.Ser128Arg, p.Ser128Arg, p.Ser128Arg | No | 4.3E−07 |
| 14:24306097:T:C | c.377A > G, c.377A > G, c.377A > G | p.Lys126Arg, p.Lys126Arg, p.Lys126Arg | No | 1.3E−06 |
| 14:24306098:T:C | c.376A > G, c.376A > G, c.376A > G | p.Lys126Glu, p.Lys126Glu, p.Lys126Glu | No | 4.3E−07 |
| 14:24306103:C:T | c.371G > A, c.371G > A, c.371G > A | p.Arg124Lys, p.Arg124Lys, p.Arg124Lys | No | 8.7E−07 |
| 14:24306105:CTCCCG:C | c.364_368delCGGGA, c.364_368delCGGGA, c.364_368delCGGGA | p.Arg122fs, p.Arg122fs, p.Arg122fs | Yes | 4.3E−07 |
| 14:24306107:C:T | c.367G > A, c.367G > A, c.367G > A | p.Glu123Lys, p.Glu123Lys, p.Glu123Lys | No | 2.1E−05 |
| 14:24306112:C:A | c.362G > T, c.362G > T, c.362G > T | p.Gly121Val, p.Gly121Val, p.Gly121Val | No | 8.7E−07 |
| 14:24306115:A:G | c.359T > C, c.359T > C, c.359T > C | p.Leu120Pro, p.Leu120Pro, p.Leu120Pro | No | 4.3E−07 |
| 14:24306118:C:G | c.356G > C, c.356G > C, c.356G > C | p.Gly119Ala, p.Gly119Ala, p.Gly119Ala | No | 4.3E−07 |
| 14:24306121:T:C | c.353A > G, c.353A > G, c.353A > G | p.Tyr118Cys, p.Tyr118Cys, p.Tyr118Cys | No | 4.3E−07 |
| 14:24306122:A:G | c.352T > C, c.352T > C, c.352T > C | p.Tyr118His, p.Tyr118His, p.Tyr118His | No | 2.2E−06 |
| 14:24306126:CAG:C | c.346_347delCT, c.346_347delCT, c.346_347delCT | p.Leu116fs, p.Leu116fs, p.Leu116fs | Yes | 4.3E−07 |
| 14:24306127:A:G | c.347T > C, c.347T > C, c.347T > C | p.Leu116Pro, p.Leu116Pro, p.Leu116Pro | No | 4.3E−07 |
| 14:24306139:T:G | c.337 − 2A > C, c.337 − 2A > C, c.337 − 2A > C | | Yes | 4.3E−07 |
| 14:24306373:C:G | c.336 + 1G > C, c.336 + 1G > C, c.336 + 1G > C | | Yes | 2.2E−06 |
| 14:24306374:C:G | c.336G > C, c.336G > C, c.336G > C | p.Arg112Ser, p.Arg112Ser, p.Arg112Ser | No | 4.3E−06 |
| 14:24306375:C:T | c.335G > A, c.335G > A, c.335G > A | p.Arg112Lys, p.Arg112Lys, p.Arg112Lys | No | 1.7E−06 |
| 14:24306382:G:T | c.328C > A, c.328C > A, c.328C > A | p.Pro110Thr, p.Pro110Thr, p.Pro110Thr | No | 1.7E−05 |
| 14:24306383:G:T | c.327C > A, c.327C > A, c.327C > A | p.Ser109Arg, p.Ser109Arg, p.Ser109Arg | No | 4.3E−07 |
| 14:24306384:C:G | c.326G > C, c.326G > C, c.326G > C | p.Ser109Thr, p.Ser109Thr, p.Ser109Thr | No | 4.3E−07 |
| 14:24306384:C:T | c.326G > A, c.326G > A, c.326G > A | p.Ser109Asn, p.Ser109Asn, p.Ser109Asn | No | 1.7E−06 |
| 14:24306386:C:G | c.324G > C, c.324G > C, c.324G > C | p.Trp108Cys, p.Trp108Cys, p.Trp108Cys | No | 1.3E−06 |
| 14:24306388:A:G | c.322T > C, c.322T > C, c.322T > C | p.Trp108Arg, p.Trp108Arg, p.Trp108Arg | No | 1.3E−06 |
| 14:24306391:T:C | c.319A > G, c.319A > G, c.319A > G | p.Ser107Gly, p.Ser107Gly, p.Ser107Gly | No | 4.3E−07 |
| 14:24306392:C:G | c.318G > C, c.318G > C, c.318G > C | p.Gln106His, p.Gln106His, p.Gln106His | No | 4.3E−07 |
| 14:24306397:C:T | c.313G > A, c.313G > A, c.313G > A | p.Gly105Ser, p.Gly105Ser, p.Gly105Ser | No | 8.7E−07 |
| 14:24306399:G:A | c.311C > T, c.311C > T, c.311C > T | p.Ser104Phe, p.Ser104Phe, p.Ser104Phe | No | 1.7E−06 |
| 14:24306402:T:A | c.308A > T, c.308A > T, c.308A > T | p.Gln103Leu, p.Gln103Leu, p.Gln103Leu | No | 2.6E−06 |
| 14:24306408:A:G | c.302T > C, c.302T > C, c.302T > C | p.Val101Ala, p.Val101Ala, p.Val101Ala | No | 3.9E−06 |
| 14:24306409:C:G | c.301G > C, c.301G > C, c.301G > C | p.Val101Leu, p.Val101Leu, p.Val101Leu | No | 4.3E−07 |
| 14:24306411:A:G | c.299T > C, c.299T > C, c.299T > C | p.Met100Thr, p.Met100Thr, p.Met100Thr | No | 1.7E−06 |
| 14:24306422:G:C | c.288C > G, c.288C > G, c.288C > G | p.Asp96Glu, p.Asp96Glu, p.Asp96Glu | No | 8.7E−07 |
| 14:24306423:T:C | c.287A > G, c.287A > G, c.287A > G | p.Asp96Gly, p.Asp96Gly, p.Asp96Gly | No | 4.3E−07 |
| 14:24306424:C:T | c.286G > A, c.286G > A, c.286G > A | p.Asp96Asn, p.Asp96Asn, p.Asp96Asn | No | 1.3E−06 |
| 14:24306426:T:G | c.284A > C, c.284A > C, c.284A > C | p.Asp95Ala, p.Asp95Ala, p.Asp95Ala | No | 4.3E−07 |
| 14:24306426:TCCTC:T | c.280_283delGAGG, c.280_283delGAGG, c.280_283delGAGG | p.Glu94fs, p.Glu94fs, p.Glu94fs | Yes | 8.7E−07 |
| 14:24306426:T:C | c.284A > G, c.284A > G, c.284A > G | p.Asp95Gly, p.Asp95Gly, p.Asp95Gly | No | 1.7E−06 |
| 14:24306427:C:T | c.283G > A, c.283G > A, c.283G > A | p.Asp95Asn, p.Asp95Asn, p.Asp95Asn | No | 6.1E−06 |
| 14:24306429:T:G | c.281A > C, c.281A > C, c.281A > C | p.Glu94Ala, p.Glu94Ala, p.Glu94Ala | No | 4.3E−07 |
| 14:24306430:C:T | c.280G > A, c.280G > A, c.280G > A | p.Glu94Lys, p.Glu94Lys, p.Glu94Lys | No | 4.3E−07 |
| 14:24306430:C:A | c.280G > T, c.280G > T, c.280G > T | p.Glu94*, p.Glu94*, p.Glu94* | Yes | 4.3E−07 |
| 14:24306430:C:G | c.280G > C, c.280G > C, c.280G > C | p.Glu94Gln, p.Glu94Gln, p.Glu94Gln | No | 4.3E−07 |

TABLE 23-continued

Missense or pLOF variants of CIDEB that were identified by exome sequencing and included in the gene burden association analyses

| Genomic coordinates for the genetic variant, C:P:R:A | Coding DNA change | Protein change | Variant classified as pLOF | AAF, fraction of 1 |
|---|---|---|---|---|
| 14:24306435:A:G | c.275T > C, c.275T > C, c.275T > C | p.Leu92Pro, p.Leu92Pro, p.Leu92Pro | No | 4.3E−07 |
| 14:24306435:A:T | c.275T > A, c.275T > A, c.275T > A | p.Leu92Gln, p.Leu92Gln, p.Leu92Gln | No | 3.0E−06 |
| 14:24306436:G:T | c.274C > A, c.274C > A, c.274C > A | p.Leu92Met, p.Leu92Met, p.Leu92Met | No | 4.3E−07 |
| 14:24306438:T:A | c.272A > T, c.272A > T, c.272A > T | p.Gln91Leu, p.Gln91Leu, p.Gln91Leu | No | 8.7E−07 |
| 14:24306448:C:G | c.262G > C, c.262G > C, c.262G > C | p.Asp88His, p.Asp88His, p.Asp88His | No | 4.3E−07 |
| 14:24306449:C:G | c.261G > C, c.261G > C, c.261G > C | p.Glu87Asp, p.Glu87Asp, p.Glu87Asp | No | 1.3E−06 |
| 14:24306450:T:TC | c.259dupG, c.259dupG, c.259dupG | p.Glu87fs, p.Glu87fs, p.Glu87fs | Yes | 1.7E−05 |
| 14:24306453:C:T | c.257G > A, c.257G > A, c.257G > A | p.Ser86Asn, p.Ser86Asn, p.Ser86Asn | No | 4.3E−07 |
| 14:24306454:T:C | c.256A > G, c.256A > G, c.256A > G | p.Ser86Gly, p.Ser86Gly, p.Ser86Gly | No | 4.3E−07 |
| 14:24306455:G:C | c.255C > G, c.255C > G, c.255C > G | p.Asp85Glu, p.Asp85Glu, p.Asp85Glu | No | 4.3E−07 |
| 14:24306457:C:T | c.253G > A, c.253G > A, c.253G > A | p.Asp85Asn, p.Asp85Asn, p.Asp85Asn | No | 4.3E−07 |
| 14:24306459:A:G | c.251T > C, c.251T > C, c.251T > C | p.Val84Ala, p.Val84Ala, p.Val84Ala | No | 8.7E−07 |
| 14:24306460:C:T | c.250G > A, c.250G > A, c.250G > A | p.Val84Met, p.Val84Met, p.Val84Met | No | 1.3E−06 |
| 14:24306467:TC:T | c.242delG, c.242delG, c.242delG | p.Gly81fs, p.Gly81fs, p.Gly81fs | Yes | 4.3E−07 |
| 14:24306468:C:G | c.242G > C, c.242G > C, c.242G > C | p.Gly81Ala, p.Gly81Ala, p.Gly81Ala | No | 1.7E−06 |
| 14:24306469:C:G | c.241G > C, c.241G > C, c.241G > C | p.Gly81Arg, p.Gly81Arg, p.Gly81Arg | No | 4.3E−07 |
| 14:24306470:A:C | c.240T > G, c.240T > G, c.240T > G | p.Asp80Glu, p.Asp80Glu, p.Asp80Glu | No | 4.3E−07 |
| 14:24306472:C:T | c.238G > A, c.238G > A, c.238G > A | p.Asp80Asn, p.Asp80Asn, p.Asp80Asn | No | 8.7E−07 |
| 14:24306474:T:C | c.236A > G, c.236A > G, c.236A > G | p.Glu79Gly, p.Glu79Gly, p.Glu79Gly | No | 8.7E−07 |
| 14:24306475:C:T | c.235G > A, c.235G > A, c.235G > A | p.Glu79Lys, p.Glu79Lys, p.Glu79Lys | No | 2.2E−06 |
| 14:24306483:A:T | c.227T > A, c.227T > A, c.227T > A | p.Val76Glu, p.Val76Glu, p.Val76Glu | No | 1.7E−06 |
| 14:24306489:G:A | c.221C > T, c.221C > T, c.221C > T | p.Thr74Ile, p.Thr74Ile, p.Thr74Ile | No | 1.3E−06 |
| 14:24306489:G:T | c.221C > A, c.221C > A, c.221C > A | p.Thr74Asn, p.Thr74Asn, p.Thr74Asn | No | 2.6E−06 |
| 14:24306498:C:T | c.212G > A, c.212G > A, c.212G > A | p.Gly71Glu, p.Gly71Glu, p.Gly71Glu | No | 4.3E−07 |
| 14:24306507:A:G | c.203T > C, c.203T > C, c.203T > C | p.Leu68Pro, p.Leu68Pro, p.Leu68Pro | No | 2.6E−06 |
| 14:24306513:G:GC | c.196_197insG, c.196_197insG, c.196_197insG | p.Thr66fs, p.Thr66fs, p.Thr66fs | Yes | 4.3E−07 |
| 14:24306513:GT:G | c.196delA, c.196delA, c.196delA | p.Thr66fs, p.Thr66fs, p.Thr66fs | Yes | 1.7E−05 |
| 14:24306514:T:A | c.196A > T, c.196A > T, c.196A > T | p.Thr66Ser, p.Thr66Ser, p.Thr66Ser | No | 1.3E−06 |
| 14:24306517:C:T | c.193G > A, c.193G > A, c.193G > A | p.Glu65Lys, p.Glu65Lys, p.Glu65Lys | No | 3.0E−06 |
| 14:24306519:A:T | c.191T > A, c.191T > A, c.191T > A | p.Leu64*, p.Leu64*, p.Leu64* | Yes | 4.3E−07 |
| 14:24306519:A:G | c.191T > C, c.191T > C, c.191T > C | p.Leu64Ser, p.Leu64Ser, p.Leu64Ser | No | 8.7E−07 |
| 14:24306522:G:T | c.188C > A, c.188C > A, c.188C > A | p.Ala63Glu, p.Ala63Glu, p.Ala63Glu | No | 3.0E−06 |
| 14:24306524:C:T | c.187 − 1G > A, c.187 − 1G > A, c.187 − 1G > A | | Yes | 4.3E−07 |
| 14:24306525:T:C | c.187 − 2A > G, c.187 − 2A > G, c.187 − 2A > G | | Yes | 8.7E−07 |
| 14:24307369:A:C | c.186 + 2T > G, c.186 + 2T > G, c.186 + 2T > G | | Yes | 2.6E−06 |
| 14:24307370:C:T | c.186 + 1G > A, c.186 + 1G > A, c.186 + 1G > A | | Yes | 4.3E−07 |
| 14:24307370:C:A | c.186 + 1G > T, c.186 + 1G > T, c.186 + 1G > T | | Yes | 4.3E−07 |
| 14:24307372:T:C | c.185A > G, c.185A > G, c.185A > G | p.Lys62Arg, p.Lys62Arg, p.Lys62Arg | No | 1.7E−06 |
| 14:24307373:T:C | c.184A > G, c.184A > G, c.184A > G | p.Lys62Glu, p.Lys62Glu, p.Lys62Glu | No | 4.3E−07 |
| 14:24307375:GC:G | c.181delG, c.181delG, c.181delG | p.Ala61fs, p.Ala61fs, p.Ala61fs | Yes | 1.7E−06 |
| 14:24307376:C:T | c.181G > A, c.181G > A, c.181G > A | p.Ala61Thr, p.Ala61Thr, p.Ala61Thr | No | 5.6E−06 |
| 14:24307376:C:G | c.181G > C, c.181G > C, c.181G > C | p.Ala61Pro, p.Ala61Pro, p.Ala61Pro | No | 4.3E−07 |
| 14:24307379:G:C | c.178C > G, c.178C > G, c.178C > G | p.Leu60Val, p.Leu60Val, p.Leu60Val | No | 1.3E−06 |
| 14:24307381:A:C | c.176T > G, c.176T > G, c.176T > G | p.Leu59Arg, p.Leu59Arg, p.Leu59Arg | No | 4.3E−07 |
| 14:24307381:A:G | c.176T > C, c.176T > C, c.176T > C | p.Leu59Pro, p.Leu59Pro, p.Leu59Pro | No | 4.3E−07 |
| 14:24307384:T:C | c.173A > G, c.173A > G, c.173A > G | p.Glu58Gly, p.Glu58Gly, p.Glu58Gly | No | 3.2E−05 |
| 14:24307391:G:T | c.166C > A, c.166C > A, c.166C > A | p.Arg56Ser, p.Arg56Ser, p.Arg56Ser | No | 4.3E−07 |
| 14:24307397:C:G | c.160G > C, c.160G > C, c.160G > C | p.Ala54Pro, p.Ala54Pro, p.Ala54Pro | No | 4.3E−07 |
| 14:24307397:C:T | c.160G > A, c.160G > A, c.160G > A | p.Ala54Thr, p.Ala54Thr, p.Ala54Thr | No | 3.5E−06 |
| 14:24307400:C:T | c.157G > A, c.157G > A, c.157G > A | p.Ala53Thr, p.Ala53Thr, p.Ala53Thr | No | 4.3E−07 |
| 14:24307406:G:T | c.151C > A, c.151C > A, c.151C > A | p.Leu51Met, p.Leu51Met, p.Leu51Met | No | 8.7E−07 |
| 14:24307408:C:A | c.149G > T, c.149G > T, c.149G > T | p.Gly50Val, p.Gly50Val, p.Gly50Val | No | 1.3E−06 |
| 14:24307412:TC:T | c.144delG, c.144delG, c.144delG | p.Gly50fs, p.Gly50fs, p.Gly50fs | Yes | 8.7E−07 |
| 14:24307414:C:T | c.143G > A, c.143G > A, c.143G > A | p.Arg48Gln, p.Arg48Gln, p.Arg48Gln | No | 1.2E−05 |
| 14:24307415:G:C | c.142C > G, c.142C > G, c.142C > G | p.Arg48Gly, p.Arg48Gly, p.Arg48Gly | No | 4.3E−07 |
| 14:24307415:G:A | c.142C > T, c.142C > T, c.142C > T | p.Arg48Trp, p.Arg48Trp, p.Arg48Trp | No | 1.1E−05 |
| 14:24307417:A:T | c.140T > A, c.140T > A, c.140T > A | p.Ile47Asn, p.Ile47Asn, p.Ile47Asn | No | 4.3E−07 |
| 14:24307418:T:C | c.139A > G, c.139A > G, c.139A > G | p.Ile47Val, p.Ile47Val, p.Ile47Val | No | 4.3E−07 |
| 14:24307420:G:T | c.137C > A, c.137C > A, c.137C > A | p.Thr46Asn, p.Thr46Asn, p.Thr46Asn | No | 4.3E−07 |
| 14:24307420:G:A | c.137C > T, c.137C > T, c.137C > T | p.Thr46Ile, p.Thr46Ile, p.Thr46Ile | No | 8.7E−07 |
| 14:24307426:T:A | c.131A > T, c.131A > T, c.131A > T | p.Lys44Met, p.Lys44Met, p.Lys44Met | No | 4.3E−07 |

TABLE 23-continued

Missense or pLOF variants of CIDEB that were identified by exome sequencing and included in the gene burden association analyses

| Genomic coordinates for the genetic variant, C:P:R:A | Coding DNA change | Protein change | Variant classified as pLOF | AAF, fraction of 1 |
|---|---|---|---|---|
| 14:24307428:G:C | c.129C > G, c.129C > G, c.129C > G | p.His43Gln, p.His43Gln, p.His43Gln | No | 4.3E−07 |
| 14:24307432:T:A | c.125A > T, c.125A > T, c.125A > T | p.Asp42Val, p.Asp42Val, p.Asp42Val | No | 6.1E−06 |
| 14:24307435:C:T | c.122G > A, c.122G > A, c.122G > A | p.Cys41Tyr, p.Cys41Tyr, p.Cys41Tyr | No | 4.3E−06 |
| 14:24307436:A:C | c.121T > G, c.121T > G, c.121T > G | p.Cys41Gly, p.Cys41Gly, p.Cys41Gly | No | 1.3E−06 |
| 14:24307436:A:G | c.121T > C, c.121T > C, c.121T > C | p.Cys41Arg, p.Cys41Arg, p.Cys41Arg | No | 4.3E−07 |
| 14:24307437:GAC:G | c.118_119delGT, c.118_119delGT, c.118_119delGT | p.Val40fs, p.Val40fs, p.Val40fs | Yes | 4.3E−07 |
| 14:24307439:C:T | c.118G > A, c.118G > A, c.118G > A | p.Val40Ile, p.Val40Ile, p.Val40Ile | No | 4.3E−07 |
| 14:24307441:C:G | c.116G > C, c.116G > C, c.116G > C | p.Arg39Pro, p.Arg39Pro, p.Arg39Pro | No | 3.0E−06 |
| 14:24307444:A:G | c.113T > C, c.113T > C, c.113T > C | p.Phe38Ser, p.Phe38Ser, p.Phe38Ser | No | 4.3E−06 |
| 14:24307444:A:C | c.113T > G, c.113T > G, c.113T > G | p.Phe38Cys, p.Phe38Cys, p.Phe38Cys | No | 4.3E−07 |
| 14:24307450:C:G | c.107G > C, c.107G > C, c.107G > C | p.Arg36Pro, p.Arg36Pro, p.Arg36Pro | No | 2.6E−06 |
| 14:24307450:C:CGCTG | c.103_106dupCAGC, c.103_106dupCAGC, c.103_106dupCAGC | p.Arg36fs, p.Arg36fs, p.Arg36fs | Yes | 4.3E−07 |
| 14:24307450:C:A | c.107G > T, c.107G > T, c.107G > T | p.Arg36Leu, p.Arg36Leu, p.Arg36Leu | No | 4.3E−07 |
| 14:24307453:T:C | c.104A > G, c.104A > G, c.104A > G | p.Gln35Arg, p.Gln35Arg, p.Gln35Arg | No | 1.7E−06 |
| 14:24307454:G:A | c.103C > T, c.103C > T, c.103C > T | p.Gln35*, p.Gln35*, p.Gln35* | Yes | 4.8E−06 |
| 14:24307459:G:T | c.98C > A, c.98C > A, c.98C > A | p.Pro33Gln, p.Pro33Gln, p.Pro33Gln | No | 4.3E−07 |
| 14:24307465:G:C | c.92C > G, c.92C > G, c.92C > G | p.Ala31Gly, p.Ala31Gly, p.Ala31Gly | No | 4.3E−07 |
| 14:24307466:C:G | c.91G > C, c.91G > C, c.91G > C | p.Ala31Pro, p.Ala31Pro, p.Ala31Pro | No | 4.3E−07 |
| 14:24307468:G:A | c.89C > T, c.89C > T, c.89C > T | p.Ser30Leu, p.Ser30Leu, p.Ser30Leu | No | 4.3E−07 |
| 14:24307472:T:A | c.85A > T, c.85A > T, c.85A > T | p.Thr29Ser, p.Thr29Ser, p.Thr29Ser | No | 4.3E−07 |
| 14:24307473:C:A | c.84G > T, c.84G > T, c.84G > T | p.Trp28Cys, p.Trp28Cys, p.Trp28Cys | No | 4.3E−07 |
| 14:24307474:C:G | c.83G > C, c.83G > C, c.83G > C | p.Trp28Ser, p.Trp28Ser, p.Trp28Ser | No | 4.3E−07 |
| 14:24307474:C:A | c.83G > T, c.83G > T, c.83G > T | p.Trp28Leu, p.Trp28Leu, p.Trp28Leu | No | 2.2E−06 |
| 14:24307477:A:C | c.80T > G, c.80T > G, c.80T > G | p.Val27Gly, p.Val27Gly, p.Val27Gly | No | 4.3E−07 |
| 14:24307478:C:T | c.79G > A, c.79G > A, c.79G > A | p.Val27Ile, p.Val27Ile, p.Val27Ile | No | 3.0E−06 |
| 14:24307480:C:T | c.77G > A, c.77G > A, c.77G > A | p.Arg26Lys, p.Arg26Lys, p.Arg26Lys | No | 1.3E−06 |
| 14:24307486:C:G | c.71G > C, c.71G > C, c.71G > C | p.Gly24Ala, p.Gly24Ala, p.Gly24Ala | No | 4.3E−07 |
| 14:24307486:C:T | c.71G > A, c.71G > A, c.71G > A | p.Gly24Glu, p.Gly24Glu, p.Gly24Glu | No | 1.3E−05 |
| 14:24307489:A:G | c.68T > C, c.68T > C, c.68T > C | p.Phe23Ser, p.Phe23Ser, p.Phe23Ser | No | 1.3E−06 |
| 14:24307489:A:C | c.68T > G, c.68T > G, c.68T > G | p.Phe23Cys, p.Phe23Cys, p.Phe23Cys | No | 8.7E−07 |
| 14:24307490:A:G | c.67T > C, c.67T > C, c.67T > C | p.Phe23Leu, p.Phe23Leu, p.Phe23Leu | No | 1.7E−06 |
| 14:24307498:CTTATA:C | c.54_58delTATAA, c.54_58delTATAA, c.54_58delTATAA | p.Asn18fs, p.Asn18fs, p.Asn18fs | Yes | 2.2E−06 |
| 14:24307501:A:G | c.56T > C, c.56T > C, c.56T > C | p.Ile19Thr, p.Ile19Thr, p.Ile19Thr | No | 3.0E−06 |
| 14:24307502:T:C | c.55A > G, c.55A > G, c.55A > G | p.Ile19Val, p.Ile19Val, p.Ile19Val | No | 1.3E−06 |
| 14:24307502:T:A | c.55A > T, c.55A > T, c.55A > T | p.Ile19Leu, p.Ile19Leu, p.Ile19Leu | No | 8.7E−07 |
| 14:24307502:T:G | c.55A > C, c.55A > C, c.55A > C | p.Ile19Leu, p.Ile19Leu, p.Ile19Leu | No | 8.7E−07 |
| 14:24307507:G:C | c.50C > G, c.50C > G, c.50C > G | p.Ser17Cys, p.Ser17Cys, p.Ser17Cys | No | 1.7E−06 |
| 14:24307508:A:C | c.49T > G, c.49T > G, c.49T > G | p.Ser17Ala, p.Ser17Ala, p.Ser17Ala | No | 4.3E−07 |
| 14:24307510:A:G | c.47T > C, c.47T > C, c.47T > C | p.Val16Ala, p.Val16Ala, p.Val16Ala | No | 1.3E−06 |
| 14:24307511:C:T | c.46G > A, c.46G > A, c.46G > A | p.Val16Ile, p.Val16Ile, p.Val16Ile | No | 1.3E−06 |
| 14:24307514:A:AC | c.42dupG, c.42dupG, c.42dupG | p.Ser15fs, p.Ser15fs, p.Ser15fs | Yes | 1.3E−06 |
| 14:24307515:C:G | c.42G > C, c.42G > C, c.42G > C | p.Arg14Ser, p.Arg14Ser, p.Arg14Ser | No | 8.7E−07 |
| 14:24307516:C:A | c.42 − 1G > T, c.42 − 1G > T, c.42 − 1G > T | | Yes | 2.6E−06 |
| 14:24307516:C:T | c.42 − 1G > A, c.42 − 1G > A, c.42 − 1G > A | | Yes | 8.7E−07 |
| 14:24307818:C:T | c.41G > A, c.41G > A, c.41G > A | p.Arg14Lys, p.Arg14Lys, p.Arg14Lys | No | 4.3E−07 |
| 14:24307818:CTGAG:C | c.37_40delCTCA, c.37_40delCTCA, c.37_40delCTCA | p.Leu13fs, p.Leu13fs, p.Leu13fs | Yes | 4.3E−07 |
| 14:24307819:T:C | c.40A > G, c.40A > G, c.40A > G | p.Arg14Gly, p.Arg14Gly, p.Arg14Gly | No | 3.0E−06 |
| 14:24307822:G:A | c.37C > T, c.37C > T, c.37C > T | p.Leu13Phe, p.Leu13Phe, p.Leu13Phe | No | 1.3E−06 |
| 14:24307830:CTG:C | c.27_28delCA, c.27_28delCA, c.27_28delCA | p.Ser10fs, p.Ser10fs, p.Ser10fs | Yes | 4.3E−06 |
| 14:24307830:C:T | c.29G > A, c.29G > A, c.29G > A | p.Ser10Asn, p.Ser10Asn, p.Ser10Asn | No | 1.3E−06 |
| 14:24307834:G:A | c.25C > T, c.25C > T, c.25C > T | p.Pro9Ser, p.Pro9Ser, p.Pro9Ser | No | 8.7E−07 |
| 14:24307835:G:T | c.24C > A, c.24C > A, c.24C > A | p.Asn8Lys, p.Asn8Lys, p.Asn8Lys | No | 8.7E−07 |
| 14:24307837:T:G | c.22A > C, c.22A > C, c.22A > C | p.Asn8His, p.Asn8His, p.Asn8His | No | 4.3E−06 |
| 14:24307840:C:G | c.19C > G, c.19C > G, c.19C > G | p.Leu7Val, p.Leu7Val, p.Leu7Val | No | 4.3E−07 |
| 14:24307842:G:A | c.17C > T, c.17C > T, c.17C > T | p.Ala6Val, p.Ala6Val, p.Ala6Val | No | 2.6E−06 |
| 14:24307843:C:T | c.16G > A, c.16G > A, c.16G > A | p.Ala6Thr, p.Ala6Thr, p.Ala6Thr | No | 4.3E−07 |
| 14:24307848:A:G | c.11T > C, c.11T > C, c.11T > C | p.Leu4Pro, p.Leu4Pro, p.Leu4Pro | No | 4.3E−07 |
| 14:24307849:G:C | c.10C > G, c.10C > G, c.10C > G | p.Leu4Val, p.Leu4Val, p.Leu4Val | No | 4.3E−07 |
| 14:24307849:G:A | c.10C > T, c.10C > T, c.10C > T | p.Leu4Phe, p.Leu4Phe, p.Leu4Phe | No | 4.3E−07 |

TABLE 23-continued

Missense or pLOF variants of CIDEB that were identified by exome sequencing and included in the gene burden association analyses

| Genomic coordinates for the genetic variant, C:P:R:A | Coding DNA change | Protein change | Variant classified as pLOF | AAF, fraction of 1 |
|---|---|---|---|---|
| 14:24307850:G:C | c.9C > G, c.9C > G, c.9C > G | p.Tyr3*, p.Tyr3*, p.Tyr3* | Yes | 4.3E−07 |
| 14:24307851:T:TA | c.7dupT, c.7dupT, c.7dupT | p.Tyr3fs, p.Tyr3fs, p.Tyr3fs | Yes | 4.3E−07 |
| 14:24307852:A:G | c.7T > C, c.7T > C, c.7T > C | p.Tyr3His, p.Tyr3His, p.Tyr3His | No | 3.5E−06 |
| 14:24307853:C:G | c.6G > C, c.6G > C, c.6G > C | p.Glu2Asp, p.Glu2Asp, p.Glu2Asp | No | 1.3E−06 |
| 14:24307853:C:A | c.6G > T, c.6G > T, c.6G > T | p.Glu2Asp, p.Glu2Asp, p.Glu2Asp | No | 8.7E−07 |
| 14:24307856:CATGG:C | c.−2__2delCCAT, c.−2__2delCCAT, c.−2__2delCCAT | p.Met1fs, p.Met1fs, p.Met1fs | Yes | 4.3E−07 |
| 14:24307856:C:T | c.3G > A, c.3G > A, c.3G > A | p.Met1?, p.Met1?, p.Met1? | Yes | 4.8E−06 |
| 14:24307857:A:T | c.2T > A, c.2T > A, c.2T > A | p.Met1?, p.Met1?, p.Met1? | Yes | 4.3E−07 |
| 14:24307857:A:G | c.2T > C, c.2T > C, c.2T > C | p.Met1?, p.Met1?, p.Met1? | Yes | 8.7E−07 |
| 14:24307858:T:C | c.1A > G, c.1A > G, c.1A > G | p.Met1?, p.Met1?, p.Met1? | Yes | 1.3E−06 |
| 14:24307921:C:A | c.−62 − 1G > T, c.−62 − 1G > T | | Yes | 1.3E−06 |
| 14:24307921:C:T | c.−62 − 1G > A, c.−62 − 1G > A | | Yes | 1.3E−06 |
| 14:24307921:CT:C | c.−62 − 2delA, c.−62 − 2delA | | Yes | 4.3E−07 |

C:P:R:A indicates the genomic coordinates of the genetic variant including chromosome (C), physical genomic position in base pairs (P), reference allele (R) and alternative allele (A) relative to build 38 of the Human Genome sequence by the Human Genome Reference Consortium. Coding DNA and protein changes follow the Human Genome Variation Society nomenclature and refer to three CIDEB transcripts annotated in the in the Ensembl database (URL: https://useast.ensembl.org/index.html). Annotations on these three transcripts are reported in the Table 23 in the following order: ENST00000258807, ENST00000554411, ENST00000336557. AAF indicates the alternative allele frequency. pLOF indicates predicted loss of function variant.

Example 3: Interaction of CIDEB Rare Coding Variants with Body Mass Index

Figure 4:
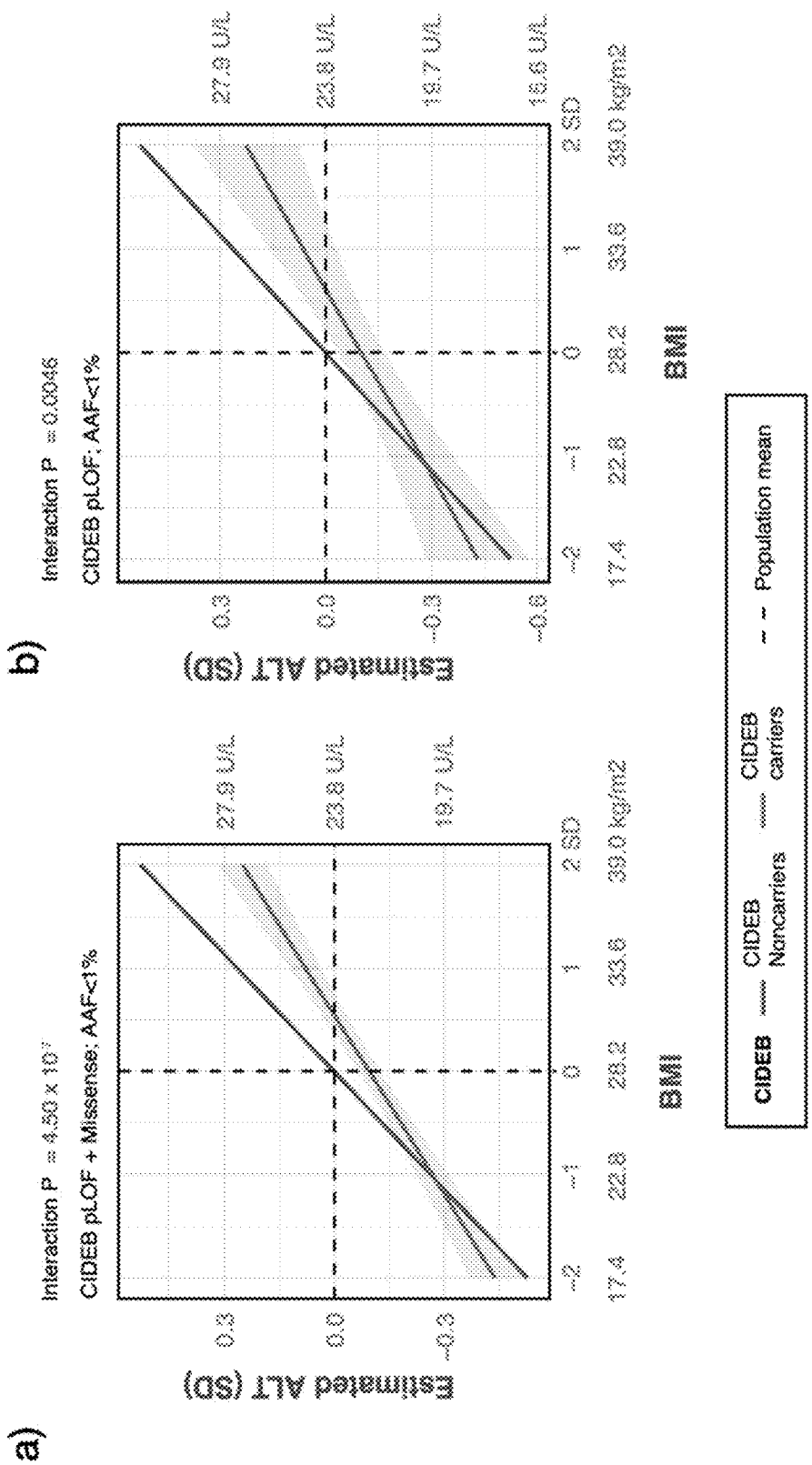
FIG. 4 shows a visualization of the interaction between the burden of rare coding variants in CIDEB and body mass index on alanine aminotransferase levels. CIDEB rare coding (pLOF and missense) variants (Panel a) and CIDEB rare pLOF variants alone (Panel b) were associated with a larger decrease in ALT when individuals have higher body mass index compared to individuals with a lower body mass index. Interaction p-values were used to determine whether this difference in association with ALT by BMI was statistically significant. Abbreviations: ALT, alanine aminotransferase; BMI, body mass index; pLOF, predicted loss of function; AAF, alternate allele frequency; SD, standard deviation; U/L, units per liter.

It was hypothesized that rare coding variants in CIDEB may protect from liver disease by preventing excessive build-up of liver fat into enlarged and inflammation-prone lipid droplets. If that were the case, the protective association of CIDEB rare pLOF and missense variants might be stronger in individuals with higher adiposity who are exposed to a higher risk of liver steatosis and injury. Thus, interactions for rare coding variants in CIDEB with body mass index (BMI), the principal epidemiological risk factor for liver steatosis, were estimated. The association of CIDEB rare coding variants with lower ALT was amplified in individuals with higher BMI when BMI was modelled as a continuous variable ($p_{interaction}$=4.5×10$^{-7}$ rare pLOF plus missense variants in CIDEB and $P_{interaction}$=0.0046 for pLOF variants in CIDEB, as shown in FIG. 4).

Figure 5:
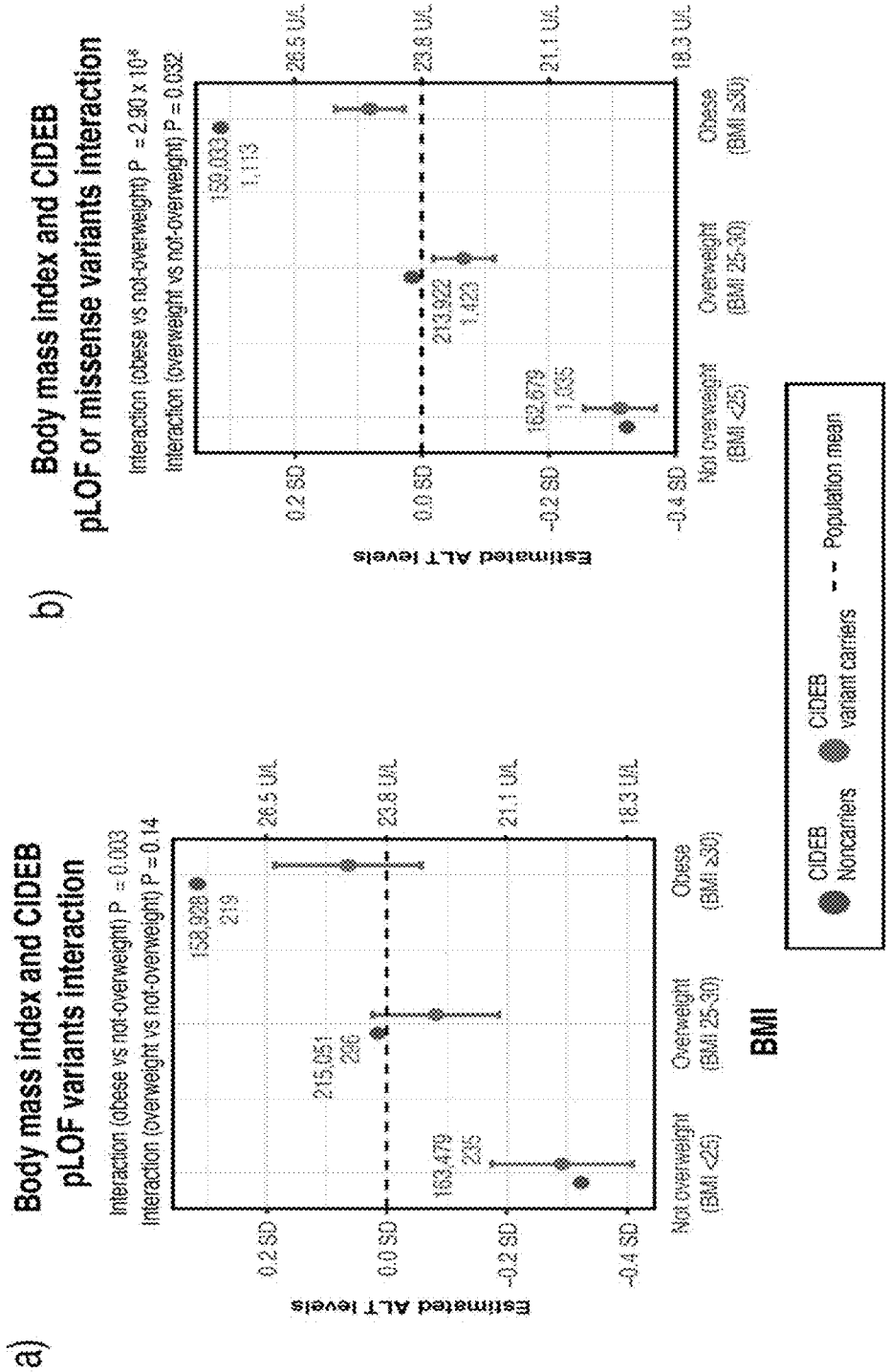
FIG. 5 shows a visualization of the interaction between rare coding variants in CIDEB and body mass index. Panel a shows the interaction of CIDEB genotype (i.e., rare pLOF variants) and body mass index on alanine aminotransferase level. Panel b shows the interaction of CIDEB genotype (i.e., rare pLOF and missense variants) and body mass index on alanine aminotransferase level. Abbreviations: pLOF, predicted loss of function; SD, standard deviation; P, p-value; ALT, alanine aminotransferase; BMI, body mass index; U/L, units per liter.

An interaction on ALT between rare coding variants in CIDEB and clinical categories of BMI was identified. Specifically, CIDEB rare coding variants were not associated with ALT levels in non-overweight individuals (per-allele beta in U/L, 0.1; 95% CI, −0.7 to 0.8; p=0.85), but were associated with −2.8 U/L lower ALT in obese individuals (95% CI, −3.6 to −2.1; p=1.7×10$^{-13}$; $p_{interaction}$ with BMI category=2.9×10$^{-8}$; FIG. 5, panel a and Table 24). This interaction was also observed for CIDEB pLOF variants (FIG. 5, panel b and Table 24). Therefore, the protective association against liver damage observed in carriers of rare pLOF variants in CIDEB is greater in individuals with higher body mass index or who are categorically classified as overweight or obese.

TABLE 24

Interaction between rare pLOF or missense variants in CIDEB and BMI on ALT levels (genetic exposure for first three data lines = burden of pLOF or missense variants in CIDEB with AAF <1%; genetic exposure for last three data lines = burden of pLOF variants in CIDEB with AAF <1%)

| BMI category | Per allele beta (95% CI) in SD units of ALT levels | p-value | Genotype counts, RR\|RA\|AA genotypes | Interaction beta (95% CI) in SD units of ALT per each additional CIDEB allele and kg/m$^2$ unit of BMI | p-value for linear interaction between CIDEB genotype and BMI |
|---|---|---|---|---|---|
| Not Overweight (<25 kg/m2) | −0.01 (−0.05, 0.06) | 8.5 × 10$^{-1}$ | 162,679\|1,035\|0 | −0.08 (−0.11, −0.05) | 4.5 × 10$^{-7}$ |

TABLE 24-continued

Interaction between rare pLOF or missense variants in CIDEB and BMI on ALT levels (genetic exposure for first three data lines = burden of pLOF or missense variants in CIDEB with AAF <1%; genetic exposure for last three data lines = burden of pLOF variants in CIDEB with AAF <1%)

| BMI category | Per allele beta (95% CI) in SD units of ALT levels | p-value | Genotype counts, RR\|RA\|AA genotypes | Interaction beta (95% CI) in SD units of ALT per each additional CIDEB allele and kg/m$^2$ unit of BMI | p-value for linear interaction between CIDEB genotype and BMI |
|---|---|---|---|---|---|
| Overweight (25 to <30 kg/m2) | −0.08 (−0.13, −0.03) | $7.9 \times 10^{-4}$ | 213,922\|1,423\|2 | | |
| Obese (≥30 kg/m2) | −0.21 (−0.26, −0.15) | $1.7 \times 10^{-13}$ | 159,033\|1,113\|1 | | |
| Not Overweight (<25 kg/m2) | 0.03 (−0.08, 0.15) | $5.7 \times 10^{-1}$ | 163,479\|235\|0 | −0.10 (−0.16, −0.03) | $4.6 \times 10^{-3}$ |
| Overweight (25 to <30 kg/m2) | −0.10 (−0.21, 0.00) | $5.8 \times 10^{-2}$ | 215,051\|296\|0 | | |
| Obese (≥30 kg/m2) | −0.25 (−0.37, −0.12) | $8.5 \times 10^{-5}$ | 159,928\|219\|0 | | |

BMI indicates body mass index. BMI categories were defined according to the World Health Organization as follows: "non-overweight" (BMI<25 kg/m$^2$), "overweight" (BMI≥25 and <30 kg/m$^2$), "obesity" (BMI≥30). RR indicates the number of individuals carrying no rare missense or pLOF variants in CIDEB (homozygous non-carriers); RA indicates the number of individuals carrying rare missense or pLOF variants in a single CIDEB allele (heterozygous carriers); AA indicates the number of individuals carrying rare missense or pLOF variants in both CIDEB alleles (homozygous carriers); SD indicates standard deviation units; AAF indicates the alternative allele frequency; pLOF indicates predicted loss of function; CI indicates confidence interval; kg/m$^2$ kilograms per square meter.

Table 24 shows the association with ALT levels of rare pLOF or missense variants in CIDEB within BMI categories in a meta-analysis of the GHS and UKB cohorts and the estimates from the linear interaction analysis.

Given the significant interactions for CIDEB with BMI (this example) and PNPLA3 (Example 4) on ALT and potential for CIDEB to affect liver fat through experimental evidence (Example 5), it was hypothesized that rare coding variants in CIDEB are associated with liver fat and that the association is more pronounced in overweight individuals. Rare coding variants in CIDEB were significantly associated with MRI-measured liver fat (Table 25): rare pLOF variants were associated with lower liver fat in overweight or obese individuals (per-allele beta in % units of liver fat fraction, −1.5%; 95% CI, −3.0% to −0.1%; p=0.04). In addition, a significant interaction was found between rare pLOF or missense variants in CIDEB and BMI on MRI-measured liver fat (p-interaction=0.02).

TABLE 25

Association results for the interaction between carriers of rare coding variant in CIDEB and overweight or obese individuals on MRI measured liver fat

| Exposure | Beta (95% CI) in SD units per allele | Clinical units, % liver fat fraction | P | Allele count |
|---|---|---|---|---|
| CIDEB (pLOF; AAF <1%) in not-overweight individuals | 0.10 (−0.30, 0.51) | 0.51 (−1.46, 2.49) | 0.61 | 14,892\|19\|0 |
| CIDEB (pLOF; AAF <1%) in Overweight or Obese individuals | −0.31 (−0.61, −0.02) | −1.54 (−2.99, −0.08) | 0.04 | 22,261\|35\|0 |
| Interaction estimate of CIDEB (pLOF; AAF <1%) * Overweight or obese | −0.42 (−0.92, 0.08) | −2.05 (−4.49, 0.40) | 0.10 | |
| CIDEB (pLOF + missense variants; AAF <1%) in not-overweight individuals | 0.18 (−0.02, 0.37) | 0.88 (−0.08, 1.84) | 0.07 | 14,947\|79\|0 |
| CIDEB (pLOF + missense variants; AAF <1%) in Overweight or Obese individuals | −0.12 (−0.27, 0.02) | −0.60 (−1.31, 0.12) | 0.10 | 22,357\|143\|0 |
| Interaction estimate of CIDEB (pLOF + missense variants; AAF <1%) * Overweight or obese | −0.30 (−0.54, −0.05) | −1.45 (−2.67, −0.23) | 0.02 | |

A linear regression was performed between PDFF and CIDEB rare coding variants within not-overweight and overweight or obese individuals separately. Interaction estimates were calculated in the full model, in each ancestry separately and meta-analyzed—same as the discovery analysis. Abbreviations: pLOF, predicted loss of function; SD, standard deviation; P, p-value; AAF, alternate allele frequency.

Figure 6:
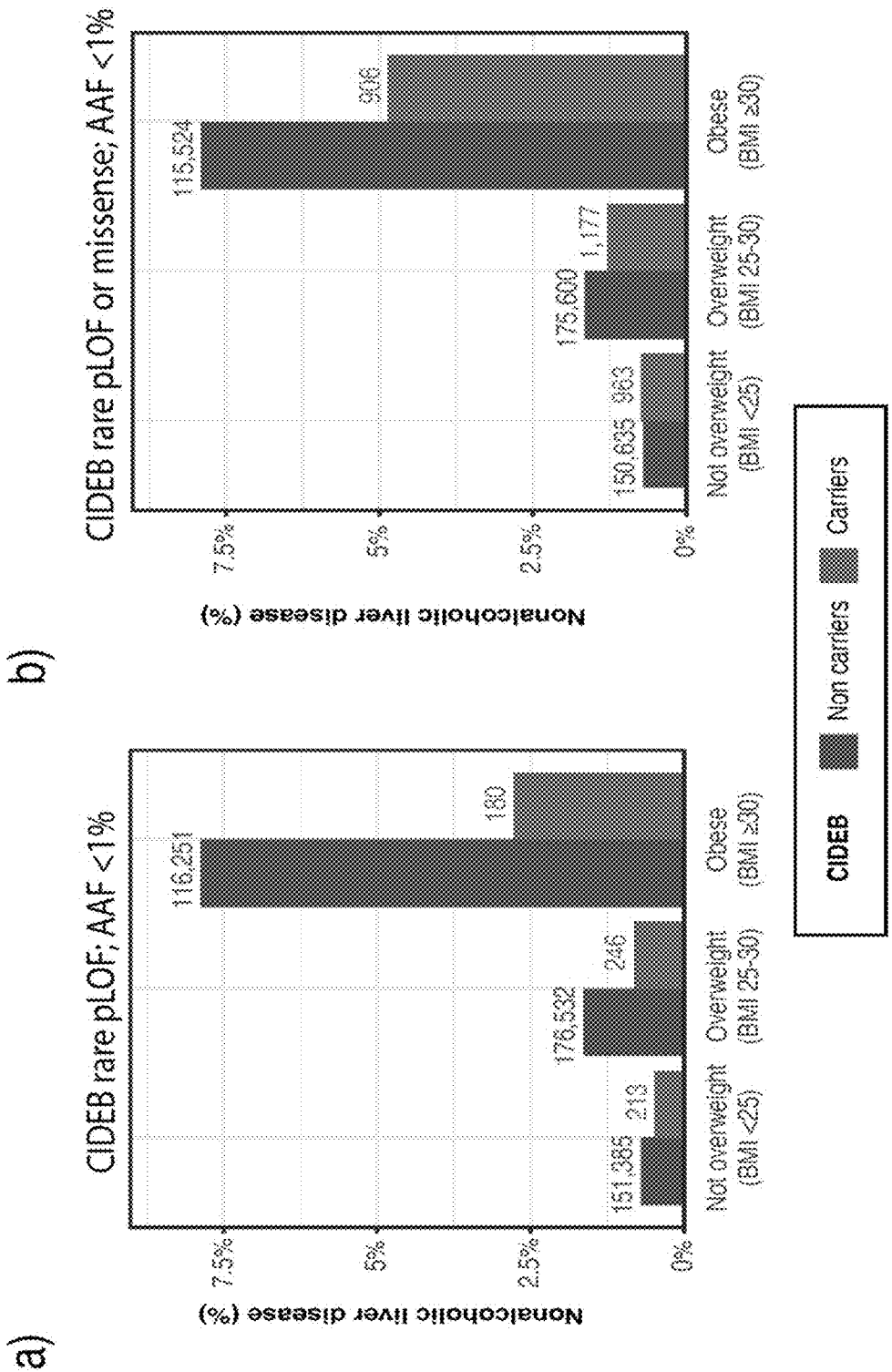
FIG. 6 shows a proportion of nonalcoholic liver disease in carriers and non-carriers of CIDEB rare coding variants across body mass index categories. The percentage of nonalcoholic liver disease is shown for carriers vs non-carriers of rare coding CIDEB variants, stratified by body mass index. Panel a shows carriers of only pLOF variants, and Panel b shows carriers of pLOF and missense variants. Abbreviations: BMI, body mass index; pLOF, predicted loss of function; AAF, alternate allele frequency. Numbers above each bar represents the observed sample size within the group being represented by the bar.

The proportion of liver disease by CIDEB genotypes and BMI categories were also estimated and it was found that the difference in proportion of liver disease in CIDEB rare coding variant carriers versus non-carriers was highest in the obesity category (FIG. 6).

Example 4: Rare Coding Variants in CIDEB Interact with PNPLA3 Genotypes and Show Additive Associations with HSD17B13 Genotypes A common missense variant in the Patatin Like Phospholipase Domain Containing 3 (PNPLA3) gene, encoding a p.Ile148Met (dbSNP rsID, r5738409; C>G substitution) missense change in the PNPLA3 protein is one of the most common and strongest genetic risk factors for liver damage (measured by ALT levels), alcoholic and non-alcoholic liver disease and cirrhosis (Nat. Genet., 2008, 40, 1461-5; and Nat. Genet., 2010, 42, 21-3). In the exome-sequencing dataset, the 148Met risk allele was strongly associated with higher ALT levels (per allele beta in SD units of ALT, 0.11; 95% confidence interval, 0.10, 0.11; $p<1.0\times10^{-300}$) consistent with previous literature.

Figure 7:
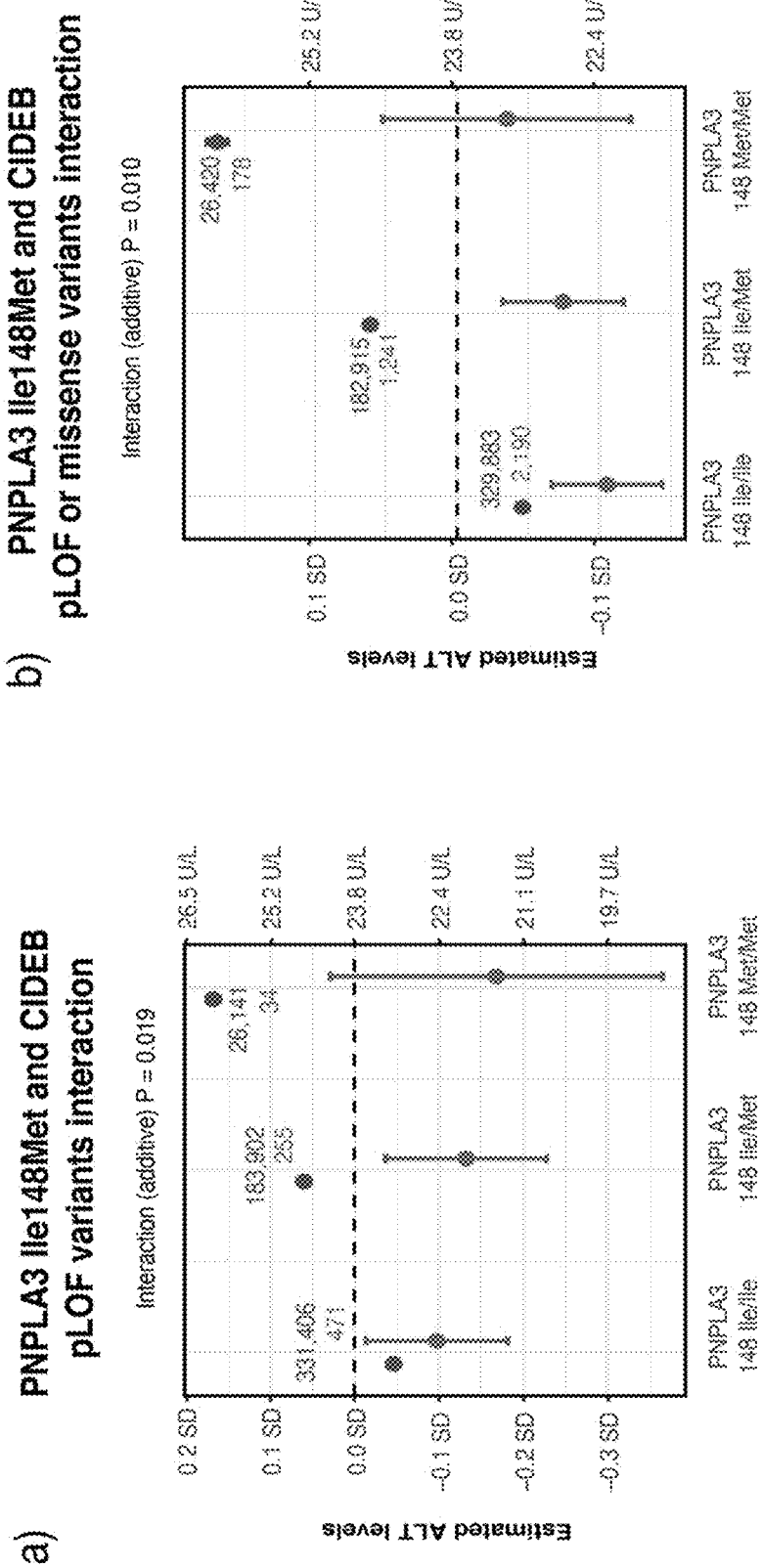
FIG. 7 shows a visualization of the interaction between rare coding variants in CIDEB with PNPLA3 Ile148Met. Panel a shows the interaction of CIDEB genotype (i.e., rare pLOF variants) and Ile148Met on alanine aminotransferase level. Panel b shows the interaction of CIDEB genotype (i.e., rare pLOF and missense variants) and Ile148Met on alanine aminotransferase level. Abbreviations: pLOF, predicted loss of function; SD, standard deviation; P, p-value; ALT, alanine aminotransferase; BMI, body mass index; U/L, units per liter.

A statistically significant interaction was observed between rare coding variants in CIDEB and the common PNPLA3 148Met risk allele on ALT (Table 26 and FIG. 7).

RR indicates the number of individuals carrying no rare missense or pLOF variants in CIDEB (homozygous non-carriers); RA indicates the number of individuals carrying rare missense or pLOF variants in a single CIDEB allele (heterozygous carriers); AA indicates the number of individuals carrying rare missense or pLOF variants in both CIDEB alleles (homozygous carriers); SD indicates standard deviation units; AAF indicates the alternative allele frequency; pLOF indicates predicted loss of function; CI indicates confidence interval.

The first section of Table 26 describes the burden of pLOF or missense variants in CIDEB with AAF<1% as the genetic exposure; second section describes the burden of only pLOF variants in CIDEB with AAF<1% as the genetic exposure. Table 26 shows the association with ALT levels of CIDEB genotype within PNPLA3 rs738409 Ile148Met genotype categories in a meta-analysis of the GHS and UKB cohorts and the estimates from the linear interaction analysis.

The association with lower ALT levels for rare pLOF variants in CIDEB was strongest in homozygous carriers of the 148Met risk allele (G/G group), with an estimated effect size that was 5 times larger in a protective direction than what was observed in homozygous carriers of the PNPLA3 148 Ile allele (C/C group; Table 26). Therefore, the protective association against liver damage observed in carriers of rare pLOF or missense variants in CIDEB is greater in individuals carrying the common PNPLA3 148Met risk allele.

No significant interactions were found between rare coding variants in CIDEB and the splice variant rs72613567 which causes loss of function in HSDB17B13 and has been shown to protect against liver disease (N. Engl. J. Med., 2018, 378, 1096-106) (Table 27). These results indicate that rare coding variants in CIDEB have additive protective associations to those of rs72613567-TA in HSD17B13.

TABLE 26

Interaction between rare pLOF or missense variants in CIDEB and PNPLA3 Ile148Met on ALT levels

| PNPLA3 rs738409 (Ile148Met) genotype group, CIDEB genotype exposure | Per allele beta (95% CI) in SD units of ALT levels | p-value | Genotype counts, RR\|RA\|AA genotypes | Interaction beta (95% CI) in SD units of ALT per each additional CIDEB allele and PNPLA3 148Met allele | p-value for linear interaction between CIDEB genotype and PNPLA3 genotype |
|---|---|---|---|---|---|
| C/C (p.148 Ile/Ile), CIDEB pLOF plus any missense | −0.06 (−0.10, −0.02) | 1.8E−03 | 329883\|2190\|0 | −0.07 (−0.12, −0.02) | 0.010 |
| C/G (p.148 Ile/Met), CIDEB pLOF plus any missense | −0.14 (−0.19, −0.09) | 4.7E−07 | 182915\|1241\|1 | | |
| G/G (p.148 Met/Met), CIDEB pLOF plus any missense | −0.18 (−0.34, −0.03) | 1.8E−02 | 26420\|178\|2 | | |
| C/C (p.148 Ile/Ile), CIDEB pLOF | −0.04 (−0.13, 0.04) | 3.3E−01 | 331406\|471\|0 | −0.14 (−0.26, −0.02) | 0.019 |
| C/G (p.148 Ile/Met), CIDEB pLOF | −0.24 (−0.36, −0.12) | 1.1E−04 | 183902\|255\|0 | | |
| G/G (p.148 Met/Met), CIDEB pLOF | −0.20 (−0.55, 0.16) | 2.8E−01 | 26141\|34\|0 | | |

TABLE 27

Interaction between rare pLOF or missense variants in CIDEB
(AAF <1%) and rs72613567 (HSD17B13 splice variant) on ALT levels

| rs72613567-TA (splice LOF variant in HSD17B13) | Per allele beta (95% CI) in SD units of ALT levels | p-value | Genotype counts, RR\|RA\|AA genotypes | p-value for linear interaction between CIDEB genotype and rs72613567 |
|---|---|---|---|---|
| T/T | −1.2 (−1.9, −0.6) | 2E−04 | 271776\|1629\|1 | 0.88 |
| T/TA | −1.7 (−2.5, −1.0) | 3E−06 | 204162\|1231\|0 | |
| TA/TA | −0.4 (−2.2, 1.3) | 6.4E−01 | 38700\|208\|0 | |

Figure 8:
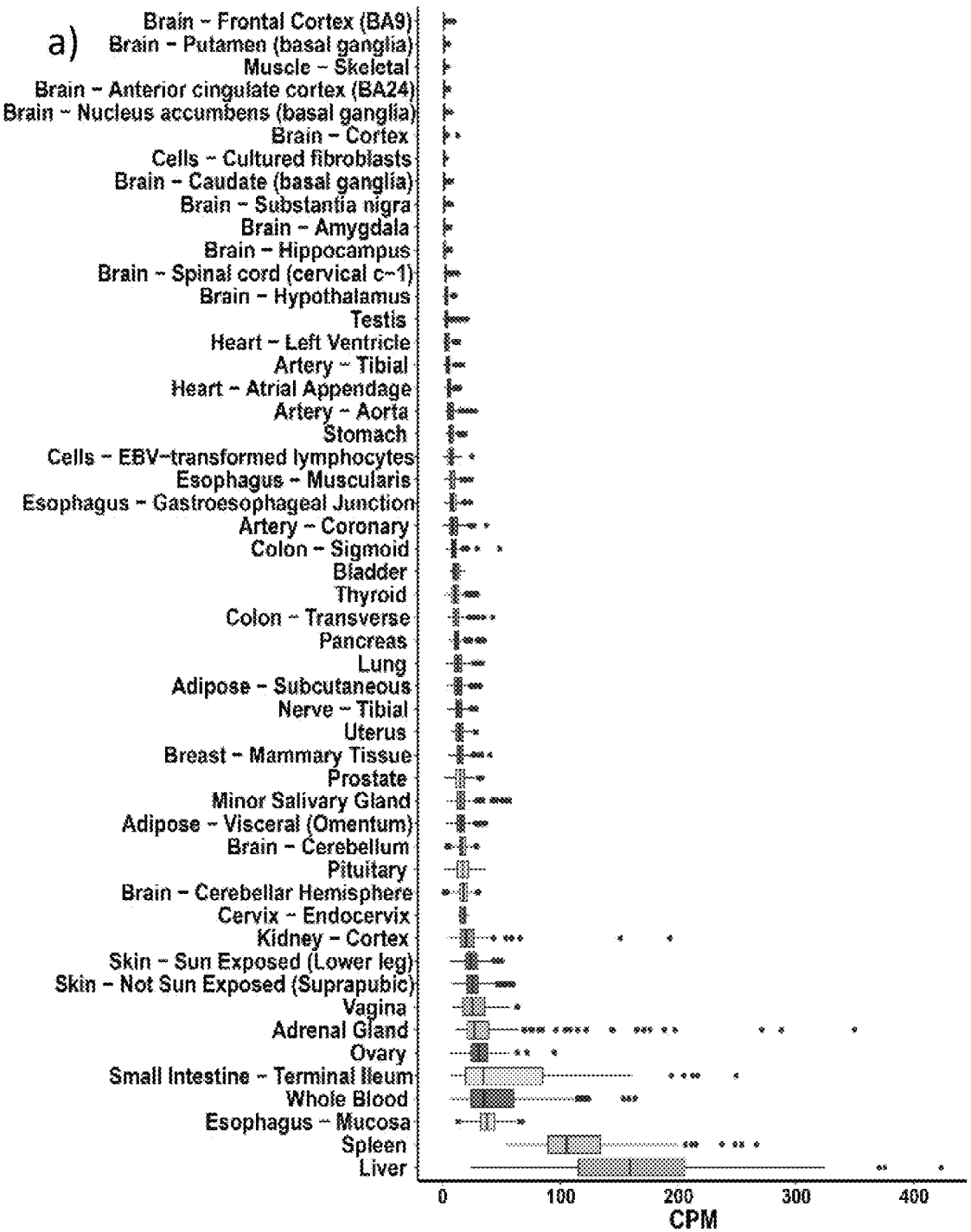
FIG. 8 shows CIDEB expression patterns across tissues (Panel a) and liver cell-types (Panel b). Panel a shows, per tissue, the normalized mRNA expression values for CIDEB in counts per million (CPM) for each individual using data from genotype tissue expression (GTEx) consortium (GTEx Portal 2021. Accessed 2021, June 1st via the world wide web at gtexportal.org/). Panel b shows normalized cell-type specific expression levels within liver, in transcripts per million protein coding genes (pTPM), obtained from the human protein atlas (HPA) (Nat. Biotechnol., 2010, 28, 1248-50). Box plots depict the median (thick black vertical bar), the interquartile range, and minimum and maximum CPM values across individuals per tissue.
Figure 8:
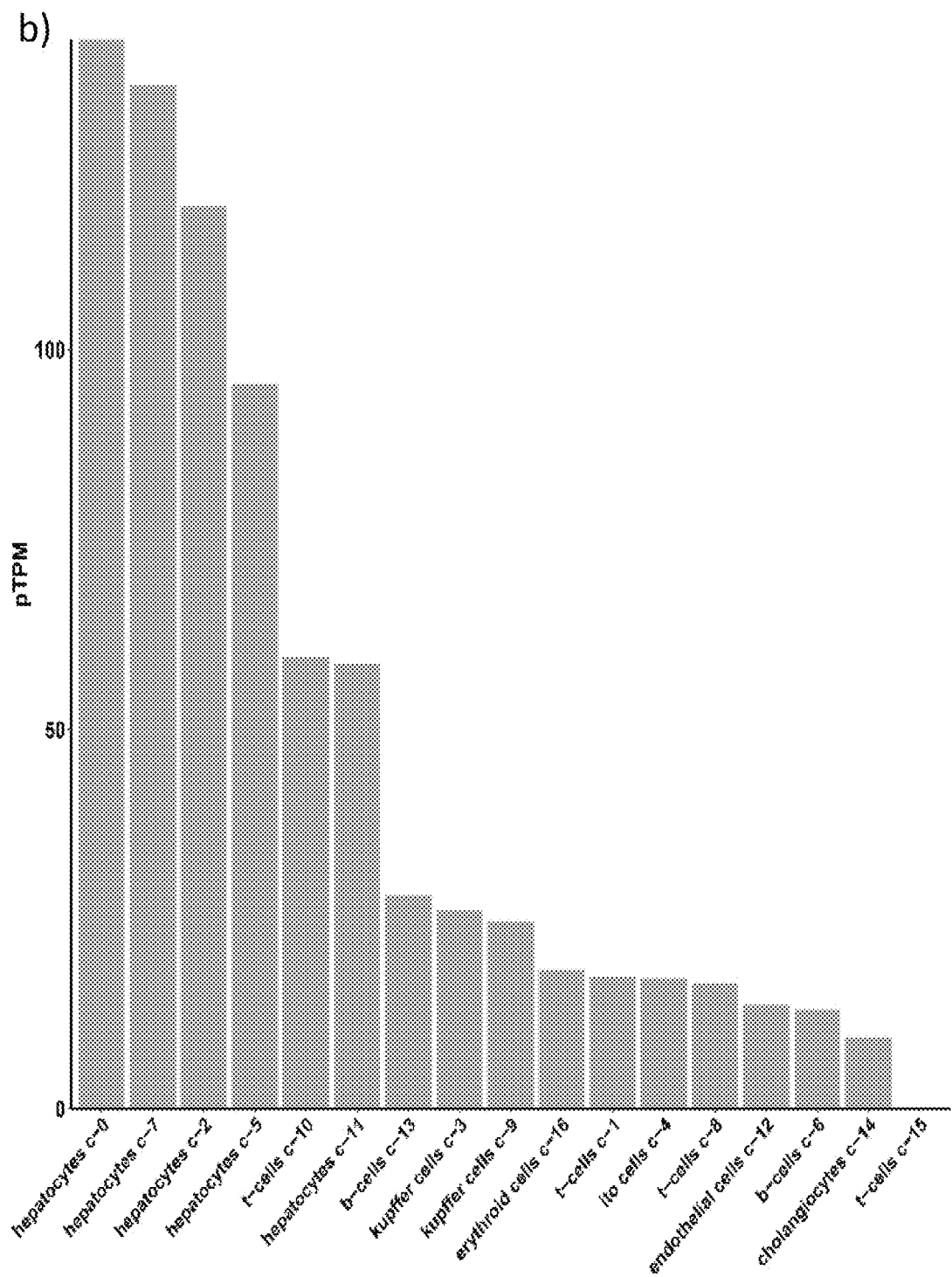

Example 5: CIDEB is Expressed in Hepatocytes at the Surface of Lipid Droplets, Predicted-Loss-of-Function Variants in CIDEB are Associated with Lower Gene Expression in Liver, and Inhibition of CIDEB Expression Via siRNA Decreases Lipid Droplet Size and Reduces Lipid Accumulation in HepG2 Cells The mRNA expression of CIDEB was examined across tissues in humans from the Genotype Tissue Expression consortium (GTEx) and it was found that CIDEB is most highly expressed in liver among the GTEx tissues (FIG. 8). The mRNA expression of CIDEB was also examined among cell types in data from the Human Protein Atlas (HPA) and found that CIDEB is most highly expressed in hepatocytes (FIG. 8).

Figure 9:
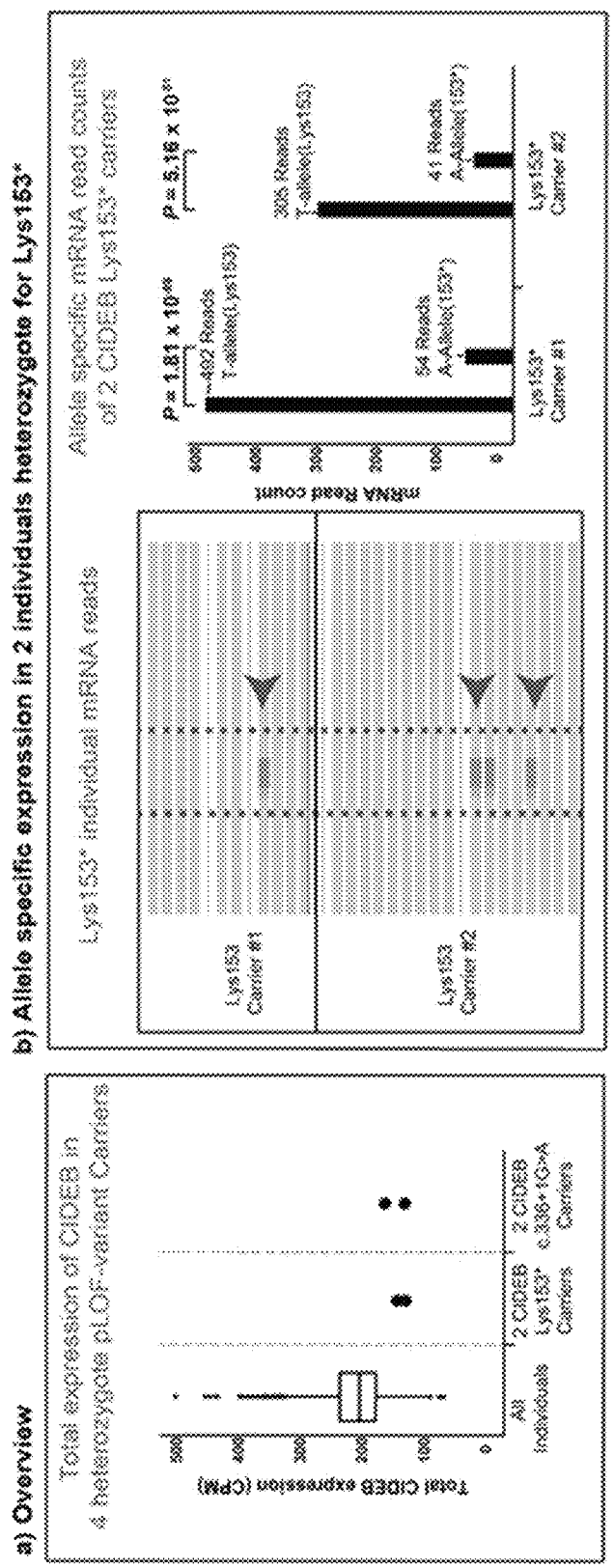
FIG. 9 shows rare pLOF variants in CIDEB impart a loss-of-function via defective mRNA processing in the liver. Panel a shows the level of mRNA expression of CIDEB in liver of bariatric surgery patients from GHS (left), that of two Lys153* heterozygous carriers (middle) and that of two c.336+1G>A heterozygous carriers (right). Panel b shows allele-specific expression results for the two Lys153* heterozygous carriers in RNA sequence reads mapped to the variant site (left; dashed red lines indicate variant site and arrows indicate rare instances where the reads carry the mutant allele) and in a comparison of read counts with or without the mutant allele (right). Panel c shows allele-specific expression results for the two c.336+1G>A heterozygous carriers. The left panel shows RNA sequence reads mapped to the variant site (dashed red lines indicate variant site and arrows indicate rare instances where the reads carry the mutant allele). The middle panel shows the number of spliced and unspliced reads in the two carriers, with unspliced reads being the less frequent occurrence. The right panel shows the allele-specific expression in unspliced reads, which disproportionally carried the variant allele. Abbreviations: pLOF, predicted loss of function; CPM, counts per million; P, p-value; mRNA, mature messenger RNA.
Figure 9:
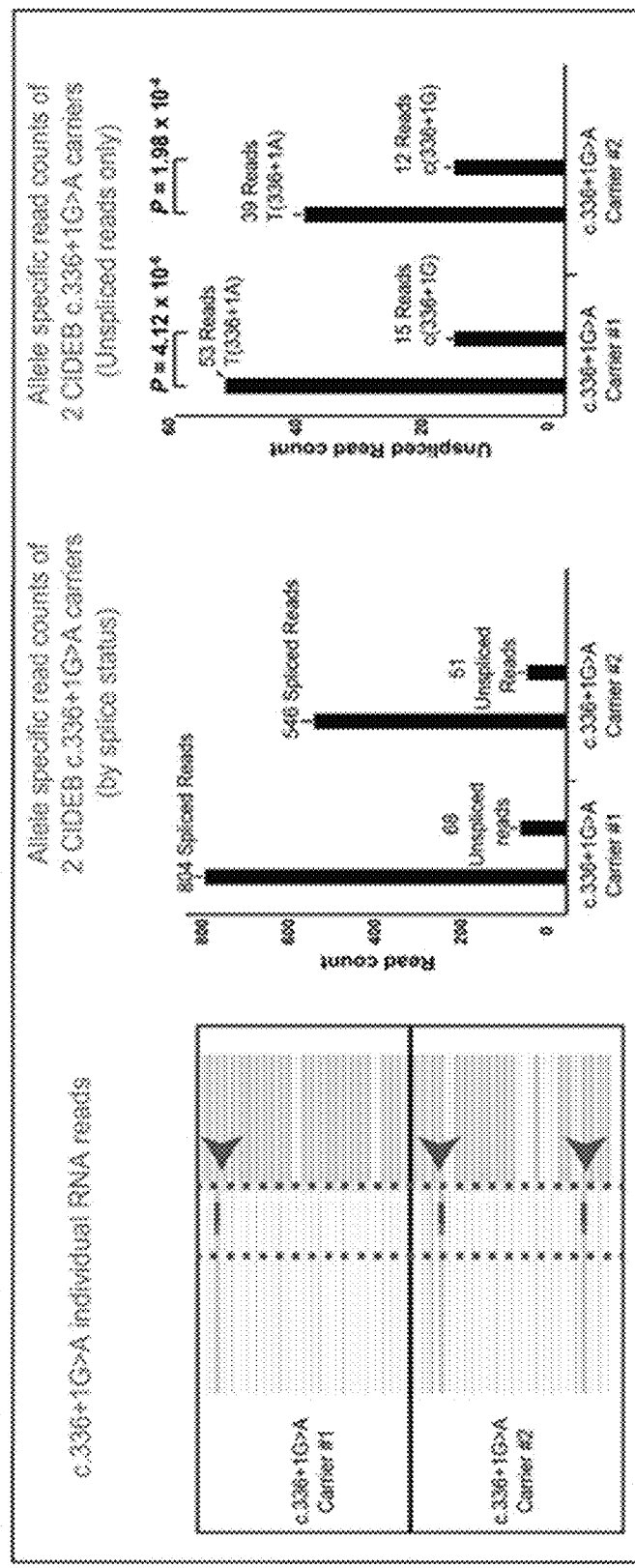

Given that CIDEB is expressed in liver, the impact of predicted loss-of-function (pLOF) variants in the gene was investigated using liver RNASeq data from bariatric surgery patients from GHS. Using liver RNASeq, the impact of two pLOF variants (c.336+1G>A, and Lys153*) was evaluated. These were the only two pLOF variants present in the 2,304 bariatric surgery patients in GHS who underwent RNASeq. Two heterozygous carriers for each of the two variant sites were found and expression levels for CIDEB below the 25th percentile in each of the four carriers were observed (FIG. 9). Both carriers of the Lys153* variant expressed reads containing the stop-gained mutation much less frequently than those carrying the reference allele (expected proportion under the assumption of no impact, 50%; Carrier 1 proportion, 9.9%; $p_{binomial}$ for the observed imbalance=$1.8 \times 10^{-89}$; Carrier 2 proportion, 11.9%; $p_{binomial}=5.2 \times 10^{-51}$; FIG. 9), indicating that the variant is subject to nonsense mediated decay and results in loss of a copy of CIDEB. In carriers of the c.336+1G>A variant, none of the RNASeq reads with spliced sequences that overlap the variant position carried the splice-donor allele. However, RNAseq reads whose unspliced sequences overlapped the position of the splice site were enriched for the splice-donor variant compared to the reference allele (expected proportion under the assumption of no impact, 50%; Carrier 3 proportion, 78.0%; $p_{binomial}=4.1 \times 10^{-06}$; Carrier 4 proportion, 76.5%; $p_{binomial}=2.0 \times 10^{-04}$; FIG. 9), indicating that the variant results in intron retention.

Figure 10:
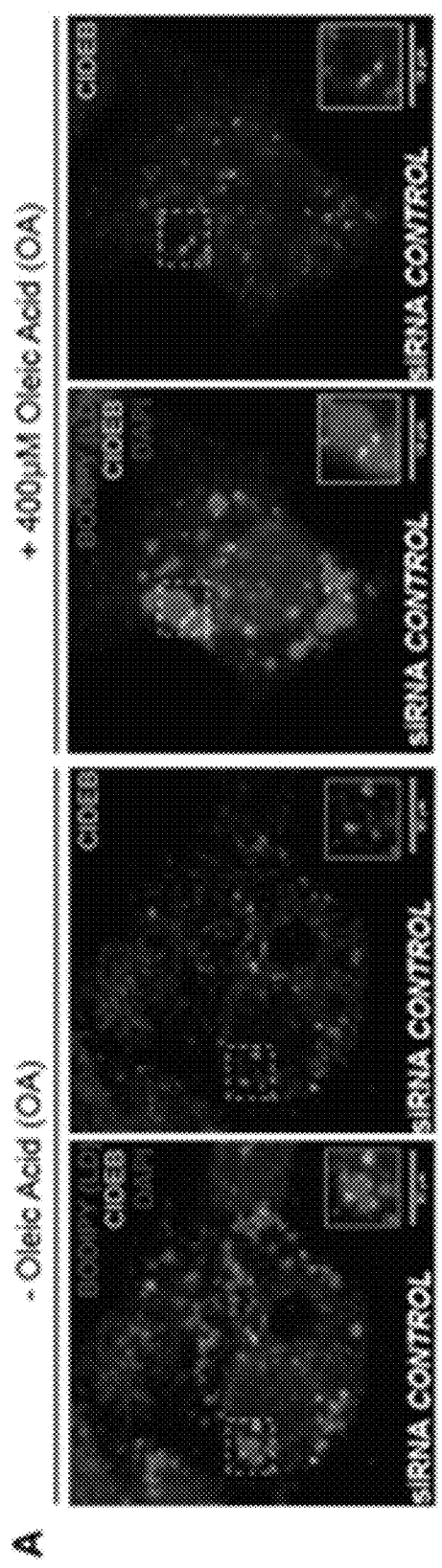
FIG. 10 shows siRNA-mediated knockdown of CIDEB prevents lipid droplet build-up in HepG2 cells. Panel A shows intracellular localization of endogenous CIDEB to the interface of lipid droplets via immunofluorescent staining under basal conditions (no oleic acid) or in the presence of 400 μM oleic acid. Panel B shows the CIDEB protein staining is detectable in cells treated with control siRNA (top) but not CIDEB siRNA (bottom), demonstrating specificity of the CIDEB antibody used in both basal conditions (left) and oleic acid treatment (right). Purple, antibody staining of CIDEB; green, neutral lipids stained by BODIPY; blue, nuclei stained by DAPI; scale bar, 10 μm. Panel C shows western blot analysis (left and center) of CIDEB protein expression and Taqman analysis of CIDEB mRNA expression (right) in control or CIDEB siRNA-treated HepG2 cells. Data are presented as mean±s.d of independent wells and Welch's t-test was performed to determine statistical significance where * represents p<0.05. Panel D shows representative images of oleic acid treatment and CIDEB siRNA impact on lipid droplet size and distribution. Red, neutral lipids stained by AdipoRed; blue, nuclei stained by DAPI; scale bar, 20 μm. Panels E, F, and H show quantification of imaging-derived lipid droplet characteristics, barplots show mean±s.d. of 4 independent wells, depicted as individual points, per condition. Panel E shows the average number of lipid droplets per cell; Panel F shows the average lipid droplet size (quantified from the three-dimensional volume of individual lipid droplets); Panel H shows the average cell lipid droplet staining (quantified as the total area of lipid droplet staining in each cell). Panel G shows average triglyceride concentration per cell quantified using an enzymatic assay; data are mean±s.d of nine independent wells, depicted as individual points, per condition. Panel I shows concentrated of proinflammatory cytokine IL-8 secreted into the cell media quantified by immunoassay; data are mean±s.d. Differences in E-I were assessed using a two-way ANOVA; Tukey's multiple comparisons tests with Sidak correction were used to assess pairwise comparisons of CIDEB siRNA or oleic acid treatment (ns, not significant; * p<0.05;  p<0.01; * p<0.001; **** p<0.0001). Panel J shows AdipoRed staining of neutral lipids demonstrating increasing concentrations of oleic acid result in a dose-dependent increase lipid droplet size and cell lipid droplet staining (left). CIDEB siRNA pretreatment reduces the size of lipid droplets relative to control siRNA pretreatment (right). Red, neutral lipids stained by AdipoRed; blue, nuclei stained by 4',6-diamidino-2-phenylindole (DAPI); scale bar, 20 μm. Abbreviations: DAPI, 4',6-diamidino-2-phenylindole; OA, oleic acid; LD, lipid droplet.
Figure 10:
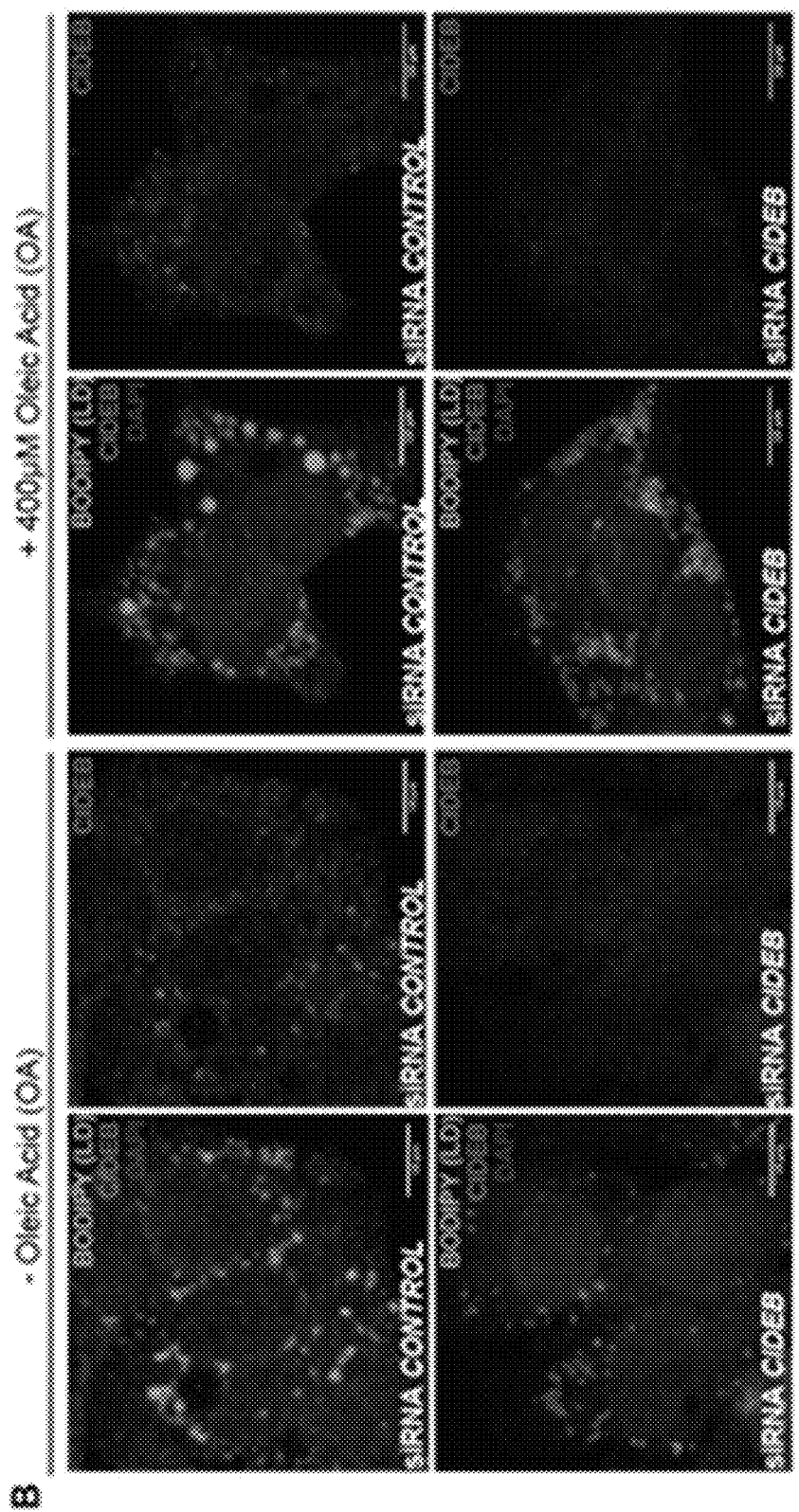
Figure 10:
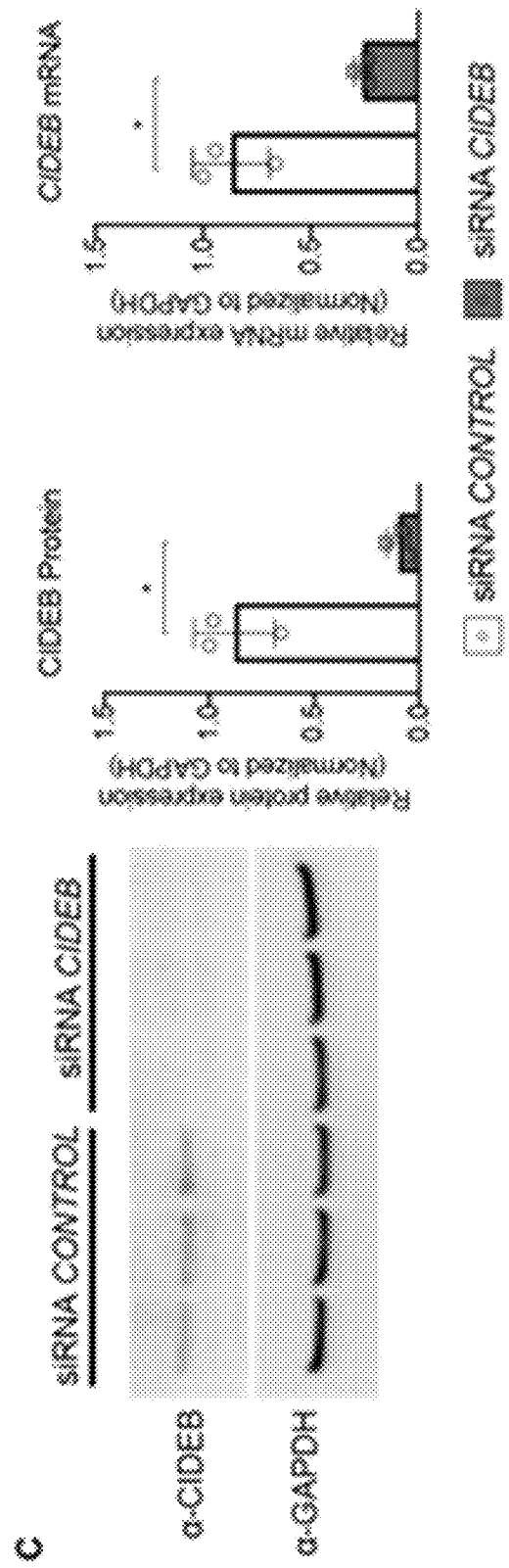
Figure 10:
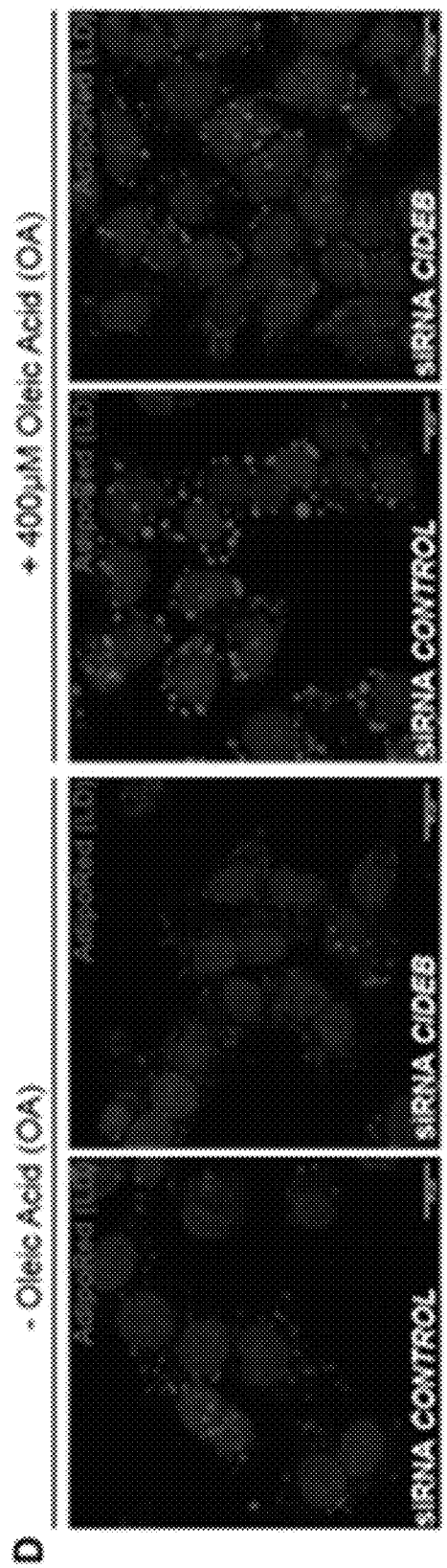
Figure 10:
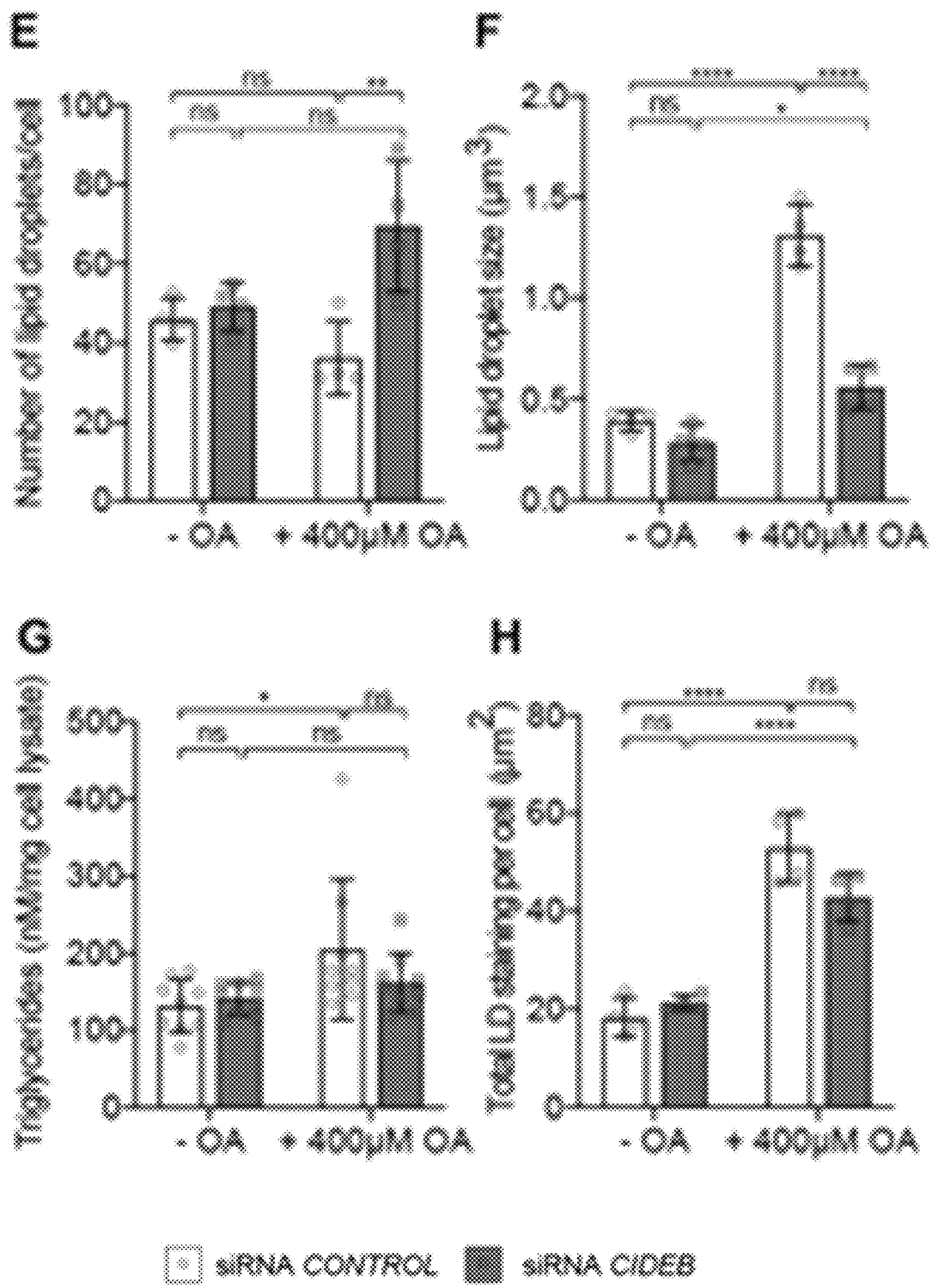
Figure 10:
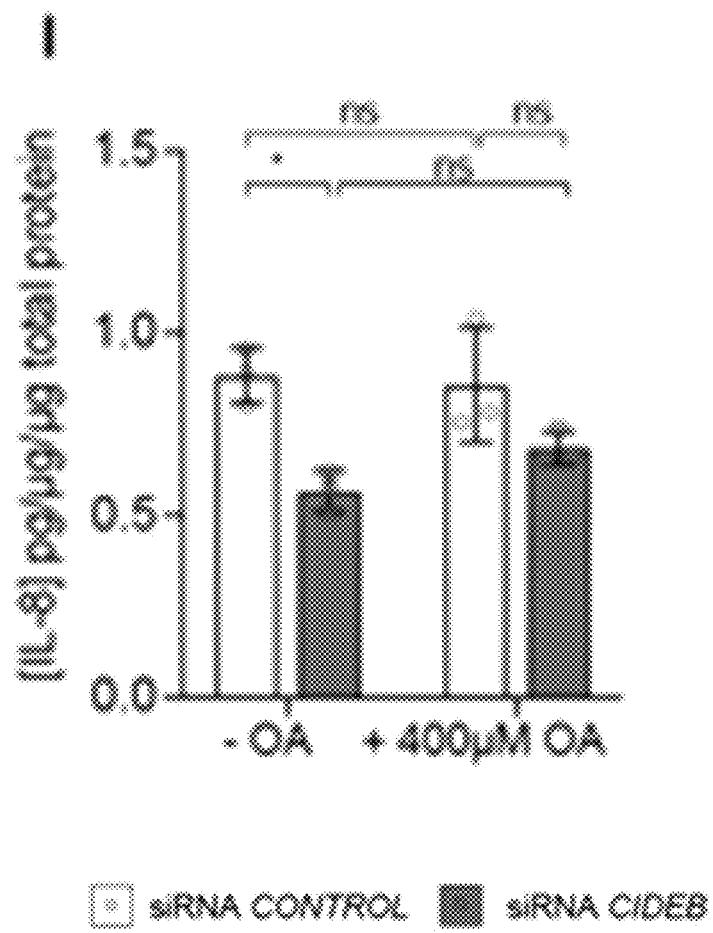
Figure 10:
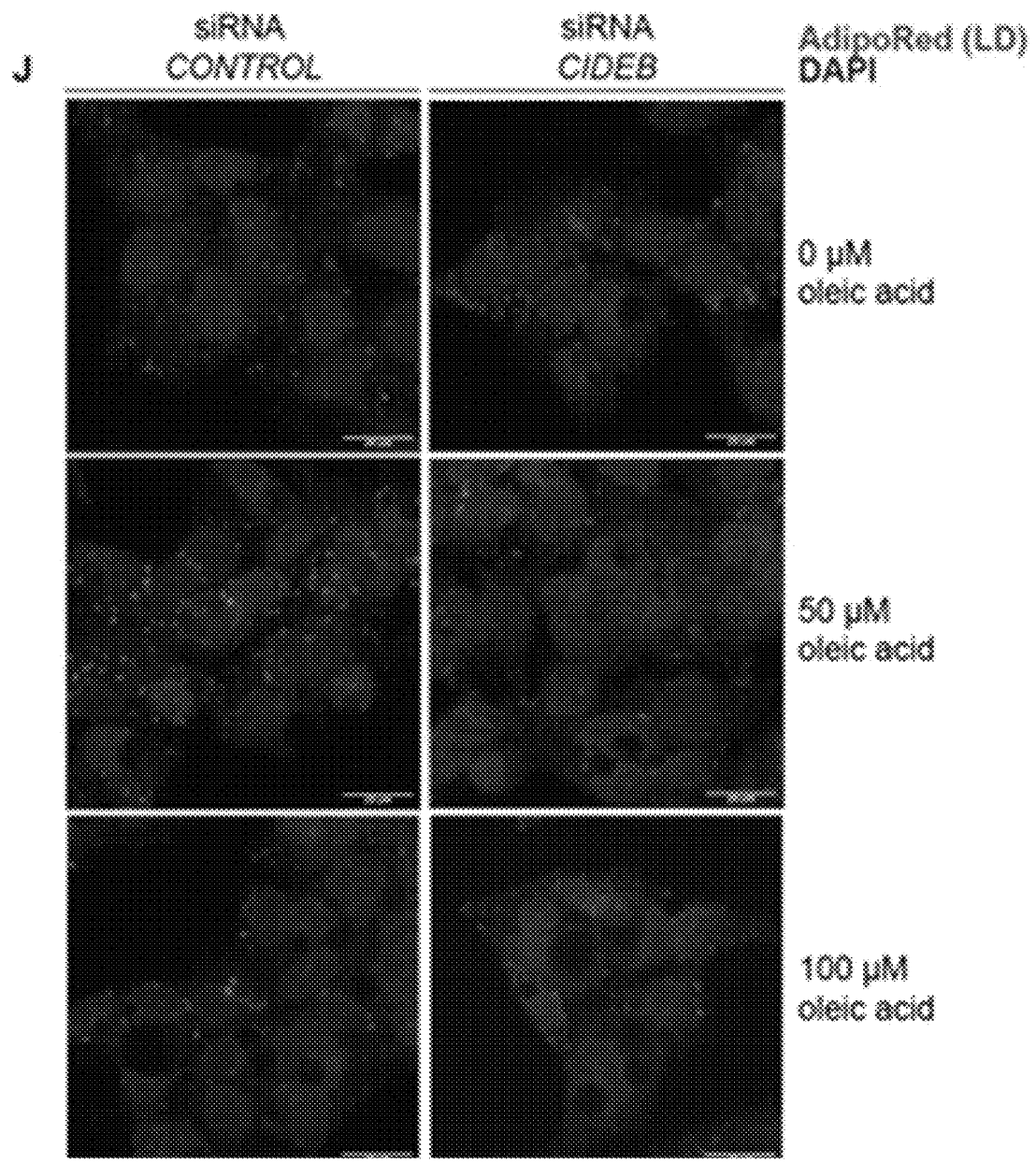
Figure 10:
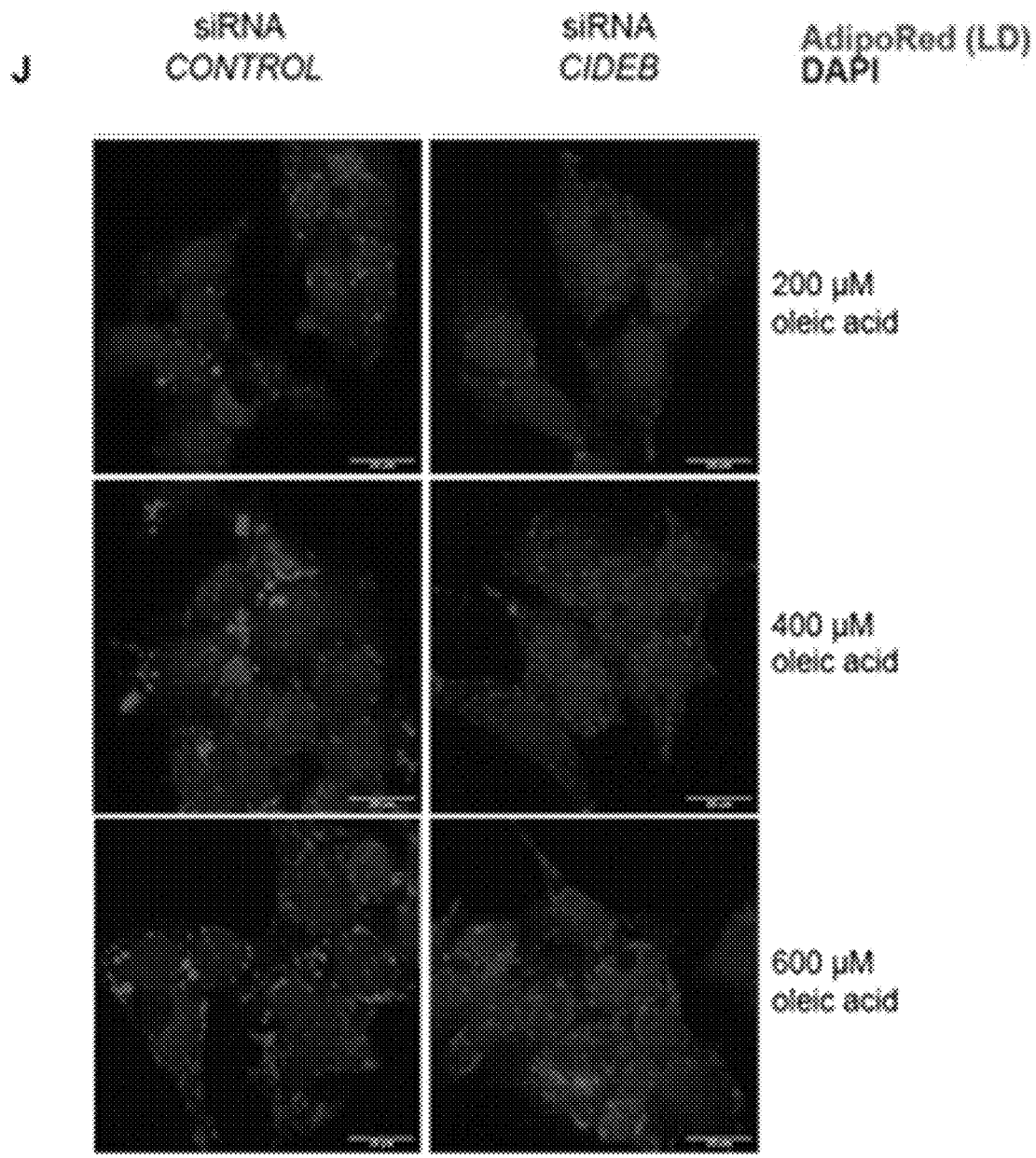

Given that the protective loss-of-function variants in CIDEB were associated with lower liver expression of this gene, the effects of siRNA-mediated knockdown of CIDEB were studied in human hepatocellular carcinoma HepG2 cells with and without treatment with oleic acid, a monosaturated omega-9 fatty acid that is routinely used to mimic steatosis conditions in vitro. In particular, HepG2 human hepatoma cells were treated with control siRNA or siRNA targeting CIDEB. 24 hours after siRNA transfection, cells were treated with 0 µM or 400 µM oleic acid for 24 hours. Endogenous CIDEB protein localized to punctae on the surfaces of lipid droplets and at the interfaces of adjacent lipid droplets in both conditions in cells treated with a non-targeting pool of control siRNA (FIG. 10, Panel A); no CIDEB staining was observed in cells treated with CIDEB siRNA to inhibit CIDEB expression (FIG. 10, Panel B), demonstrating the specificity of the CIDEB antibody used. For each treatment, the left-side image shows the merge of all three stains and the right-side image shows staining of CIDEB only. Further quantification showed that the CIDEB siRNA inhibited CIDEB mRNA expression by 71% and inhibited CIDEB protein expression by 89% (FIG. 10, Panel C). GAPDH was used as loading and normalization control.

Silencing of CIDEB did not affect lipid droplet number or average lipid droplet size, cell triglyceride content or cell lipid droplet staining in the basal condition (FIG. 10, Panels D, E, F, G, and H). CIDEB siRNA-treated cells secreted less IL-8 (FIG. 10, Panel I), a proinflammatory cytokine linked to NAFLD progression, consistent with the genetic associations showing decreased risk of inflammatory liver diseases such as NASH and cirrhosis. Cells were next treated with oleic acid to induce fat accumulation. Oleic acid resulted in the appearance of larger lipid droplets in cells treated with control siRNA in a manner proportional to the amount of oleic acid administered (FIG. 10, Panel J), with increased average lipid droplet size, cell triglyceride content and cell lipid droplet staining (FIG. 10, Panels E, F, G, and H). Numerical, non statistically-significant reductions in average cell triglyceride content or cell lipid droplet staining were observed in CIDEB siRNA-treated cells (FIG. 10, Panels G and H), in line with the genetic association results for liver fat fraction. However, inhibition of CIDEB expression prior to oleic acid treatment resulted in an increased number of smaller lipid droplets compared to cells treated with control siRNA, with significantly reduced average lipid droplet size (p<0.0001) and increased number of lipid droplets per cell (p<0.01) (FIG. 10, Panels D, E, and F).

Various modifications of the described subject matter, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety.

SEQUENCE LISTING

The patent contains a lengthy sequence listing. A copy of the sequence listing is available in electronic form from the USPTO web site (https://seqdata.uspto.gov/?pageRequest=docDetail&DocID=US11773393B2). An electronic copy of the sequence listing will also be available from the USPTO upon request and payment of the fee set forth in 37 CFR 1.19(b)(3).

What is claimed is:

1. A method of treating a subject with a cell death inducing DFFA like effector B (CIDEB) inhibitor, wherein the subject has a liver disease or is at risk of developing a liver disease, the method comprising the steps of:
    determining whether the subject has a CIDEB variant nucleic acid molecule by:
        obtaining or having obtained a biological sample from the subject; and
        performing or having performed a sequence analysis on the biological sample to determine if the subject has a genotype comprising the CIDEB variant nucleic acid molecule, wherein the CIDEB variant nucleic acid molecule is a missense variant, a splice-site variant, a stop-gain variant, a start-loss variant, a stop-loss variant, a frameshift variant, or an in-frame indel variant, or a variant that encodes a truncated CIDEB polypeptide; and
    administering or continuing to administer the CIDEB inhibitor in a standard dosage amount to a CIDEB reference subject; and
    administering or continuing to administer the CIDEB inhibitor in a dosage amount that is the same as or less than a standard dosage amount to a subject that is heterozygous for the CIDEB variant nucleic acid molecule;
    wherein the presence of a genotype having the CIDEB variant nucleic acid molecule indicates the subject has a decreased risk of developing the liver disease or has a decreased risk of developing a more severe form of the liver disease.

2. The method of claim 1, wherein the subject is CIDEB reference, and the subject is administered or continued to be administered the CIDEB inhibitor in a standard dosage amount.

3. The method of claim 1, wherein the subject is heterozygous for the CIDEB variant nucleic acid molecule, and the subject is administered or continued to be administered the CIDEB inhibitor in a dosage amount that is the same as or less than a standard dosage amount.

4. The method of claim 1, wherein the CIDEB variant nucleic acid molecule is a genomic nucleic acid molecule.

5. The method of claim 1, wherein the CIDEB variant nucleic acid molecule is an mRNA molecule.

6. The method of claim 1, wherein the CIDEB variant nucleic acid molecule is a cDNA molecule produced from an mRNA molecule.

7. The method of claim 1, wherein the CIDEB variant nucleic acid molecule comprises 14:24305635:A:AGTAG, 14:24305641:A:C, 14:24305650:G:A, 14:24305657:C:A, 14:24305662:G:T, 14:24305667:T:C, 14:24305671:C:A, 14:24305671:C:G, 14:24305701:A:T, 14:24305709:C:T, 14:24305718:A:G, 14:24305721:T:C, 14:24305728:G: GGCCTT, 14:24305743:T:C, 14:24305948:T:C, 14:24305966:C:T, 14:24305974:T:C, 14:24305980:TCA:T, 14:24305988:C:T, 14:24306014:C:T, 14:24306034:A:C, 14:24306041:C:G, 14:24306044:G:A, 14:24306047:G:A, 14:24306051:T:G, 14:24306064:T:C, 14:24306074:A:G, 14:24306077:G:C, 14:24306082:A:G, 14:24306083:T:A, 14:24306095:G:A, 14:24306122:A:G, 14:24306134:C:G, 14:24306373:C:G, 14:24306379:T:C, 14:24306382:G:A, 14:24306383:G:T, 14:24306426:T:G, 14:24306437:C:G, 14:24306439:G:C, 14:24306442:A:G, 14:24306444:A:G, 14:24306457:C:T, 14:24306463:C:T, 14:24306469:C:T, 14:24306480:A:G, 14:24306486:A:C, 14:24306504:A:G, 14:24306519:A:G, 14:24307382:G:C, 14:24307405:A:G, 14:24307417:A:T, 14:24307421:T:A, 14:24307441:C:A, 14:24307444:A:C, 14:24307444:A:G, 14:24307450:C: CGCTG, 14:24307461:TG:T, 14:24307469:AG:A, 14:24307474:C:T, 14:24307475:A:G, 14:24307833:G:C, 14:24307851:T:TAC, 14:24306426:T:C, 14:24307849:G:C, 14:24307448:G:T, 14:24305671:C:T, 14:24305663:C:T, 14:24305686:C:G, 14:24307829:A:C, 14:24307818:CT-GAG:C, 14:24307856:C:T, 14:24306423:T:C, 14:24306061:AC:A, 14:24307390:C:T, 14:24306382:G:T, 14:24306373:C:T, 14:24305733:T:C, 14:24307858:T:C, 14:24306387:C:T, 14:24305637:T:C, 14:24306062:C:T, 14:24307853:C:G, 14:24307450:C:G, 14:24306052:TG:T, 14:24305673:G:A, 14:24306043:C:T, 14:24307834:G:A, 14:24306417:C:T, 14:24307451:G:A, 14:24307436:A:C, 14:24305953:ACTTT:A, 14:24306489:G:T, 14:24307441:C:T, 14:24306375:C:T, 14:24305657:C:G, 14:24306427:C:T, 14:24306524:C:T, 14:24307516:C:A, 14:24307840:G:C, 14:24307501:A:G, 14:24305968:A:C, 14:24305986:C:T, 14:24307441:C:G, 14:24307459:G:T, 14:24306017:T:A, 14:24307424:G:A, 14:24306072:G:T, 14:24307423:C:T, 14:24307450:C:T, 14:24306420:G:A, 14:24307454:G:A, 14:24305653:C:T, 14:24307442:G:A, 14:24306002:C:T, 14:24306076:C:T, 14:24305664:C:T, 14:24305961:TG:T, 14:24305706:A:G, 14:24305946:C:T, 14:24306455:G:C, 14:24307468:G:A, 14:24307825:A:C, 14:24306110:G:A, 14:24305710:C:T, 14:24307483:C:T, 14:24306459:A:G, 14:24305754:C:T, 14:24305650:G:C, 14:24305691:C:T, 14:24306508:G:C, 14:24306039:G:T, 14:24306139:T:C, 14:24306391:T:C, 14:24306373:C:A, 14:24307498:C:T, 14:24307415:G:A, 14:24306138:CTG:C, 14:24307453:T:C, 14:24305692:G:A, 14:24305683:C:G, 14:24307484:G:A, 14:24307385:C:T, 14:24306519:A:T, 14:24307839:A:C, 14:24305965:C:T, 14:24305988:CAT:C, 14:24306087:C:G, 14:24307439:C:T, 14:24307477:A:C, 14:24306436:G:T, 14:24306507:A:G, 14:24307397:C:T, 14:24307495:G:A, 14:24306034:A:T, 14:24306013:G:A, 14:24307381:A:G, 14:24306383:G:C, 14:24305638:A:G, 14:24307420:G:A, 14:24306020:C:T, 14:24306470:A:C, 14:24307435:C:T, 14:24306469:C:G, 14:24306451:C:T, 14:24306403:G:A, 14:24307515:C:G, 14:24307489:A:G, 14:24307414:C:T, 14:24306483:A:G, 14:24305755:G:A, 14:24305766:C:T, 14:24306064:T:G, 14:24307516:C:G, 14:24305766:C:G, 14:24306489:G:A, 14:24306097:T:C, 14:24305763:T:G, 14:24307447:G:A, 14:24307402:G:A, 14:24305972:C:G, 14:24306423:T:G, 14:24305974:T:TG, 14:24307411:T:C, 14:24306121:T:C, 14:24307516:C:T, 14:24306424:C:T, 14:24306039:G:C, 14:24307853:C:A, 14:24306388:A:G, 14:24305990:T:C, 14:24307822:G:GT, 14:24305640:G:A, 14:24307418:T:C, 14:24305758:G:C, 14:24306131:C:T, 14:24305953:A:G, 14:24305730:C:A, 14:24306418:A:G, 14:24306059:AC:A, 14:24307842:G:A, 14:24307837:T:G, 14:24306095:G:T, 14:24306109:C:T, 14:24307822:G:A, 14:24306077:G:A, 14:24307824:A:T, 14:24306080:C:T, 14:24305649:C:T, 14:24306433:G:GA, 14:24306420:G:C, 14:24305658:T:G, 14:24306472:C:T, 14:24307412:TC:T, 14:24306062:C:A, 14:24306044:G:C, 14:24306047:G:T, 14:24306126:CAG:C, 14:24306449:C:G, 14:24307391:G:A, or 14:24307857:A:C, according to GRCh38/hg38 human genome assembly coordinates.

8. The method of claim 1, wherein the sequence analysis comprises sequencing at least a portion of the nucleotide sequence of the CIDEB genomic nucleic acid molecule, CIDEB mRNA molecule, or CIDEB cDNA molecule produced from an mRNA molecule in the biological sample.

9. The method of claim 8, wherein the sequence analysis comprises:
   a) contacting the biological sample with a primer hybridizing to a portion of the nucleotide sequence of the CIDEB nucleic acid molecule that is proximate to a CIDEB variant nucleic acid molecule position;
   b) extending the primer at least through the CIDEB variant nucleic acid molecule position; and
   c) determining whether the extension product of the primer comprises a variant nucleotide at the CIDEB variant nucleic acid molecule position.

10. The method of claim 8, wherein the sequence analysis comprises sequencing the entire nucleic acid molecule in the biological sample.

11. The method of claim 1, wherein the sequence analysis comprises:
   a) amplifying at least a portion of the CIDEB nucleic acid molecule in the biological sample, wherein the portion comprises a CIDEB variant nucleic acid molecule position;
   b) labeling the amplified nucleic acid molecule with a detectable label;
   c) contacting the labeled nucleic acid molecule with a support comprising an alteration-specific probe, wherein the alteration-specific probe comprises a nucleotide sequence which hybridizes under stringent conditions to the CIDEB variant nucleic acid molecule position; and
   d) detecting the detectable label.

12. The method of claim 1, wherein the sequence analysis comprises:
   contacting the CIDEB nucleic acid molecule in the biological sample with an alteration-specific probe comprising a detectable label, wherein the alteration-specific probe comprises a nucleotide sequence which hybridizes under stringent conditions to a CIDEB variant nucleic acid molecule position; and
   detecting the detectable label.

13. The method of claim 1, further comprising determining the subject's gene burden of having a CIDEB variant nucleic acid molecule.

14. The method of claim 1, further comprising administering a patatin-like phospholipase domain containing 3 (PNPLA3) inhibitor.

15. The method of claim 1, further comprising administering a hydroxysteroid 17-beta dehydrogenase 13 (HSD17B13) inhibitor.

16. The method of claim 14, further comprising detecting the presence or absence of a PNPLA3 variant nucleic acid molecule encoding PNPLA3 Ile148Met or Ile144Met polypeptide in a biological sample from the subject.

17. The method of claim 14, wherein the subject has a PNPLA3 variant nucleic acid molecule encoding PNPLA3 Ile148Met or Ile144Met polypeptide, and the subject is administered a PNPLA3 inhibitor.

18. The method of claim 14, wherein the PNPLA3 inhibitor is AZD2693.

19. The method of claim 15, further comprising detecting the presence or absence of a nucleic acid molecule encoding a reference HSD17B13 polypeptide or a functional HSD17B13 polypeptide and/or a reference HSD17B13 polypeptide or a functional HSD17B13 polypeptide in a biological sample from the subject.

20. The method of claim 15, wherein the HSD17B13 inhibitor is ARO-HSD or ALN-HSD.

21. The method of claim 1, further comprising administering a therapeutic agent for treating a liver disease to the subject.

22. The method of claim 21, wherein the therapeutic agent for treating a liver disease comprises semaglutide.

23. The method of claim 1, wherein the liver disease is fatty liver disease.

24. The method of claim 1, wherein the liver disease is non-alcoholic fatty liver disease (NAFLD).

25. The method of claim 1, wherein the liver disease is non-alcoholic steatohepatitis (NASH).

26. The method of claim 1, wherein the liver disease is liver cirrhosis.

27. The method of claim 1, wherein the liver disease is liver fibrosis.

* * * * *